(12) United States Patent
Markert et al.

(10) Patent No.: US 12,364,715 B2
(45) Date of Patent: Jul. 22, 2025

(54) METHODS OF DETERMINING THE SUITABILITY OF CULTURED THYMUS TISSUE FOR IMPLANTATION INTO HUMANS AND ASSOCIATED METHODS OF USE

(71) Applicants: Duke University, Durham, NC (US); Sumitomo Pharma Switzerland GmbH, Basel (CH)

(72) Inventors: Mary Louise Markert, Durham, NC (US); Laura P. Hale, Durham, NC (US); Joanne Kurtzberg, Durham, NC (US); Lynn Cheatham, Durham, NC (US); Gregory D. Sempowski, Durham, NC (US); Andrew N. MacIntyre, Durham, NC (US); Alex Tracy, Cambridge, MA (US); Kristin Marks, Cambridge, MA (US); Karin Pihel, Cambridge, MA (US)

(73) Assignees: Enzyvant Therapeutics GMBH, Basel (CH); Duke University, Durham, NC (US)

( * ) Notice: Subject to any disclaimer, the term of this patent is extended or adjusted under 35 U.S.C. 154(b) by 21 days.

(21) Appl. No.: 16/994,061

(22) Filed: Aug. 14, 2020

(65) Prior Publication Data
US 2020/0405771 A1   Dec. 31, 2020

Related U.S. Application Data

(63) Continuation of application No. PCT/US2020/046341, filed on Aug. 14, 2020, and a continuation-in-part of application No. 16/283,007, filed on Feb. 22, 2019, now Pat. No. 11,819,520, which is a continuation of application No. PCT/US2019/019137, filed on Feb. 22, 2019.

(60) Provisional application No. 63/039,153, filed on Jun. 15, 2020, provisional application No. 62/888,799, filed on Aug. 19, 2019, provisional application No. 62/634,377, filed on Feb. 23, 2018.

(51) Int. Cl.
| | |
|---|---|
| *C12N 5/077* | (2010.01) |
| *A61K 35/26* | (2015.01) |
| *A61K 35/35* | (2015.01) |
| *A61L 27/36* | (2006.01) |
| *C12N 5/078* | (2010.01) |

(52) U.S. Cl.
CPC .............. *A61K 35/35* (2013.01); *A61K 35/26* (2013.01); *A61L 27/3604* (2013.01); *A61L 27/3687* (2013.01); *C12N 5/0634* (2013.01); *C12N 5/065* (2013.01); *C12N 5/0653* (2013.01); *A61L 2400/06* (2013.01); *A61L 2430/40* (2013.01); *C12N 2533/30* (2013.01); *C12N 2533/80* (2013.01)

(58) Field of Classification Search
None
See application file for complete search history.

(56) References Cited

U.S. PATENT DOCUMENTS

| | | | |
|---|---|---|---|
| 5,614,187 | A | 3/1997 | Sachs et al. |
| 5,624,823 | A | 4/1997 | Sachs et al. |
| 5,658,564 | A | 8/1997 | Sykes et al. |
| 5,766,944 | A | 6/1998 | Ruiz |
| 5,876,708 | A | 3/1999 | Sachs |
| 6,296,846 | B1 | 10/2001 | Sachs et al. |
| 6,911,220 | B1 | 6/2005 | Sachs |
| 7,173,016 | B2 | 2/2007 | DiMartino et al. |
| 8,933,194 | B2 | 1/2015 | Yang et al. |
| 10,612,092 | B2 | 4/2020 | Suthanthiran |
| 11,819,520 | B2 | 11/2023 | Markert |
| 2004/0086508 | A1 | 5/2004 | Skurkovich et al. |
| 2006/0110387 | A1 | 5/2006 | Brunetta |
| 2006/0147428 | A1 | 6/2006 | Sachs |
| 2007/0202085 | A1 | 8/2007 | Hu et al. |
| 2009/0041854 | A1 | 2/2009 | Markert |

(Continued)

FOREIGN PATENT DOCUMENTS

| | | |
|---|---|---|
| CN | 101438977 A | 5/2009 |
| CN | 102061286 A | 5/2011 |

(Continued)

OTHER PUBLICATIONS

Singapore Search Report and Written Opinion dated Mar. 31, 2022 for Singapore Application No. 11202007498Y, 11 pages.

(Continued)

*Primary Examiner* — Allison M Fox
(74) *Attorney, Agent, or Firm* — Hamilton, Brook, Smith & Reynolds, P.C.

(57) ABSTRACT

Methods and compositions for promoting donor-specific tolerance and immunocompetence to a recipient of a solid organ transplant, by implanting an allogeneic solid organ in a recipient in need of a solid organ transplant and further comprising surgical implantation of a tissue-engineered allogeneic cultured postnatal thymus tissue product in the recipient of a solid organ from a donor.

Methods of producing an allogeneic cultured postnatal thymus tissue-derived product suitable for implantation into a human; methods of culturing allogeneic cultured postnatal thymus tissue-derived product suitable for implantation into a human and methods of using allogeneic cultured postnatal thymus tissue-derived product by implantation in a human subject.

7 Claims, 196 Drawing Sheets
(67 of 196 Drawing Sheet(s) Filed in Color)

(56) References Cited

U.S. PATENT DOCUMENTS

| | | |
|---|---|---|
| 2012/0263737 A1 | 10/2012 | Taylor |
| 2015/0110754 A1 | 4/2015 | Bai et al. |
| 2020/0012845 A1* | 1/2020 | Tracy .................. G06K 9/6218 |

FOREIGN PATENT DOCUMENTS

| | | |
|---|---|---|
| JP | 2002-542174 A | 12/2002 |
| WO | 2000/062657 A2 | 10/2000 |
| WO | 2009/120341 A2 | 10/2009 |
| WO | 2012/0092578 A1 | 7/2012 |
| WO | 2018013585 A | 1/2018 |
| WO | 2019/0165195 A1 | 8/2019 |

OTHER PUBLICATIONS

Extended European Search Report mailed Feb. 9, 2022 in European Application No. 19757113.6, 12 pages.
Markert, et al: "Successful Formation of a Chimeric Human Thymus Allograft Following Transplantation of Cultured Postnatal Human Thymus", The Journal of Immunology, Jan. 15, 1997 (Jan. 15, 1997), p. 998.
Rice, et al: "Thymic Transplantation for Complete DiGeorge Syndrome: Medical and Surgical Considerations", Journal of Pediatric Surgery, W. B. Saunders Company, US, vol. 39, No. 11, Nov. 1, 2004 (Nov. 1, 2004), pp. 1607-1615.
Kwun, et al: "Cultured Thymus Tissue Implementation Promotes Donor-specific Tolerance to Allogeneic Heart Transplants", JCI Insight, Apr. 30, 2020 (Apr. 30, 2020), XP055738728, DOI: 10.1172/jci.insight.129983.
Zachary A. A. et al, "HLA Mismatching Strategies for Solid Organ Transplantation—a Balancing Act," Front Immunol, Dec. 7, 2016, vol. 7, Article 575: pp. 1-14.
International Preliminary Report of Patentability mailed Feb. 17, 2022 in International Application No. PCT/US2020/046341, 8 pages.
Amatuni, et al., "Newborn Screening for Severe Combined Immunodeficiency and T-cell Lymphopenia in California, 2010-2017", Pediatrics. Feb. 2019;143(2).
Albuquerque, et al., "Human FOXN1-Deficiency Is Associated With αβ Double-Negative and FoxP3+ T-Cell Expansions That Are Distinctly Modulated Upon Thymic Transplantation." PLoS One, 2012; 7(5):e37042.
Chinn, et al., "Induction of Tolerance to Parental Parathyroid Grafts Using Allogeneic Thymus Tissue in Patients With DiGeorge Anomaly", J Allergy Clin Immunol. Jun. 2011;127(6):1351-5.
Chinn, et al., "Thymus Transplantation Restores the Repertoires of Forkhead Box Protein 3 (FoxP3)+ and FoxP3- T Cells in Complete DiGeorge Anomaly." Clin Exp Immunol. Jul. 2013;173(1):140-9.
Heimall, et al., "Diagnosis of 22q11.2 Deletion Syndrome and Artemis Deficiency in Two Children With T-B-NK+ Immunodeficiency." J Clin Immunol. Oct. 2012;32(5):1141-4.
Lee, et al., "Clinical Course and Outcome Predictors of Critically Ill Infants With Complete DiGeorge Anomaly Following Thymus Transplantation", Pediatr Crit Care Med. Sep. 2014;15(7):e321-6.
Li , et al., 2011, "Thymic Microenvironment Reconstitution After Postnatal Human Thymus Transplantation," Clin Immunology, Apr. 16, 2011, 140(3): 244-259.
Markert, et al., "First Use of Thymus Transplantation Therapy for FOXN1 Deficiency (nude/SCID): a Report of 2 Cases." Blood. Jan. 13, 2011;117(2):688-96.
Rendell, et al., "Complete Thymectomy in Adult Rats With Non-Invasive Endotracheal Intubation," J Vis Exp 2014, (94).
Stone, Jr. et al., "A Case of Atypical, Complete DiGeorge Syndrome Without 22q11 Mutation", Ann Allergy Asthma Immunol. May 2017;118(5):640-642.
International Search Report and Written Opinion for International Application No. PCT/US2020/046341 mailed Oct. 22, 2020 from the International Searching Authority (16 pages).

Biron-Pain K, Grosset AA, Poirier F, Gaboury L, St-Pierre Y (2013) Expression and functions of galectin-7 in human and murine melanomas PLoS One 8:e63307 doi:10.1371/journal.pone.0063307.
Bunting MD, Comerford I, McColl SR (2011) Finding their niche: chemokines directing cell migration in the thymus Immunol Cell Biol 89:185-196 doi:10.1038/icb.2010.142.
Fitzhugh DJ, Shan S, Dewhirst MW, Hale LP (2008) Bromelain treatment decreases neutrophil migration to sites of Inflammation Clin Immunol 128:66-74 doi:10.1016/j.clim.2008.02.015.
Flores KG, Li J, Sempowski GD, Haynes BF, Hale LP (1999) Analysis of the human thymic perivascular space during aging J Clin Invest 104:1031-1039 doi:10.1172/JCI7558.
Gruver AL, Hudson LL, Sempowski GD (2007) Immunosenescence of ageing J Pathol 211:144-156 doi:10.1002/path.2104.
Hafezi-Moghadam A, Thomas KL, Prorock AJ, Huo Y, Ley K (2001) L-selectin shedding regulates leukocyte recruitment J Exp Med 193:863-872 doi:10.1084/jem.193.7.863.
Hernandez-Lopez C, Varas A, Sacedon R, Jimenez E, Munoz JJ, Zapata AG, Vicente A (2002) Stromal cell-derived factor 1/CXCR4 signaling is critical for early human T-cell development Blood 99:546-554 doi:10.1182/blood.v99.2.546.
Hong R, Moore AL (1996) Organ culture for thymus transplantation Transplantation 61:444-448 doi:10.1097/00007890-199602150-00023.
Hu Z, Lancaster JN, Ehrlich LI (2015) The Contribution of Chemokines and Migration to the Induction of Central Tolerance in the Thymus Front Immunol 6:398 doi:10.3389/fimmu.2015.00398.
Ito R et al. (2017) Late Effects of Exposure to Ionizing Radiation and Age on Human Thymus Morphology and Function Radiat Res 187:589-598 doi:10.1667/RR4554.1.
Ivetic A, Hoskins Green HL, Hart SJ (2019) L-selectin: a Major Regulator of Leukocyte Adhesion, Migration and Signaling Front Immunol 10:1068 doi:10.3389/fimmu.2019.01068.
Kozai M et al. (2017) Essential role of CCL21 in establishment of central self-tolerance in T cells J Exp Med 214:1925-1935 doi:10.1084/jem.20161864.
Kuwabara I et al. (2002) Galectin-7 (PIG1) exhibits pro-apoptotic function through JNK activation and mitochondrial cytochrome c release J Biol Chem 277:3487-3497 doi:10.1074/jbc.M109360200.
Le PT, Kurtzberg J, Brandt SJ, Niedel JE, Haynes BF, Singer KH (1988) Human thymic epithelial cells produce granulocyte and macrophage colony-stimulating factors J Immunol 141:1211-1217.
Liu C et al. (2005) The role of CCL21 in recruitment of T-precursor cells to fetal thymi Blood 105:31-39 doi:10.1182/blood-2004-04-1369.
Lkhagvasuren E, Sakata M, Ohigashi I, Takahama Y (2013) Lymphotoxin beta receptor regulates the development of CCL21-expressing subset of postnatal medullary thymic epithelial cells J Immunol 190:5110-5117 doi:10.4049/immunol.1203203.
Markert ML et al. (2007) Review of 54 patients with complete DiGeorge anomaly enrolled in protocols for thymus transplantation: outcome of 44 consecutive transplants Blood 109:4539-4547 doi:10.1182/blood-2006-10-048652.
Markert ML et al. (2003) Thymus transplantation in complete DiGeorge syndrome: immunologic and safety evaluations in 12 patients Blood 102:1121-1130 doi:10.1182/blood-2002-08-2545.
Palmer S, Albergante L, Blackburn CC, Newman TJ (2018) Thymic involution and rising disease incidence with age Proc Natl Acad Sci U S A 115:1883-1888 doi:10.1073/pnas.1714478115.
Sun DP et al. (2016) Thymic hyperplasia after chemotherapy in adults with mature B cell lymphoma and its influence on thymic output and CD4(+) T cells repopulation Oncoimmunology 5:e1137417 doi:10.1080/2162402X.2015.1137417.
Weiss JM, Cufi P, Bismuth J, Eymard B, Fadel E, Berrih-Aknin S, Le Panse R (2013) SDF-1/CXCL12 recruits B cells and antigen-presenting cells to the thymus of autoimmune myasthenia gravis patients Immunobiology 218:373-381 doi:10.1016/j.imbio.2012.05.006.
Wickemeyer JL, Sekhsaria S (2014) Prolonged severe immunodeficiency following thymectomy and radiation: a case report J Med Case Rep 8:457 doi:10.1186/1752-1947-8-457.

(56) References Cited

OTHER PUBLICATIONS

Zaitseva M, Kawamura T, Loomis R, Goldstein H, Blauvelt A, Golding H (2002) Stromal-derived factor 1 expression in the human thymus J Immunol 168:2609-2617 doi:10.4049/jimmunol.168.6.2609.
Lancaster JN, Li Y, Ehrlich LIR. Chemokine-Mediated Choreography of Thymocyte Development and Selection. Trends Immunol. 2018;39(2):86-98. Epub Nov. 23, 2017. doi: 10.1016/j.it.2017.10.007. PubMed PMID: 29162323; PMCID: PMC5800975.
Hale LP, Neff J, Cheatham L, Cardona D, Markert ML, Kurtzberg J. Histopathologic assessment of cultured human thymus. PLOS One, in press, 2020.
Sharabi Y, et al., "Mixed Chimerism and Permanent Specific Transplantation Tolerance Induced by a Nonlethal Preparative Regimen," J Exp Med (1989), 169(2):493-502.
Manilay, et al., 1998, "Intrathymic Deletion of Alloreactive T Cells in Mixed Bone Marrow Chimeras Prepared With a Nonmyeloablative Conditioning Regimen," Transplantation 66(1):96-102.
Yamada K, et al., 1997, "Role of the Thymus in Transplantation Tolerance in Miniature Swine: I. Requirement of the Thymus for Rapid and Stable Induction of Tolerance to Class I-Mismatched Renal Allografts," J Exp Med 186(4):497-506.
Yamada K, et al., 2003, "Thymic Transplantation in Miniature Swine: III. Induction of Tolerance by Transplantation of Composite Thymokidneys Across Fully Major Histocompatibility Complex-Mismatched Barriers," Transplantation 76(3):530-536.
Nobori S, et al., 2006, "Thymic Rejuvenation and the Induction of Tolerance by Adult Thymic Grafts," Proc Natl Acad Sci U S A 103(50):19081-19086.
Davies et al., "Thymus Transplantation for Complete DiGeorge Syndrome: European Experience", J Allergy Clin Immunol. Dec. 2017;140(6):1660-1670.
Collard HR, et al., Possible Extrathymic Development of Nonfunctional T Cells in a Patient With Complete DiGeorge Syndrome. Clin Immunol. May 1999;91(2):156-62.
Markert, et al., "Postnatal Thymus Transplantation With Immunosuppression as Treatment for DiGeorge Syndrome," Blood Oct. 15, 2004; 104(8):2574-2581.
Markert, et al., "Transplantation of Thymus Tissue in Complete DiGeorge Syndrome," N Engl J Med. Oct. 14, 1999; 341(16):1180-1189.
Markert, et al., "The human Thymic Microenvironment During Organ Culture." Clin Immunol Immunopathol. Jan. 1997;82(1):26-36.
Markert, et al., "Factors Affecting Success of Thymus Transplantation for Complete DiGeorge Anomaly", Am J Transplant. Aug. 2008;8(8):1729-36.
Markert, et al., "Successful Formation of a Chimeric Human Thymus Allograft Following Transplantation of Cultured Postnatal Human Thymus." J Immunol. Jan. 15, 1997;158(2):998-1005.
Markert, M. Louise, 2014, "Thymus Transplantation." Sullivan KE & Stiehm ER (Eds) (Academic Press), Chapter 60, pp. 1059-1067.
Markert, et al. "Effect of Highly Active Antiretroviral Therapy and Thymic Transplantation on Immunoreconstitution in HIV Infection", AIDS Res Hum Retroviruses. Mar. 20, 2000;16(5):403-13.
Markert, et al., "Thymus Transplantation," Clin Immunology, May 2010, 135(2): 236-246.
Markert ML, "Perspective: Research Highlights at the Duke University Center for AIDS Research. Immunoreconstitution in HIV Infection: The Role of the Thymus", AIDS Res Hum Retroviruses. Jun. 10, 1996;12(9):751-5.
Markert, et al. "Complete DiGeorge Syndrome: Persistence of Profound Immunodeficiency", J Pediatr. Jan. 1998;132(1):15-21.
Markert, et al., "Thymopoiesis in HIV-Infected Adults After Highly Active Antiretroviral Therapy", AIDS Res Hum Retroviruses. Nov. 20, 2001;17(17):1635-43.
Yin, et al., "Disseminated *Mycobacterium kansasii* Disease in Complete DiGeorge Syndrome", J Clin Immunol. Jul. 2015;35(5):435-8.
Selim, et al., "The Cutaneous Manifestations of Atypical Complete DiGeorge Syndrome: a Histopathologic and Immunohistochemical Study." J Cutan Pathol. Apr. 2008;35(4):380-5.
Boehm, et al., 2014, "Thymic Development and Selection of T Lymphocytes." Heidelberg: Springer-Verlag. vol. 373, pp. 1-132.
Isakovic, et al., 1965, "Immunologic Tolerance in Thymectomized, Irradiated Rats Grafted with Thymus from Tolerant Donors," Science 148(3675):1333-1335.
Neufeld, M. et al., 1981, "Two Types of Autoimmune Addison's Disease Associated With Different Polyglandular Autoimmune (PGA) Syndromes," Medicine 60: 355-362.
Hong, et al., 1979, "Transplantation of Cultured Thymic Fragments. II. Results in Nude Mice," J Exp Med., 149(2):398-415.
Li, et al., 2009, "Characterization of Cultured Thymus Tissue Used for Transplantation With Emphasis on Promiscuous Expression of Thyroid Tissue-specific Genes," Immunol Res. 2009; 44 (1-3):71-83.
Haynes, et al., The Role of the Thymus in Immune Reconstitution in Aging, Bone Marrow Transplantation, and HIV-1 Infection. Annu Rev Immunol. 2000;18:529-60.
Rice, et al., "Thymic Transplantation for Complete DiGeorge Syndrome: Medical and Surgical Considerations", J Pediatr Surg. Nov. 2004; 39(11):1607-15.
Parker, W. et al., "Specificity and Function of 'Natural' Antibodies in Immunodeficient Subjects: Clues to B Cell Lineage and Development," 1997, J Clin Immunol., 17:311-321.
Heron, I., "A Technique for Accessory Cervical Heart Transplantation in Rabbits and Tats," 1971 Acta Pathol Microbiol Scand A 79(4):366-372).
Ahonen, P., 1985, "Autoimmune Polyendocrinopathy—Candidosis—Ectodermal Dystrophy (APECED): Autosomal Recessive Inheritance," Clinical Genetics, 27: 535-542.
Ahonen, P., et al., 1987, "Adrenal and Steroidal Cell Antibodies in Patients With Autoimmune Polyglandular Disease Type I and Risk of Adrenocortical and Ovarian Failure," J. Clin. Endocrinology and Metabolism, 64: 494-500.
Ahonen, P., et al., 1988, "The Expression of Autoimmune Polyglandular Disease Type I Appears Associated With Several HLA-A Antigens But Not With HLA-DR", J. Clin. Endocrinology and Metabolism, 66, 1152-1157.
Ahonen, P., et al., 1990, "Clinical Variation of Autoimmune Polyendocrinopathy-Candidiasis-Ectodermal Dystrophy (APECED) in a Series of 68 Patients," New Engl. J. Med. 322: 1829-1836.
Arulanantham, K., et al., 1979, "Evidence for Defective Immunoregulation in the Syndrome of Familial Candidiasis Endocrinopathy," New Eng. J. Med. 300:164-168.
Blizzard, R. M. et al., 1963, "Studies of the Adrenal Antigens and Antibodies in Addison's Disease," J. Clin. Invest. 42:1653-1660.
Krohn, K., et al., 1992, "Identification by Molecular Cloning of an Autoantigen Associated With Addison's Disease as Steroid 17α-hydroxylase," Lancet 339:770-773.
Perheentupa J., 2002, "APS-I/APECED: the Clinical Disease and Therapy," Endocrinol. Metab. Clin. North Am. 31:295-320.
Davis, CM, et al., "Normalization of the Peripheral Blood T Cell Receptor V Beta Repertoire After Cultured Postnatal Human Thymic Transplantation in DiGeorge Syndrome." J Clin Immunol. Mar. 1997;17(2):167-75.
Schoenecker, et al., 2000, "Exposure to Topical Bovine Thrombin During Surgery Elicits a Response Against the Xenogeneic Carbohydrate Galactose α1-3Galactose," J Clin Immunol., 20:434-444.
Uibo R., et al., 1994, "Autoantibodies to Cytochrome P450 Enzymes P450scc, P450c17, and P450c21 in Autoimmune Polyglandular Disease Types I and II and in Isolated Addison's Sisease," J. Clin. Endocrinol. Metab. 78: 323-328.
Zlotogora, J., et al., 1992, "Polyglandular Autoimmune Syndrome Type I Among Iranian Jews," J. Med. Genet, 29, 824-826.
Schmid, et al., 1994,"Successful Heterotopic Heart Transplantation in Rat," Microsurgery 15(4):279-281.
Curcio, et al., "Robotic-Assisted Thoracoscopic Surgery Thymectomy," Journal of Visualized Surgery, Nov. 7, 2017 (Nov. 7, 2017), vol. 3, Iss. 162, pp. 1-4.

(56) References Cited

OTHER PUBLICATIONS

DeWolf, et al., "A New Window into the Human Alloresponse," Transplantation, Aug. 31, 2016 (Aug. 31, 2016), vol. 100, Iss. 9, pp. 1639-1649.

Furudate, et al., "Sequential Therapy with Nivolumab Followed by Ipilimumab Induces Complete Response in Metastatic Melanoma of the Lung but with Severe Hepatotoxicities," Case Reports in Oncology, Oct. 17, 2016 (Oct. 17, 2016), vol. 9, No. 3, pp. 644-649.

Zachary, et al., "HLA Mismatching Strategies for Solid Organ Transplantation—A Balancing Act," Frontiers in Immunology, Dec. 7, 2016 (Dec. 7, 2016), vol. 7, No. 575, pp. 1-14.

Gebel, et al., "HLA Antibody Detection With Solid Phase Assays: Great Expectations or Expectations Too Great?," American Journal of Transplantation, Aug. 1, 2014 (Aug. 1, 2014 ), vol. 14, No. 9, pp. 1964-1975.

Shichkin, et al., "Effect of Cryopreservation on Viability and Growth Efficiency of Stromal-epithelial Cells Derived From Neonatal Human Thymus," Cryobiology, Jun. 28, 2017 (Jun. 28, 2017), vol. 78, pp. 70-79.

International Search Report and Written Opinion for International application No. PCT/US2019/019137 mailed May 9, 2019 from the International Searching Authority (31 pages).

CFR Title 21; 1271, "Human Cells, Tissues, and Cellular and Tissue-Based Products; Establishment Registration and Listing." Agency: Food and Drug Adminstration, HHS. Fed. Reg. vol. 69, No. 17, Jan. 27, 2004, pp. 3823-3826.

Russia Official Action of the Substantive Examination dated Aug. 9, 2022 for Russian Application No. 2020124312, 21 pages.

Li, B. et al., "Thymic Microenvironment Reconstitution After Postnatal Human Thymus Transplantation.". Clin Immunol, Apr. 16, 2011, vol. 140, No. 3, Author's manuscript from PubMed: pp. 1-27p. 2 last para., p. 3 third para., p. 5 first—second para., p. 6 third para., Citation is not enclosed due to copyright restrictions.

Markert M. L. et al., "Factors Affecting Success of Thymus Transplantation for Complete DiGeorge Anomaly," Am J Transplant, Jun. 28, 2008, vol. 8, No. 8, pp. 1729-1736.

Khubutia, M. Sh., et al., "Immunological Tolerance in Organ Transplantation," Transplantology, 2017; 9(3):211-225. DOI:10.23873/2074-0506-2017-9-3-211-225. 37 pages with translation.

Curico, Carlo et al., "Robotic-assisted Thoracoscopic Surgery Thymectomy," Journal of Visualized Sugery, (Nov. 7, 2017), vol. 3, No. 162, doi: 10.21037/jovs.2017.10.01, pp. 1-4.

Onischenko NA et al., "Donor Bone Marow Cells as Regulators of Immune Tolerance Induction in the Recipient's Body During Allogeneic Organ Transplantation," Bulletin of Transplantology and Artificial Organs. T.Xi. N Apr. 2009, pp. 97-102, (15 pages with translation). file:///C:/Users/i_a_b/Desktop/276-590-1-SM.pdf.

Zhao, et al., "A Model of Isolated, Vascular Whole Thymus Transplantation in Nude Rats", Transplantation Proceedings, 44, 1394-1398 (2012).

Zhao, et al., "Vascularized Whole Thymus Transplantation in Rowett Nude Rats: Effect of Thymus Allograft Volume on Tolerance Induction", Transplant Immunology 23 (2010) 40-44.

Zinkernagel RM, et al., "Cytotoxic T Cells Learn Specificity for Self H-2 During Differentiation in the Thymus," Nature. 1978; 271(5642):251-253.

"Anti-Cytokeratin AE1/AE3 Antibody, recognizes acidic & basic cytokeralins, clone AE1/AE3", www.sigmaaldrich.com/US/en/producl/mm/mab3412, 8 pages.

"Anti-pan Cytokeratin antibody [AE1/AE3] (ab27988)", www.abcam.com/pan-cytokeralin-anlibody-ae1ae3-ab27988.html, 4 pages.

"Cytokeratin, Multi (AE1/AE3) Antibody—MCK Immunohistochemical Slain", https://shop.leicabiosystems.com/us/ihc-sh/ihc-primary-antibodies/pid-cytokeralin-multi-ae1-ae3, 3 pages.

"Keratin, type I cytoskelelal 14 [*Homo sapiens*]," 3 pages. www.ncbi.nlm.gov/protein/NP _000517.3.

Ariyoshi, et al, "Antibody Reactivity with New Antigens Revealed in Multitransgenic Triple Knockout Pigs May Cause Early Loss of Pig Kidneys in Baboons", Xenotransplantation. 2021;28:e12642. 1 of 9 pages.

Armstrong, et al., Analysis of Primate Renal Allografts After T-Cell Depletion with Anti-CD3-CRM9. Transplantation, Jul. 15, 1998;66(1):5-13. 20 Pages.

Ashton-Rickardt PG, et al., "Peptide Contributes to the Specificity of Positive Selection of COB+ T Cells in the Thymus," Cell. 1993; 73(5):1041-1049.

Atkinson K, et al., Thymus Transplantation After Allogeneic Bone Marrow Grall to Prevent Chronic Graft-Versus-Host Disease in Humans, Transplantation. 1982;33(2):168-173. http://www.ncbi.nlm.nih.gov/pubmed/7036469. Accessed Sep. 8, 2018.

Bhagra, et al., "Cardiac Transplantation: Indications, Eligibility and Current Outcomes", Heart (2019);105:252-260.

Black, et al., "Solid Organ Transplantation in the 21st Century", Ann Transl Med (2018) 6(20):409, 12 pages.

Born W, et al., "Expression and Role of the T Cell Receptor in Early Thymocyte Differentiation In Vitro," J Immunol. 1987; 138(4):999-1008. http://www.ncbi.nlm.nih.gov/pubmed/3492547. Accessed Sep. 17, 2018.

Braunberger, et al., "Tolerance Induced Without Immunosuppression in a T-Lymphocyte Suicide-Gene Therapy Cardiac Allograft Model in Mice", J Thorac Cardiovasc Surg. (Jan. 2000); 119(1):46-51.

Brent L, et al., "Transplantation Tolerance," Br Med Bull. 1976; 32(2):101-106. http://www.ncbi.nlm.nih.gov/pubmed/60159. Accessed Sep. 17, 2018.

Brown, et al, "A Humanized Mouse Model Generated Using Surplus Neonatal Tissue" Stem Cell Report, vol. 10, Issue 4, Apr. 10, 2018, pp. 1175-1183.

Campos L, et al., "Prolonged Survival of Rat Orthotopic Liver Allografts After Intrathymic Inoculation of Donor-Strain Cells," Transplantation. 1993; 55(4):866-870. http://www.ncbi.nlm.nih.gov/pubmed/8475562. Accessed Sep. 18, 2018.

Chinn IK, et al., "Long-term Tolerance to Allogeneic Thymus Transplants in Complete DiGeorge Anomaly," Clin Immunol. 2008;126(3):277-281.

Chowdhury NC, et al., "Acquired Systemic Tolerance to Rat Cardiac Allografts Induced by Intrathymic Inoculation of Synthetic Polymorphic MHC Class I Allopeptides," Transplantation. 1996; 62(12):1878-1882. http://www.ncbi.nlm.nih.Jov/pubmed/8990380. Accessed Sep. 18, 2018.

Ciupe SM, et al., "The Dynamics of T-Cell Receptor Repertoire Diversity Following Thymus Transplantation for DiGeorge Anomaly," PLoS Comput Biol. Jun. 2009; 5(6):e1000396. doi: 10.1371/joumal.pcbi.1000396. Epub Jun. 12, 2009. PubMed PMID: 19521511; PubMed Central PMCID: PMC2690399.

Duggan, et al,"Progress Towards Xenogenic Tolerance", www.co-transplantation.com, vol. 25, No. 5, Oct. 2020, pp. 457-463.

Griesemer AD, et al. "Results of gal-knockout porcine thymokidney xenografts," Am J Transplant 9:2669-2678 (2009).

Hale et al., "Corticosteroids Regulate Epithelial Cell Differentiation and Hassan Body Formation in the Human Thymus", J Immunol. Jan. 1, 2004; 172(1):617-24.

Hall BM, et al., "The Cellular Basis of Allograft Rejection In Vivo. I. The Cellular Requirements for First-set Rejection of Heart Grails," J Exp Med. 1978; 148(4):878-889. http://www.ncbi.nlm.nih.gov/pubmed/359750.

Hall BM, et al., "The Cellular Basis of Allograft Rejection In Vivo. II. The Nature of Memory Cells Mediating Second Set Heart Graft Rejection," J Exp Med. 1978; 148(4):890-902.

Hammerman, Marc R., "Xenotransplantation in the Kidney: A Historical Perspective", Kidney Development, Disease, Repair and Regeneration, Chapter 37, pp. 507-519 (2016).

Hornik CP, et al., "Successful Extracorporeal Membrane Oxygenation for Respiratory Failure in an Infant with DiGeorge Anomaly, Following Thymus Transplantation," Respir Care. Jun. 2011; 56(6):866-70. doi: 10.4187/espcare.01051. Epub Feb. 11, 2011. PubMed PMID: 21333090.

Isakovic K, et al., "Role of the Thymus in Tolerance. I. Tolerance to Bovine Gamma Globulin in Thymectomized, Irradiated Rats Grafted with Thymus From Tolerant Donors," J Exp Med. 1965; 122(6):1103-1123.

(56) References Cited

OTHER PUBLICATIONS

J.O., et al, "Heart En Bloc Thymus Cotransplantation in NHPs -ATC Abstracts", ATC Meeting Abstracts, January 5, J021, https://atcmeetingabstracts.com/abstracl/heart-en-bloc-thymus-cotransplantation-in-nhps/, 4 pages.

Japanese Office Action dated Feb. 14, 2023 in Japanese Application No. 2020-543913, 10 pages.

Johnston, et al, "Heart and En-bloc Thymus Transplantation in Miniature Swine", Cardiothoracic Transplantation, The Journal of Thoracic and Cardiovascular Surgery, vol. 130, No. 2, pp. 554-559 (Aug. 2005).

Jones, et al., "Assessing Solid Organ Donors and Monitoring Transplant Recipients or Human Immunodeficiency Virus, Hepatitis B Virus, and Hepatitis C Virus Infection—U.S. Public Health Service Guideline, 2020" MMWR, vol. 69, No. 4, Jun. 26, 2020, 20 pages.

Kappler JW, et al., "T Cell Tolerance by Clonal Elimination in the Thymus," Cell. 1987; 49(2):273-280.

Kawai T, et al "Tolerance—One Transplant for Life," Transplantation. Jul. 27, 2014; 98(2): 117-121, 8 pages.

Kawai, et al., "CD154 Blockade for Induction of Mixed Chimerism and Prolonged Renal Allograft Survival in Nonhuman Primates", Am J Transplant 4: 1391-1398 (2004).

Kawai, et al., Effect of Mixed Hematopoietic Chimerism on Cardiac Allograft Survival in Cynomolgus Monkeys. Transplantation 73: 1757-1764 (2002). 8 pages.

Kawai, et al., "HLA-Mismatched Renal Transplantation Without Maintenance Immunosuppression," N Engl J Med 358:353-361 (2008).

Kawai, et al., "Long-term Outcome and Alloantibody Production in a Non-Myeloablative Regimen for Induction of Renal Allograft Tolerance", Transplantation (1999) 68: 1767-1775. 16 pages.

Kawai, et al., "Mixed Allogeneic Chimerism and Renal Allograft Tolerance in Cynomolgus Monkeys", Transplantation (1995) 59:256-262.

Kirk et al., "Optimization of De Novo Belatacept-based Immunosuppression Administered to Renal Transplant Recipients", Am J Transplant; 21:1691-1698 (2021).

Kisielow P, et al., "Positive Selection of Antigen-Specific T Cells in Thymus by Restricting MHC Molecules," Nature. 1988; 335(6192):730-733.

Kwun J, et al., "Thymus Co-Transplantation Promotes Donor-Specific Tolerance in Allogeneic Heart Transplantation—ATC Abstracts." In: Abstract A423. ; 2018. https:/atcmeetingabstracts.com/abstract/thymus-co-transplantation-promotes-donor-specific-tolerance-in-allogeneic-heart-transplantation/.

Lambrigts, et al, "Implantation of Autologous Thymus Into The Heart Prior to Procurement", Transplantation, vol. 66, No. 6, pp. 810-814 (Sep. 27, 1998).

LoCascio SA, et al., "Mixed Chimerism, Lymphocyte Recovery, and Evidence for Early Donor-specific Unresponsiveness in Patients Receiving Combined Kidney and Bone Marrow Transplantation to Induce Tolerance", Transplantation. Dec. 2, 20107;90(12):1607-15.

Lu, et al. "Cardiac Allograft Tolerance Induced by Isogeneic CD4+ CD25+ Regulatory T Cells", Exp Clin Transplant, Apr. 2014;12(2):133-8.

Lund LH, et al., "The Registry of the International Society for Heart and Lung Transplantation: Thirty-first Official Adult Heart Transplant Report-2014; Focus Theme: Retransplantation," J Hear Lung Transplant. 2014; 33(10):996-1008.

Lynch HE, et al., "Thymic Involution and Immune Reconstitution," Trends Immunol. 2009; 30(7):366-373.

MacDonald HR, et al., "T-Cell Receptor Vil Use Predicts Reactivity and Tolerance to Mlsa—Encoded Antigens," Nature. 1988; 332(6159):40-45.

Madariaga, et al, "Organ-specific Differences in Achieving Tolerance", Curr Opin Organ Transplant. (Aug. 2015); 20 4): 392-399, 16 pages.

Magee CN, et al., "Notch-1 Inhibition Promotes Immune Regulation in Transplantation via Regulatory T Cell-Dependent Mechanisms", Circulation. Sep. 9, 2019; 140(10):846-863.

Markert et al., "Complete DiGeorge syndrome: Development of Rash, Lymphadenopathy, and Oligoclonal T Cells in 5 Cases," J Allergy Clin Immunol. Apr. 2004; 113(4):734-41.

Markert ML et al., "Thymus Transplantation in Complete DiGeorge Anomaly." Immunol Res. 2009; 44(1-3):61-70.

Markert ML, et al., "Use of Allograft Biopsies to Assess Thymopoiesis After Thymus Transplantation," J Immunol. May 1, 2008; 180(9):6354-6364.

Maron BJ, et al., "American College of Cardiology/European Society of Cardiology Clinical Expert Consensus Document on Hypertrophic Cardiomyopathy," J Am Coll Cardiel. 2003; 42(9): 1687 -1713.

Maron BJ, et al., "Sudden Deaths in Young Competitive Athletes," Circulation. 2009; 119(8):1085-1092.

Matthews, et al, "New-Onset Diabetes Mellitus Aller Transplantation in a Cynomolgus Macaque (Macaca fasicularis)", Comparitive Medicine, American Association for Laboratory Animal Science, vol. 65, No. 4, pp. 352-356, Aug. 2015.

Mehra MR, et al., "The 2016 International Society for Heart Lung Transplantation Listing Criteria For Heart Transplantation: A 10-year Update," J Hear Lung Transplant. 2016; 35(1):1-23.

Menard MT, et al., "Composite "Thymoheart" Transplantation Improves Cardiac Allograft Survival", Am J Transplant. J004; 4(1): 79-86.

Menard, et al, "Immunosuppression in Experimental Heart Transplantation", Organtransplantation in Rats and Mice, Chapter 38, pp. 375-384 (1998).

Mezrich, et al, "Role of the Thymus and Kidney Graft in the Maintenance of Tolerance to Heart Grafts in Miniature Swine", Transplantation, vol. 79, No. 12, pp. 1663-1673. Jun. 27, 2005.

Mezrich, et al, "The Role of the Thymus in the Maintenance Phase of Tolerance in Miniature Swine", The Journal of Heart and Lung Transplantation, vol. 21, No. 1, (66), pp. 78-79, Jan. 2002.

Miller, Rodney T., "Cytokeralin AE1/AE3," the Focus—Immunohislochemisry, Nov. 2003, 2 pages.

Muniappan, et al., "En-Bloc Heart and Thymus Transplantation in Cynomolgus Monkeys", Transplantation, Jul. 27, 2004, vol. 78, No. 2, 2004, p. 631.

Niimi, et al., "Importance of Thymus to Maintain Operational Tolerance to Fully Allogeneic Cardiac Grafts", Ann Thorac Surg., 2001, 72:735-739.

Ohuchi, et al, "A Novel Technique for En Bloc, Vascularized, Composite Thymic, and Cardiac Co-transplantation", Transplantation, vol. 74, 403-415, No. 3, Aug. 15, 2002.

Ohzato H, et al., "Induction of Specific Unresponsiveness {tolerance) to Skin Allografts by Intrathymic Donor-Specific Splenocyte Injection in Anlilymphocyte Serum-Treated Mice," Transplantation. 1992; 54(6):1090-1095.

Perico N, et al., "Thymus-Mediated Immune Tolerance to Renal Allograft Is Donor but Not Tissue Specific," J Am Soc Nephrol. 1991; 2(6):1063-1071.

Pham SM, et al., "A Clinical Trial Combining Donor Bone Marrow Infusion and Heart Transplantation: Intermediate-term Results", J Thorac Cardiovasc Surg. Apr. 2000; 119(4 PI 1):673-81.

Pierson RN 3rd, et al., "Prolongation of Primate Cardiac Allograft Survival by Treatment with ANTI-CD40 Ligand CD154) Antibody", Transplantation. Dec. 15, 1999; 68(11):1800-5. 10 pages.

Pilat N., Sabler P, Klaus C, Mahr B, Unger L, Hock K, et al. "Blockade of adhesion molecule lymphocyte function-associaled antigen-1 improves long term heart allograft survival in mixed chimeras", J Heart Lung Transplant. Sep. 2018;37(9):1119-1130.

Posselt AM, et al., "Induction of Donor-Specific Unresponsiveness by Intrathymic Islet Transplantation," Science. 1990; 249(4974):1293-1295.

Rajab, et al., "Heart Transplantation Following Donation After Cardiac Death: History, Current Techniques, and Future", The Journal of Thoracic and Cardiovascular Surgery, vol. 161, No. 4, pp. 1337-1340 (2021).

(56) References Cited

OTHER PUBLICATIONS

Remuzzi G, et al., "Kidney Graft Survival in Rats Without Immunosuppressants After Intrathymic Glomerular Transplantation," Lancet (London, England). 1991; 337(8744):750-752.

Rota IA et al., "FOXN1 deficiency nude severe combined immunodeficiency", Orphanel Journal of Rare Diseases. 2017; 12:6.

Sahara, H., Weiss, MJ., et al., "Thymectomy Does Not Abrogate Long-Term Acceptance of MHC Class I-Disparate Lung Allografts in Miniature Swine", Transplantation Proceedings, Dec. 2006; 38(10): 3253-3255. 6 pages.

Salvadori M., et al., "Enteric-coated mycophenolate sodium is therapeutically equivalent to mycophenolate mofetil in denovo renal transplant patients." Am J Transplant 2004;4(2):231-6.

Sayegh MH, et al., "Thymic Recognition of Class II Major Hislocompalibility Complex Allopeplides Induces Donor-Specific Unresponsiveness to Renal Allografts", Transplantation. 1993; 56(2):461-465.

Scalea, et al., "Abrogation of Renal Allograft Tolerance in MGH Miniature Swine: The Role of Intra-Graft and Peripheral Factors in Long-Term Tolerance", American Journal of Transplantation 2014; 14: 2001-2010.

Scalea, et al., "An Overview of the Necessary Thymic Contributions to Tolerance in Transplantation", Clinical Immunology 173 (2016) 1-9.

Schmitz R. et al., "Kidney Transplantation Using Alemtuzumab, Belatacept, and Sirolimus: Five-year Follow-up", Am J Transplant. Dec. 2020; 20(12):3609-3619.

Spitzweg C, et al., "Expression of Thyroid-Related Genes in Human Thymus," Thyroid. 1999;9(2):133-141.

Sprent J, et al., "T Cell Selection in the Thymus," Immunol Rev. 1988; 101:173-190.

Stehlik, J., et al., "The Registry of the International Society for Heart and Lung Transplantation: 29th official adult heartransplant report", 2012. J Heart Lung Transplant 31: 1052-1064.

Summary of FY 2001 Research Report: "An Attempt to Induce Immune Tolerance by Whole Thymus Organ Transplantation after Autologous Thymectomy/Lymphocyte Removal" (Japanese with translation), 2003, 5 pages, https://kaken.nii.ac.jp/grant/KAKENHI-PROJECT-11671153.

Taub DD, et al., "Insights Into Thymic Aging and Regeneration," Immunol Rev. 2005; 205(1):72-93.

Tonsho, et al, "Heart En Bloc Thymus Transplantation Permits Long-Term, Acute Rejection-Free Cardiac Allograft Survival in Nonhuman Primates (NHPs)", American Transplant Congress (ATC) Meeting Abstracts, Abstract No. A251, May 2, 2015, 5 pages.

Tonsho, et al, "Heart Transplantation: Challenges Facing the Field", Cold Spring Harb Perspect Med 2014; 4:a015636, pp. 1-22.

Tonsho, et al, "Successful Tolerance Induction of Cardiac Allografts in Nonhuman Primates through Donor Kidney Co-Transplantation", American Transplant Congress (ATC) Meeting Abstracts, Abstract No. 490, 2013, 4 pages.

Von Moos, et al., "Assessment of Organ Quality in Kidney Transplantation by Molecular Analysis and Why II May Not Have Been Achieved, Yet", Frontiers in Immunology, vol. 11, Article 833, May 2020. 12 Pages.

Waer M, et al., "Induction of Transplantation Tolerance in Mice Across Major Hislocompalibility Barrier by Using Allogeneic Thymus Transplantation and Total Lymphoid Irradiation," J Immunol. 1990; 145(2):499-504.

Watanaba, et al., "Intra-bone Bone Marrow Transplantation From hCD47 Transgenic Pigs to Baboons Prolongs Chimerism to >60 Days and Promotes Increased Porcine Lung Transplant Survival", Xenotransplantation, 2020;27:e12552, 15 pages.

Wood, Kathyn J., "The Induction of Tolerance to Alloantigens Using MHC Class I Molecules", Immunology, 1993,6:759-762.

Xie B., et al., :Monoclonal Antibody Treatment to Prolong the Secondary Cardiac Allograft Survival in Alloantigen-primed Mice, Scand J Immunol. May 2010; 71(5):345-52.

Yamada et al., "Tolerance in Xenotransplantation", Curr Opin Organ Transplant 22:522-528 (2017).

Yamada K, et al., "Thymic Transplantation in Miniature Swine. I. Development and Function of the "Thymokidney"", Transplantation. 1999; 68(11), 1684-1692.

Yamada, et al, "Intra-bone Bone Marrow Transplantation in Pig-to-Nonhuman Primates for the Induction of Tolrance Across Xenogeneic Barriers", Methods Mol Biol. (2020), 2110: 151-171, 20 pages.

Yamada, et al, "Both Central and Peripheral Mechanisms Play a Role in Tolerance Induction and in the Prevention of Cardiac Allograft Vasculopathy (Cav) in Recipients of Heart/Kidney Transplants", Transplantation, Jun. 27, 1998—vol. 65—Issue 12—p. S 183, 3 pages.

Yamada, et al, "Co-transplantation of Vascularized Thymic Grall with Kidney in Pig-to-Nonhuman Primates for the nduction of Tolerance Across Xenogeneic Barriers", Methods Mol Biol. 2020 ; 2110: 151-171.

Yamada, et al, "Repeated Injections of IL-2 Break Renal Allograft Tolerance Induced via Mixed Hemalopoielic Chimerism in Monkeys", American Journal of Transplantation 2015; 15: 3055-3066.

Yamada, et al, "Role of the Thymus in Transplantation Tolerance in Miniature Swine: II. Effect of Steroids and Age on the Induction of Tolerance to Class I Mismatched Renal Allografts", Transplantation, vol. 67—Issue 3, 1999, pp. 158-467.

Yamada, et al, "Thymic Transplantation in Miniature Swine. II. Induction of Tolerance by Transplantation of Composite Thymokidneys to Thymectomized Recipients", J Immunol, 2000, 164:3079-3086.

Yamamoto, et al., "Role of the Thymus in Helerotopic Cardiac Allograft Survival in Miniature Swine: Evidence for the Need of Thymic Emigrants Immediately Post-Transplantation, and Thymic Immigrants for Long Term Tolerance Induction", The Journal of Heart and Lung Transplantation, 273, Jan. 2003, 1 page.

Kaken, 2001 Fiscal Year Final Research Report Summary, A Trial to Obtain a Donor-Specific Immunotorelance Using a Vascularized Thymus Allograft after Host Thymectomy andHost Lymphocyte Depletion; 2 pages (Sep. 17, 2003).

Chinn, I. K., et al., "Mechanisms of Tolerance to Parental Parathyroid Tissue when Combined with Human Allogeneic Thymaus Transplantation", J Allergy Clin Immunol, 126(4):814-820 (2010).

Dem'yanenko, S.V., et al., "Age Changes Thymus-Dependent Part of Immune System", Fundamental Medicine and Biology, 611(4):17-29 (2012)-with English Abstract.

* cited by examiner

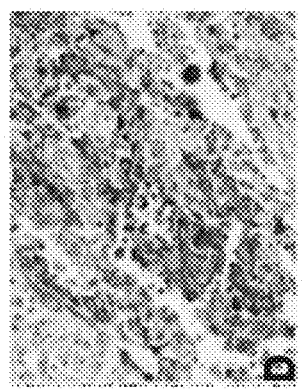
FIG. 34B
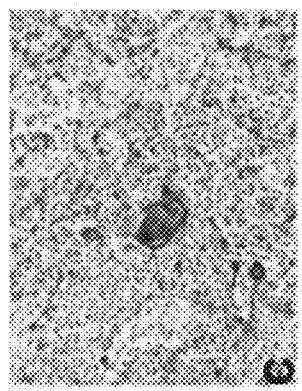
FIG. 34D
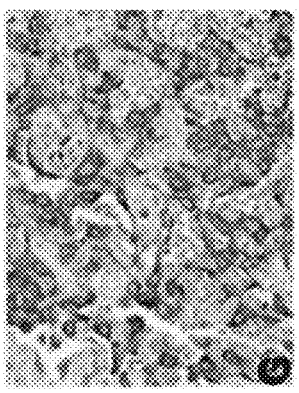
FIG. 34C
FIG. 34A
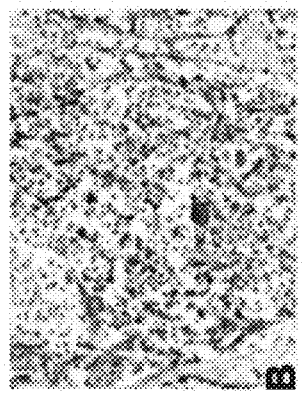
FIG. 34F
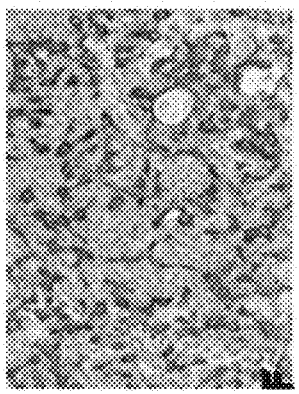
FIG. 34H
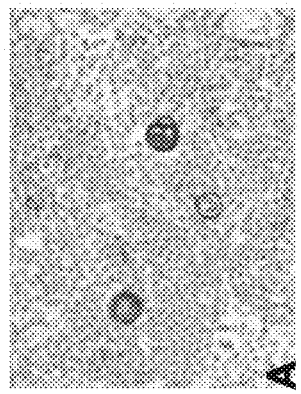
FIG. 34E
FIG. 34G

| WK | donor monkey (Mamu-A:01 negative) ||||
|---|---|---|---|---|
| | donor monkey surgery | donor monkey other procedure | donor thymus processing | donor monkey testing (blood) |
| WK | | | | |
| 1 | 1 | | | | MLR#1 |
| 2 | 2 | | | | flow cytometry CBCdiff, chemistry, CMV level |
| WK | | | | |
| 3 | 1 | | | | |
| 4 | 2 | | | | |

FIG. 38A

| recipient blood testing | recipient thymus processing | Recipient other procedures | Recipient medical therapy | Recipient surgery |
|---|---|---|---|---|
| colspan=5 | recipient monkey (Mamu-A:01 positive) | | | |
| colspan=5 | STAGE 1 (MHC type animals prior to coming to Duke - ask DLAR for one blood sample during quarantine) | | | |
| MLR#1 blood sample for storage | | | | |
| flow cytometry CBCdiff, chemistry, CMV level | | | | |
| colspan=5 | STAGE 2 | | | |
| CMV level | Culture recipient thymus from day 1.3 to 3.1 | 1,3,5,7 days post thymectomy, sedation for weighing | | thymectomy day 1.3 |
| DSA (2ml) blood sample for storage CMV level | | | | |

FIG. 38B

|  | control monkey |  | notes |
| --- | --- | --- | --- |
|  | control drugs | testing (blood) procedure |  |
|  |  |  |  |
|  |  | MLR#1 (ml) | determine pairing for experiments based on MLR reactivity and Mamu-A*01 allele (recipient positive; donor, negative) |
|  |  | flow cytometry, CBCdiff, chemistry, CMV level |  |
|  |  |  |  |
|  |  |  | 1<br>2<br>3<br>4<br>5<br>6<br>7 |
|  |  |  | 1<br>2<br>3<br>4<br>5<br>6<br>7 | put valganciclovir and ganciclovir as possible drugs thymectomize recipient and culture recipient thymus

FIG. 38C

| WK | | donor monkey (Mamu-A:01 negative) | | | |
|---|---|---|---|---|---|
| | | donor monkey surgery | donor monkey other procedure | donor thymus processing | donor monkey testing (blood) |
| 5 | 3 | | | | flow cytometry, CBC, CMV level, day 3.1 |
| 6 | 4 | | | | weekly CBC flow until recipient has no RTE |
| 7 | 5 | | | | weekly CBC flow until recipient has no RTE |
| WK | | | | | |
| 8 | 1 | thymectomy, and skin biopsies, day 1.3 | | culture donor thymus 12 days (day 1.3 to 3.1 total of 12 days) | |

FIG. 38D

| recipient blood testing | recipient thymus processing | Recipient other procedures | Recipient medical therapy | Recipient surgery |
|---|---|---|---|---|
| colspan=5 | recipient monkey (Mamu-A:01 positive) | | | |
| CBCdiff day 3.1, (CMV level) flow to show no RTE day 3.1 | One day 3.1 crypreserve thymus | | | |
| weekly CBCdiff flow until recipient has no RTE; when no RTE, go to STAGE 3. Chemistry this week CMV level | | | | |
| weekly CBCdiff flow until recipient has no RTE; when no RTE, go to STAGE 3. Chemistry this week CMV level | | | | |

If the recipient continues to have recent thymic emigrants (RTE), this monkey did not have a complete thymectomy. If this is the case, <u>start stage 2 again (at week 1) with another Mamu-A:01 positive monkey as the recipient or switch the recipient and donor and have the donor be Mamu-A:01 positive, and the recipient negative.</u>

STAGE 3

| recipient blood testing | recipient thymus processing | Recipient other procedures | Recipient medical therapy | Recipient surgery |
|---|---|---|---|---|
| CBCdiff, (CMV level), chemistry blood sample for storage | | | start tacrolimus BID day 1.1 | |

FIG. 38E

| | control monkey | | notes |
|---|---|---|---|
| | control drugs | testing (blood) procedure | |
| | | CMV level | 1 cropreserve<br>2 recipient<br>3 culture recipient<br>4 thymus<br>5<br>6<br>7 |
| | | | |
| | | | If thymectomy is insufficient, the recipient becomes the control, use all males |
| | | | 1 start tacro, MMF in recipient<br>2<br>3 thymectomize<br>4 donor<br>5<br>6<br>7 |

FIG. 38F

| WK | | donor monkey (Mamu-A:01 negative) | | | |
|---|---|---|---|---|---|
| | | donor monkey surgery | donor monkey other procedure | donor thymus processing | donor monkey testing (blood) |
| 9 | 2 | | | total of 2 days<br><br>then transplant half and cryopreserve half on day 2.7 | |
| 10 | 3 | | | | chemistry, CMV |
| 11 | 4 | | | | |
| 12 | 6 | | | | |
| 13 | 6 | | | | |

FIG. 38G

| recipient monkey (Mamu-A:01 positive) ||||||
| --- | --- | --- | --- | --- |
| recipient blood testing | recipient thymus processing | Recipient other procedures | Recipient medical therapy | Recipient surgery |
| flow day 2.4 to document T cell depletion, CBCdiff, tacro level, CMV level | | | Start rhATG (5 days) days 2.1 to 2.5 then 2 days of rest before transplant continue tacrolimus BID | |
| tacro level (0.5 ml), DSA. CMV level, chemistry | | no weighing | continue tacro BID | Cultured thymus transplant (from donor) day 3.1 |
| CBCdiff, tacro level, CMV level | | | continue tacro BID | |
| tacro level, CMV level, chemistry blood for storage | | | continue tacro BID | |
| flow, CBCdiff, tacro level, CMV level | | | continue tacro BID | |

FIG. 38H

| | control monkey | | notes |
|---|---|---|---|
| | control drugs | testing (blood) procedure | |
| | | flow control, CBCdiff, day 2.3, CMV level | | 1 start ATG<br>2<br>3<br>4 flow to show T cell depletion - recipient<br>5 start last ATG<br>6<br>7 |
| | | | | 1 thymus transplant<br>2<br>3<br>4<br>5<br>6<br>7 |
| | | | |
| | | | |
| | | flow control, CBCdiff, CMV level | |

FIG. 38I

| WK | | donor monkey (Mamu-A:01 negative) | | | |
|---|---|---|---|---|---|
| | | donor monkey surgery | donor monkey other procedure | donor thymus processing | donor monkey testing (blood) |
| 14 | 7 | | | | chemistry, CMV |
| 15 | 8 | | | | |
| 16 | 9 | | | | |
| 17 | 10 | | | | |
| 18 | 11 | | | | chemistry, CMV |
| 19 | 12 | | | | |

FIG. 38J

| recipient monkey (Mamu-A:01 positive) | | | | |
|---|---|---|---|---|
| recipient blood testing | recipient thymus processing | Recipient other procedures | Recipient medical therapy | Recipient surgery |
| tacro level, CMV level, chemistry, | | | continue tacro BID | |
| CBCdiff, tacro level, CMV level, | | | continue tacro BID | |
| tacro level, CMV level, chemistry, blood for storage | | | continue tacro BID | |
| flow, CBCdiff, serum for DSA, tacro level, CMV level | no weighing | Evaluate CTTT biopsy by IHC for thymopoiesis | continue tacro BID | Day 10.3 Biopsy of CTTT transplant; transplant Cryo-CTTT into other leg |
| tacro level, CMV level, chemistry | | | continue tacro BID | |
| CBCdiff, serum for DSA, tacro level, CMV level | | | continue tacro BID | |

FIG. 38K

| control monkey | | notes |
|---|---|---|
| control drugs | testing (blood) procedure | |
| | CMV level | |
| | | |
| | flow control, CBCdiff, CMV level | 1<br>2<br>3 Biopsy of CTTT, transplant cryo-CTTT<br>4<br>5<br>6<br>7 |
| | CMV level | If biopsy is good, it hasn't been rejected and the plan should work.<br><br>flow CBC optional this week |

FIG. 38L

| WK | donor monkey (Mamu-A:01 negative) | | | |
|---|---|---|---|---|
| | donor monkey surgery | donor monkey other procedure | donor thymus processing | donor monkey testing (blood) |
| 20 / 13 | | | | |
| 21 / 14 | | | | |
| 22 / 15 | | | | chemistry, CMV |
| 23 / 16 | | | | |
| 24 / 17 | | | | |
| 25 / 18 | | | | |
| 26 / 19 | | | | chemistry, CMV |
| 27 / 20 | | | | |

FIG. 38M recipient monkey (Mamu-A:01 positive)

| recipient blood testing | recipient thymus processing | Recipient other procedures | Recipient medical therapy | Recipient surgery |
|---|---|---|---|---|
| tacro level, CMV level, chemistry, blood for storage | | | continue tacro BID | |
| flow, CBCdiff, tacro level, CMV level, | | | continue tacro BID | |
| tacro level, CMV level, chemistry, blood for storage | | | continue tacro BID | |
| CBCdiff, serum for DSA, tacro level, CMV level, | | | continue tacro BID | |
| tacro level, CMV level, chemistry, blood for storage | | | continue tacro BID | |
| flow, CBCdiff, tacro level, CMV level | | | continue tacro BID, if naive T cell>15% - go to stage 4; | |
| tacro level, CMV level, chemistry | | | continue tacro BID, if naive T cell>15% - go to stage 4; | |
| CBCdiff, tacro level, CMV level | | | continue tacro BID, if naive T cell>15% - go to stage 4; | |

FIG. 38N

| | control monkey | | notes |
|---|---|---|---|
| | control drugs | testing (blood) procedure | |
| | | | |
| | | flow control, CBCdiff, CMV level | |
| | | | |
| | | CMV level | flow optional this week |
| | | | |
| | | flow control, CBCdiff, CMV level | |
| | | | |
| | | CMV level | flow optional this week |

FIG. 38O

| WK | donor monkey (Mamu-A:01 negative) | | | |
|---|---|---|---|---|
| | donor monkey surgery | donor monkey other procedure | donor thymus processing | donor monkey testing (blood) |
| 28 | | | | |
| 29 | | | | |
| 30 | 18 | | | chemistry, CMV |
| 31 | 1 | | | |
| 32 | 2 | | | chemistry, CMV |

FIG. 38P

| | recipient monkey (Mamu-A:01 positive) | | | | |
|---|---|---|---|---|---|
| recipient blood testing | recipient thymus processing | Recipient other procedures | Recipient medical therapy | Recipient surgery | |
| tacro level, CMV level, chemistry, blood for storage | | | Continue tacro BID, if naïve T cell>15% - go to stage 4; | | |
| flow, CBCdiff, tacro level, CMV level, | | | Continue tacro BID, if naïve T cell>15% - go to stage 4; | | |
| CBCdiff, CMV level, tacro level | | | Continue the pattern of the last 4 weeks until naïve T cell>15% - then go to stage 4; If naïve T cells don't reach 15% go to Stage 5. Tacro BID | | |
| Stage 4 | | | | | |
| CMV level, chemistry, tacro | | | | | |
| flow, CBCdiff, tacro level, CMV level, blood for storage | | | continue tacro BID | | |

FIG. 38Q

| | control monkey | | notes |
|---|---|---|---|
| | control drugs | testing (blood) procedure | |
| | | | |
| | | flow control, CBCdiff, CMV level | |
| | | CBCdiff, CMV level | |
| | | | |
| | | flow control, CBCdiff, CMV level | |

FIG. 38R

| WK | | donor monkey (Mamu-A:01 negative) | | | |
|---|---|---|---|---|---|
| | | donor monkey surgery | donor monkey other procedure | donor thymus processing | donor monkey testing (blood) |
| 33 | 3 | | | | |
| 34 | 4 | non survival heart donation, skin biopsies, all on day 4.1 | Save blood for transfusion into recipient if necessary | | |
| 35 | 5 | | | | |
| 36 | 6 | | | | |
| 37 | 7 | | | | |
| 38 | 8 | | | | |

FIG. 38S

| recipient monkey (Mamu-A:01 positive) | | | | |
|---|---|---|---|---|
| recipient blood testing | recipient thymus processing | Recipient other procedures | Recipient medical therapy | Recipient surgery |
| CMV level, serum for DSA tacro level, chemistry | | | continue tacro BID | |
| CBCdiff, serum for DSA, tacro level, CMV level | 1,3,5,7 days post heart tx, sedation for weighing<br><br>check thymus biopsy | Monitor heart beating, 2x/week Assess thymus biopsies for thymopoiesis by IHC | continue tacro BID | heterotopic heart transplant from donor, day 4.1, biopsy Cryo-CTTT. Only repeat CTTT biopsy if the first CTTT biopsy demonstrated lack of thymus tissue in the leg |
| tacro level, CMV level, chemistry | | Monitor heart beating, 2x/week (ECHO). If heart stops beating, sacrifice monkey | continue tacro BID | |
| flow, CBCdiff, tacro level, CMV level | | Monitor heart beating, 2x/week (ECHO). If heart stops beating, sacrifice monkey | wean tacro BID over 4 weeks | |
| chemistry, CMV level blood for storage | | Monitor heart beating, 1x/week (ECHO). If heart stops beating, sacrifice monkey | wean tacro BID over 3 weeks | |
| CBCdiff, tacro level, CMV level | | Monitor heart beating, 1x/week (ECHO). If heart stops beating, sacrifice monkey | wean tacro BID over 2 weeks | |

FIG. 38T

| control monkey | | notes |
|---|---|---|
| control drugs | testing (blood) procedure | |
| | | |
| | | 1 heterotopic heart transplant from donor, bx of Cryo-CTTT
2
3
4
5
6
7 |
| | flow control, CBCdiff, CMV level | |
| | | |
| | | |

FIG. 38U

| WK | | donor monkey (Mamu-A:01 negative) | | | |
|---|---|---|---|---|---|
| | | donor monkey surgery | donor monkey other procedure | donor thymus processing | donor monkey testing (blood) |
| 39 | 9 | | | | |
| 40 | 10 | | | | MLR#3 recipient and 3rd party |
| 41 | 11 | | | | |
| 45 | 15 | note that this is week 15, 4 weeks after week 11 | | | |
| 49 | 19 | note that this is week 19, 4 weeks after week 15 | | | |
| 53 | 23 | etc | | | |
| 53 | 27 | etc | | | |

FIG. 38V

| recipient blood testing | recipient thymus processing | Recipient other procedures | Recipient medical therapy | Recipient surgery |
|---|---|---|---|---|
| | | recipient monkey (Mamu-A:01 positive) | | |
| chemistry, CMV level | | Monitor heart beating, 1x/week (ECHO). If heart stops beating, sacrifice monkey | wean tacro BID over 1 week | |
| CMV level, MLR#3 | no weighing, visualize rejection and take photos under anesthesia | Monitor skin, Monitor heart beating, 1- 2x/week, If heart stops beating, sacrifice monkey | off racro | If heart is beating, apply fresh recipient skin, and fresh 3rd party skin |
| monthly CBCdiff flow, CMV level, chemistry, blood for storage | | Monitor skin, Monitor heart beating, 1- 2x/week, If heart stops beating, sacrifice monkey | | |
| monthly CBCdiff flow, CMV level, chemistry, blood for storage | | Monitor skin, Monitor heart beating, 1- 2x/week, If heart stops beating, sacrifice monkey | | |
| monthly CBCdiff flow, CMV level, chemistry, blood for storage | | Monitor skin, Monitor heart beating, 1- 2x/week, If heart stops beating, sacrifice monkey | | |
| monthly CBCdiff flow, CMV level, chemistry, blood for storage | | Monitor skin, Monitor heart beating, 1- 2x/week, If heart stops beating, sacrifice monkey | | |
| monthly CBCdiff flow, CMV level, chemistry, blood for storage | | Monitor skin, Monitor heart beating, 1- 2x/week, If heart stops beating, sacrifice monkey | | |

FIG. 38W

| | control monkey | notes |
|---|---|---|
| control drugs | testing (blood) procedure | |
| | | |
| | obtain fresh skin for grafting. MLR#3 CMV level | draw MLR prior to skin grafting, want MLR in case skin graft doesn't work |
| | monthly control flow and CBCDiff, CMV level | |
| | monthly control flow and CBCDiff, CMV level | |
| | monthly control flow and CBCDiff, CMV level | |
| | monthly control flow and CBCDiff, CMV level | |
| | monthly control flow and CBCDiff, CMV level | |

FIG. 38X

| WK | donor monkey (Mamu-A:01 negative) | | | |
|---|---|---|---|---|
| | donor monkey surgery | donor monkey other procedure | donor thymus processing | donor monkey testing (blood) |
| 57 / 30 | etc | | | |
| 60 | 180 days after heart transplantation, if monkey has beating heart, we will find more money to keep monkey alive for another 6 months and then sacrifice | | | |
| 1 | | | | |
| 2 | | | | |
| 3 | | | | |

FIG. 38Y

| | | | | | |
|---|---|---|---|---|---|
| \multicolumn{6}{c}{recipient monkey (Mamu-A:01 positive)} |
| recipient blood testing | recipient thymus processing | Recipient other procedures | Recipient medical therapy | Recipient surgery |
| monthly CBCdiff flow, CMV level, chemistry, blood for storage | | montor skin, Monitor heart beating, 1-2 x/week, If heart stops beating, sacrifice monkey | | |
| flow, CBCdiff flow, CMV level, chemistry, blood for storage | | | | sacriface monkey, harvest heart for path, recipient and donor thymus for IHC and thotacic tissue for IHC |
| \multicolumn{5}{c}{Stage 5 (continue tacro)} |
| flow, CBCdiff tacro level, chemistry, CMV level | | | continue tacro, if naïve T cells>15% go to Stage 4 | |
| serum for DSA, tacro level, CMV level | | | continue tacro, if naïve T cells>15% go to Stage 4 | |
| CBCdiff tacro level, chemistry, CMV level | | | continue tacro, if naïve T cells>15% go to Stage 4 | |

FIG. 38Z

| | control monkey | | notes |
|---|---|---|---|
| | control drugs | testing (blood) procedure | |
| | | monthly control for flow and CBCdiff, CMV level | |
| | | flow control, CBCdiff, CMV level | |
| | | flow control, CBCdiff, CMV level | flows starting here are to watch for thymus rejection |
| | | | |
| | | | |

FIG. 38AA

| WK | donor monkey (Mamu-A:01 negative) | | | |
|---|---|---|---|---|
| | donor monkey surgery | donor monkey other procedure | donor thymus processing | donor monkey testing (blood) |
| 4 | | | | |
| 5 | | | | |
| 6 | | | | |
| 7 | | | | |

FIG. 38BB

| recipient monkey (Mamu-A:01 positive) ||||| 
|---|---|---|---|---|
| recipient blood testing | recipient thymus processing | Recipient other procedures | Recipient medical therapy | Recipient surgery |
| tacro level, blood for storage, CMV level | | | continue tacro, if naïve T cells>15% go to Stage 4 | |
| flow, CBCdiff tacro level, chemistry, CMV level | | | continue tacro, if naïve T cells>15% go to Stage 4 | |
| tacro level, CMC level | | | continue tacro, if naïve T cells>15% go to Stage 4 | |
| CBCdiff tacro level, chemistry, CMV level | | | continue tacro, if naïve T cells>15% go to Stage 4 | |

FIG. 38CC

| | control monkey | | notes |
|---|---|---|---|
| | control drugs | testing (blood) procedure | |
| | | | |
| | | flow control, CBCdiff, CMV level | |
| | | | |
| | | | |

FIG. 38DD

| WK | donor monkey (Mamu-A:01 negative) | | | |
|---|---|---|---|---|
| | donor monkey surgery | donor monkey other procedure | donor thymus processing | donor monkey testing (blood) |
| 8 | | | | |
| 9 | | | | |
| 10 | | | | |
| 11 | | | | |
| 12 | | | | |

FIG. 38EE

| recipient monkey (Mamu-A:01 positive) | | | | |
|---|---|---|---|---|
| recipient blood testing | recipient thymus processing | Recipient other procedures | Recipient medical therapy | Recipient surgery |
| tacro level, CMV level, blood for storage | | | continue tacro if naïve T cells>15% go to Stage 4 | |
| flow, CBCdiff tacro level, chemistry, CMV level | | | continue tacro if naïve T cells>15% go to Stage 4 | |
| tacro level, CMV level | | | continue tacro if naïve T cells>15% go to Stage 4 | |
| CBCdiff tacro level, chemistry, CMV level | | | continue tacro if naïve T cells>10% go to Stage 4 | |
| tacro level, CMV level, blood for storage | | | continue tacro, if naïve T cells<10% go to Stage 6 | |

FIG. 38FF

| | control monkey | notes |
|---|---|---|
| control drugs | testing (blood) procedure | |
| | | |
| | flow control, CBCdiff, CMV level | |
| | | |
| | | |

FIG. 38GG

| WK | donor monkey (Mamu-A:01 negative) | | | |
|---|---|---|---|---|
| | donor monkey surgery | donor monkey other procedure | donor thymus processing | donor monkey testing (blood) |
| 1 | | | | |
| 2 | | | | |
| 3 | | | | |
| 4 | | | | |
| 5 | | | | |
| 6 | | | | |
| 7 | | | | |
| 8 | | | | |
| 9 | | | | |

FIG. 38HH

| recipient monkey (Mamu-A:01 positive) ||||| 
|---|---|---|---|---|
| recipient blood testing | recipient thymus processing | Recipient other procedures | Recipient medical therapy | Recipient surgery |
| Stage 6 ||||| 
| flow, CBCdiff, DSA level, CMV level, chemistry | | no weighing | wean tacro over 4 weeks | Cryo-CTTT from RECIPIENT (day 1.1) |
| | | | wean tacro over 3 weeks | |
| CBCdiff, CMV level, chemistry | | | wean tacro over 2 weeks | |
| blood for storage | | | wean tacro over 1 weeks | |
| flow, CBCdiff, CMV level, chemistry | | | off tacro | |
| CBCdiff, CMV level, chemistry | | | | |
| flow, CBCdiff, chemistry DSA level, blood for storage | assess recipient thymus biopsy | | | biopsy RECIPIENT Crro-CTTT graft sacrifice monkey harvest organs |

FIG. 38II

| | control monkey | | notes |
|---|---|---|---|
| | control drugs | testing (blood) procedure | |
| | | flow control CBCdiff, CMV level | This graft is to show that we can transplant thymus in a NHP |
| | | | |
| | | | |
| | | | |
| | | flow control, CBCdiff, CMV level | |
| | | | |
| | | flow control, CBCdiff, CMV level | This biopsy is to show that the recipient thymus has thymopoiesis, that we can do grafts in NHP |

FIG. 38JJ

| WK | donor monkey (Mamu-A:01 negative) | | | |
|---|---|---|---|---|
| | donor monkey surgery | donor monkey other procedure | donor thymus processing | donor monkey testing (blood) |
| | | | | |
| 1 | | | | MLR #1 (5ml) |
| 2 | | | | flow cytometry, CBCdiff, chemistry, CMV level, MHC typing |
| | | | | |
| 1 | | | | |
| 2 | | | | |

FIG. 39A

| recipient monkey (Mamu-A:01 positive) | | | | |
|---|---|---|---|---|
| recipient blood testing | recipient thymus processing | Recipient other procedures | Recipient medical therapy | Recipient surgery |
| STAGE 1 (MHC type animals prior to coming) | | | | |
| MLR#1 (5ml) | | | | |
| flow cytometry CBCdiff, chemistry, CMV level, MHC typing | | | | |
| STAGE 2 | | | | |
| CMV level | Cryopreserve skin on day 1.3 Culture recipient thymus from day 1.3 to 3.1 | | | thymectomy and skin biopsies day 1.3 |
| DSA (5ml), | | | | |

FIG. 39B

| notes | all other monkey, |
|---|---|
| | monkey testing (blood) |
| | |
| determine pairing for experiments based on MLR reactivity and Mamu-A*01 allele (recipient positive; donor, nagative) | MLR #1 (5ml) |
| | flow cytometry, CBCdiff, chemistry, CMV level |
| | |
| | 1<br>2<br>3 thymectomize recipient<br>4 and culture recipient<br>5 thymus, skin biopsy<br>6<br>7 |
| | 1<br>2<br>3<br>4<br>5<br>6<br>7 |

FIG. 39C

| WK | donor monkey (Mamu-A:01 negative) ||||
| --- | --- | --- | --- | --- |
| | donor monkey surgery | donor monkey other procedure | donor thymus processing | donor monkey testing (blood) |
| 3 | | | | flow cytometry, CBC, CMV level, day 3.1 |
| 4 | | | | weekly CBC flow until recipient has no RTE |
| 5 | | | | |
| 1 | thymectomy, and skin biosies, day 1.3 | | culture donor thymus 12 days (day 1.3 to 3.1 otal of 12 days), then transplant half and cryopreserve half on day 2.7 | |
| 2 | | | | |

FIG. 39D recipient monkey (Mamu-A:01 positive)

| recipient blood testing | recipient thymus processing | Recipient other procedures | Recipient medical therapy | Recipient surgery |
|---|---|---|---|---|
| flow, CBCdiff day 3.1, (CMV level) flow to show no RTE day 3.1 | One day 3.1 crypreserve thymus | | | |
| weely CBCdiff flow until recipient has no RTE; when no RTE, go to STAGE 3. | | | | |
| If the recipient continues to have recent thymic emigrants (RTE), this monkey did not have a complete thymectomy. If this is the case, <u>start stage 2 again (at week 1) with another Mamu-A:01 positive monkey as the recipient or switch the recipient and donor and have the donor be Mamu-A:01 positive, and the recipient negative.</u> | | | | |
| STAGE 3 | | | | |
| flow day 1.1 CBCdiff, (CMV level) | | | | |
| CBCdiff, tacro level | | | | |

FIG. 39E

|  | notes | all other monkeys |
|---|---|---|
|  |  | monkey testing (blood) |
|  |  | 1 cropreserve<br>2 recipient<br>3 cultured<br>4 thymus<br>5<br>6<br>7 |
|  |  |  |
|  |  |  |
|  |  | 1<br>2<br>3 thymectomize donor<br>4<br>5<br>6<br>7 |
|  |  | 1<br>2<br>3<br>4 flow to show T cell<br>5 depletion<br>6 - recipient<br>7 start last ATG |

FIG. 39F

| WK | donor monkey (Mamu-A:01 negative) | | | |
|---|---|---|---|---|
| | donor monkey surgery | donor monkey other procedure | donor thymus processing | donor monkey testing (blood) |
| 3 | | | | |
| 4 | | | | |
| 5 | | | | |
| 6 | | | | |
| 7 | | | | |
| 8 | | | | |

FIG. 39G

| | | recipient monkey (Mamu-A:01 positive) | | | |
|---|---|---|---|---|---|
| | recipient blood testing | recipient thymus processing | Recipient other procedures | Recipient medical therapy | Recipient surgery |
| | tacro level (0.5 ml), DSA, CMV level | | | on day 3.1, start tacro, MMF and rhATG (5 days) | Cultured thymus transplant (from donor) day 3.1 |
| | flow, CBCdiff, tacro level, CMV level | | | continue tacro, MMF | |
| | tacro level, CMV level, creatinine, ALT | | | continue tacro, MMF | |
| | flow, CBCdiff, tacro level, | | | continue tacro, MMF | |
| | tacro level, CMV level, creatinine, ALT | | | continue tacro, MMF | |
| | flow, CBCdiff, tacro level, | | | continue tacro, MMF | |

FIG. 39H

| | notes | all other monkeys, |
|---|---|---|
| | | monkey testing (blood) |
| | | 1 thymus transplant<br>2<br>3<br>4<br>5<br>6<br>7 |
| | | flow control, CBCdiff, day 2,3, CMV level |
| | | |
| | | flow control, CBCdiff |
| | | |
| | | flow control, CBCdiff |

FIG. 39I

| WK | donor monkey (Mamu-A:01 negative) ||||
| --- | --- | --- | --- | --- |
| | donor monkey surgery | donor monkey other procedure | donor thymus processing | donor monkey testing (blood) |
| 9 | | | | |
| 10 | | | | |
| 11 | | | | |
| 12 | | | | |
| 13 | | | | |
| 14 | | | | |

FIG. 39J

| recipient monkey (Mamu-A:01 positive) | | | | |
|---|---|---|---|---|
| recipient blood testing | recipient thymus processing | Recipient other procedures | Recipient medical therapy | Recipient surgery |
| tacro level, CMV level, creatinie, ALT | | | continue tacro, MMF | |
| flow, CBCdiff, serum for DSA, tacro level | | Evaluate CTTT biopsy by IHC for thymopoiesis | continue tacro, MMF | Dat 10.3 Biopsy of CTTT transplant; transplant Cryo-CTTT into other leg |
| tacro level, CMV level, creatinine, ALT | | | continue tacro, MMF | |
| flow, CBCdiff, serum for DSA, tacro level | | | continue tacro, MMF | |
| tacro level, CMV level, creatinine, ALT | | | continue tacro, MMF | |
| flow, CBCdiff, tacro level, | | | continue tacro, MMF | |

FIG. 39K

| notes | all other monkeys, |
|---|---|
| | monkey testing (blood) |
| | |
| | flow control, CBCdiff |
| If biopsy is good, it hasn't been rejected and the plan should work. | |
| If biopsy on day 10.3 is good, start next pair of monkeys | flow control, CBCdiff |
| | |
| | flow control, CBCdiff |

1
2
3 Biopsy of CTTT, transplant cryo-CTTT
4
5
6
7

FIG. 39L

| WK | donor monkey (Mamu-A:01 negative) ||||
| --- | --- | --- | --- | --- |
| | donor monkey surgery | donor monkey other procedure | donor thymus processing | donor monkey testing (blood) |
| 15 | | | | |
| 16 | | | | |
| 17 | | | | |
| 18 | | | | |
| 1 | | | | MLR#2 |
| 2 | | | | |

FIG. 39M

| | | | | |
|---|---|---|---|---|
| \multicolumn{5}{c}{recipient monkey (Mamu-A:01 positive)} |||||
| recipient blood testing | recipient thymus processing | Recipient other procedures | Recipient medical therapy | Recipient surgery |
| tacro level, CMV level, creatinie, ALT | | | continue tacro, MMF | |
| flow, CBCdiff, serum for DSA, tacro level | | | continue tacro, MMF | |
| tacro level, CMV level | | | continue tacro, MMF | |
| flow, CBCdiff, CMV level, tacro level | | | Continue the pattern of the last 4 weeks until naïve T cells >15%-then go to Stage 4; If naïve T cells don't reach 15% go to Stage 5. | |
| Stage 4 | | | | |
| MLR#2 CMV level | | | If MLR shows tolerance to donor and response to 3rd party go to weeks 2, if no tolerance with response to 3rd party, go to Stage 6. | |
| flow, CBCdiff, tacro level, | | | continue tacro, drop MMF to BID | |

FIG. 39N

| notes | all other monkeys, |
|---|---|
| | monkey testing (blood) |
| | |
| | flow control, CBCdiff |
| | |
| | flow control, CBCdiff |
| purpose is to show that recipient is tolerance of donor and donor is still reactive against the recipient. (which should be the case even without thymus in the donor) | MLR#2 |
| flows starting here are to watch for thymus rejection | flow control, CBCdiff |

FIG. 39O

| WK | donor monkey (Mamu-A:01 negative) | | | |
|---|---|---|---|---|
| | donor monkey surgery | donor monkey other procedure | donor thymus processing | donor monkey testing (blood) |
| 3 | | | | |
| 4 | | | | |
| 5 | | | | |
| 6 | | | | MLR#3 |
| 7 | non survival heart donation, skin biopsoes, all on day 7.1 | Cryo-preserve skin, day 7.1 Save blood for transfusion into recipient if necessary | | |
| 8 | | | | |

FIG. 39P

| | | | | |
|---|---|---|---|---|
| recipient monkey (Mamu-A:01 positive) ||||||
| recipient blood testing | recipient thymus processing | Recipient other procedures | Recipient medical therapy | Recipient surgery |
| CMV level, serum for DSA, tacro level | | | continue tacro, drop MMF to daily | |
| flow, CBCdiff, creatinine, ALT, tacro level | | | continue tacro, MMF | |
| flow, CBCdiff, CMV level, tacro level | | | continue tacro | |
| MLR#3 tacro level | | | regardless of result, go to week 7 | |
| flow, CBCdiff, CMV level, serum for DSA, tacro level | assess thymus biopsies | Monitor heart beating, 2x/week, Assess thymus biopsiesis for thymopoiesis by IHC | continue tacro | heterotopic heart transplant from donor, day 7.1, biopsy Cryo-CTTT. Only repeat CTTT biopsy if the first CTTT biopsy demonstrated lack of thymus tissue in the leg |
| tacro level | | Monitor heart beating, 2x/week (ECHO). If heart stops beating, sacrifice monkey | continue tacro | |

FIG. 39Q

| notes | all other monkeys, |
|---|---|
| | monkey testing (blood) |
| | |
| | flow control, CBCdiff |
| | flow control, CBCdiff |
| We certainly hope that the MLR is neg from recipient to donor off MMF | MLR#3 |
| | flow control, CBCdiff |
| | in stage 4, obtain skin from control NHP for upcoming cryo-preserved skin grafting |

1 heterotopic heart transplant from donor, bx of Cryo-CTTT
2
3
4
5
6
7

FIG. 39R

| WK | donor monkey (Mamu-A:01 negative) ||||
|----|---|---|---|---|
| | donor monkey surgery | donor monkey other procedure | donor thymus processing | donor monkey testing (blood) |
| 9 | | | | |
| 10 | | | | |
| 11 | | | | |
| 12 | | | | MLR#4, draw prior to skin grafting |
| 13 | | | | |
| 14 | | | | |
| 180 days after heart ransplantation |||||

FIG. 39S

| recipient monkey (Mamu-A:01 positive) | | | | |
|---|---|---|---|---|
| recipient blood testing | recipient thymus processing | Recipient other procedures | Recipient medical therapy | Recipient surgery |
| flow, CBCdiff, CMV level, tacro level | | Monitor heart beating, 2x/week (ECHO). If heart stops beating, sacrifice monkey | wean tacro over 4 week | |
| | | Monitor heart beating, 1x/week (ECHO). If heart stops beating, sacrifice monkey | wean tacro over 3 week | |
| flow, CBCdiff, CMV level, | | Monitor heart beating, 1x/week (ECHO). If heart stops beating, sacrifice monkey | wean tacro over 3 week | |
| ALT creatinine, DSA, MLR#4 | | Monitor heart beating, 1x/week (ECHO). If heart stops beating, sacrifice monkey | wean tacro over 1 week | If heart is beating, apply fresh recipient skin, cryopreserved recipient skin, cryopreserved donor skin and fresh and cryopreserved 3rd party skin |
| CMV level | | monitor skin | off tacro | |
| montly CBCdiff flow, CMV, ALT, creatinine | | | | |
| flow, CBCdiff, CMV level, serum for DSA | | | | sacrafice monkey, harvest heart for path), recipient and donor thymus for IHC and throracic tissue for IHC |
| Stage 5 (drop MMF, continue tacro) | | | | |

FIG. 39T

| | notes | all other monkeys, |
|---|---|---|
| | | monkey testing (blood) |
| | | flow control, CBCdiff |
| | | |
| | | flow control, CBCdiff |
| | | MLR#4, fresh skin biopsy for grafting |
| | | montly control for flow and CBCDiff |
| | | flow control, CBCdiff |

FIG. 39U

| WK | donor monkey (Mamu-A:01 negative) | | | |
|---|---|---|---|---|
| | donor monkey surgery | donor monkey other procedure | donor thymus processing | donor monkey testing (blood) |
| 1 | | | | |
| 2 | | | | |
| 3 | | | | |
| 4 | | | | |
| 5 | | | | |

FIG. 39V recipient monkey (Mamu-A:01 positive)

| recipient blood testing | recipient thymus processing | Recipient other procedures | Recipient medical therapy | Recipient surgery |
|---|---|---|---|---|
| flow, CBCdiff, tacro level, creatinie, ALT | | | continue tacro, drop MMF to BID | |
| CMV level, serum for DSA, tacro level | | | continue tacro, drop MMF to daily | |
| flow, CBCdiff, creatinine, ALT, tacro level | | | continue tacro, stop MMF | |
| CMV level, tacro level, creatinine, ALT | | | contine tacro, if naïve T cells>15% go to Stage 4 (although MMF has already been weaned) | |
| flow, CBCdiff, tacro level, creatinine, ALT | | | contine tacro, if naïve T cells>15% go to Stage 4 (although MMF has already been weaned) | |

FIG. 39W

| notes | all other monkeys, |
|---|---|
| | monkey testing (blood) |
| flow starting here are to watch for thymus rejection | flow control, CBCdiff |
| | |
| | flow control, CBCdiff |
| | flow control, CBCdiff |

FIG. 39X

| WK | donor monkey (Mamu-A:01 negative) | | | |
| --- | --- | --- | --- | --- |
| | donor monkey surgery | donor monkey other procedure | donor thymus processing | donor monkey testing (blood) |
| 6 | | | | |
| 7 | | | | |
| 8 | | | | |
| 9 | | | | |

FIG. 39Y

| recipient monkey (Mamu-A:01 positive) | | | | |
|---|---|---|---|---|
| recipient blood testing | recipient thymus processing | Recipient other procedures | Recipient medical therapy | Recipient surgery |
| tacro level, CMV level | | | contine tacro, if naïve T cells>15% go to Stage 4 (although MMF has already been weaned) | |
| flow, CBCdiff, tacro level, creatinine, ALT | | | contine tacro, if naïve T cells>15% go to Stage 4 (although MMF has already been weaned) | |
| tacro level, CMV level | | | contine tacro, if naïve T cells>15% go to Stage 4 (although MMF has already been weaned) | |
| flow, CBCdiff, tacro level, creatinine, ALT | | | contine tacro, if naïve T cells>15% go to Stage 4 (although MMF has already been weaned) | |

FIG. 39Z

| notes | all other monkeys, |
|---|---|
| | monkey testing (blood) |
| | |
| | flow control, CBCdiff |
| | |
| | flow control, CBCdiff |

FIG. 39AA

| WK | donor monkey (Mamu-A:01 negative) | | | |
|---|---|---|---|---|
| | donor monkey surgery | donor monkey other procedure | donor thymus processing | donor monkey testing (blood) |
| 10 | | | | |
| 11 | | | | |
| 12 | | | | |
| 1 | | | | |
| 2 | | | | |
| 3 | | | | |
| 4 | | | | |
| 5 | | | | |
| 6 | | | | |

FIG. 39BB recipient monkey (Mamu-A:01 positive)

| recipient blood testing | recipient thymus processing | Recipient other procedures | Recipient medical therapy | Recipient surgery |
|---|---|---|---|---|
| tacro level, CMV level | | | contine tacro, if naïve T cells>15% go to Stage 4 (although MMF has already been weaned) | |
| flow, CBCdiff, tacro level, creatinine, ALT | | | contine tacro, if naïve T cells>10% go to Stage 4 (although MMF has already been weaned) | |
| tacro level, CMV level | | | contine tacro, if naïve T cells<10% go to Stage 6 | |
| Stage 6 | | | | |
| flow, CBCdiff, DSA level | | | | Cryo-CTTT from RECIPIENT (day 1.1) |
| CMV level, creatinine, ALT | | | | |
| flow, CBCdiff, DSA level | | | | |
| CMV level, creatinine, ALT | | | | |
| flow, CBCdiff, DSA level | | | | |
| CMV level, creatinine, ALT | | | | |

FIG. 39CC

| | notes | all other monkeys, |
|---|---|---|
| | | monkey testing (blood) |
| | | |
| | | flow control, CBCdiff |
| | | |
| | This graft is to show that we can transplant thymus in a NHP | flow control, CBCdiff |
| | | |
| | | flow control, CBCdiff |
| | | flow control, CBCdiff |
| | | |

FIG. 39DD

| WK | donor monkey (Mamu-A:01 negative) | | | |
|---|---|---|---|---|
| | donor monkey surgery | donor monkey other procedure | donor thymus processing | donor monkey testing (blood) |
| 7 | | | | |
| 8 | | | | |
| 9 | | | | |

FIG. 39EE

| recipient monkey (Mamu-A:01 positive) | | | | |
|---|---|---|---|---|
| recipient blood testing | recipient thymus processing | Recipient other procedures | Recipient medical therapy | Recipient surgery |
| flow, CBCdiff, DSA level | | | | |
| CMV level, creatinine, ALT | | | | |
| flow, CBCdiff, creatinine, ALT | assess recipient thymus biopsy | | | biopsy RECIPIENT Cryo-CTTT graft, sacrifice monkey, harvest organs |

FIG. 39FF

| notes | all other monkeys, |
|---|---|
| | monkey testing (blood) |
| | flow control, CBCdiff |
| | |
| This biopsy is to show that the recipient thymus has thymopoiesis, that we can do grafts in NHP | flow control, CBCdiff |

FIG. 39GG

Table S1: Proteins Present in Spent Media of Thymic Organ Cultures, as Determined by Multiplex Antibody Arrays

| Target | Mean Change/ Day in ln(pg/mL) | e^(mean daily change), i.e., the average daily multiplicative change | P-value | FDR Corrected P-value | # of Thymi Contributing to Analysis | AUC Summed over Thymi |
|---|---|---|---|---|---|---|
| L-Selectin | -0.151 | 0.859 | 0.000 | 0.038 | 3 | 202.586 |
| CXCL16 | 0.064 | 1.066 | 0.001 | 0.038 | 3 | 209.210 |
| MCSF | -0.055 | 0.946 | 0.001 | 0.038 | 3 | 92.920 |
| 6Ckine/CCL21 | 0.161 | 1.174 | 0.002 | 0.038 | 3 | 252.435 |
| Galectin-7 | -0.076 | 0.927 | 0.002 | 0.038 | 3 | 140.538 |
| MIF | -0.148 | 0.862 | 0.002 | 0.052 | 3 | 199.764 |
| GDNF | 0.073 | 1.075 | 0.003 | 0.061 | 1 | 5.394 |
| CTACK | -0.086 | 0.918 | 0.006 | 0.064 | 1 | 27.773 |
| MIP-3b | 0.023 | 1.023 | 0.006 | 0.064 | 3 | 172.044 |
| ICAM-1 | -0.076 | 0.927 | 0.006 | 0.064 | 3 | 203.589 |
| PECAM-1 | -0.113 | 0.893 | 0.008 | 0.064 | 3 | 133.303 |
| IL-2 Rg | -0.036 | 0.965 | 0.008 | 0.064 | 3 | 153.295 |
| SCF R | -0.062 | 0.940 | 0.008 | 0.064 | 3 | 124.307 |
| IL-16 | -0.174 | 0.840 | 0.008 | 0.064 | 3 | 163.768 |

FIG. 56A

| | | | | | | |
|---|---|---|---|---|---|---|
| GDF-15 | 0.106 | 1.112 | 0.009 | 0.064 | 3 | 186.913 |
| PDGF-AA | -0.023 | 0.977 | 0.009 | 0.064 | 3 | 52.074 |
| SDF-1a/CXCL12 | 0.225 | 1.252 | 0.009 | 0.064 | 3 | 29.952 |
| MIP-3a | -0.142 | 0.868 | 0.009 | 0.064 | 3 | 31.062 |
| IL-2 Ra | -0.015 | 0.985 | 0.010 | 0.064 | 1 | 9.608 |
| ICAM-3 | -0.108 | 0.897 | 0.012 | 0.075 | 2 | 21.766 |
| LIGHT | 0.039 | 1.040 | 0.012 | 0.075 | 3 | 85.066 |
| IGFBP-1 | -0.202 | 0.817 | 0.014 | 0.080 | 3 | 99.912 |
| BCMA | -0.038 | 0.962 | 0.015 | 0.080 | 2 | 21.790 |
| EGF R | -0.182 | 0.834 | 0.015 | 0.080 | 3 | 154.229 |
| uPAR | 0.106 | 1.111 | 0.018 | 0.089 | 3 | 242.266 |
| MIP-1b | 0.010 | 1.010 | 0.019 | 0.090 | 3 | 107.695 |
| PlGF | 0.090 | 1.095 | 0.019 | 0.090 | 3 | 167.824 |
| PF4 | -0.145 | 0.865 | 0.023 | 0.104 | 3 | 62.902 |
| Eotaxin/CCL11 | 0.161 | 1.174 | 0.025 | 0.106 | 3 | 101.421 |
| HVEM | -0.084 | 0.919 | 0.026 | 0.106 | 3 | 52.502 |
| IGFBP-6 | 0.055 | 1.056 | 0.027 | 0.106 | 3 | 223.281 |
| IL-6R | -0.085 | 0.919 | 0.027 | 0.106 | 3 | 108.855 |
| IL-12p40 | -0.454 | 0.635 | 0.031 | 0.119 | 2 | 13.349 |
| RANTES | -0.027 | 0.973 | 0.034 | 0.127 | 3 | 134.204 |
| MICA | -0.030 | 0.971 | 0.035 | 0.127 | 3 | 124.223 |

FIG. 56B

| | | | | | | |
|---|---|---|---|---|---|---|
| GCP-2 | 0.050 | 1.052 | 0.038 | 0.130 | 3 | 196.666 |
| OPN | 0.040 | 1.041 | 0.038 | 0.130 | 3 | 249.803 |
| ALCAM | -0.094 | 0.911 | 0.039 | 0.130 | 3 | 97.825 |
| NRG1-b1 | -0.092 | 0.912 | 0.045 | 0.142 | 3 | 96.152 |
| CEACAM-1 | -0.056 | 0.945 | 0.045 | 0.142 | 3 | 70.163 |
| IL-1b | -0.026 | 0.975 | 0.047 | 0.145 | 3 | 79.821 |
| DKK-1 | 0.326 | 1.386 | 0.0495 | 0.148 | 2 | 37.394 |
| ANG-1 | 0.046 | 1.047 | 0.0502 | 0.148 | 3 | 85.812 |
| ErbB3 | -0.072 | 0.930 | 0.057 | 0.163 | 1 | 9.214 |
| IL-9 | 0.014 | 1.014 | 0.058 | 0.163 | 1 | 43.672 |
| LIMPII | -0.041 | 0.960 | 0.063 | 0.175 | 3 | 95.957 |
| Contactin-2 | -0.120 | 0.887 | 0.066 | 0.178 | 1 | 14.559 |
| PAI-1 | 0.027 | 1.028 | 0.070 | 0.186 | 3 | 228.849 |
| HGF | -0.033 | 0.967 | 0.076 | 0.196 | 3 | 159.181 |
| ENA-78 | 0.008 | 1.008 | 0.079 | 0.199 | 3 | 234.838 |
| MCP-2 | 0.031 | 1.032 | 0.081 | 0.199 | 3 | 139.076 |
| TNF RII | -0.052 | 0.949 | 0.082 | 0.199 | 3 | 193.497 |
| OPG | 0.122 | 1.130 | 0.083 | 0.199 | 3 | 137.668 |
| VEGF | 0.130 | 1.139 | 0.096 | 0.226 | 3 | 129.469 |
| TNF RI | -0.020 | 0.980 | 0.102 | 0.235 | 3 | 218.058 |
| PARC | 0.021 | 1.021 | 0.105 | 0.238 | 3 | 207.288 |

FIG. 56C

| | | | | | | |
|---|---|---|---|---|---|---|
| gp130 | -0.084 | 0.919 | 0.111 | 0.245 | 3 | 131.722 |
| I-TAC | 0.044 | 1.045 | 0.112 | 0.245 | 3 | 41.093 |
| TIMP-2 | 0.033 | 1.033 | 0.116 | 0.250 | 3 | 238.942 |
| TRAIL R3 | -0.072 | 0.931 | 0.118 | 0.250 | 2 | 13.700 |
| Follistatin | 0.099 | 1.104 | 0.123 | 0.254 | 3 | 181.874 |
| Resistin | -0.071 | 0.932 | 0.124 | 0.254 | 3 | 106.468 |
| 4-1BB | -0.056 | 0.945 | 0.129 | 0.261 | 1 | 20.040 |
| VEGF R1 | -0.049 | 0.953 | 0.138 | 0.274 | 3 | 228.018 |
| Fas | -0.049 | 0.952 | 0.148 | 0.286 | 3 | 118.996 |
| Lipocalin-2 | -0.031 | 0.969 | 0.152 | 0.286 | 3 | 176.082 |
| TGFb1 | 0.028 | 1.028 | 0.153 | 0.286 | 2 | 49.932 |
| Angiogenin | -0.019 | 0.982 | 0.154 | 0.286 | 3 | 175.004 |
| Eotaxin-2 | 0.047 | 1.048 | 0.155 | 0.286 | 3 | 108.763 |
| IGFBP-2 | 0.063 | 1.065 | 0.159 | 0.288 | 3 | 192.496 |
| G-CSF | -0.092 | 0.912 | 0.162 | 0.290 | 3 | 158.850 |
| HCC-1 | -0.073 | 0.929 | 0.165 | 0.291 | 3 | 142.157 |
| Cripto-1 | -0.016 | 0.984 | 0.170 | 0.295 | 2 | 34.201 |
| Lymphotactin | 0.013 | 1.013 | 0.172 | 0.295 | 3 | 122.650 |
| TARC | -0.093 | 0.911 | 0.183 | 0.308 | 3 | 106.087 |
| AR | -0.107 | 0.899 | 0.184 | 0.308 | 3 | 46.829 |
| VEGF R2 | 0.012 | 1.012 | 0.204 | 0.336 | 2 | 39.193 |
| CD40 | -0.203 | 0.816 | 0.211 | 0.343 | 2 | 22.631 |

FIG. 56D

| | | | | | | |
|---|---|---|---|---|---|---|
| Flt-3L | 0.023 | 1.023 | 0.214 | 0.343 | 3 | 90.290 |
| MIP-1a | -0.054 | 0.947 | 0.216 | 0.343 | 3 | 58.799 |
| LAP(TGFb1) | -0.033 | 0.967 | 0.223 | 0.350 | 3 | 146.542 |
| GITR | 0.028 | 1.029 | 0.237 | 0.368 | 1 | 14.837 |
| Endoglin | 0.039 | 1.040 | 0.257 | 0.392 | 2 | 49.988 |
| IL-2 Rb | -0.004 | 0.996 | 0.259 | 0.392 | 3 | 188.704 |
| IL-17F | 0.038 | 1.039 | 0.279 | 0.417 | 2 | 47.061 |
| GRO | 0.011 | 1.011 | 0.319 | 0.469 | 3 | 148.212 |
| IL-13 | -0.010 | 0.990 | 0.321 | 0.469 | 3 | 29.440 |
| MCP-3 | 0.038 | 1.038 | 0.360 | 0.519 | 3 | 116.129 |
| CD14 | 0.075 | 1.077 | 0.364 | 0.519 | 3 | 206.167 |
| Fcg RIIBC | -0.023 | 0.978 | 0.374 | 0.528 | 3 | 154.387 |
| MCP-1 | -0.007 | 0.993 | 0.385 | 0.535 | 3 | 131.410 |
| ICAM-2 | -0.021 | 0.979 | 0.390 | 0.535 | 3 | 231.645 |
| Dtk | -0.028 | 0.972 | 0.392 | 0.535 | 1 | 23.534 |
| IL-4 | -0.033 | 0.968 | 0.396 | 0.535 | 2 | 11.786 |
| MIG | -0.053 | 0.948 | 0.400 | 0.535 | 3 | 153.182 |
| IL-10 | -0.014 | 0.986 | 0.431 | 0.564 | 1 | 8.219 |
| TIMP-1 | 0.003 | 1.003 | 0.431 | 0.564 | 3 | 214.968 |
| TSLP | 0.068 | 1.071 | 0.436 | 0.564 | 2 | 23.874 |
| Siglec-5 | -0.026 | 0.974 | 0.455 | 0.581 | 3 | 146.401 |

FIG. 56E

| | | | | | | |
|---|---|---|---|---|---|---|
| IL-8 | -0.005 | 0.995 | 0.461 | 0.581 | 3 | 91.165 |
| Axl | 0.003 | 1.003 | 0.465 | 0.581 | 3 | 140.204 |
| CCL28 | 0.017 | 1.017 | 0.466 | 0.581 | 2 | 41.134 |
| IGFBP-4 | 0.016 | 1.016 | 0.473 | 0.584 | 3 | 139.780 |
| MCP-4 | 0.022 | 1.022 | 0.480 | 0.586 | 3 | 137.942 |
| BTC | 0.017 | 1.017 | 0.527 | 0.636 | 1 | 22.810 |
| MDC | 0.006 | 1.006 | 0.533 | 0.636 | 3 | 166.883 |
| Cathepsin S | -0.006 | 0.994 | 0.536 | 0.636 | 3 | 156.492 |
| IL-1ra | -0.016 | 0.984 | 0.557 | 0.649 | 3 | 137.561 |
| IL-6 | 0.003 | 1.003 | 0.557 | 0.649 | 3 | 158.523 |
| IL-1 RI | 0.007 | 1.007 | 0.568 | 0.656 | 2 | 43.751 |
| NAP-2 | 0.010 | 1.010 | 0.642 | 0.735 | 3 | 130.999 |
| FGF-7 | -0.015 | 0.985 | 0.654 | 0.735 | 2 | 55.305 |
| TREM-1 | -0.003 | 0.997 | 0.654 | 0.735 | 3 | 73.081 |
| MPIF-1 | 0.015 | 1.015 | 0.675 | 0.749 | 3 | 87.617 |
| E-Selectin | 0.013 | 1.013 | 0.678 | 0.749 | 1 | 24.599 |
| LIF | -0.012 | 0.988 | 0.726 | 0.790 | 3 | 132.040 |
| BMP-7 | 0.005 | 1.005 | 0.728 | 0.790 | 1 | 15.782 |
| IP-10 | -0.008 | 0.992 | 0.754 | 0.812 | 3 | 167.405 |
| BLC | 0.022 | 1.022 | 0.777 | 0.826 | 3 | 21.017 |
| MICB | 0.007 | 1.007 | 0.781 | 0.826 | 1 | 29.761 |
| VEGF-C | -0.022 | 0.979 | 0.836 | 0.877 | 2 | 50.465 |

FIG. 56F

| | | | | | | |
|---|---|---|---|---|---|---|
| VCAM-1 | -0.007 | 0.993 | 0.849 | 0.884 | 3 | 233.065 |
| IGFBP-3 | 0.004 | 1.004 | 0.866 | 0.894 | 3 | 258.861 |
| IL-11 | -0.002 | 0.998 | 0.911 | 0.933 | 3 | 144.132 |
| LYVE-1 | 0.001 | 1.001 | 0.967 | 0.975 | 3 | 139.215 |
| Trappin-2 | 0.001 | 1.001 | 0.967 | 0.975 | 3 | 234.720 |
| MCSFR | 0.000 | 1.000 | 0.992 | 0.992 | 3 | 183.716 |
| Activin A | ND | ND | ND | ND | 0 | ND |
| AgRP | ND | ND | ND | ND | 0 | ND |
| Angiostatin | ND | ND | ND | ND | 0 | ND |
| B7-1 | ND | ND | ND | ND | 0 | ND |
| BDNF | ND | ND | ND | ND | 0 | ND |
| bFGF | ND | ND | ND | ND | 0 | ND |
| BMP-4 | ND | ND | ND | ND | 0 | ND |
| BMP-5 | ND | ND | ND | ND | 0 | ND |
| b-NGF | ND | ND | ND | ND | 0 | ND |
| CD30 | ND | ND | ND | ND | 0 | ND |
| CD40L | ND | ND | ND | ND | 0 | ND |
| DAN | ND | ND | ND | ND | 0 | ND |
| DR6 | ND | ND | ND | ND | 0 | ND |
| E-Cadherin | ND | ND | ND | ND | 0 | ND |
| EGF | ND | ND | ND | ND | 0 | ND |
| EG-VEGF | ND | ND | ND | ND | 0 | ND |
| Eotaxin-3 | ND | ND | ND | ND | 0 | ND |
| EpCAM | ND | ND | ND | ND | 0 | ND |
| FASL | ND | ND | ND | ND | 0 | ND |
| FGF-4 | ND | ND | ND | ND | 0 | ND |
| GH | ND | ND | ND | ND | 0 | ND |
| GM-CSF | ND | ND | ND | ND | 0 | ND |
| HB-EGF | ND | ND | ND | ND | 0 | ND |

FIG. 56G

| | | | | | | |
|---|---|---|---|---|---|---|
| HCC-4 | ND | ND | ND | ND | 0 | ND |
| I-309 | ND | ND | ND | ND | 0 | ND |
| IFNg | ND | ND | ND | ND | 0 | ND |
| IGF-1 | ND | ND | ND | ND | 0 | ND |
| IL-10 Rb | ND | ND | ND | ND | 0 | ND |
| IL-12p70 | ND | ND | ND | ND | 0 | ND |
| IL-13 R1 | ND | ND | ND | ND | 0 | ND |
| IL-13 R2 | ND | ND | ND | ND | 0 | ND |
| IL-15 | ND | ND | ND | ND | 0 | ND |
| IL-17 | ND | ND | ND | ND | 0 | ND |
| IL-17B | ND | ND | ND | ND | 0 | ND |
| IL-17R | ND | ND | ND | ND | 0 | ND |
| IL-18 BPa | ND | ND | ND | ND | 0 | ND |
| IL-1a | ND | ND | ND | ND | 0 | ND |
| IL-2 | ND | ND | ND | ND | 0 | ND |
| IL-21R | ND | ND | ND | ND | 0 | ND |
| IL-23 | ND | ND | ND | ND | 0 | ND |
| IL-28A | ND | ND | ND | ND | 0 | ND |
| IL-29 | ND | ND | ND | ND | 0 | ND |
| IL-31 | ND | ND | ND | ND | 0 | ND |
| IL-5 | ND | ND | ND | ND | 0 | ND |

FIG. 56H

| | | | | | | |
|---|---|---|---|---|---|---|
| IL-7 | ND | ND | ND | ND | 0 | ND |
| Insulin | ND | ND | ND | ND | 0 | ND |
| MIP-1d | ND | ND | ND | ND | 0 | ND |
| MSP | ND | ND | ND | ND | 0 | ND |
| NGF R | ND | ND | ND | ND | 0 | ND |
| NrCAM | ND | ND | ND | ND | 0 | ND |
| NT-3 | ND | ND | ND | ND | 0 | ND |
| NT-4 | ND | ND | ND | ND | 0 | ND |
| PDGFRb | ND | ND | ND | ND | 0 | ND |
| PDGF-AB | ND | ND | ND | ND | 0 | ND |
| PDGF-BB | ND | ND | ND | ND | 0 | ND |
| RAGE | ND | ND | ND | ND | 0 | ND |
| SCF | ND | ND | ND | ND | 0 | ND |
| SDF-1b | ND | ND | ND | ND | 0 | ND |
| Shh-N | ND | ND | ND | ND | 0 | ND |
| ST2 | ND | ND | ND | ND | 0 | ND |
| TECK | ND | ND | ND | ND | 0 | ND |
| TGFa | ND | ND | ND | ND | 0 | ND |
| TGFb2 | ND | ND | ND | ND | 0 | ND |
| TGFb3 | ND | ND | ND | ND | 0 | ND |
| Tie-2 | ND | ND | ND | ND | 0 | ND |

FIG. 56I

| | | | | | | |
|---|---|---|---|---|---|---|
| TIM-1 | ND | ND | ND | ND | 0 | ND |
| TNFa | ND | ND | ND | ND | 0 | ND |
| TNFb | ND | ND | ND | ND | 0 | ND |
| TPO | ND | ND | ND | ND | 0 | ND |
| TRAIL R4 | ND | ND | ND | ND | 0 | ND |
| VEGF R3 | ND | ND | ND | ND | 0 | ND |
| VEGF-D | ND | ND | ND | ND | 0 | ND |

FIG. 56J

METHODS OF DETERMINING THE SUITABILITY OF CULTURED THYMUS TISSUE FOR IMPLANTATION INTO HUMANS AND ASSOCIATED METHODS OF USE

CROSS REFERENCE TO RELATED APPLICATIONS

This application is a continuation of PCT/US2020/046341, filed on Aug. 14, 2020, which is a continuation in part of U.S. application Ser. No. 16/283,007 filed Feb. 22, 2019, which is a continuation of PCT/US2019/19137, filed Feb. 22, 2019, and claims the benefit of U.S. Provisional Application Nos. 62/634,377, filed Feb. 23, 2018; U.S. Provisional Application No. 62/888,799, filed Aug. 19, 2019; and U.S. Provisional Application No. 63/039,153, filed Jun. 15, 2020, the subject matter of which is incorporated herein in their entirety by reference.

STATEMENT REGARDING FEDERALLY SPONSORED RESEARCH OR DEVELOPMENT

This invention was made with United States government support awarded by NIH Grant P01-AG052359 to J. Nikolich-Zigich. The United States government has certain rights in this invention.

FIELD OF INVENTION

Biomarkers useful for determining the viability and suitability of T cell-depleted cultured pediatric thymus tissue, also known as allogeneic cultured postnatal thymus tissue-derived product (or, sometimes "CTT"), for implantation and T cell reconstitution in subjects having thymus disorders, including congenital athymia and other immune system dysfunction due to thymus disorders. Methods and compositions for promoting donor-specific tolerance to allogeneic solid organ transplants in a recipient receiving an allogeneic solid organ transplant from a donor.

BACKGROUND OF THE INVENTION

Organ transplantation requires the preparation and harvesting of a human solid organ from a donor and transplantation into the recipient. The major problem in solid organ transplantation is that the recipient is not tolerant of the donor. The recipient T cells will reject the organ and the recipient B cells will develop antibodies to the organ causing its eventual failure. The holy grail of solid organ transplantation is development of tolerance to the transplanted human organ by the recipient. More than 36,000 organ transplants are estimated to be performed per year in the U.S., and many more in in Europe, and other major countries. It is further estimated that there are more than 120,000 patients on waiting lists in the U.S. for organ transplants. Demand for healthy organs significantly exceeds the supply of suitable organs. In 2018, approximately 10,000 donors were identified. See https://optn.transplant.hrsa.gov.

Transplant rejection is a substantial challenge in solid organ transplantation. Transplant rejection by both T cells and B cells can lead to significant complications in organ function or even to transplant failure. The 5-year graft survival, for example, for heart transplants is 77.7%, for kidney transplants is 78.6%, for liver transplants is 72.8%, and for lung transplants is 53.4%. Typically, this problem has been addressed, in part, through the matching of donors and recipients for major histocompatibility complex (MHC) antigens and by avoiding recipients with antibodies to the recipient tissue types. In addition, the use of immunosuppressive regimens to manage the immunological response underlying transplant rejection has improved. However, tolerance has not been achieved and the mean survival for many organs is only 10 years.

Preservation of organ viability prior to and during the implantation procedure is a second significant challenge. The removal, storage and transplantation of an organ may profoundly affect the internal structure and function of the organ and can influence significantly the degree to which the return of normal organ function is delayed or prevented after transplantation is completed.

The time period in which solid human organs may be effectively preserved varies by organ, with kidneys ranging from 24-36 hours, pancreas from 12-18 hours, liver from 8-12 hour and heart and lung from 4-6 hours. See https://unos.org/transplantation/matching-organs.

Organ injury occurs primarily as a result of ischemia and hypothermia, but may also be related to reperfusion of the organ ex vivo or during implantation.

Techniques for organ preservation, including ex vivo perfusion, are known in the art and serve to minimize organ damage and promote optimal graft survival and function.

The principal solid organs which have been the subject of transplantation procedures, include kidney, liver, heart, and lungs. Success in transplanting these solid organs has been achieved with varying degrees of success. The principal variability resides in the techniques that are used to interfere with immune-mediated graft rejection. Experience has shown that there is no one single immunosuppressive agent or technique that is useful in all settings involving solid organ transplantation. The limiting factor usually resides in the toxicity associated with each individual immunosuppressive agent. The toxicity associated with a given immunosuppressive agent may frequently hinder the normal functioning of the transplanted solid organ or of other organs such as the kidneys which can fail when calcineurin inhibitors are used to prevent rejection.

The toxicity drawbacks associated with known immunosuppressive agents normally used to prevent graft rejection in solid organ transplants presents a need to find new methods for preventing graft rejection of solid organ transplants.

The ability to discriminate between self and non-self antigens is central to the immune response. This discrimination results in self-tolerance. Autoimmunity develops when there has been a loss of self-tolerance. An unmet need exists in transplantation procedures to induce tolerance to solid organ transplants.

Preservation of thymus tissue viability prior to and during the implantation procedure for allogeneic cultured postnatal thymus tissue-derived product in subjects with thymus disorders, including congenital athymia and other immune system dysfunction due to thymus disorders is an important factor in the practice of the various aspects and embodiments of the present disclosure.

The thymus is necessary for development of T cells that can appropriately respond to foreign antigens and pathogens, while avoiding damaging self-reactivity.

The thymus is large in infancy due to its need to establish the initial T cell repertoire, but soon becomes homeostatic, followed by a slow process of involution that continues throughout adulthood. Work over the last two to three decades has established that while the overall output of adult thymus is decreased, the organ remains critical for producing T cells with novel specificities that can protect against infectious disease or cancer and repopulate the repertoire following immune insults such as radiation, chemotherapy, and some infections such as human immunodeficiency virus (HIV) (Gruver et al. 2007; Palmer et al. 2018; Sun et al. 2016; Wickemeyer and Sekhsaria 2014). Thus, recent attention has been focused on identifying the mechanisms that govern age-related thymus involution and methods to facilitate thymus regeneration following immune injury in adults.

Age-related thymus involution in humans is characterized by loss of developing thymocytes and decreased numbers of thymic epithelial cells, with replacement of thymus parenchyma by adipose tissue. Determining whether the mechanisms driving these changes are thymus-intrinsic versus thymus-extrinsic is difficult to address using animal models due to constant trafficking to and from the thymus, and such questions are generally not possible to address in live humans.

Organ cultures of thymus tissue derived from young donors are useful for evaluating these questions, since in vitro culture of human thymus slices results in depletion of thymocytes, while generally maintaining the viability and function of the thymic epithelial and stromal cells. This is demonstrated by the ability of these slices to grow out monolayers (Markert et al. 1997b) and to facilitate T cell reconstitution when implanted into congenitally athymic recipients (Davies et al. 2017; Davis et al. 1997; Markert et al. 2004; Markert et al. 1999; Markert et al. 2007; Markert et al. 2010; Markert et al. 1997a; Markert et al. 2011; Markert et al. 2003). We hypothesized that the loss of thymocytes that occurs during thymic organ cultures could mimic acute and chronic involution and help to identify mechanisms that drive changes in the thymic microenvironment during aging.

Allogeneic cultured postnatal thymus tissue-derived product has been shown to be useful for the treatment of T cell immunodeficiency (primary immune deficiency) resulting from congenital athymia, for example in the treatment of complete DiGeorge Anomaly (cDGA) associated with 22q11.2 deletion and CHARGE (coloboma, heart defect, choanal atresia, growth or mental retardation, genital hypoplasia and ear anomalies or deafness) syndrome associated with mutations in the chd7 (chromodomain-helicase-DNA-binding protein 7) gene and in athymic patients with forkhead box protein N1 (FOXN1) deficiency. Congenital athymia is a rare, fatal condition and currently has no drug treatment options utilizing regulatory approved drug products.

Experimental implantation of an allogeneic cultured postnatal thymus tissue-derived product that retains thymus epithelial cells (TECs) has been successfully applied to treat pediatric patients with congenital athymia (Markert M L, Devlin B H, McCarthy E A, 2010, "Thymus transplantation," Clin Immunol., 135(2): 236-46; Markert M L, et al., 2004, "Postnatal thymus transplantation with immunosuppression as treatment for DiGeorge syndrome," Blood 104 (8):2574-2581; Markert M L, et al., 1999, "Transplantation of thymus tissue in complete DiGeorge syndrome," N c J Med 341(16):1180-1189 27).

In this reference, DiGeorge Syndrome is defined as a condition in which there are variable defects in the heart, thymus and parathyroid gland. Approximately 1% of infants with DiGeorge syndrome have athymia and hence cannot make naïve T cells that mature and fight infection. These infants are said to have complete DiGeorge syndrome. Without intending to be inclusive, there are subgroups of children who meet the criteria of complete DiGeorge syndrome, 22q11.2 deletion syndrome, CHARGE, infants of diabetic mothers, and infants with no syndromic or genetic defects. Congenital athymia may also be associated with mutations in the TBX1 or TBX2 genes.

Allogeneic cultured postnatal thymus tissue-derived product is a tissue-engineered product that is prepared, cultured and stored for up to 21 days (for example, a culturing regimen of about 6 to about 21 days) to produce partially T cell-depleted thymus tissue slices and which is differentiated from native thymus by a conditioning process. The conditioning regimen partially depletes the donor thymocytes from the cultured thymus tissue slices. Based on in vitro data (immunohistochemistry) a culture period between 6 and 21 days preserves the epithelial network as assessed using cytokeratin antibodies. The culturing is preferably done at 37° C. in a 5% $CO_2$ incubator.

The culturing process significantly modifies the biological characteristics of the donor thymus tissue and constituent cells contained therein in the following manner to optimize the effective therapeutic properties of the allogeneic cultured postnatal thymus tissue-derived product slices. The culturing process assures that a defined composition of the cultured cells/tissue having the pre-requisite biological characteristics is obtained in a manner suitable for surgical implantation into a subject to enable reconstitution of the subject's immune system.

The culturing process results in a loss of thymocytes and relative enrichment of TECs and other stromal cells in the donor thymus tissue slices. The culturing process further results in depletion of thymocytes and maintenance of TECs to enable reconstitution of the recipient's immune system and allows tolerance to develop in the recipient to HLA antigens in the donor thymus. Overall, the culturing process is designed to deplete many of the thymocytes from the donor thymus tissue and to preserve the functional architecture of the thymic stroma (thymic epithelial cells and fibroblasts). Common lymphoid progenitors that develop from stem cells migrate to the thymus and enter the thymus as thymus settling progenitors.

The culturing process is described in WO2019/165197A1, Cultured Thymus Tissue Transplantation Promotes Donor-Specific Tolerance to Allogeneic Solid Organ Transplants, Markert, M. L., which is hereby incorporated by reference in its entirety. The analysis of the suitability of allogeneic cultured postnatal thymus tissue-derived product slices is described in PCT/US2019/040275, which is incorporated by reference herein in its entirety.

The surgical administration of allogeneic, cultured postnatal thymus tissue-derived product (e.g., also known as "RVT-802") in athymic patients leads to a cascade of events resulting in the development of a functional immune system. Following surgical placement of allogeneic, cultured postnatal thymus tissue-derived product in a recipient, T cells are educated by donor TECs and recipient dendritic cells (DCs). Donor TECs in conjunction with recipient DCs enable tolerance to the implanted donor thymus tissue, which is implanted as cultured thymus tissue slices. This is the same tolerance induction as in a normal thymus. The donor TECs in conjunction with recipient DCs lead to tolerance to self.

Thymopoiesis in implanted donor thymus tissue has been documented by allograft biopsies and the presence of recipient naive T cells in the periphery (Markert M L, 2010; Markert M L, et al., 2008, "Use of allograft biopsies to assess thymopoiesis after thymus transplantation," J Immunol 180(9):6354-6364; Markert M L, et al., 2007, "Review of 54 patients with complete DiGeorge anomaly enrolled in protocols for thymus transplantation: outcome of 44 consecutive transplants," Blood 109(10):4539-454728), which are incorporated herein by reference.

Studies of children treated with investigational allogeneic, cultured postnatal thymus tissue-derived product show tolerance to donor major histocompatibility complex (MHC) by mixed lymphocyte reactions (Chinn I K, Devlin B H, Li Y J, & Markert M L, 2008, "Long-term tolerance to allogeneic thymus transplants in complete DiGeorge anomaly," Clin Immunol 126(3):277-281). In addition, the infants with congenital athymia, after allogeneic, cultured postnatal thymus tissue-derived transplantation, are able to control infections such as Epstein Barr virus (Markert M L, 2014, Thymus Transplantation. Stiehm's Immune Deficiencies, eds Sullivan K E & Stiehm E R (Academic Press), 1st Ed, pp 1059-1067.

Historically, allogeneic cultured postnatal thymus tissue-derived product release criteria has included histopathological evaluation of H&E and immunostained sections of tissue at the mid-point of the manufacturing process, which was later refined to days 6-21 of the culture period. This histopathological evaluation has served as the potency assay, and has been performed as a qualitative analysis by a board-certified pathologist. Samples were prepared for evaluation either by freezing or formalin fixation prior to the tissue slice being sectioned and then fixed onto a slide. Samples prepared in this manner are stable over long periods of time, allowing for reanalysis to be performed.

The historical samples available from the 20+ years of development history can be linked to positive clinical outcomes, and thus provide a strong data set for development of a quantitative histology assay for evaluation of product quality.

A new digital histology assay was developed using scanned images of H&E slides from previous clinical lots and from experimental lots of allogeneic, cultured postnatal thymus-tissue derived product. These images were analyzed for development into a quantitative release assay. The digital histology assay is described more completely in PCT/US2019/040275.

Cellular migration in response to chemoattractant cytokines (chemokines) and other soluble molecules is a critical, but less intuitive, mechanism that regulates thymus function (Hu et al. 2015). Early thymocyte progenitors migrate from the bone marrow to the thymus under the influence of chemokine gradients. Chemokine gradients also influence their migration within the thymus. Early thymocyte progenitors and their CD4–/CD8– double negative (DN) progeny interact with cortical thymic epithelial cells, differentiate into CD4+/CD8+ double positive (DP) thymocytes, and then are positively selected to differentiate into CD4+ or CD8+ single positive thymocytes (Lancaster 2018) that migrate to the thymic medulla. After self-reactive cells are deleted by negative selection, the resulting naïve mature T cells are released into the periphery.

Notwithstanding the foregoing success of implanting allogeneic, cultured postnatal thymus-tissue derived product in children having congenital athymia, there is still a need to identify cultured thymus tissue that is viable, functional and suitable for implantation in order to achieve immune-reconstitution.

SUMMARY OF THE INVENTION

Achieving donor-specific immune tolerance remains the ultimate immunologic goal in transplantation. Most of the current approaches focus on controlling peripheral mature donor-reactive T cells by depletion (e.g. alemtuzumab, thymoglobulin, etc.) or suppression (e.g. calcineurin inhibitors, basiliximab, etc.) without targeting the production of alloreactive T cells in thymus. However, even with the dramatic advancement of immunosuppressive drugs and new immunomodulatory regimens, transplant tolerance has not yet been consistently achieved.

The present inventors have shown that tolerance to solid organ transplants may be achieved through the implantation of allogeneic cultured postnatal thymus tissue-derived product (referred to herein also as "CTT" or as "RVT-802"), in a thymectomized recipient, to shorten the time period of use of post-transplantation immunosuppressive agents to prevent rejection of the transplanted organ. The removal of the recipient's thymus and substitution of an allogeneic cultured postnatal thymus tissue-derived product results in reconstitution of the solid organ recipient's immune system and tolerance to the recipient's self as well as to the transplanted allogeneic solid organ.

Tolerance induction by surgical insertion of allogeneic cultured postnatal thymus tissue-derived product is similar to tolerance induction via donor dendritic cells ("DC") in hematopoietic stem cell transplantation (Sharabi Y & Sachs D H, 1989, "Mixed chimerism and permanent specific transplantation tolerance induced by a nonlethal preparative regimen," *J Exp Med* 169(2):493-502; Manilay J O, Pearson D A, Sergio J J, Swenson K G, & Sykes M, 1998, "Intrathymic deletion of alloreactive T cells in mixed bone marrow chimeras prepared with a nonmyeloablative conditioning regimen," *Transplantation* 66(1):96-102). A series of studies from Transplantation Biology Research Center (TBRC, Boston, MA) showed the crucial role of thymus in tolerance induction (Yamada K, et al., 1997, "Role of the thymus in transplantation tolerance in miniature swine. I. Requirement of the thymus for rapid and stable induction of tolerance to class I-mismatched renal allografts," *J Exp Med* 186(4):497-506) and tested thymus transplantation with tolerance induction in a large animal model (Yamada K, et al., 2000, "Thymic transplantation in miniature swine. II. Induction of tolerance by transplantation of composite thymokidneys to thymectomized recipients," *J Immunol* 164(6):3079-3086; 5; Yamada K, et al., 2003, "Thymic transplantation in miniature swine: III. Induction of tolerance by transplantation of composite thymokidneys across fully major histocompatibility complex-mismatched barriers," Transplantation 76(3):530-536; Nobori S, et al., 2006, "Thymic rejuvenation and the induction of tolerance by adult thymic grafts," *Proc Nat Acad Sci USA* 103(50): 19081-19086. In their series of studies, this group successfully used HLA-Class II matched/Class I mismatched donor (thymus and kidney or heart) as thymus composite tissues (thymokidney and thymoheart) with 12 days of cyclosporine ("CsA") for transplant tolerance induction. They claimed that non-vascularized thymus did not induce tolerance in their model. More precisely, however, non-vascularized thymus that was not cultured did not engraft long-term. As they indicated, the failure of engraftment of the uncultured thymus may have been due to ischemic injury in addition to alloimmunity (Yamada K, et al., 2000). This elegant concept of generating vascularized thymus prior to transplantation to induce tolerance, would be difficult to translate to the clinic without using xenotransplantation. (Kwun, Jean, Li, Jie, Rouse, Clay, Park, Jae Berm, Farris, Alton B., Kuchibhatla, Maragatha, Turek, Joseph W. Knechtle, Stuart J. Kirk, Allan D. and Markert, M Louise, *Cultured thymus tissue implantation promotes donor-specific tolerance to allogeneic heart transplants*, JCI Insight. 2020 Jun. 4; 5(11):e129983. doi: 10.1172/jci.insight.129983).

The limitation of non-vascularized thymus transplantation can be overcome with a culture system as well as T cell depletion. Experimental transplantation of allogeneic cultured postnatal thymus tissue-derived product (CTT) that retains TECs has been successfully applied to treat pediatric patients with congenital athymia (Markert M L, Devlin B H, McCarthy E A, 2010, "Thymus transplantation," *Clin Immunol.,* 135(2): 236-46; Markert M L, et al., 2004, "Postnatal thymus transplantation with immunosuppression as treatment for DiGeorge syndrome," *Blood* 104(8):2574-2581; Markert M L, et al., 1999, "Transplantation of thymus tissue in complete DiGeorge syndrome," *N Engl J Med* 341(16): 1180-1189 27).

In foregoing reference, DiGeorge Syndrome is defined as a condition in which there are variable defects in the heart, thymus and parathyroid gland. Approximately 1% of infants with DiGeorge syndrome have athymia and hence no T cells to fight infection. These infants are said to have complete DiGeorge syndrome. There are 4 subgroups of children who meet the criteria of complete DiGeorge syndrome, 22q11.2 deletion syndrome, CHARGE, infants of diabetic mothers, and infants with no syndromic or genetic defects. In all four groups, the infants with athymia represent a very tiny group, possibly 1% of the total children carrying the diagnosis, such as the diagnosis of 22q11.2 deletion syndrome.

Thympoiesis has been documented by allograft biopsies and the presence of recipient naive T cells in the periphery (Markert M L, 2010; Markert M L, et al., 2008, "Use of allograft biopsies to assess thymopoiesis after thymus transplantation," *J Immunol* 180(9):6354-6364; Markert M L, et al., 2007, "Review of 54 patients with complete DiGeorge anomaly enrolled in protocols for thymus transplantation: outcome of 44 consecutive transplants," *Blood* 109(10): 4539-454728). Studies of children treated with investigational CTT show tolerance to donor MHC by mixed lymphocyte reactions (Chinn I K, Devlin B H, Li Y J, & Markert M L, 2008, "Long-term tolerance to allogeneic thymus transplants in complete DiGeorge anomaly," *Clin Immunol* 126(3):277-281). In addition, the infants with congenital athymia, after CTT implantation, are able to control infections such as Epstein Barr virus (Markert M L, 2014, Thymus Transplantation. *Stiehm's Immune Deficiencies*, eds Sullivan K E & Stiehm E R (Academic Press), 1st Ed, pp 1059-1067). Based on these data in humans with congenital athymia, it was determined that allogeneic cultured postnatal thymus tissue-derived product expressing the MHC of a solid organ donor after surgical insertion in the recipient will develop tolerance to both self and to the donor, while producing functional T cells that will protect the recipient from infection.

*Thymus Gland and Education of Thymocytes.* (Kwun, Jean, Li, Jie, Rouse, Clay, Park, Jae Berm, Farris, Alton B., Kuchibhatla, Maragatha, Turek, Joseph W. Knechtle, Stuart J. Kirk, Allan D. and Markert, M Louise, *Cultured thymus tissue implantation promotes donor-specific tolerance to allogeneic heart transplants*, JCI Insight. 2020 Jun. 4; 5(11):e129983. doi: 10.1172/jci.insight.129983.

The thymus gland normally is located on top of the heart. The thymus provides an essential microenvironment for T cell development and is critical to the establishment and maintenance of the adaptive immune system (Boehm T and Takahama Y, 2014, *Thymic Development and Selection of T Lymphocytes.* Heidelberg: Springer-Verlag). During postnatal development, the thymus educates hematopoietic stem cells migrating from the bone marrow to the thymus gland. The progenitor stem cells colonize the thymus thereby forming thymocytes. The thymocytes thereafter undergo a series of maturation steps. This is evidenced by the expression of a number of observable cell surface markers appearing on the thymocytes.

T cells are critical for the protection of the body from infections. T cells that develop in a normally functioning thymus develop a diverse set of T cell receptors (generally proteins on the surface of the cell), which enable the mature T cell to fight a wide variety of infections. During this education process the developing T cells are instructed by the thymus not to attack the body's normal proteins, such as insulin or parathyroid hormone (which regulate glucose and calcium levels in the blood). These instructions are carried out under the influence of the autoimmune regulator gene ("AIRE gene)."

Briefly, the education process occurs in the normally functioning thymus gland. Thymocytes, present in the thymus gland, are formed from bone marrow stem cells. Thymocytes, are taught by thymus epithelial cells ("TECs") and dendritic cells ("DCs"), located within the thymus, to not attack recipient major histocompatibility complex (MHC) proteins (antigens) such as HLA-A, HLA-B, HLA-C, HLA-DRB1, HLA-DQB1, HLA-DQA1, HLA-DPB1, HLA-DPA1 antigens. The HLA antigens have 2 proteins that hold a self-peptide in a groove. The self-peptide could be from a thyroid protein or an insulin peptide or almost any other protein expressed in the body. Thymocytes developing in the thymus form a T cell receptor (TCR) composed of two proteins that cross the membrane. The TCR is expressed on the cell surface of the T cells. Each T cell expresses many copies of its unique TCR. If the TCR binds too tightly to the self peptide: MHC on a dendritic cell, the dendritic cell provides a signal to make the T cell undergo apoptosis and die. This mechanism prevents the development of autoimmunity to self. The TEC can also provide a signal to thymocytes that they are binding too tightly. Lastly the DC can grab bits of membrane from the TEC and present the TEC self peptide: MHC to the developing thymocyte. If the thymocytes bind too tightly, the DC sends a signal so that the thymocyte undergoes apoptosis and dies. By these mechanisms, T cells that leave the thymus are not self-reactive. The T cells that leave the thymus are very variable and can recognize infections but they do not attack proteins of the body.

The two major constituents of thymus are epithelium and thymocytes that are produced in the thymus in the following manner. Cells derived from bone marrow stem cells, common lymphoid progenitors ("CLPs"), migrate to the thymus as early thymic progenitors. The CLPs enter the thymus in response to signals (chemokines) produced by the thymus epithelium and endothelium. In the thymus the CLPs differentiate into thymocytes and proliferate. Thymocytes develop a unique T-cell receptor ("TCR") that is expressed on the cell surface. Thymocytes also begin to express the T cell molecules CD3, CD4 and CD8. A vast diversity of T cells develop rendering the cells capable of responding to infections throughout the life of the recipient. Mixed lymphocyte reactions show tolerance of the recipient T cells in children who are treated with cultured thymus tissue (RVT-802) to thymus donor MHC.

Self-reactive recipient thymocytes are deleted prior to exit from the thymus. This occurs by interaction of recipient thymocytes and recipient DCs that migrate to the thymus. Apoptosis is induced in recipient thymocytes that bind too tightly to the DCs as a measure to protect the body from autoimmune disease. After completion of this process, the thymocytes exit the thymus. The new circulating T cells, i.e., recent thymus emigrants, express the markers CD31, CD45RA and CD62L. After a few weeks, the CD31 marker is no longer expressed. The T cells expressing CD45RA and CD62L are called naive T cells. These recipient T cells proliferate normally in response to mitogens. They protect the recipient from infection without having autoreactivity to self.

Allogeneic Cultured Postnatal Thymus Tissue-Derived Product.

Allogeneic cultured postnatal thymus tissue-derived product has been shown to be useful for the treatment of T cell immunodeficiency (primary immune deficiency) resulting from congenital athymia. T cell immunodeficiency due to athymia is associated with congenital disorders which prevent the development of a functional thymus, such as complete DiGeorge Anomaly (cDGA) associated with 22q11.2 deletion and CHARGE (coloboma, heart defect, choanal atresia, growth or mental retardation, genital hypoplasia and ear anomalies or deafness) syndrome associated with mutations in the chd7 (chromodomain-helicase-DNA-binding protein 7) gene and in athymic patients with forkhead box protein N1 (FOXN1) deficiency. Other genetic defects causing athymia include TBX1, TBX2, PAX1 and semaphorine 3E (SEMA3E), and Bernstock, Joshua D, Totten, A, and Atkinson, T. Prescott, "Recurrent microdeletions at chromosome 2p11.2," Bernstock, Joshua D, Totten, A, and Atkinson, T. Prescott, JACI 145:358-367. Congenital athymia is a rare fatal condition and currently has no drug treatment options utilizing regulatory approved drug products. If left untreated and no therapeutic reconstitution of the child's immune system occurs, the primary immunodeficiency due to congenital athymia is fatal, with almost all infants dying before the age of three years, most often by severe infections.

Allogeneic cultured postnatal thymus tissue-derived product is a tissue-engineered product. Based on disclosures in this specification and Examples, CTT is expected to be useful for the development of tolerance in a recipient receiving a transplanted solid organ.

As described more fully in this specification and Examples, the surgical administration of allogeneic, cultured postnatal thymus tissue-derived product (e.g., "RVT-802") in athymic patients leads to a cascade of events resulting in the development of a functional immune system. Following surgical placement of allogeneic, cultured postnatal thymus tissue-derived product (e.g., RVT-802) in the recipient, T cells are educated by donor TECs and recipient DCs. Donor TECs in conjunction with recipient DCs enable tolerance to the implanted donor thymus tissue, which is implanted as cultured thymus tissue slices. This is the same tolerance induction as in a normal thymus. The recipient TECs in conjunction with recipient DCs lead to tolerance to self as described in this specification.

This complex process has been shown clinically to lead to >70% survival in patients with congenital athymia receiving allogeneic, cultured postnatal thymus tissue derived product (e.g., RVT-802) due to the recipient's capacity to fight infections (Markert M L, Devlin B H, Alexieff M J, Li J, McCarthy E A, Gupton S E, et al., 2007, "Review of 54 patients with complete DiGeorge anomaly enrolled in protocols for thymus transplantation: outcome of 44 consecutive transplants," Blood, 109(10): 4539-47; Markert M L, Devlin B H, McCarthy E A. Thymus transplantation. 2010, Clin. Immunol. 135(2): 236-46). The recipients are able to control viral infections such as Epstein-Barr virus that would have been fatal prior to CTT. (Chinn I K, Devlin B H, Li Y J, & Markert M L, 2008).

Overview of Tolerance Induction in Solid Organ Transplant in Combination with Implantation of CTT In accordance with the description, figures, examples and claims of the present specification, the inventor has demonstrated that CTT induces donor-specific tolerance in a rat heart transplantation model. The experiments reported herein used comparable CTT implantation methods that have been used clinically in subjects with congenital athymia, such as subjects afflicted by cDGA. cDGA infants have essentially no naïve T cells prior to surgical placement of CTT. Following surgical placement of CTT, the infants developed naïve T cells approximately 6 months after the surgical procedure. (Markert M L, et al., 2004, "Postnatal thymus transplantation with immunosuppression as treatment for DiGeorge syndrome," Blood 104(8):2574-2581; Markert M L, Devlin B, & McCarthy E A, 2010, "Thymus transplantation," Clin Immunol 135(2):236-246). The studies of tolerance induction in a rat model were based on the results of investigations of transplantation of allogeneic postnatal cultured thymus tissue-derived product (CTT) from 1993 to 2017 in athymic infants with complete DiGeorge anomaly. Favorable results were obtained in the reported studies of surgical placement of CTT in infants having congenital athymia. The published results showed an overall survival rate of 71% (61/86) (essentially all the deaths occurred in the first 9-12 months; median 11.7 years, range 1.2 to 25 years at the time of this assessment) in this otherwise fatal condition (Markert, M L, et al., 2010). Biopsies of the implanted cultured thymus tissue have demonstrated thymopoiesis on immunohistochemistry (Markert, M L, et al., 2008). Flow cytometry and spectra-typing have shown development of a diverse T cell repertoire. Mixed lymphocyte reactions show tolerance of the recipient T cells to thymus donor antigen presenting cells (Chinn I K, Devlin B H, Li Y J, & Markert M L, 2008).

Importantly, the recipients of CTT are able to control viral infections such as Epstein-Barr virus that would have been fatal prior to CTT (Markert, M L, 2014, Thymus Transplantation. Stiehm's Immune Deficiencies, eds Sullivan K E & Stiehm E R (Academic Press), 1st Ed, pp 1059-1067). Based on these human data showing tolerance to unmatched thymus MHC antigens, implantation of CTT in a rat model was evaluated using the same methods used clinically, for its ability to induce donor-specific tolerance in a rat heart transplantation model. These studies showed that transplanting unmatched hearts along with donor CTT expressing the heart donor's MHC class I and class II antigens (with initial T cell depletion by anti CD5 and immunosuppression with cyclosporine) induces tolerance to the antigens of the donor heart while preserving alloreactivity toward other MHC antigens.

The present invention substantiates donor thymus co-transplantation with solid organs as a method of tolerance induction with regard to the transplanted solid organ in the recipient. The patient groups that would most benefit from the procedure is adults with heart failure as well as infants needing heart transplants. Since postnatal thymic tissue is present and could be removed from deceased infants, and the recipient thymus is routinely removed from infants undergoing heart transplantation, no additional procedure aside from cultured thymus tissue implantation (CTT) would be needed to transfer this approach to the clinic. Similar transplants may also be performed in adults.

Overview of Preparation of Allogeneic, Cultured Postnatal Thymus-Tissue Derived Product Allogeneic, cultured postnatal thymus-tissue derived product is prepared, cultured and stored for up to 21 days (for example, a culturing regimen of about 6 days to about 21 days), and, on the day of implantation, placed in individual sterile cups for transport to the operating room, as described in more detail herein.

The CTT (cultured thymus tissue) is aseptically processed and cultured under current Good Manufacturing Practices ("cGMP"), for example, cGMPs established by the U.S. Food & Drug Administration ("FDA"), to produce partially T cell-depleted thymus tissue slices. CTT is differentiated from native thymus by a conditioning process described in detail below. CTT effects the normal positive and negative selection process of developing T cells in the thymus after implantation, enabling the T cells to be tolerant to both the donor thymus and the donor solid organ transplant plus recipient tissues. In addition, these T cells can recognize foreign antigens in the context of recipient major histocompatibility (MHC) proteins so as to fight infection.

The route of administration is by surgical implantation of CTT, in the manner described below. A single administration is typically 1,000 to 22,000 $mm^2$ of CTT surface area per recipient body surface area ("BSA") in $m^2$. The surface area is the total of all the surface areas of all cultured tissue slices. The individual CTT slices are implanted in a single administration surgical procedure.

Surgical implantation of allogeneic cultured postnatal thymus tissue-derived product in athymic patients leads to a cascade of events resulting in the development of a functional immune system. (Markert M L, 2007; Markert M L, et al., 2010; Markert M L, Devlin B H, McCarthy E A. Chapter 84 *Thymic reconstitution*. 2013. In: Fleisher T A, Shearer W T, Schroeder H W, Frew A J, Weyand C M, editors. Clinical Immunology (Fourth Edition). London; pp. 1032-8).

Recipient CLPs of the bone marrow migrate to the thymus allograft, enter as early thymic progenitors and there develop into recipient T cells. The donor thymus graft provides a microenvironment in which the recipient thymocytes develop a broad repertoire of TCRs capable of recognizing pathogens.

Migration of recipient DCs to the donor thymus depletes self-reactive recipient thymocytes that would attack the recipient's tissues after the new T cells leave the thymus and enter the circulation. Genetically-recipient naïve T cells are readily detectable in the circulation approximately 5-12 months after administration. These recipient T cells have diverse TCR repertoires and proliferate normally in response to mitogens. They protect the recipient from infection without having autoreactivity to self.

Recipient bone marrow CLPs migrate to the thymus allograft where they develop into recipient T cells. Negative selection by recipient DCs that have migrated to the donor thymus results in tolerance to the recipient MHC antigens. Immunohistochemical evidence of thymopoiesis is observed in biopsies of the implanted cultured thymus tissue taken within approximately 2-3 months of transplantation. The thymopoiesis reflects the ability of the T cells to defend against and control infection, and prevent autoimmune disease.

Naïve T cells are detected in the circulation 5-12 months post-transplantation, resulting in the ability to defend against and control infection, and the prevention of autoimmune disease.

Implantation of cultured thymus tissue was first shown to be beneficial in treating primary immune deficiency resulting from congenital athymia associated with conditions such as complete DiGeorge anomaly (cDGA) or forkhead box protein N1 (FOXN1) deficiency. It was discovered that replacement of defective thymus tissue with normal thymus tissue after culture (e.g. CTT and RVT-802) may also obviate the lack of tolerance observed in recipients of transplanted solid organs.

The non-clinical and clinical work underlying the treatment of congenital athymia through placement of cultured thymus tissue led to the realization that placement of CTT (e.g., RVT-802) in patients may permit the development of tolerance to a transplanted solid organ. Specifically, placement of CTT will reconstitute an immune system and induce tolerance to the donor organ if the subject is first thymectomized and immunosuppressed prior to the implantation of the CTT that expresses the MHC of the donor organ.

Measurement of the expression and distribution of certain markers associated with the cellular components of the thymus establish a phenotype following ex vivo culturing of thymus tissue. The culturing conditions described in this specification and Examples support the observation of in vivo thymopoiesis following placement of CTT in an athymic subject.

Importantly, after the surgical placement of CTT in an athymic recipient, the development of naïve T cells and the presence of a broad range of TCR-variable regions provides clear evidence that culturing of thymus tissue can foster the development of a functional endogenous T cell population. In addition, the expression of key regulatory and structural genes was noted in thymus tissue during culturing. Circulating naïve (CD45RA+CD62L+) T cells can be first detected 3-5 months after surgical insertion of CTT. These observations have been noted in the treatment of patients with complete DiGeorge Anomaly (Markert M L, 2010; Markert M L. 2013).

The nonclinical data described in the literature for thymus tissue implantation aligns with the robust clinical efficacy of implanting allogeneic cultured postnatal thymus tissue and supports its use in humans. (Markert M L, Watson T J, Kaplan I, Hale L P, Haynes B F, 1997, "The human thymic microenvironment during organ culture," *Clin Immunol Immunopathol*. January; 82(1):2 6-36; Hong R, Schulte-Wissermann H, Jarrett-Toth E, Horowitz S D, Manning D D, 1979, "Transplantation of cultured thymic fragments. II. Results in nude mice," *J Exp Med.,* 149(2): 398-415. Li B, Li J, Hsieh C S, Hale L P, Li Y J, Devlin B H, Markert M L, 2009, "Characterization of cultured thymus tissue used for transplantation with emphasis on promiscuous expression of thyroid tissue-specific genes," *Immunol Res.* 2009; 44 (1-3):71-83; Li B, Li J, Devlin B H, Markert M L, 2011, "Thymic microenvironment reconstitution after postnatal human thymus transplantation," *Clin Immunol*., September; 140(3): 244-59).

Complete DiGeorge Anomaly patients may have defects in three glands that develop in the neck in the young embryo, the heart, the thymus and the parathyroid gland. Normally the heart and thymus descend into the chest and the parathyroid gland regulates calcium levels, and remain in the neck. Treatment of cDGA subjects with CTT led to the survival rates at two years of age of 75% compared to a survival rate of 6% in patients treated by other modalities (unpublished data). As noted above, almost all deaths are in the first year prior to development of naive T cells. (Markert, et al., 2010). Of note, the CTT implantation does not affect the problems of the heart and the parathyroid gland that must be managed separately.

An aspect of the present disclosure provides methods for the surgical placement of allogeneic cultured postnatal thymus tissue-derived product in a recipient to induce tolerance to a solid organ transplant in an immunologically normal recipient. Such methods comprise, consist of, or consist essentially of, removal of the thymus gland in an immunocompetent recipient followed by depleting the recipient's T cells with an induction immunosuppressive regimen, comprising one or more immunosuppressive agent, such as with one or more antibody and/or one or more calcineurin inhibitor. The induction immunosuppressive regimen is administered in a therapeutically effective amount to deplete mature T cells in the subject and/or to suppress the recipient's T cells from rejecting the transplanted solid organ. A suitable solid human organ and a thymus gland from a deceased donor is obtained and the solid organ is transplanted into the recipient. A maintenance immunosuppressive regimen is administered for a period of time to suppress transplant rejection. The thymus gland from the deceased donor is subjected to a conditioning regimen for a period up to 21 days (for example, a conditioning regimen of about 6 days to about 21 days), to aseptically process the donor thymus tissue in a thymus organ medium to produce partially T-cell depleted donor thymus tissue slices thereby comprising the allogeneic cultured postnatal thymus tissue-derived product. The partially T-cell depleted donor thymus tissue slices show areas positive for keratin AE1/AE3 scattered throughout the tissue, the presence of at least one Hassall body, CK14 staining scattered throughout the tissue and presence of intact nuclei. The allogeneic cultured postnatal thymus tissue-derived product is then surgically placed in the recipient, typically in the quadriceps muscle of the thigh. The allogeneic cultured postnatal thymus tissue-derived product enables the recipient to develop naïve T cells after implantation. All new T cells that develop are genetically recipient and are tolerant to both the recipient and to the donor. The dosage of thymus tissue slices is about 1,000-22,000 mm$^2$ of thymus tissue surface area/recipient body surface area m$^2$. Following implantation, the allogeneic cultured postnatal thymus tissue-derived product induces thymopoiesis and tolerance in the subject.

Taking as an example a heart transplant, the donor would be a deceased donor. The thymus would be removed from the donor at the same time that the heart is removed. A heart transplantation is performed immediately with induction immunosuppression to decrease T cell numbers and suppress the remaining recipient T cells preventing them from attacking the donor heart. The donor thymus is processed to form human allogeneic cultured postnatal thymus tissue-derived product that can be used for implantation to induce tolerance after a period of at least about 6 days to about 21 days of conditioning. As a precaution, approximately half of the allogeneic cultured postnatal thymus tissue-derived product can be cryopreserved after conditioning, so that if there was a problem with later rejection of the heart necessitating the administration of high doses of steroids or other immunosuppressive agents to treat the rejection, and whereby the very high doses of steroid damage the allogeneic cultured postnatal thymus tissue-derived product, the cryopreserved allogeneic cultured postnatal thymus tissue-derived product would be available to implant after the rejection episode was controlled.

Importantly, after implantation of allogeneic cultured postnatal thymus tissue-derived product, immune tolerance is maintained even in the presence of infections. With other approaches such as co-stimulatory blockade, viral infections can led to loss of tolerance, because approximately a third of CD8 T cells have alloreactivity. When the immune system is activated to fight an infection, the alloreactive CD8 T cells start to reject the solid organ transplant. In contrast, when using thymus tissue processed into allogeneic cultured postnatal thymus tissue-derived product to induce tolerance, potentially alloreactive T cells against the donor are deleted through the process of negative selection in the thymus.

In an embodiment, the donor thymus tissue matches the HLA alleles in the donor organ that are not in the recipient. All new T cells that develop are genetically recipient and are tolerant to both the recipient and to the donor.

In another aspect of the present disclosure, there is provided a method for promoting donor-specific tolerance to an allogeneic solid organ transplant obtained from a deceased donor, in a recipient in need of a solid organ transplant, the method comprising the steps of:
  (a) removal of the thymus of the recipient;
  (b) treating the recipient with an induction immunosuppressive regimen comprising one or more immunosuppressive agent to deplete the recipient's T cells and/or to suppress the recipient's T cells from rejecting the transplanted solid organ;
  (c) providing both a suitable solid human organ and a thymus gland from a deceased donor;
  (d) transplanting the solid human organ into the recipient;
  (e) treating the recipient with a maintenance immunosuppressive regimen;
  (f) providing an allogeneic cultured postnatal thymus tissue-derived product, wherein the allogeneic cultured postnatal thymus tissue-derived product is obtained from suitable thymus tissue of the solid organ donor; wherein the donor thymus tissue is subjected to a conditioning regimen for a period up to 21 days (for example, a conditioning regimen of about 6 days to about 21 days) to produce allogeneic cultured postnatal thymus tissue-derived product; further wherein the conditioning regimen for the donor thymus tissue comprises aseptically processing the donor thymus tissue in a thymus organ medium to produce partially T-cell depleted donor thymus tissue slices; wherein the partially T-cell depleted donor thymus tissue slices show areas positive for cytokeratin (CK) (using antibody AE1/AE3) scattered throughout the tissue, the presence of at least one Hassall body, CK14 staining scattered throughout the tissue and presence of intact nuclei; and
  (g) implanting the allogeneic cultured postnatal thymus tissue-derived product into the recipient after about 6 to about 21 days of conditioning regimen, wherein the dosage of thymus tissue slices is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient.

In an embodiment, a method of promoting donor-specific tolerance to an allogeneic heart transplant in a recipient in need of a deceased donor heart is provided. The method comprises the following steps:
  (a) obtaining a suitable human heart from a deceased donor for transplantation;
  (b) removing the deceased donor thymus at the same time as the heart is obtained for conditioning into allogeneic cultured postnatal thymus tissue-derived product; wherein the donor thymus matches the HLA alleles in the donor transplanted organ;
  (c) treating the recipient with an induction immunosuppressive regimen comprising one or more immunosuppressive agents to deplete and/or suppress the recipient's T cells wherein the one or more immunosuppressive agents comprises glucocorticoids administered at the induction of anesthesia and after reperfusion;
(d) transplanting the heart into the recipient;
(e) treating the recipient with a maintenance immunosuppressive regimen comprising one or more immunosuppressive agents selected from the group consisting of a calcineurin inhibitor, an inosine monophosphate dehydrogenase inhibitor and an anti-thymocyte globulin for a period of time sufficient to prevent or suppress transplant rejection of the heart;
(f) between day 6 and 21 providing an allogeneic cultured postnatal thymus tissue-derived product, wherein the allogeneic cultured postnatal thymus tissue-derived product is obtained from the donor thymus tissue, wherein the donor thymus tissue is subjected to a conditioning regimen for a period of from about 6 to about 21 days to produce allogeneic cultured postnatal thymus tissue-derived product; further wherein the conditioning regimen for the donor thymus tissue comprises aseptically processing the donor thymus tissue in a thymus organ medium to produce partially T-cell depleted donor thymus tissue slices; wherein the partially T-cell depleted donor thymus tissue slices show areas positive for keratin AE1/AE3 scattered throughout the tissue, the presence of at least one Hassall body, CK14 staining scattered throughout the tissue and presence of intact nuclei;
(g) implanting a portion of the allogeneic cultured postnatal thymus tissue-derived product into the recipient, wherein the dosage of thymus tissue slices is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient; and
(h) cryopreserving a portion of the allogeneic cultured postnatal thymus tissue-derived product to be used in the recipient in the event that there is an early rejection episode requiring high doses of steroids that would damage the portion of allogeneic cultured postnatal thymus tissue-derived product that was implanted in step (g).

In an embodiment, a method of promoting donor-specific tolerance to an allogeneic heart transplant in a recipient in need of a deceased donor heart is provided. The method comprises the following steps:
(a) obtaining a suitable solid human heart from a deceased donor for transplantation;
(b) removing the deceased donor thymus at the same time as the heart is obtained for conditioning into allogeneic cultured postnatal thymus tissue-derived product; wherein the donor thymus matches the HLA alleles in the donor transplanted organ;
(c) treating the recipient with an induction immunosuppressive regimen comprising one or more immunosuppressive agents to deplete and/or suppress the recipient's T cells wherein the one or more immunosuppressive agents comprises glucocorticoids administered at the induction of anesthesia and after reperfusion;
(d) surgically removing the heart and thymus of the recipient;
(e) transplanting the donor human heart into the recipient;
(f) treating the recipient with a maintenance immunosuppressive regimen comprising one or more immunosuppressive agents selected from the group consisting of a calcineurin inhibitor, an inosine monophosphate dehydrogenase inhibitor and an anti-thymocyte globulin for a period of time sufficient to prevent or suppress transplant rejection of the heart;
wherein, if the post-operative condition of the recipient is too unstable to allow weaning of the glucocorticoids and safely implanting the allogeneic cultured postnatal thymus tissue-derived product in the recipient, the allogeneic cultured postnatal thymus tissue-derived product is cryopreserved to be implanted at a later time when the recipient is stable, wherein the donor thymus tissue is subjected to a conditioning regimen for a period of from about 6 to about 21 days to produce allogeneic cultured postnatal thymus tissue-derived product; further wherein the conditioning regimen for the donor thymus tissue comprises aseptically processing the donor thymus tissue in a thymus organ medium to produce partially T-cell depleted donor thymus tissue slices; wherein the partially T-cell depleted donor thymus tissue slices show areas positive for keratin AE1/AE3 scattered throughout the tissue, the presence of at least one Hassall body, CK14 staining scattered throughout the tissue and presence of intact nuclei;
(h) implanting a portion of the allogeneic cultured postnatal thymus tissue-derived product into the recipient after the patient is stable, wherein the dosage of thymus tissue slices is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient; and
(i) cryopreserving a portion of the allogeneic cultured postnatal thymus tissue-derived product to be used in the recipient in the event that there is a rejection episode requiring high doses of steroids that would damage the portion of allogeneic cultured postnatal thymus tissue-derived product that was implanted in step (h).

In another aspect of the present disclosure, there is provided a method for promoting donor-specific tolerance to an allogeneic solid organ transplant obtained from a living human donor, in a human recipient in need of a solid organ transplant, the method comprising the steps of:
(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing a suitable solid organ from a living human donor;
(d) transplanting the solid organ into the recipient;
(e) treating the recipient with a maintenance immunosuppressive regimen;
(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product was processed from thymus tissue from a thymus donor expressing HLA alleles matched to HLA alleles in the recipient that are not present in the solid organ transplant; wherein the donor thymus tissue was subjected to a conditioning regimen for a period from about 6 days to about 21 days; further wherein the conditioning regimen for the donor thymus tissue comprises aseptically processing the donor thymus tissue in a thymus organ medium to produce partially T-cell depleted thymus tissue slices, wherein the thymus tissue slices show areas positive for keratin AE1/AE3 scattered throughout the tissue, the presence of at least one Hassall body, CK14 staining scattered throughout the tissue and presence of intact nuclei upon completion of the conditioning regimen;

(g) thawing the cryopreserved allogeneic cultured postnatal thymus tissue-derived product; and (h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient.

A fourth aspect of the present disclosure provides a method for promoting donor-specific tolerance to an allogeneic solid organ transplant obtained from a deceased human donor, in a human recipient in need of a solid organ transplant, the method comprising the steps of:

(a) removal of the thymus of the recipient;

(b) treating the recipient with an induction immunosuppressive regimen comprising one or more immunosuppressive agent to deplete the recipient's T cells and/or to suppress the recipient's T cells from rejecting the transplanted solid organ;

(c) providing a suitable solid organ from a living human donor;

(d) transplanting the solid organ into the recipient;

(e) treating the recipient with a maintenance immunosuppressive regimen;

(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product is processed from thymus tissue from a thymus donor expressing HLA alleles matched to HLA alleles in the recipient that are not present in the solid organ transplant; wherein the donor thymus tissue was subjected to a conditioning regimen for a period from about 6 days to about 21 days; further wherein the conditioning regimen for the donor thymus tissue comprises aseptically processing the donor thymus tissue in a thymus organ medium to produce partially T-cell depleted thymus tissue slices, wherein the thymus tissue slices show areas positive for keratin AE1/AE3 scattered throughout the tissue, the presence of at least one Hassall body, CK14 staining scattered throughout the tissue and presence of intact nuclei upon completion of the conditioning regimen;

(g) thawing the cryopreserved allogeneic cultured postnatal thymus tissue-derived product; and (h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient.

In an embodiment of the foregoing aspects of the present disclosure, the allogeneic cultured postnatal thymus tissue-derived product, wherein the thymus, on the day of harvest, demonstrates that >50% of areas are positive for keratin in a lacy staining pattern, that Hassall bodies are present, that CK14 stains in a lacy pattern, and that >90% of nuclei are intact.

In an aspect of the present disclosure there is provided an allogeneic cultured postnatal thymus tissue-derived product for implantation into a subject undergoing a solid organ transplant prepared by obtaining suitable thymus tissue from a donor wherein the donor thymus tissue is subjected to a conditioning regimen for a period up to 21 days (for example, a conditioning regimen of about 6 days to about 21 days); further wherein the conditioning regimen for the donor thymus tissue comprises aseptically processing the donor thymus tissue in a thymus organ medium to produce partially T-cell depleted donor thymus tissue slices; wherein the donor thymus tissue slices show, between days 5 and 9 post-harvest, areas positive for keratin AE1/AE3 scattered throughout the tissue, the presence of at least one Hassall body, CK14 staining scattered throughout the tissue and presence of intact nuclei; recovering the partially T-cell depleted donor thymus tissue slices as allogeneic cultured postnatal thymus tissue-derived product.

In an embodiment of the foregoing aspects of the present disclosure, the thymus, on the day of harvest from the donor, demonstrates that >50% of areas are positive for keratin in a lacy staining pattern, that Hassall bodies are present, that CK14 stains in a lacy pattern, and that >90% of nuclei are intact.

In an embodiment of the foregoing aspects of the present disclosure, the allogeneic cultured postnatal thymus tissue-derived product is cryopreserved.

In an embodiment, the cryopreserved allogeneic cultured postnatal thymus tissue-derived product is maintained in liquid nitrogen for future use.

In another embodiment, the cryopreserved allogeneic cultured postnatal thymus tissue-derived product is maintained in a cryopreserved tissue bank.

In an embodiment, the allogeneic cultured postnatal thymus tissue-derived product is prepared from suitable thymus tissue from a donor comprising HLA alleles matched to HLA alleles in a proposed recipient that are not present in the solid organ transplant.

In an embodiment the HLA alleles are: HLA-A, HLA-B, HLA-C, HLA-DRB1, HLA-DQB1, HLA-DRB3, HLA-DRB4, HLA-DRB5, HLA-DQA1, HLA-DPB1, and HLA-DPA1.

In an aspect of the present disclosure there is provided a cryopreserved allogeneic cultured postnatal thymus tissue-derived product, prepared by method comprising the steps of:

(a) obtaining suitable thymus tissue from a donor;

(b) typing HLA alleles: HLA-A, HLA-B, HLA-C, HLA-DRB1, HLA-DQB1, HLA-DRB3, HLA-DRB4, HLA-DRB5, HLA-DQA1, HLA-DPB1, HLA-DPA1;

(c) subjecting the thymus tissue to a conditioning regimen for a period from about 6 days to about 21 days; wherein the conditioning regimen for the donor thymus tissue comprises aseptically processing the donor thymus tissue in a thymus organ medium to produce partially T-cell depleted donor thymus tissue slices; further wherein the donor thymus tissue slices show, on days 6 to 21, areas positive for keratin AE1/AE3 scattered throughout the tissue, the presence of at least one Hassall body, CK14 staining scattered throughout the tissue and presence of intact nuclei upon completion of the conditioning regimen;

(d) harvesting the partially T-cell depleted donor thymus tissue slices as allogeneic cultured postnatal thymus tissue-derived product;

(e) cryopreserving the allogeneic cultured postnatal thymus tissue-derived product in liquid nitrogen; and (f) maintaining the cryopreserved allogeneic cultured postnatal thymus tissue-derived product in liquid nitrogen in a cryopreserved allogeneic cultured postnatal thymus tissue-derived product bank.

In an embodiment, the thymus, on the day of harvest, demonstrates that >50% of areas are positive for keratin in a lacy staining pattern, that Hassall bodies are present, that CK14 stains in a lacy pattern, and that >90% of nuclei are intact.

In an embodiment, the cryopreserved allogeneic cultured postnatal thymus tissue-derived product in liquid nitrogen is held for future use by the recipient.

In an aspect of the present disclosure, there is provided a method of preparing the donor thymus for implanting into a recipient subject. Such methods comprise, consist of, or consist essentially of culturing the donor thymus for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, or up to about 21 days, and then surgically placing the cultured thymus tissue into the recipient, as further described herein. A culture period between about 6 and about 21 days results in good function. For successful transplantation of cryopreserved thymus tissue, the tissue is typically cultured for about 6 to about 21 days, and then cryopreserved.

In an aspect of the present disclosure, there is provided an allogeneic cultured postnatal thymus tissue-derived product (CTT; RVT-802) for implantation into a subject undergoing a solid organ transplant manufactured by the method of subjecting thymus tissue from a suitable donor to a conditioning regimen for a period up to 21 days (for example, a conditioning regimen of about 6 days to about 21 days); wherein the conditioning regimen for the allogeneic cultured postnatal thymus tissue-derived product comprises aseptically processing the donor thymus tissue in a thymus organ medium to produce partially T-cell depleted thymus tissue slices, wherein the thymus tissue slices show areas positive for keratin AE/AE3 scattered throughout the tissue, the presence of at least one Hassall body, CK14 staining scattered throughout the tissue and presence of intact nuclei.

In an embodiment, the donor thymus, on the day of harvest, demonstrates that >50% of areas are positive for keratin in a lacy staining pattern, that Hassall bodies are present, that CK14 stains in a lacy pattern, and that >90% of nuclei are intact.

In an embodiment of the foregoing aspects and embodiments, the recipient's thymus is obtained by surgery.

In an embodiment of the foregoing aspects and embodiments, the recipient's thymus is obtained by robotic surgery.

In an embodiment of the foregoing aspects and embodiments, the recipient's thymus is obtained by thoracoscopic surgery.

In an embodiment of the foregoing aspects and embodiments, the solid organ is a portion of a whole organ.

In an embodiment of the foregoing aspects and embodiments, the method of the first to fourth aspects further comprises the step of cryopreserving peripheral blood mononuclear cells from the deceased donor for future use in a mixed lymphocyte reaction to demonstrate cellular tolerance.

In an embodiment of the foregoing aspects and embodiments, the mixed lymphocyte reaction to demonstrate cellular tolerance is performed using peripheral blood mononuclear cells from the recipient and cryopreserved peripheral blood mononuclear cells from the donor following the implantation of allogeneic cultured postnatal thymus tissue-derived product in accordance the implantation procedure of CTT in this specification.

In an embodiment of the foregoing aspects and embodiments, the mixed lymphocyte reaction to demonstrate cellular tolerance is performed with peripheral blood mononuclear cells from the recipient and cryopreserved peripheral blood mononuclear cells from the donor about 6 to 12 months following the implantation of allogeneic cultured postnatal thymus tissue-derived product.

In an embodiment of the foregoing aspects and embodiments, the mixed lymphocyte reaction to demonstrate cellular tolerance is performed with peripheral blood mononuclear cells from the recipient and cryopreserved peripheral blood mononuclear cells from the donor after naïve T cells constitute about 10% of total T cells in the recipient.

In an embodiment of the foregoing aspects and embodiments, the implanted allogeneic cultured postnatal thymus tissue-derived product induces thymopoiesis in the subject within 12 months following the implantation of allogeneic cultured postnatal thymus tissue-derived product.

In an embodiment of the foregoing aspects and embodiments, the development of tolerance is determined by a mixed lymphocyte reaction performed with cryopreserved peripheral blood mononuclear cells from the deceased donor and T cells from the recipient.

In an embodiment of the foregoing aspects and embodiments, humoral tolerance is determined by the development of humoral immunity and the absence of donor reactive antibodies.

In an embodiment of the foregoing aspects and embodiments, the solid organ transplant is a heart transplant, a kidney transplant, a liver transplant, a lung transplant, a heart/lung transplant, a pancreas transplant, an intestine transplant, a stomach transplant, an abdominal wall transplant, a craniofacial transplant, a scalp transplant, a penile transplant, a uterus transplant, a unilateral or bilateral upper limb transplant, a unilateral vascularized composite allograft, or combination thereof.

In an embodiment of the foregoing aspects and embodiments, the method further comprises evaluating the recipient for HLA-Class I and HLA-Class II panel reactive antibodies ("PRA") score prior to transplanting the solid organ.

In an embodiment of the foregoing aspects and embodiments, the solid organ transplant is a heart transplant.

In an embodiment of the foregoing aspects and embodiments, the solid organ transplant is a pediatric heart transplant.

In an embodiment of the foregoing aspects and embodiments, the solid organ transplant is an adult heart transplant.

In an embodiment of the foregoing aspects and embodiments, the method further comprises evaluating the recipient for HLA-Class I and HLA-Class II panel reactive antibodies ("PRA") score prior to transplanting the solid organ.

In an embodiment of the foregoing aspects and embodiments, recipients with HLA antibodies are cross-matched with potential donors.

In an embodiment of the foregoing aspects and embodiments, recipients with HLA antibodies are virtually cross-matched with UNET.

In an embodiment of the foregoing aspects and embodiments, if a PRA score of >20% virtual cross-match is recorded, the method will further comprise the step of performing plasmapheresis in the operating room at the time of solid organ transplant in the recipient.

In an embodiment of the foregoing aspects and embodiments, if a PRA score of >70% virtual cross-match is recorded, the method will further comprise the step of performing an actual prospective donor cross-match and performing plasmapheresis in the operating room at the time of solid organ transplant in the recipient. Typically, transplants are not performed under these circumstance because of poor success rates.

In an embodiment of the foregoing aspects and embodiments, the method further comprises the step of evaluating recipients with HLA antibodies by cross-matching virtually with UNET.

In an embodiment of the foregoing aspects and embodiments, the method further comprises performing plasmapheresis in the operating room at the time of solid organ transplant in the recipient if the HLA panel reactive antibodies have a score >20%.

In an embodiment of the foregoing aspects and embodiments, the method further comprises performing an actual prospective donor cross-match and performing plasmapheresis in the operating room at the time of solid organ transplant in the recipient if the HLA panel reactive antibodies have a score >70%.

In an embodiment of the foregoing aspects and embodiments, the solid organ is HLA-matched, in for instance, from a living related donor of the kidney, partial liver and partial intestine transplants to the recipient.

In an embodiment of the foregoing aspects and embodiments, the solid organ is HLA-mismatched.

In an embodiment of the foregoing aspects and embodiments, the solid organ is HLA matched. In another embodiment, the HLA match is determined by typing HLA alleles: HLA-A, HLA-B, HLA-C, HLA-DRB1, HLA-DQB1, HLA-DRB3, HLA-DRB4, HLA-DRB5, HLA-DQA1, HLA-DPB1, HLA-DPA1 in the donor and the recipient.

In an embodiment of the foregoing aspects and embodiments, the solid organ transplants are ABO compatible.

In an embodiment of the foregoing aspects and embodiments, the solid organ is HLA-mismatched. In an embodiment, HLA-mismatched is determined by typing HLA-A, HLA-B, HLA-C, HLA-DRB1, HLA-DQB1, HLA-DQA1, HLA-DPB1, HLA-DPA1 in the donor and the recipient.

In an embodiment of the foregoing aspects and embodiments, the cultured thymus tissue slices are surgically implanted into the quadriceps thigh muscle of the subject.

In an embodiment of the foregoing aspects and embodiments, the cultured thymus tissue slices are surgically implanted into the body of the subject in an area other than the quadriceps.

In an embodiment of the foregoing aspects and embodiments, a portion of the allogeneic cultured postnatal thymus tissue-derived product is surgically implanted into the quadriceps thigh muscle of the recipient.

In an embodiment of the foregoing aspects and embodiments, wherein the remaining portion of the allogeneic cultured postnatal thymus tissue-derived product is cryopreserved in liquid nitrogen for future transplantation.

In an embodiment of the foregoing aspects and embodiments, the conditioning regimen is for a period of about 6 days to about 21 days.

In an embodiment of the foregoing aspects and embodiments, the conditioning period of the donor thymus tissue is about 5 days to about 21 days, or about 5 days, or about 6 days, or about 7 days, or about 8 days, or about 9 days, or about 10 days, or about 11 days, or about 12 days, or about 13 days, or about 14 days, or about 15 days, or about 16 days, or about 17 days, or about 18 days, or about 19 days, or about 20 days, or about 21 days.

It will be appreciated by the person of ordinary skill in the art that there are numerous potential induction immunosuppressive regimens and maintenance immunosuppressive regimens known in the art, and that a suitable induction and maintenance immunosuppressive agent may be selected by the person of skill in the art without undue burden. The following illustrative induction immunosuppressive regimens and maintenance immunosuppressive regimens are exemplary of the practice of the methods of the first to the fourth aspects of the invention and support the inventions as claimed.

In an embodiment of the foregoing aspects and embodiments, the induction immunosuppressive regiment comprises an induction immunosuppressive agent selected from the group of glucocorticoid, anti-thymocyte globulin (rabbit), anti-thymocyte globulin (equine), and alemtuzumab.

In an embodiment of the foregoing aspects and embodiments, the ATG is antithymocyte globulin (rabbit).

In an embodiment of the foregoing aspects and embodiments, the induction immunosuppressive regimen comprises administration of a glucocorticoid. In an embodiment, the glucocorticoid comprises methylprednisolone. In another embodiment, the glucocorticoid is methylprednisolone sodium succinate. In a further embodiment, methylprednisolone sodium succinate is administered intravenously at no greater than 4 mg/kg/day.

In an embodiment of the foregoing aspects and embodiments, the induction immunosuppressive regimen comprises rabbit-derived anti-thymocyte globulin. In another embodiment, the rabbit-derived anti-thymocyte globulin is administered intravenously in a dose of about 1.5 mg/kg. In a further embodiment, the anti-thymocyte globulin is administered daily for four days. In another embodiment the ATG is equine derived ATG.

In an embodiment of the foregoing aspects and embodiments, the induction immunosuppressive regimen comprises basiliximab. In another embodiment, the basiliximab is administered at a dose of 10 mg intravenously for recipients less than 35 kg in body weight. In another embodiment, the basiliximab is administered at a dose of 20 mg intravenously for recipients more than 35 kg in body weight.

In an embodiment of the foregoing aspects and embodiments, the second immunosuppressive regimen comprises one or more immunosuppressive agent selected from the group consisting of a glucocorticoid, calcineurin inhibitor, an inosine monophosphate dehydrogenase inhibitor, azathioprine, and anti-thymocyte globulin ("ATG").

In an embodiment of the foregoing aspects and embodiments, the immunosuppressive agent of the maintenance immunosuppressive regiment is anti-thymocyte globulin (ATG).

In an embodiment of the foregoing aspects and embodiments, the ATG is administered intravenously at a dose of about 1.5 mg/kg for a period of 3-14 days starting with administration in the operating room.

In an embodiment of the foregoing aspects and embodiments, the anti-thymocyte globulin is administered daily for 3-14 days at about 15 mg/kg/day by intravenous administration.

In an embodiment of the foregoing aspects and embodiments, the first immunosuppressive regimen comprises alemtuzumab.

In an embodiment of the foregoing aspects and embodiments, the alemtuzumab is administered at a dose of about 0.25 mg/kg for 4 days intravenously for recipients less than 35 kg in body weight. In another, embodiment the alemtuzumab is administered at a dose of about 3 to 20 mg for 4 days intravenously for recipients more than 35 kg in body weight.

In an embodiment of the foregoing aspects and embodiments, the second immunosuppressive regimen comprises one or more immunosuppressive agent selected from the group consisting of a calcineurin inhibitor, and inosine monophosphate dehydrogenase inhibitor, or azathioprine.

In an embodiment of the foregoing aspects and embodiments, the immunosuppressive agent of the maintenance immunosuppressive regimen the immunosuppressive agent is a calcineurin inhibitor.

In an embodiment, the immunosuppressive agent of the maintenance immunosuppressive regimen the immunosuppressive agent is an inosine monophosphate dehydrogenase inhibitor.

In an embodiment of the foregoing aspects and embodiments, the immunosuppressive regimen comprises an inosine monophosphate dehydrogenase inhibitor, for example, mycophenolate mofetil. In an embodiment, mycophenolate mofetil is administered intravenously in a dose of about 15 to about 25 mg/kg. In an embodiment, the mycophenolate mofetil is administered intravenously two to three times a day.

In an embodiment of the foregoing aspects and embodiments, inosine monophosphate dehydrogenase inhibitor is mycophenolic acid. In another embodiment, the mycophenolic acid is administered at a dose of about 25 to about 50 mg/kg in 2 or 3 divided doses.

In an embodiment of the foregoing aspects and embodiments, the mycophenolic acid is administered at a dose of about for children about 400 mg/m$^2$/dose twice daily with a maximum dose 720 mg, or BSA 1.19 to 1.59 m$^2$ about 540 mg twice daily, or for BSA>1.58 m$^2$ about 720 mg twice daily.

In an embodiment of the foregoing aspects and embodiments, the mycophenolate mofetil is administered for children at a dose of about 15 to about 25 mg/kg/dose twice a day or for adults about 1500 mg orally or intravenously twice daily and adjusted for a WBC of >3500.

In an embodiment of the foregoing aspects and embodiments, the second immunosuppressive regimen may further comprise a glucocorticoid selected from the group consisting of methylprednisolone, prednisone and prednisolone. In an embodiment, the dose of glucocorticoid is kept below 4 mg/kg/day.

In an embodiment of the foregoing aspects and embodiments, the glucocorticoid is administered in a tapered dosage reduction, as described elsewhere in the present disclosure.

In an embodiment of the foregoing aspects and embodiments, the calcineurin inhibitor is tacrolimus. In another embodiment, the calcineurin inhibitor is cyclosporine A.

In an embodiment of the foregoing aspects and embodiments, the administration of the second immunosuppressant regimen is weaned after naïve T cells reach 10% of total T cells. In yet another embodiment, the second immunosuppressant regimen is weaned after implantation of allogeneic cultured postnatal thymus tissue-derived product.

To evaluate how thymus production and/or release of chemokines and other soluble molecules may regulate these processes of cellular migration changes as thymocytes are depleted during preparation of donor thymus tissue for CTT, we screened conditioned media from human thymus organ cultures for the presence of 200 soluble molecules using antibody microarrays.

Expression of selected potentially mechanistically important candidate molecules was validated using additional thymic organ cultures and compared with a panel of well-characterized human thymus tissues obtained from donors ranging from age 5 days to 78 years. Through this analysis we identified certain potentially important biomarkers of thymocyte content.

A potentially important biomarker for thymocyte content of cultured thymus slices is L-selectin. Another important biomarker for thymic epithelial cell viability and function relies on the secretion of the chemokine CCL21 6Ckine.

Numerous additional potential biomarkers are set forth in FIGS. 50 and 56. Of particular interest are the biomarkers set forth on FIG. 50, namely L-selectin, CCL21, CXCL16, M-CSF, galectin-7, CCL11, IL-16 and CXCL12. Also, of particular interest, are biomarkers set forth on FIG. 56, particularly biomarkers having a P-value of less than 0.05. These biomarkers would include: L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, CCL20 (MIP-3a), IL-2Ra, ICAM-3, LIGHT, IGFBP-1, BCMA, EGF R, uPAR (CD87), MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1.

The data reported in the Examples and in the literature support that the following biomarkers are indicative of TEC function: CCL21 (6Ckine, CXCL16, Osteopontin (OPN), CCL11, uPAR (CD87) and CXCL12. CXCL16: This chemokine has been shown to be produced by TECs (Bunting 2011).

Osteopontin (OPN; encoded by the SPP1 gene): This cytokine is increased during thymic stress and increased levels are associated with thymic atrophy (decrease in thymocyte number), decrease thymocyte numbers is a desirable state for cultured thymus (Wang 2009; Gridley 2013). OPN is required to make corticosteroids, which have been well-established to induce thymocyte apoptosis.

CCL11 (Eotaxin): This chemokine is made by medullary TE (Bunting 2011). It was initially named for its ability to attract eosinophils and we have shown that eosinophil infiltrates may be prominent in thymus tissues with active thymopoiesis (Flores 1999). However, eotaxin has also been shown to serve as a chemoattractant for both double-positive (DP) and single-positive (SP) human thymocytes (Bunting 2011).

uPAR (CD87; encoded by the PLAUR gene): Urokinase receptor, also known as urokinase plasminogen activator receptor, is expressed in both soluble and membrane-bound forms based on alternative splicing. It aids in local degradation of extracellular matrix. It has been shown to be expressed in human thymus and interestingly, by migrating epidermal keratinocytes (EK) at the edge of a wound (Loughner 2016). This latter characteristic is most interesting since TE cells mirror EK in expression of many genes (Patel 1995). Progressive increases in secretion by cultured thymus slices may reflect the activation of TE and thus be a marker for TE outgrowth following implantation.

CXCL12 (SDF-1a): This chemokine had an expression pattern that was different than the other analytes, in that it was only detected during the final ⅓ of the culturing period. First detectable on days 13-15, it rose linearly (in the in plots) to a much higher level over the next week in culture. CXCL12 has been documented to be produced by subcapsular cortical and medullary TE (Bunting 2011; Hernandez-Lopez 2002; Zaitseva 2002), but also can be made by thymic fibroblasts and endothelial cells present within the thymus. CXCL12 has been shown to recruit B cells and antigen-presenting cells (APC) to the thymus (Weiss 2003), which is expected to be important in generation of full thymic function. It is also involved in localization of thymocyte subsets within the thymus and it enhances thymocyte proliferation to IL-7 (Hernandez-Lopez 2002). Of note, antibodies that neutralize CXCL12 have been shown to decrease thymopoiesis in human thymus organ cultures in vitro and addition of CXCL12 increases thymopoiesis in these cultures (Hernandez-Lopez 2002).

Additional biomarkers that may reflect thymocyte presence include L-selectin. This molecule is expressed at high levels on developing and naïve T cells. It is released from the cell surface when thymocytes are cultured. Usually rapidly re-expressed when shed by healthy cells in vivo (Fitzhugh 2008), progressively decreased levels of shedding likely reflects the progressive loss of thymocyte viability because they normally do not re-express this molecule on their surface during culture (A. Macintyre, unpublished data).

Another biomarker that may reflect thymocyte presence is IL-16. This cytokine was included since its pattern (as described below) corresponded with that hypothesized for thymocytes. This biomarker is known to be made by lymphocytes.

Yet another biomarker that may reflect thymocyte presence is MIF. This chemokine was included since its pattern corresponded with that hypothesized for thymocytes.

Still another biomarker that may reflect thymocyte presence is CCL20 (MIP-3a): This chemokine was included since its pattern corresponded with that hypothesized for thymocytes.

Another biomarker that may reflect thymocyte presence is IGFBP-1. IGFBP2-6 are known to be expressed by thymic epithelium, which does not express IGFBP-1 (Gosteli-Peter 1994; Ketcha 1999).

Other biomarkers that showed initially high levels that then decreased with time, a hypothesized characteristic of thymocyte-derived biomarkers, which, based on the data in the Examples and the literature, correlate with the presence of viable thymocytes: L-selectin, IL-16, MIF. CCL20 (MIP-3a), and IGFBP-1. Decreases in these biomarkers over time is consistent with our more qualitative observations that T cells are depleted while the thymus tissue slices are in culture.

CCL21 has been shown to be expressed by thymic epithelial cells (Lkhagvasuren et al. 2013) and to be functionally important due to its chemotactic activity for thymocyte precursors (Liu et al. 2005), as well as for thymocyte migration within the thymus (Hu et al. 2015). This chemotactic property for thymocytes may be a critical determinant for successful immune reconstitution of the recipients following implantation of cultured thymus tissue, as described herein.

The results reported here should also be broadly applicable toward understanding mechanisms of age-related thymus involution as well as for understanding mechanisms involved in immune reconstitution of athymic recipients via implantation of cultured thymus tissue.

In the Examples and on FIG. 56, it is reported that at least 127 different analytes can be detected in spent/conditioned culture medium obtained from cultured human thymus tissue slices and that 42 of these analytes show progressive increases or decreases with culture time. Of these analytes, the amount of soluble L-selectin released was validated as a non-destructive marker for residual content of viable thymocytes in cultured thymus. Expression and/or secretion of the chemokines CCL21, CXCL16, CXCL12 and CCL11 by thymic epithelium was demonstrated to increase as thymocytes decrease, both during thymus organ culture in vitro and in vivo in unmanipulated thymus tissues obtained from healthy donors across the lifespan. Similarly, the expression or secretion of L-selectin, M-CSF, galectin-7 and IL-16 were observed to decrease in the thymus organ culturing medium during the course of the culturing process. These findings are directly relevant for understanding mechanisms of age-related thymus involution, as well as qualities of human thymus tissues that facilitate immune reconstitution. Parallels between the changes seen during culture of infant thymus and those associated with aging suggest that cultured human infant thymus also provides a model that may be useful for studying mechanisms that mediate age-related thymic involution.

To our knowledge, this is the first large screen of soluble molecules produced and released or secreted by the human thymus as thymocytes are depleted. Many of the 42 analytes that were found to have significantly increased or decreased release into media as cultures progressed are cytokines and/or chemokines that have previously been shown to be produced by cell types present within the thymus. Others are novel in this respect. While the experimental work focused primarily on release of L-selectin as a marker for thymocyte content and on CCL21 as a marker for TEC viability and function, the data reported from the antibody microarray screening can be used to identify additional analytes from FIG. 56 that can identify novel pathways that govern acute atrophy, chronic involution and/or regeneration of human thymus in vivo. These would include in particular the biomarkers set forth on FIG. 50. For example, some analytes that met pre-specified selection criteria were not considered further since they are known to be expressed or released during cell injury and/or hypoxic stress and their levels may reflect culture-associated tissue damage and inflammatory responses rather than thymus-specific biology. Additional biomarkers noted in the culture supernatant from cultured thymus tissue slices include CC25(TECK), osteopontin (OPN), uPAR (CD87), MIF, CCL20 (MIP-3a) and IGFBP-1. Study of additional analytes whose release may reflect the viability and/or activation of critical cell types in human thymus may lead to clinically and mechanistically important insights, particularly regarding responses to thymocyte loss.

CCL25 (TECK): Although detectable levels of TECK were only present in a few samples of supernatant late in the culture period of 2 of the 3 thymus cultures examined, it is of interest since this chemokine has been shown to be chemotactic for thymocytes (Liu 2005). It is known to be expressed by thymic dendritic cells (DC) and by both FoxN1+ and FoxN1− TE cells (Bunting 2011). However, its activity does not appear to be critical for thymus development based on studies of mice in which CCR9, the sole receptor for this chemokine, was deleted (Wurbel 2001).

Based on the microarray studies, it was determined that soluble L-selectin levels in conditioned culture media could serve as a potential biomarker of thymocyte presence and viability in cultured thymus slices. This is very plausible, since expression of L-selectin is limited to hematopoietic cells and is shed constitutively as well as during migration (Hafezi-Moghadam et al. 2001), then is usually rapidly re-expressed by healthy cells in vivo (Fitzhugh et al. 2008).

The experimental results show that the loss of L-selectin release temporally correlates with thymocyte death, as indicated by loss of thymocyte membrane integrity via histology and CD3 immunohistochemistry, as well as lack of characteristic thymocyte proliferation by Ki-67 immunohistochemistry.

Being able to non-destructively monitor thymocyte content of cultured human thymus slices is important to identify the most appropriate harvest time points for experimental studies. This can also provide clinically important information, since opening developmental niches for colonization by recipient thymocytes through depletion of donor thymocytes is believed to be critical for successful immune reconstitution of athymic patients via thymic implantation. Taken together, the studies presented in the Examples suggest that decreased L-selectin release is a useful biomarker for monitoring thymocyte depletion in cultured thymus slices.

Biomarkers that reflect the presence and function of thymic epithelium also can provide critical mechanistic information. Studies set forth in the Examples focused on CCL21, since the microarray screen indicated that this chemokine began to be secreted into the media at high levels soon after the start of culturing. CCL21 was previously shown to be expressed by thymic epithelium and to be chemotactic for thymocytes and their precursors (Liu et al. 2005). Our studies showed that expression of CCL21 could also be readily quantitated by enzyme immunoassay. Immunohistochemistry confirmed CCL21 expression by TECs in cultured as well as non-cultured thymus, with strongest expression in the medullary and subcapsular cortical thymic epithelium.

It is also important to note that CCL21 immunoreactivity of thymus slices did not necessarily increase as CCL21 secretion increased during culture. This may reflect that the additional CCL21 produced is secreted rather than being retained in the cytoplasm where it can be detected via immunohistochemistry. CCL21 is a transcriptionally regulated, high turnover molecule with a short half-life (Dudal et al. 2015), so the positive immunohistochemical reactivity observed represents cells that are actively producing this chemokine. That production of CCL21 markedly increases as thymocytes decrease in both cultured thymus and non-manipulated aging thymus suggests that thymic epithelial cells can sense thymocyte content and react in a homeostatic attempt to counteract thymocyte loss.

The identification of CCL21 as a secreted biomarker that reflects the viability and function of TECs is also important clinically with regards to thymus transplantation. Most established methods that can assess the quality of tissue to be implanted (e.g. flow cytometry, immunohistochemistry, gene expression analysis) destroy the samples during analysis. In addition to decreasing the amount of tissue available for eventual implantation, such results are subject to sampling error since the slice(s) tested is not part of the slices that are eventually implanted. As shown in FIG. 53C, assay of pooled spent media for CCL21 can integrate across all slices in a lot derived from any given thymus donor, providing a non-destructive picture of overall lot quality.

The chemokine CXCL12 (SDF-1a) differed from most other analytes in the screening, in that it became detectable in conditioned media relatively late during the culturing period (FIG. 50H). First detectable on days 13-15, it rose linearly (in the in plots) to a much higher level over the next week in culture. CXCL12 has been documented to be produced by subcapsular cortical and medullary TECs, but may also be made by thymic fibroblasts and endothelial cells present within the thymus (Bunting et al. 2011; Hernandez-Lopez et al. 2002; Zaitseva et al. 2002). CXCL12 recruits B cells and antigen-presenting cells to the thymus (Weiss et al. 2013), which is expected to be important in generation of full thymic function. CXCL12 is also involved in localization of thymocyte subsets within the thymus and it enhances thymocyte proliferation to IL-7 (Hernandez-Lopez et al. 2002). Of note, antibodies that neutralize CXCL12 have been shown to decrease thymopoiesis in human thymus organ cultures in vitro and addition of CXCL12 increases thymopoiesis in these cultures (Hernandez-Lopez et al. 2002). The later timing of CXCL12 secretion during in vitro thymic organ cultures shown here, combined with its increased expression in vivo in thymus derived from donors >18 years, compared with younger, suggest that expression of this chemokine is induced by more long-standing depletion of thymocytes than is required to induced secretion of CCL21.

The screening data suggest that other chemokines, including CXCL16 and CCL11, are likely biomarkers for assessing the viability and function of cultured thymus, since they also increase as thymocytes are lost during thymus organ culture. Both CXCL16 and CCL11 have previously been shown to be made by TECs (Bunting et al. 2011).

CCL11 was originally named eotaxin for its ability to attract eosinophils. We previously showed that eosinophil infiltrates may be prominent adjacent to thymus tissues with active thymopoiesis (Flores et al. 1999), although CCL11 levels were not directly measured in those studies. However, CCL11 was subsequently also shown to serve as a chemoattractant for both double-positive and single-positive human thymocytes (Bunting et al. 2011). Evidence for a specific role of CXCL16 in thymopoiesis is less clear.

The studies presented in the Examples validate the use of L-selectin as a biomarker for the presence of viable thymocytes and CCL21 as a biomarker for TEC viability that may also be predictive of efficient immune reconstitution if thymocyte precursors are made available. Production of CCL21 is typically low when thymopoiesis is robust and is markedly induced when thymopoiesis becomes compromised, in both cultured thymus slices and non-cultured thymus tissues from older adults. Interestingly, after normalization to either TEC area or active cortical area, thymus tissues from younger donors (≤18 years) continued to express more CD3epsilon and CD1A mRNAs and less keratin8 (KRT8) and keratin14 (KRT14) mRNAs than thymus from older adults. This suggests that thymopoiesis and TEC maintenance may potentially be more efficient in these younger donors. Further, for both normalization methods, the production of CCL21 and CXCL12 are markedly increased for tissues derived from donors >18 years, a timeframe when TEC content and active thymopoiesis is decreased compared to younger donors. That expression of CCL21 and CXCL12 both increase as numbers of thymocytes decrease in both in vitro in thymus organ cultures and in vivo during aging raises the possibility that induction of these chemokines is part of homeostatic mechanisms that attempt to counter the decreased thymocyte numbers through enhanced recruitment of T cell precursors. Increased secretion of thymocyte-attracting chemokines by thymocyte-depleted cultured thymus slices would be expected to enhance their colonization and ability to result in immunoreconstitution, as is observed when such slices are implanted into athymic infant recipients (Markert et al. 2008). In contrast, abundant secretion of CCL21 and CXCL12 may provide less benefit during aging, if the availability of thymocyte precursors or other critical aspects of the thymic microenvironment are limiting.

Together, these studies show that organ cultures of thymus derived from pediatric donors can be used to model at least some aspects of age-related thymic involution in humans, particularly those that are more directly related to loss of thymocytes. However, it is clear that T cell-depleted cultured pediatric thymus must differ substantially from aged adult thymus in other ways, since implantation of T cell-depleted cultured pediatric thymus into athymic recipients results in immune reconstitution and protection from infections, whereas aged adults with involuted thymus are more vulnerable to infections than younger adults with more robust thymus function. Palmer, S, Albergante L, Blackburn C C, Newman T J. Thymic involution and rising disease incidence with age. Proc Natl Acad Sci USA 11colk:1883-1888, 2018.

The results presented here in FIG. 56 provide a rich source of additional molecules and pathways as potential biomarkers to model some aspects of human thymus aging in vitro using cultured infant thymus. This is important, since infant thymus is typically more readily available for research given the need to remove a portion of thymus from most infants to properly expose the operative field for corrective cardiac surgery. Adult thymus tissue is typically less readily available, since it is generally not necessary to remove thymus tissue to provide access for many types of cardiac surgery common in adults. Furthermore, any adult thymus tissue removed is not typically made available for research since it appears less organoid and grossly resembles fat. However, adult thymus tissue would potentially be cultured and used to co-transplant with a solid organ if tolerance is desired in adult solid organ recipients. The biomarkers also are useful in determining the suitability, functionality and viability of allogeneic, cultured postnatal thymus tissue-derived product derived from adult donors.

Thymus production of the thymocyte chemoattractants CCL21, CXCL16, CXCL12 and CCL11 increase as thymocyte content decreases. This suggests that thymocyte loss may activate homeostatic mechanisms that attempt to counteract potential atrophy, although ultimately unsuccessfully in the setting of aging, future studies to more fully elucidate these mechanisms will be useful for understanding and potentially reversing mechanisms that drive age-related thymus involution and may help to enhance thymus-driven immune reconstitution at all ages.

In an aspect of the present disclosure, there is provided a method of producing an allogeneic cultured postnatal thymus tissue-derived product suitable for implantation into a human, comprising the steps of subjecting donor thymus to a conditioning regimen for a period from about 6 to about 21 days; wherein the conditioning regimen for the donor thymus tissue comprises aseptically processing the donor thymus tissue in a thymus organ medium to produce partially T-cell depleted donor thymus tissue slices; further comprising detecting increasing levels of CCL21 in the thymus organ medium during the course of the conditioning regimen; and recovering the partially T-cell depleted donor thymus tissue slices as allogeneic cultured postnatal thymus tissue-derived product suitable for implantation.

In an embodiment of the aspects and embodiments of the present disclosure, the method further comprises the step of cryopreserving the allogeneic cultured postnatal thymus tissue-derived product in liquid nitrogen for future implantation.

In an embodiment of the aspects and embodiments of the present disclosure, the method further comprises detecting decreasing levels of L-selectin in the thymus organ medium during the course of the conditioning regimen.

In an embodiment of the aspects and embodiments of the present disclosure, the method comprises detecting one or more of CCL21, CXCL12, CXCL16 or CCL11 in the thymus organ medium during the course of the conditioning regimen.

In an embodiment of the aspects and embodiments of the present disclosure, the method comprises detecting increasing levels of one or more of CXCL12, CXCL16 or CCL11 in the thymus organ medium during the course of the conditioning regimen.

In an embodiment of the aspects and embodiments of the present disclosure, the method comprises detecting increasing levels of CXCL12 in the thymus organ medium during the course of the conditioning regimen.

In an embodiment of the aspects and embodiments of the present disclosure, the method comprises detecting increasing CXCL16 in the thymus organ medium during the course of the conditioning regimen.

In an embodiment of the aspects and embodiments of the present disclosure, the method comprises detecting increasing levels of CCL11 in the thymus organ medium during the course of the conditioning regimen.

In an embodiment of the aspects and embodiments of the present disclosure, the method comprises detecting one or more of M-CSF, galectin-7 or IL-16 in the thymus organ medium during the course of the conditioning regimen.

In an embodiment of the aspects and embodiments of the present disclosure, the method comprises detecting decreasing levels of one or more of M-CSF, galectin-7 or IL-16 in the thymus organ medium during the course of the conditioning regimen.

In an embodiment of the aspects and embodiments of the present disclosure, the method comprises detecting decreasing levels of M-CSF in the thymus organ medium during the course of the conditioning regimen.

In an embodiment of the aspects and embodiments of the present disclosure, the method comprises detecting decreasing levels of galectin-7 in the thymus organ medium during the course of the conditioning regimen.

In an embodiment of the aspects and embodiments of the present disclosure, the method comprises detecting decreasing levels of IL-16 in the thymus organ medium during the course of the conditioning regimen.

In an embodiment of the aspects and embodiments of the present disclosure, the conditioning regimen is for a period of five days, or six days, or seven days, or eight days, or nine days, or 10 days, or 11 days, or 12 days, or 13 days, or 14 days, or 15 days, or 16 days, or 17 days, or 18 days or 19 days, or 20 days, or 21 days; or for a period of 5-6 days, or 5-7 days, or 5-8 days, or 5-9 days, or 5-10 days, or 6 to 7 days, or 6 to 8 days, or 6 to 9 days, or 6 to 10 days, or 6 to 11 days, or 6 to 12 days, or 6 to 21 days, or 7 to 21 days, or 8 to 21 days, or 9 to 21 days, or 10 to 21 days, or 11 to 21 days, or 12 to 21 days, 13 to 21 days or 14 to 21 days, or 15 to 21 days, or 16 to 21 days or 17 to 21 days or 18 to 21 days, or 19 to 21 days, or 20 to 21 days.

In an embodiment of the aspects and embodiments of the present disclosure, the levels of CCL21 approximate the levels in FIG. 50E, and/or the levels of L-selectin approximate the levels in FIG. 50A, and/or the levels of M-CSF approximate the levels in FIG. 50B, and/or the levels of galectin-7 approximate the levels in FIG. 50C, and/or the levels of IL-16 approximate the levels in FIG. 50D, and/or the levels of CXCL16 approximate the levels in FIG. 50F, and/or wherein the levels of CCL11 approximate the levels in FIG. 50G, and/or the levels of CXL21 approximate the levels in FIG. 50H.

In an embodiment of the aspects and embodiments of the present disclosure, the method further comprises the step of determining in the donor thymus tissue slices between days 6 and 21, preferably between days 6 and 9 of the conditioning regimen areas positive for keratin AE1/AE3 scattered throughout the donor thymus tissue slices the presence of at least one Hassall body, CK14 staining scattered throughout the donor thymus tissue slices and the presence of intact nuclei.

In an embodiment of the aspects and embodiments of the present disclosure, the method further comprises detecting the level of at least one marker in the thymus organ medium during the culturing regimen, or at least two, or at least three, or at least four, or at least five, or at least six, or at least seven, or detecting at least eight markers in the thymus organ medium during the conditioning regimen, selected from L-selectin, M-CSF, galectin-7, IL-16, CCL21, CXCL12, CXCL16, and CCL11.

In an embodiment of the aspects and embodiments of the present disclosure, the method further comprises detecting the level of at least one marker in the thymus organ medium during the culturing regimen selected from L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PlGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1.

In an aspect of the present disclosure, there is provided a method for determining whether allogeneic cultured post-natal thymus tissue-derived product is suitable for implantation into a human, the method comprising the steps of conditioning donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; and detecting the level of at least one marker selected from L-selectin, M-CSF, galectin-7, IL-16, CCL21, CXCL12, CXCL16, and CCL11 in the thymus organ medium.

In an embodiment of the aspects and embodiments of the present disclosure, the at least one marker is L-selectin, and wherein the levels of L-selectin in the thymus organ medium decrease over time, i.e., during the course of the course of the conditioning regimen.

In an embodiment of the aspects and embodiments of the present disclosure, the at least one marker is M-CSF, and wherein the levels of M-CSF in the thymus organ medium decrease during the course of the conditioning regimen.

In an embodiment of the aspects and embodiments of the present disclosure, the at least one marker is galectin-7, and wherein the levels of galectin-7 in the thymus organ medium decrease during the course of the conditioning regimen.

In an embodiment of the aspects and embodiments of the present disclosure, the at least one marker is IL-16, and wherein the levels of IL-16 in the thymus organ medium decrease during the course of the conditioning regimen.

In an embodiment of the aspects and embodiments of the present disclosure, the at least one marker is CCL21, and wherein the levels of CCL21 in the thymus organ medium increase during the course of the conditioning regimen.

In an embodiment of the aspects and embodiments of the present disclosure, the at least one marker is CXCL12, and wherein the levels of CXCL12 in the thymus organ medium increase during the course of the conditioning regimen.

In an embodiment of the aspects and embodiments of the present disclosure, the at least one marker is CXCL16, and wherein the levels of CXCL16 in the thymus organ medium increase during the course of the conditioning regimen.

In an embodiment of the aspects and embodiments of the present disclosure of the present disclosure, the at least one marker is CCL11, and wherein the levels of CCL11 in the thymus organ medium increase during the course of the conditioning regimen.

In an aspect of the present disclosure, there is provided a method for determining whether allogeneic cultured post-natal thymus tissue-derived product is suitable for implantation into a human, the method comprising the steps of conditioning donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; and detecting the level of at least one marker in the thymus organ medium during the course of the conditioning regimen selected from L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PlGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1.

In an embodiment of the aspects and embodiments of the present disclosure, the method further comprises the step of determining in the donor thymus tissue slices between days 6 and 21 of the conditioning regimen areas positive for keratin AE/AE3 scattered throughout the donor thymus tissue slices the presence of at least one Hassall body, CK14 staining scattered throughout the donor thymus tissue slices and the presence of intact nuclei.

In an embodiment of the aspects and embodiments of the present disclosure, the conditioning regimen is for a period of five days, or six days, or seven days, or eight days, or nine days, or 10 days, or 11 days, or 12 days, or 13 days, or 14 days, or 15 days, or 16 days, or 17 days, or 18 days or 19 days, or 20 days, or 21 days; or for a period of 5-6 days, or 5-7 days, or 5-8 days, or 5-9 days, or 5-10 days, or 6 to 7 days, or 6 to 8 days, or 6 to 9 days, or 6 to 10 days, or 6 to 11 days, or 6 to 12 days, or 6 to 21 days, or 7 to 21 days, or 8 to 21 days, or 9 to 21 days, or 10 to 21 days, or 11 to 21 days, or 12 to 21 days, 13 to 21 days or 14 to 21 days, or 15 to 21 days, or 16 to 21 days or 17 to 21 days or 18 to 21 days, or 19 to 21 days, or 20 to 21 days.

In an embodiment of the aspects and embodiments of the present disclosure, the levels of CCL21 approximate the levels in FIG. 50E, and/or the levels of L-selectin approximate the levels in FIG. 50A, and/or the levels of M-CSF approximate the levels in FIG. 50B, and/or the levels of galectin-7 approximate the levels in FIG. 50C, and/or the levels of IL-16 approximate the levels in FIG. 50D, and/or the levels of CXCL16 approximate the levels in FIG. 50F, and/or wherein the levels of CCL11 approximate the levels in FIG. 50G, and/or the levels of CXL21 approximate the levels in FIG. 50H.

In an embodiment of the aspects and embodiments of the present disclosure, the method further comprises detecting the level of at least one marker in the thymus organ medium during the course of the conditioning regimen, or the levels of at least two, at least three, at least four, at least five, at least six, at least seven, or detecting at least eight markers, selected from L-selectin, M-CSF, galectin-7, IL-16, CCL21, CXCL12, CXCL16, and CCL11, and wherein the levels of L-selectin, M-CSF, galectin-7, IL-16 decrease in the thymus organ medium during the course of the conditioning regimen, and further wherein the levels of CCL21, CXCL12, CXCL16, and CCL11 increase in the thymus organ medium during the course of the conditioning regimen.

In an aspect of the invention, there is a method for determining whether allogeneic cultured postnatal thymus tissue-derived product is suitable for implantation into a human, the method comprising the steps of conditioning donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; and detecting the level of at least one marker selected from the markers in FIG. 56.

In an embodiment of the aspects and embodiments of the present disclosure, there is a method for determining whether allogeneic cultured postnatal thymus tissue-derived product is suitable for implantation into a human, the method comprising the steps of conditioning donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; and detecting the level of at least one marker in the thymus organ medium during the course of the conditioning regimen selected from L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1.

In an aspect of the present disclosure, there is a method of treating a thymic disorder, the improvement comprising implanting into a subject having a thymic disorder allogeneic cultured postnatal thymus tissue-derived slices subjected to a conditioning regimen in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; and detecting the level of at least one marker selected from L-selectin, M-CSF, galectin-7, IL-16, CCL21, CXCL12, CXCL16, and CCL11.

In another aspect of the present disclosure, there is a method of treating thymic disorders, the improvement comprising implanting into a subject having a thymic disorder allogeneic cultured postnatal thymus tissue-derived slices subjected to a conditioning regimen in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; and detecting the level of at least one marker in the thymus organ medium during the course of the conditioning regimen is selected from L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1.

In an embodiment of the aspects and embodiments of the present disclosure, at least one marker is L-selectin, and wherein the levels of L-selectin in the thymus organ medium decrease during the course of the conditioning regimen.

In an embodiment of the aspects and embodiments of the present disclosure, at least one marker is M-CSF, and wherein the levels of M-CSF in the thymus organ medium decrease during the course of the conditioning regimen.

In an embodiment of the aspects and embodiments of the present disclosure, at least one marker is galectin-7, and wherein the levels of galectin-7 in the thymus organ medium decrease during the course of the conditioning regimen.

In an embodiment of the aspects and embodiments of the present disclosure, at least one marker is IL-16, and wherein the levels of IL-16 in the thymus organ medium decrease during the course of the conditioning regimen.

In an embodiment of the aspects and embodiments of the present disclosure, at least one marker is CCL21, and wherein the levels of CCL21 in the thymus organ medium increase during the course of the conditioning regimen.

In an embodiment of the aspects and embodiments of the present disclosure, at least one marker is CXCL12, and wherein the levels of CXCL12 in the thymus organ medium increase during the course of the conditioning regimen.

In an embodiment of the aspects and embodiments of the present disclosure, at least one marker is CXCL16, and wherein the levels of CXCL16 in the thymus organ medium increase during the course of the conditioning regimen.

In an embodiment of the aspects and embodiments of the present disclosure, at least one marker is CCL11, and wherein the levels of CCL11 in the thymus organ medium increase during the course of the conditioning regimen.

In an embodiment of the aspects and embodiments of the present disclosure, the method further comprises the step of determining in the donor thymus tissue slices during the conditioning regimen areas positive for keratin AE1/AE3 scattered throughout the donor thymus tissue slices the presence of at least one Hassall body, CK14 staining scattered throughout the donor thymus tissue slices and the presence of intact nuclei.

In an embodiment of the aspects and embodiments of the present disclosure, the thymic disorder is congenital athymia associated with complete DiGeorge syndrome, 22q11.2 deletion, CHARGE (coloboma, heart defect, choanal atresia, growth or mental retardation, genital hypoplasia and ear anomalies or deafness), mutations in the CHD7 (chromodomain-helicase-DNA-binding protein 7) gene or forkhead box protein N1 (FOXN1) deficiency.

In an embodiment of the aspects and embodiments of the present disclosure, the thymic disorder is thymic involution. In another embodiment, thymic disorder is congenital athymia associated with mutations in the TBX-1 or TBX-2 gene.

In an embodiment of the aspects and embodiments of the present disclosure, the thymic disorder is related to paired box 1 (PAX1), semaphorine 3E (SEMAE) and recurrent microdeletions at chromosome 2p11.2.

In an embodiment of the aspects and embodiments of the present disclosure, the thymic disorder is associated with a thymoma. In still a further embodiment the thymoma is either non-malignant or malignant.

In an embodiment of the aspects and embodiments of the present disclosure, the thymic disorder is associated with myasthenia gravis (MG), pure red cell aplasia and hypogammaglobulinemia.

In an aspect of the present disclosure there is provided a method for providing immune-competence in a human subject, the improvement comprising the steps of conditioning donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regimen selected from the markers L-selectin, M-CSF, galectin-7, IL-16, CCL21, CXCL12, CXCL16, or CCL11; wherein the level is decreased if the marker is L-selectin, M-CSF, galectin-7, or IL-1 or increased if the marker is CCL21, CXCL12, CXCL16, or CCL11; and implanting the partially T-cell depleted donor thymus tissue slices into the human subject.

In an aspect of the present disclosure, there is provided a method for providing immune-competence in a human subject, the improvement comprising the steps of conditioning donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regimen is selected from the markers from L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1; and implanting the partially T-cell depleted donor thymus tissue slices into the human subject.

In an aspect of the present disclosure, there is provided a method for providing immune-competence in a human subject undergoing a solid organ transplant, the method comprising the following steps of removing the thymus of the human subject; obtaining thymus tissue from a donor matching HLA-Class I and HLA-Class II alleles in the solid organ; slicing the donor thymus; conditioning the donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regimen selected from the markers L-selectin, M-CSF, galectin-7, IL-16, CCL21, CXCL12, CXCL16, or CCL11; wherein the level is decreased if the marker is L-selectin, M-CSF, galectin-7, or IL-1 or increased if the marker is CCL21, CXCL12, CXCL16, or CCL11; implanting the solid organ; and implanting the partially T-cell depleted donor thymus tissue slices into the human subject.

For better understanding of the development of tolerance in this model, one can refer to FIG. 38 which has a primate model of this procedure that will provide data to support a human study for generating donor-specific tolerance. The experiment in FIG. 38 has 3 monkeys. One is the thymus and heart donor (information in the left hand columns). The second is the thymus and heart recipient (information in the middle column on the $2^{nd}$ page. This column has the STAGE of the experiment). The third is the control (information in the right hand columns on the $3^{rd}$ page). Please note that the original spreadsheet had the procedures for all three animals one page wide by many pages long. Because the spread sheet was wider than the width allowed, each row of the spread sheet was divided into 3 pages. The table continues in groups of 3 panels for many weeks and several stages.

In an aspect of the present disclosure, there is provided a method for providing immune-competence in a human subject undergoing a solid organ transplant, the method comprising the following steps of removing the thymus of the human subject; obtaining thymus tissue from a donor matching HLA-Class I and II alleles in the solid organ; slicing the donor thymus; conditioning the donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regiment is selected from the markers L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1; implanting the solid organ; and implanting the partially T-cell depleted donor thymus tissue slices into the human subject.

In an aspect of the present disclosure, there I provided a method for providing immune-competence in a human subject undergoing a solid organ transplant, the method comprising the following steps of removing the thymus of the human subject; obtaining thymus tissue from a donor matching both HLA-Class I and HLA-Class II alleles in the solid organ; slicing the donor thymus; conditioning the donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regimen selected from the markers L-selectin, M-CSF, galectin-7, IL-16, CCL21, CXCL12, CXCL16, or CCL11; wherein the level is decreased if the marker is L-selectin, M-CSF, galectin-7, or IL-1 or increased if the marker is CCL21, CXCL12, CXCL16, or CCL11; implanting the solid organ; and implanting the partially T-cell depleted donor thymus tissue slices into the human subject.

In an aspect of the present disclosure, there is provided a method for providing immune-competence in a human subject undergoing a solid organ transplant, the method comprising the following steps of removing the thymus of the human subject; obtaining thymus tissue from a donor matching both HLA-Class I and HLA-Class II alleles in the solid organ; slicing the donor thymus; conditioning the donor thymus tissue slices in a thymus organ medium for a period of about 6 days to about 21 days; wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regimen is selected from the markers L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1; implanting the solid organ; and implanting the partially T-cell depleted donor thymus tissue slices into the human subject.

In an aspect of the present disclosure, there is provided a method of promoting donor-specific tolerance to an allogeneic solid organ transplant obtained from a deceased donor, in a recipient in need of a solid organ transplant, the method comprising the following steps:
(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing both a suitable solid human organ and a thymus gland from a deceased donor;
(d) transplanting the solid human organ into the recipient;
(e) treating the recipient with a maintenance immunosuppressive regimen;
(f) providing an allogeneic cultured postnatal thymus tissue-derived product, wherein the allogeneic cultured postnatal thymus tissue-derived product is subjected to a conditioning regimen in a thymus organ medium for a period of about 6 days to about 21 days to produce allogeneic cultured postnatal thymus tissue-derived product slices; further wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regimen selected from the markers L-selectin, M-CSF, galectin-7, IL-16, CCL21, CXCL12, CXCL16, or CCL11; wherein the level of the marker in the thymus organ medium is decreased if the marker is L-selectin, M-CSF, galectin-7, or IL-1 or increased if the marker is CCL21, CXCL12, CXCL16, or CCL11; and
(g) implanting the allogeneic cultured postnatal thymus tissue-derived product into the recipient after about 6 days to about 21 days of conditioning regimen, wherein the dosage of thymus tissue slices is about 1,000-22,000 mm² of thymus tissue surface area/recipient body surface area in m², and further wherein the implanted allogeneic cultured postnatal thymus tissue-derived product induces thymopoiesis and tolerance in the recipient.

In an aspect of the present disclosure, there is provided a method of promoting donor-specific tolerance to an allogeneic solid organ transplant obtained from a deceased donor, in a recipient in need of a solid organ transplant, the method comprising the following steps:
(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing both a suitable solid human organ and a thymus gland from a deceased donor;
(d) transplanting the solid human organ into the recipient;
(e) treating the recipient with a maintenance immunosuppressive regimen;
(f) providing an allogeneic cultured postnatal thymus tissue-derived product, wherein the allogeneic cultured postnatal thymus tissue-derived product is subjected to a conditioning regimen in a thymus organ medium for a period of about 6 days to about 21 days to produce allogeneic cultured postnatal thymus tissue-derived product slices; further wherein the conditioning regimen for the donor thymus tissue comprises aseptically processing the donor thymus tissue in the thymus organ medium to produce partially T-cell depleted donor thymus tissue slices; detecting the level of at least one marker in the thymus organ medium during the course of the conditioning regimen is selected from the markers L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1; and
(g) implanting the allogeneic cultured postnatal thymus tissue-derived product into the recipient after about 6 days to about 21 days of conditioning regimen, wherein the dosage of thymus tissue slices is about 1,000-22,000 mm² of thymus tissue surface area/recipient body surface area in m², and further wherein the implanted allogeneic cultured postnatal thymus tissue-derived product induces thymopoiesis and tolerance in the recipient.

In an aspect of the present disclosure, there is provided a method for promoting donor-specific tolerance to an allogeneic solid organ transplant obtained from a living human donor, in a human recipient in need of a solid organ transplant, the method comprising the steps of:
(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing a suitable solid organ from a living human donor;
(d) transplanting the solid organ into the recipient;
(e) treating the recipient with a maintenance immunosuppressive regimen;
(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product was processed from thymus tissue from a thymus donor expressing HLA alleles matched to HLA-Class I and HLA-Class II alleles in the recipient that are not present in the solid organ transplant; wherein the donor thymus tissue was subjected to a conditioning regimen for a period of about 6 days to about 21 days; further wherein the conditioning regimen for the donor thymus tissue comprises aseptically processing the donor thymus tissue in a thymus organ medium to produce partially T-cell depleted thymus tissue slices; detecting the level of at least one marker in the thymus organ medium during the course of the conditioning regimen selected from the markers L-selectin, M-CSF, galectin-7, IL-16, CCL21, CXCL12, CXCL16, or CCL11; wherein the level of the marker in the thymus organ medium is decreased if the marker is L-selectin, M-CSF, galectin-7, or IL-1 or increased if the marker is CCL21, CXCL12, CXCL16, or CCL11;

(g) thawing the cryopreserved allogeneic cultured postnatal thymus tissue-derived product, and (h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient In an embodiment of the aspects and embodiments of the present disclosure, permissive mismatches for HLA-DP can be allowed (Pidala J et al 2014 Blood 124:2596-2606). In addition, nonpermissive mismatches for HLA-DPB1 can be allowed if there is sufficient numerical functional distance (Crivello P et al 2016 Blood 128:120-129).

In an aspect of the present invention, there is provided a method for promoting donor-specific tolerance to an allogeneic solid organ transplant obtained from a living human donor, in a human recipient in need of a solid organ transplant, the method comprising the steps of:

(a) removal of the thymus of the recipient;

(b) treating the recipient with an induction immunosuppressive regimen comprising one or more immunosuppressive agent to deplete the recipient's T cells and/or to suppress the recipient's T cells from rejecting the transplanted solid organ;

(c) providing a suitable solid organ from a living human donor;

(d) transplanting the solid organ into the recipient;

(e) treating the recipient with a maintenance immunosuppressive regimen;

(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product was processed from thymus tissue from a thymus donor expressing HLA alleles matched to HLA-Class I and HLA-Class II alleles in the recipient that are not present in the solid organ transplant; wherein the donor thymus tissue was subjected to a conditioning regimen for a period of about 6 days to about 21 days; further wherein the conditioning regimen for the donor thymus tissue comprises aseptically processing the donor thymus tissue in a thymus organ medium to produce partially T-cell depleted thymus tissue slices; detecting the level of at least one marker in the thymus organ medium during the course of the conditioning regimen is selected from the markers L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1 in the thymus organ medium; wherein the level of the marker in the thymus organ medium is increased or decreased in accordance with the levels for the marker in FIG. 56;

(g) thawing the cryopreserved allogeneic cultured postnatal thymus tissue-derived product; and (h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient In an embodiment of the aspects and embodiments of the present disclosure, about one-half of the thawed cryopreserved allogeneic cultured postnatal thymus tissue-derived product is transplanted into the recipient and the remainder is cryopreserved for future use.

In an embodiment of the aspects and embodiments of the present disclosure, step (h) is performed about one month or more after the transplantation of the solid organ.

In an aspect of the present disclosure, there is provided a method for promoting donor-specific tolerance to an allogeneic solid organ transplant obtained from a deceased human donor, in a human recipient in need of a solid organ transplant, the method comprising the steps of:

(a) removal of the thymus of the recipient;

(b) treating the recipient with an induction immunosuppressive regimen comprising one or more immunosuppressive agent to deplete the recipient's T cells and/or to suppress the recipient's T cells from rejecting the transplanted solid organ;

(c) providing a suitable solid organ from a living human donor;

(d) transplanting the solid organ into the recipient;

(e) treating the recipient with a maintenance immunosuppressive regimen;

(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product is processed from thymus tissue from a thymus donor expressing HLA alleles matched to HLA alleles in the recipient that are not present in the solid organ transplant; wherein the donor thymus tissue was subjected to a conditioning regimen for a period of about 6 days to about 21 days; further wherein the conditioning regimen for the donor thymus tissue comprises aseptically processing the donor thymus tissue in a thymus organ medium to produce partially T-cell depleted thymus tissue slices, detecting the level of at least one marker in the thymus organ medium during the course of the conditioning regimen selected from the markers L-selectin, M-CSF, galectin-7, IL-16, CCL21, CXCL12, CXCL16, or CCL11; wherein the level of the marker in the thymus organ medium is decreased if the marker is L-selectin, M-CSF, galectin- 7, or IL-1 or increased if the marker is CCL21, CXCL12, CXCL16, or CCL11;

(g) thawing the cryopreserved allogeneic cultured postnatal thymus tissue-derived product; and (h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient.

In an aspect of the present disclosure, there is provided a method for promoting donor-specific tolerance to an allogeneic solid organ transplant obtained from a deceased human donor, in a human recipient in need of a solid organ transplant, the method comprising the steps of:

(a) removal of the thymus of the recipient;

(b) treating the recipient with an induction immunosuppressive regimen comprising one or more immunosuppressive agent to deplete the recipient's T cells and/or to suppress the recipient's T cells from rejecting the transplanted solid organ;

(c) providing a suitable solid organ from a living human donor;

(d) transplanting the solid organ into the recipient;

(e) treating the recipient with a maintenance immunosuppressive regimen;

(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product is processed from thymus tissue from a thymus donor expressing HLA alleles matched to HLA alleles in the recipient that are not present in the solid organ transplant; wherein the donor thymus tissue was subjected to a conditioning regimen for a period of about 6 days to about 21 days; further wherein the conditioning regimen for the donor thymus tissue comprises aseptically processing the donor thymus tissue in a thymus organ medium to produce partially T-cell depleted thymus tissue slices, detecting the level of at least one marker in the thymus organ medium during the course of the conditioning regimen selected from the markers L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1; wherein the level of the marker in the thymus organ medium is increased or decreased in accordance with the levels in FIG. 7;

(g) thawing the cryopreserved allogeneic cultured postnatal thymus tissue-derived product; and (h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient.

In an aspect of the present disclosure, there is provided a cryopreserved allogeneic cultured postnatal thymus tissue-derived product, prepared by a method comprising the steps of:

(a) obtaining suitable thymus tissue from a donor;

(b) typing HLA alleles: HLA-A, HLA-B, HLA-C, HLA-DRB1, HLA-DQB 1, HLA-DRB3, HLA-DRB4, HLA-DRB5, HLA-DQA1, HLA-DPB1, HLA-DPA1;

(c) subjecting the thymus tissue to a conditioning regimen for a period of about 6 days to about 21 days; wherein the conditioning regimen for the donor thymus tissue comprises aseptically processing the donor thymus tissue in a thymus organ medium to produce partially T-cell depleted donor thymus tissue slices;

(d) detecting the level of at least one marker in the thymus organ medium during the course of the conditioning regimen selected from the markers L-selectin, M-CSF, galectin-7, IL-16, CCL21, CXCL12, CXCL16, or CCL11; wherein the level of the marker in the thymus organ medium is decreased if the marker is L-selectin, M-CSF, galectin-7, or IL-1 or increased if the marker is CCL21, CXCL12, CXCL16, or CCL11;

(e) retrieving the partially T-cell depleted donor thymus tissue slices as allogeneic cultured postnatal thymus tissue-derived product;

(f) cryopreserving the allogeneic cultured postnatal thymus tissue-derived product in liquid nitrogen; and (g) maintaining the cryopreserved allogeneic cultured postnatal thymus tissue-derived product in liquid nitrogen in a cryopreserved allogeneic cultured postnatal thymus tissue-derived product bank.

In an aspect of the present disclosure, there is a cryopreserved allogeneic cultured postnatal thymus tissue-derived product, prepared by a method comprising the steps of:

(a) obtaining suitable thymus tissue from a donor;

(b) typing HLA alleles: HLA-A, HLA-B, HLA-C, HLA-DRB 1, HLA-DQB 1, HLA-DRB3, HLA-DRB4, HLA-DRB5, HLA-DQA1, HLA-DPB1, HLA-DPA1;

(c) subjecting the thymus tissue to a conditioning regimen for a period from about 6 days to about 21 days; wherein the conditioning regimen for the donor thymus tissue comprises aseptically processing the donor thymus tissue in a thymus organ medium to produce partially T-cell depleted donor thymus tissue slices;

(d) detecting the level of at least one marker in the thymus organ medium during the course of the conditioning regimen selected from the markers L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1; wherein the level of the marker in the thymus organ medium is increased or decreased in accordance with the levels in FIG. 7;

(e) retrieving the partially T-cell depleted donor thymus tissue slices as allogeneic cultured postnatal thymus tissue-derived product;

(f) cryopreserving the allogeneic cultured postnatal thymus tissue-derived product in liquid nitrogen; and (g) maintaining the cryopreserved allogeneic cultured postnatal thymus tissue-derived product in liquid nitrogen in a cryopreserved allogeneic cultured postnatal thymus tissue-derived product bank.

In an aspect of the present disclosure, there is provided a method for promoting donor-specific tolerance to an allogeneic solid organ transplant obtained from a deceased human donor, in a human recipient in need of a solid organ transplant, the method comprising the steps of:
(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing a suitable solid organ from a living human donor;
(d) transplanting the solid organ into the recipient;
(e) treating the recipient with a maintenance immunosuppressive regimen;
(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product is processed from thymus tissue from a thymus donor expressing HLA alleles matched to HLA alleles in the recipient that are not present in the solid organ transplant; wherein the donor thymus tissue was subjected to a conditioning regimen for a period of a about 6 days to about 21 days; further wherein the conditioning regimen for the donor thymus tissue comprises aseptically processing the donor thymus tissue in a thymus organ medium to produce partially T-cell depleted thymus tissue slices, detecting the level of at least one marker in the thymus organ medium during the course of the conditioning regiment selected from the markers L-selectin, M-CSF, galectin-7, IL-16, CCL21, CXCL12, CXCL16, or CCL11 in the thymus organ medium; wherein the level of the marker in the thymus organ medium is decreased if the marker is L-selectin, M-CSF, galectin-7, or IL-1 or increased if the marker is CCL21, CXCL12, CXCL16, or CCL11;
(g) thawing the cryopreserved allogeneic cultured postnatal thymus tissue-derived product; and
(h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient.

In an aspect of the present disclosure, there is provided a cryopreserved allogeneic cultured postnatal thymus tissue-derived product, prepared by a method comprising the steps of:
(a) obtaining suitable thymus tissue from a donor;
(b) typing HLA alleles: HLA-A, HLA-B, HLA-C, HLA-DRB 1, HLA-DQB 1, HLA-DRB3, HLA-DRB4, HLA-DRB5, HLA-DQA1, HLA-DPB1, HLA-DPA1;
(c) subjecting the thymus tissue to a conditioning regimen for a period of about 6 days to about 21 days; wherein the conditioning regimen for the donor thymus tissue comprises aseptically processing the donor thymus tissue in a thymus organ medium to produce partially T-cell depleted donor thymus tissue slices;
(d) detecting the level of at least one marker in the thymus organ medium during the course of the conditioning regimen selected from the markers L-selectin, M-CSF, galectin-7, IL-16, CCL21, CXCL12, CXCL16, or CCL11 in the thymus organ medium; wherein the level of the marker in the thymus organ medium is decreased if the marker is L-selectin, M-CSF, galectin-7, or IL-1 or increased if the marker is CCL21, CXCL12, CXCL16, or CCL11;
(e) retrieving the partially T-cell depleted donor thymus tissue slices as allogeneic cultured postnatal thymus tissue-derived product;
(f) cryopreserving the allogeneic cultured postnatal thymus tissue-derived product in liquid nitrogen; and
(g) maintaining the cryopreserved allogeneic cultured postnatal thymus tissue-derived product in liquid nitrogen in a cryopreserved allogeneic cultured postnatal thymus tissue-derived product bank.

In an aspect of the present disclosure, there is provided a method for promoting donor-specific tolerance to an allogeneic solid organ transplant obtained from a deceased human donor, in a human recipient in need of a solid organ transplant, the method comprising the steps of:
(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing a suitable solid organ from a living human donor;
(d) transplanting the solid organ into the recipient;
(e) treating the recipient with a maintenance immunosuppressive regimen;
(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product is processed from thymus tissue from a thymus donor expressing HLA alleles matched to HLA alleles in the recipient that are not present in the solid organ transplant; wherein the donor thymus tissue was subjected to a conditioning regimen for a period of about 6 days to about 21 days; further wherein the conditioning regimen for the donor thymus tissue comprises aseptically processing the donor thymus tissue in a thymus organ medium to produce partially T-cell depleted thymus tissue slices, detecting the level of at least one marker in the thymus organ medium during the course of the conditioning regimen selected from the markers L-selectin, CXCL16, M-CSF, CCL21/6Ckine, galectin-7, MIF, GDNF, CTACK, MIP-3b, ICAM-1, PECAM-1, IL-2Rg, SCF R, IL-16, GDF-15, PDGF-AA, CXCL12/SDFF-1a, MIP-3a, IL-2Ra, ICAM-3, LIGHT, IGFBP-1, BCMA, EGF R, uPAR, MIP-1b, PIGF, PF4, CCL11/Eotaxin, HVEM, IGFBP-6, IL-6R. IL-12p40, RANTES, MICA, GCP-2, OPN, ALCAM, NRG1-B1, CEACAM-1, IL-1b, DKK-1 and ANG-1; wherein the level of the marker in the thymus organ medium is increased or decreased in accordance with the levels for the marker in FIG. 56;
(g) thawing the cryopreserved allogeneic cultured postnatal thymus tissue-derived product; and
(h) implanting the thawed cryopreserved allogeneic cultured postnatal thymus tissue-derived product into the recipient, wherein the dosage of the cryopreserved allogeneic cultured postnatal thymus tissue-derived product is about 1,000-22,000 mm$^2$ of thymus tissue surface area/recipient body surface area in m$^2$, and further wherein the implanted allogeneic cultured postnatal thymus tissue-derived product induces thymopoiesis and tolerance in the recipient In an embodiment of the aspects and embodiments of the present disclosure, the solid organ transplant is a heart transplant, a kidney transplant, a liver transplant, a lung transplant, a heart/lung transplant, a pancreas transplant, an intestine transplant, a stomach transplant, an abdominal wall transplant, a craniofacial transplant, a scalp transplant, a penile transplant, a uterus transplant, a unilateral or bilateral upper limb transplant, a unilateral vascularized composite allograft, or combination thereof.

In an embodiment of the aspects and embodiments of the present disclosure, the solid organ transplant is a heart transplant, or a pediatric heart transplant, or an adult heart transplant.

In an embodiment of the aspects and embodiments of the present disclosure, the conditioning regimen is for a period of five days, or six days, or seven days, or eight days, or nine days, or 10 days, or 11 days, or 12 days, or 13 days, or 14 days, or 15 days, or 16 days, or 17 days, or 18 days or 19 days, or 20 days, or 21 days; or for a period of 5-6 days, or 5-7 days, or 5-8 days, or 5-9 days, or 5-10 days, or 6 to 7 days, or 6 to 8 days, or 6 to 9 days, or 6 to 10 days, or 6 to 11 days, or 6 to 12 days, or 6 to 21 days, or 7 to 21 days, or 8 to 21 days, or 9 to 21 days, or 10 to 21 days, or 11 to 21 days, or 12 to 21 days, 13 to 21 days or 14 to 21 days, or 15 to 21 days, or 16 to 21 days or 17 to 21 days or 18 to 21 days, or 19 to 21 days, or 20 to 21 days.

In an aspect of the present disclosure, there is provided a cryopreserved allogeneic cultured postnatal thymus tissue-derived product suitable for implantation into a human, comprising the steps of:
  (a) obtaining suitable thymus tissue from a human donor;
  (b) subjecting the thymus tissue to a conditioning regimen for a period of about 6 days to about 21 days; wherein the conditioning regimen for the donor thymus tissue comprises aseptically processing the donor thymus tissue in a thymus organ medium to produce partially T-cell depleted donor thymus tissue slices; wherein levels of L-selectin, and/or M-CSF and/or galectin-7 and/or IL-16 in the thymus organ medium decrease during the course of the conditioning regimen; further wherein levels of CCL21 and/or CXCL12 and/or CXCL16 and/or CCL11 in the thymus organ medium increase during the course of the conditioning regimen;
  (c) harvesting the partially T-cell depleted donor thymus tissue slices as allogeneic cultured postnatal thymus tissue-derived product;
  (d) cryopreserving the allogeneic cultured postnatal thymus tissue-derived product in liquid nitrogen; and
  (e) maintaining the cryopreserved allogeneic cultured postnatal thymus tissue-derived product in liquid nitrogen in a cryopreserved allogeneic cultured postnatal thymus tissue-derived product bank In an embodiment of the aspects and embodiments of the present disclosure, the levels of CCL21 in the thymus organ medium increase during the course of the conditioning regimen In an embodiment of the aspects and embodiments of the present disclosure, the levels of L-selectin in the thymus organ medium decrease during the course of the conditioning regimen.

In an embodiment of the aspects and embodiments of the present disclosure, the levels of one or more of M-CSF, galectin-7, and IL-16 in the thymus organ medium decrease during the course of the conditioning regimen.

In an embodiment of the aspects and embodiments of the present disclosure, the levels of one or more of CCL21, CXCL12, CXCL16, and CCL11 in the thymus organ medium increase during the course of the conditioning regimen.

In an embodiment of the aspects and embodiments of the present disclosure, the method further comprises the step of determining in the donor thymus tissue slices during the conditioning regimen areas positive for keratin AE1/AE3 scattered throughout the donor thymus tissue slices presence of at least one Hassall body, CK14 staining scattered throughout the donor thymus tissue slices and the presence of intact nuclei.

In an aspect of the present disclosure, there is provided a kit for performing the methods of any of the foregoing aspects and embodiments, together with instructions for use in determining whether allogeneic cultured postnatal thymus tissue-derived product is suitable for implantation into a human.

In an embodiment of the aspects and embodiments of the present disclosure, the kit comprises at least one antibody that specifically binds marker L-selectin, M-CSF, galectin-7, IL-16, CCL21, CXCL12, CXCL16, or CCL11.

In an embodiment of the aspects and embodiments of the present disclosure, the kit comprises one or more antibody that specifically finds a marker set forth in FIG. 56.

In an aspect of the present disclosure, there is provided a kit for determining whether cryopreserved allogeneic cultured postnatal thymus tissue-derived product cultured in accordance with any one of the foregoing aspects and embodiments is suitable for implantation into a human together with instructions for use In an embodiment of the aspects and embodiments of the present disclosure, the kit comprises at least one antibody that specifically binds marker L-selectin, M-CSF, galectin-7, IL-16, CCL21, CXCL12, CXCL16, or CCL11.

It is further appreciated that certain features described herein, which are, for clarity, described in the context of different aspects of the present disclosure and/or in separate embodiments, can also be provided in combination in a single embodiment. Conversely, various features which are, for brevity, described in the context of a single aspect of the present disclosure and/or in a single embodiment, can also be provided separately or in any suitable subcombination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the principles disclosed herein, and the advantages thereof, reference is made to the following descriptions taken in conjunction with the accompanying drawings, in which:

FIG. 6E and FIG. 6F are predominantly epithelial cells. Condensation of the epithelium of the subcapsular cortex occurs as the thymocytes are depleted with time. Similar condensation occurs in medullary areas of the thymus. Photo by Laura P. Hale, MD, PhD, Department of Pathology, Duke University.

FIG. 11A. Day 0; FIG. 11B. Day 5; FIG. 11C. Day 9; FIG. 11D. Day 12; and FIG. 11E. Day 21. The structure of the thymic epithelial network remains intact as the culture progresses. Bar represents 400 µm. Photo by Laura P. Hale, MD, PhD, Department of Pathology, Duke University.

FIG. 12A depicts the cortex at day 9 after exposure to forced degradation conditions. FIG. 12B depicts the cortex at day 21 after exposure to forced degradation conditions. In FIG. 12A the smear of blue is DNA released from cells. The majority of cells show evidence of degradation although small foci of cells with intact nuclei can be identified. Photo by Laura P. Hale, MD, PhD, Department of Pathology, Duke University.

FIG. 17C is a photograph of CTT implanted under the kidney capsule of an LW rat. FIG. 17D is a photograph of a thymus graft harvested at 6 months after implantation. Arrows indicate the CTT under the kidney capsule.

FIG. 18A shows a comparison of medullary differentiation in H&E stained fresh thymus tissue (top frame) and CTT cultured for 5 days (bottom frame), as described in Example 5. FIG. 18B shows the typical lacey pattern observable in CTT cultured for 5 days (bottom frame) when stained for cytokeratin compared with fresh thymus tissue (top frame), as described in Example 5. FIG. 18C shows fresh thymus tissue (top frame) and CTT depleted of T cells (bottom frame) when stained for Ki-67. FIG. 18D shows fresh thymus tissue stained for CD3 (top frame) and CTT thymus tissue cultured for 5 days and then stained for CD3 (bottom frame). The brown stain noted in the CD3 stained CTT (FIG. 18D, bottom frame), likely represents some viable cells plus the detritus of dead T cells that have not washed out of the tissue.

FIG. 19A shows a comparison of medullary differentiation in H&E stained fresh thymus tissue (top frame) and CTT cultured for 5 days (bottom frame), as described in Example 5. FIG. 19B shows the typical lacey pattern observable in CTT cultured for 5 days (bottom frame) when stained for cytokeratin compared with fresh thymus tissue (top frame), as described in Example 5. FIG. 19C shows fresh thymus tissue (top frame) and CTT depleted of T cells (bottom frame) when stained for Ki-67. FIG. 19D shows fresh thymus tissue stained for DC3 (top frame) and CTT thymus tissue cultured for 5 days and then stained for CD3 (bottom frame). The brown stain noted in the CD3 stained CTT (FIG. 19D, bottom frame), likely represents some viable cells plus the detritus of dead T cells that have not washed out of the tissue.

In FIG. 30A, after immunosuppression was removed and the BN heart transplanted, the BN heart was quickly rejected and thus is very large because of all the inflammation. The LW heart is normal sized for the heart pumping blood through the body. The DA heart is small as it was placed in the abdomen and didn't need to pump blood. In FIG. 30B, the rat is immunodeficient and cannot reject either the BN or DA heart after immunosuppression is removed. This figure appears in Kwun, J. et al., JCI Insight (2020) June 4; 5(11).

FIG. 31A depicts quantification of inflammatory cells in the primary abdominal DA cardiac allograft. The syngeneic control shows that LW rats do not reject LW hearts. The DA control shows that LW rats do reject DA hearts. The CTT group does not reject the DA heart because of tolerance. The group without CTT doesn't reject the DA heart because of immunodeficiency from lack of a thymus. FIG. 31B depicts quantification of inflammatory cells in secondary cervical BN cardiac allografts. The syngeneic control shows that LW rats do not reject LW hearts. The BN control shows that LW rats do reject BN hearts. The CTT group rejects the BN heart because it is immunocompetent. The group without CTT doesn't reject the BN heart because of immunodeficiency from lack of a thymus.

FIG. 32A shows representative histogram plots for post-transplant donor-specific alloantibody (anti-DA and anti-BN antibodies) measured by T cell flow crossmatch. The upper left panel of FIG. 32A (DA control) shows the development of anti-DA antibody (thick line) in a normal LW rat after receiving a heterotopic abdominal DA heart transplant. The upper middle panel of FIG. 32A shows lack of anti DA antibody in the LW rats that received CTT; this indicates tolerance. The upper right panel shows no response by the LW rats without CTT; this reflects the immunodeficiency of the rats after thymectomy and T cell depletion without receipt of a donor thymus. The lower left panel of FIG. 32A shows normal anti BN antibody formed by a normal LW rat receiving a cervical BN heart. The lower middle panel of FIG. 32A shows a normal response of the LW rats with CTT against BN after receiving a cervical BN heart transplant, showing immunocompetence and ability to reject $3^{rd}$ party. The lower right panel of FIG. 32A shows that there is no response of the LW rats without CTT against BN after having received a cervical BN heart transplant, showing immune-incompetence and lack of ability to reject $3^{rd}$ party. FIG. 32B shows levels of anti-DA antibody after primary DA heart transplantation. The LW rats with CTT from an LW×DA thymus donor do not make anti-DA antibody after a DA heart transplant because they are tolerant to DA. The LW rats without CTT do not make anti-DA antibody after DA heart transplantation because they are immunodeficient. FIG. 32C shows levels of anti-BN antibody after secondary cervical BN heart transplantation. The LW rats with CTT from an LW×DA donor make antibodies against BN showing immunocompetence against 3 party. The LW rats without CTT do not make antibodies against BN showing immunocompetence. This figure appears in Kwun, J. et al., JCI Insight (2020) June 4; 5(11).

FIG. 34P shows Ki-67 staining of proliferating T cells at the same time points. Staining with Ki-67 is absent by day 6 (FIG. 34N), as the T cells have mainly died. This figure shows the ability to cryopreserve non-human primate thymus similarly to how cultured thymus tissue will be cryopreserved for patients. All pictures are at 40× magnification.

FIG. 38 presents an outline of the experimental design of Example 8 directed to an assessment of successful engraftment of cultured thymic tissue followed by tolerance to matched heart and rejection of unmatched skin in a CMV-free NHP model. In particular, after thymectomy of the recipient (week 1 of Stage 2) and confirmation of complete thymectomy, the recipient is T cell depleted and started on immunosuppression with tacrolimus. Unmatched cultured donor thymus tissue from an unrelated NHP is engrafted into the recipient at week 3 of Stage 3. A biopsy is done of the thymus graft at week 10 of Stage 3 to evaluate for thymopoiesis. After naïve T cells develop a few months later, the recipient should be tolerant to the donor. The recipient is then given a heterotopic heart transplant from the thymus donor (Week 4 of Stage 4). Immunosuppression is weaned off. The beating of the heart is followed (demonstrating tolerance). And a mixed lymphocyte reaction at week 10 of Stage 4 in done to show tolerance to cryopreserved donor cells and rejection of third party cells. Stage 5 is used if more time is needed for naïve T cells to develop. Stage 6 is used if tolerance didn't develop. Recipient thymus would be transplanted into the recipient NHP to prove that the thymus tissue transplant procedure is working in the NHP.

It is helpful to know how FIG. 38 was formatted. The experiment has 3 monkeys. Please note that the original spreadsheet had the procedures for all three animals in a document one page wide by many pages long. Because the spread sheet was wider than the width allowed in this patent application, each row of the spread sheet was divided into 3 pages. The first monkey is the thymus and heart donor; procedures on this monkey are in the left hand columns on the $1^{st}$, $4^{th}$, $7^{th}$ etc pages. The second monkey is the thymus and heart recipient; information in the middle columns are the $2^{nd}$, $5^{th}$, $8^{th}$ etc pages). The third monkey is the control; information in the right hand columns are on the $3^{rd}$, $6^{th}$, $9^{th}$ etc pages).

FIG. 39 presents an outline of the experimental design of Example 9 which is the same as that in Example 8 except that an additional immunosuppression medication is added, mycophenylate mofetil (MMF). The drug MMF is used routinely in heart transplantation. This study will assess if there is any detrimental effect of MMF on the cultured thymus tissue transplant.

Figure 40:
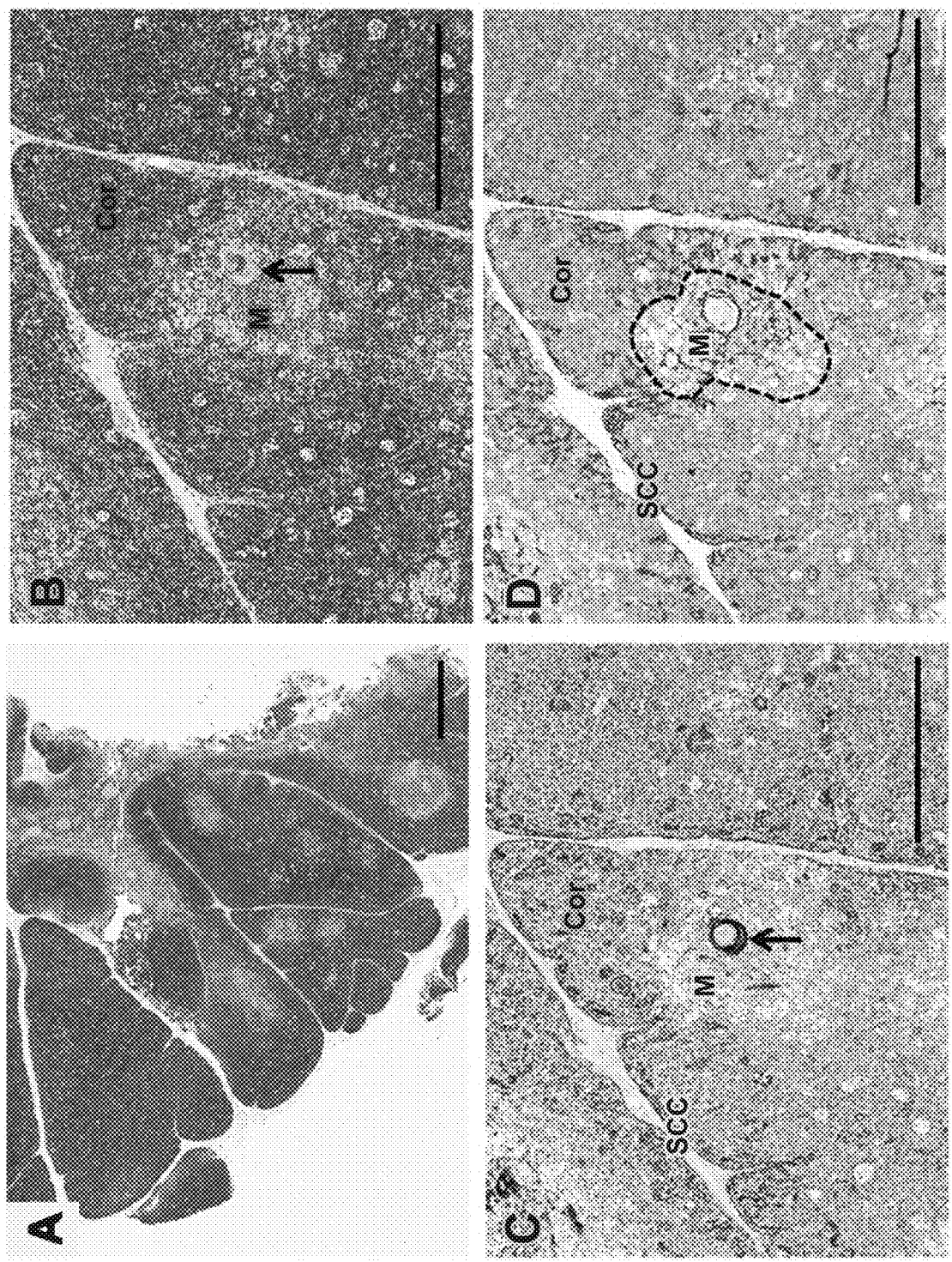

FIGS. 40A-D presents photomicrographs of slices of fresh thymus, d0 of culture, showing thymic architecture. In FIGS. 40A-B, hematoxylin and eosin (H&E) staining shows well-defined cortical and lighter-staining medullary areas, as expected for normal pediatric thymus. FIG. 40C shows immunohistochemistry with a cocktail of pan-cytokeratin antibodies (AE1/AE3) that together detect all types of epithelial cells demonstrates that thymic epithelial cells are present beneath the capsule and in a light lacy network in both cortex and medulla (brown staining shows positive antibody reaction). Arrows in FIG. 40B and FIG. 40C point to a Hassall body. FIG. 40D shows Cytokeratin 14 (CK14) antibody staining (brown). CK14 antibody reacts with thymic epithelial cells in the sub-capsular cortex and in the medulla, as well as with scattered thymic epithelial cells in the cortex. The dotted line highlights an area of medulla that is surrounded by cortex. SCC denotes sub-capsular cortex, Cor denotes cortex, and M denotes medulla. Scale bar in FIG. 40A represents 1 mm; scale bars in FIGS. 40B-D represent 500 µm.

Figure 41:
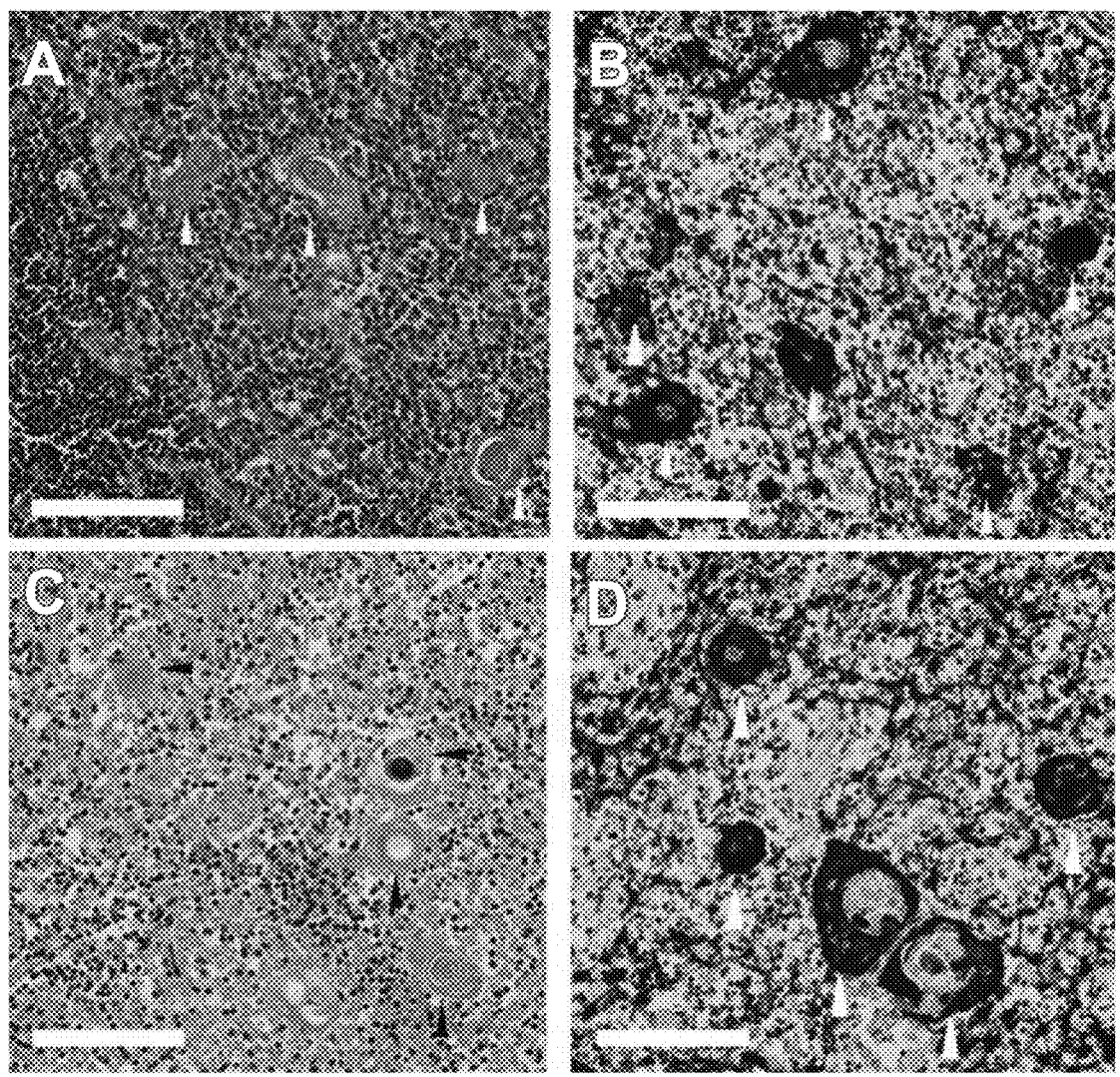

FIGS. 41A-D present photomicrographs showing examples of Hassall bodies in cultured thymic slices. The histologic appearance of Hassall bodies is shown on day 0 (FIGS. 41A-B) and day 9 (FIGS. 41C-D) of culture. FIG. 41A and FIG. 41C show hematoxylin and eosin (H&E) staining; FIG. 41B and FIG. 41D show reactivity with pan-cytokeratin (AE/AE3) antibodies (brown color indicates a positive reaction). Arrowheads in FIGS. 41A-D point out representative Hassall bodies, which appear less prominent on H&E-stained sections of cultured thymus due to depletion and necrosis of surrounding thymocytes. However, Hassall bodies can still be readily identified by careful examination or by using immunohistochemistry. Scale bar in FIGS. 41A-D represents 100 µm.

Figure 42:
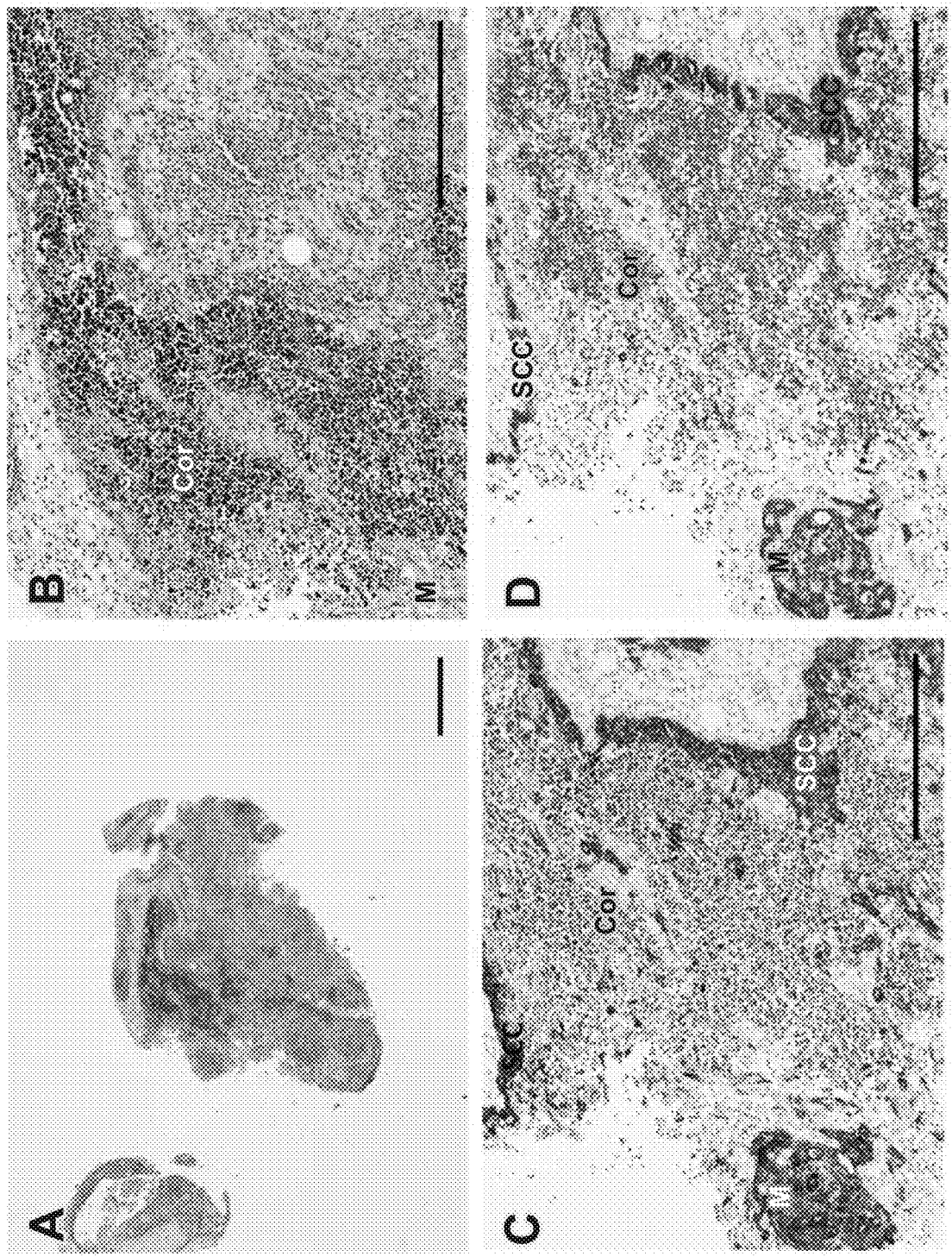

FIGS. 42A-D presents photomicrographs showing the architecture of cultured thymus, day 7. Hematoxylin and eosin (H&E) staining in FIGS. 42A-B shows marked depletion of thymocytes, although some cortical areas (Cor) still contain large numbers of thymocytes with retained nuclei. Pan-cytokeratin (AE1/AE3) in FIG. 42C and cytokeratin 14 (CK14) immunohistochemistry in FIG. 42D show condensation of the thymic epithelium in the subcapsular cortex (SCC) and in the medulla (M). Brown color in FIGS. 42C-D indicates a positive reaction with antibody. Scale bar represents 1 mm in FIG. 42A and 500 µm in FIGS. 42B-D.

FIGS. 43A-D present photomicrographs showing the architecture of cultured thymus, day 9. FIGS. 43A-B show hematoxylin and eosin (H&E) staining. Few if any live T cells or thymic epithelial cells are present in the pale-staining area in FIG. 43A that is enclosed by the dotted line, which is almost completely necrotic (Necr). Most nuclei formerly present in this region have been degraded via karyolysis. Other areas where the nuclei from residual thymocytes have not been completely degraded continue to stain dark blue with hematoxylin. Arrow in FIG. 43B points to a Hassall body. FIG. 43C shows pan-cytokeratin (AE/AE3) immunoreactivity (brown); FIG. 43D shows cytokeratin 14 (CK14) immunoreactivity (brown). Scale bar represents 1 mm in FIG. 43A and 500 µm in FIGS. 43B-D.

Figure 44:
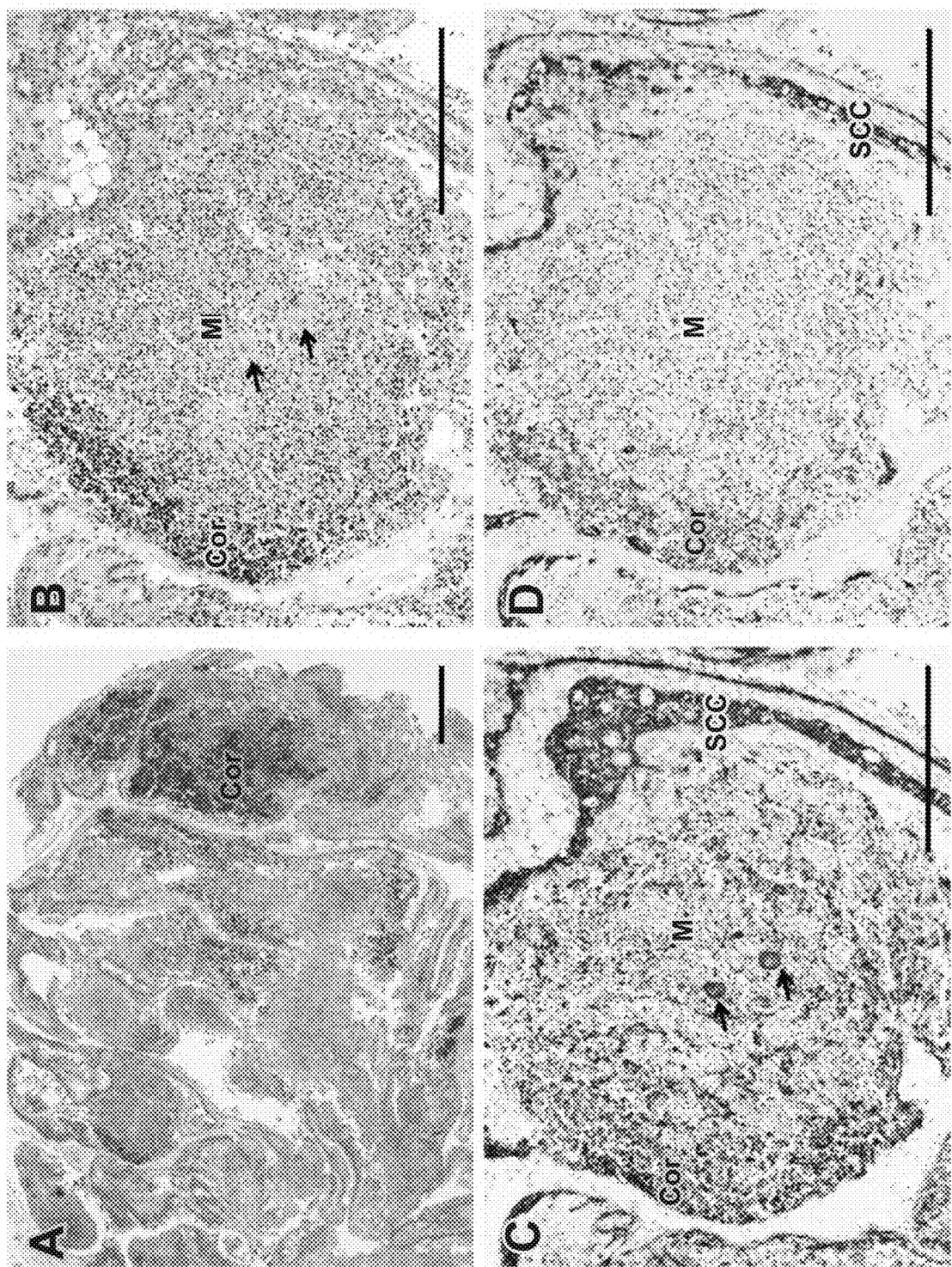

FIGS. 44A-D presents photomicrographs showing the architecture of cultured thymus, day 12. FIGS. 44A-B show hematoxylin and eosin (H&E) staining. At this time point, many thymocytes have either been lost from the tissue or have died and their nuclei have been dissolved, making the tissue more eosinophilic (pink). Some areas retain architecture characteristic of normal uncultured thymus with cortical-like areas (Cor) that stain more basophilic (blue) and medullary-like areas (M), although with greatly decreased thymocyte cellularity. FIG. 44C shows pan-cytokeratin (AE1/AE3) immunoreactivity (brown); FIG. 44D shows cytokeratin 14 (CK14) immunoreactivity (brown). At this time point, the sub-capsular cortex (SCC) has thickened and epithelial cells appear more prominent due to the decreased numbers of thymocytes present. Arrows point to representative Hassall bodies. Bar represents 1 mm in FIG. 44A and 500 µm in FIGS. 44B-D.

Figure 45:
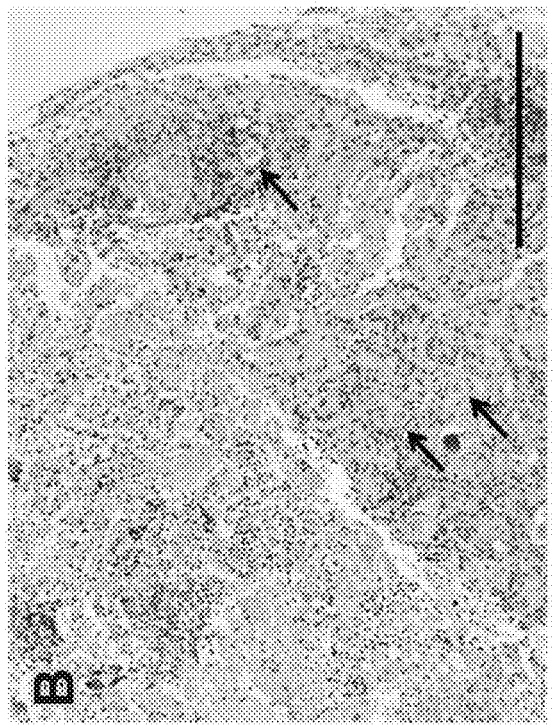
Figure 45:
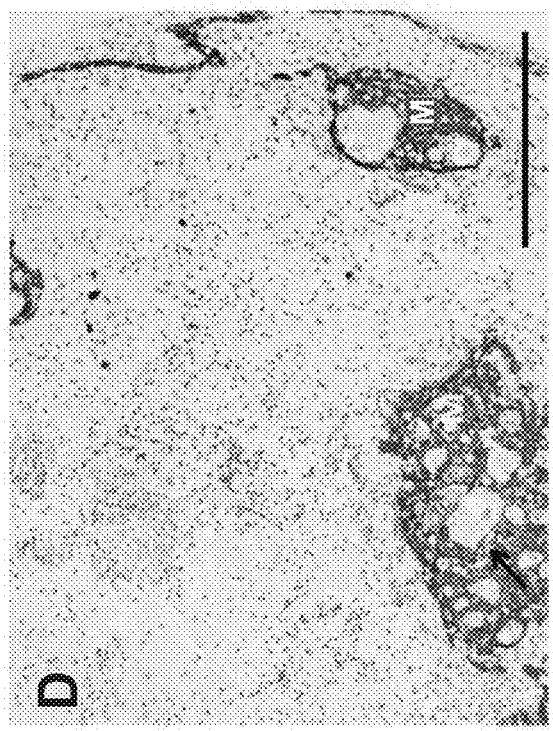
Figure 45:
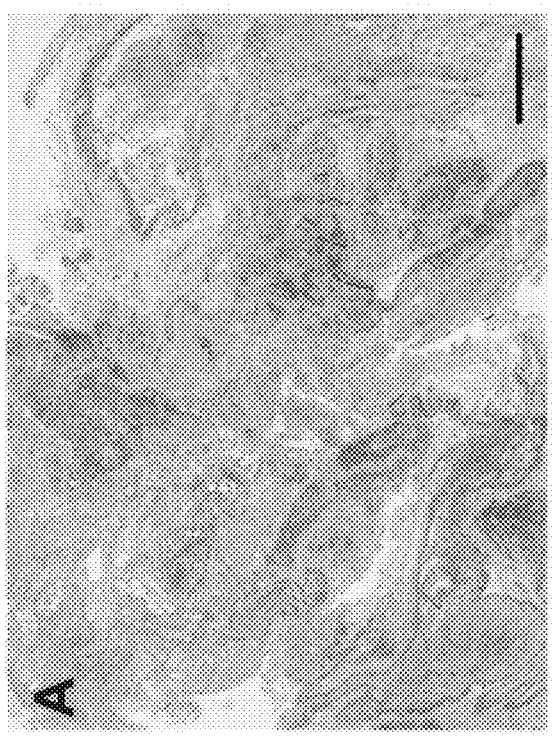
Figure 45:

FIGS. 45A-D presents photomicrographs showing the architecture of cultured thymus, day 20. FIGS. 45A-B shows hematoxylin and eosin (H&E) staining. At this time point, most thymocytes have either been lost from the tissue or have died and their nuclei have been dissolved, making the tissue more eosinophilic (pink). Large groups of residual thymocytes are rare, although scattered cells with nuclear characteristics of thymocytes are evident. FIG. 45C shows pan-cytokeratin (AE1/AE3) immunoreactivity (brown). Much of the epithelium present in formerly medullary areas (M) is condensed due to loss of medullary thymocytes, but scattered epithelial cells indicative of a residual light, lacy, three-dimensional network of thymic epithelial cells remain. In FIG. 45D, cytokeratin 14 (CK14) immunohistochemistry (brown) highlights former medullary areas and the subcapsular cortex. Arrows point to representative Hassall bodies. Scale bar represents 1 mm in FIG. 45A and 500 µm in FIGS. 45B-D.

Figure 46:
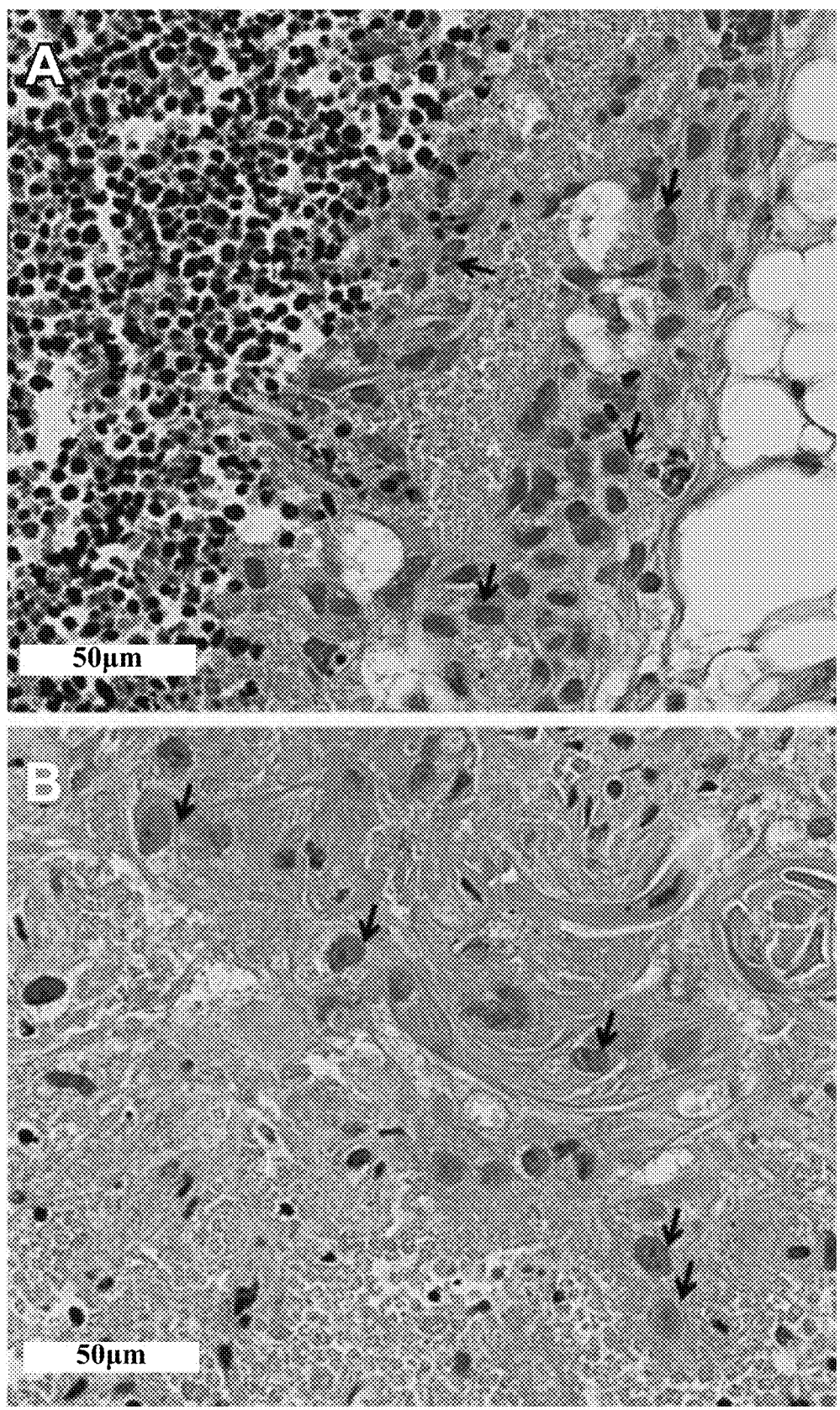

FIGS. 46A-B present photomicrographs showing examples of intact nuclei in thymus slices. Examples of intact thymic epithelial cell nuclei (arrows) are shown in the subcapsular cortex on day 9 (FIG. 46A) and in the medulla on day 21 (FIG. 46B). Hematoxylin and eosin stain; scale bar represents 50 µm.

Figure 47:
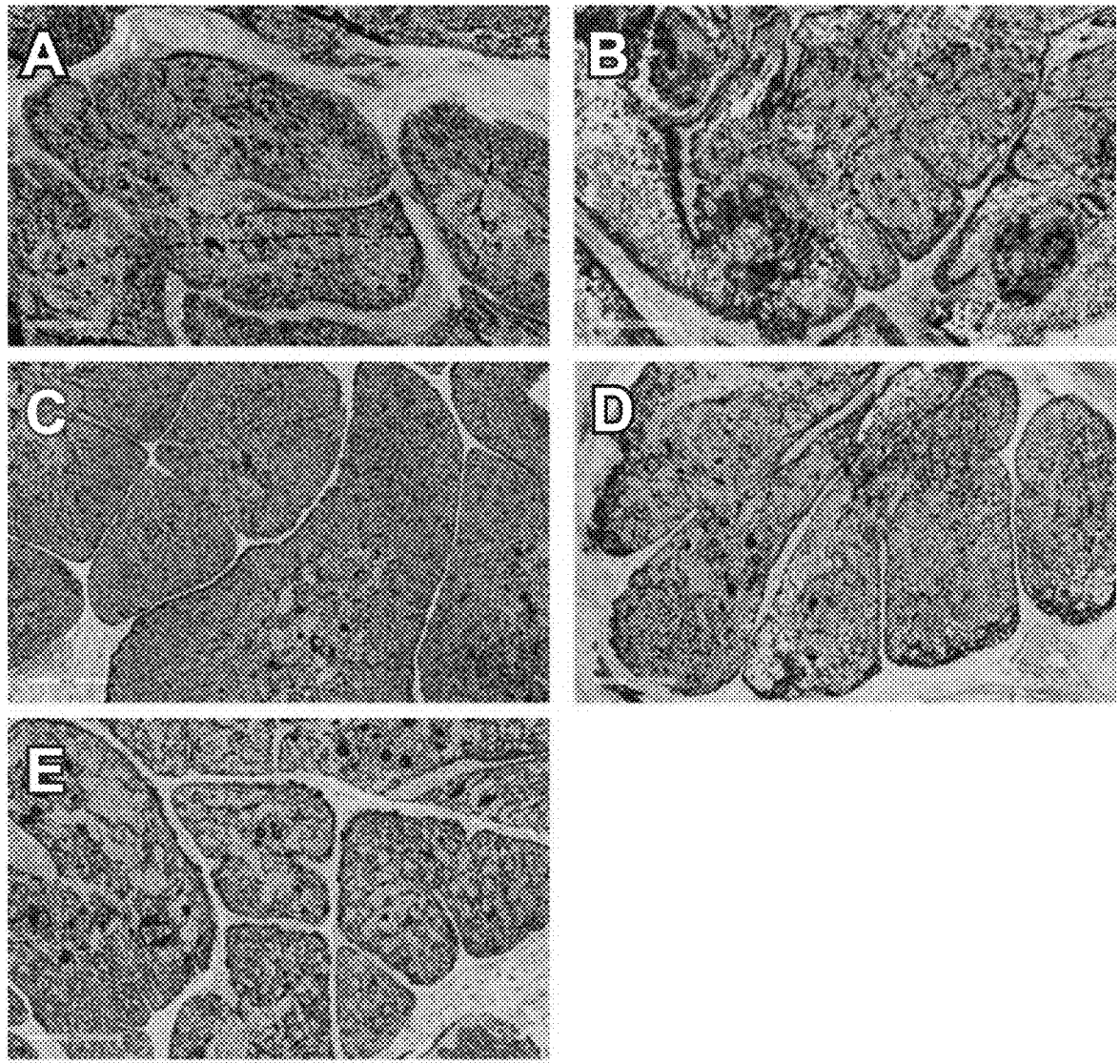

FIGS. 47A-E present photomicrographs showing a comparison of the thymic epithelial network of cultured thymus tissue at different time points. FIG. 47A shows day 0, FIG. 47B shows day 5, FIG. 47C shows day 9, FIG. 47D shows day 12, and FIG. 47E shows day 21. Although there are time point-related differences in thymocyte depletion and the amount of necrosis such that the tissue become less basophilic (blue) with time, the structure of the thymic epithelial network (brown) remains intact as the culture progresses. Both cortical and medullary epithelium may condense as intervening thymocytes are depleted. Brown color indicates a positive reaction with a cocktail of anti-cytokeratin antibodies (AE/AE3); hematoxylin counterstain. Scale bar represents 400 µm.

Figure 48:
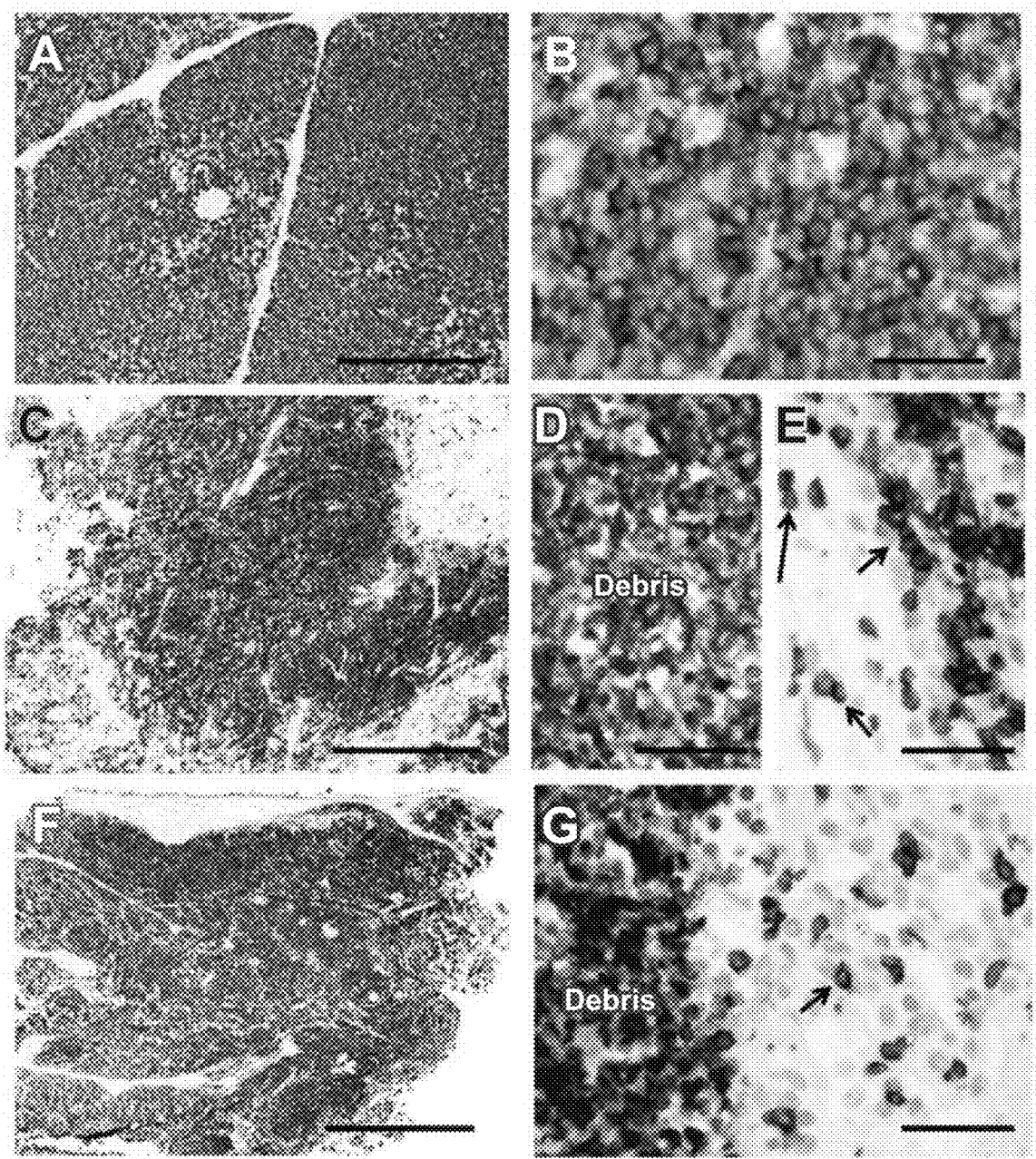
Figure 48:
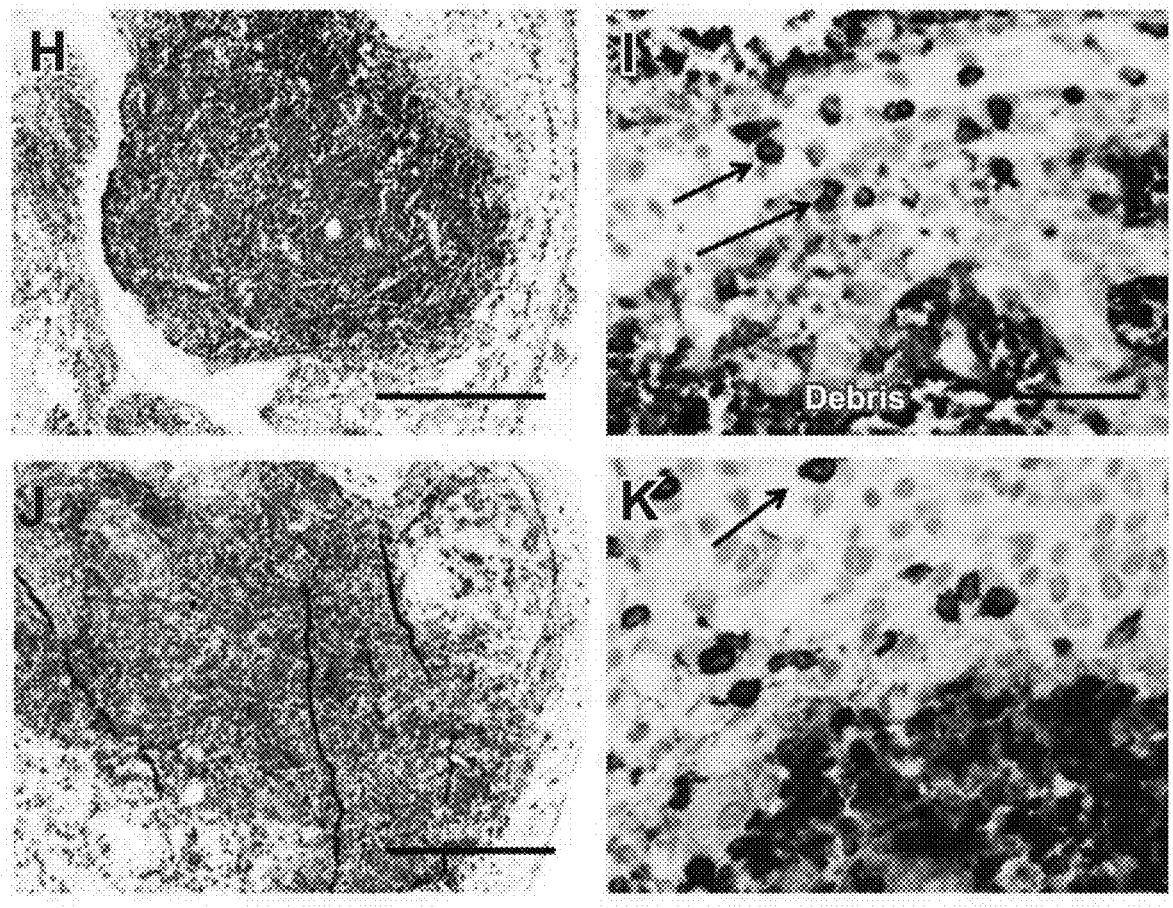
Figure 49:
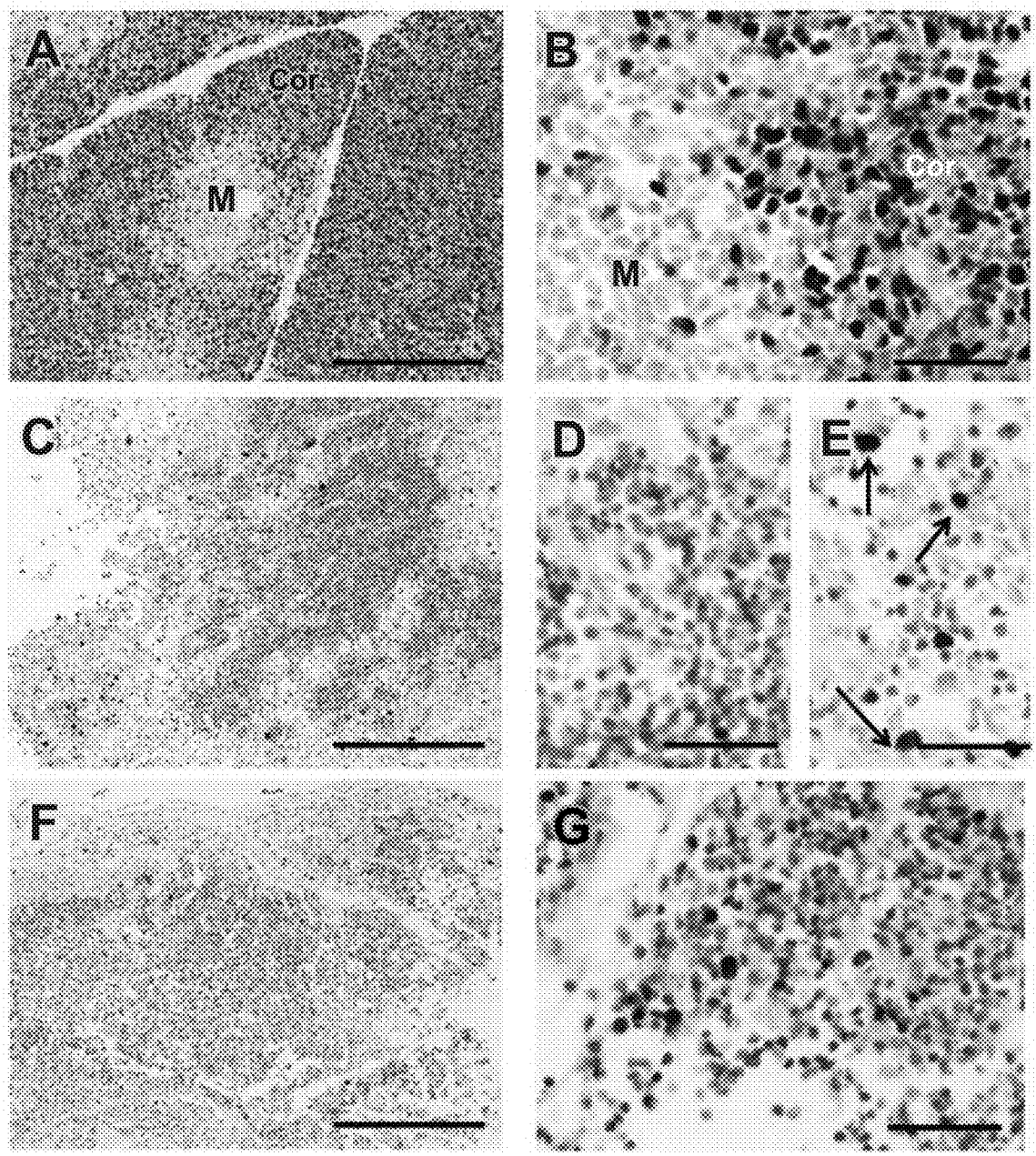
Figure 49:
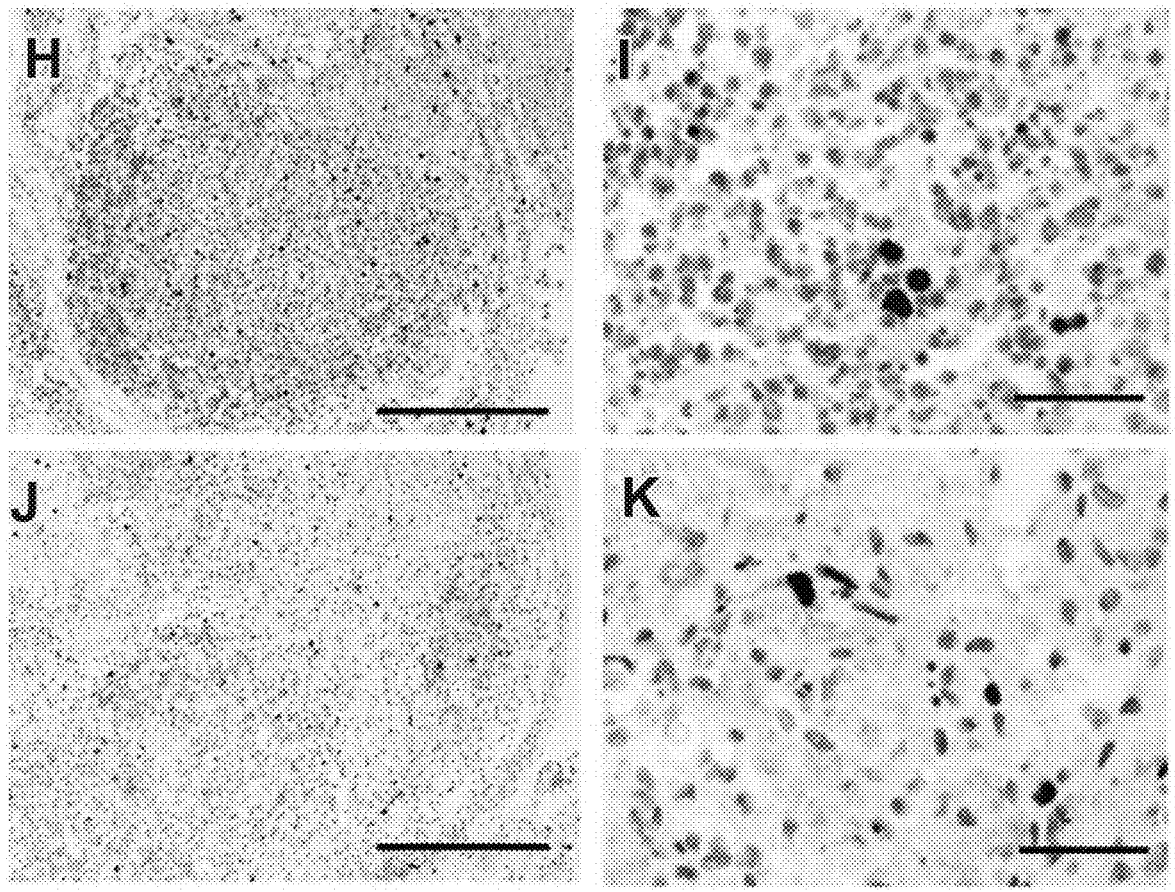
Figure 50:
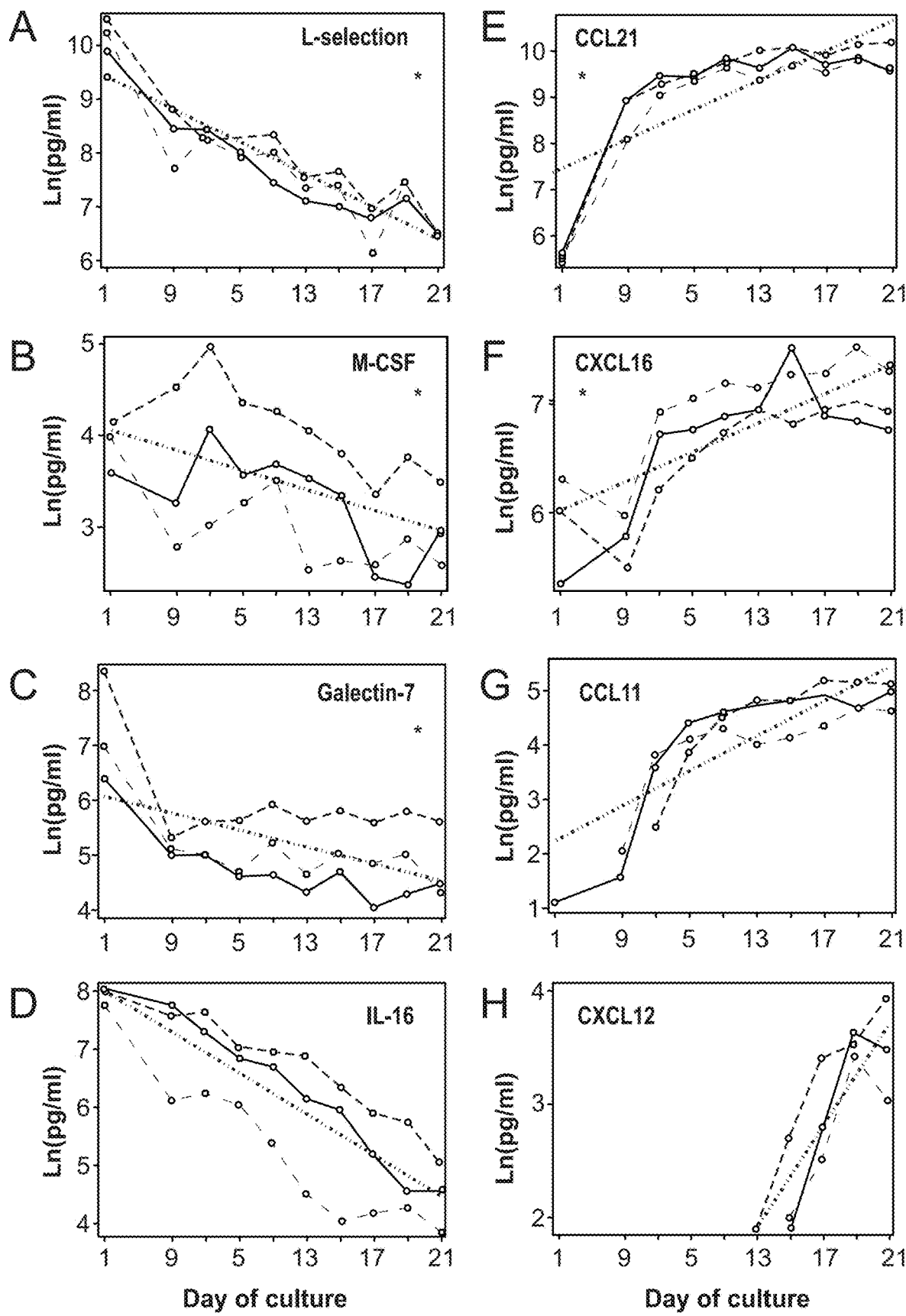

FIGS. 48A-K presents photomicrographs showing examples of CD3 immunohistochemistry in thymus slices as a function of time in culture. FIGS. 48A-B shows that on day 0, essentially all immature T cells in the cortex and more mature cells in the medulla react strongly with CD3 antibody. Higher magnification (FIG. 48B) shows pale blue nuclei surrounded by a ring of brown immunoreactivity, consistent with membrane expression of CD3. In FIGS. 48C-E, tissue still shows extensive reactivity with CD3 antibody on day 7. However, FIGS. 48D-E shows that when viewed under higher magnification, the majority of the immunoreaction (brown) is associated with debris from dead thymocytes, as most brown foci lack evidence of nuclei (FIG. 48D). Small foci of cells that demonstrate intact nuclei and membrane staining (arrows) can still be identified in areas away from the debris (FIG. 49E). As cultures progress through day 9 (FIGS. 48F-G), day 12 (FIGS. 48H-I), and day 21 (FIGS. 48J-K), reactivity with thymocyte cellular debris remains strong, making it difficult to reliably detect potentially intact cells amidst the debris. The slices shown are all from a single lot that is representative of multiple lots examined at these time points. Scale bar represents 500 µm in FIG. 48A, FIG. 48C, FIG. 48F, FIG. 48H, and FIG. 48J, and 50 µm in FIG. 48B, FIG. 48D, FIG. 48E, FIG. 48G, FIG. 48, and FIG. 48K.

FIGS. 49A-K presents photomicrographs showing examples of Ki-67 immunohistochemistry in thymus slices as a function of time in culture. The slices shown are all from a single lot that is representative of multiple lots examined at similar time points. FIGS. 49A-B shows that on day 0, the nuclei of the majority of immature T cells in the cortex (Cor) react strongly with antibody specific for Ki-67. Higher magnification (FIG. 49B) shows strong positive reactivity with the nuclei of cortical thymocytes (brown), whereas only rare lymphocytes in the medulla (M) react with Ki-67 antibody. FIGS. 49C-E show that by day 7, the nuclei of most thymocytes that remain in cortical areas are small with indistinct nuclear borders consistent with apoptosis, and they fail to react with Ki-67-specific antibody. The cells that react with antibody (FIG. 49E, arrows) have larger nuclei, suggesting that they are thymic epithelial cells. A similar lack of Ki-67 labeling of residual thymocyte nuclei is seen on days 9 (FIGS. 49F-G), 12 (FIGS. 49H-I) and 21 (FIGS. 49J-K). Scale bar represents 500 µm in FIG. 49A, FIG. 49C, FIG. 49E, FIG. 49G, and FIG. 49I and 50 µm in FIG. 49B, FIG. 49D, FIG. 49F, FIG. 4950H, and FIG. 49J.

Figure 1:
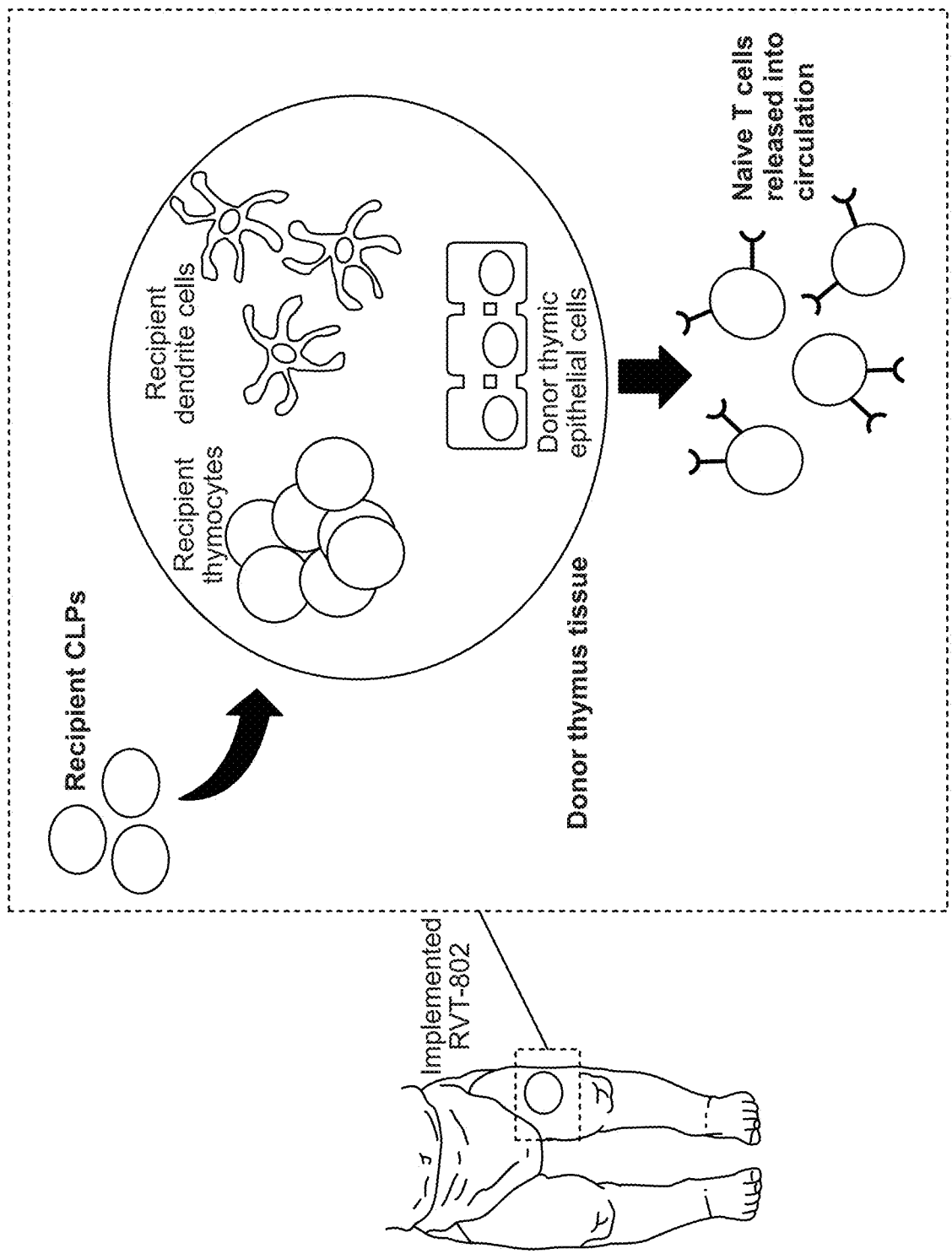
FIG. 1 describes the manner in which allogeneic, cultured postnatal thymus tissue-derived product (e.g., CTT, RVT-802) provides for immune reconstitution in congenital athymia following implantation.
Figure 2:
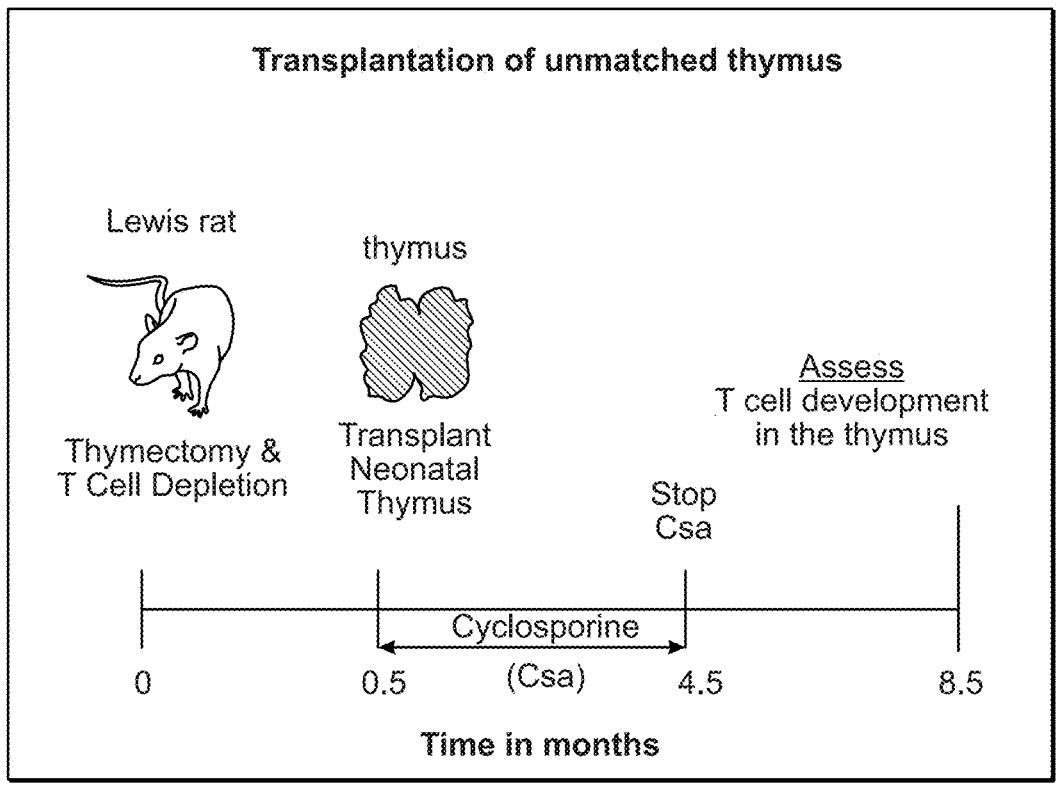
FIG. 2 shows a schematic of the steps for reconstituting the immune system in a rat, as described elsewhere in Example 5, by removing the thymus in an immunologically normal Lewis rat, administering an antibody to kill the recipient rat's T cells, implanting cultured neonatal thymus tissue from a donor rat into the recipient rat, administering an immunosuppressive agent for about 4 months and evaluating T cell development in the recipient rat. Of note, all rats in the treatment group had over 10% naïve T cells prior to stopping the cyclosporine.
Figure 3:
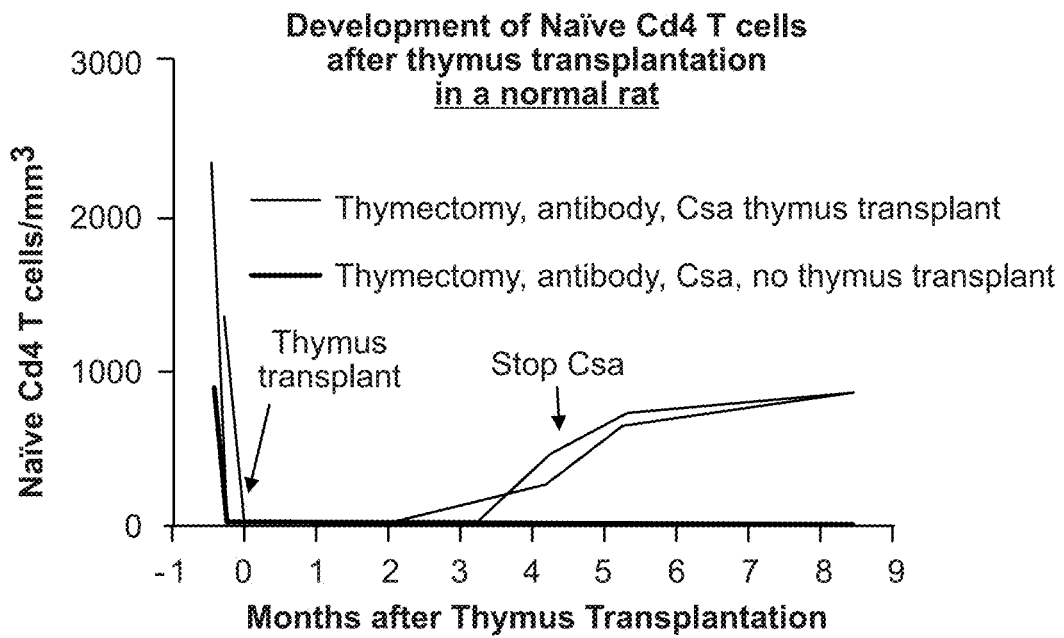
FIG. 3 shows the development of naïve T cells in two experimental recipient rats of Example 5 (rising lines on right) versus two controls rat not receiving a thymus tissue implant (thick lines at baseline).

FIG. 50A to FIG. 50H shows plots of selected soluble molecules detected in conditioned media from human thymus organ cultures. FIG. 50A is a plot of L-selectin in Ln/pg versus days in culture; FIG. 50B is a plot of M-CSF in Ln/pg versus days in culture; FIG. 50C is a plot of galectin-7 in Ln/pg versus days in culture; FIG. 1D is a plot of IL-16 in Ln/pg versus days in culture; FIG. 50E is a plot of CCL21 in Ln/pg versus days in culture; FIG. 50F is a plot of CXCL16 in Ln/pg versus days in culture; FIG. 50G is a plot of CCL11 in Ln/pg versus days in culture; and FIG. 50H is a plot of CXCL12 in Ln/pg versus days in culture.

Figure 51:
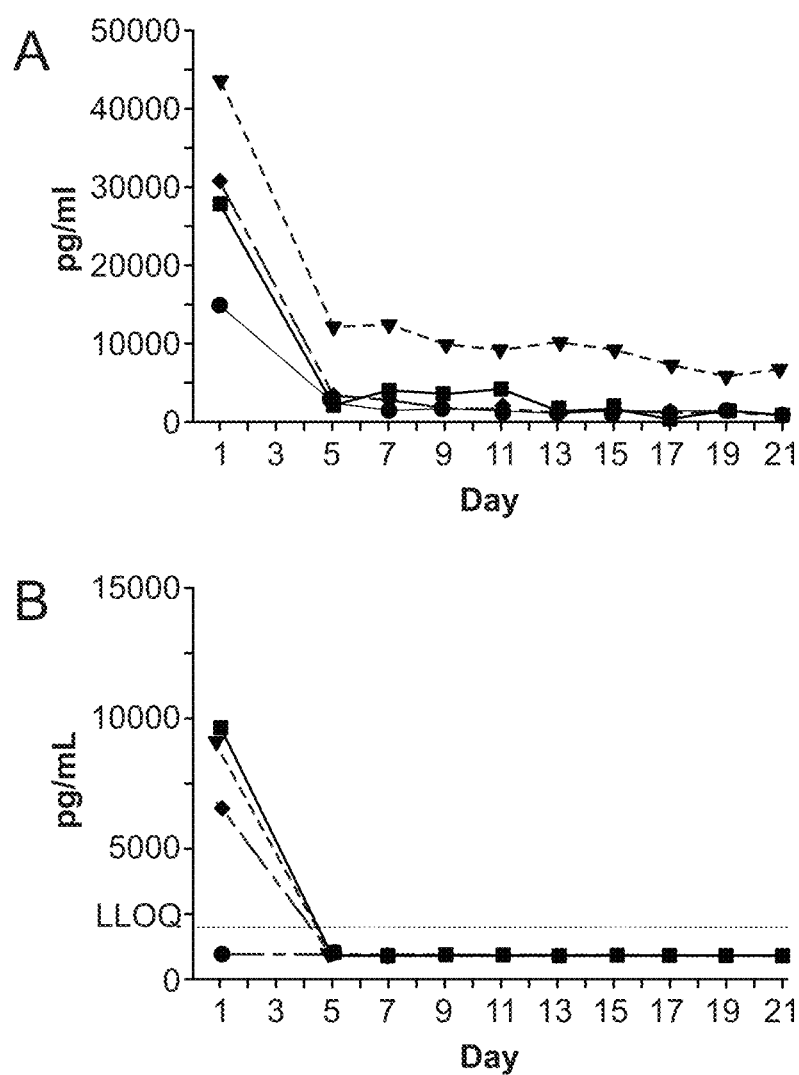

FIG. 51 shows plots assessing thymocyte content in cultured slices of human thymus in pg/ml from days 1 to 21 of the culturing process.

Figure 52:
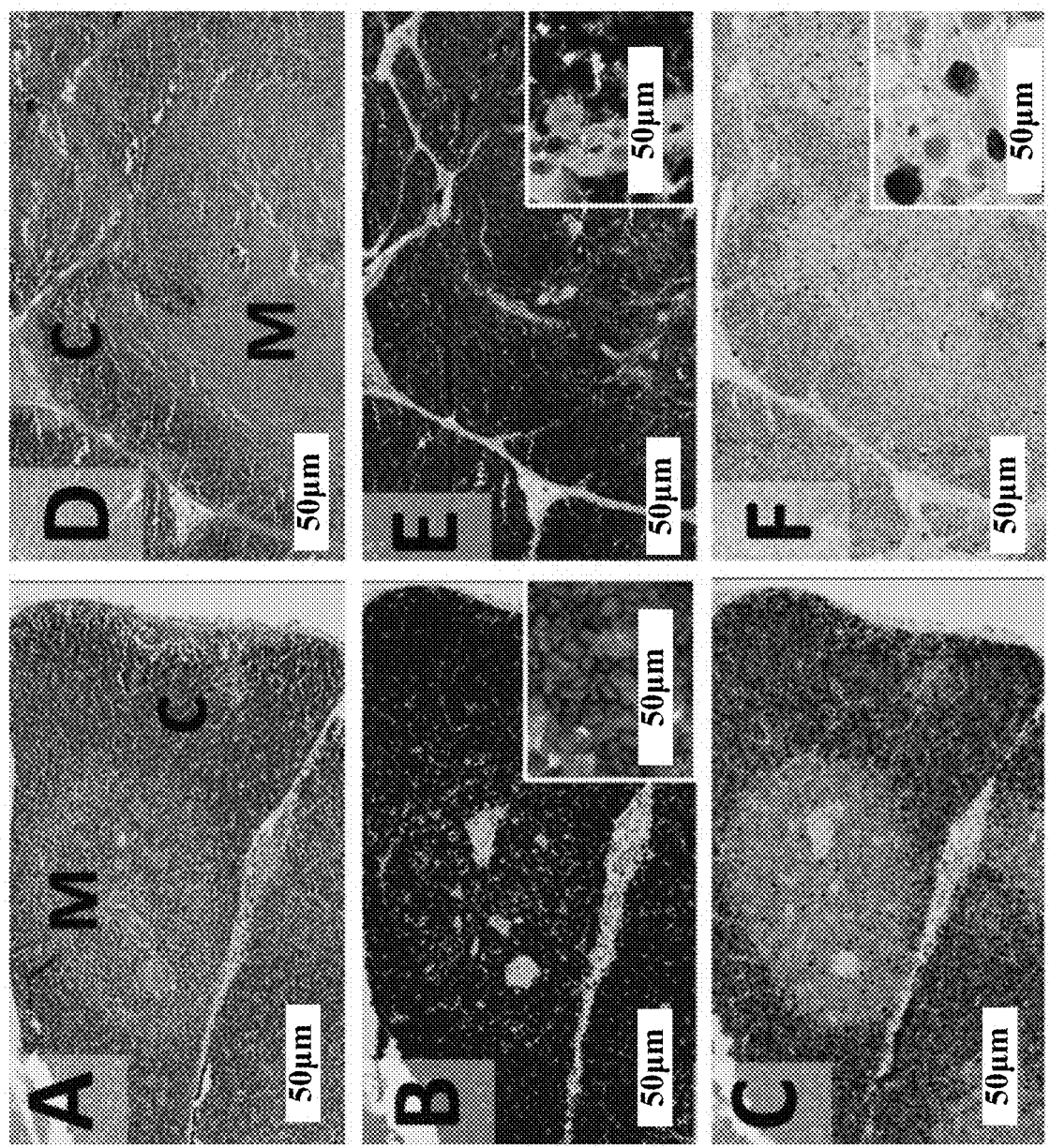

FIG. 52 shows photos of the immunohistochemical assessment of viable thymocytes in cultured slices of human thymus tissue as a function of time. FIG. 52A is a photo of the immunohistochemistry with anti-CD3 antibodies that identify cells as T lineage and with anti-Ki-67 antibody that identifies proliferating cells, demonstrates the rapid loss of thymocyte viability early in culture. FIG. 52B is a photo on day 0 depicting the plasma membranes of essentially all immature T cells in the cortex and the medulla appear strongly reactive with anti-CD3 in a membrane pattern. FIG. 52C depicts immunohistochemistry using antibody specific for the Ki-67 proliferation marker shows abundant reactivity with cortical thymocytes on day. FIG. 52D shows histology of cultured thymus on day 9, using hematoxylin and eosin stain. The decreased basophila (blue color) is indicative of loss of donor thymocytes during culture; FIG. 52E depicts after several days of culture, the majority of the brown color is due to the anucleate, but still immunoreactive, debris that remains after dead thymocytes undergo karyolysis/nuclear dissolution. FIG. 52F depicts thymocyte death that occurs during organ culture results in Ki-67 immunoreactivity only with larger cells morphologically consistent with TE cells at later time points during culture.

Figure 53:
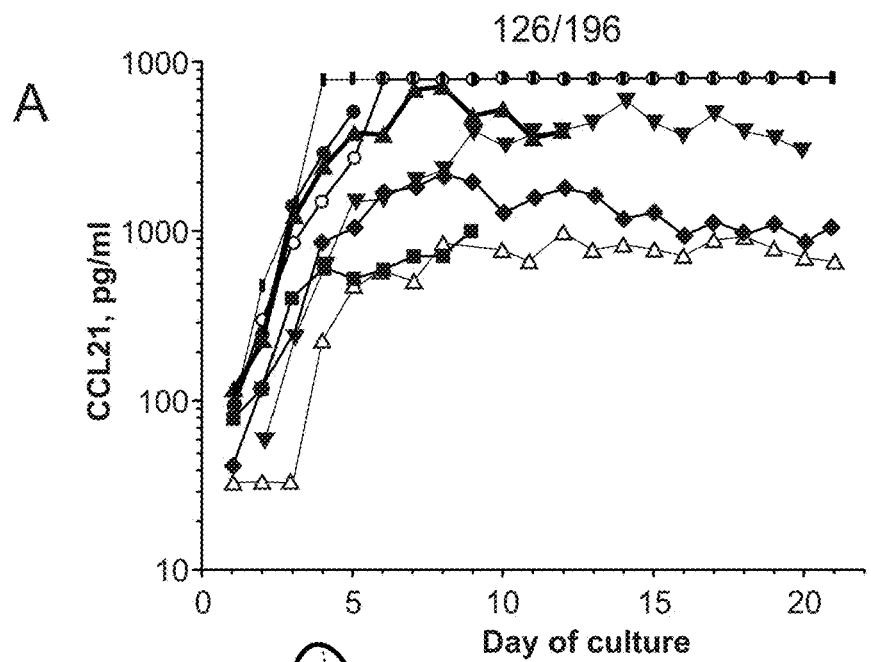
Figure 53:
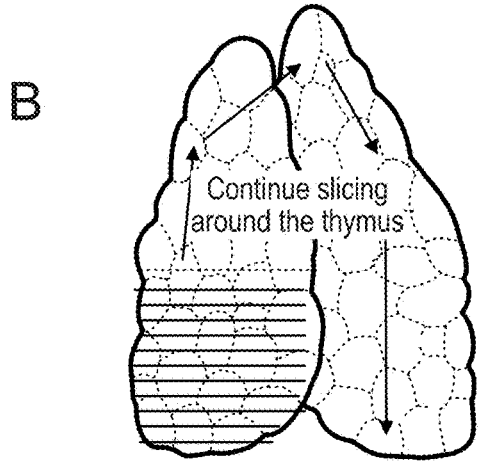
Figure 53:
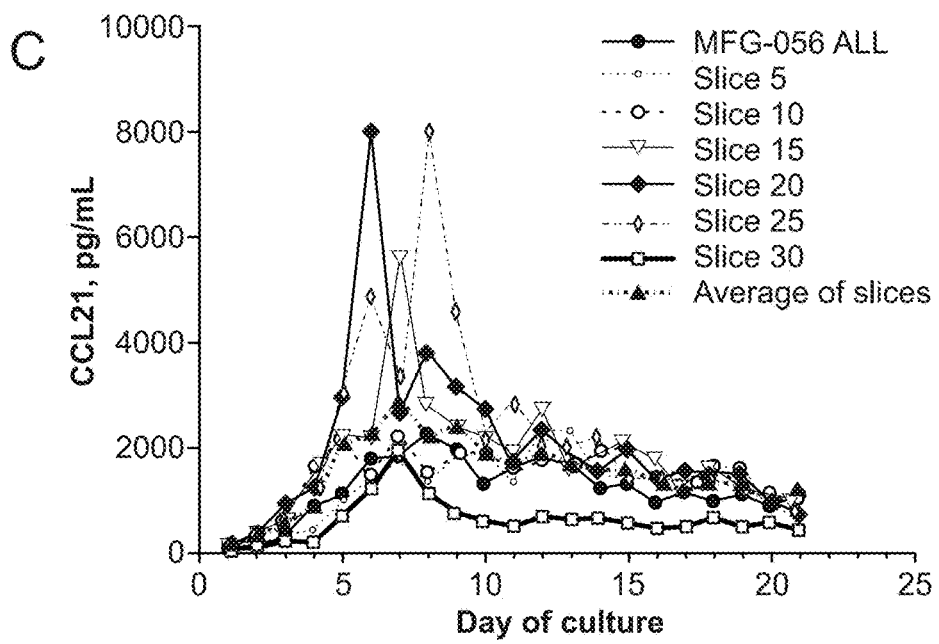

FIG. 53A shows a plot of CCL21 levels in pg/ml of conditioned media from cultured thymus tissue versus the number of days in culture. FIG. 53B is an illustration of the slicing procedure for thymus tissue to be subjected to conditioning. FIG. 53C is a plot of the secretion of CCL21 by slice of thymus organ tissue cultures as a function of time.

Figure 54:
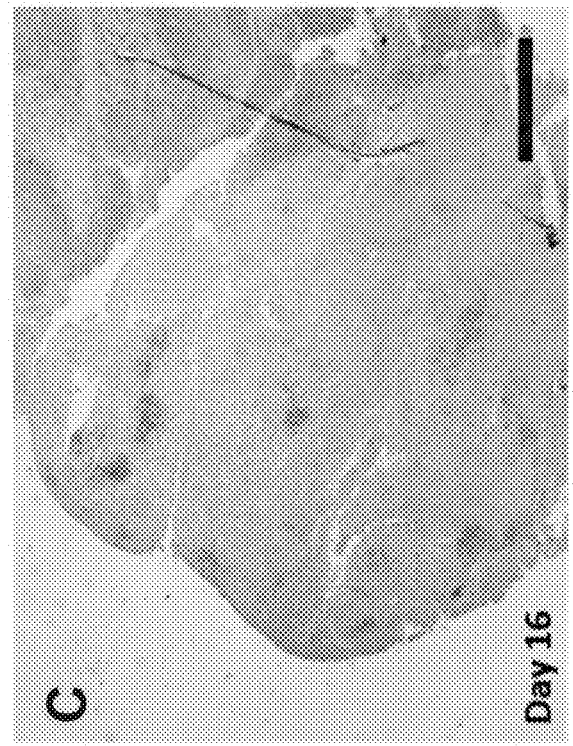
Figure 54:
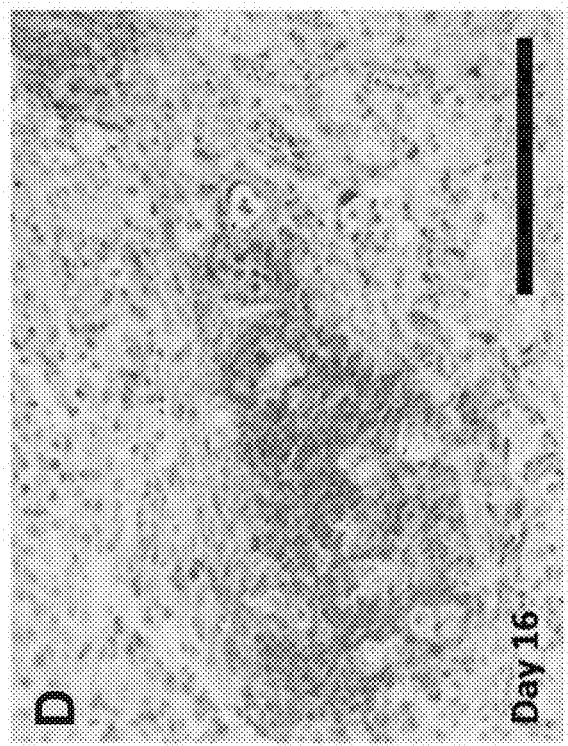
Figure 54:
Figure 54:
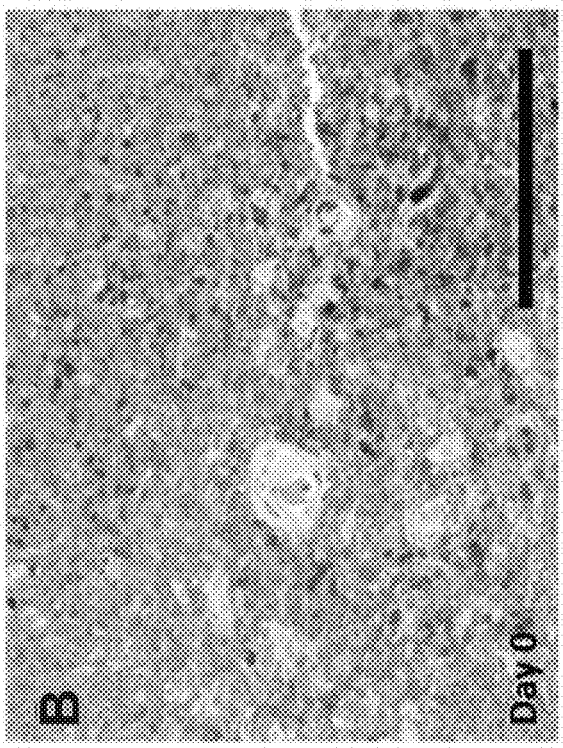

FIG. 54A to FIG. 54D are photographs depicting the immunoreactivity in cultured and non-cultured thymus tissue. FIG. 54A is a photograph of the medullary region, but also includes TECS scattered throughout the cortex at Day 0 of culturing; FIG. 54B is as photograph of the medullary region, but also includes TECS scattered throughout the image at Day 16 of culturing; FIG. 54C is a photograph of TECs in medullary regions as well as in scattered TECs in cortical areas on Day 0 of culturing. FIG. 54D is a photograph of TECs in medullary regions as well as in scattered TECs in cortical areas on Day 16 of culturing.

FIG. 55A to FIG. 55F are plots of the expression of selected mRNAs in thymus tissue from across the lifespan. The relative amounts of the target mRNAs present in FFPE sections of thymus tissue were quantitated using the QuantiGene assay (Thermo Fisher) in accordance with the manufacturer's directions. Data for each target mRNA is presented normalized to GAPDH ("Not adjusted"), then further normalized to the % area containing thymic epithelium ("Adjusted by TE") or to the % area containing CD1a-positive cortical thymocytes ("Adjusted by Cor"). Data shown was obtained from 47 samples of thymus, derived from donors ranging in age from 5 days to 78 years. FIGS. 55A and 55B are thymus tissues obtained from donors ≤18 years (n=25) showed higher expression of mRNAs encoding the T cell marker CD3ε and the cortical thymocyte marker CD1a (FIG. 55A, B) relative to GAPDH when compared to donors older than 18 years, respectively. FIGS. 55C and 55D are photos depicting mRNAs encoding cytokeratins 8 (KRT8) and 14 (KRT14) were decreased relative to GAPDH in donors ≤18 years compared with older adults (FIG. 55C, D), respectively. FIG. 55E is a photo depicting unadjusted CCL21 gene expression which was consistently low relative to GAPDH in thymus from donors ≤18 years of age. FIG. 55F is a photo depicting unadjusted CXCL12 gene expression which was consistently low relative to GAPDH in thymus from donors ≤18 years of age.

FIG. 56 is a table of proteins present in spent media of thymic organ cultures, as determined by multiplex antibody arrays.

Figure 57:
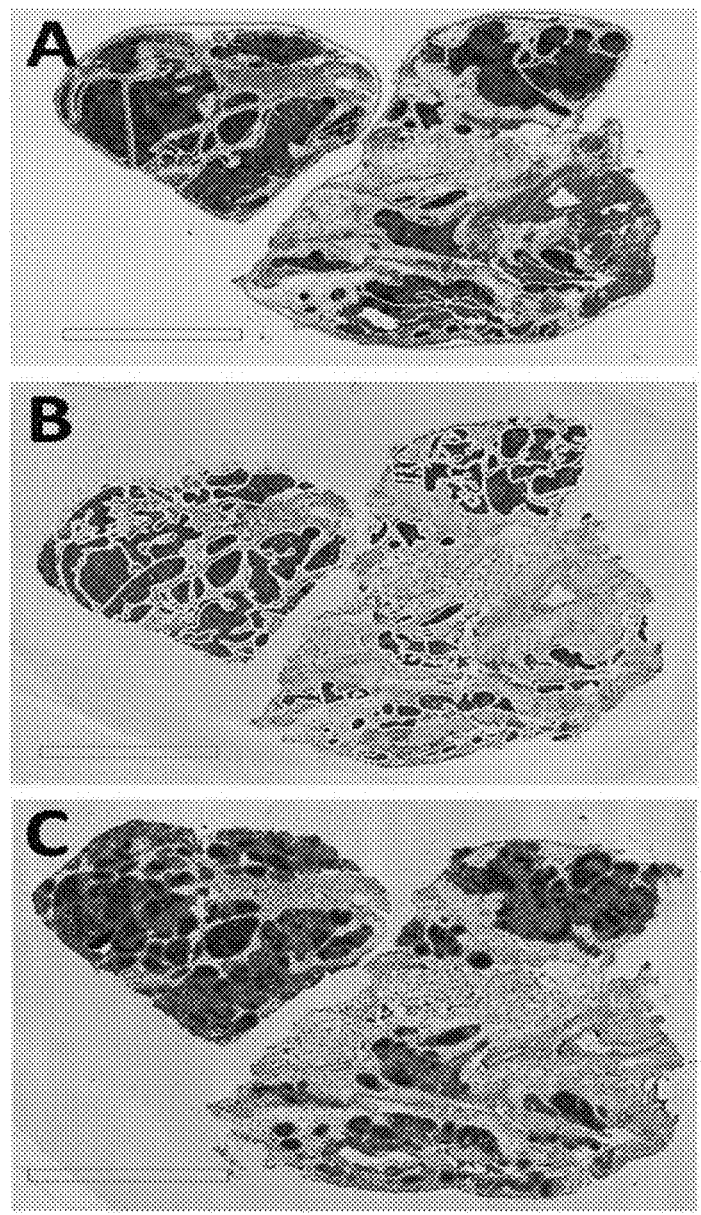

FIGS. 57A to 57C are photographs of morphological measurements of thymus tissues. Areas included in each measurement were outlined using the "pen tool" provided by the ImageScope software (Aperio Technologies, Leica Biosystems imaging, Inc.) in accordance with the manufacturer's instructions. FIG. 57A shows the total area of thymus tissue on the H&E-stained slide outlined in green. The proportion of this area that contains lymphocytes is further outlined in aqua. FIG. 57B is a photo showing areas containing thymic epithelium ("TE area") outlined in yellow on the section reacted with AE/AE3 cocktail to identify pan-cytokeratins. FIG. 57C is a photo showing Areas containing immature thymocytes ("cortical area") outlined in red on the section reacted with CD1a antibody. The thymus shown was derived from a 32 year old female at the time of aortic valve replacement surgery. Scale bar=4 mm for each panel. In panels of FIGS. 57B and 57C, brown color indicates a positive reaction with antibody.

Figure 58:
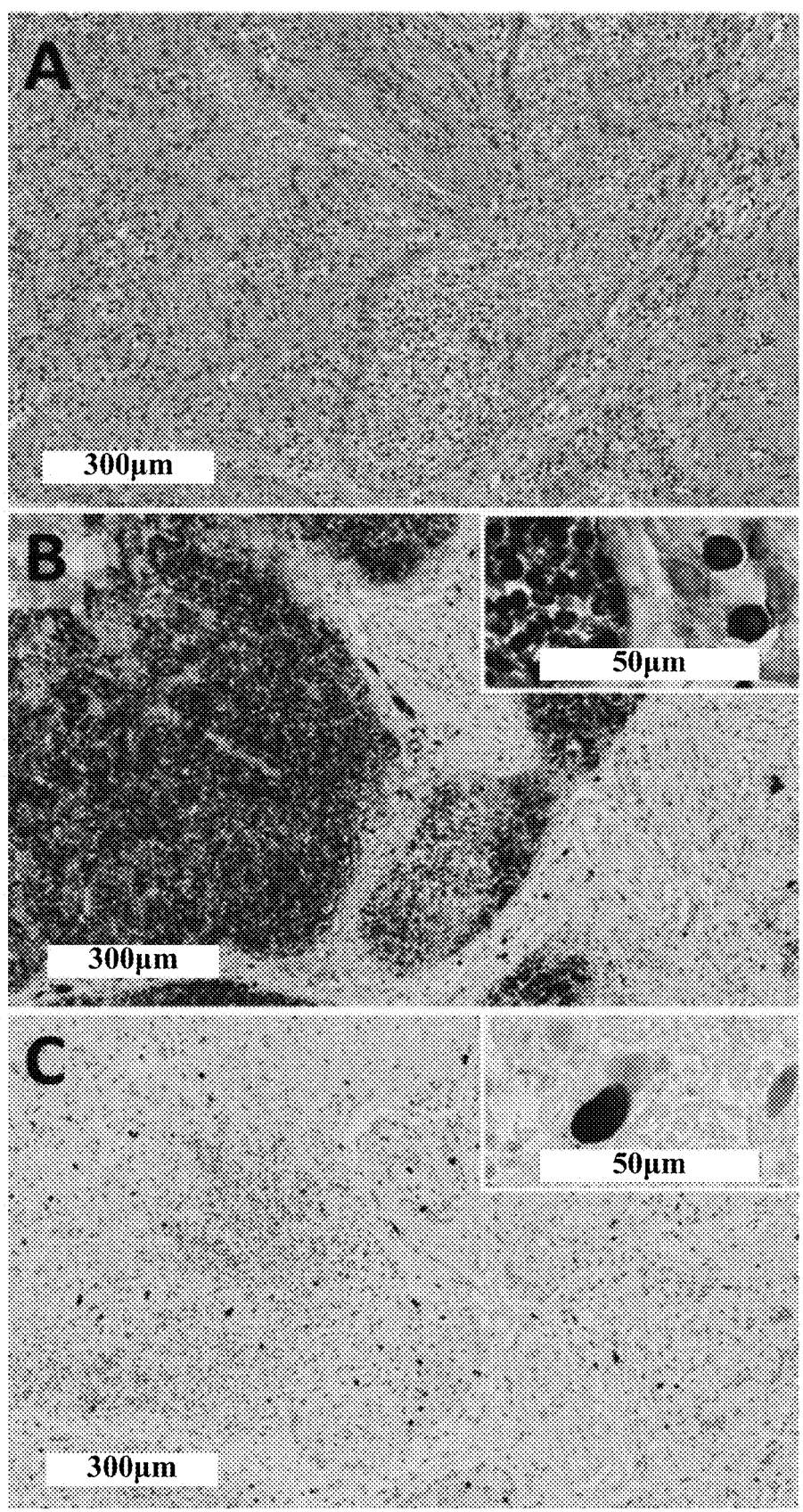

FIGS. 58A to 58C are photographs depicting the few viable thymocytes in thymus tissue slices cultured for 21 days. FIG. 58A is a photo depicting thymus slices containing few intact thymocytes on day 21 of culture, as indicated by the marked lack of basophilia (blue color) in H&E sections. FIG. 58B is a photo depicting cultured thymus tissue slices in which most of the strong brown immunoreaction seen with CD3 immunohistochemistry is associated with anucleate cellular debris, although dead thymocytes that exhibit nuclear and cytoplasmic staining characteristic of necrotic cells that have not yet undergone karyolysis (inset) are not uncommon. FIG. 58C is a photo depicting Ki-67 immunoreactivity on day 21 is limited to cells with larger nuclei that are characteristic of thymic epithelial cells. Bar represents 300 µm in the main panels and 50 µm in the insets.

FIGS. 59A to 59C are graphs showing characteristics of human thymus tissues used for gene expression analysis. FIG. 59A depicts the age and sex distribution of the thymus tissues studied, with the lower black-filled circles designating females, upper open circles designating males, and the middle gray circle designating the one donor of unknown sex. FIG. 59B plots the % area containing thymic epithelial cells as a function of age for this panel of thymus tissues. FIG. 59C plots the % area with active thymopoiesis as defined by CD1a-positive thymocytes as a function of age for this panel of thymus tissues.

Figure 60:

FIG. 60 is a photograph of freshly harvested thymus tissue.

Figure 61:
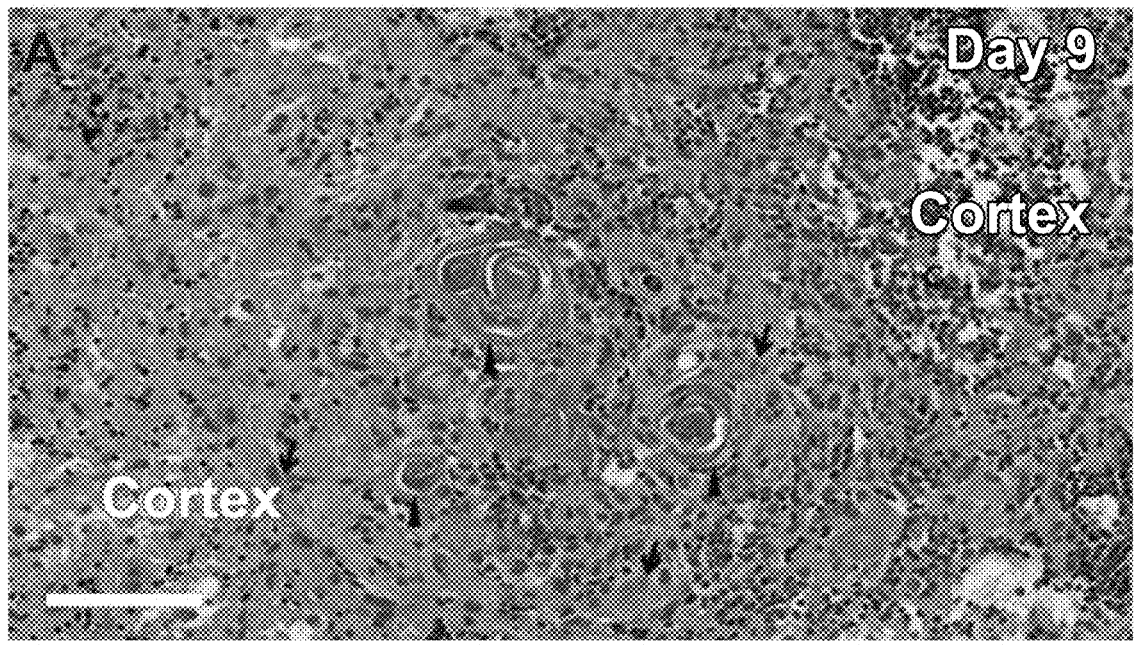
Figure 61:
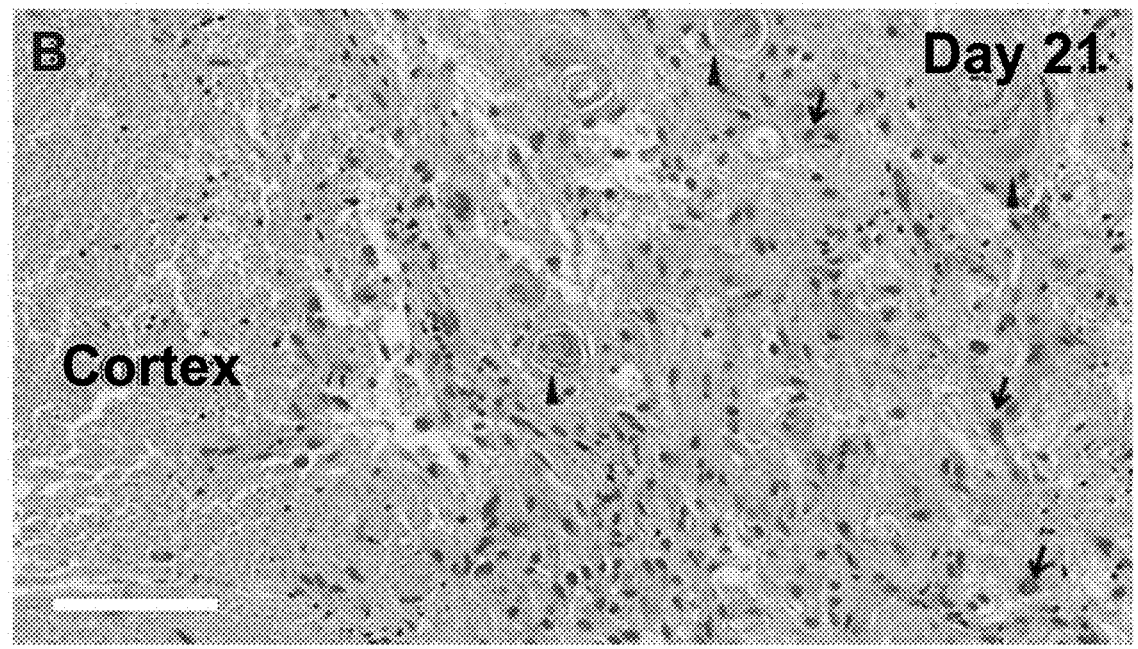

FIGS. 61A and 61B depict the histology of thymus tissue slides after exposure to forced degradation conditions of 10×PBS. FIG. 61A depicts the cortex at day 9 after exposure to forced degradation conditions. FIG. 61B depicts the cortex at day 21 after exposure to forced degradation conditions. In FIG. 61A the smear of blue is DNA released from cells. The majority of cells show evidence of degradation although small foci of cells with intact nuclei can be identified. Photo by Laura P. Hale, MD, PhD, Department of Pathology, Duke University.

Figure 62A:
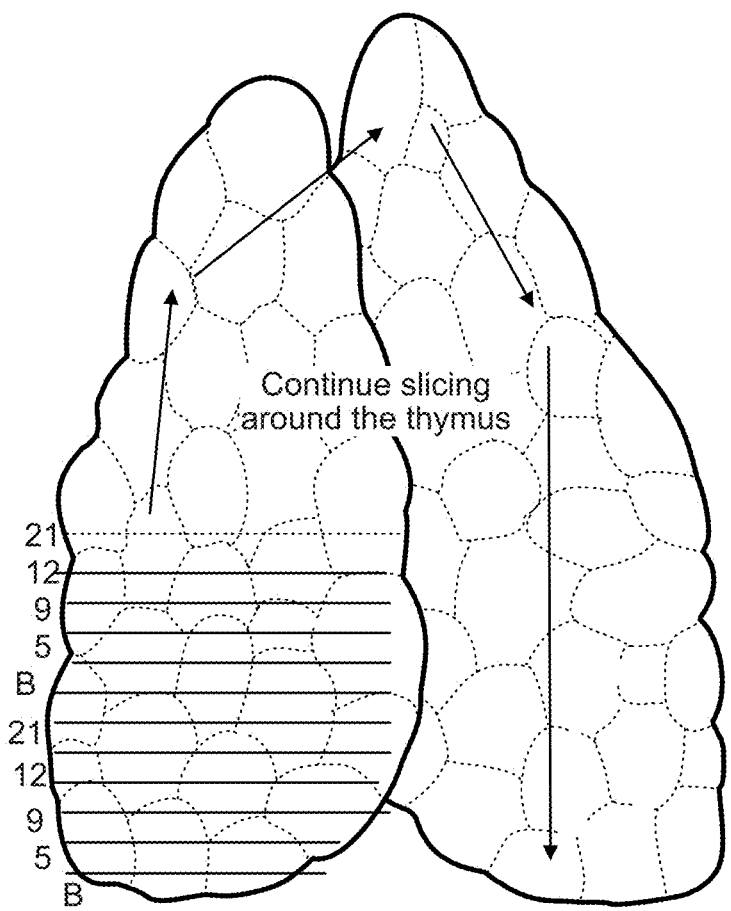
Figure 62B:
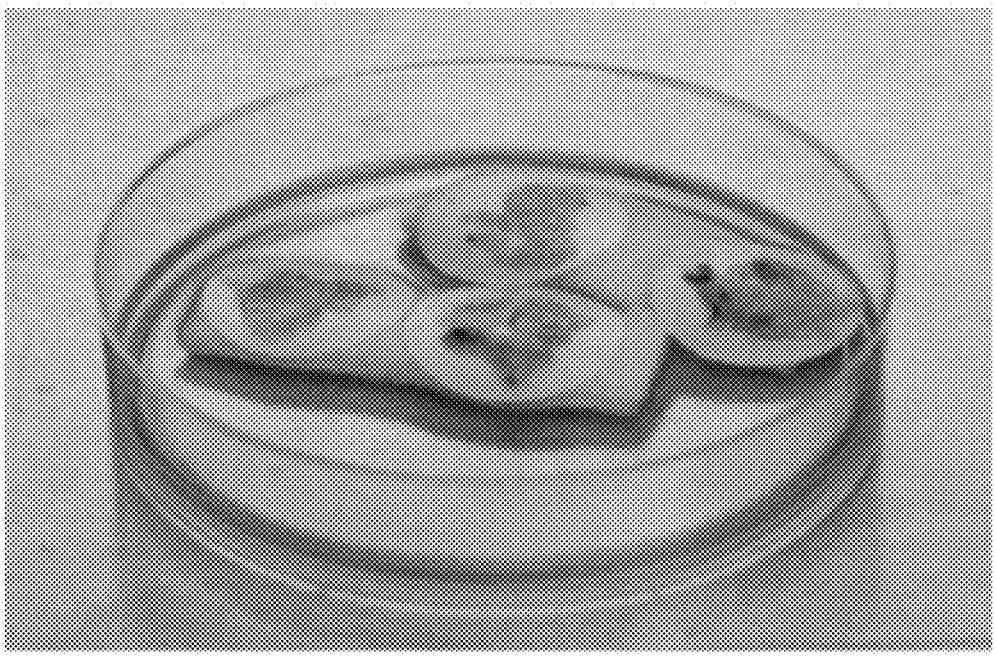

FIG. 62A shows a schematic showing the slicing of thymus tissue for characterization testing, as discussed in section [00520]. FIG. 62B is a figure showing slices of thymus tissue on cellulose filters on surgical sponges in a tissue culture dish as is used for culture of the thymus.

Figure 14:
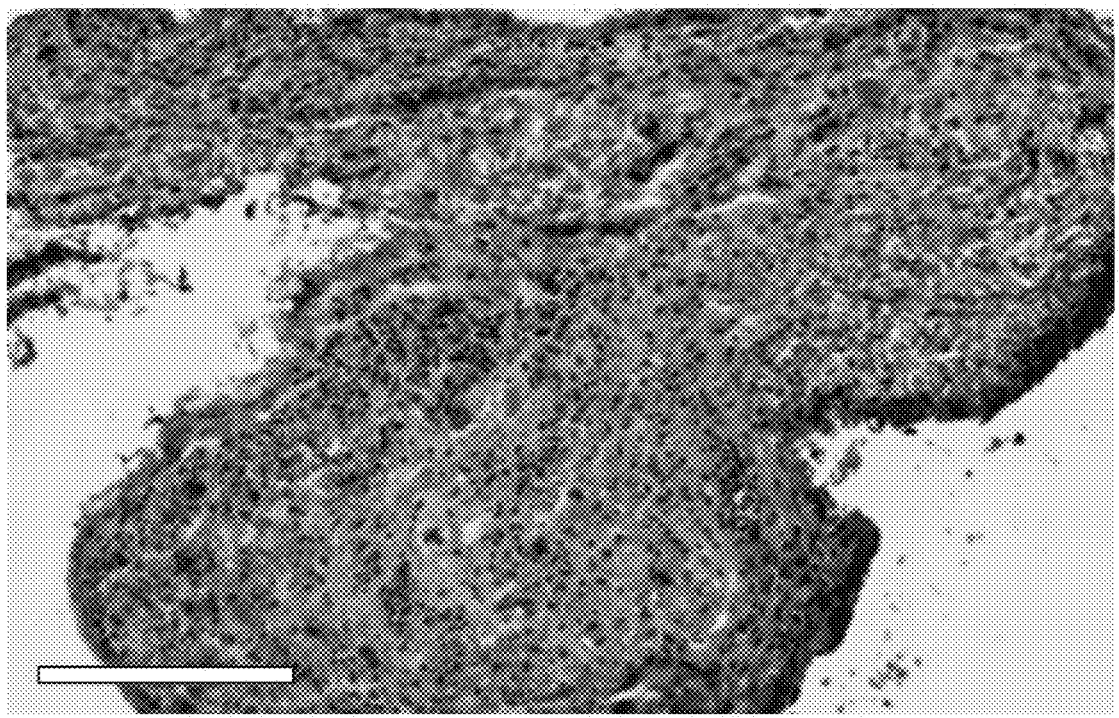
FIG. 14 Frozen section, H&E stained histology sections for clinical sample MLM219. This is a frozen section so the tissue looks different from paraffin embedded formalin fixed tissue that was cultured and presented above. Nevertheless, the important histologic characteristics of thymocyte depletion and robust viability of TEC are well represented. Photo by Laura P. Hale, MD, PhD, Department of Pathology, Duke University.
Figure 63:
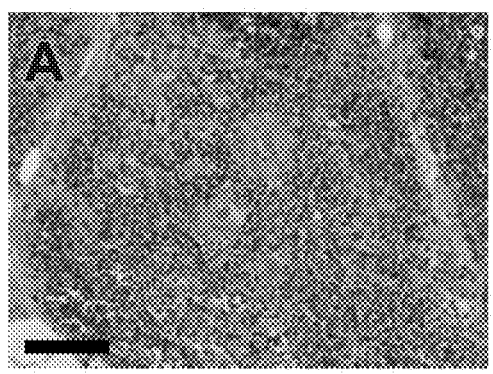
Figure 63:
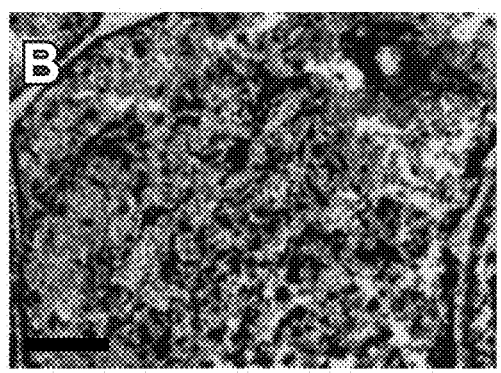
Figure 63:
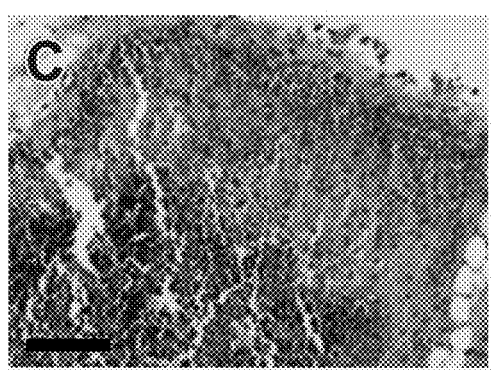
Figure 63:
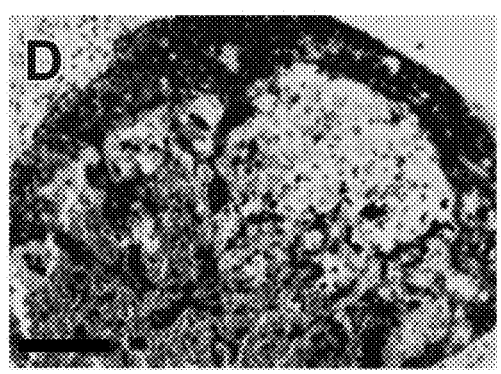
Figure 63:
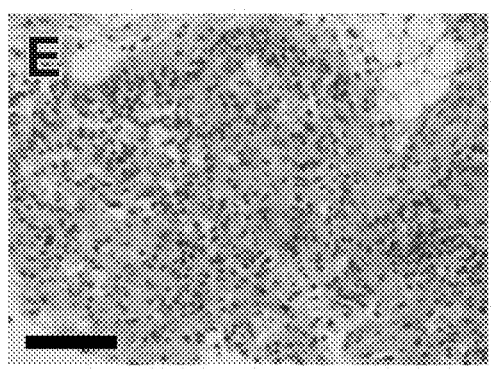
Figure 63:
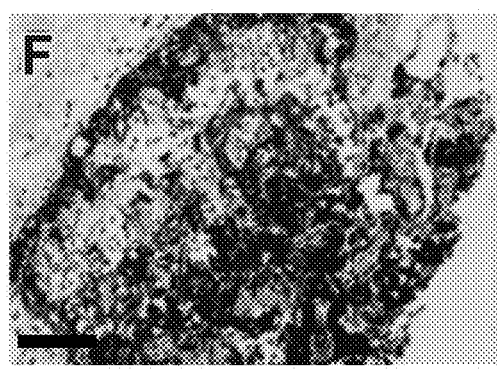
Figure 63:
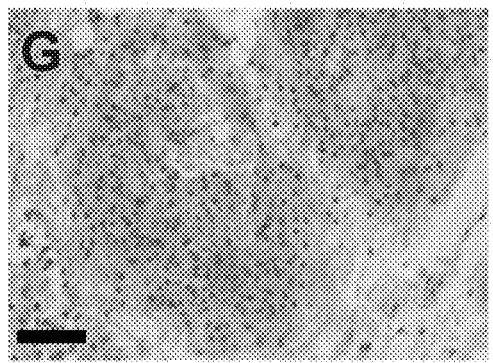
Figure 63:

FIGS. 63A to 63H depict histology testing of thymus tissue slices from a lot (MFG-056) of cultured thymus tissue on day 5, 9, 12 and 21 after harvest of the thymus from a donor. Hematoxylin and eosin-stained slices (left panels) and their corresponding reactivity with a cocktail of the anti-cytokeratin antibodies AE1/AE3 (right panels; brown color denotes positive reactivity) are shown at day 5 (FIG. 63A, FIG. 63B), day 9 (FIG. 63C, FIG. 63D), day 12 (FIG. 63E, FIG. 63F), and day 21 (FIG. 63G, FIG. 63H), respectively. Bars in the lower left of each panel represent 100 µm. Panels with H&E show progression depletion of T cells with time. FIG. 14E and FIG. 63F are predominantly epithelial cells. Condensation of the epithelium of the subcapsular cortex occurs as the thymocytes are depleted with time. Similar condensation occurs in medullary areas of the thymus. Photo by Laura P. Hale, MD, PhD, Department of Pathology, Duke University.

Figure 64A:
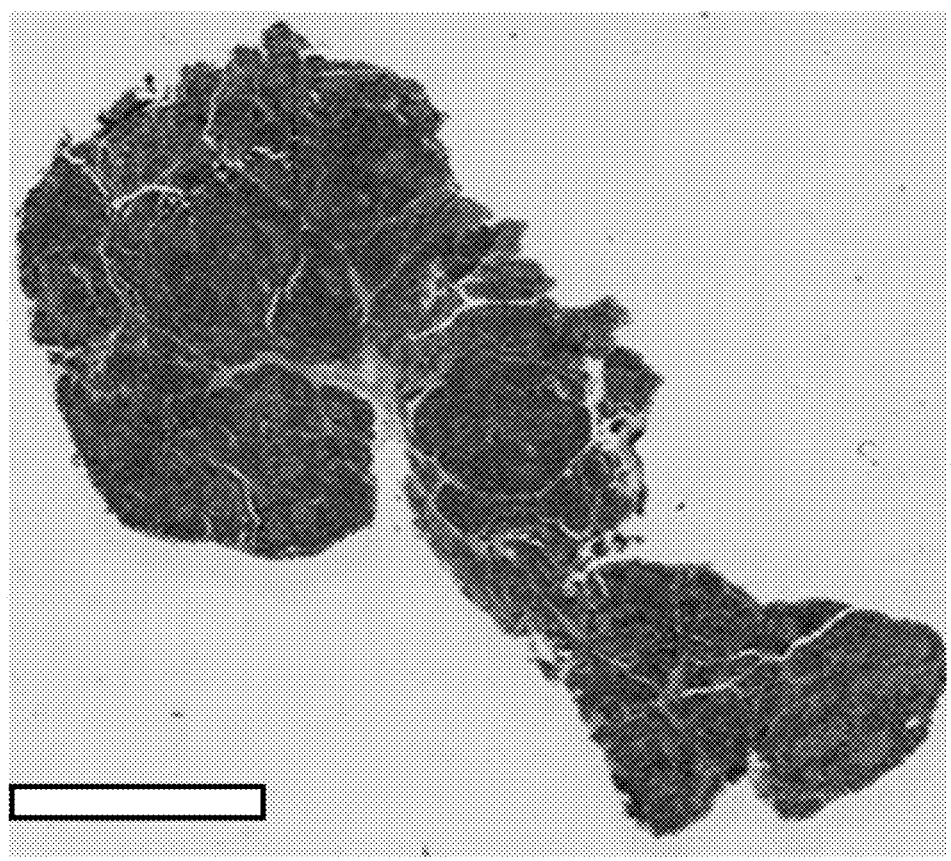
Figure 64B:
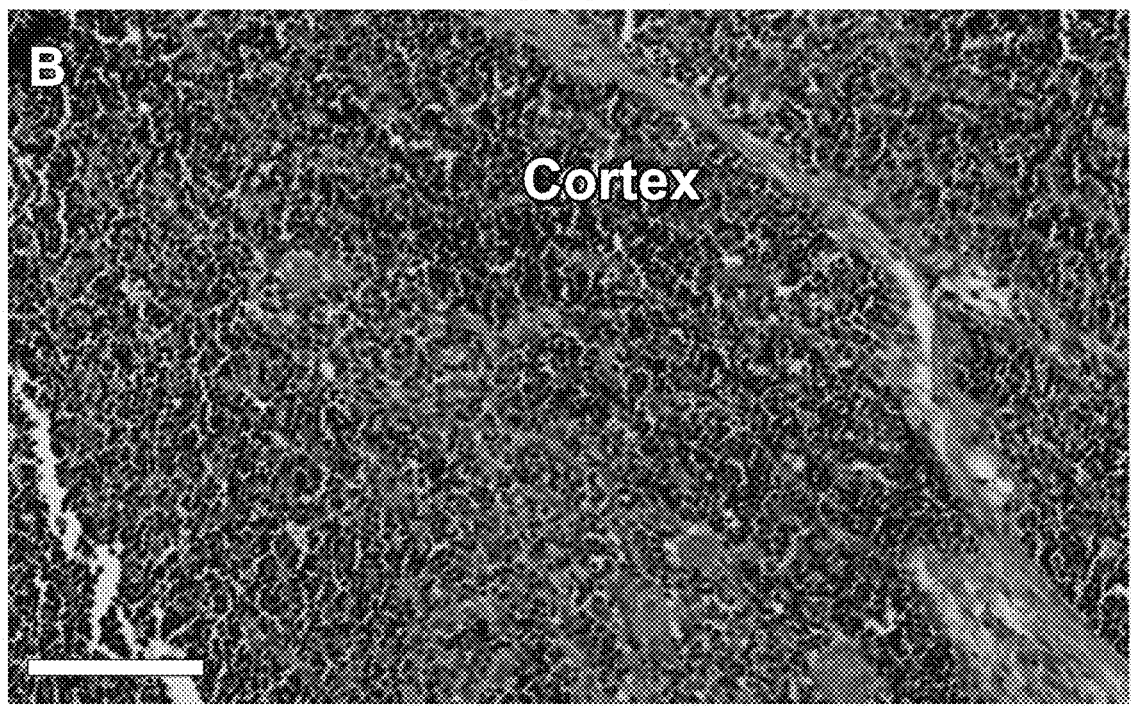

FIGS. 64A and 64B depict the histology of thymus tissue slices on day 0 of the time course in a scale of 5 mm (FIG. 64A) and 100 µm (FIG. 64B), respectively. This shows the thymus and thymocytes at low power (bar 5 mm) and high power (bar 100 um) on day 0. This is normal thymus. At this time the cortex and medulla both have large numbers of thymocytes with dark blue nuclei contributing to the overall dark blue appearance of the tissue. Photo by Laura P. Hale, MD, PhD, Department of Pathology, Duke University.

Figure 65A:
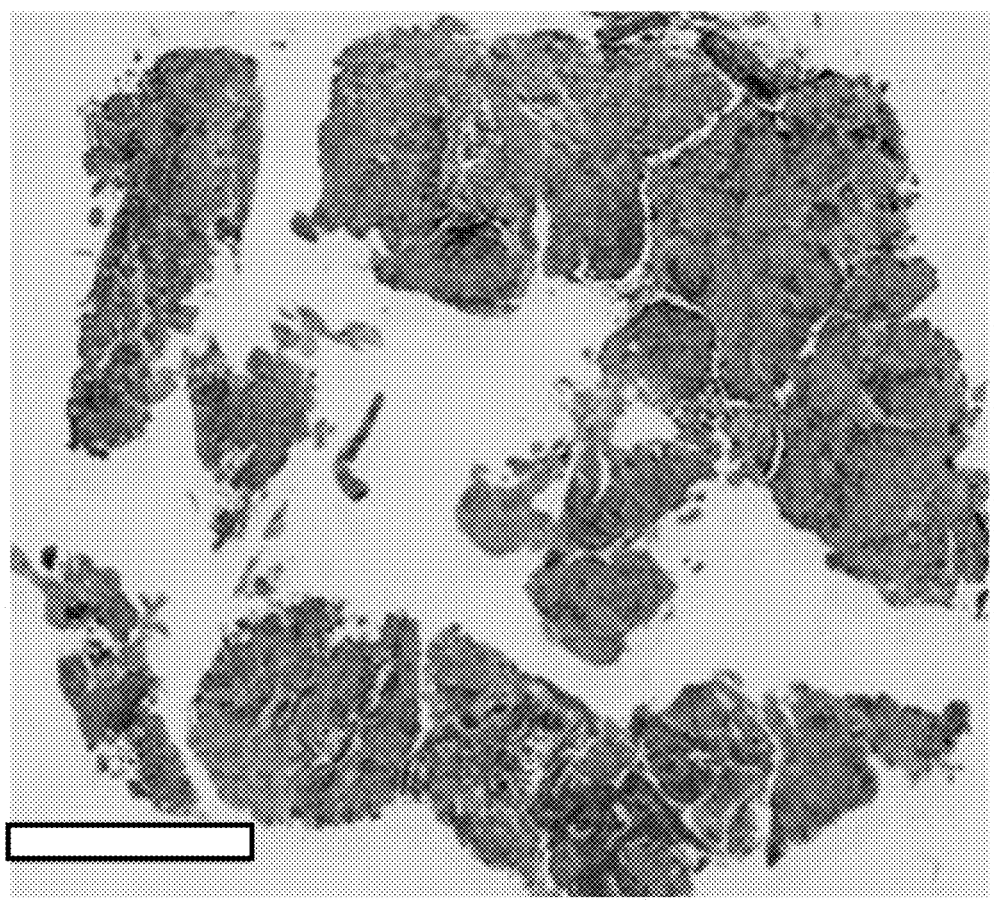
Figure 65B:
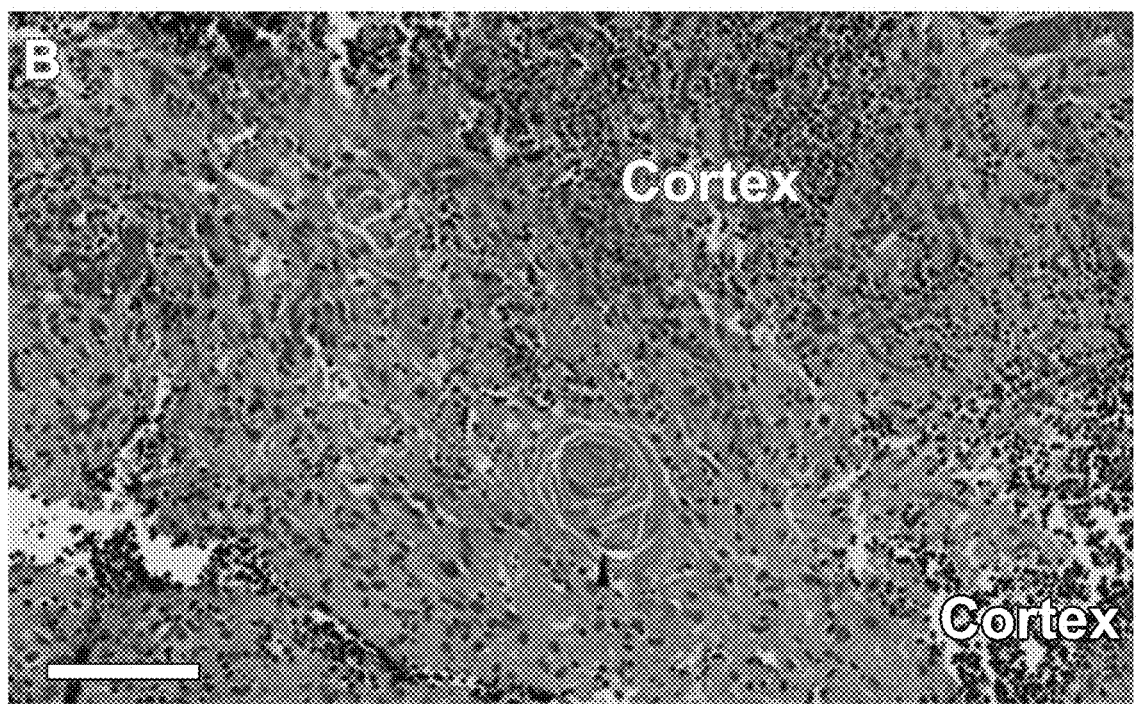

FIGS. 65A and 65B are images from H&E stained slide that depict the histology of thymus tissue slices on day 5 of the time course in a scale of 5 mm (FIG. 65A) and 100 µm (FIG. 65B), respectively. Progression of depletion of the thymocytes results in a more eosinophilic (pink) appearance of the tissue. Photo by Laura P. Hale, MD, PhD, Department of Pathology, Duke University.

Figure 66A:
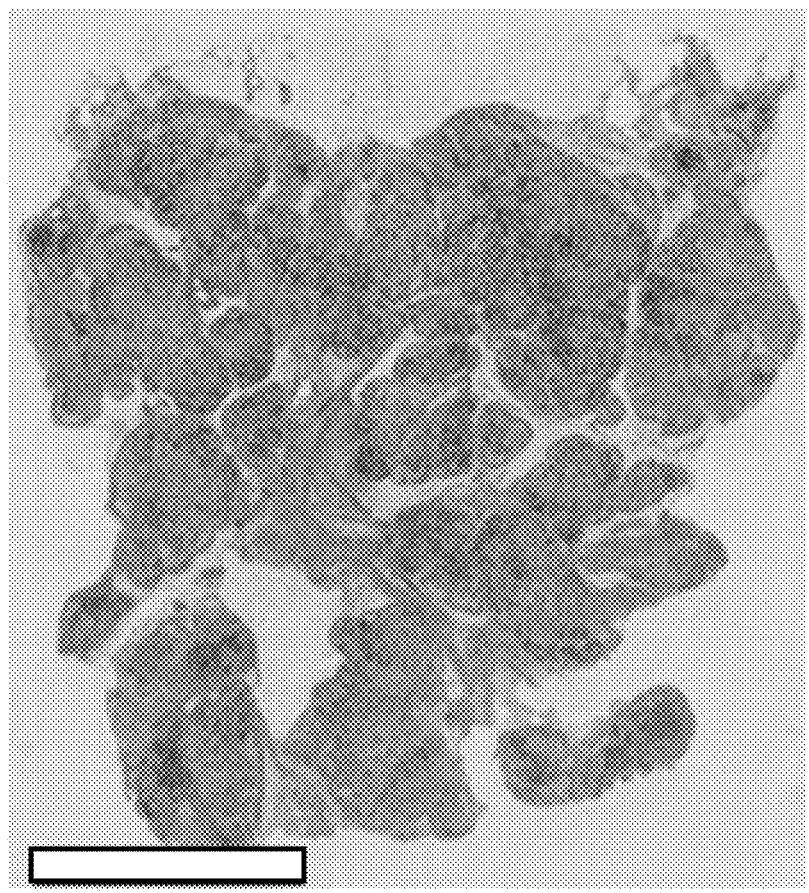
Figure 66B:
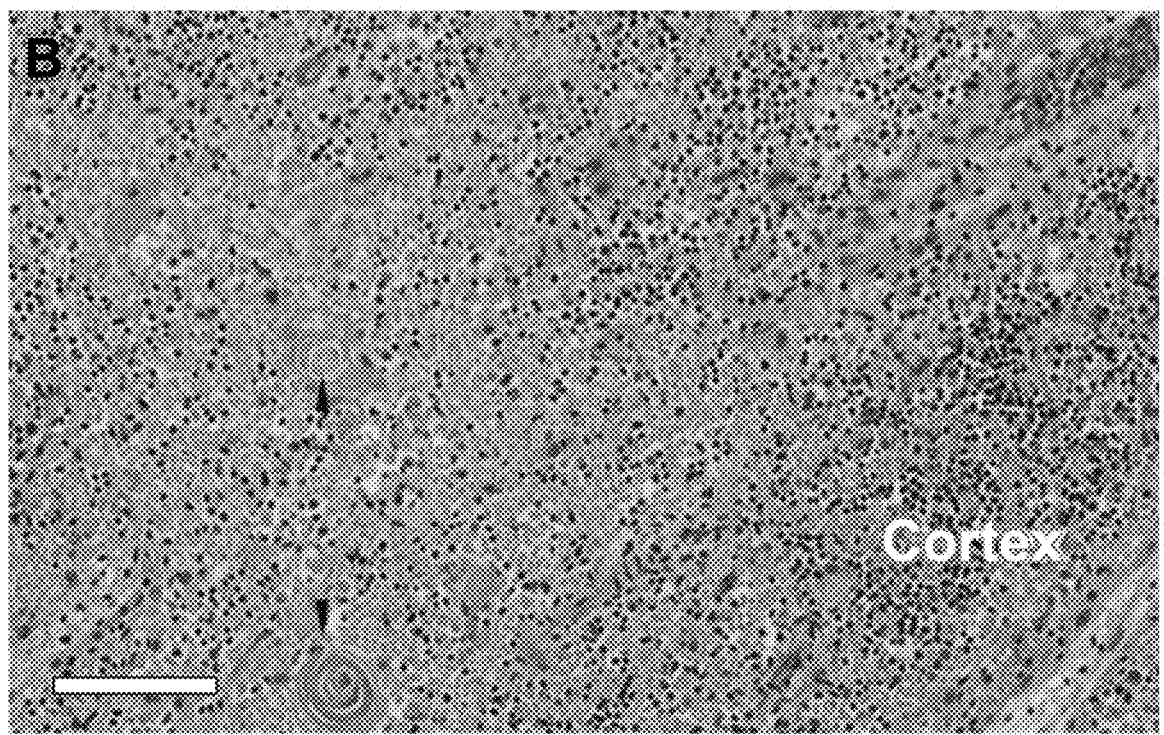

FIG. 66A and FIG. 66B depict H&E staining of the thymus tissue slices on day 12 of the time course in a scale of 5 mm (FIG. 66A) and 100 µm (FIG. 66B), respectively. We see progressive depletion of thymocytes. The higher magnification shows numerous eosinophilic cell bodies lacking nuclei which are diagnostic of necrotic cells that have undergone karyolysis (dissolution of the nuclei). This degree of necrosis is expected at this time in culture. Photo by Laura P. Hale, MD, PhD, Department of Pathology, Duke University.

Figure 67A:
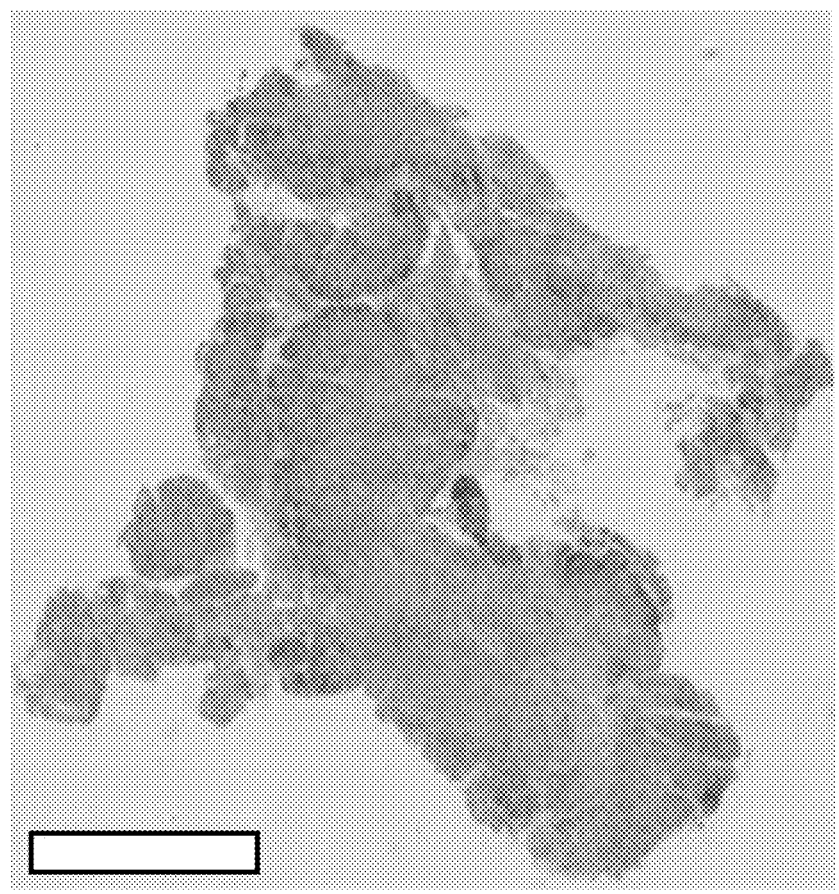
Figure 67B:
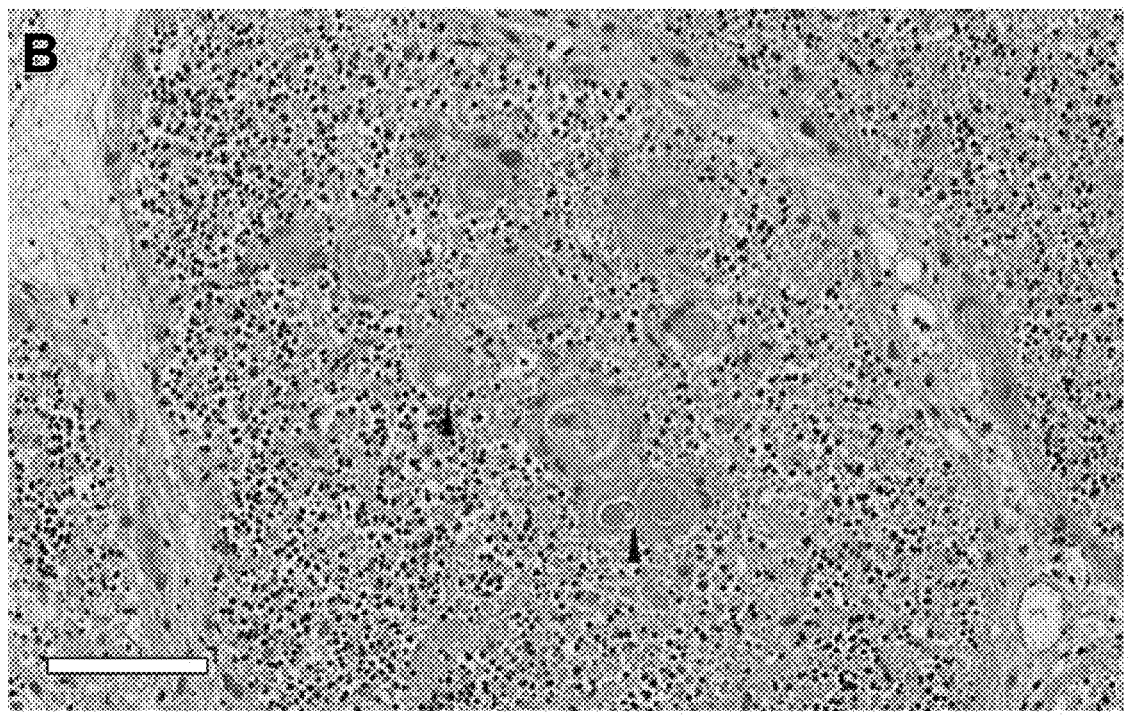

FIG. 67A and FIG. 67B depict H&E staining of thymus tissue slices on day 21 of the time course in a scale of 5 mm (FIG. 67A) and 100 µm (FIG. 67B), respectively. Note the preservation of the overall architecture of the tissue including in FIG. 67B the subcapsular cortex, cortical region and medullary region containing numerous Hassall bodies. The small dark cells are mostly necrotic thymocytes that have not yet undergone karyolysis. Photo by Laura P. Hale, MD, PhD, Department of Pathology, Duke University.

FIGS. 68A-E depict representative thymus slices which were immuno-stained with a cocktail of anti-cytokeratin antibodies (AE/AE3). FIG. 68A. Day 0; FIG. 68B. Day 5; FIG. 68C. Day 9; FIG. 68D. Day 12; and FIG. 68E. Day 21. The structure of the thymic epithelial network remains intact as the culture progresses. Bar represents 400 µm. Photo by Laura P. Hale, MD, PhD, Department of Pathology, Duke University.

Figure 69:
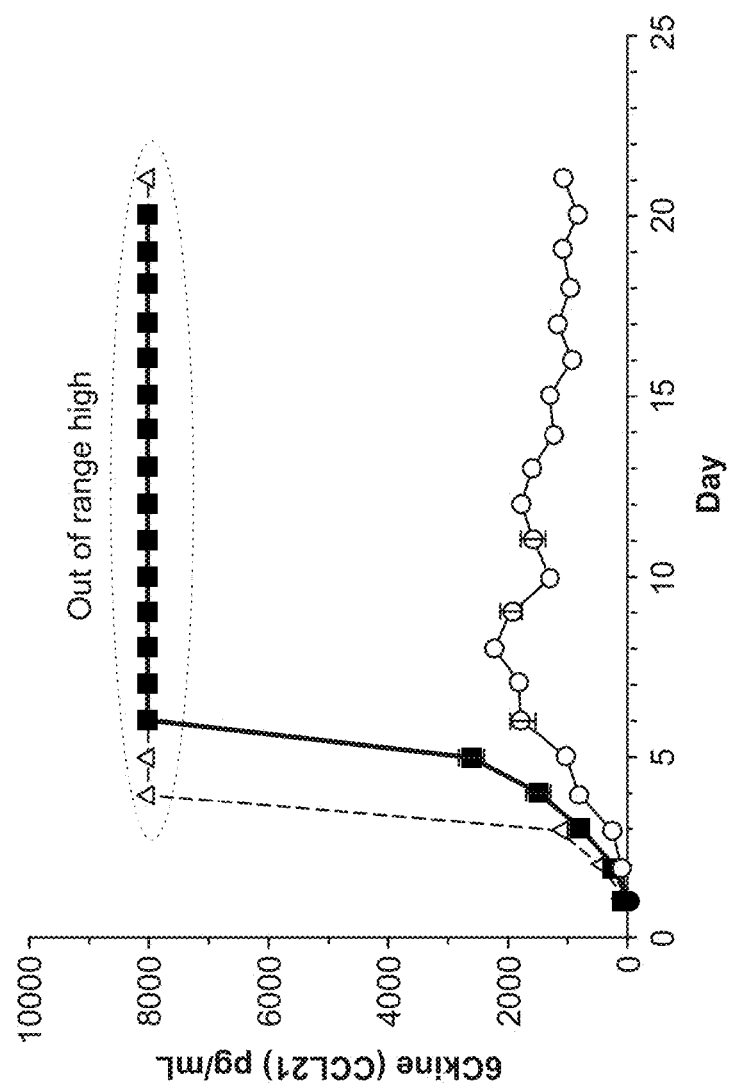
Figure 69:
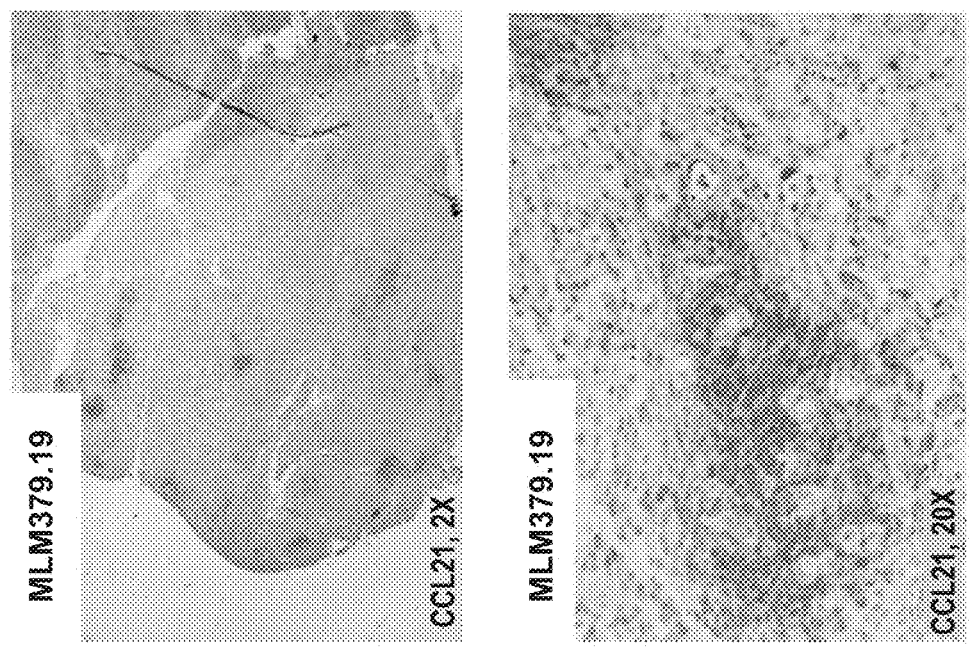

FIG. 69 presents photomicrographic images and a graph of CCL21 assessment in cultured infant thymus. CCL21 is produced at high levels by cultured infant thymus. Immunohistochemical reactivity with CCL21 antibody (Ab) (brown staining) on day 16 of culture is shown in the left panels (upper left panel, 2× magnification; lower left panel, 20× magnification). A corresponding time course measuring daily CCL21 secretion into culture media is shown on the right for 3 infant thymus cultures (R&D Systems Duo-Set ELISA). Thus, the cultured thymus tissue can produce a functionally important biomolecule, CCL21, the chemokine responsible for attracting immature thymocyte precursors to the thymus.

Figure 70:
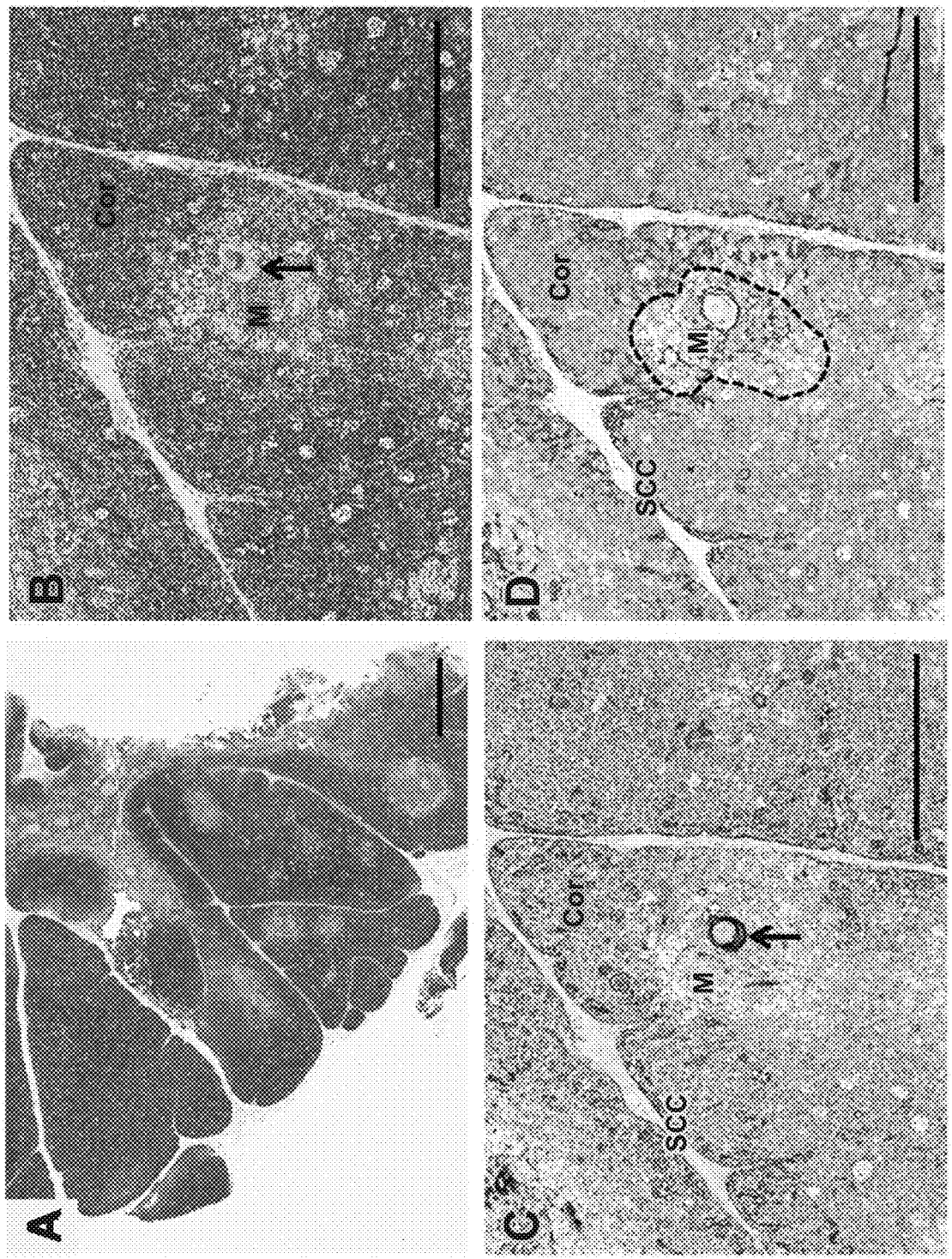

FIGS. 70A to 70D presents photomicrographs of slices of fresh thymus, d0 of culture, showing thymic architecture. In FIGS. 70A-B, hematoxylin and eosin (H&E) staining shows well-defined cortical and lighter-staining medullary areas, as expected for normal pediatric thymus. FIG. 70C shows immunohistochemistry with a cocktail of pan-cytokeratin antibodies (AE1/AE3) that together detect all types of epithelial cells demonstrates that thymic epithelial cells are present beneath the capsule and in a light lacy network in both cortex and medulla (brown staining shows positive antibody reaction). Arrows in FIG. 70B and FIG. 70C point to a Hassall body. FIG. 70D shows Cytokeratin 14 (CK14) antibody staining (brown). CK14 antibody reacts with thymic epithelial cells in the sub-capsular cortex and in the medulla, as well as with scattered thymic epithelial cells in the cortex. The dotted line highlights an area of medulla that is surrounded by cortex. SCC denotes sub-capsular cortex, Cor denotes cortex, and M denotes medulla. Scale bar in FIG. 70A represents 1 mm; scale bars in FIGS. 70B-D represent 500 µm.

FIGS. 71A to 71D present photomicrographs showing examples of Hassall bodies in cultured thymic slices. The histologic appearance of Hassall bodies is shown on day 0 (FIGS. 71A-B) and day 9 (FIGS. 71C-D) of culture. FIG. 71A and FIG. 71C show hematoxylin and eosin (H&E) staining; FIG. 71B and FIG. 71D show reactivity with pan-cytokeratin (AE1/AE3) antibodies (brown color indicates a positive reaction). Arrowheads in FIGS. 71A-D point out representative Hassall bodies, which appear less prominent on H&E-stained sections of cultured thymus due to depletion and necrosis of surrounding thymocytes. However, Hassall bodies can still be readily identified by careful examination or by using immunohistochemistry. Scale bar in FIGS. 71A-D represents 100 µm.

Figure 72:
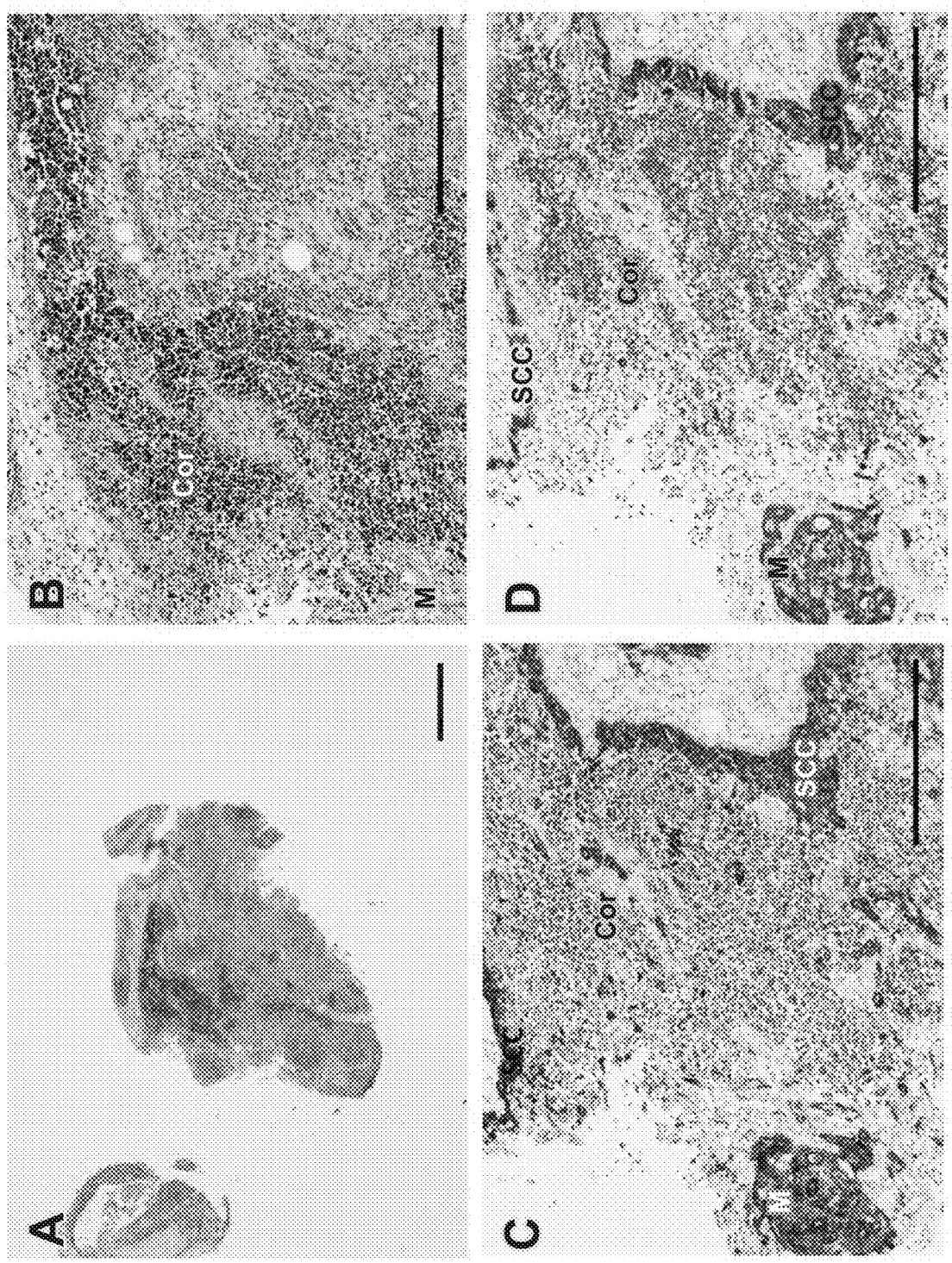

FIGS. 72A to 72D presents photomicrographs showing the architecture of cultured thymus, day 7. Hematoxylin and eosin (H&E) staining in FIGS. 72A-B shows marked depletion of thymocytes, although some cortical areas (Cor) still contain large numbers of thymocytes with retained nuclei. Pan-cytokeratin (AE1/AE3) in FIG. 72C and cytokeratin 14 (CK14) immunohistochemistry in FIG. 72D show condensation of the thymic epithelium in the subcapsular cortex (SCC) and in the medulla (M). Brown color in FIGS. 72C-D indicates a positive reaction with antibody. Scale bar represents 1 mm in FIG. 23 and 500 µm in FIGS. 72B-D.

FIGS. 73A to 73D present photomicrographs showing the architecture of cultured thymus, day 9. FIGS. 73A-B show hematoxylin and eosin (H&E) staining. Few if any live T cells or thymic epithelial cells are present in the pale-staining area in FIG. 73A that is enclosed by the dotted line, which is almost completely necrotic (Necr). Most nuclei formerly present in this region have been degraded via karyolysis. Other areas where the nuclei from residual thymocytes have not been completely degraded continue to stain dark blue with hematoxylin. Arrow in FIG. 73B points to a Hassall body. FIG. 73C shows pan-cytokeratin (AE/AE3) immunoreactivity (brown); FIG. 73D shows cytokeratin 14 (CK14) immunoreactivity (brown). Scale bar represents 1 mm in FIG. 73A and 500 µm in FIGS. 73B-D.

Figure 74:
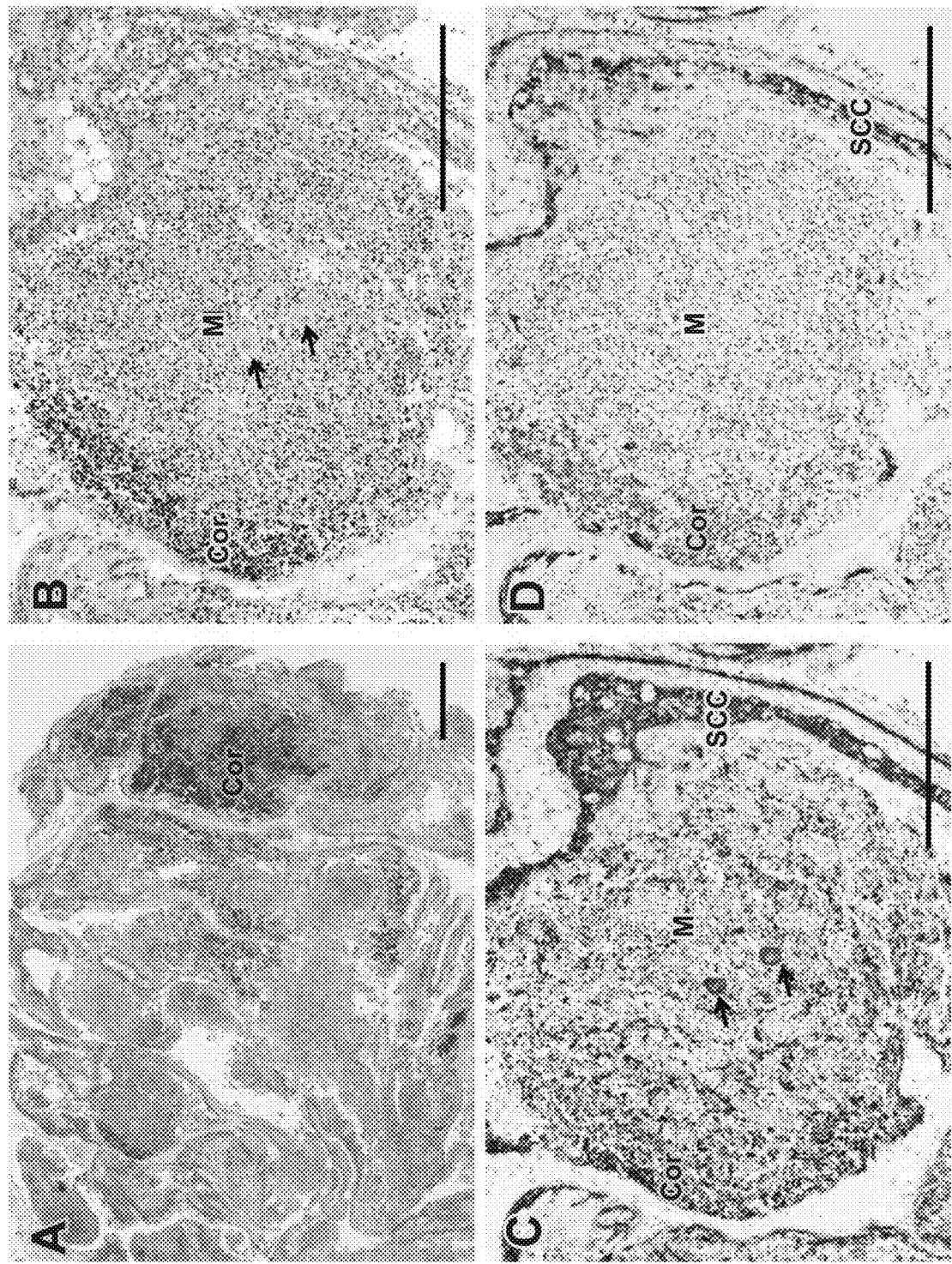

FIGS. 74A to 74D presents photomicrographs showing the architecture of cultured thymus, day 12. FIGS. 74A-B show hematoxylin and eosin (H&E) staining. At this time point, many thymocytes have either been lost from the tissue or have died and their nuclei have been dissolved, making the tissue more eosinophilic (pink). Some areas retain architecture characteristic of normal uncultured thymus with cortical-like areas (Cor) that stain more basophilic (blue) and medullary-like areas (M), although with greatly decreased thymocyte cellularity. FIG. 74C shows pan-cytokeratin (AE1/AE3) immunoreactivity (brown); FIG. 74D shows cytokeratin 14 (CK14) immunoreactivity (brown). At this time point, the sub-capsular cortex (SCC) has thickened and epithelial cells appear more prominent due to the decreased numbers of thymocytes present. Arrows point to representative Hassall bodies. Bar represents 1 mm in FIG. 74A and 500 µm in FIGS. 74B-D.

Figure 75:
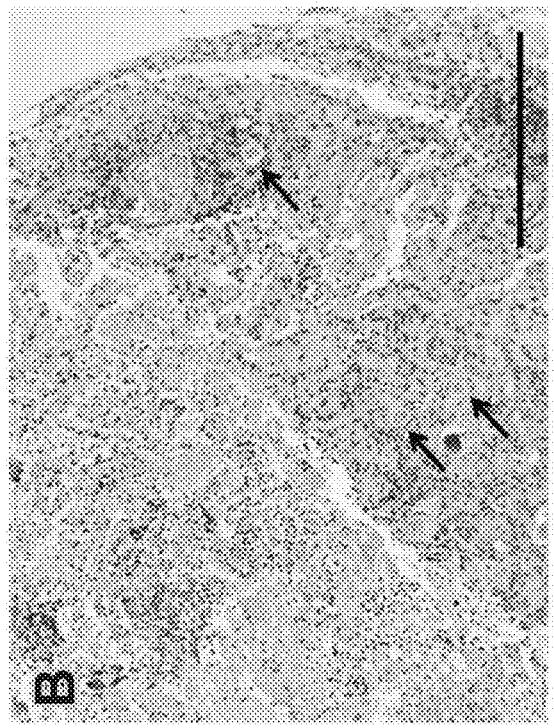
Figure 75:
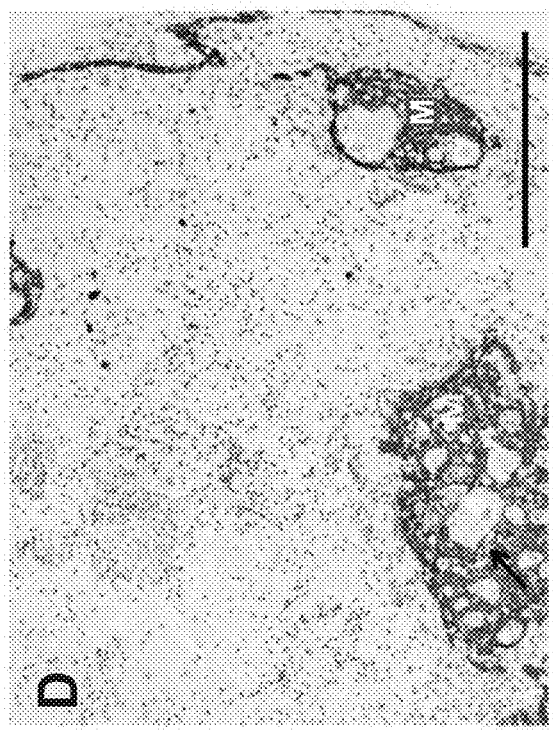
Figure 75:
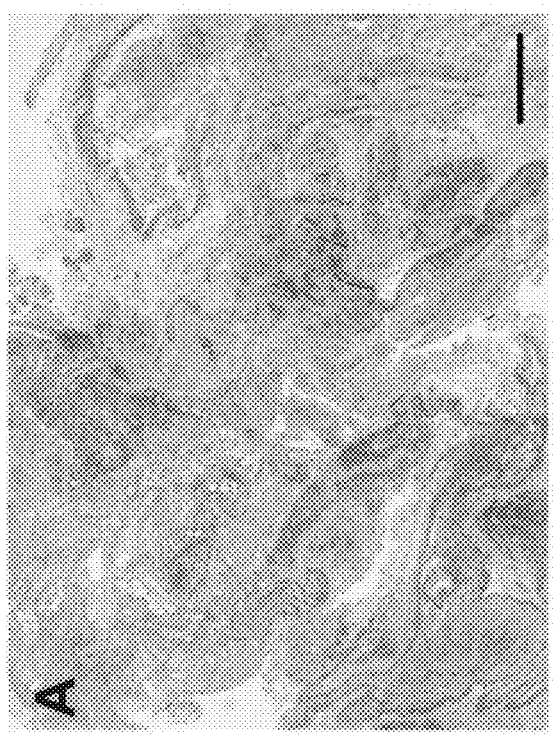
Figure 75:

FIGS. 75A-B shows hematoxylin and eosin (H&E) staining. At this time point, most thymocytes have either been lost from the tissue or have died and their nuclei have been dissolved, making the tissue more eosinophilic (pink). Large groups of residual thymocytes are rare, although scattered cells with nuclear characteristics of thymocytes are evident. FIG. 75C shows pan-cytokeratin (AE1/AE3) immunoreactivity (brown). Much of the epithelium present in formerly medullary areas (M) is condensed due to loss of medullary thymocytes, but scattered epithelial cells indicative of a residual light, lacy, three-dimensional network of thymic epithelial cells remain. In FIG. 75D, cytokeratin 14 (CK14) immunohistochemistry (brown) highlights former medullary areas and the subcapsular cortex. Arrows point to representative Hassall bodies. Scale bar represents 1 mm in FIG. 75A and 500 µm in FIGS. 75B-D.

Figure 76:
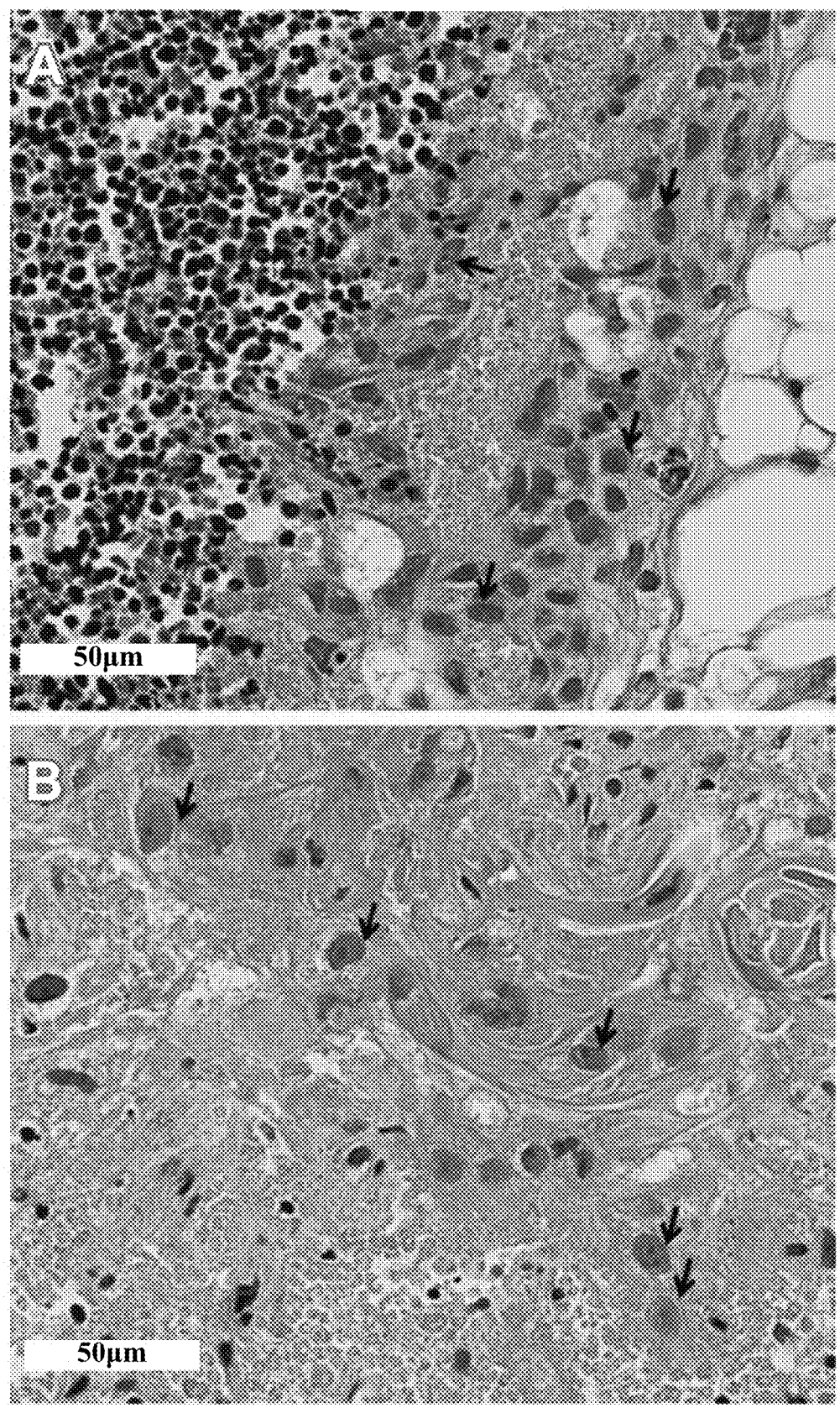

FIGS. 76A-B present photomicrographs showing examples of intact nuclei in thymus slices. Examples of intact thymic epithelial cell nuclei (arrows) are shown in the subcapsular cortex on day 9 (FIG. 76A) and in the medulla on day 21 (FIG. 76B). Hematoxylin and eosin stain; scale bar represents 50 µm.

Figure 77:
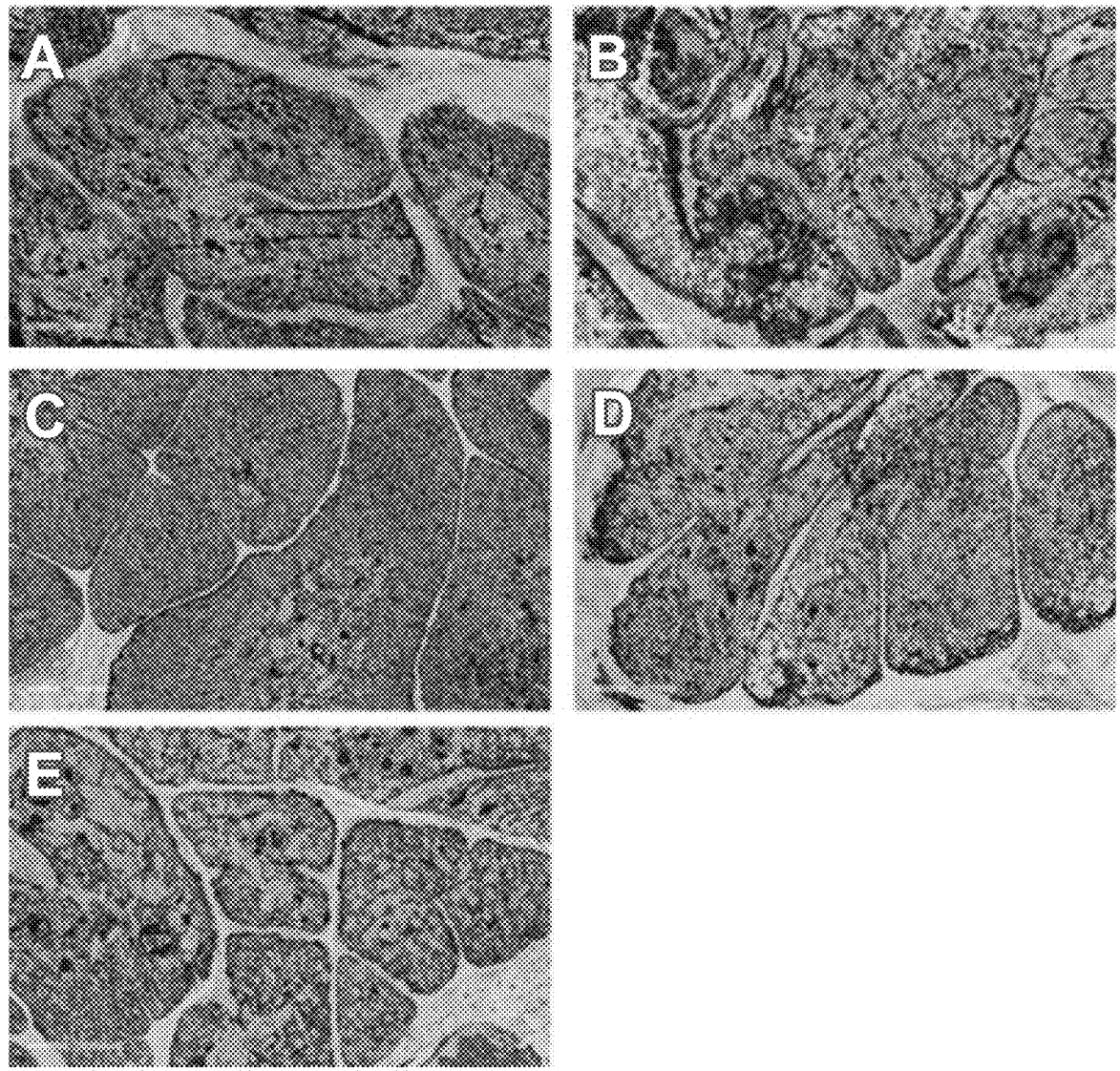

FIGS. 77A to 77E present photomicrographs showing a comparison of the thymic epithelial network of cultured thymus tissue at different time points. FIG. 77A shows day 0, FIG. 77B shows day 5, FIG. 77C shows day 9, FIG. 77D shows day 12, and FIG. 77E shows day 21. Although there are time point-related differences in thymocyte depletion and the amount of necrosis such that the tissue become less basophilic (blue) with time, the structure of the thymic epithelial network (brown) remains intact as the culture progresses. Both cortical and medullary epithelium may condense as intervening thymocytes are depleted. Brown color indicates a positive reaction with a cocktail of anti-cytokeratin antibodies (AE/AE3); hematoxylin counterstain. Scale bar represents 400 µm.

Figure 78:
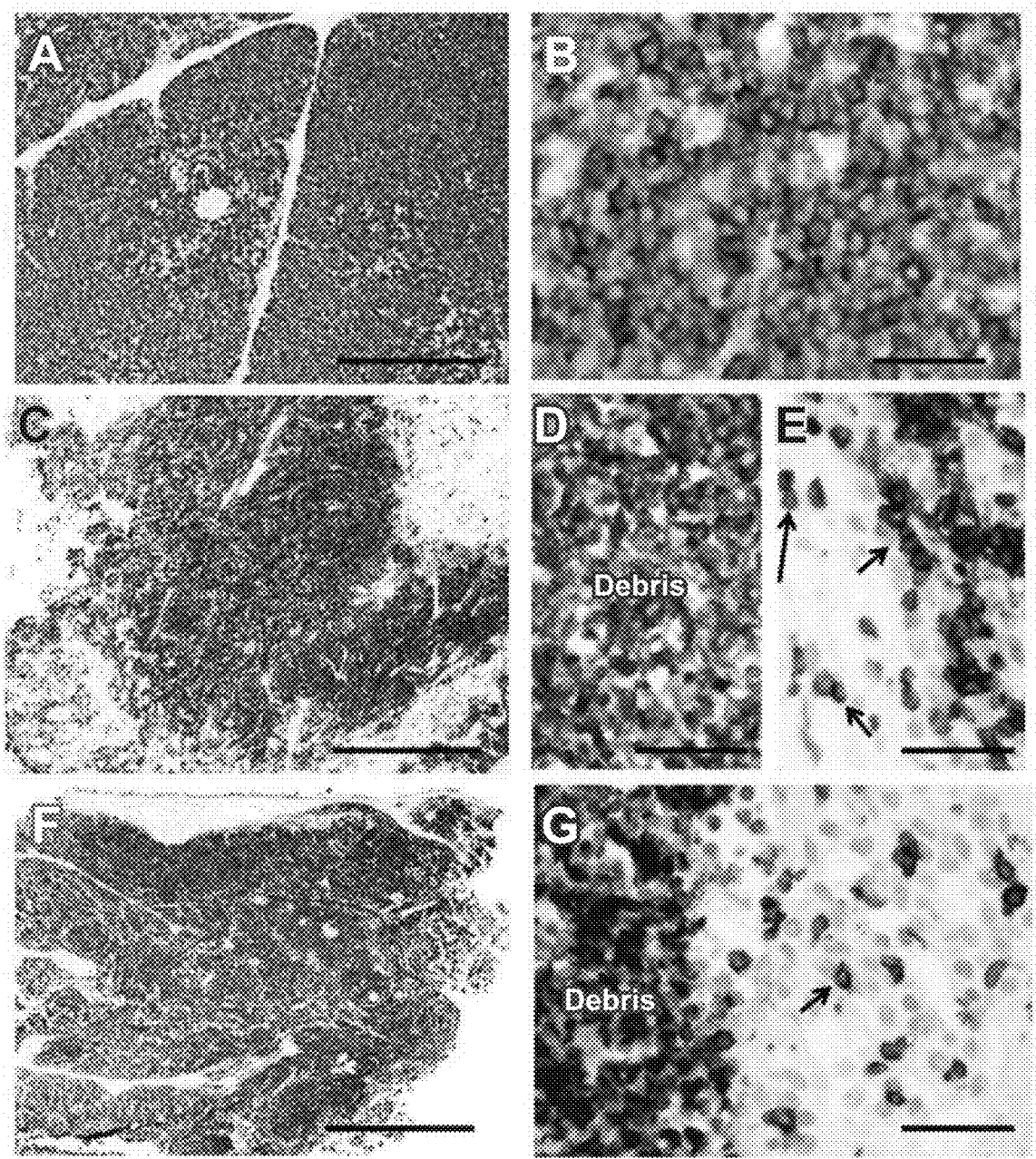
Figure 78:
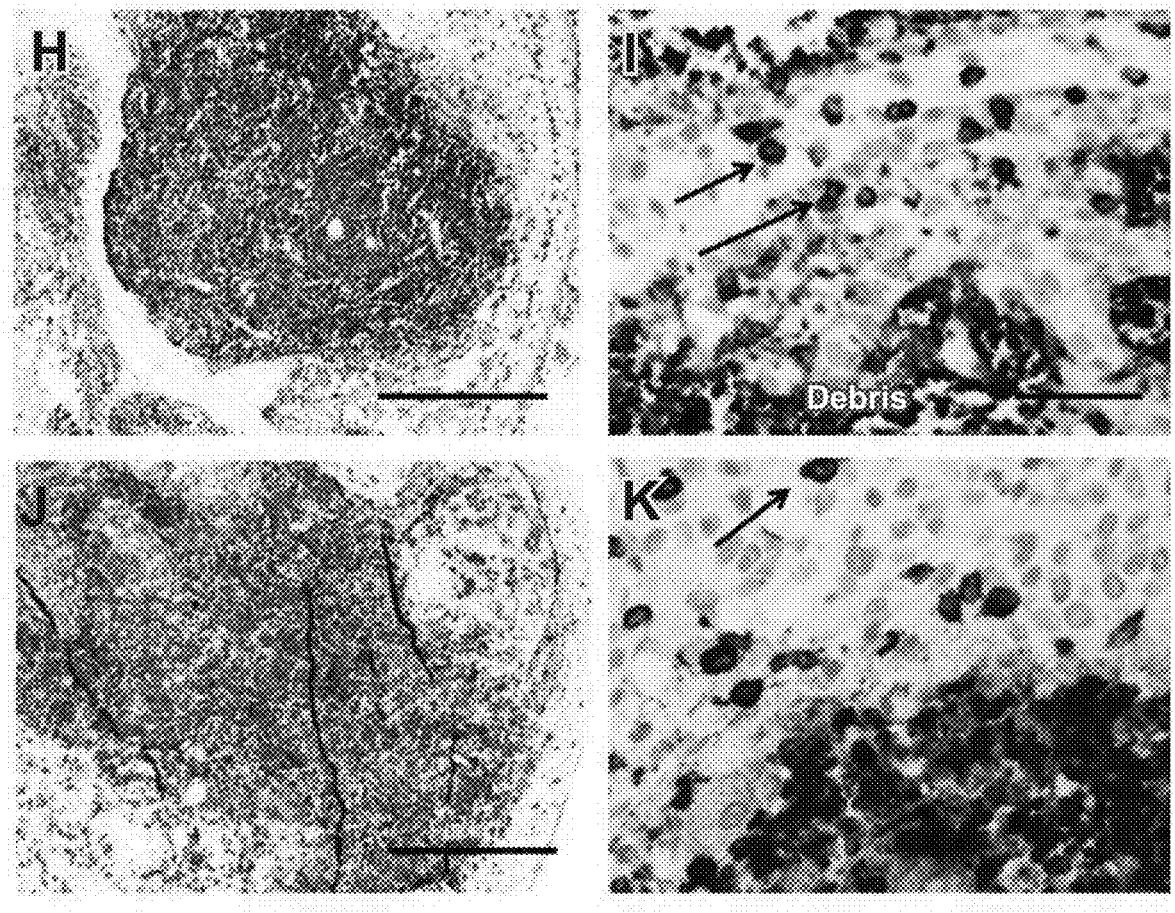

FIGS. 78A-K presents photomicrographs showing examples of CD3 immunohistochemistry in thymus slices as a function of time in culture. FIGS. 78A-B shows that on day 0, essentially all immature T cells in the cortex and more mature cells in the medulla react strongly with CD3 antibody. Higher magnification (FIG. 78B) shows pale blue nuclei surrounded by a ring of brown immunoreactivity, consistent with membrane expression of CD3. In FIGS. 78C-E, tissue still shows extensive reactivity with CD3 antibody on day 7. However, FIGS. 78D-E shows that when viewed under higher magnification, the majority of the immunoreaction (brown) is associated with debris from dead thymocytes, as most brown foci lack evidence of nuclei (FIG. 78D). Small foci of cells that demonstrate intact nuclei and membrane staining (arrows) can still be identified in areas away from the debris (FIG. 78E). As cultures progress through day 9 (FIGS. 78F-G), day 12 (FIGS. 78H-I), and day 21 (FIGS. 78J-K), reactivity with thymocyte cellular debris remains strong, making it difficult to reliably detect potentially intact cells amidst the debris. The slices shown are all from a single lot that is representative of multiple lots examined at these time points. Scale bar represents 500 µm in FIG. 78A, FIG. 78C, FIG. 78F, FIG. 78H, and FIG. 78J, and 50 µm in FIG. 78B, FIG. 78D, FIG. 78E, FIG. 78G, FIG. 78, and FIG. 78K.

Figure 79:
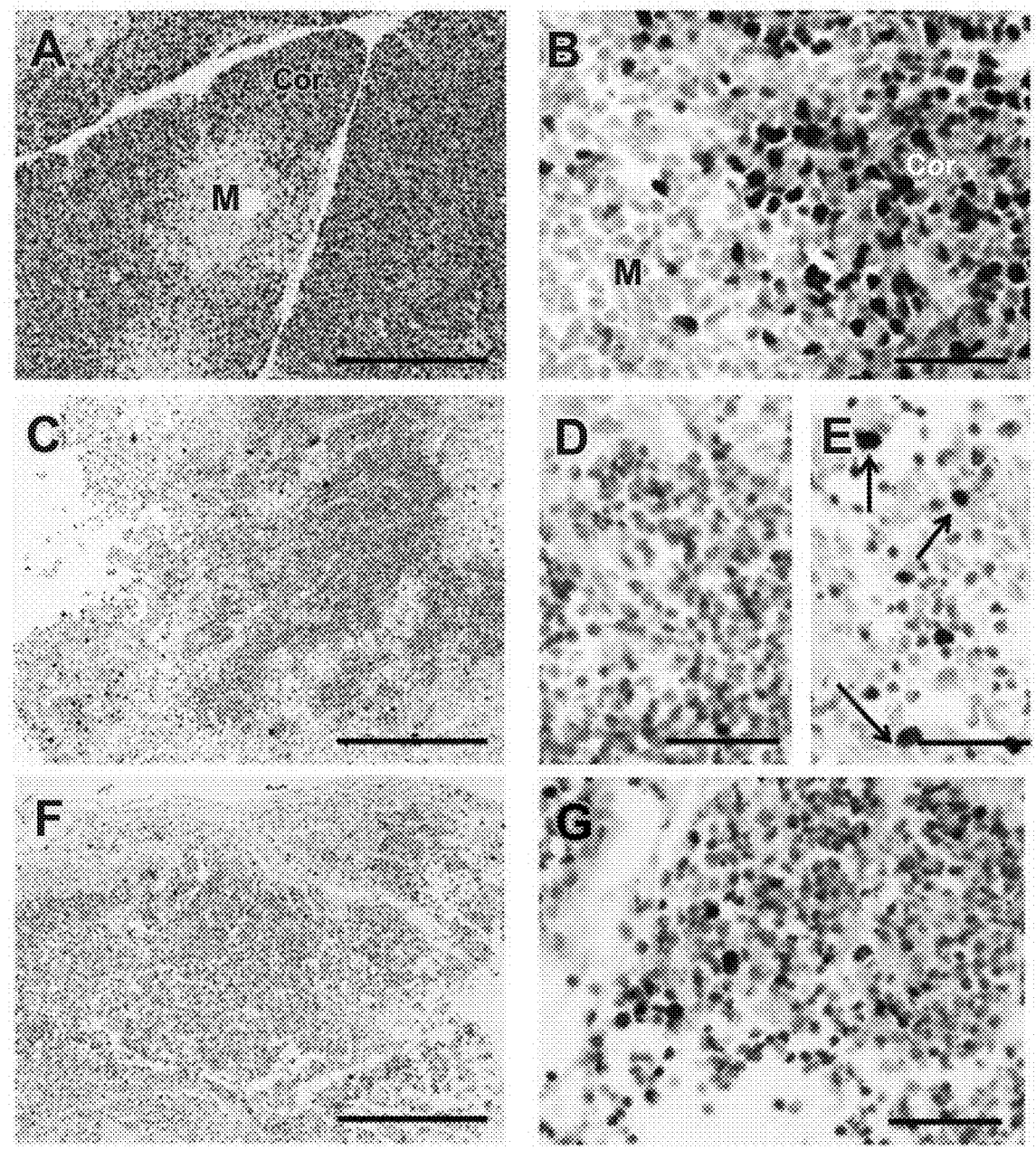
Figure 79:
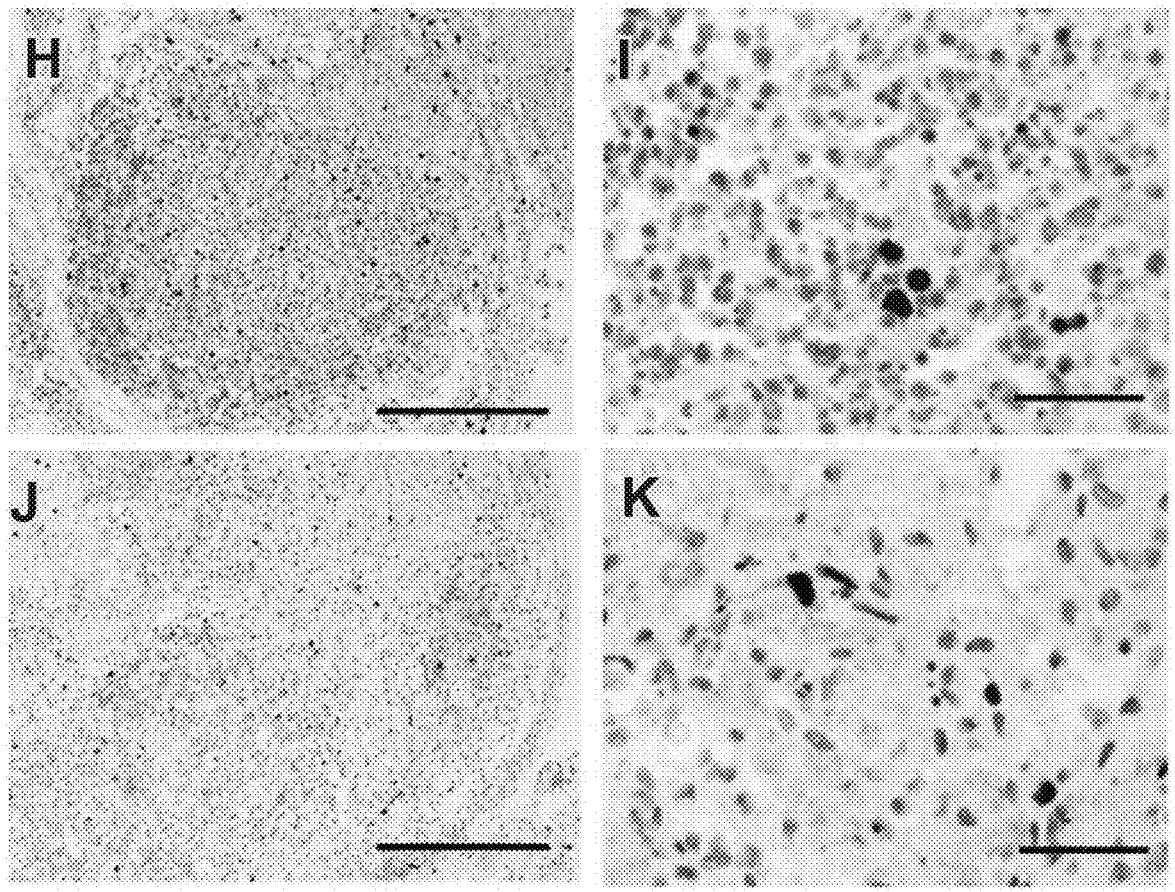

FIGS. 79A-K presents photomicrographs showing examples of Ki-67 immunohistochemistry in thymus slices as a function of time in culture. The slices shown are all from a single lot that is representative of multiple lots examined at similar time points. FIGS. 79A-B shows that on day 0, the nuclei of the majority of immature T cells in the cortex (Cor) react strongly with antibody specific for Ki-67. Higher magnification (FIG. 79B) shows strong positive reactivity with the nuclei of cortical thymocytes (brown), whereas only rare lymphocytes in the medulla (M) react with Ki-67 antibody. FIGS. 79C-E show that by day 7, the nuclei of most thymocytes that remain in cortical areas are small with indistinct nuclear borders consistent with apoptosis, and they fail to react with Ki-67-specific antibody. The cells that react with antibody (FIG. 79E, arrows) have larger nuclei, suggesting that they are thymic epithelial cells. A similar lack of Ki-67 labeling of residual thymocyte nuclei is seen on days 9 (FIGS. 79F-G), 12 (FIGS. 79H-I) and 21 (FIGS. 79J-K). Scale bar represents 500 µm in FIG. 79A, FIG. 79C, FIG. 79E, FIG. 79G, and FIG. 79I and 50 µm in FIG. 79B, FIG. 79D, FIG. 79F, FIG. 79, and FIG. 79J.

Figure 80:
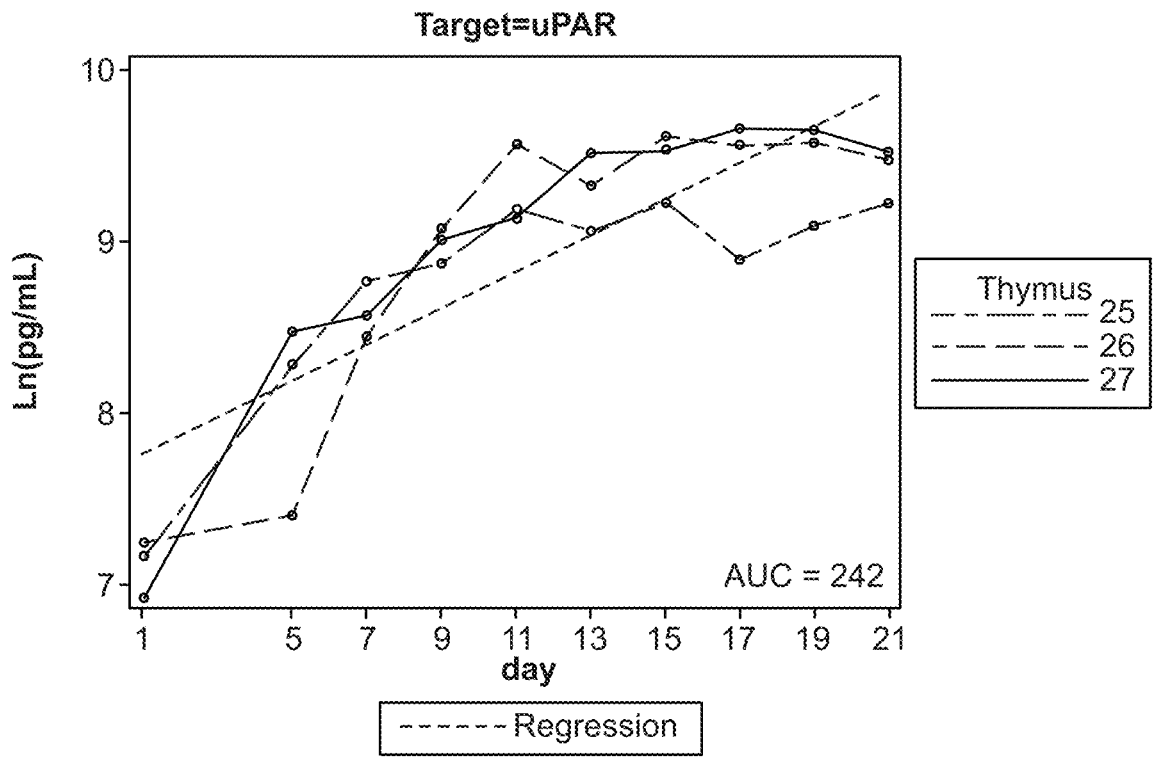

FIG. 80 is a plot of uPAR detected in conditioned media from human thymus organ cultures.

Figure 81:
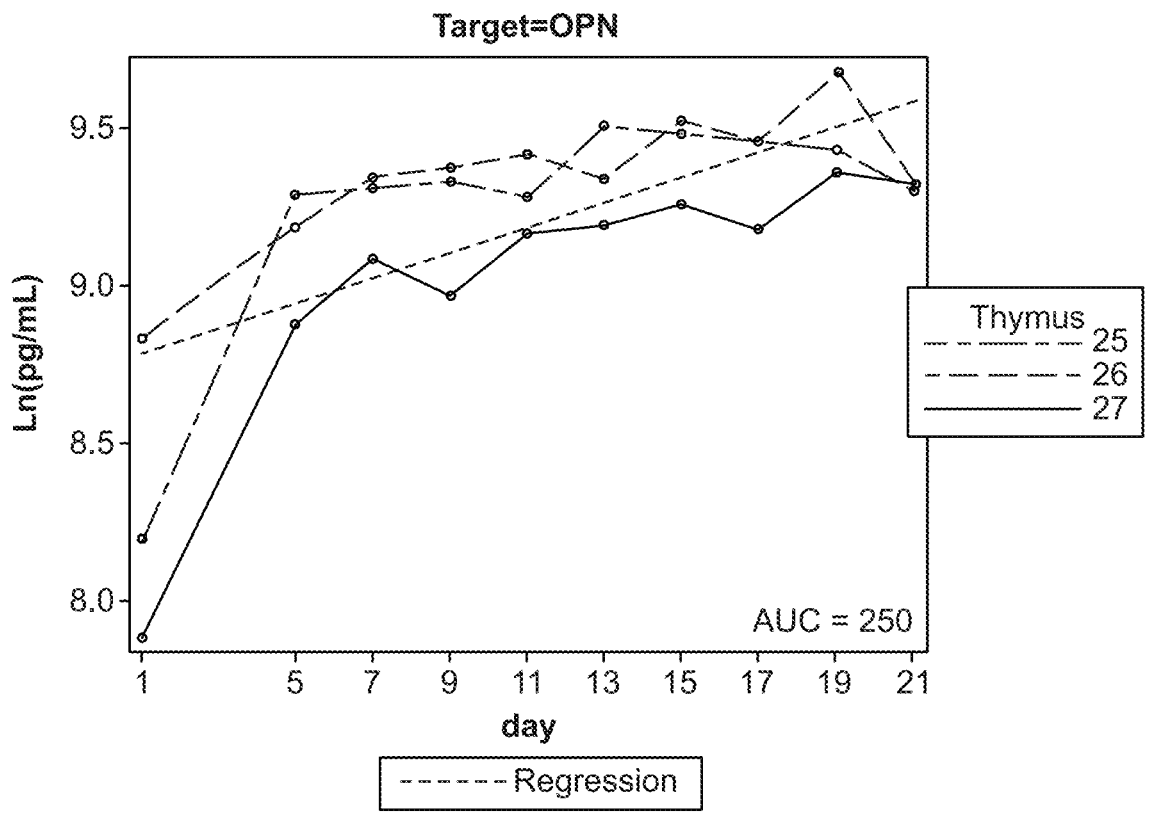

FIG. 81 is a plot of OPN detected in conditioned media from human thymus organ cultures.

Figure 82:
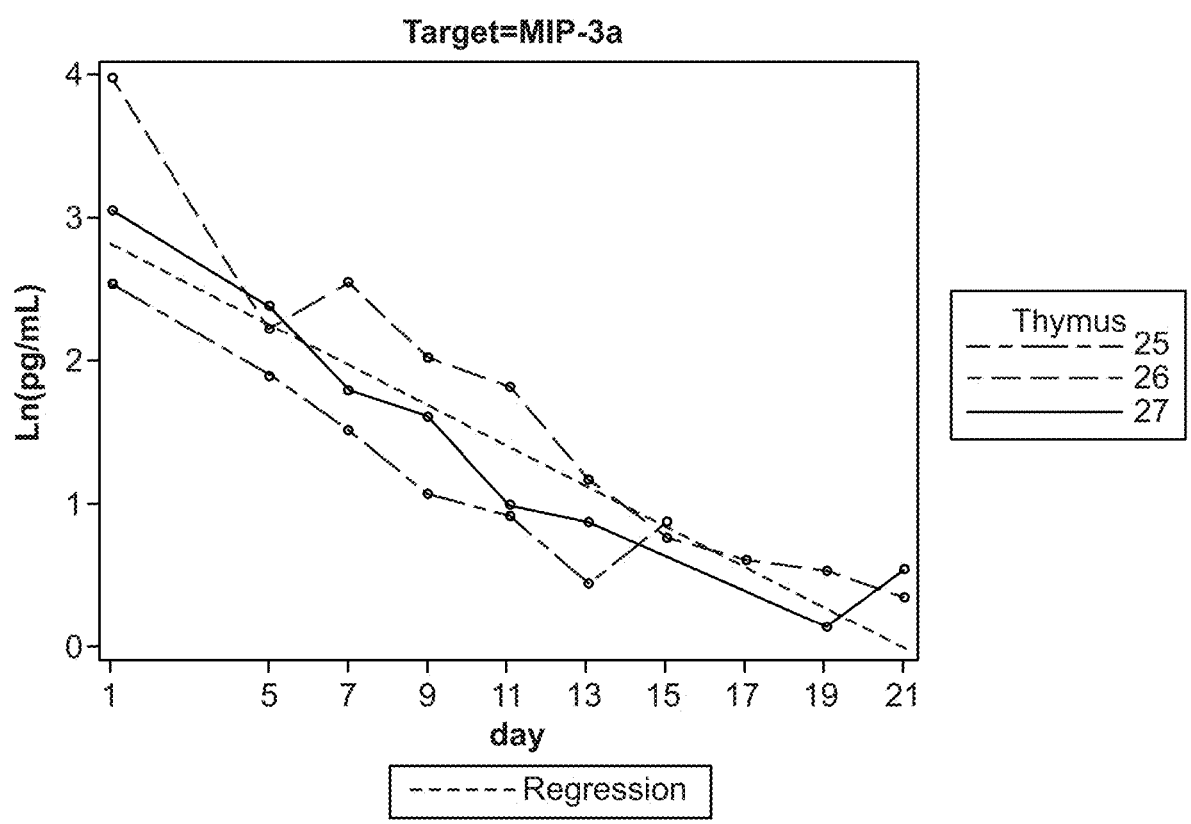

FIG. 82 is a plot of MIP3a detected in conditioned media from human thymus organ cultures.

Figure 83:
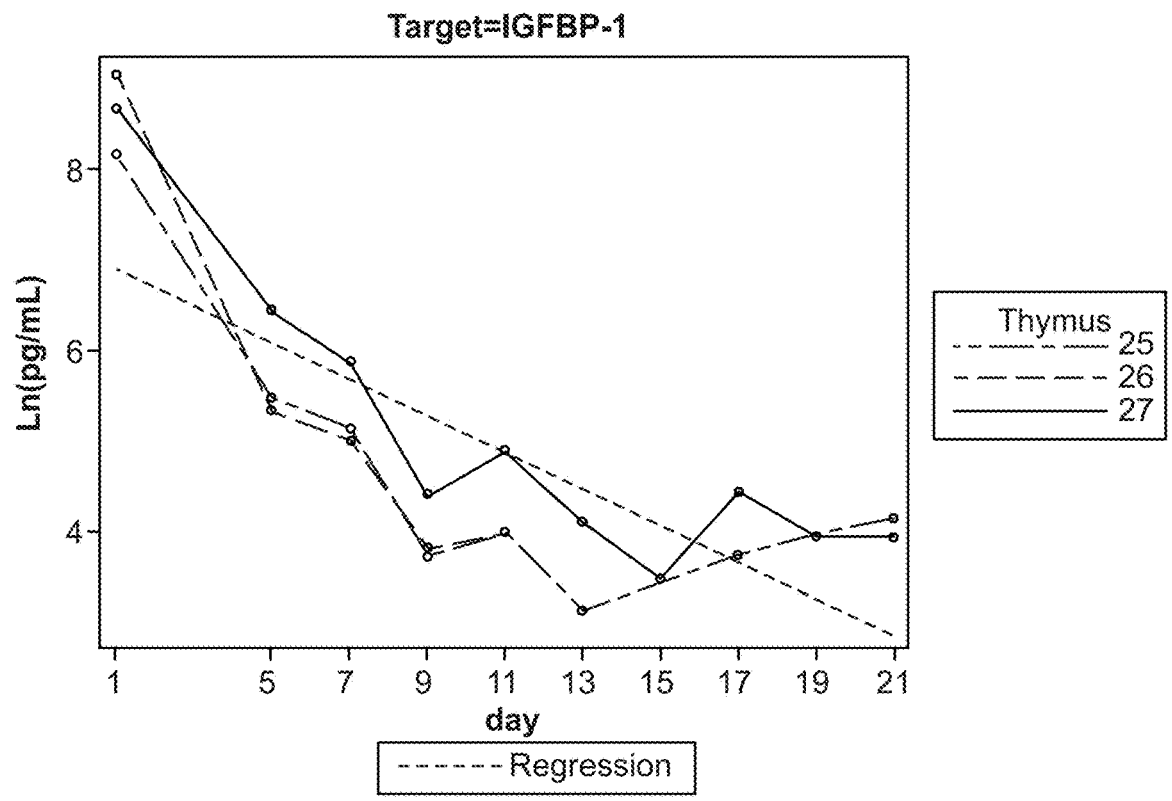

FIG. 83 is a plot of IGFBP-1 detected in conditioned media from human thymus organ cultures.

Figure 84:
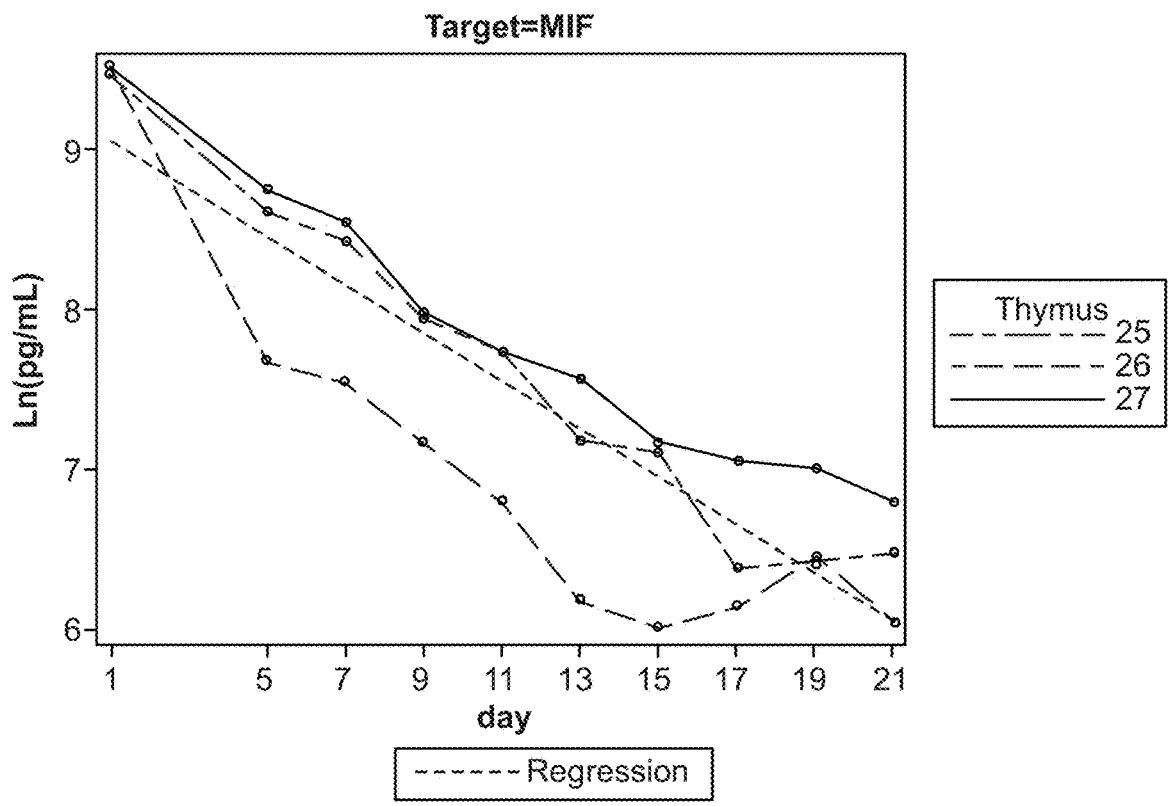

FIG. 84 is a plot of MIF detected in conditioned media from human thymus organ cultures.

Figure 85:
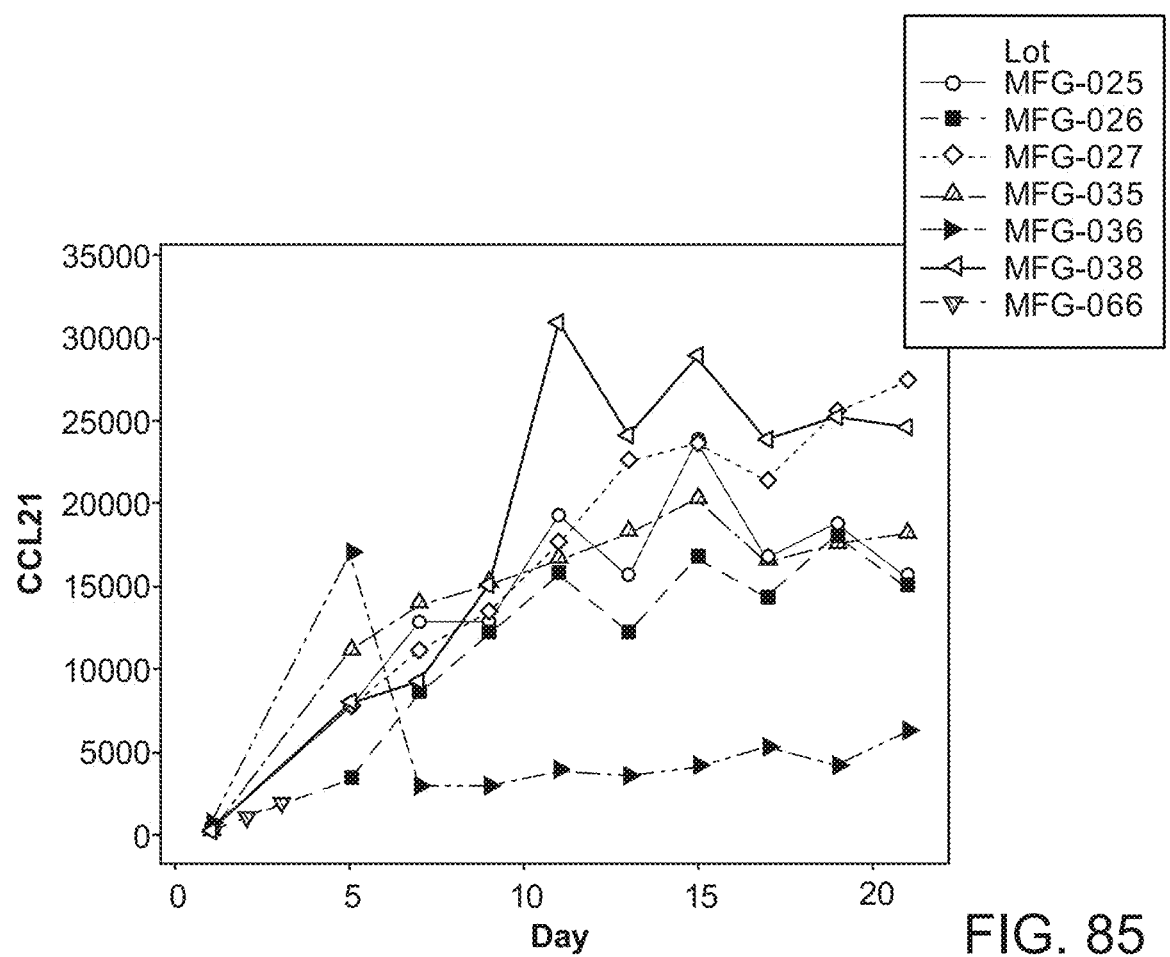

FIG. 85 is a scatterplot of CCL21 Concentration in Spent Media vs. Day.

Figure 86:
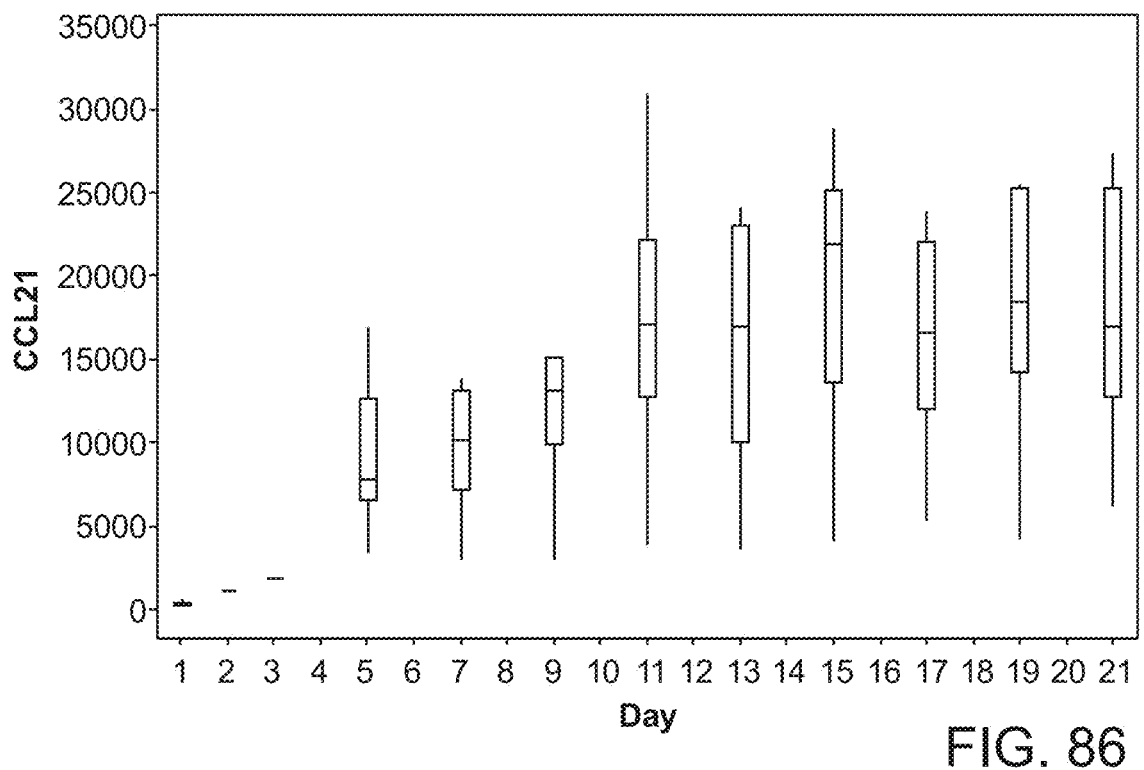

FIG. 86 is a boxplot of CCL21 Concentration in Spent Media vs. Day.

Figure 4:
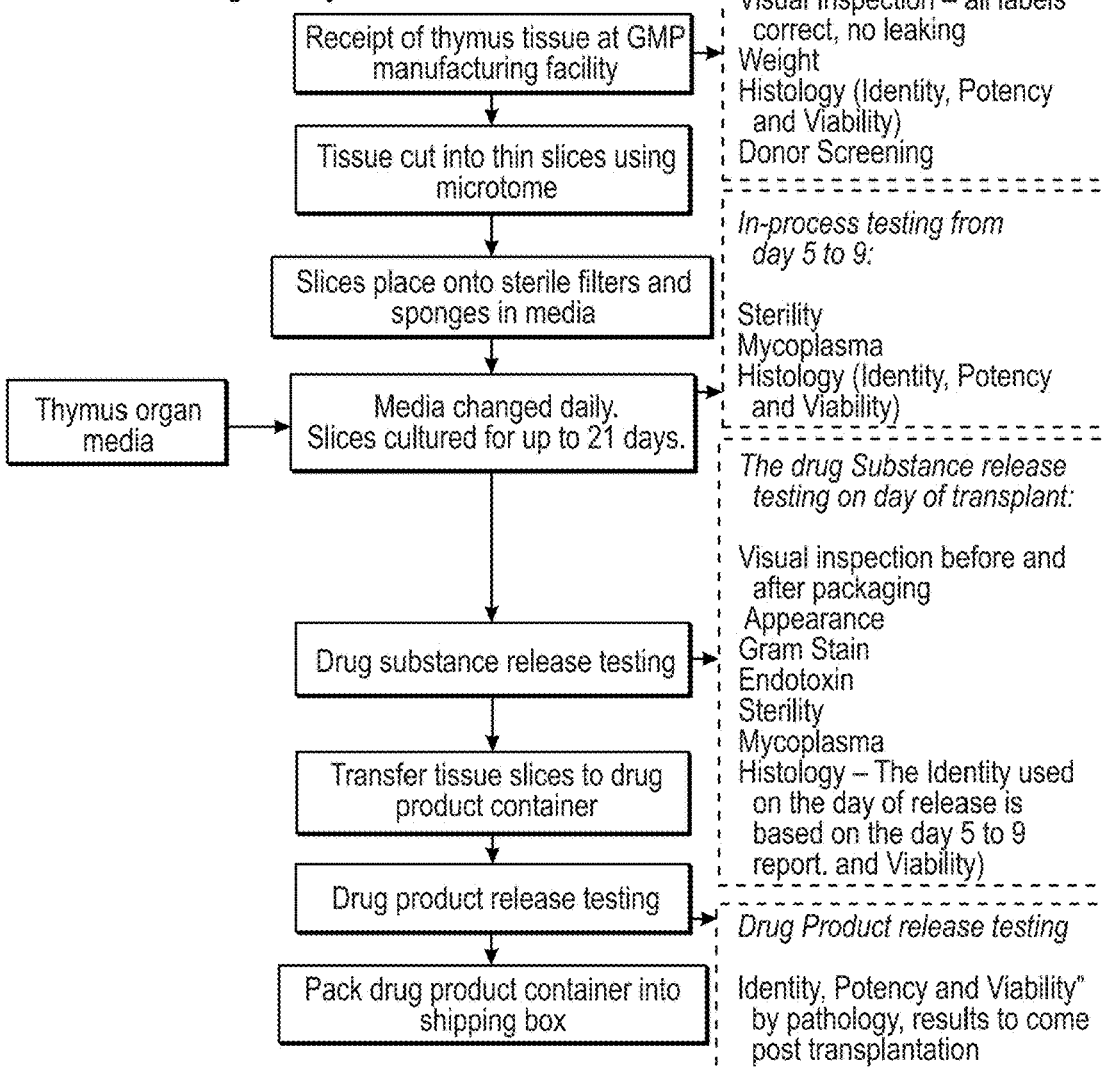
FIG. 4 shows a schematic of the manufacturing process for harvesting a thymus from a donor, culturing thin slices of the donor thymus tissue made with a hand microtome for up to 21 days and implanting the cultured thymus tissue in the quadriceps muscle of the recipient.
Figure 87:
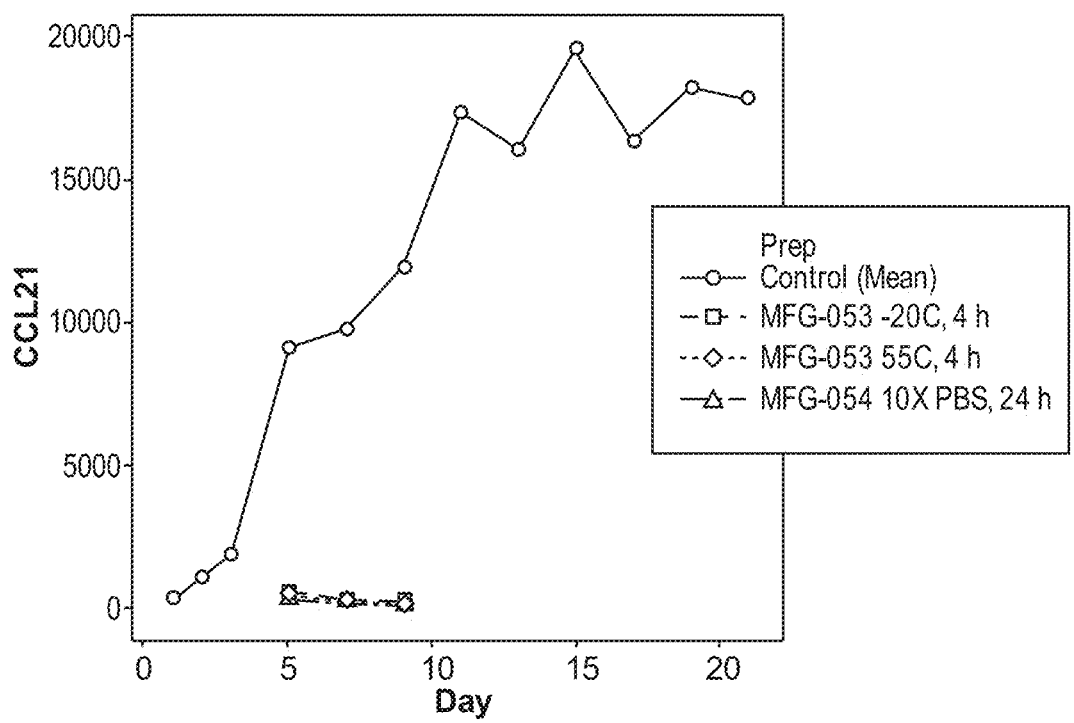

FIG. 87 is a graph of FIG. 4: CCL21 Levels (pg/mL) in Forced Degradation Study—Lot MFG-053 and Lot-054.

Figure 88:
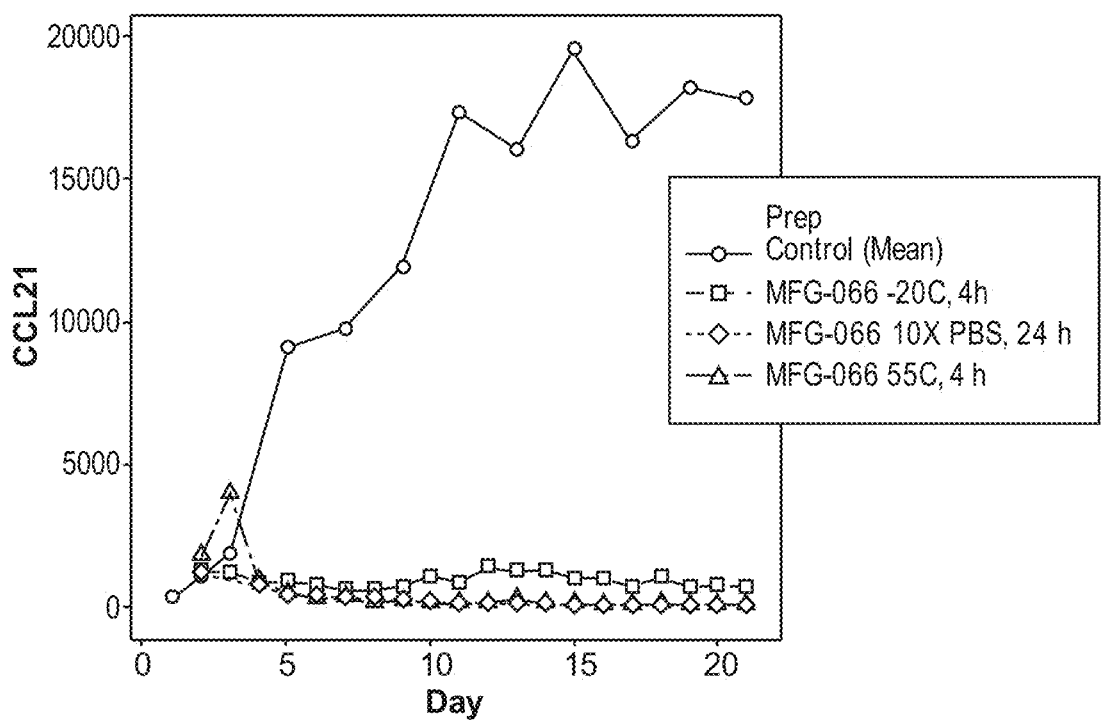

FIG. 88 is a graph of CCL21 Levels (pg/mL) in Forced Degradation Study—Lot MFG-066.

Figure 89:
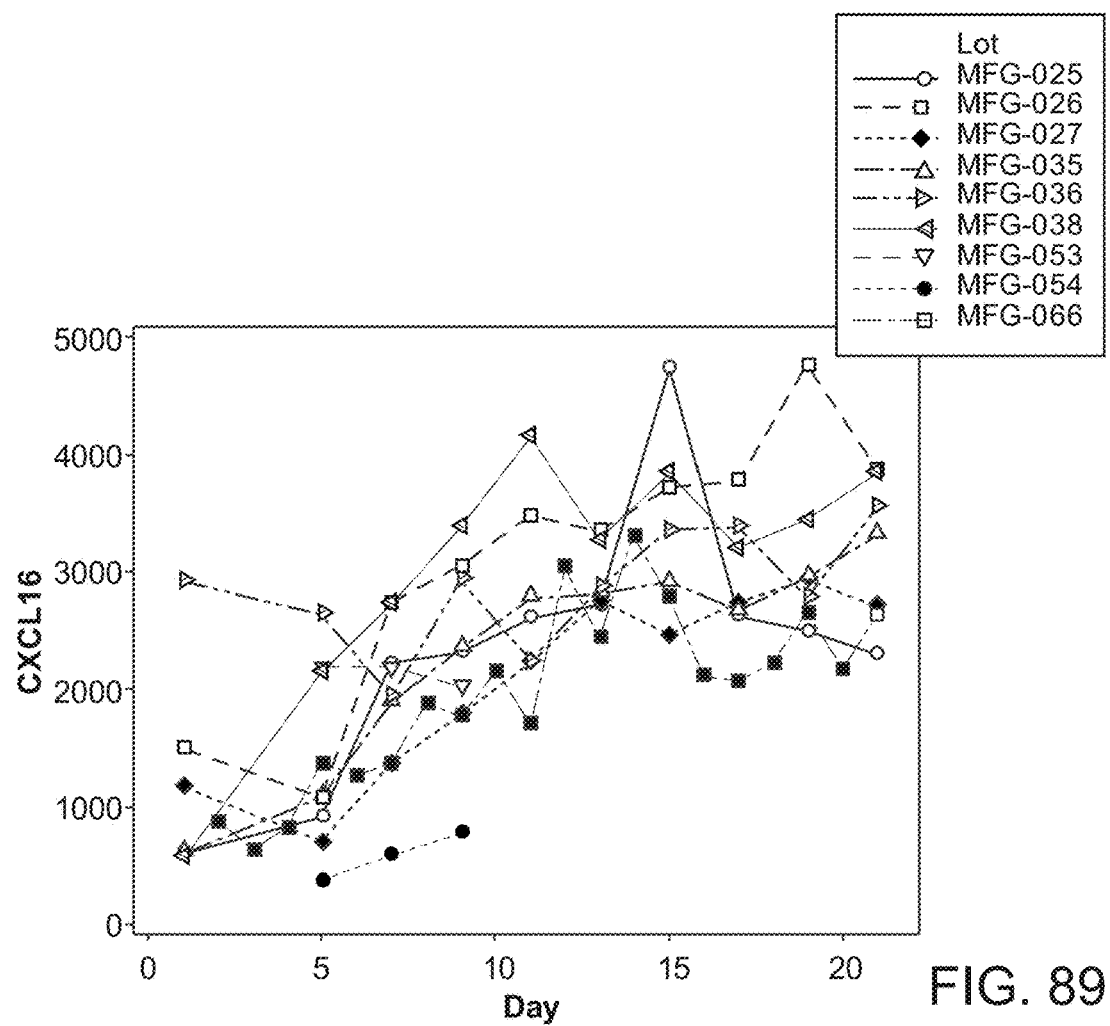

FIG. 89 is a scatterplot of CXCL16 Concentration in Spent Media vs. Day.

Figure 90:
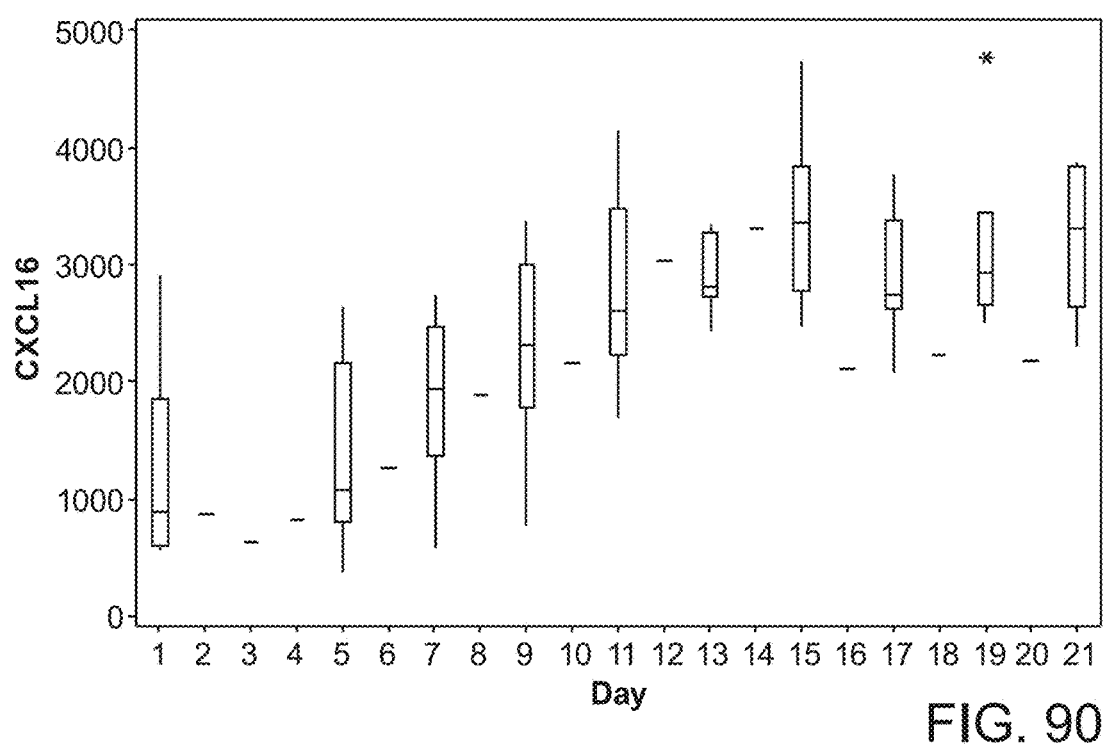

FIG. 90 is a boxplot of CXCL16 Concentration in Spent Media vs. Day.

Figure 91:
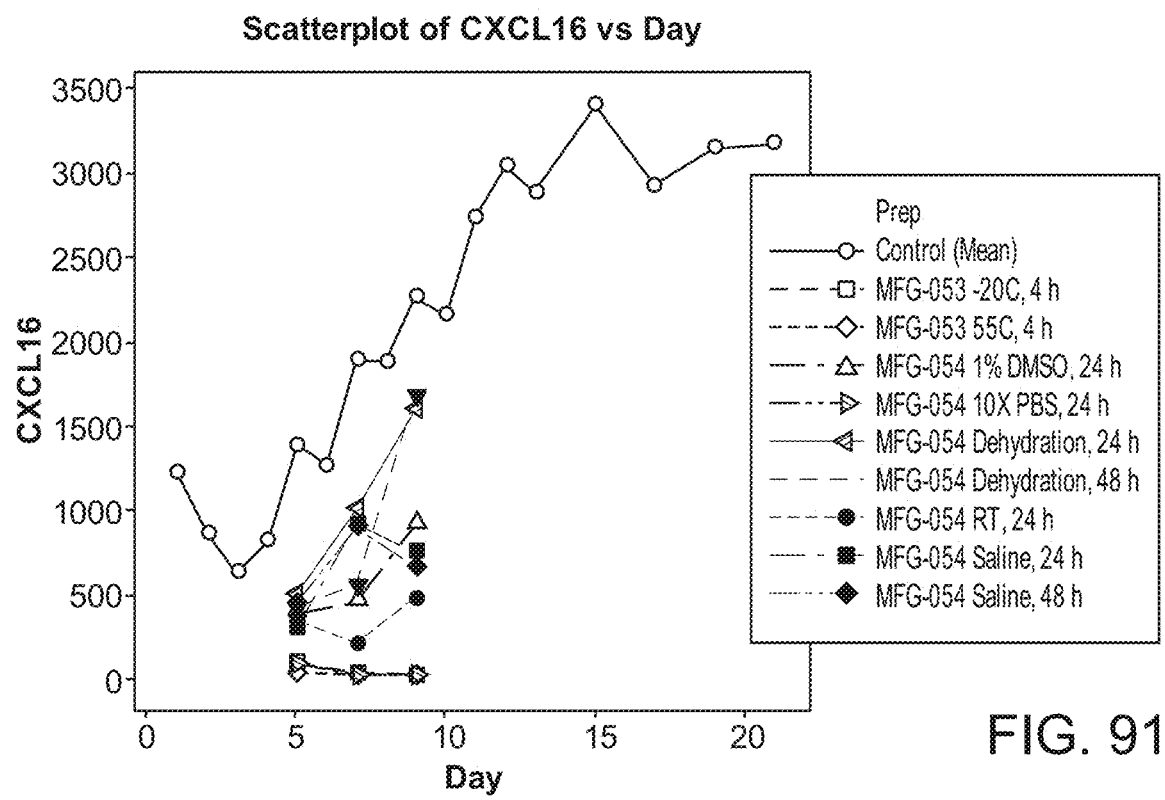

FIG. 91 is a scatterplot of CXCL16 Levels (pg/mL) in Forced Degradation Study—Lot MFG-053 and Lot MFG-054.

Figure 92:
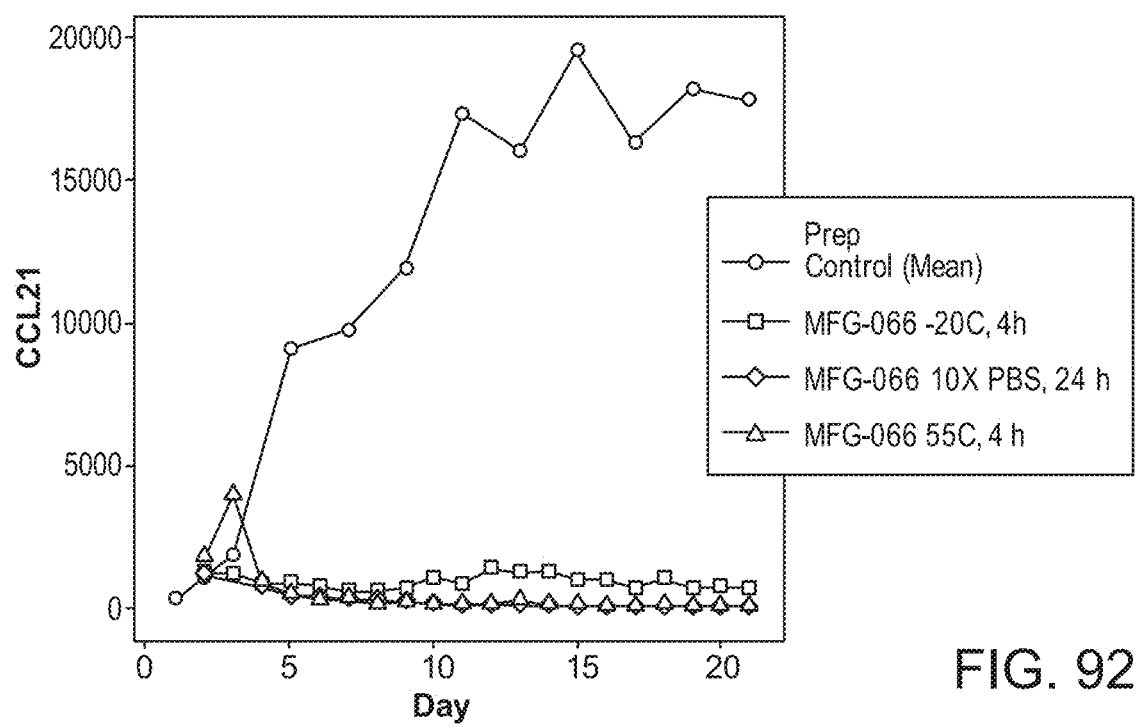

FIG. 92 is a scatterplot of CXCL21 Levels in Forced Degradation Study—Lot MFG-066.

Figure 93:
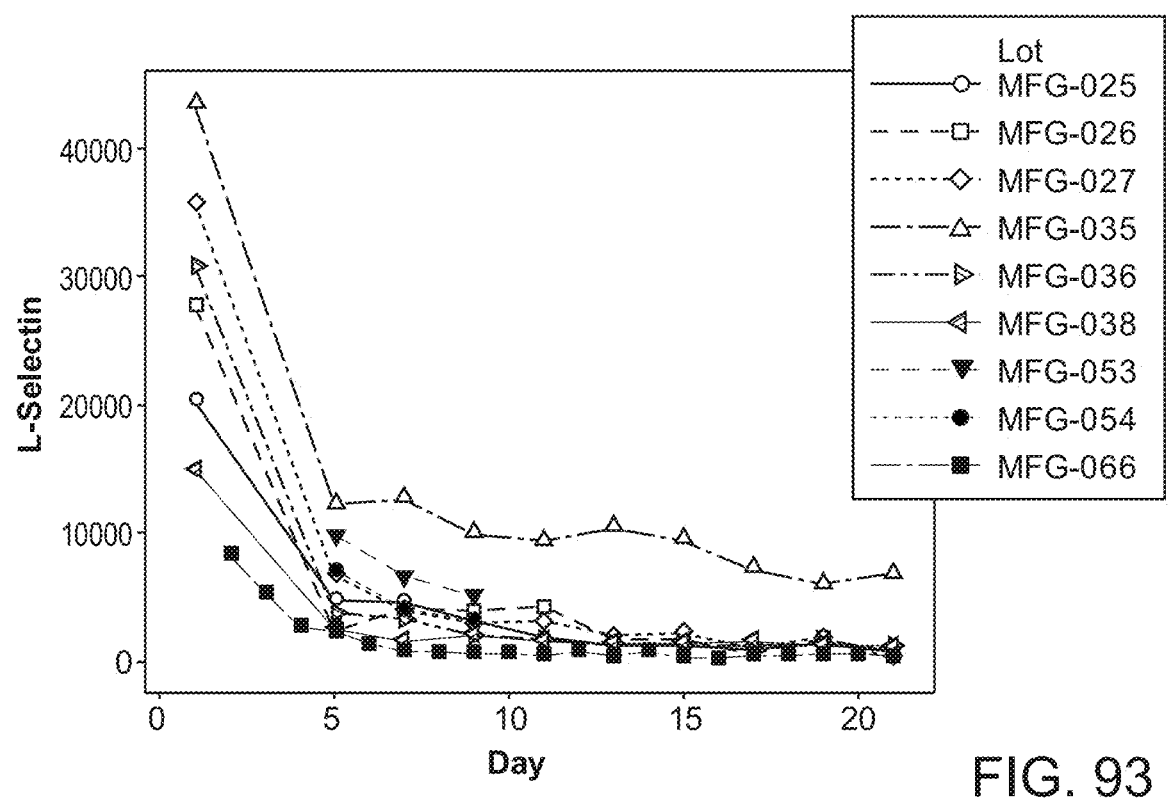

FIG. 93 is a scatterplot of L-Selectin Concentration in Spent Media vs. Day.

Figure 94:
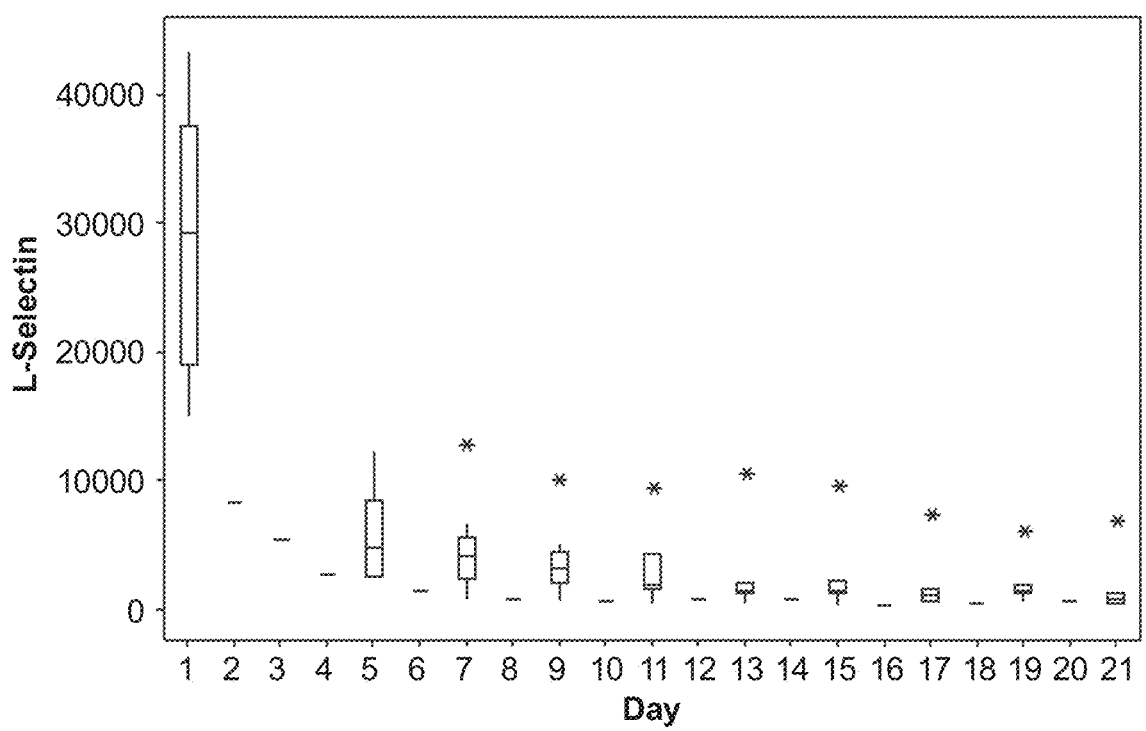

FIG. 94 is a boxplot of L-Selectin Concentration in Spent Media vs. Day.

Figure 95:
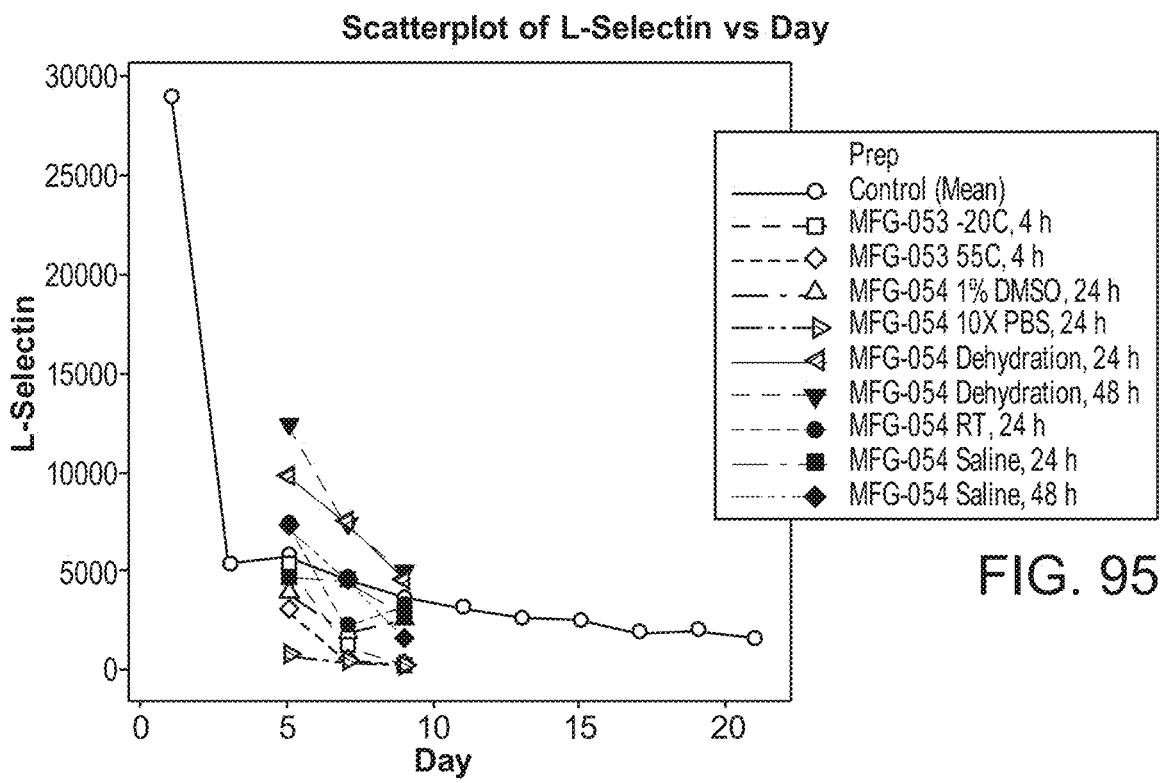

FIG. 95 is a scatterplot of L-Selectin Levels (pg/mL) in Forced Degradation Study—Lot MFG-053 and Lot MFG-054.

Figure 96:
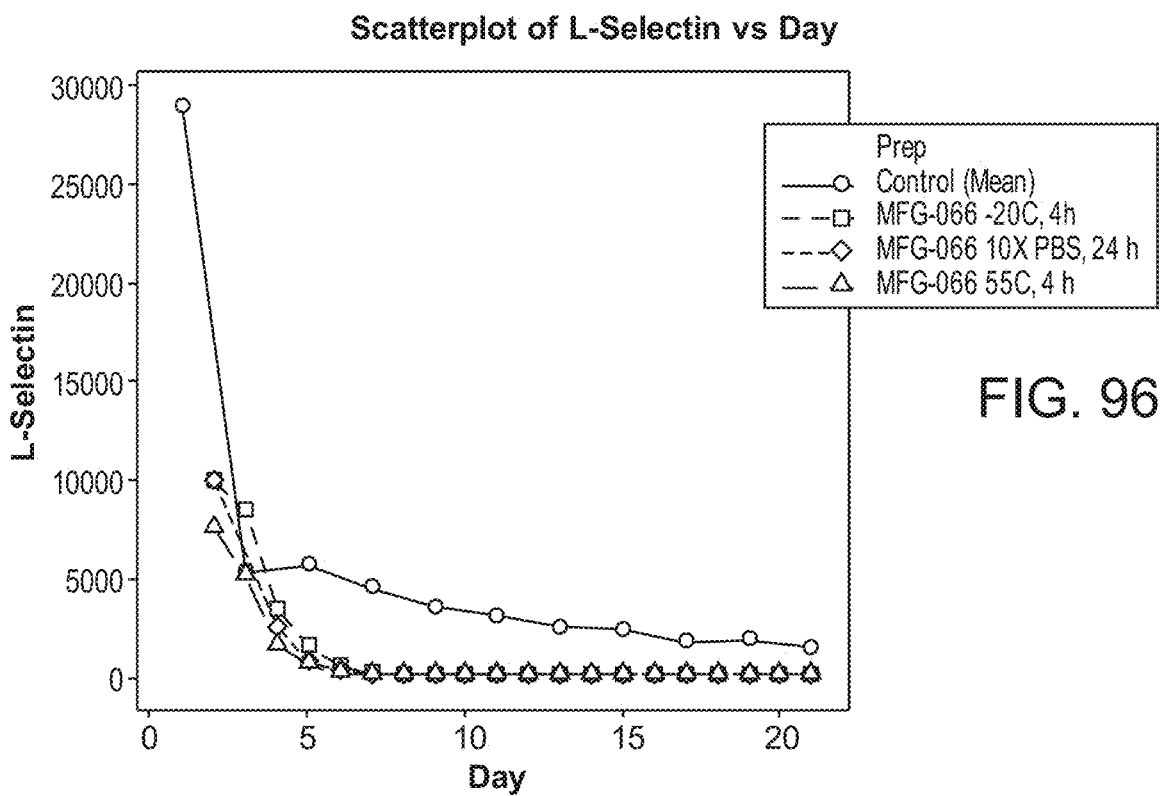

FIG. 96 is a scatterplot of L-Selectin Levels in Forced Degradation Study—Lot MFG-066.

Figure 97:
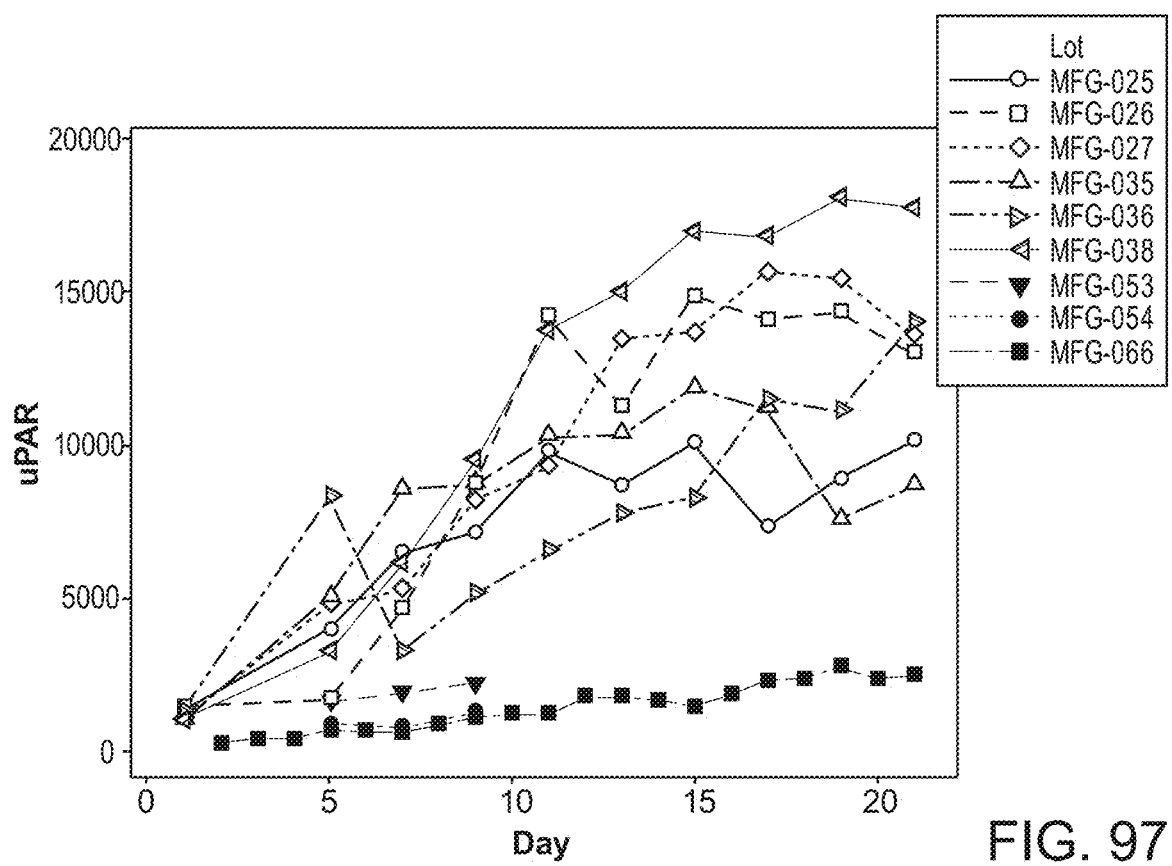

FIG. 97 is a scatterplot of uPAR Concentration in Spent Media vs. Day.

Figure 98:
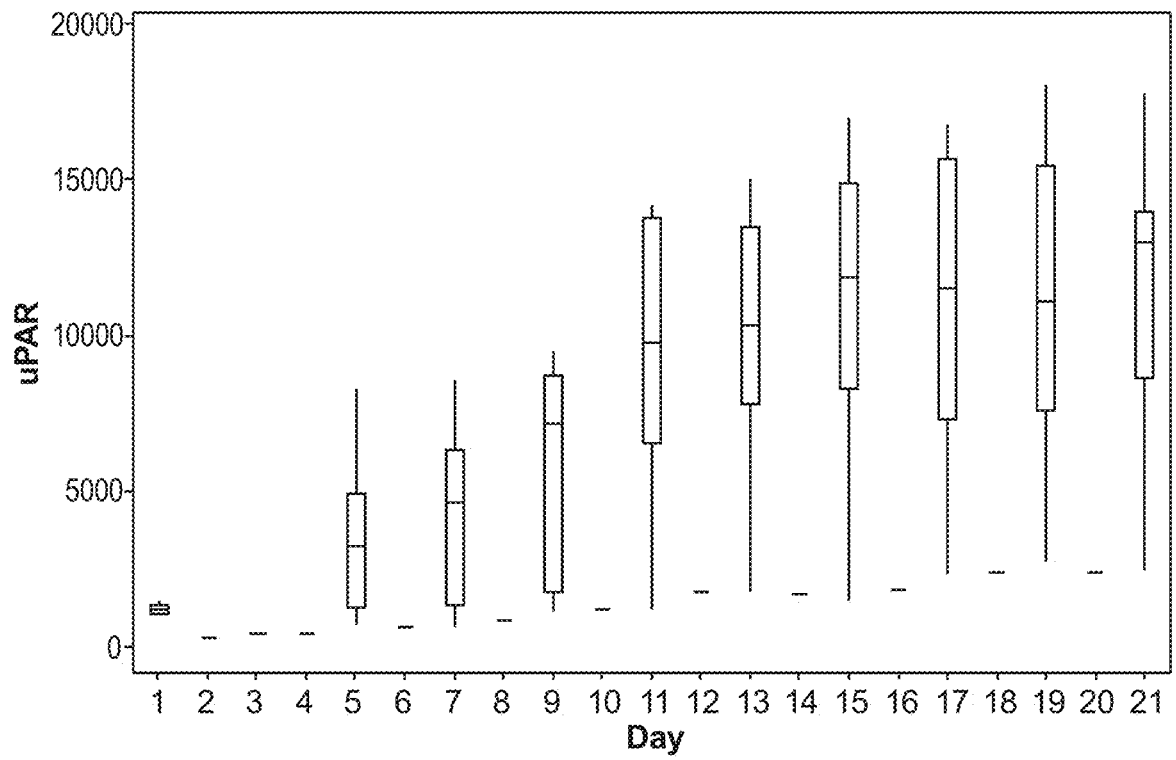

FIG. 98 is a boxplot of uPAR Concentration in Spent Media vs. Day.

Figure 99:
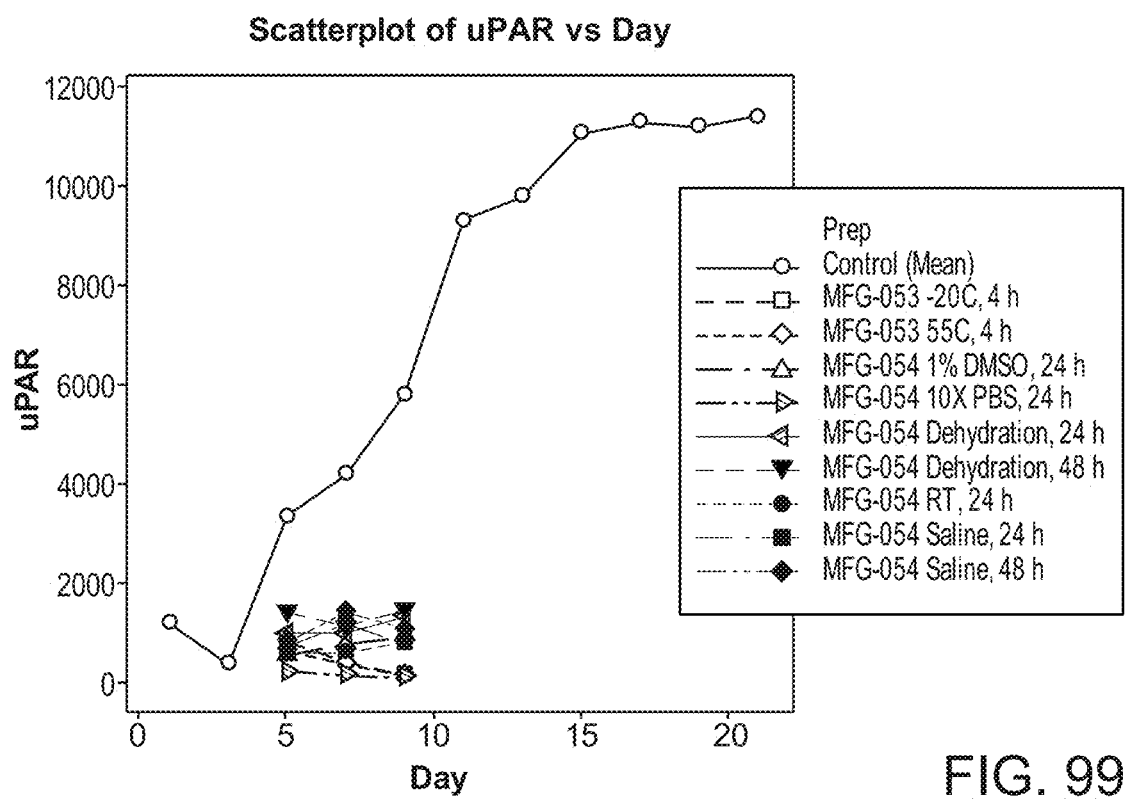

FIG. 99 is a scatterplot of uPAR Levels (pg/mL) in Forced Degradation Study—Lot MFG-053 and Lot MFG-054.

Figure 100:
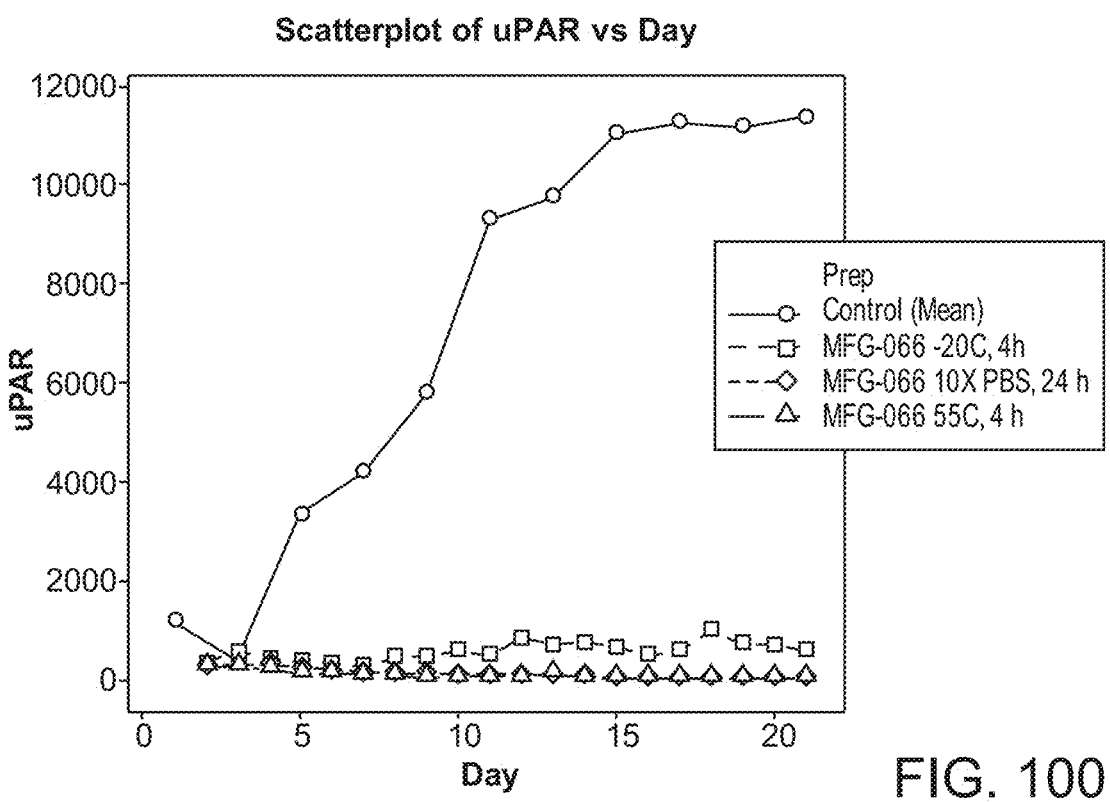

FIG. 100 is a scatterplot of uPAR Levels in Forced Degradation Study—Lot MFG-066.

Figure 101:
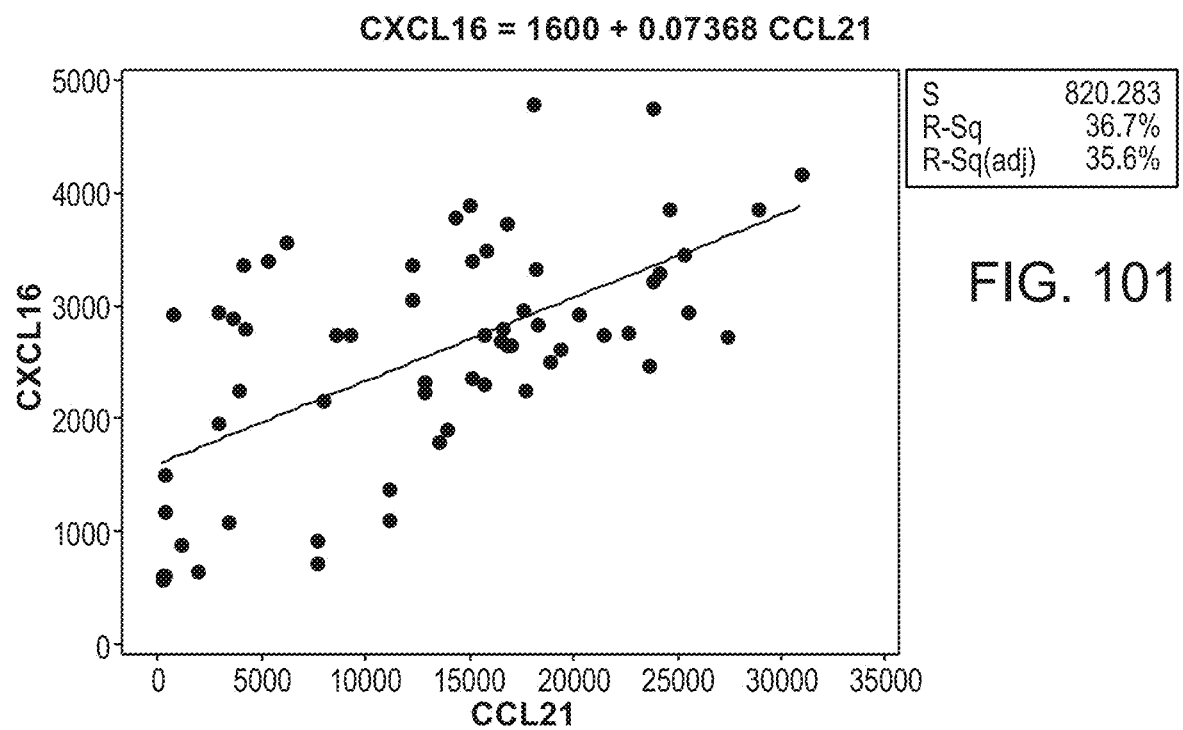

FIG. 101 is a scatterplot of CXCL16 vs. CCL21.

Figure 102:
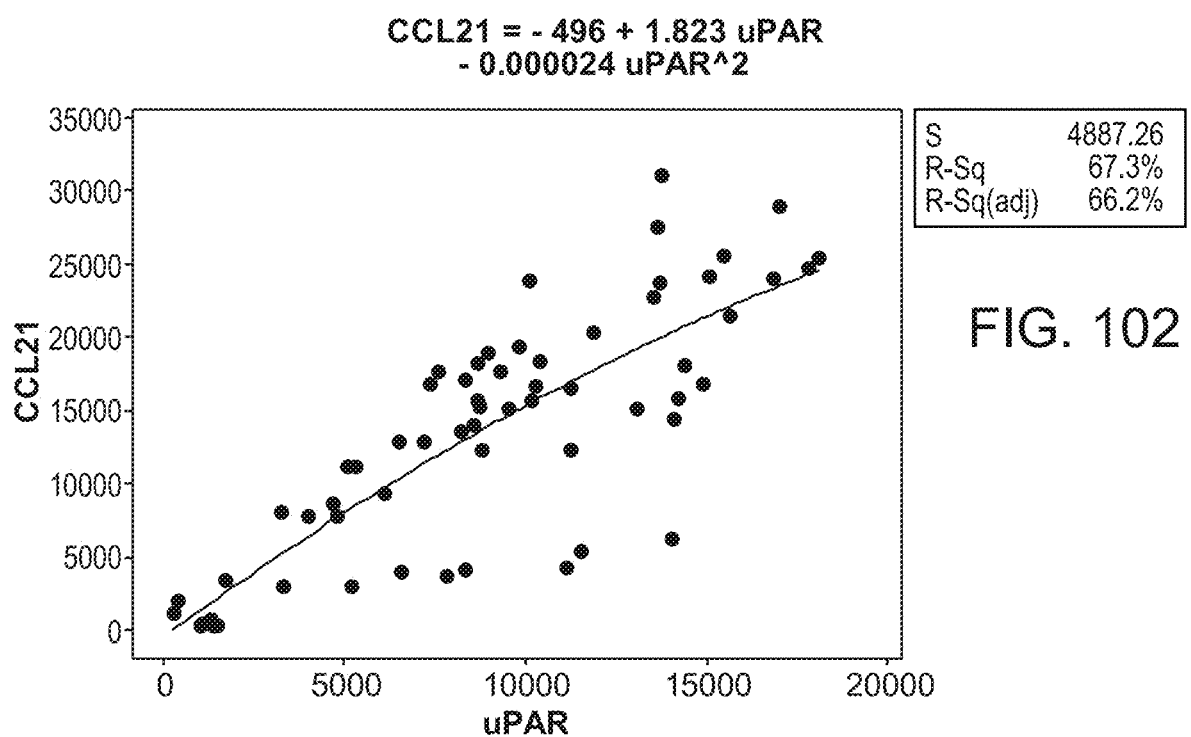

FIG. 102 is a quadratic regression model of CCL21 vs. uPAR.

Figure 103:
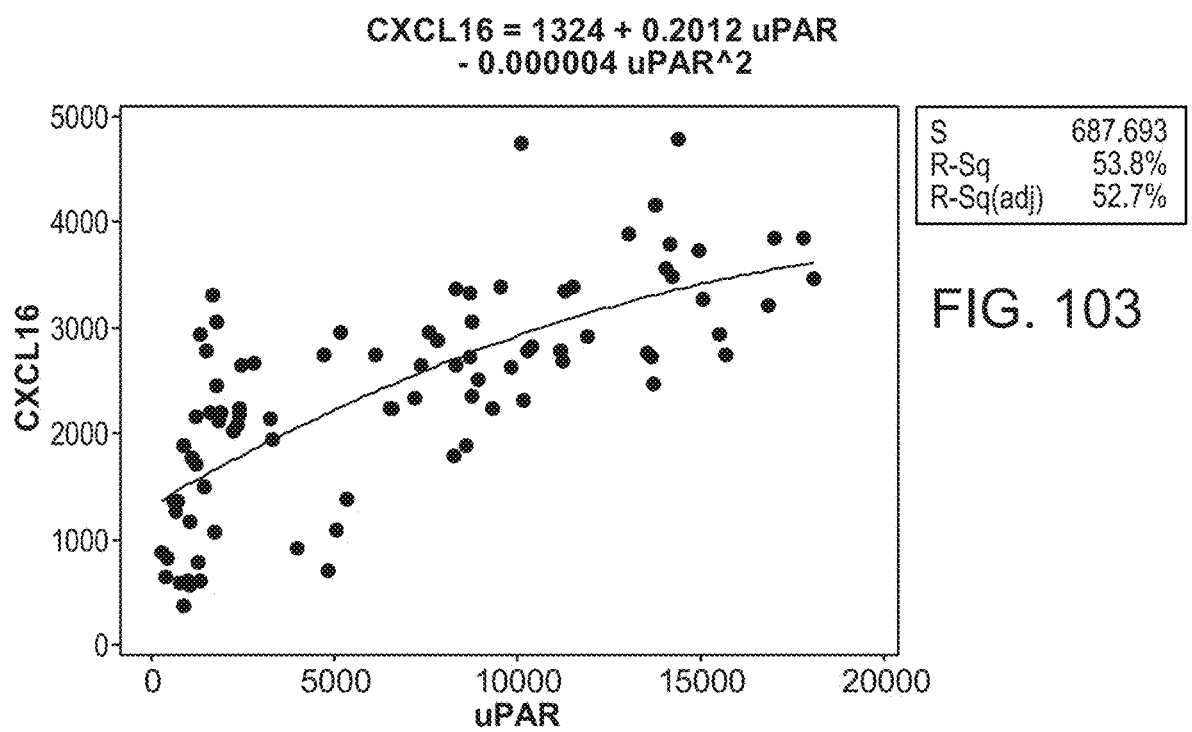

FIG. 103 is a quadratic regression model of CXCL16 vs. uPAR.

Figure 104:
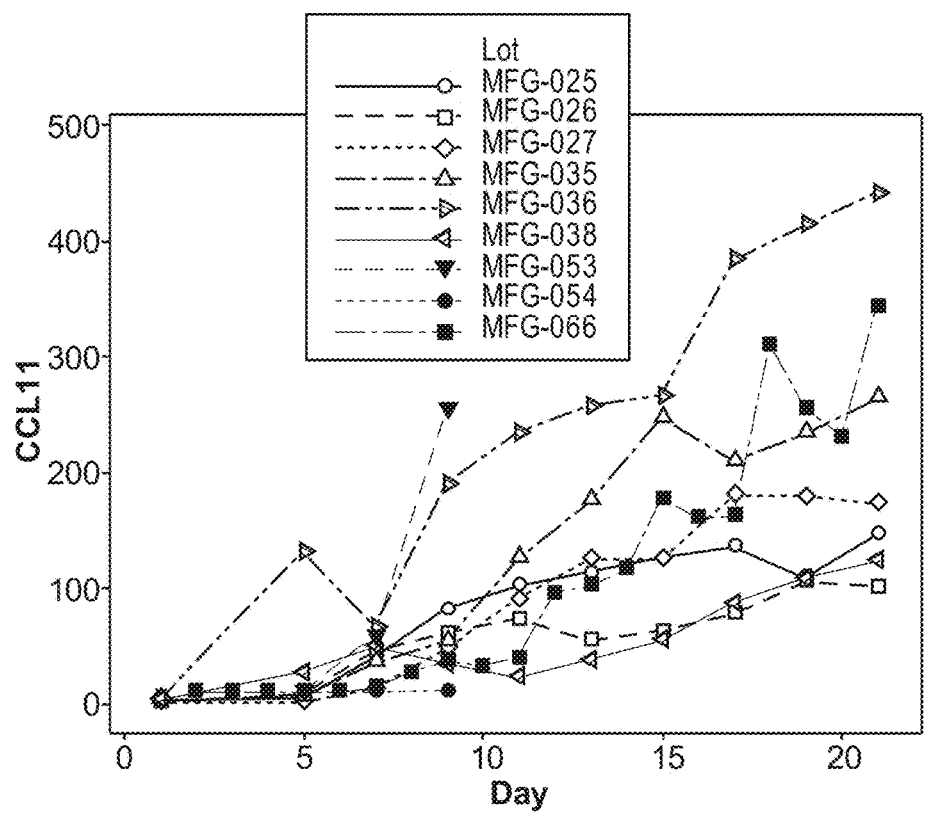

FIG. 104 is a scatterplot of CCL11 Concentration in Spent Media vs. Day.

Figure 105:
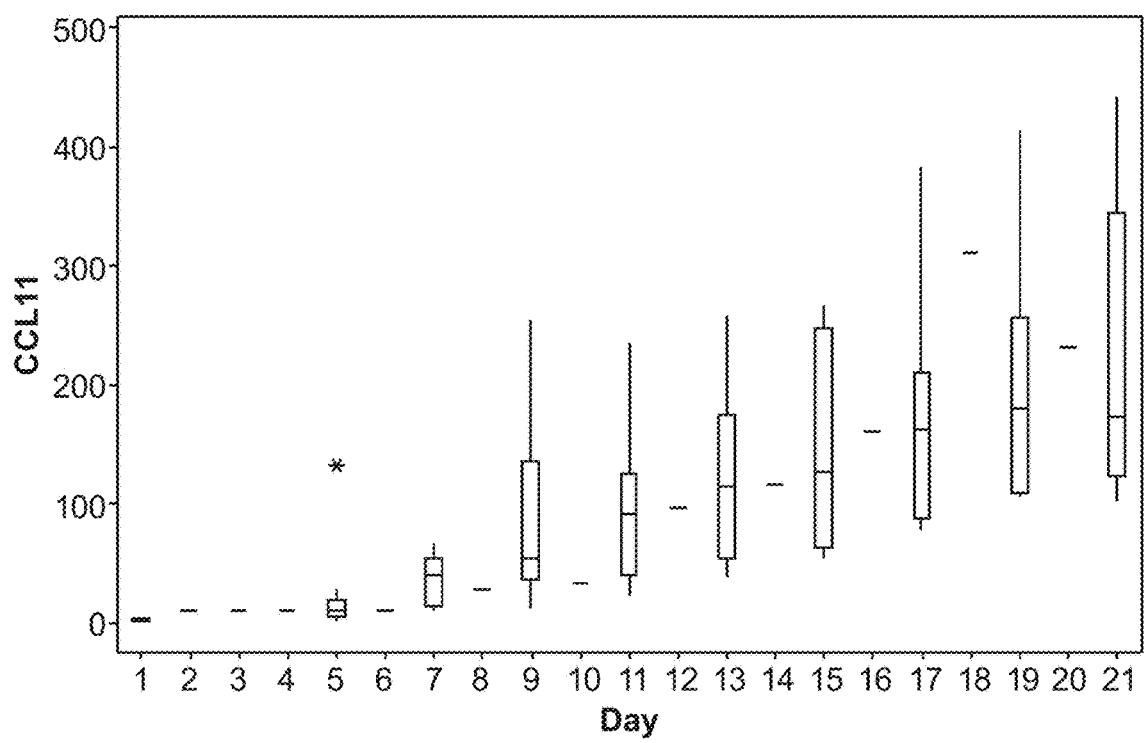

FIG. 105 is a boxplot of CCL11 Concentration in Spendt Media vs. Day.

Figure 106:
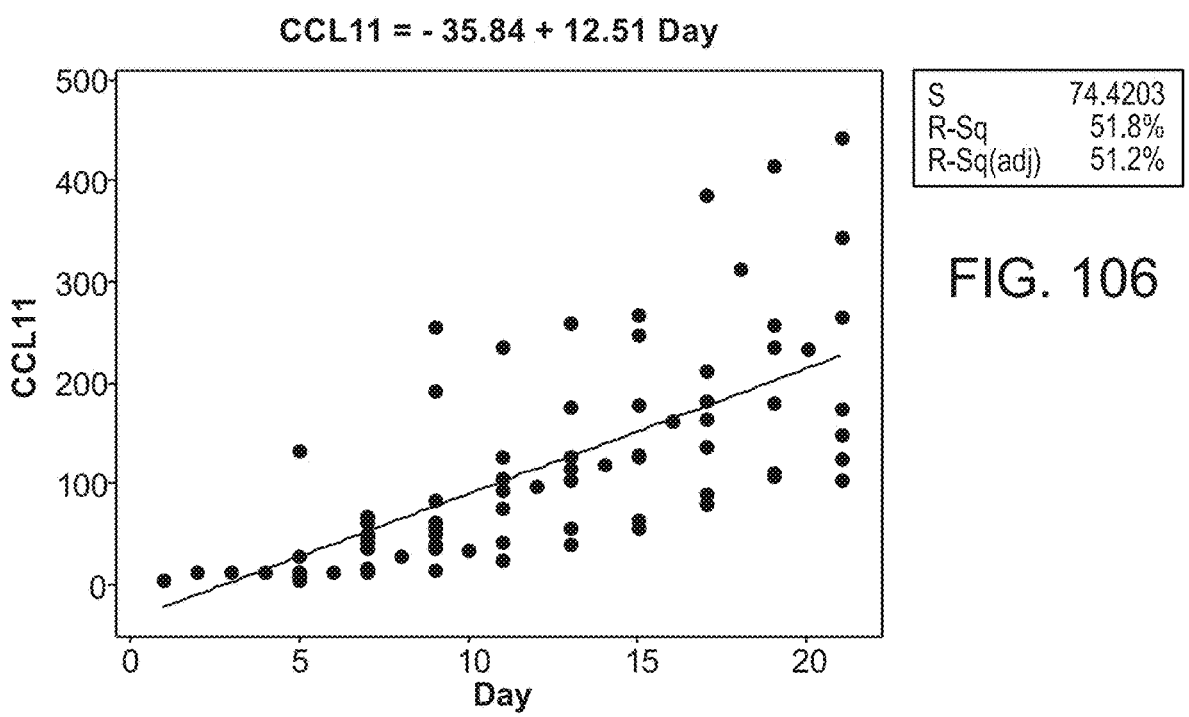

FIG. 106 is a linear regression model of CCL11 Concentration in Spent Media vs. Day.

Figure 107:
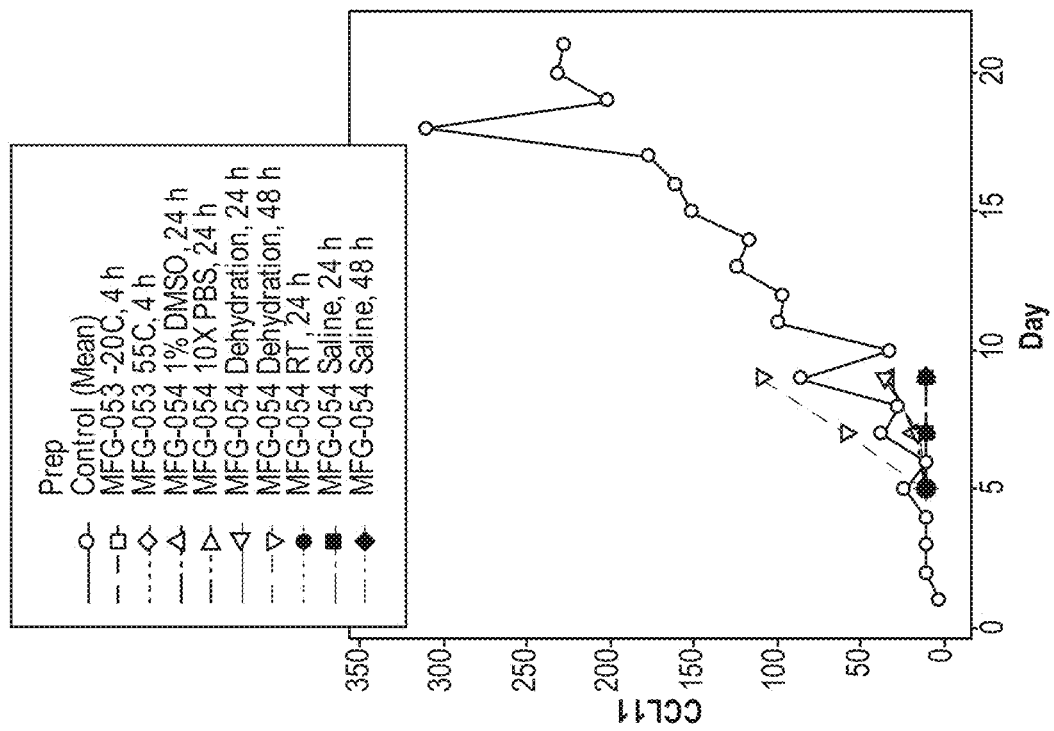

FIG. 107 is a plot of CCL11 Levels (pg/mL) in Forced Degradation Study—Lot MFG-053 and Lot MFG-054.

Figure 108:
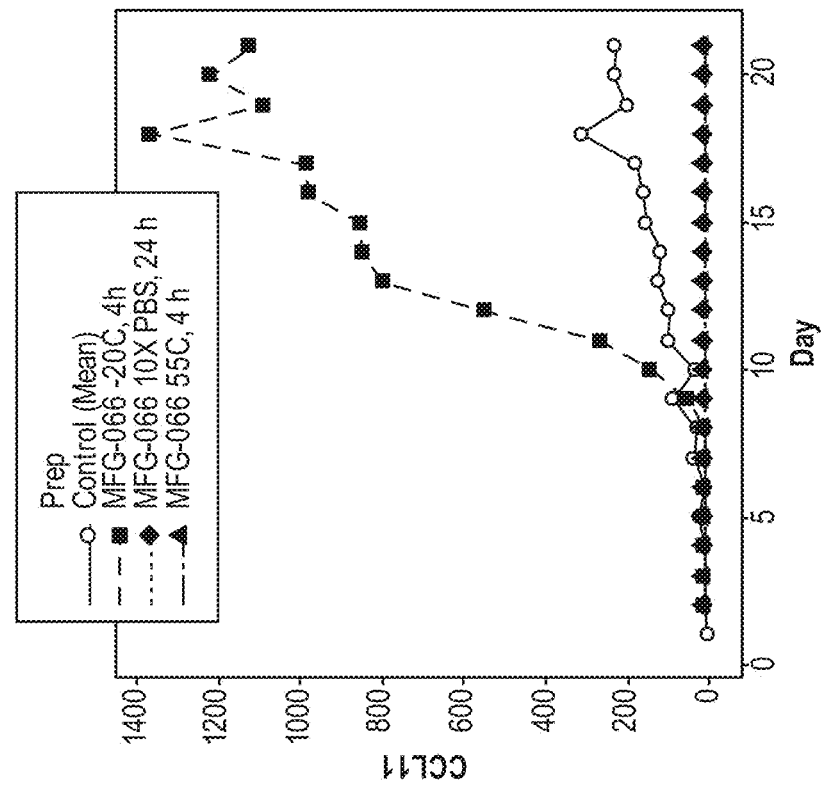

FIG. 108 is a lot of CCL11 Levels in Forced Degradation Study-Lot MFG-066.

Figure 109:
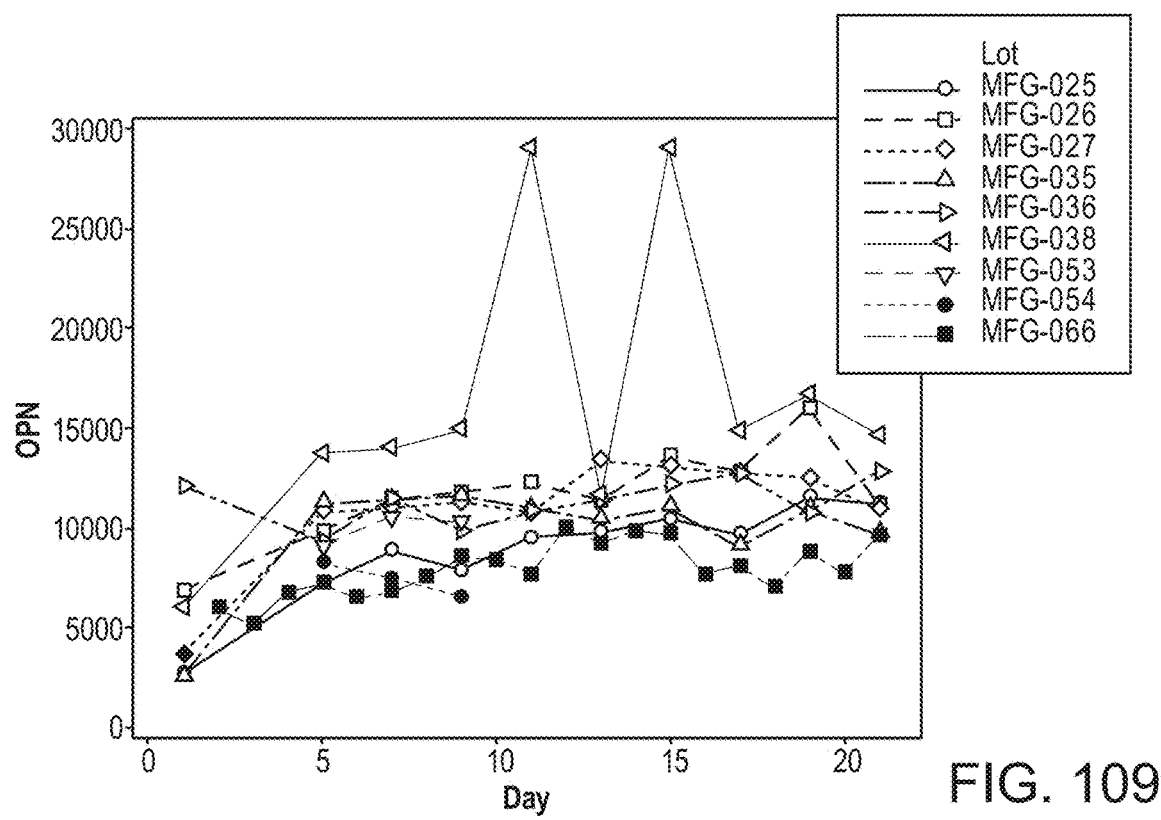

FIG. 109 is a scatterplot of OPN Concentration in Spent Media vs. Day.

Figure 110:
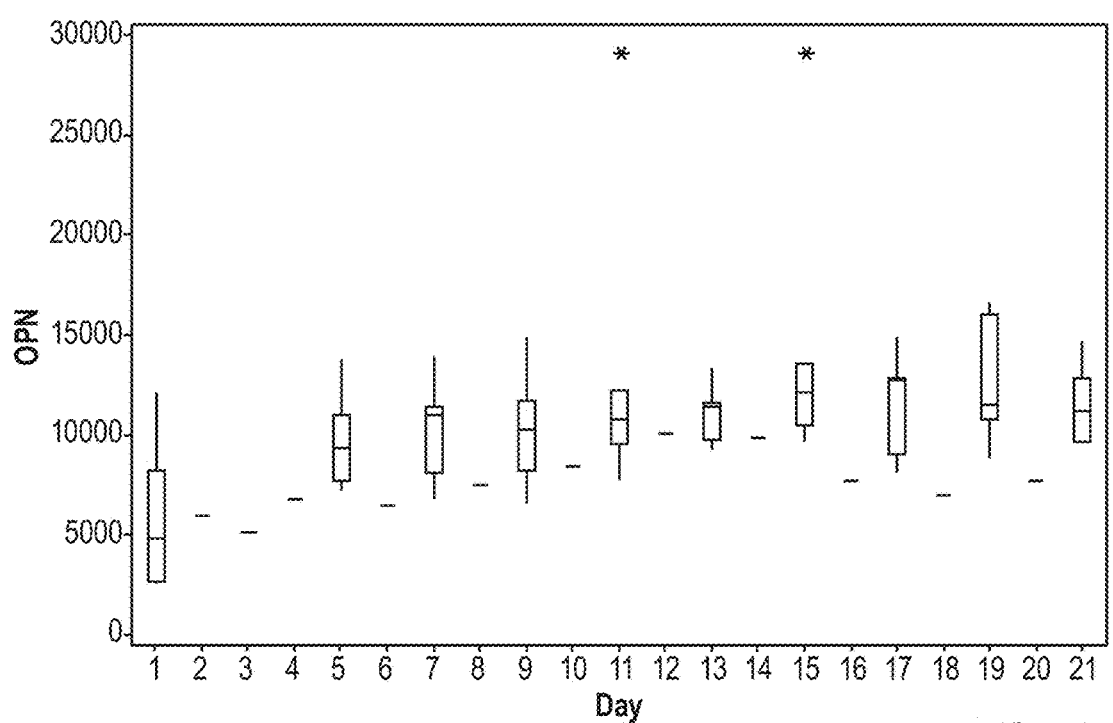

FIG. 110 is a boxplot of OPN Concentration in spent Media vs. Day.

Figure 111:
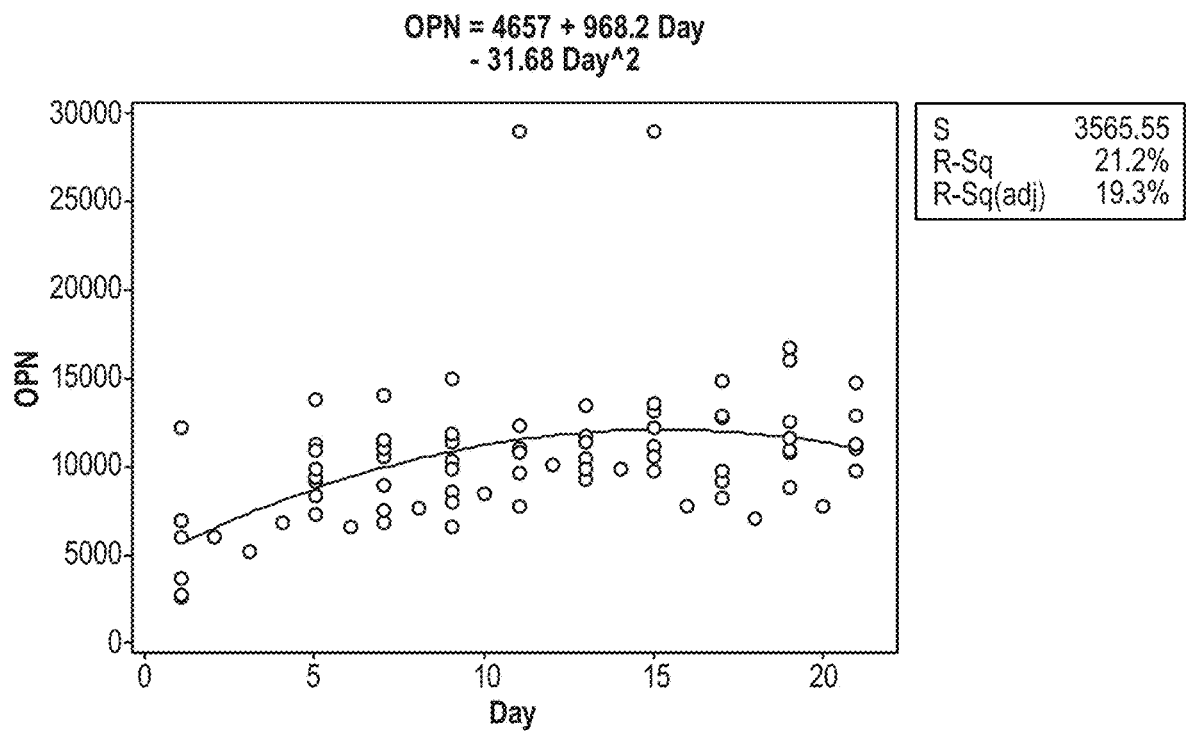

FIG. 111 is a quadratic regression model of OPN Concentration in Spent Media vs. Day.

Figure 112:
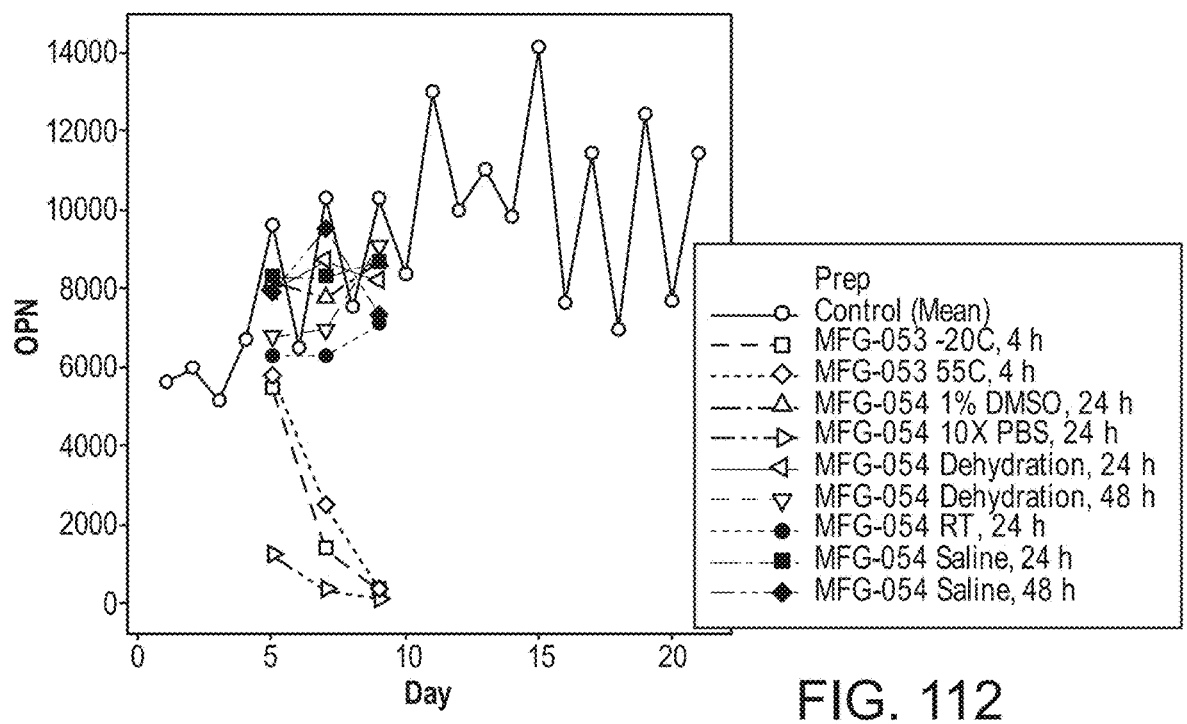

FIG. 112 is a plot of OPN Levels (pg/mL) in Forced Degradation Study-Lot MFG-053 and Lot MFC-054.

Figure 113:
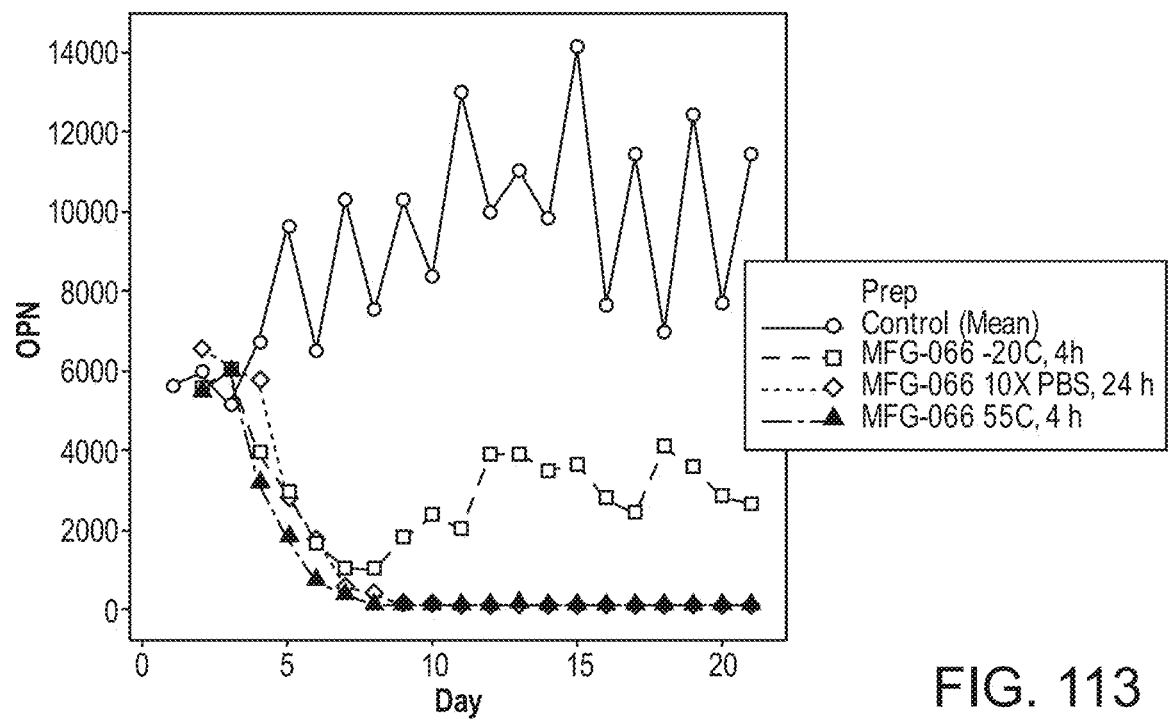

FIG. 113 is a plot of OPN Levels in Forced Degradation Study-Lot MFG-066.

Figure 114:
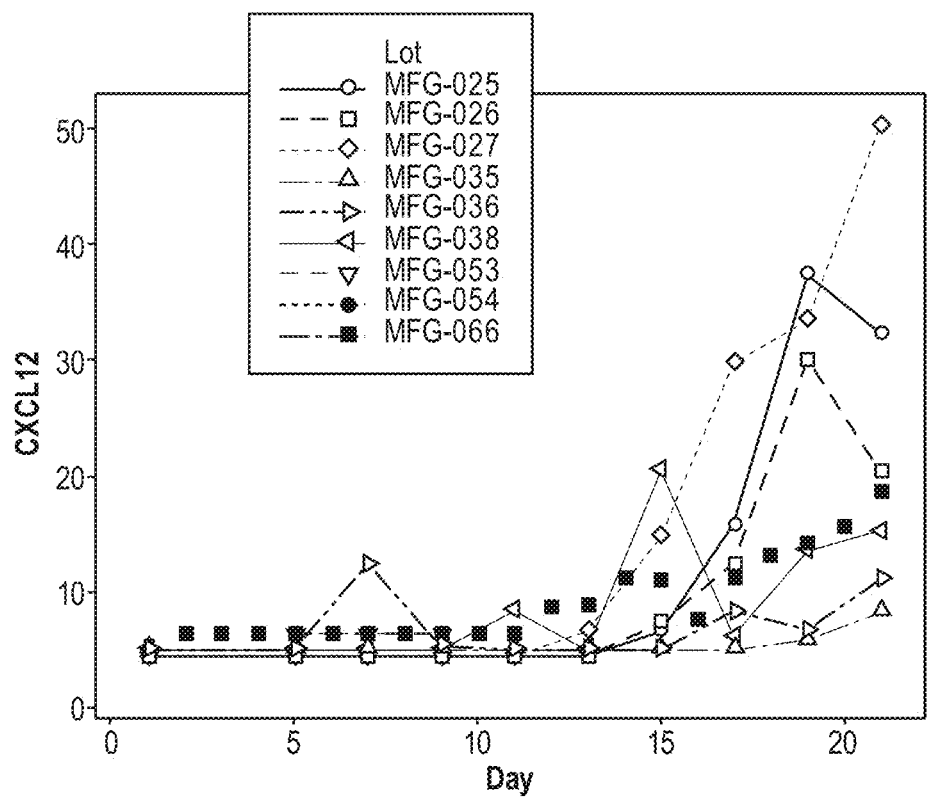

FIG. 114 is a scatterplot of CXCL12 Concentration in Spent Media vs. Day.

Figure 115:
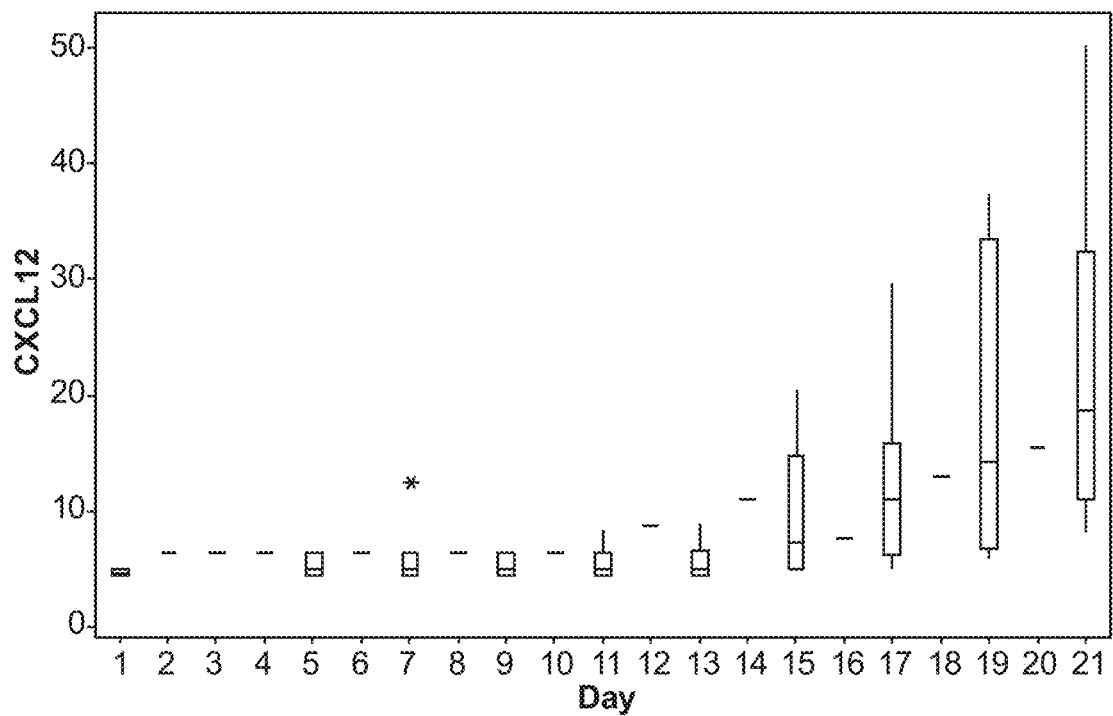

FIG. 115 is a boxplot of CXCL12 Concentration in Spent Media vs. Day.

Figure 116:
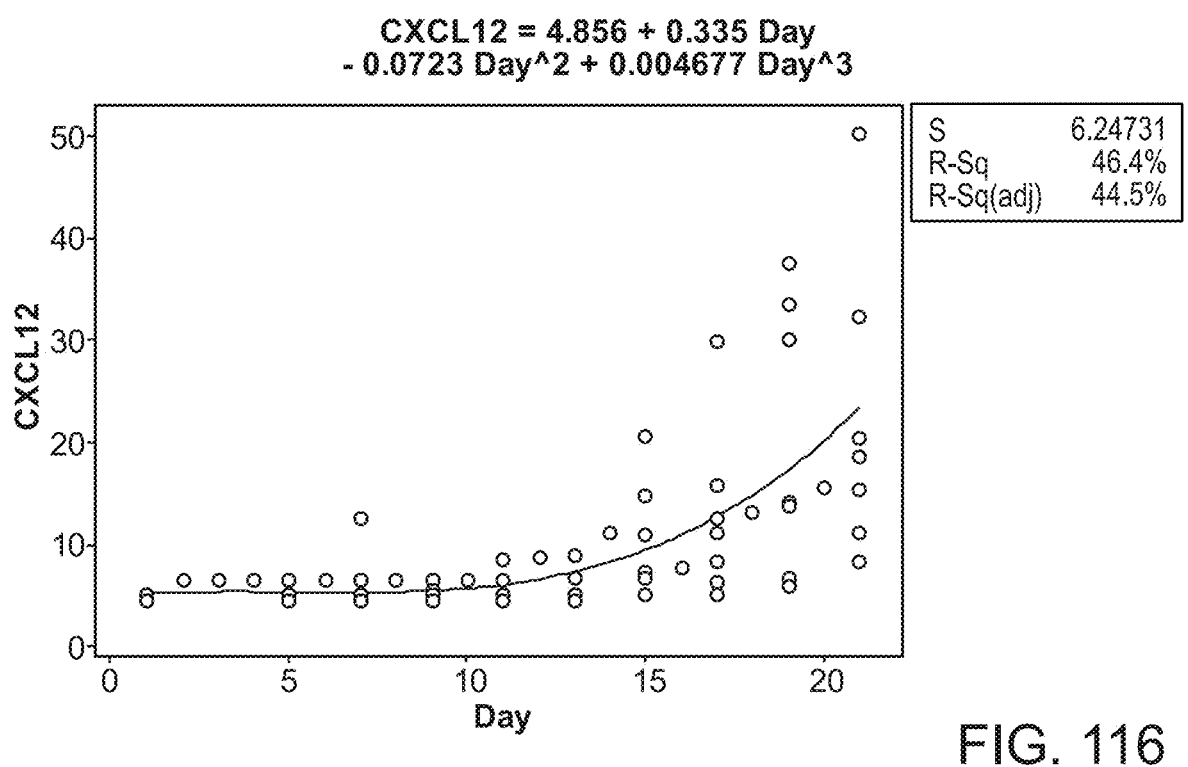

FIG. 116 is a fitted line plot of CXCL12 Concentration in Spent Media vs. Day.

Figure 117:
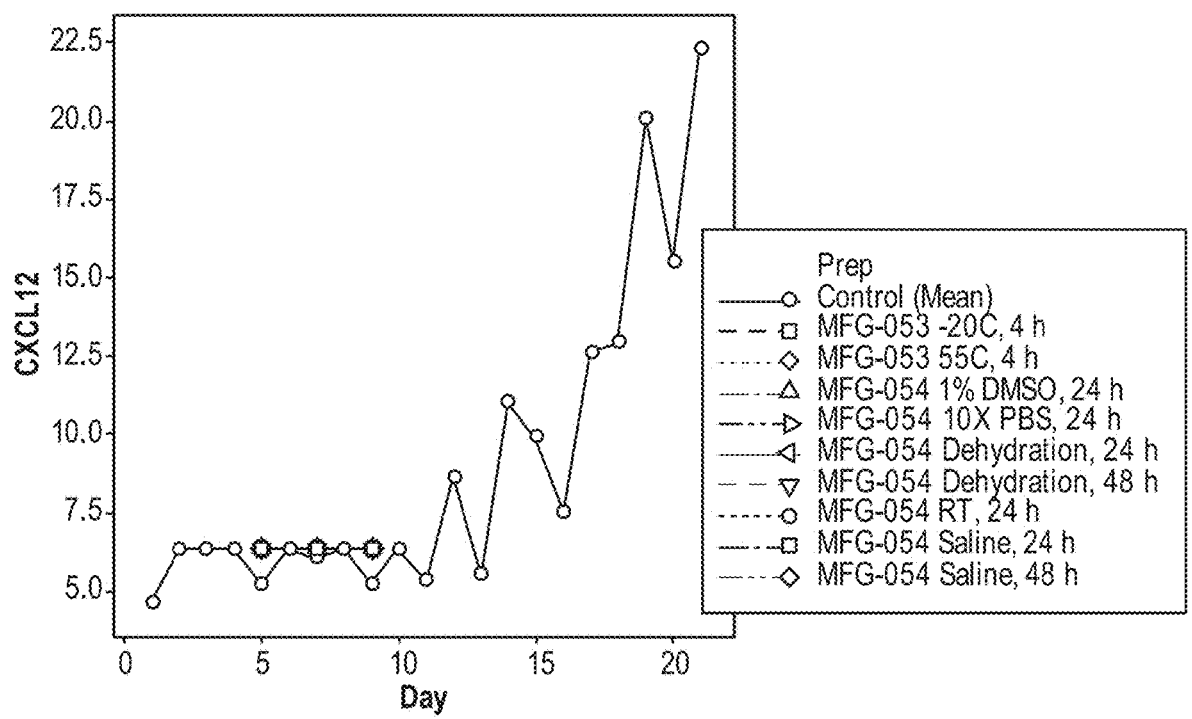

FIG. 117 is a scatterplot of CXCL12 Levels (pg/mL) in Forced Degradation Study-Lot MFG-053 and Lot MFG-054.

Figure 118:
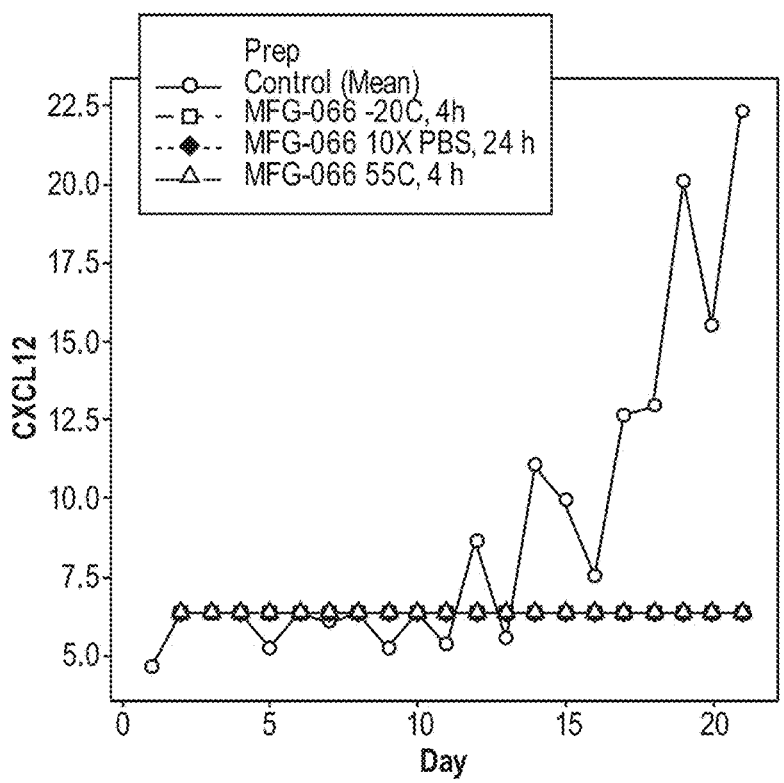

FIG. 118 is a scatterplot of CXCL12 Levels in Forced Degradation Study-Lot MFG-066.

Figure 119:
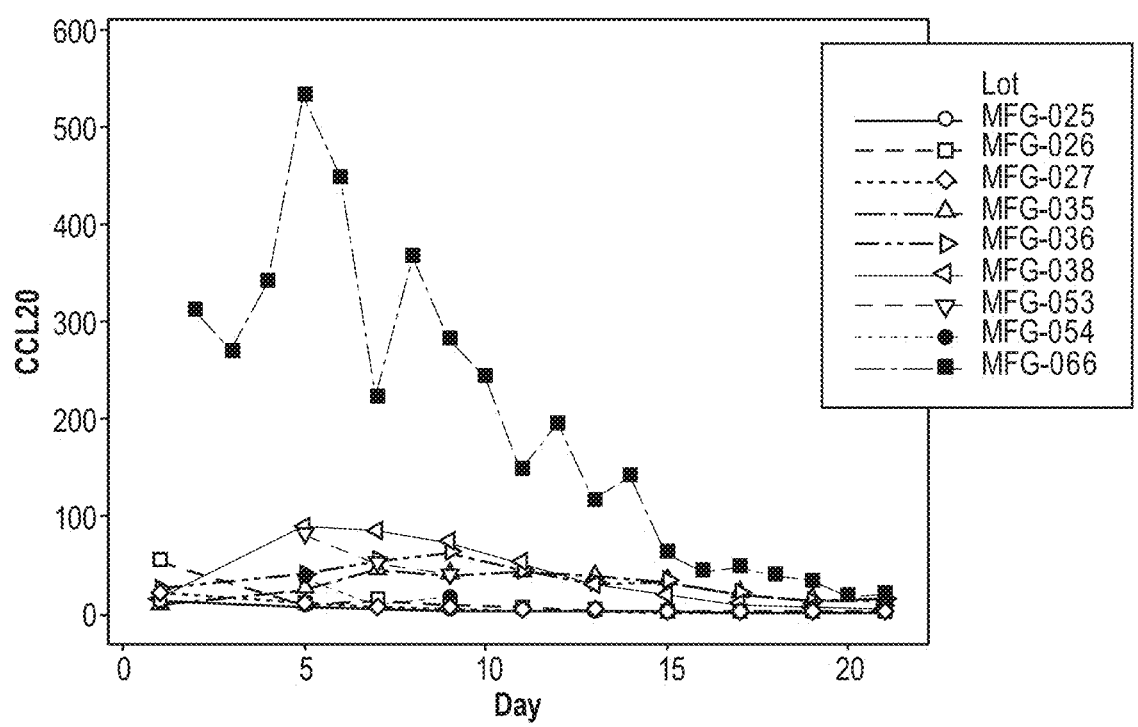

FIG. 119 is a scatterplot of CCL20 Concentration in Spent Media vs. Day.

Figure 120:
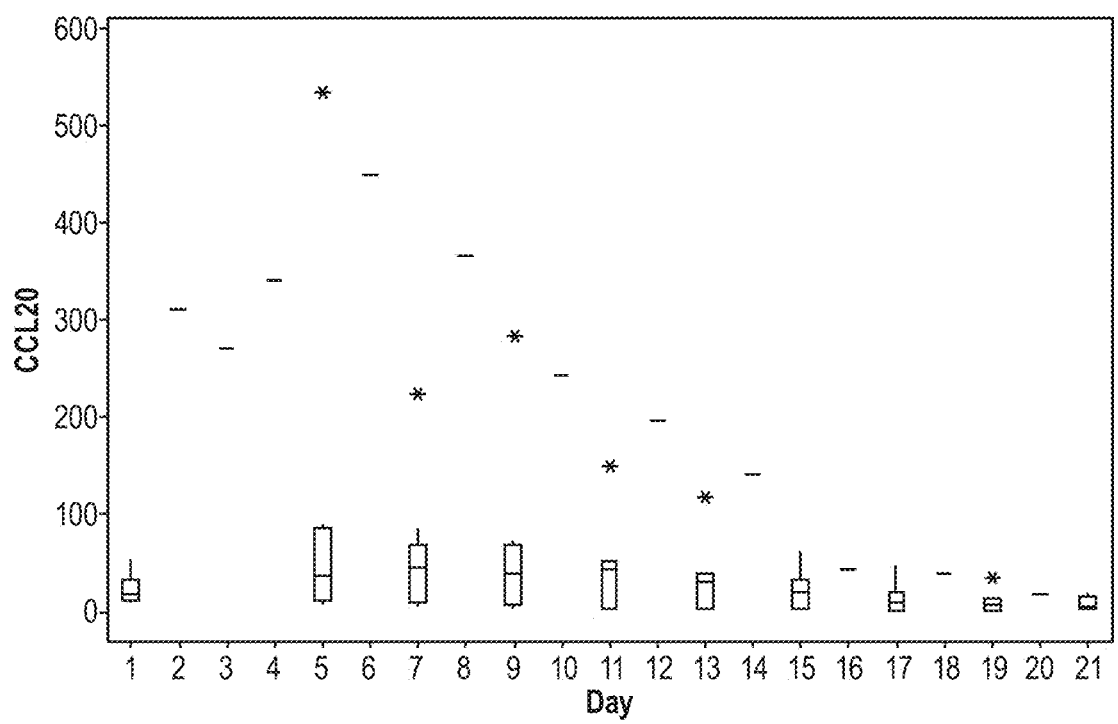

FIG. 120 is a boxplot of CCL20 Concentration in Spent Media vs. Day.

Figure 121:
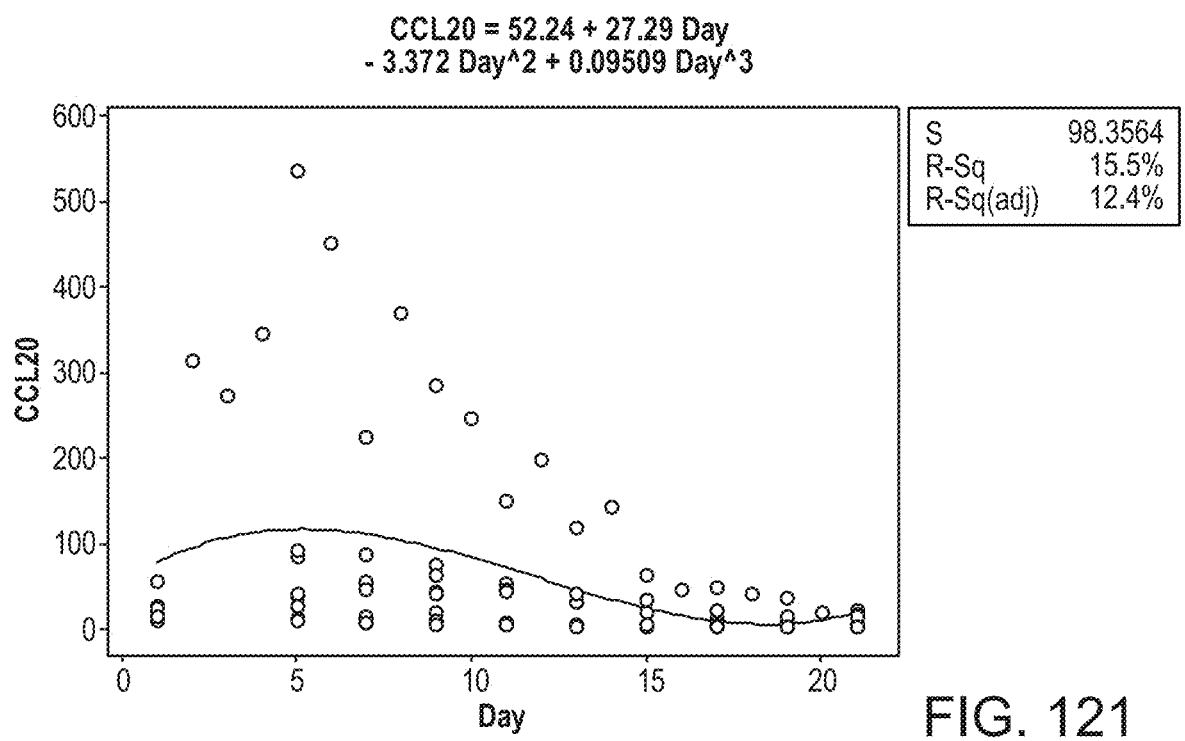

FIG. 121 is a cubic regression model of CCL20 Concentration in Spent media vs. Day.

Figure 122:
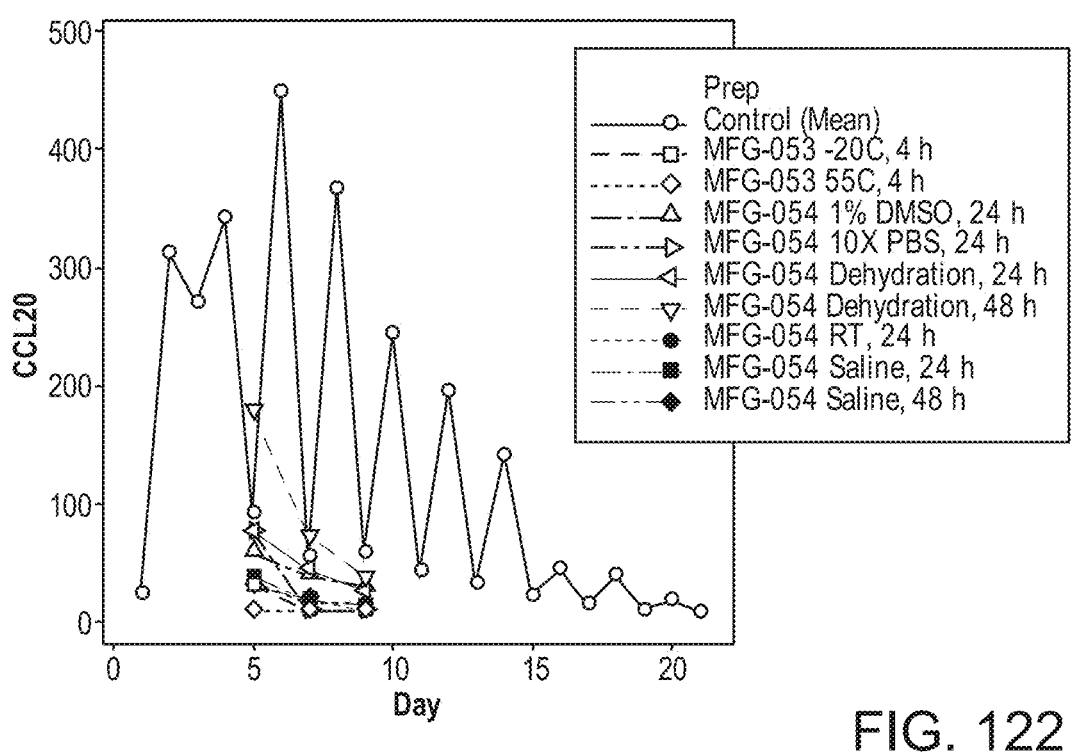

FIG. 122 is a scatterplot of CCL20 Levels (pg/mL) in Forced Degradation Study-Lot MFG-053 and Lot MFG-054.

Figure 123:
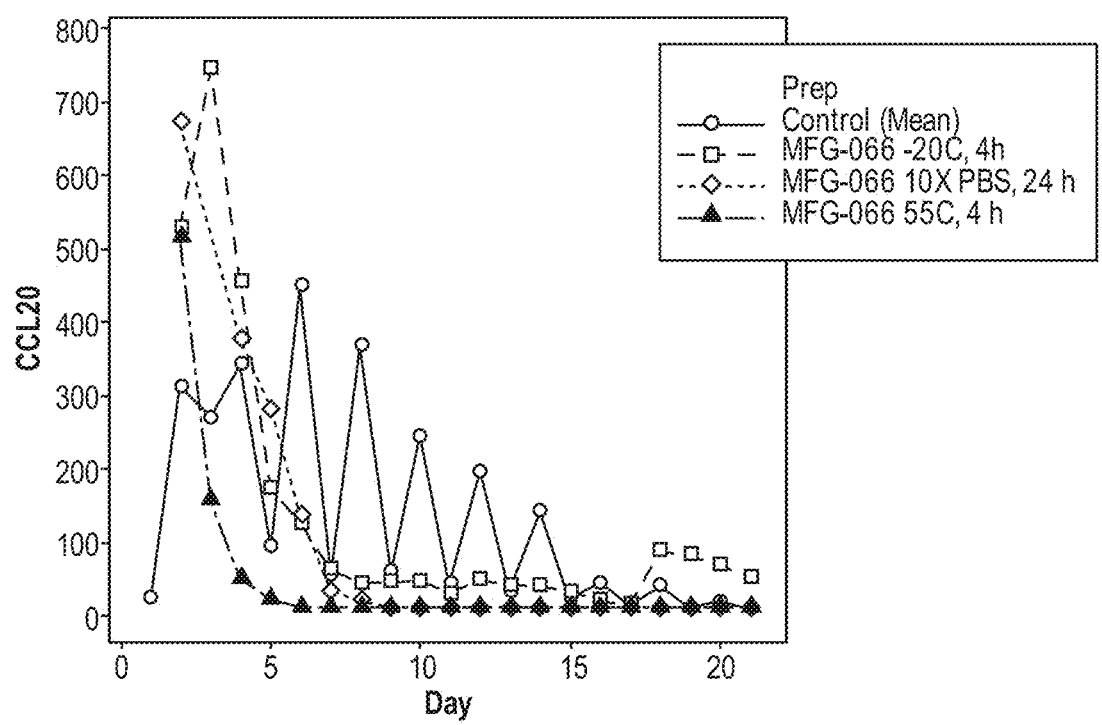

FIG. 123 is a scatterplot of CCL20 Levels in Forced Degradation Study-Lot MFG-066.

Figure 124:
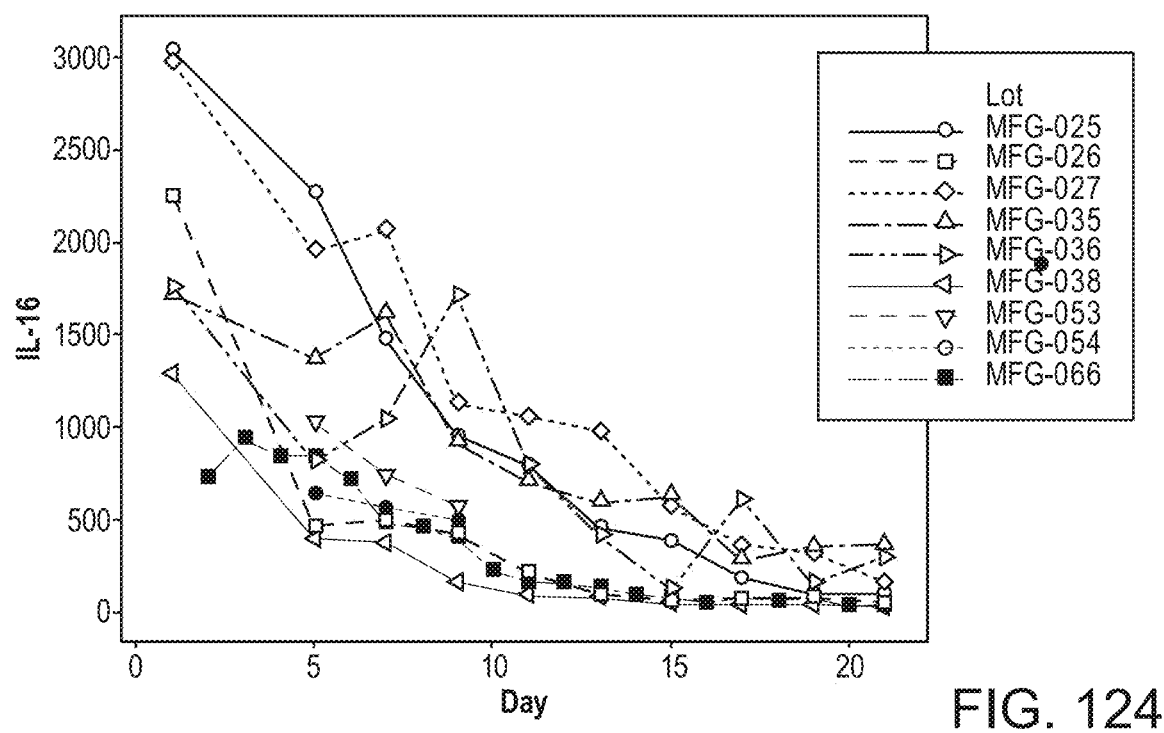

FIG. 124 is a scatterplot of IL-16 Concentration in Spent Media vs. Day.

Figure 125:
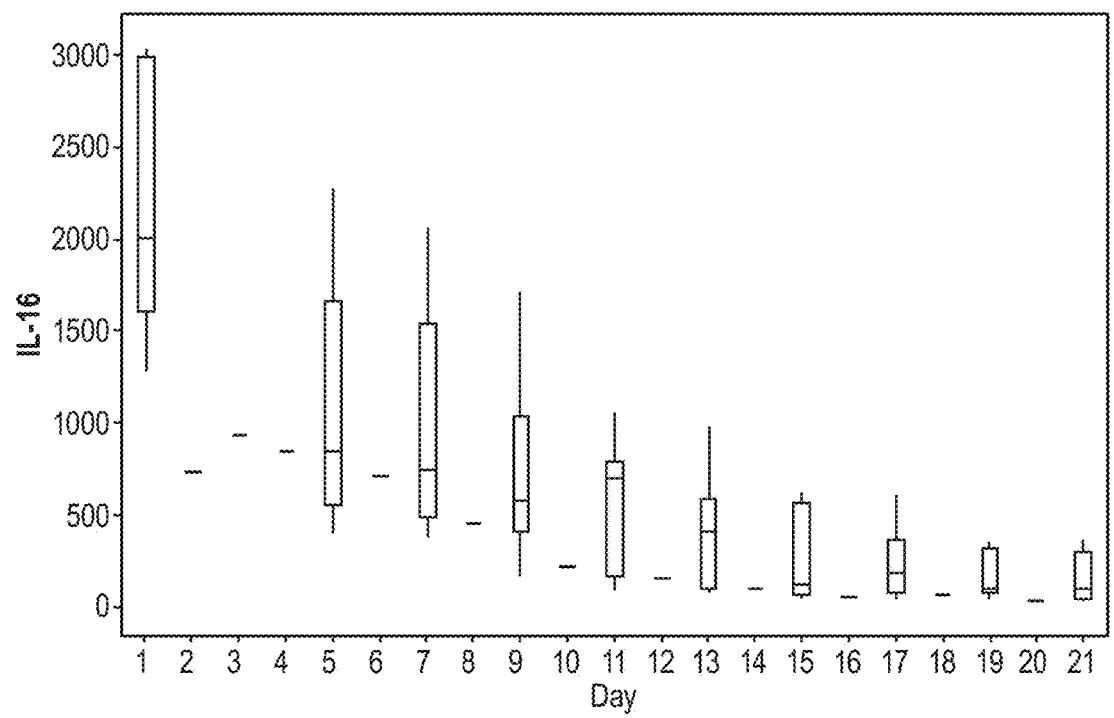

FIG. 125 is a boxplot of IL-16 Concentration in Spent Media vs. Day.

Figure 126:
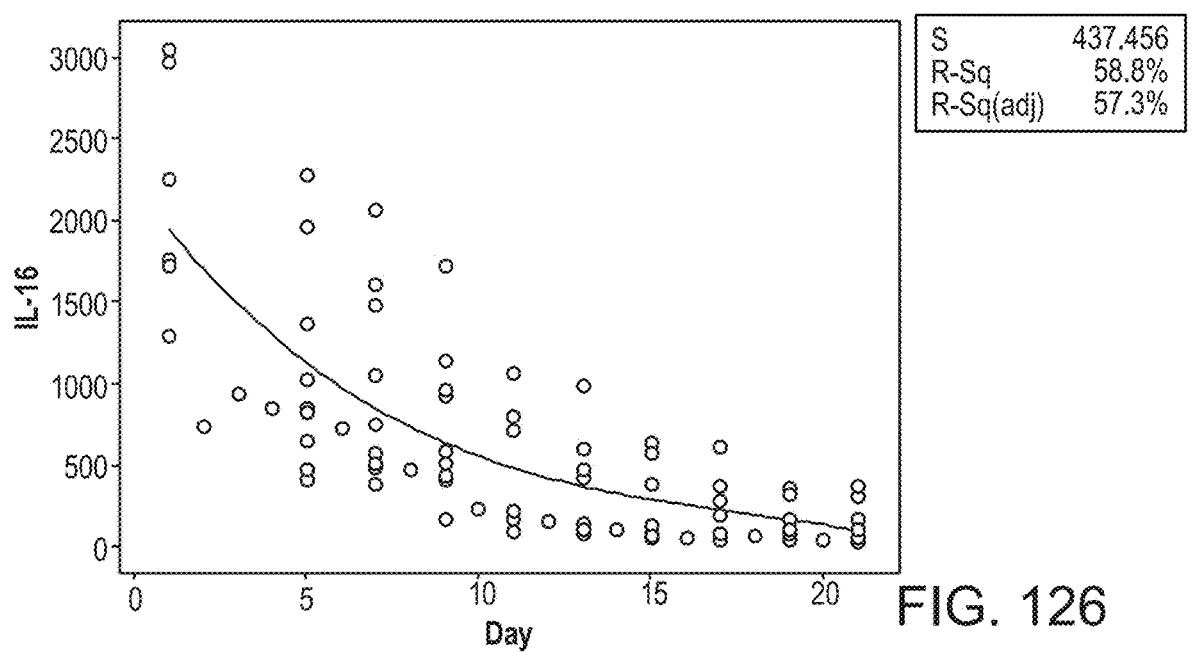

FIG. 126 is a fitted line plot of IL-16 Concentration in Spent Media vs. Day.

Figure 127:
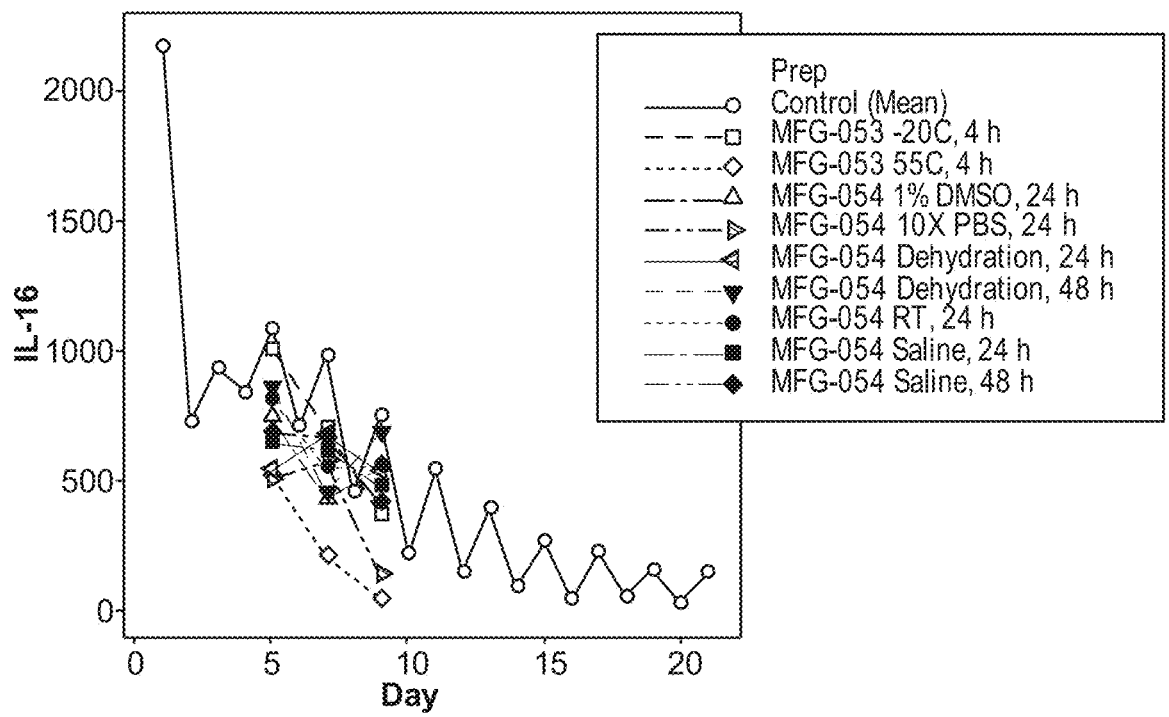

FIG. 127 is a scatterplot of IL-16 Levels (pg/mL) in Forced Degradation Study—Lot MFG-053 and Lot MFG-054.

Figure 128:
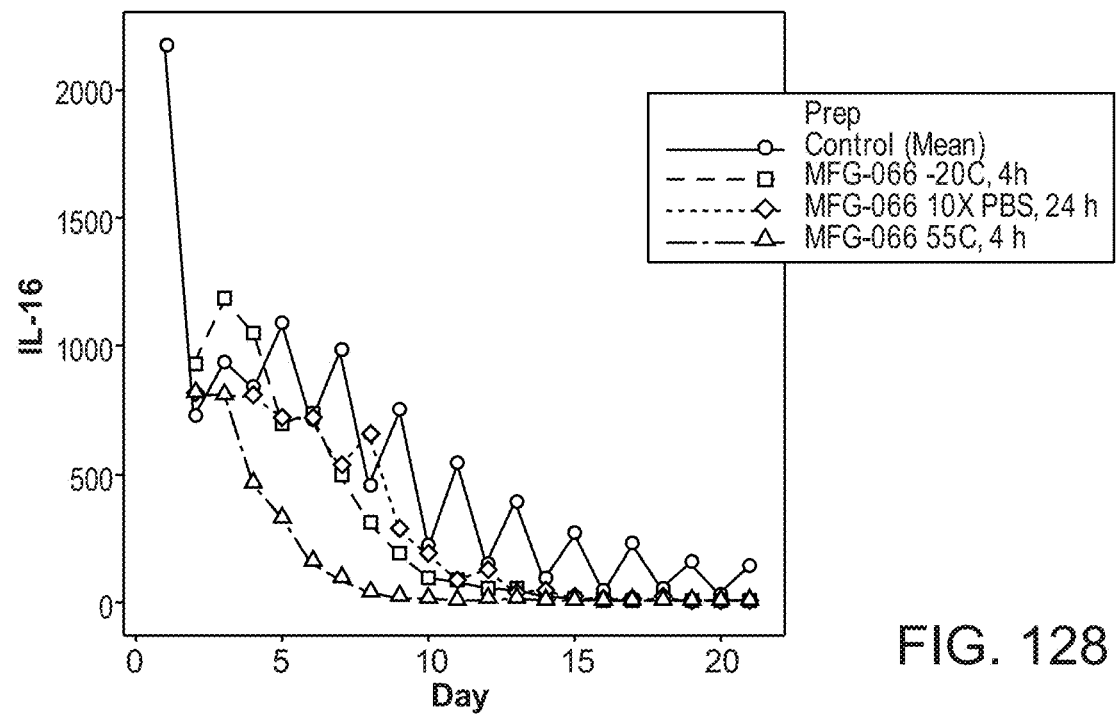

FIG. 128 is a scatterplot of IL-16 Levels in Forced Degradation Study-Lot MFG-066.

Figure 129:
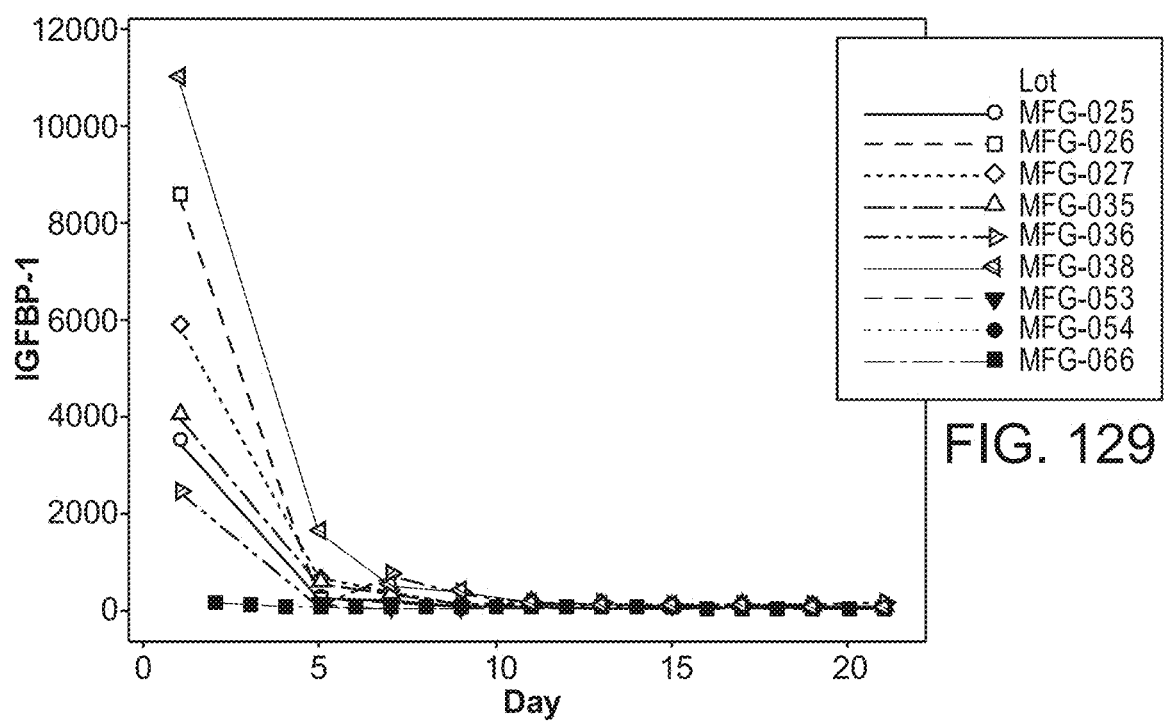

FIG. 129 is a scatterplot of IGFBP-1 Concentration in Spent Media vs. Day.

Figure 130:
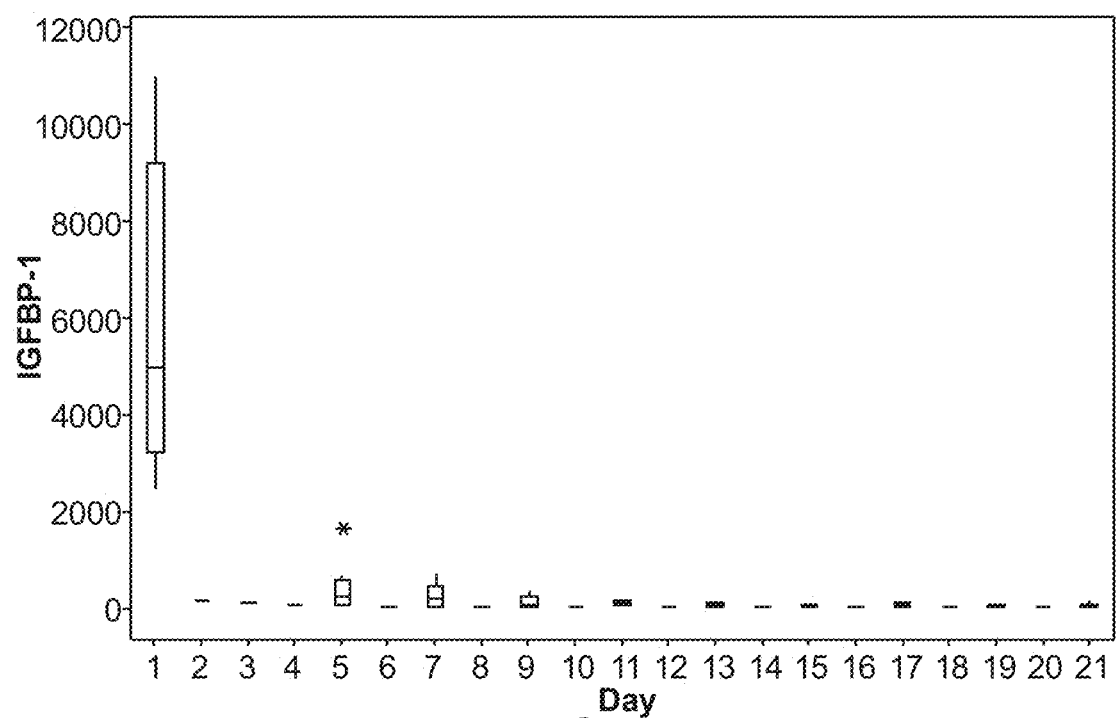

FIG. 130 is a boxplot of IGFBP-1 Concentration in Spent Media vs. Day.

Figure 131:
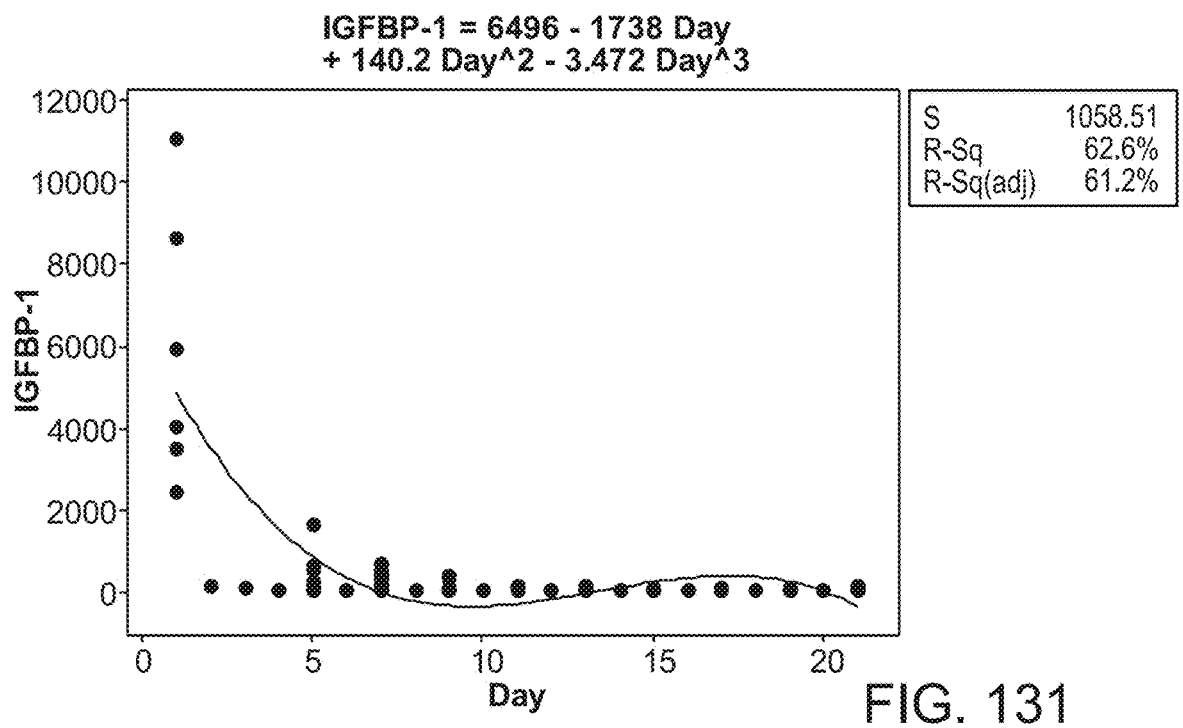

FIG. 131 is a fitted line plot of IGFBP-1 Concentration in Spent Media vs. Day.

Figure 132:
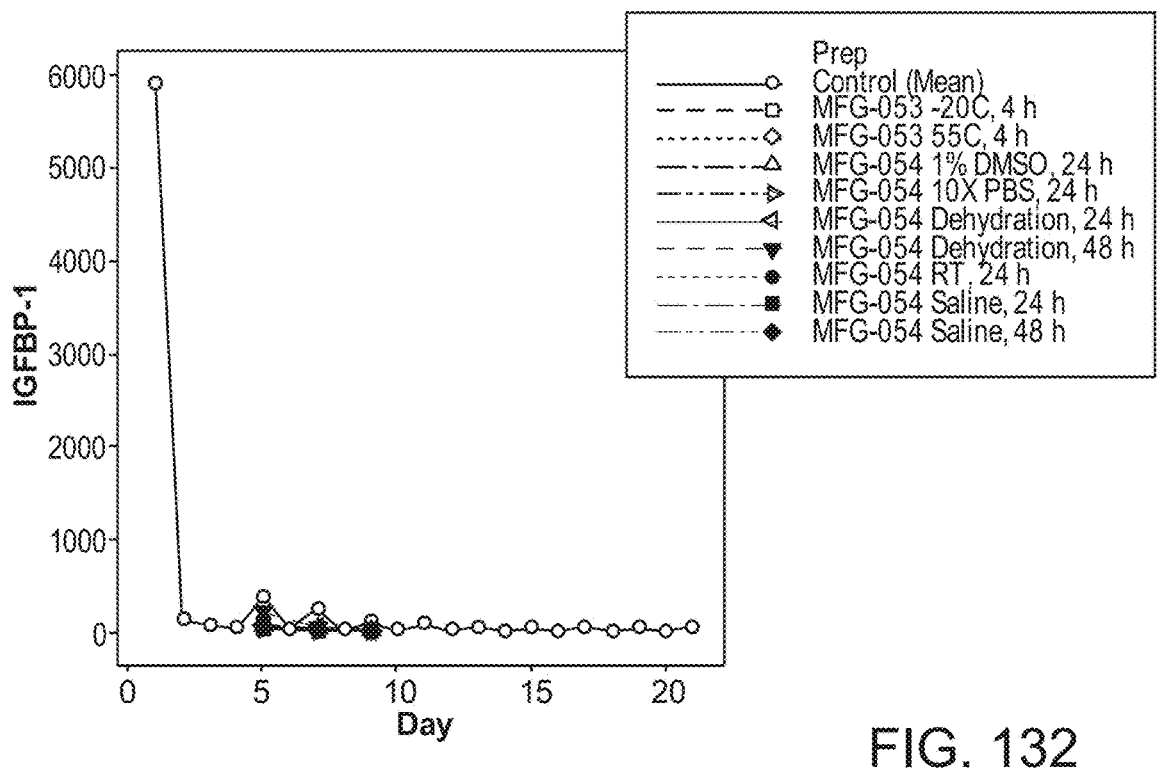

FIG. 132 is a scatterplot of IGFBP-1 Levels (pg/mL) in Forced Degradation Study-Lot MFG-053.

Figure 133:
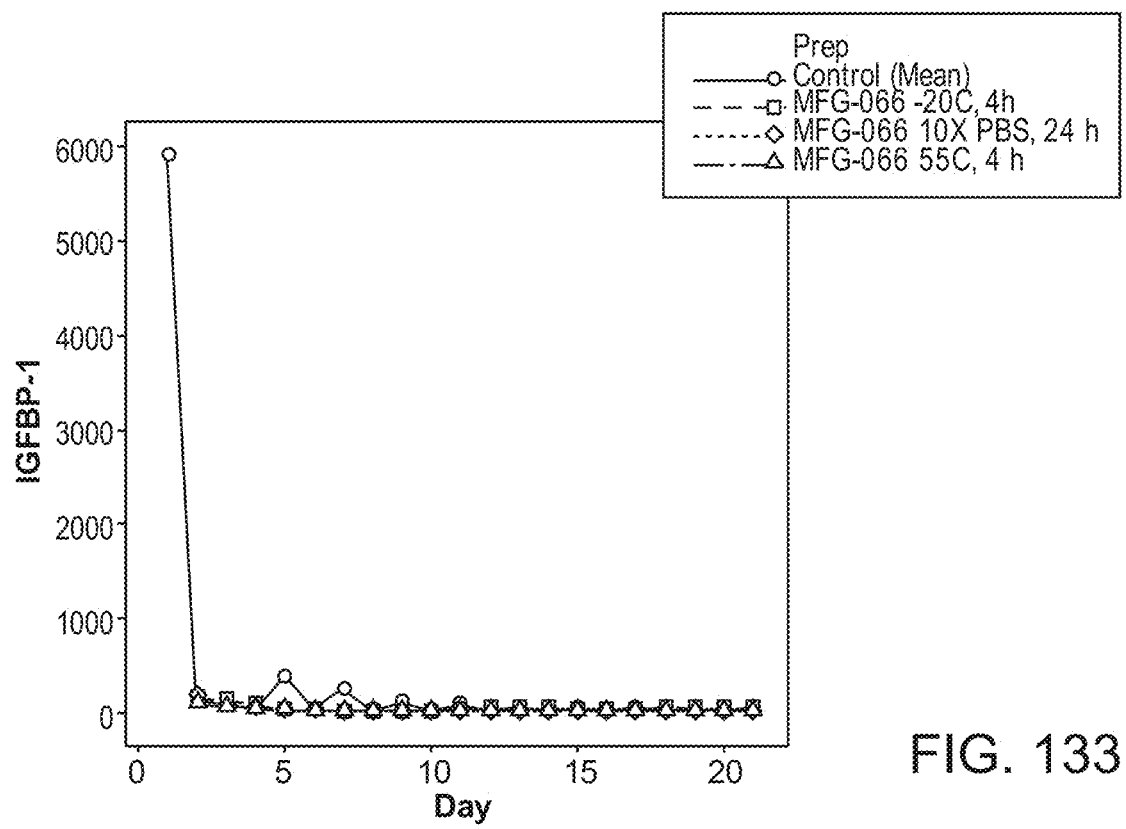

FIG. 133 is a scatterplot of OGFBP-1 Levels in Forced Degradation Study-Lot MFG-066.

Figure 134:
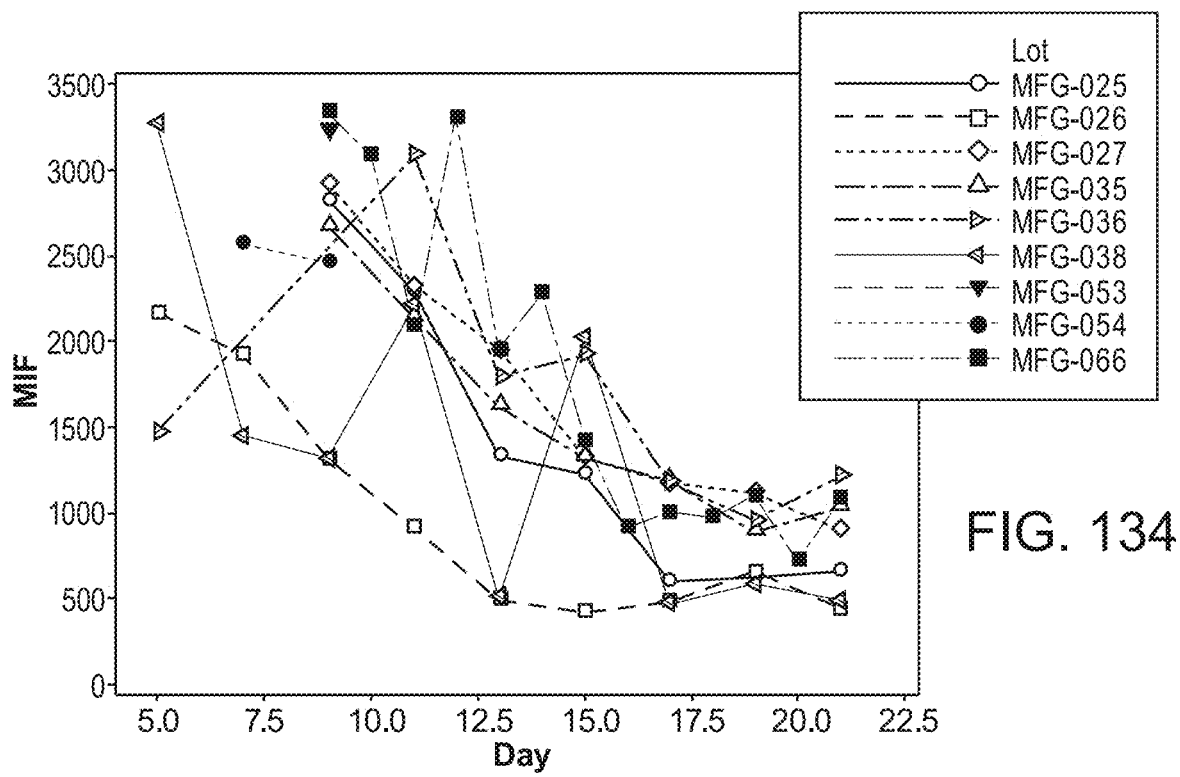

FIG. 134 is a scatterplot of MIF Concentration in Spent Media vs. Day.

Figure 135:
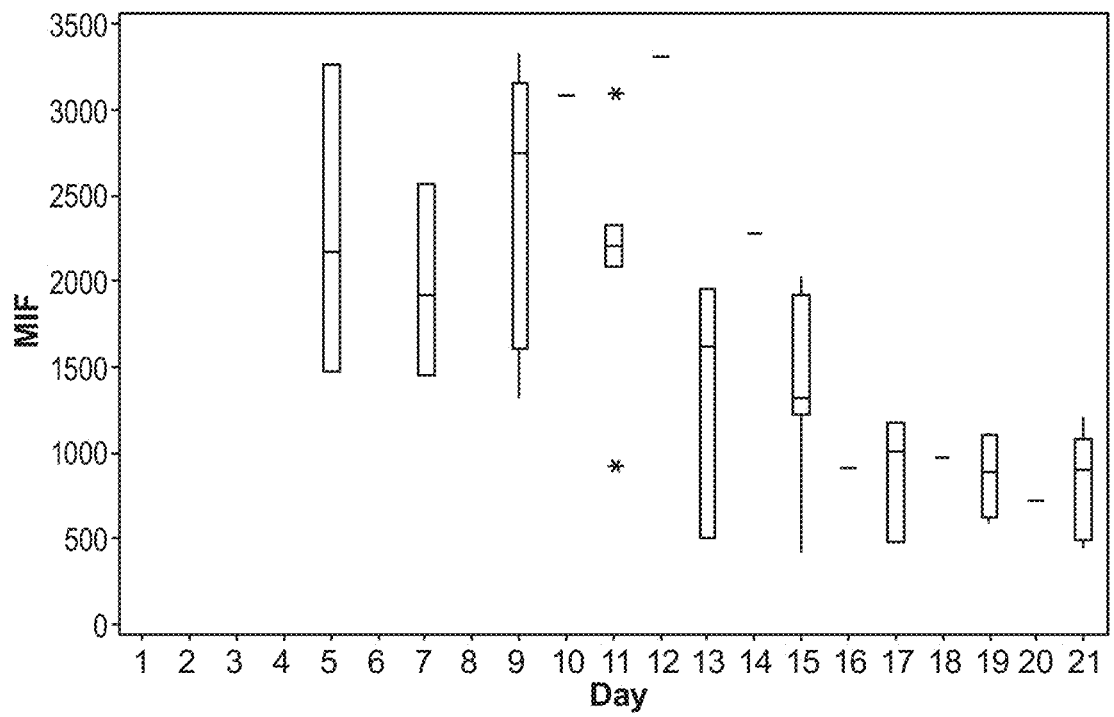

FIG. 135 is a boxplot of MIF Concentration in Spent Media vs. Day.

Figure 136:
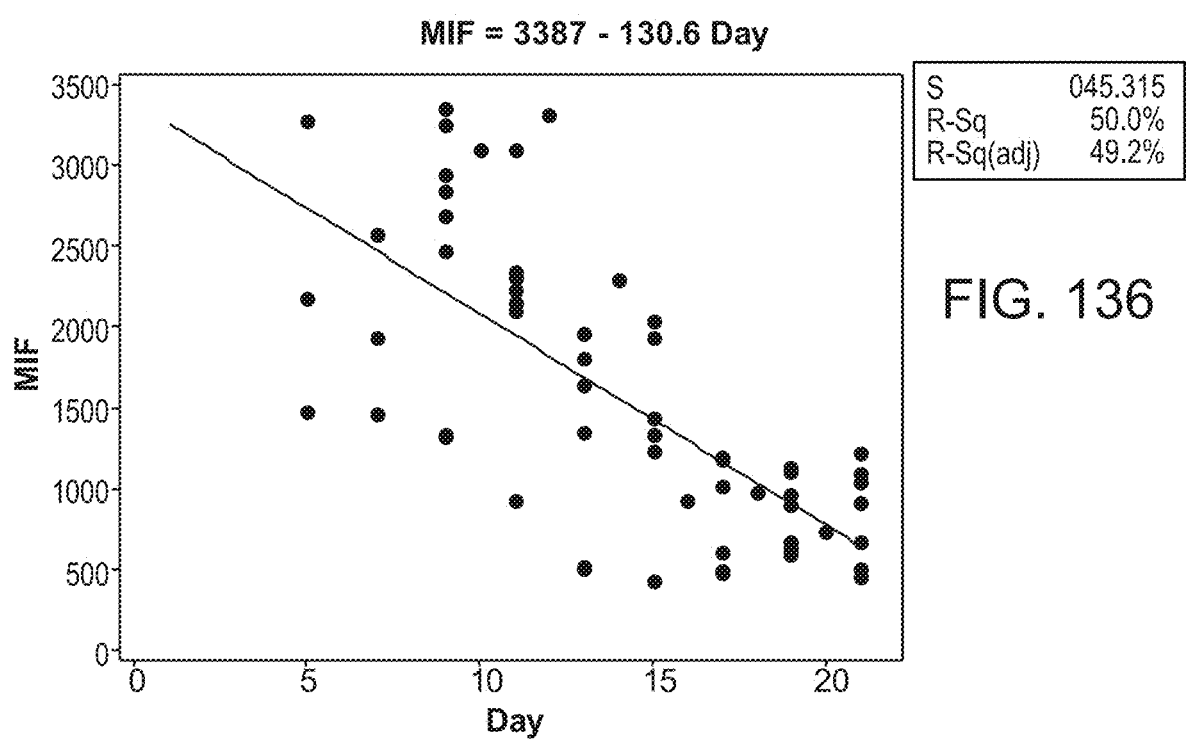

FIG. 136 is a linear regression model of MIF Concentration in Spent Media vs. Day.

Figure 137:
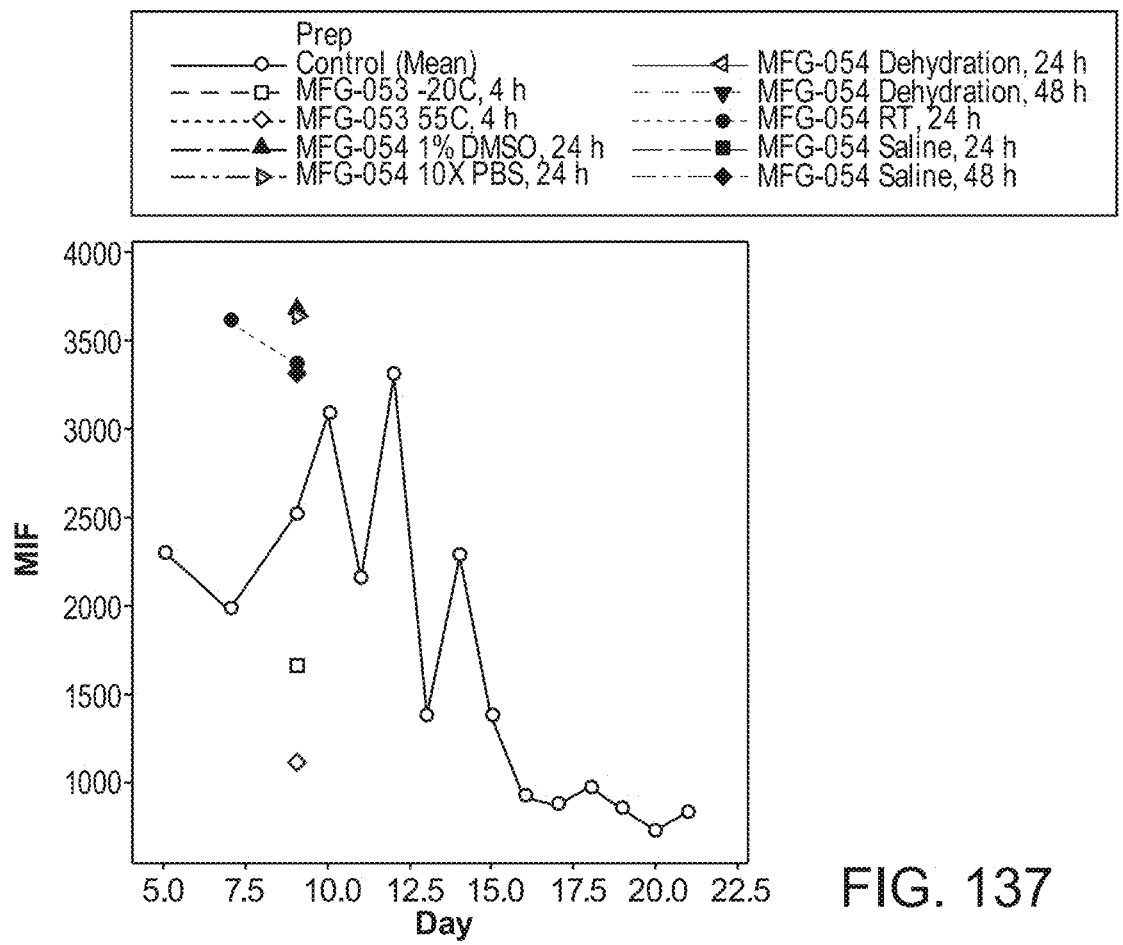

FIG. 137 is a scatterplot of MIF Levels (pg/mL) in Forced Degradation Study-Lot-MFG-053 and Lot MFG-054.

Figure 138:
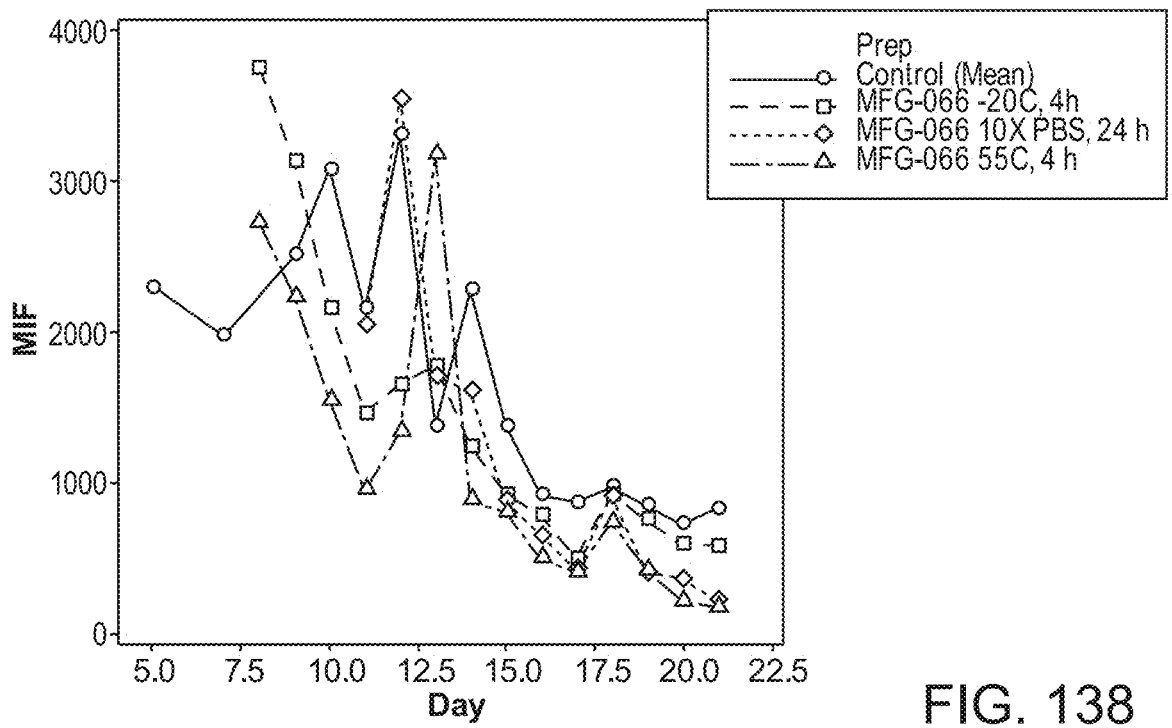

FIG. 138 is a scatterplot of MIF Levels in Forced Degradation Study-Lot MFG-066.

Figure 139:
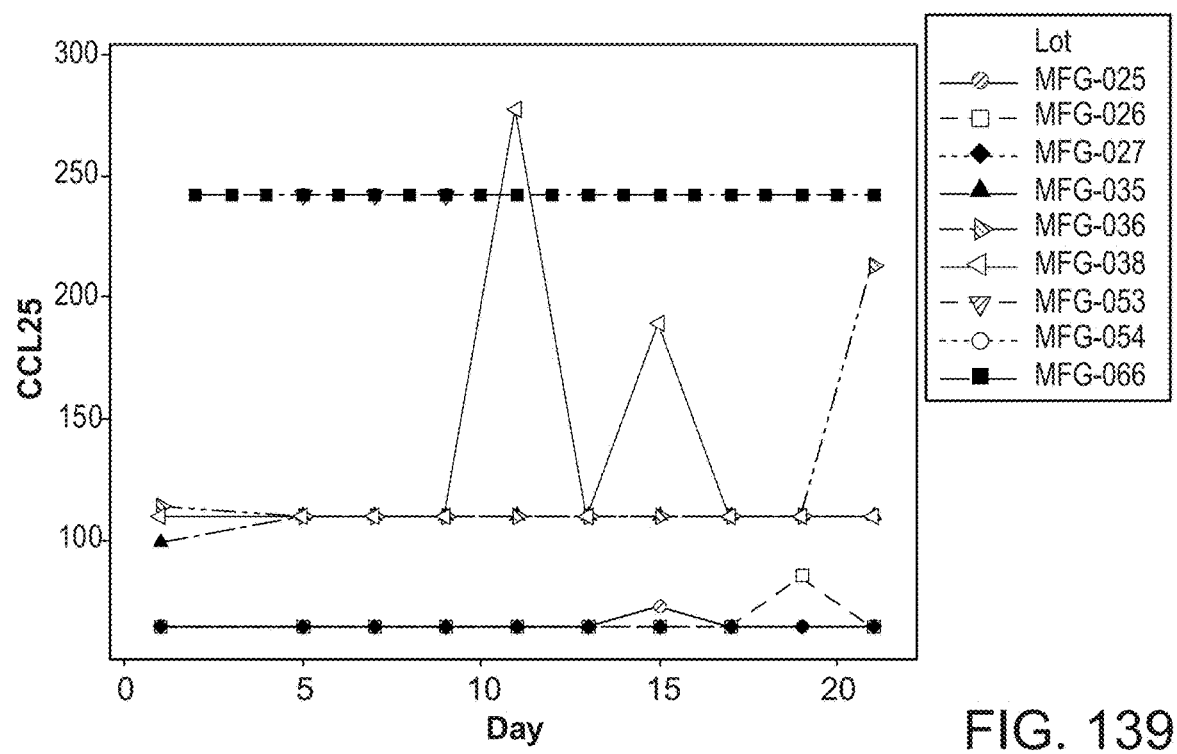

FIG. 139 is a scatterplot of CCL25 Concentration in Spent Media vs. Day.

Figure 140:
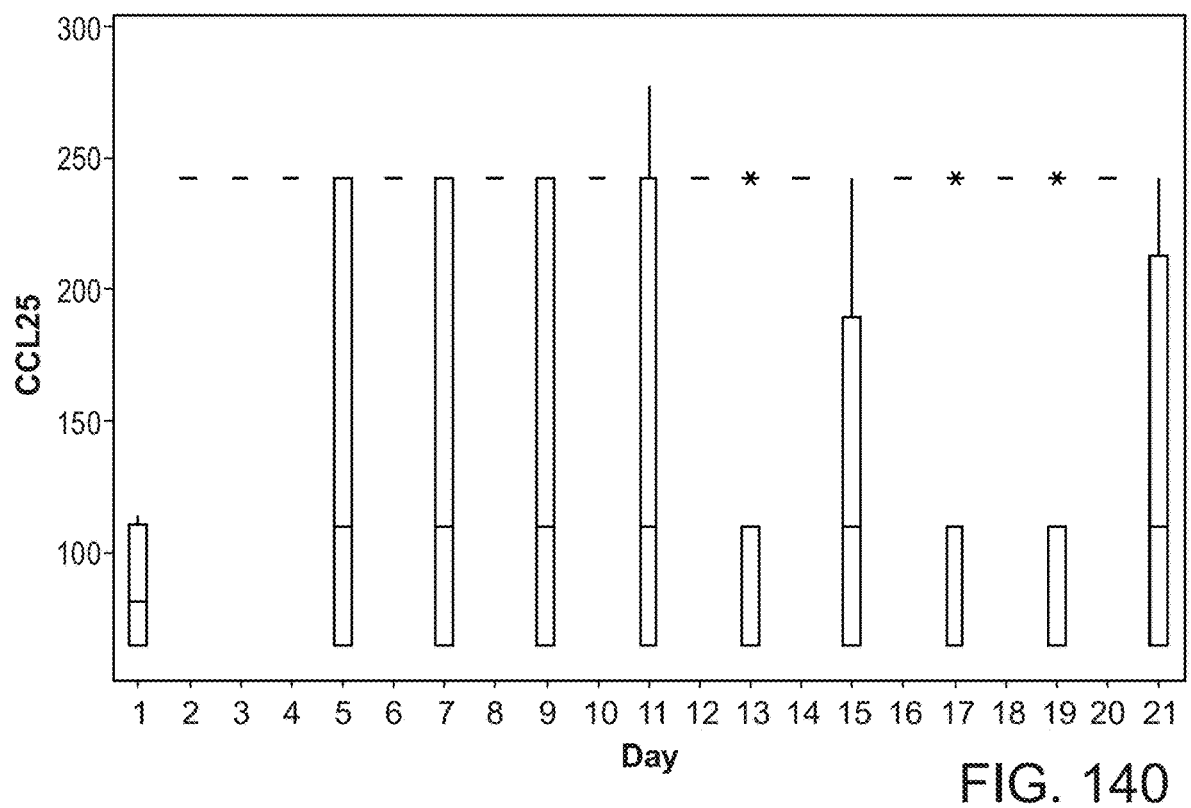

FIG. 140 is a boxplot of CCL25 Concentration in Spent Media vs. Day.

Figure 141:
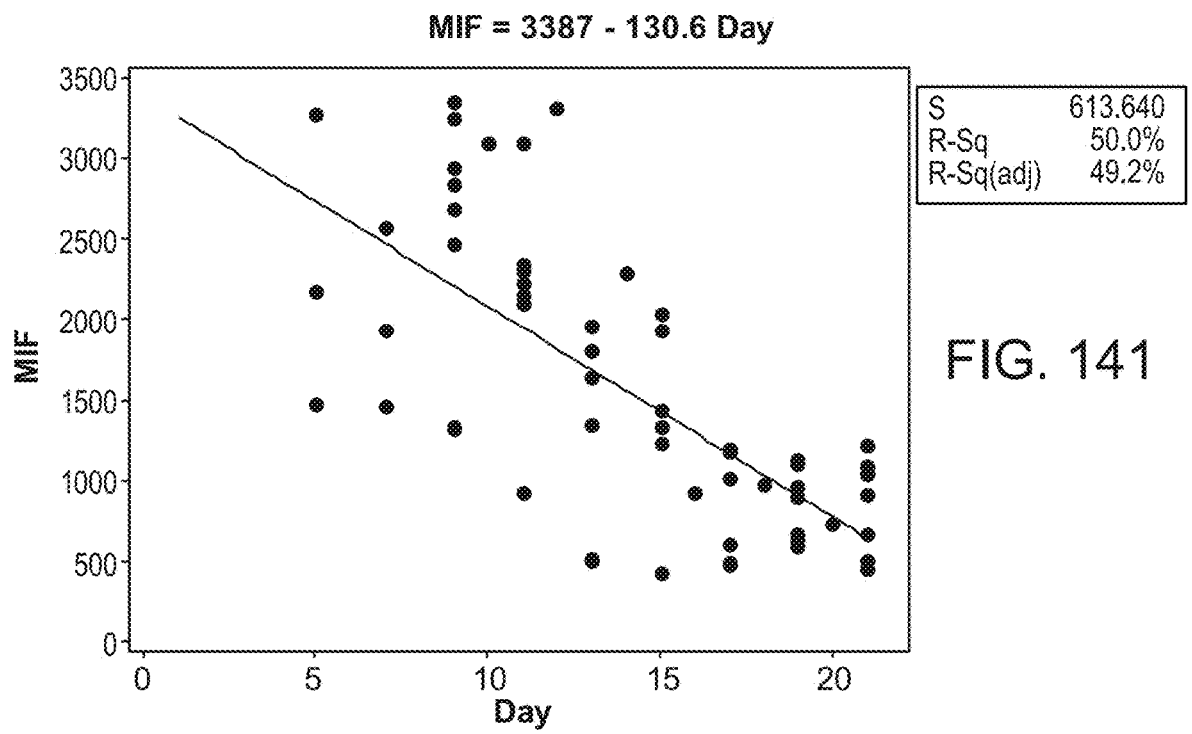

FIG. 141 is a linear regression model plot of MIF Concentration in Spent Media vs. Day.

Figure 142:
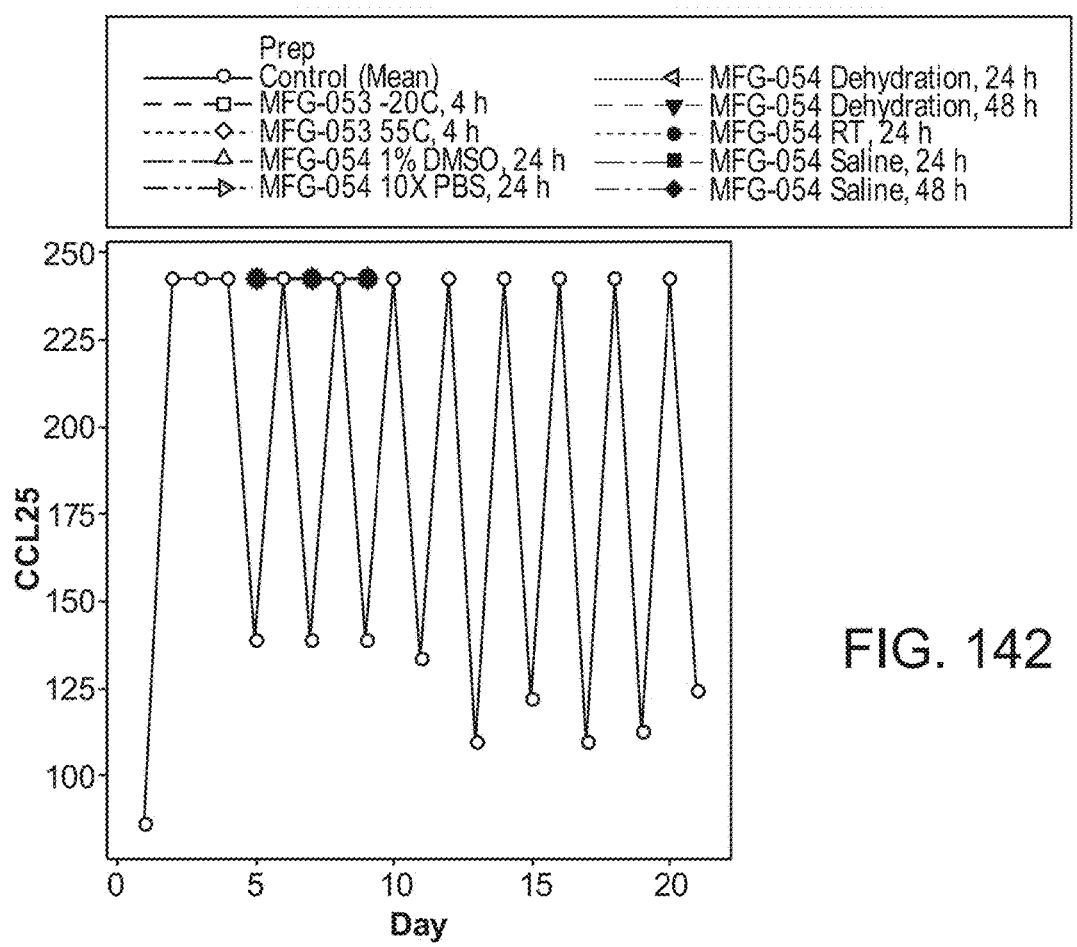

FIG. 142 is a scatterplot of CCL25 Levels (pg/mL) in Forced Degradation Study-Lot-053 and Lot-054.

Figure 143:
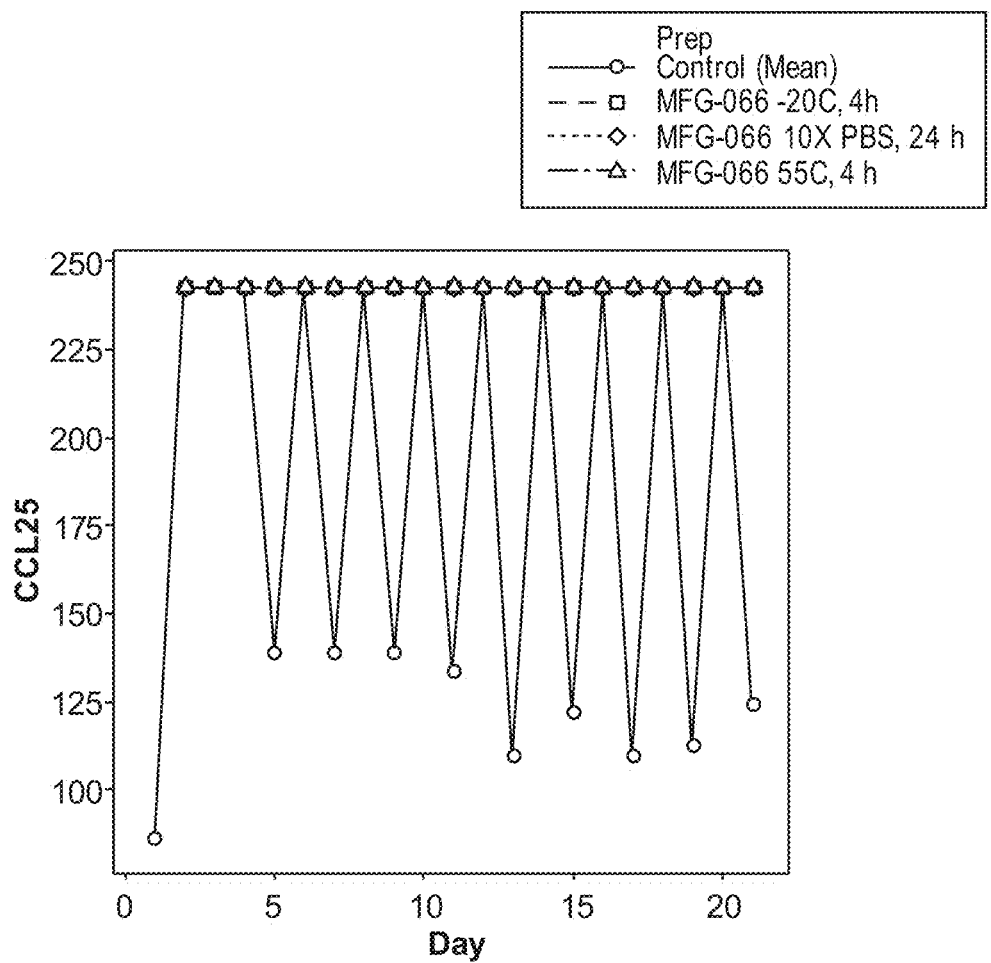

FIG. 143 is a scatterplot of CCL25 Levels in Forced Degradation Study-Lot MFG-066.

DETAILED DESCRIPTION OF THE INVENTION

The titles, headings and subheadings provided herein should not be interpreted as limiting the various aspects of the disclosure. Accordingly, the terms defined below are more fully defined by reference to the specification in its entirety. All references cited herein are incorporated by reference in their entirety.

Unless otherwise defined, scientific and technical terms used herein shall have the meanings that are commonly understood by those of ordinary skill in the art. Further, unless otherwise required by context, singular terms shall include pluralities and plural terms shall include the singular. In this application, the use of "or" means "and/or" unless stated otherwise. In the context of a multiple dependent claim, the use of "or" refers back to more than one preceding independent or dependent claim in the alternative only.

It is further noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

The instant invention is most clearly understood with reference to the following definitions:

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of +/−10%. As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

As used herein, the term "animal" includes, but is not limited to, humans and non-human vertebrates such as wild, domestic, and farm animals. The animal can also be referred to as a "subject."

As used herein, the term "biomarkers" refer to the substances listed in FIG. 56. It is to be further understood that references to "decreased" and "increased" levels with respect to the appearance of the biomarkers in the thymus organ medium refers to increased measurements or decreased measurements of the particular biomarker over the time course of the conditioning regimen.

As used here, "biocompatible" refers to any material, which, when implanted in a mammal, does not provoke an adverse response in the mammal.

"Chronic transplant rejection" generally occurs in humans within several months to years after engraftment, even in the presence of successful immunosuppression of acute rejection. Fibrosis is a common factor in chronic rejection of all types of organ transplants.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, un-recited elements or method steps. Additionally, a term that is used in conjunction with the term "comprising" is also understood to be able to be used in conjunction with the term "consisting of" or "consisting essentially of."

As used herein, a "graft" refers to a tissue or organ that is implanted into an individual, typically to replace, correct or otherwise overcome a defect. The tissue or organ may consist of cells that originate from the same individual; this graft is referred to herein by the following interchangeable terms: "autograft", "autologous transplant", "autologous implant" and "autologous graft". A graft from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the term "HLA matched" refers to a donor recipient pair in which none of the HLA antigens are mismatched between the donor and recipient. HLA matching in the methods of the invention comprise: HLA alleles: HLA-A, HLA-B, HLA-C, HLA-DRB1, HLA-DQB1, HLA-DQA1, HLA-DPB1, and HLA-DPA1.

As used herein, the term "HLA mismatched" refers to matching in a donor and recipient HLA antigens, typically with respect to HLA-A, HLA-B, HLA-C, HLA-DRB1, HLA-DQB1, HLA-DQA1, HLA-DPB1, and HLA-DPA1 wherein an HLA mismatch between the donor and recipient occurs. In some cases, one haplotype is matched and the other is mismatched. This situation is frequently found with organs from living or deceased donors. An HLA mismatch in donor-recipient pairs results in an increased risk of graft rejection relative to HLA-matched pairs.

As background to the foregoing definitions, HLA antigens correspond to "human leukocyte antigens," which are protein molecules expressed on the surface of cells that confer a unique antigenic identity to these cells. They are also known as "major histocompatibility complex antigens." Thus the MHC or HLA antigens are target molecules that are recognized by T-cells as being "self" or "non-self." If the HLA antigens are derived from the same source of hematopoietic stem cells as the immune effector cells they are considered "self." If, the HLA antigens are derived from another source of hematopoietic reconstituting cells, they are considered "non-self."

Two main classes of HLA antigens are recognized: HLA-Class I and HLA-Class II. HLA-Class I antigens (A, B, and C in humans) render each cell recognizable as "self." HLA-Class II antigens (DRB1, DPB1, DPA1, DQB1, and DQA1 in humans) are involved in reactions between lymphocytes and antigen presenting cells. Both classes of HLA antigens have been implicated as targets of rejection of transplanted organs.

HLA genes are clustered on human chromosome position 6p21. This cluster of genes encodes the six classical transplantation HLA genes. The segment of 6p21 also encodes genes encoding proteins having important roles in the regulation of the immune system and other fundamental molecular and cellular processes. The complete cluster measures roughly 3.6 Mb, with at least 224 gene loci. As a result of the clustering certain "haplotypes" occur (the set of alleles present on a single chromosome). The haplotypes inherited from one parent tend to be inherited as a group. The set of alleles inherited from each parent forms a haplotype, in which some alleles tend to be associated together. HLA matching is used to identify the recipient's haplotypes and help in identifying suitable matching donors. Certain haplotypes are more prevalent than others and they vary in frequency in different racial and ethnic groups.

As used herein, the phrase "in need thereof" means that the subject has been identified as having a need for the particular method or treatment. In some embodiments, the identification can be by any means of diagnosis. In any of the methods and treatments described herein, the subject can be in need thereof.

As used herein, the phrase "integer from X to Y" means any integer that includes the endpoints. For example, the phrase "integer from X to Y" means 1, 2, 3, 4, or 5.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein the term "organ" refers to a solid vascularized organ that performs a specific function or group of functions within an organism. The term organ includes, but is not limited to heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus.

As used herein, the terms "prevent", "preventing" and "prevention" refer to the administration of therapy to an individual who may ultimately manifest at least one symptom of a disease, disorder, or condition, but who has not yet done so, to reduce the chance that the individual will develop the symptom of the disease, disorder, or condition over a given period of time. Such a reduction may be reflected, for example, in a delayed onset of the at least one symptom of the disease, disorder, or condition in the patient.

As used herein, the terms "subject," "individual" or "patient," used interchangeably, means any animal, including mammals, such as mice, rats, other rodents, rabbits, dogs, cats, swine, cattle, sheep, horses, or primates, such as humans.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

The term "tissue" as used herein refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

"Tissue bank" in the context of the present disclosure refers to long-term storage of cryopreserved allogeneic cultured postnatal thymus tissue-derived product stored under liquid nitrogen. General guidance for establishment of a repository for allogeneic cultured postnatal thymus tissue-derived product may be drawn from Guidance for Industry. Current Good Tissue Practice (CGTP) and Additional Requirements for Manufacturers of Human Cells, Tissues, and Cellular and Tissue-Based Products (HCT/Ps) available at https://www.fda.gov/downloads/BiologicsBloodVaccines/GuidanceComplianceRegulatoryInformation/Guidances/Tissue/UCM285223.pdf.

"Tissue engineer(ing-ed)" refers to the process of generating tissues ex vivo for use in tissue replacement or reconstruction. Tissue engineering is an example of "regenerative medicine" which encompasses approaches to the repair or replacement of tissues and organs by incorporation of cells, genes or other biological building blocks, along with bioengineered materials and technologies.

The term "transplant rejection" encompasses both acute and chronic transplant rejection. "Acute rejection" is the rejection by the immune system of a tissue transplant recipient when the transplanted tissue is immunologically foreign. Acute rejection is characterized by infiltration of the transplant tissue by immune cells of the recipient, which carry out their effector function and destroy the transplant tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

As used herein, the terms "treat," "treated," or "treating" mean both therapeutic treatment and prophylactic measures wherein the object is to slow down (lessen) an undesired physiological condition, disorder or disease, or obtain beneficial or desired clinical results. For example, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease.

As described herein, any concentration range, percentage range, ratio range or integer range is to be understood to include the value of any integer within the recited range and, when appropriate, fractions thereof (such as one tenth and one hundredth of an integer), unless otherwise indicated. Ranges are approximate and may vary by more than an integer.

Units, prefixes, and symbols are denoted in their Système International de Unites (SI) accepted form. Numeric ranges are inclusive of the numbers defining the range. Measured values are understood to be approximate, taking into account significant digits and the error associated with the measurement.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

Harvesting of Donor Thymus Tissue.

Donor thymus tissue may be may be discarded during post-natal heart operations and may be used for CTT with informed consent of the donor's family. The removal of some thymus may be necessary to reveal the operative site. Thus, a portion of the thymus may be removed during the heart operation in post-natal heart surgeries, due to the nature of the surgical procedure.

During postnatal heart surgeries a portion of the thymus tissue may be discarded during the surgical procedure. For all heart surgeries, whether or not the thymus is being screened for transplantation, the surgeon places the thymus tissue that has been discarded into a sterile container.

Thymus tissue donors for thymus tissue transplantation in infants with complete DiGeorge syndrome have been infants under nine months of age. The drug substance allogeneic cultured postnatal thymus tissue-derived product is manufactured by processing and culturing the discarded thymus tissue as described herein.

Consent for use of the thymus in cultured thymus tissue implantation may be obtained before or after the thymus is harvested. However, consent allowing blood to be obtained from the infant prior to undergoing bypass is necessary and is always obtained prior to the surgery. This blood sample is used for donor screening.

The discarded thymus tissue is placed into a sterile container. Routine testing is done on the donor and donor's birth mother in accordance with FDA guidelines for tissue transplantation. Tissue type matching is not required in the surgical procedures described herein, but such tissue type matching can be performed in certain situations.

Tissue may be processed immediately or stored refrigerated overnight for next day processing. If the thymus tissue is to be stored overnight, the tissue is aseptically added to thymus organ medium ("TOM" medium described below) sufficient to completely cover the thymus tissue in the original container. The container with the thymus is placed in refrigerator until ready to process the next day.

Overview of Conditioning of Thymus Tissue

The conditioning regimen depletes the donor thymocytes from the cultured thymus tissue slices. Based on in vitro data (immunohistochemistry) a culture period between 12 and 21 days preserves the epithelial network as assessed using cytokeratin antibodies. The culturing is preferably done at 37° C. in a 5% $CO_2$ incubator.

For successful culture, the thymus tissue is preferably sliced and put on Millipore® cellulose or equivalent filters and placed on surgical sponges in tissue culture dishes. The medium comprises the thymus organ medium (TOM) and is changed daily.

The thymus on receipt is assessed by pathology. The test for identity must show >50% of areas positive for keratin in lacy staining pattern. The test for potency must show Hassall bodies; it must also show CK14 staining in lacy pattern. The test for viability must show >90/intact nuclei observed in sections. The lot release for the tissue is done on one day between day 5 and day 21 (inclusive) and is performed by pathology. For identity, areas on tissue between days 5 and 21 must be positive for keratin, AE1/AE3. For potency, the cultured thymus tissue between days 5 and 21 must show cytokeratin CK14 staining scattered throughout, and there must be at least one Hassall body identified. For viability, the cultured thymus tissue between days 5 and 21 must show intact nuclei.

In an embodiment, the thymus tissue slices are conditioned for about 12 days and then cryopreserved. In another embodiment all of the thymus tissue slices are conditioned for about 12 days, then about half are implanted in the recipient and the remaining thymus tissue slices are cryopreserved for future use.

Within 24 hours of harvest, the thymus is cut into thin slices. The slices are held in culture for 12-21 days. This culturing process, as described in detail below, depletes viable donor T cells and ultimately enables the surgically implanted tissue slices to reconstitute the athymic subject's immune system, albeit at a immunologically effective level, although most subjects will have T cell counts below the 10th percentile for age. The culturing process, as outlined below, significantly modifies the biological characteristics of the donor thymus tissue and constituent cells contained therein in the following manner to optimize the effective therapeutic properties of the CTT slices.

The culturing process assures that a defined composition of the cultured cells/tissue having the pre-requisite biological characteristics is obtained in a manner suitable for surgical implantation into a subject to enable reconstitution of the subject's immune system.

The culturing process results in a loss of thymocytes and relative enrichment of thymic epithelial cells and other stromal cells in the donor thymus tissue slices.

The culturing process further results in depletion of thymocytes and maintenance of TECs to enable reconstitution of the recipient's immune system and allows tolerance to develop in the recipient to HLA antigens in the donor thymus.

Overall, the manufacturing process is designed to deplete thymocytes from the donor thymus tissue and to preserve the functional architecture of the thymic stroma (thymic epithelial cells and fibroblasts).

In an embodiment, processed donor thymus tissue is an engineered thymus tissue product capable of inducing tolerance to the thymus tissue types (HLA antigens) in a subject in need thereof following a surgical implantation procedure.

To keep the sliced thymus tissue viable, the thymus sections are placed on Millipore cellulose filters and surgical sponges inserted into medium-containing tissue culture dishes. The culture medium in each tissue culture dish is replaced daily from the day of harvest from the donor to the day of implantation (day 12 to day 21).

The culturing of donor thymus tissue depletes thymocytes in such processed tissue which minimizes the risk of graft versus host disease ("GvHD"), which could be highly problematic in profoundly immunodeficient subjects following a thymectomy.

During the first few days in culture, many thymocytes "fall out" of the tissue slices into the culture medium and are discarded during media changes. As culturing continues during the culturing period, donor thymocytes continue to die but their cellular remnants are retained within the CTT slices.

Without being bound by theory, the presence of these non-viable thymocytes and their remnants that lack nuclei are hypothesized to be important for the intended function of the tissue-engineered product, because they help to preserve the open pockets in the three-dimensional network of thymic epithelial cells that is necessary for the entry of recipient bone marrow stem cells post-treatment. The importance of having "space" for the entering bone marrow stem cells is supported by experience with patient DIG003 in Markert, 1999 (See list of reference infra). The patient described in the foregoing reference had been given a very large dose of steroids (40 mg/kg/day×3 days of methylprednisolone) 35 days after CTT implantation, which led to apoptosis of the thymocytes and condensation of the epithelium. No naïve T cells ever developed, and the patient succumbed to infection. At autopsy, the inserted thymus was a mass of viable epithelium with no space between the epithelial cells for thymocytes to enter.

During the culturing period, HLA typing is performed to see if the patient (recipient) and donor tissue share any HLA alleles. Anti-HLA antibody testing is performed in the recipient to determine if the recipient has any antibodies against HLA antigens in the thymus. If the recipient has antibodies targeting the donor's MHC, another thymus would be sought. The donor and the mother of the donor are checked for infection per the FDA guidance document "Guidance for Industry. Eligibility Determination for Donors of Human Cells, Tissues and Cellular and Tissue-Based Products (HCT/Ps)" and more recent Guidance documents. The tissue is processed aseptically under the Code of Federal Regulations (CFR) 1271 subpart D "Current Good Tissue Practice."

Following review of the batch records and QC testing the tissue is released from manufacturing and provided to the surgical team for implantation, the tissue is surgically implanted into the recipient, as described in this specification.

Cultured thymus tissue is produced in a process more completely described below and in the Examples set forth in this specification.

In summary, the culturing process of the harvested thymus tissue significantly modifies the biological characteristics of the donor tissue and constituent cells contained therein in the following manners: loss of donor thymocytes and enrichment of thymic epithelial cells and other stromal cells, and depletion of donor thymocytes modifies the physiologic functions of the tissue (e.g., secretion of cytokines and growth factors) as well as its structural properties.

During the first few days in culture, many thymocytes "fall out" of the tissue slices into the culture medium and are discarded during media changes.

Manipulations that occur during the manufacturing process result in changes in the gross and histologic appearance of the resulting cells contained in the finished product as compared with the source or starting material obtained from the donor.

Figure 15:
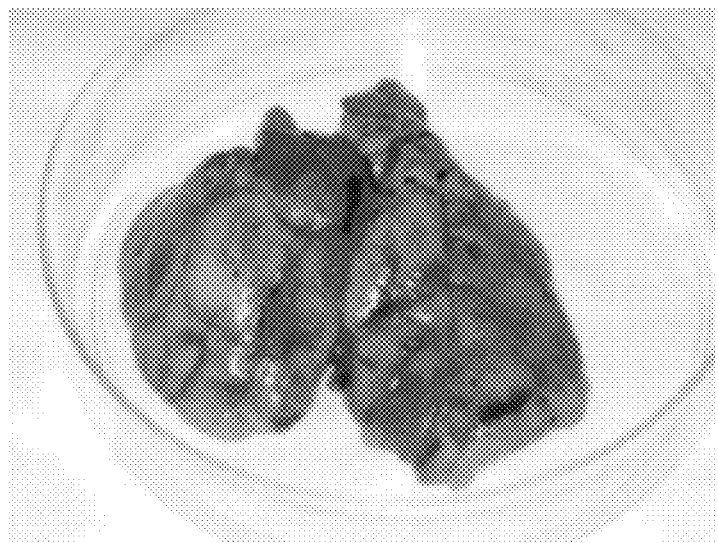
FIG. 15 is a photograph of freshly harvested thymus tissue.
Figure 16:
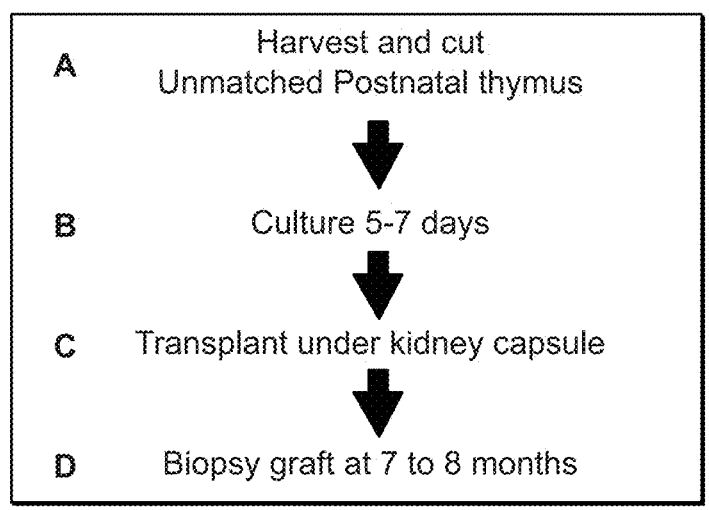
FIG. 16 is a schematic describing the harvesting, culturing, implantation and biopsy of the implantation of CTT under the rat kidney capsule, as presented in Example 5.

Thymus tissue during the first few days of culturing appears red due to residual blood on and within the tissue. See, e.g., FIG. 15.

Between days 5 to 21 viable tissue is observed minus the blood contamination that was evident on day 1.

During the remaining days of culturing the depth of the tissue decreases as thymocytes are depleted. The decrease in density of thymocytes in the tissue is documented by immunohistochemistry and described in detail below.

On day 0 following harvesting of the discarded thymus tissue the tissue is densely populated with viable thymocytes embedded in a stroma that contains thymic epithelial cells and fibroblasts. AE1/AE3 and CK14 staining confirm the presence of cytokeratin (CK)-positive thymic epithelial cells, which are characteristic of normal thymus. The thymic epithelial cells form a lacy three-dimensional network with delicate processes that surround neighboring thymocytes.

During the culturing process, slices of thymus are cultured, as described below. Numerous thymocytes are washed out of the tissue, especially over the first 3 days. This depletion can be identified histologically as early as day 2 by H&E stains that show decreased thymocyte density, particularly in medullary areas. The majority of the thymocytes that remain in the tissue show nuclear changes consistent with apoptosis and/or necrosis or demonstrate karyolysis (complete loss of nuclei). Many of these dead thymocytes and their cellular remnants remain present throughout the thymus tissue and are believed to prevent total collapse of the space between epithelial cells.

Some epithelial condensation can be seen in external areas, such as in the subcapsular cortex where loss of thymocytes has led the epithelial cell network to collapse. These condensed subcapsular cortical epithelial cells can form linear arrays several cell layers thick, which may add to the mechanical strength of the slices. Some medullary epithelium may also condense to form patches of contiguous epithelial cells.

Death of thymocytes continues as the culture progresses, with retention of necrotic thymocyte debris within the tissue. Further condensation of medullary and subcapsular cortical epithelium is minimal between approximately days 7 and 19 of culture.

Areas with epithelial architecture similar to normal thymus can still be observed late in culture for each thymus using the AE1/AE3 stains. For tissues cultured longer, the epithelial architecture of cortex and medulla can still be readily discerned; for instance, Hassall bodies remain in the medullary areas. The degree of thymocyte depletion, however, results in a substantially different overall histologic appearance on H&E compared to that of normal thymus at time points later than day 0.

Detailed Culturing of Thymus Tissue.

The general procedure in preparing allogeneic cultured thymus tissue-derived product is that thymus tissue for infants with complete DiGeorge syndrome is obtained as discarded tissue from infants under the age of 9 months undergoing cardiac surgery, as described previously. For solid organ transplantation, discarded thymus will be obtained from individuals up to 50 years of age. Use of the thymus tissue will depend on whether it meets criteria for use as set forth in this specification.

The thymus tissue is aseptically processed and cultured under cGMP conditions to produce partially T cell-depleted thymus tissue slices.

The manufacture of cultured thymus tissue (CTT) consists of the following general steps: receipt and processing of incoming thymus tissue, slicing, culturing, media changes, dose calculation, packaging and transporting the thymus to the operating room. In addition, incoming thymus tissue is tested for acceptability and in-process and release testing is conducted on thymus tissue slices.

In an embodiment, the thymus tissue slicing process entails using sterile, single-use scissors and forceps to cut off a piece of thymus tissue. The operator removes the capsule of the thymus with forceps and scissors and places the capsule in the lid of the plate for disposal later.

The piece of thymus tissue is placed in the single-use tissue slicer using forceps. The top of the slicer (e.g., Stadie-Riggs hand microtome (Thomas Scientific, Swedesboro, NJ)), is placed onto the middle portion of the slicer and tightened in place. The operator runs the blade through the tissue piece to cut off a slice. The slices are approximately 0.5 to 1 mm thick. Approximately 50-90% of the filter space is filled without overlap of the tissue slices.

Typically, three in-process pieces are cut off of the tissue at the beginning of slicing, all of which are roughly 3×3 mm. One is sent for histology, and two are retained. Thymocytes flow freely into the medium as the thymus is sliced.

In an embodiment, the filter and thymus slices are transferred to a gelatin surgical sponge saturated with TOM in a tissue culture dish. The TOM wicks up wetting the Millipore filters, keeping the tissue moist. Two filters are placed per sponge and 2 sponges are used per tissue culture dish. The process of slicing pieces of thymus is repeated until the required number of slices has been prepared. Culture dishes are labeled with an operation number, dish number, and ISBT barcode label. Completed dishes are placed in a humidified incubator at 37° C. with 5% $CO_2$.

The tissue engineered drug substance comprises thymus tissue slices after they have been placed in a culture dish in media and cultured for about 6 days to about 21 days, as described below. The tissue-engineered drug product comprises the thymus tissue slices after transfer into a drug product container. No other processing is conducted to create the drug product from the drug substance; the only processing of drug substance to create drug product is transfer of slices into the leak proof container and corresponding media change.

The culturing of thymus tissue slices is more specifically set forth in the following paragraphs.

In an embodiment, thymus tissue is obtained from the operating room as discarded tissue from infants aged 9 months and under undergoing cardiac surgery. The tissue is then placed in a sterile specimen cup with a screw-cap top by the surgical team and transported to a GMP facility under ambient conditions for processing. The sterile specimen container in which the thymus is received is labeled, including a barcode, with the donor's name and medical record number. The donor screening group gives the thymus a unique identifier (thymuses are numbered consecutively) and a unique medical record number. For manufacturing, each tissue has an operation number, and a unique label. All identifiers are recorded on a "Confidential Thymus Donor Form" that is maintained separately from the batch record and kept confidential.

In an embodiment, the drug substance container closure system may be a cell culture dish with lid. One slice of thymus tissue is placed on a filter and two filters are placed on each gelatin sponge in thymus organ media in the dish. Four slices are placed in each culture dish and the dishes are stored in the incubator, with daily media changes, until ready for release.

In an embodiment, the culture dishes can be obtained from Corning. The dishes may be sterile, non-pyrogenic Falcon® 100 mm polystyrene cell culture dishes (product #353003). The dishes are cleaned by vacuum-gas plasma treatment and sterilized by gamma irradiation. The dimensions of the dish are 89.43 mm O.D.×19.18 mm.

In an exemplary embodiment, the Surgifoam® sponge may be manufactured by Ethicon and it meets the requirements for Absorbable Gelatin Sponge, USP. A suitable sponge is a sterile, water-insoluble, malleable, porcine gelatin absorbable sponge that is intended for hemostatic use. An illustrative example of the mixed cellulose esters filter is manufactured by Millipore (product #SMWP 02500). The 25 mm hydrophilic membrane has a 5.0 µm pore size. It is made of biologically inert mixtures of cellulose acetate and cellulose nitrate. The filter is sterilized by ethylene oxide prior to use.

After release and acceptance of the donor thymus into the processing laboratory, the thymus is cut into thin slices, which are placed on sterile filter papers that are put on the surgical sponges in sterile culture dishes. If the tissue is not processed immediately, it is stored in thymus organ media (TOM), as described below, at 2-8° C. for up to 24 hours after harvest from the donor before processing is initiated. TOM consists of Ham's F-12 culture media, HEPES buffer, L-glutamine and heat-inactivated fetal bovine serum (FBS).

In an embodiment, processing occurs in an ISO 5 space of a biological safety cabinet (BSC) in an ISO 7 manufacturing clean room. Only one lot of thymus tissue from a single thymus is processed in the BSC at any time. The BSC is cleaned before use. The thymus is tested for appearance by visual inspection and weighed. The thymus is then placed in a 150-mm tissue culture dish in TOM. The capsule of the thymus is removed with sterile, single-use forceps and scissors. Tissue pieces are taken for testing and as retained samples. The incoming thymus tissue is tested for identity by histology. Donor eligibility is also confirmed. Processing continues prior to receipt of histologic results and all donor screening results.

The acceptance criteria for donor screening is that all donor eligibility requirements must be met. Donor screening is required per 21 CFR 1271 to protect the safety of the thymus tissue implant recipient. This screening minimizes the risk of disease transmission from donor to recipient.

Thymus Organ Media (TOM)

The medium is made with ingredients approved for use in humans which are unlikely to cause allergic reactions, whenever such reagents are available.

All reagents must be tracked such that all ingredients can be identified after implantation if any problems develop.

Fetal Bovine Serum (FBS) must be manufactured using US material because of the concern of Creutzfeldt-Jakob Disease. Information on each lot must be sent to the FDA prior to use.

Medium must be tested for bacterial, fungal, and mycoplasmal contamination prior to use.

In an embodiment, the following materials are used to prepare TOM:

HAMS F12, Gibco #11765-054 (or case 11765-062), 500 ml bottles or equivalent source.

HEPES, Gibco #15630-080 or equivalent, 1M solution, 100 ml bottles. Final concentration 25 mM.

L-Glutamine, Gibco #25030-081 or equivalent source, (stock 200 mM).

Fetal Bovine Serum, Gibco, #16140 (Heat Inactivated) or #10082-147 (heat inactivated, certified).

In an embodiment FBS that is HI may be used in the following manner:

FBS must be heat inactivated at 56° C. for 30 min.

To decrease the likelihood of contamination of the medium, medium must be divided into aliquots and no aliquot should be used more than once.

Aliquots of remaining FBS may be stored frozen (-20° C.) in 25 ml aliquots for research use.

In an embodiment, TOM may be prepared in the following manner.

Thaw fetal bovine serum overnight in the refrigerator, or at 37° C. with frequent gentle swirling.

If non-Heat inactivated fetal bovine serum is used, heat inactivate at 56° C. for 30 minutes.

Put all media components together into 4 liter flask if making 4 liters at a time, stir for 3-5 minutes with stir bar on magnetic stir plate on medium speed (no frothing).

Sterilize using the 0.2 micron filter units.

In an embodiment, sterilization of the TOM preparation may be performed in the following manner. Dispense 1 liter TOM into one liter flask. Measure 80 ml TOM in a disposable sterile cylinder. Pour the 80 ml TOM into a 150 ml Corning filter sterilization unit. Attach house vacuum to filter and filter sterilize per manufacturer's directions. Remove the filter unit from the container and discard. Cap the collection bottle with the sterile cap (provided with the unit). Label with TOM Lot No. Test one aliquot for bacterial culture with anaerobes; fungal culture, other; and *Mycoplasma* culture. Test one aliquot for endotoxin. Store all TOM aliquots in the -20° C. freezer upright.

TOM media may be released for use if: LAL result must equal to or less than 2 EU/ml for samples diluted 20 fold for testing or 1 EU/ml for samples diluted 10 fold for testing; all culture results must be negative for growth.

A BSC must be used for the filtering and dispensing the medium.

TOM is tested for sterility and endotoxin before release. TOM is not released for culturing a donor thymus until after the 14-day sterility testing acceptance criterion has been met. Once prepared, TOM is stored at -20° C. until thawed, at which point it may be stored for use in the refrigerator for up to two weeks.

In an embodiment, the 14-day sterility testing, may, for example, be conducted using the BacT/ALERT culture system. The BacT/ALERT (BioMerieux, Durham, NC) is a commercially available culture system that can be used to test samples using an automated microbial detection system.

All in-process and drug substance cultures are incubated for 14 days or reported immediately if the product becomes positive. For positive tests, the organism(s) are identified and their antibiotic sensitivities determined. Culture bottles containing medium for aerobic growth and bottles containing medium for anaerobic growth are inoculated with samples to be tested on day 1, day 7 and the day of release. All bottles are incubated for 14 days at 35-37° C.

FBS may be obtained from GIBCO brand, Life Technologies. The FBS is prepared by an aseptic, validated process. FBS meets USDA requirements for abattoir-sourced animals, traceability and country of origin. All fetal blood is collected from fetuses derived from healthy dams that have passed pre- and post-mortem certified veterinary inspection.

All FBS are traceable by date and location of collection. FBS collected and processed in the United States is from USDA approved and inspected slaughter establishments. The United States is recognized by the USDA as being free of foot and mouth disease and rinderpest. To qualify the supplier, FBS is tested for pH, osmolality, endotoxin, total protein and identity before use Completed dishes are placed in a humidified incubator at 37° C. with 5% $CO_2$. Each lot of thymus tissue is stored in a separate incubator. After the thymus slices have been placed in the incubator, particle sampling and personnel monitoring is conducted.

Thymus slices are cultured for up to 21 days (for example a conditioning regimen of about 6 days to about 21 days), and during culture the medium is changed daily. These thymus slices are considered the drug substance. During the culture period, many thymocytes are washed out of the thymus tissue slices or the thymocytes undergo apoptosis while preserving the thymic stroma. All manufacturing steps are conducted using sterile, disposable equipment and supplies. Media is aspirated by pipette from the culture dish and pooled into a sterile collection container for in-process testing. Ten (10) mL of fresh thymus organ media is then gently dispensed to each culture dish in a rinsing manner over the tissue slices. After the media change is completed, samples are taken from the pooled media for sterility and histology, if needed. Particle sampling and personnel monitoring are completed and line clearance is performed.

The medium is changed daily.

The slices are cultured for up to 21 days (for example a conditioning regimen of about 6 days to about 21 days).

In-process testing is conducted to provide insight into the process and product quality and to help ensure the safety and quality of the final drug product.

In-Process Testing

Samples are collected for sterility in-process testing on day 1 and day 7. Samples are collected for *mycoplasma* in-process testing on day 7. Samples are collected for in-process histology testing between days 5 and 9. The dose is determined on the day prior to release. Gram stain, BacT, *mycoplasma* and endotoxin are tested on the day of release.

The Gram stain is a bacteriological laboratory technique used to differentiate bacterial species into two groups, Gram-positive and Gram-negative. Gram stain is tested on pooled spent culture medium from the culture dishes. The method uses a staining technique to determine the classification based on the physical properties of the cell wall. This method is used to make a preliminary morphologic identification or to establish whether there are significant numbers of bacteria in a clinical specimen. Staining is conducted either manually or using an automated stainer. It has been demonstrated that the two different staining methods showed no qualitative differences that would impact culture results.

Histology testing is performed prior to implantation, and includes in an embodiment at a minimum: (1) determination that areas positive for keratin AE/AE3 are scattered throughout tissue; (2) at least 1 Hassall body is microscopically identified; (3) CK14 staining of the tissue slices is scattered throughout the thymus tissue; and (4) intact nuclei are microscopically observed. In an embodiment, histology testing is performed between about days 6 to about 21 days) The presence of Hassall bodies and intact nuclei as well as successful CK14 staining are indicative of normal healthy thymus tissue that has been cultured.

Culture time is an important process parameter. As noted, culturing is performed for up to 21 days.

Testing of thymus samples in culture prior to implantation is conducted to confirm whether histology results generated in culture are representative of histology testing of historical specimens of cultured thymus tissue. Based on the observations made by the pathologist for the samples discussed in the Examples, the histologic appearance of the tissue slices at day 5 reflects what is observed at each of the later time points (day 9, 12 and 21) of culturing. In an embodiment testing of thymus tissue may be performed at various timer periods and intervals between days 5 and 21 of culturing. For example, the testing may be performed during the conditioning regimen which is for a period of five days, or six days, or seven days, or eight days, or nine days, or 10 days, or 11 days, or 12 days, or 13 days, or 14 days, or 15 days, or 16 days, or 17 days, or 18 days or 19 days, or 20 days, or 21 days; or for a period of 5-6 days, or 5-7 days, or 5-8 days, or 5-9 days, or 5-10 days, or 6 to 7 days, or 6 to 8 days, or 6 to 9 days, or 6 to 10 days, or 6 to 11 days, or 6 to 12 days, or 6 to 21 days, or 7 to 21 days, or 8 to 21 days, or 9 to 21 days, or 10 to 21 days, or 11 to 21 days, or 12 to 21 days, 13 to 21 days or 14 to 21 days, or 15 to 21 days, or 16 to 21 days or 17 to 21 days or 18 to 21 days, or 19 to 21 days, or 20 to 21 days. In an embodiment, the conditioning regimen may be anytime between about 6 days and about 21 days prior to implantation of the cultured thymus tissue.

Histologic examination of any one slice corroborates the conclusion regarding acceptability of the entire lot. The relevant characteristics of any one slice from a thymus reflect those of the entire thymus, supporting the continued use of a single slice of tissue for histology testing.

Figure 12A:
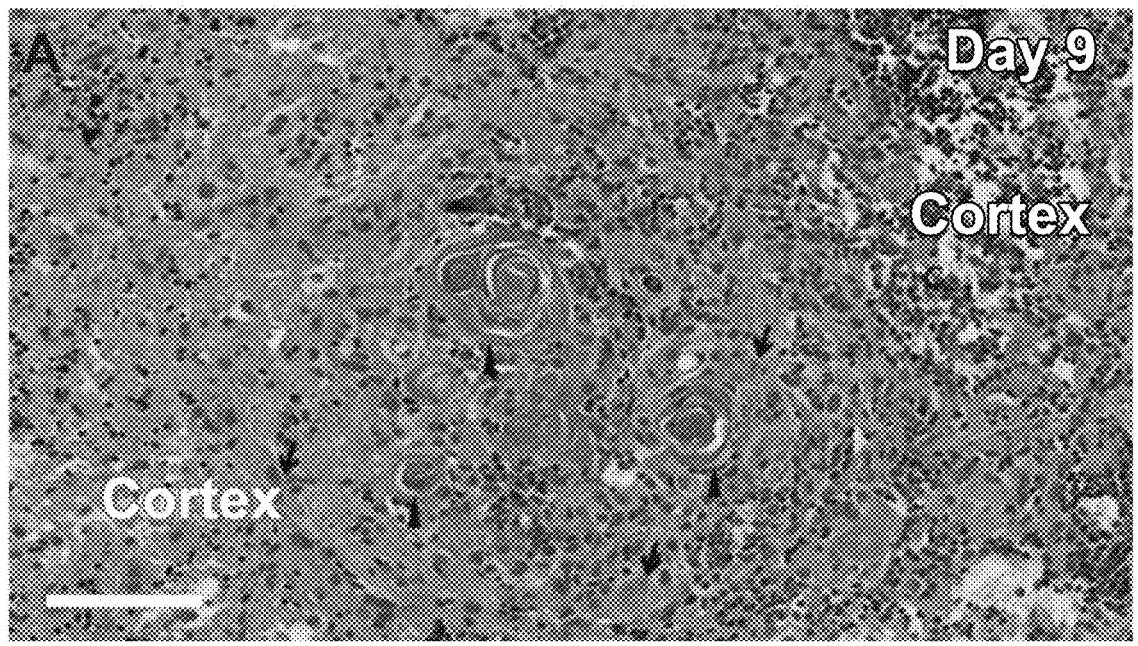
FIGS. 12A and 12B depict the histology of thymus tissue slides after exposure to forced degradation conditions of 10×PBS.
Figure 12B:
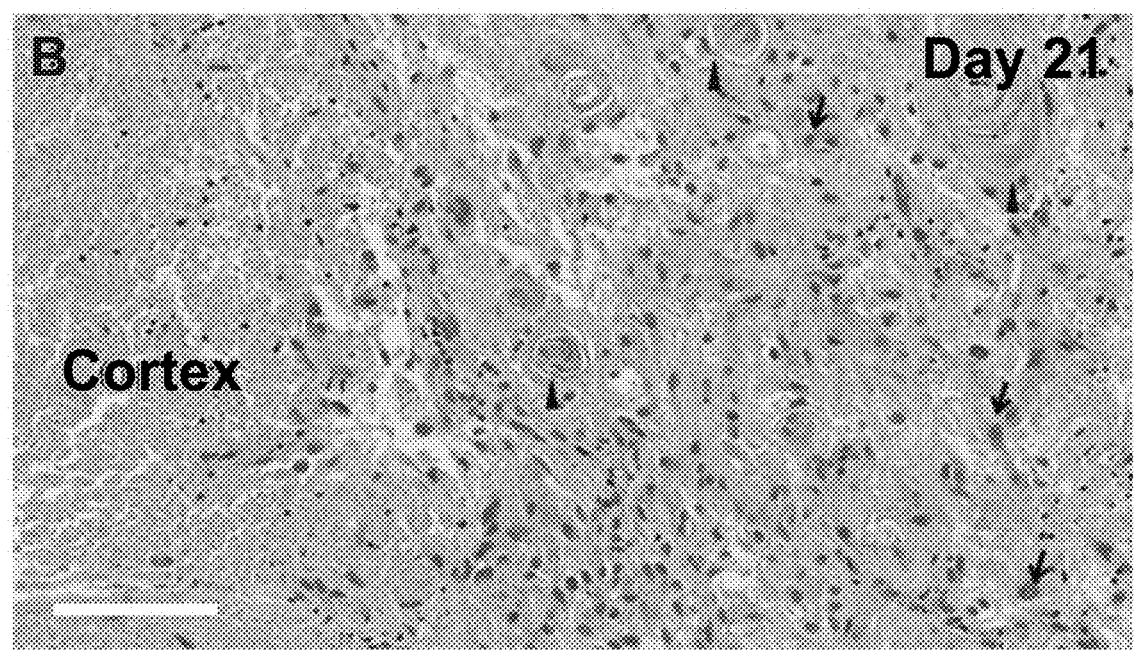
Figure 13:
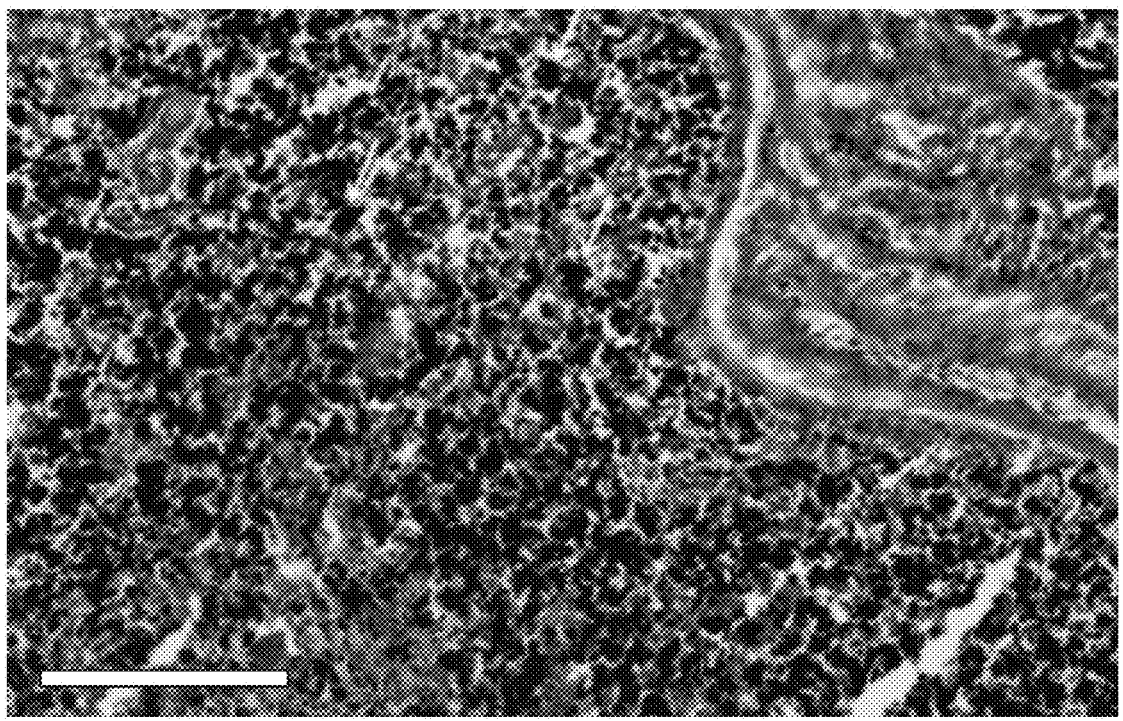
FIG. 13 depicts H&E stained histology sections for clinical sample MLM247. This is Day 0 of culture. The bar is 200 um. This is a frozen section from day 0. Because this was frozen, the tissue looks different from paraffin embedded formalin fixed tissue on day 0. Photo by Laura P. Hale, MD, PhD, Department of Pathology, Duke University.

Forced degradation testing indicated as indicated in FIGS. 12A and 12B demonstrated that the cultured thymus tissue product is not easily degraded and is most sensitive to freeze/thaw as well as changes in osmolarity. Other conditions tested during forced degradation showed little to no effect on the cultured thymus tissue product.

Control of Cultured Thymus Product Drug Substance

Acceptance criteria for incoming thymus tissue product include the tests identified in Table 1 below.

TABLE 1

| Incoming Thymus Tissue | | | |
|---|---|---|---|
| Attribute | Day of Test | Test Parameter | Acceptance Criteria |
| Process Step: Incoming Thymus Tissue | | | |
| Safety | Day 0 | Donor Screening | Donor eligibility requirements are met per 21 CFR 1271 |
| Identity | Day 0 | Visual Inspection | Container intact Label accurate Pink to dark red, black marks may be present |

TABLE 1-continued

| Incoming Thymus Tissue | | | |
|---|---|---|---|
| Attribute | Day of Test | Test Parameter | Acceptance Criteria |
| | Day 0 | Histology | >50% of areas positive for keratin in lacy staining pattern Hassall bodies identified CK14 staining in lacy pattern >90% intact nuclei observed in sections |
| Quality | Day 0 | Weight | ≥3 grams |

Abbreviations: CK, cytokeratin; EU, endotoxin unit; USP, United States Pharmacopeia. A thymus tissue is processed prior to obtaining all donor screening results.

Generally, the acceptance criterion for weight is greater than or equal to 3 grams. This is the minimal thymus weight that is accepted to ensure sufficient material is available for proper dosing of the final product. The acceptance criterion is based on experience in processing thymus tissue.

Acceptance criteria for in-process testing is identified in Table 2 below.

TABLE 2

| In-process Testing: | | | |
|---|---|---|---|
| Attribute | Day of Test | Test Parameter | Acceptance Criteria |
| Process Step: Drug Substance In-Process Testing | | | |
| Safety | Day 1 | Sterility | No growth |
| Safety | Day 7 | Sterility | No growth |
| | Day 7 | Mycoplasma | Negative for the presence of mycoplasma |
| Potency | Days 5-9 | Histology | Areas positive for keratin AE1/AE3 scattered throughout tissue on days 5-9 At least 1 Hassall body identified CK14 staining scattered throughout tissue Intact nuclei observed |

Acceptance criteria for cultured thymus tissue drug substance testing is identified in Table 3 below.

TABLE 3

| Cultured Thymus Tissue Drug Substance Testing | | | |
|---|---|---|---|
| Attribute | Day of Test | Test Parameter | Acceptance Criteria |
| Process Step: Drug Substance Release Testing | | | |
| Appearance | Day of release | Visual inspection | No evidence of tampering or damage to containers Yellow to brown slices of tissue with varying thickness and shape |
| Identity | Days 5-9 | Histology | Thymus tissue identity is confirmed by histology on day 1 and at midpoint (days 5-9). |
| | Day of release | Barcode | A barcode is used for tracking of the tissue throughout the processing and the barcode is confirmed at release. |

TABLE 3-continued

Cultured Thymus Tissue Drug Substance Testing

| Attribute | Day of Test | Test Parameter | Acceptance Criteria |
| --- | --- | --- | --- |
| Strength | Day before release | Dose | 1000-22,000 mm$^2$ of thymus tissue/recipient body surface area in m$^2$ |
| Safety | Day of release | Endotoxin (USP <85>) | <5 EU/kg body weight/hr |
| | Day of release | Sterility | No growth |
| | Day of release | Mycoplasma | Negative for the presence of mycoplasma |
| | Day of release | Gram stain | Negative |

The acceptance criterion for identity is that thymus tissue identity is confirmed by histology on day 1 and at the midpoint (days 5-9). A barcode is used for tracking of the tissue throughout the processing and the barcode is confirmed at release to verify the correct identity of the product.

Histology by Immunochemistry

The histology method is a standard method used by hospitals for all tissue types, as is known by a person of skill in the art.

Samples of the product are fixed in 10%/formalin and transported to the laboratory. Containers are labeled with a coded identifier instead of the patient's name to protect patient privacy, along a medical record number. Upon arrival in pathology, the specimens are assigned a unique pathology accession number, and barcoded. The subsequent blocks, slides, and paperwork are all barcoded with this pathology accession number.

After the specimen is received in the lab, the formalin-fixed tissue is grossly examined, and a written gross description of the material is prepared that will become part of the final report. The formalin-fixed tissue is then processed and embedded into a paraffin block by standard methodology on an automated processor. Sections are cut from the paraffin block and the following stains are performed by ASCP-certified histotechnologists:

Hematoxylin & eosin.

Cytokeratin AE1/AE3 immunohistochemistry.

Cytokeratin 14 immunohistochemistry.

CD3 immunohistochemistry.

Ki-67 immunohistochemistry.

During performance of the foregoing immunohistochemistry tests, appropriate control slides are also tested and reviewed. All control slides and internal controls demonstrate the expected immunoreactive patterns. The incoming thymus sample also serves as a control for tissue slices that have been in culture for about 6 days to about 21 days, when samples are tested as part of potency testing. The incoming thymus sample appears as a typical thymus sample and then changes occur to the tissue slices while they are cultured and then tested after about 6 days to about 21 days in culture. After about 6 days to about 21 days in culture, the sample must show areas positive for keratin AE1/AE3 scattered throughout the tissue, the presence of at least one Hassall body, CK14 staining scattered throughout the tissue and presence of intact nuclei.

Slides are interpreted by a pathologist certified in Anatomic Pathology, with additional experience in the histologic evaluation of thymic tissue. The final report is issued by the pathologist and the report documents the results.

Acceptance criteria for cultured thymus tissue drug substance testing is identified in Table 4 below.

TABLE 4

Cultured Thymus Tissue Drug Substance Release Testing

Process Step Drug Product Release Testing

| Identity | Day of release | Visual inspection | No evidence of tampering or damage to containers Yellow to brown slices of tissue with varying thickness and shape, adhered to round white filter paper |
| --- | --- | --- | --- |
| | Days 5-9 | Histology | Thymus tissue identity is confirmed by histology on day 1 and at midpoint (days 5-9). |
| | Day of release | Barcode | A barcode is used for tracking of the tissue throughout the processing and the barcode is confirmed at release. |

The cultured thymus tissue must be free of microorganisms. In the sterility test performed on day 1 and day 7, there should be no growth of microorganisms. *Mycoplasma* should be negative upon testing on day 7. The sterility test should be gram stain negative.

Product sterility is maintained using appropriate controls including aseptic technique; employing a training program and verifying the qualification of operators; utilizing appropriate clean room qualification procedures; employing establish clean media fill procedures and utilizing ready-to-use sterilized apparatus or apparatus sterilized utilizing validated sterilization cycles.

The containers of processed thymus tissue are visually examined for damage. Tissue slices normally exhibit a yellow to reddish brown appearance with varying thickness and shape.

Thymus tissue identity is confirmed by histology on day 1 and at midpoint (days 5-9).

A barcode is used for tracking of the tissue throughout the processing and the barcode is confirmed at release.

The dosage (area) is 1,000-22,000 mm$^2$ of thymus tissue/recipient body surface area in m2. Dose is controlled by the surface area of slices released to the operating room as appropriate for the patient's body surface area.

The acceptable dose range is defined as 1,000-22,000 mm$^2$ of thymus tissue per recipient body surface area (BSA) in m$^2$. The area of the thymus tissue is determined by photograph using software analysis (PAX-it Image Analysis Software). BSA is determined using the patient's height in cm and weight in kg. The DuBois and DuBois formula is used to calculate the BSA:

$$BSA = 0.007184 \times [\text{height (cm)}]^{0.725} \times [\text{weight (kg)}]^{0.425}.$$

The cultured thymus tissue is tested for endotoxin. The specification is ≤5 EU/kg body weight/hr.

Endotoxin testing may be performed, for example, by using the Endosafe PTS system. The cartridges used with the Endosafe PTS use a chromogenic kinetic Limulus Amebocyte Lysate (LAL) test. Each cartridge contains precise amounts of LAL reagent, chromogenic substrate and control standard endotoxin. Test sample is pipetted into four sample reservoirs. The instrument draws and mixes the sample with LAL reagent in two channels (sample channels) and with the LAL reagent and positive product control in the other two (spike channels). The sample is incubated then combined with the chromogenic substrate. After mixing, the optical density of the wells is measured and compared to a standard curve archived in the instrument. The instrument measures the reaction time in each channel. The archived standard curve specific for each batch of cartridges is constructed using the log of the reaction time versus the log of the endotoxin standard concentration. The sample and spike values are calculated by interpolation off the standard curve using the reaction time. This testing meets the requirements of United States Pharmacopeia (USP).

Testing for *mycoplasma* may be performed in the following manner. A sample of the pooled media is removed from the plates on day 7 and tested before product release.

In the event of a positive culture during manufacturing, the lot will be discarded and will not be administered. In the event of a positive culture after clinical product administration, the patient's attending physician and sponsor will treat the patient appropriately. A positive culture requires that the species of the contaminating organism be identified and its antibiotic sensitivity determined. The attending physician will institute antibiotic therapy for the thymus recipient, if indicated.

The drug product undergoes similar visual inspections and histology testing before use.

After the thymus tissue slices have been cultured for up to 21 days, the slices are transferred into drug product containers for transport to the operating room. Once received in the operating room, the slices are inserted into the thigh muscle of the recipient patient The container should be intact with no visible damage and the thymus tissue slices should appear as yellow to reddish-brown slices of tissue with varying thickness and shape. The tissue slices are visually examined to confirm that these acceptance criteria are met.

Cryopreservation and Thawing of Allogeneic Cultured Post-Natal Thymus Tissue Derived Product Cryopreservation of the allogeneic cultured post-natal thymus tissue derived product may be performed in the following manner.

A cryopreserved allogeneic cultured postnatal thymus tissue-derived product, prepared by method comprising the steps of:
(a) obtaining suitable thymus tissue from a donor;
(b) typing HLA alleles: HLA-A, HLA-B, HLA-C, HLA-DRB1, HLA-DQB1, HLA-DRB3, HLA-DRB4, HLA-DRB5, HLA-DQA1, HLA-DPB1, HLA-DPA1;
(c) subjecting the thymus tissue to a conditioning regimen for a period from about 6 days to about 21 days; wherein the conditioning regimen for the donor thymus tissue comprises aseptically processing the donor thymus tissue in a thymus organ medium to produce partially T-cell depleted donor thymus tissue slices; further wherein the donor thymus tissue slices show, on about 6 days to about 21 days, areas positive for keratin AE/AE3 scattered throughout the tissue, the presence of at least one Hassall body, CK14 staining scattered throughout the tissue and presence of intact nuclei upon completion of the conditioning regimen;
(d) harvesting the partially T-cell depleted donor thymus tissue slices as allogeneic cultured postnatal thymus tissue-derived product;
(e) cryopreserving the allogeneic cultured postnatal thymus tissue-derived product in liquid nitrogen; and
(f) maintaining the cryopreserved allogeneic cultured postnatal thymus tissue-derived product in liquid nitrogen in a cryopreserved allogeneic cultured postnatal thymus tissue-derived product bank. In an embodiment, the cryopreserved allogeneic cultured postnatal thymus tissue-derived product, wherein the thymus, on the day of harvest, demonstrates that >50% of areas are positive for keratin in a lacy staining pattern, that Hassall bodies are present, that CK14 stains in a lacy pattern, and that >90% of nuclei are intact.

In an embodiment, the donor thymus is sliced and divided into roughly two equal portions, putting each slice with its cellulose filter in a separate cryovial (Nunc tube). The filter is folded in half to insert it into the tube. About 1 to about 1.5 ml of freezing medium [sterile filtered 90% heat inactivated fetal bovine serum (FBS) and 10% dimethyl sulfoxide (DMSO)] at room temperature is added to cover the tissue. The sterile cap of the cryovial is replaced on the tube. Put all the tubes in a Biocision Cool Cell or equivalent container which is at room temperature. Any empty slots in the CoolCell should be filled with tubes that have 1 ml of freezing media. The tubes are placed overnight in a −80° C. freezer. Alternatively place each tissue plus filter in a 5 ml CryoELITE tissue Vial (Wheaton). Put 3 to 5 ml of freezing medium at room temperature to cover the tissue. Put in a Styrofoam box and put in −80° freezer overnight. The vials are then transferred to the vapor phase of a liquid nitrogen freezer. Alternatively a controlled rate freezer can be used to bring the temperature of the cryovials to liquid nitrogen temperature.

To recover the tissue, remove the cryovial or the CryoELITE tissue Vial from the liquid nitrogen freezer. Thaw the thymic pieces in the vial rapidly with a swirling motion in a 37° C. water bath. The tube is sprayed with 70% ethanol and then is placed in the Biological Safety Cabinet (BSC). The thymic tissue and filter are removed from either the Nunc cryovial or the CryoELITE tissue Vial using forceps. The tissue and filter are placed in a 50 ml conical tube containing 20 ml of 4° C. TOM. Up to 5 filters can be placed in each 50 ml conical tube that contains 20 ml of 4° C. TOM. Immediately transfer the 5 filters with tissue to a fresh conical tube with 20 ml of 4° C. TOM media and put at 4° C. for 15 minutes. Repeat the wash 3 times. Keeping the tissue at 4° C., transfer each piece to its own 120 ml Starplex container with 5 mls 4° TOM. All containers are brought to the surgical suite in a temperature-controlled container with a cold pack in it. The Starplex containers with the tissue are brought into the operating room. The tissue on the filters are transferred to the sterile field into a tissue culture dish with approximately 2 ml of sterile saline. The scrub nurse removes the tissue from the filter paper by scrapping or pulling with forceps. The scrub nurse places the tissue, in an amorphous pile, back on the filter paper. The tissue culture dish with approximately 4 filters and the tissue is transferred to the operative site where the surgeon can easily access the tissue. The tissue is placed in the quadriceps muscles similarly to the procedure with CTT (RVT-802). The Cryo-CTT resembles the CTT in that it is partially T-cell depleted, the thymus tissue slices show areas positive for keratin AE1/AE3 scattered throughout the tissue, slices contain at least one Hassall body, CK14 staining is scattered throughout the tissue and presence of intact nuclei.

Transplantation of CIT

In an embodiment, unmatched thymus tissue slices from the donor are cultured for about 6 days to about 21 days. On the day of the solid organ transplantation steroids are usually given at the induction of anesthesia. For heart or lung transplants, the thymus of the recipient is surgically removed at the time of the solid organ transplant. For other organ transplants the thymectomy may be done prior to the day of transplantation or on that day. The thymectomy method would be surgical, thoracoscopic or robotic. At the end of the surgery after reperfusion, the recipient is given more steroids prior to receiving equine anti-thymocyte globulin (e.g., rabbit anti-thymocyte globulin) over 3 to 7 days to kill most of the residual T cells (and NK cells) in the recipient or alemtuzumab over 4 days to kill the T, B and NK cells. Administration of an immunosuppressant (such as cyclosporine or tacrolimus) and mycophenylate is then started until T cells develop and show greater than 10% naïve T cells. It may take 6 to 12 months for the naïve T cells to increase to this number. Cultured thymus tissue is processed for the thymus of the donor of the solid organ. Half of the CTT can be implanted into the quadriceps muscle between about 6 days to about 21 days. The other half of the thymus will be cryopreserved for future use of the recipient. The immunosuppressive regimens will suppress any remaining T cells until naïve T cells are released by the cultured thymus tissue slices implanted in the recipient and the recipient meets criteria for weaning off the maintenance immunosuppression regimen. (Over 10% naïve T cells are needed to wean the immunosuppression.)

Thymectomy Protocol

The patient is taken to the operating room and is placed under general anesthesia by endotracheal tube.

The chest and abdomen are prepped and draped in a sterile fashion.

The patient undergoes a full sternotomy through a skin incision of approximately 4 cm.

Both pleural spaces are entered to guarantee a complete resection.

The phrenic nerves are visualized on both sides and care is taken to not compromise them.

The thymus is identified and carefully dissected away from the pleural investment of the lung, starting with the inferior horns and extending to the superior horns.

A complete thymectomy is performed.

Hemostasis is attained within the mediastinum.

Chest tube placement. One chest tube is always inserted (into the mediastinum). If a single pleural space is entered during the operation, the chest tube is continued from the mediastinum into that pleural space. If both pleural spaces are entered, a second chest tube is used in a similar fashion from the mediastinum to the other pleural space.

Drain size. #15 Blake drains are used for infants up to 2 years of age. #19 Blake drains are used for children 2 years and older.

Sternum closure: In neonates or infants, 0-Ticron sutures are used to close the sternum. At about 1-2 year of age, #1 sternal wires are used. At about 2-5 years of age, #4 sternal wires are used.

The fascia, subcutaneous tissue and skin are closed with running absorbable suture.

A skin wound vac is placed on the sternum.

The patient is extubated in the operating room.

A sponge, instrument and needle counts are taken and must be correct at the end of the case.

Surgical Implantation of Allogeneic Cultured Postnatal Thymus Tissue-Derived Product.

Allogeneic cultured postnatal thymus tissue-derived product should be implanted in accordance with the following instructions. Implantation of thymus tissue into the thigh requires a healthy bed of muscle tissue.

Preparation for Implantation Procedure

The maximum and minimum dosage of planned implanted allogeneic cultured postnatal thymus tissue-derived product should be calculated for each individual patient. Properly identify the intended recipient prior to administration.

Under sterile conditions within a laminar flow hood, the tissue slices on the filter papers that are on surgical sponges in medium are removed from the tissue culture dishes and placed in 120 ml sterile cups with 20 ml medium, packaged to maintain sterility, and delivered to the operating room or packaged for shipment. Tissue slices are not removed from the individual containers until ready to be used. Verify the product expiration date and time.

Always handle allogeneic cultured postnatal thymus tissue-derived product (tissue slices) using strict sterile technique. Inspect each container for leaks or evidence of damage. Do not use if there is evidence of contamination. Outside the sterile field, unpack allogeneic cultured postnatal thymus tissue-derived product containers from the shipping box. Remove racks containing polypropylene containers from the outer bag. When ready, a team member outside the sterile field, but adjacent to the sterile prep table, will open and remove the cap from each container, one at a time. Each open container is then held by the team member outside the sterile field extending his/her arm over the sterile field without touching the sterile field.

The sterile field team member will use a pair of forceps to remove the individual tissue slice with its filter paper from the container and place it in a sterile tissue culture dish containing approximately 2 ml preservative-free saline on the sterile prep table. Four tissue slices with the filter papers taken from four containers are placed in one sterile tissue culture dish that is on the sterile field in front of the sterile field team member. Using sterile forceps, the sterile field team member then peels the tissue slice away from the filter paper using two pairs of forceps, one of which holds the filter in place while the other pulls the tissue or scrapes the tissue into a pile. The tissue removed from each filter paper is than put on that filter paper in a pile in the middle of the filter paper. The sterile tissue culture dish is then transferred to the sterile field. The next set of four allogeneic cultured postnatal thymus tissue-derived product containers will then be processed the same way while the surgeon is implanting the first 4 slices. When the surgeon finishes implanting the first four slices, the next dish with 4 pieces of tissue is put in the surgical field and the initial tissue culture dish is returned to the sterile field in front of the sterile field team member for loading the $3^{rd}$ set of four tissue slices. Continue this cycle until all the desired tissue is implanted. All of the tissue slices are not transferred at the beginning to avoid contamination from the air in the operating room.

Surgical Procedure

Step 1. Skin Opening.

After induction of general anesthesia, make a vertical skin incision (typically ~5 cm in length) over one of the anterior thigh compartment. Note: The size of the incision and the use of one or both legs for the implantation procedure is determined by the size of the patient, planned amount of implanted tissue, and his/her muscle mass. If all or most of the tissue can be implanted in one leg, then only one leg should be used.

Step 2. Open the fascia to expose the anterior compartment muscles.

Step 3. Muscle spreading and implantation.

Separate the muscle using a tonsil clamp or similar instrument along the natural furrows of the quadriceps muscle. The allogeneic cultured postnatal thymus tissue-derived product individual thymus slices should be implanted without cutting muscle tissue. Place individual tissue slices in "pockets" approximately 1 cm apart and approximately 1 cm in depth within the quadriceps muscle along the natural furrows. Depending on the size of the patient, the surgeon may place approximately 6-7 slices into 6 to 7 pockets along each furrow. Individual allogeneic cultured postnatal thymus tissue-derived product slices may be cut in half prior to implantation depending on the mass of tissue on each filter. A thick slice of tissue that had fully covered the filter paper should be cut in half for optimal vascularization of each tissue. Implant as much required tissue within each anterior compartment up to the maximum planned dose.

Step 4. Muscle closure.

Close the muscle with a single suture over the site where the thymus tissue was implanted to prevent muscle reopening and graft coming out of muscle. Ensure that the implanted tissue is entirely covered by muscle tissue with no exposed thymus tissue prior to closing the incision.

Step 5. Repeat Steps 3-4 for each allogeneic cultured postnatal thymus tissue-derived product tissue slice up to the maximum intended dose.

Step 6. Incision closing.

Confirm hemostasis. Close the skin incision with two layers of absorbable sutures and apply standard dressing such as wound closure strips or skin glue. Leave the fascia open to allow room for the muscle compartment swelling. An occlusive dressing may be used to prevent contamination.

Post-Operative Surgical/Medical Management.

Use mild analgesics as needed. Monitor for signs of infection or dehiscence.

If the donor is a living related donor as for lung, kidney, intestine, or partial liver, a portion of that solid organ donors' thymus may be adequate for culture and implantation. The pathology criteria listed above for the day of harvest and until implantation would need to be met.

Cryopreserved-cultured thymus tissue may be available from a $3^{rd}$ party donor. However, the $3^{rd}$ party donor must express all the recipient HLA alleles that are not expressed by the solid organ donor. This includes HLA-A, HLA-B, HLA-C, HLA-DRB1, HLA-DQB1, HLA-DQA1, HLA-DPB1, and HLA-DPA1. Mismatching in HLA-DP alleles is acceptable if the mismatch is "permissive." In other alleles minor mismatching is allowed, e.g., HLA-A*01:02 into a recipient carrying HLA-A*01:01, in other words, the second field (after the colon) can be different, the first field (before the colon) must be identical.

Human Heart Transplant Procedures

Eligibility of a subject is determined based on a number of criteria including: Poor 12 to 24 month prognosis without cardiac transplantation despite current maximum supportive therapies; congenital or acquired heart disease with failure to thrive as defined by UNOS criteria; symptoms of advanced heart failure in the setting of congenital or acquired heart disease refractory to medical therapy; abnormal hemodynamics or increasing pulmonary vascular resistance; inoperable structural heart disease; symptomatic arrhythmias not amenable to medication or device therapy or poor exercise tolerance.

A number of absolute and relative contraindications to heart transplant surgery are assessed, including, for example, reversible renal dysfunction unless the subject is a candidate for heart/kidney transplant; irreversible liver disease unless candidate for heart/liver transplant; irreversible pulmonary dysfunction, use of non-conventional mechanical ventilator support (i.e. high frequency ventilator, maximal settings of CMV) or fixed pulmonary hypertension (TPG>15) unless the subject is a candidate for a heart-lung transplant; Diabetes mellitus with microvascular disease; or active, uncontrolled seizure disorder.

Other contraindications may include other diseases limiting long term survival and rehabilitation following a heart transplant; substance abuse, morbid obesity, malignancies; active psychiatric disorder; and other reasons such as documented medical non-compliance.

Relative contraindications include active infections; cognitive dysfunction; inadequate vascular access and significant allosensitization.

Donor and recipient histocompatibility management is also considered. Patients are evaluated for panel reactive antibodies ("PRA") for pre-formed HLA antibodies that the recipient may have formed in response to a "sensitizing event" such as prior transfusions or major surgeries using bypass/blood products or homograft materials.

An assessment is made of the recipient's presensitization history, for example, previous blood transfusions; number, dates; previous surgeries; previous pregnancies; immunization history and IVIG administration (with dates).

Patients with an excessively high HLA-Class I or Class-II PRA or those undergoing repeat transplant may be candidates for desensitization strategies. Specific strategies will be individualized to the potential recipient and may include use of plasmapheresis, IVIG, rituximab and/or bortezomib. Significant antibodies are those that remain present after a 1:16 dilution.

Pre-sensitized patients may require an actual prospective cross-match with potential donors. Patients with a history of HLA antibodies will undergo virtual cross-match in UNET at the time a transplant is being considered.

Pre-sensitized patients may require an actual prospective cross-match with potential donors via the following general guidelines. All patients with a history of HLA antibodies will undergo virtual cross-match in UNET at the time an offer is being considered.

If the cPRA<20%: virtual cross-match in UNET, no additional measures are needed; proceed with routine retrospective donor cross-match and routine immunosuppression.

If cPRA>20%: virtual cross-match in UNET, recipient receives plasmapheresis in the operating room ("OR") at the time of transplant.

If cPRA>70%: virtual cross-match, consider obtaining an actual prospective donor cross-match if time allows; administer plasmapheresis in the OR. Consider placement of a pheresis catheter in the OR for post-op continuation of pheresis.

Ongoing antibody reduction interventions are determined by donor cross-match, DSA's and clinical course.

For all pre-sensitized patients, blood will be sent for donor-specific antibodies within the first two weeks post-transplant and repeated as clinically indicated. Routine testing for DSA will be done on all post-transplant patients at least every 6 months post-transplant and as needed if any clinical concerns.

Standard blood product transfusion protocols are followed both pre- and post-transplantation.

Immunosuppression Management

Immunosuppression management is determined based on the solid organ to be transplanted.

Pediatric Heart Transplants

All patients will receive induction therapy with basiliximab or anti-thymocyte globulin based on their clinical situation and risk factors. The type of induction therapy used will be determined prior to transplant (First Immunosuppression Regimen drug therapy).

In an embodiment, pre-transplant/induction therapy typically comprises administration of:

Mycophenolate mofetil (CellCept®) 25 mg/kg IV prior to the operating room.

Methylprednisolone 10 mg/kg IV on induction (max dose 500 mg).

Methylprednisolone 10 mg/kg IV on release of x-clamp (max dose 500 mg).

ATG (antithymocyte globulin) 1.5 mg/kg IV on release of x-clamp.

Alternatively use Basiliximab (Simulect®), dosed by weight of recipient.

<35 kg, 10 mg on release of x-clamp and 2nd dose 4 days later.

>35 kg, 20 mg on release of x-clamp and 2nd dose 4 days later.

In an embodiment pre-transplant induction immunosuppressive therapy for heart and CTT implant candidates may comprise:

Basiliximab (Simulect®)—(if cannot give ATG).

Dosing:

<35 kg: Initial dose: 10 mg IV administered preoperatively by anesthesia on induction of anesthesia (after stable and methylprednisolone given).

Second dose: 10 mg IV administered 4 days after transplantation; hold second dose if complications occur (including severe hypersensitivity reactions or graft loss)

>35 kg: Initial dose: 20 mg IV administered preoperatively by anesthesia on induction of anesthesia when stable.

Second dose: 20 mg IV administered 4 days after transplantation; hold second dose if complications occur (including severe hypersensitivity reactions or graft loss.

Administration: IV infusion over 20-30 minutes. Half-life children 1-11 years: 9.5 days, adolescents 12-16 years: 9.1 days, adults: 7.2 days.

In an embodiment, antithymocyte globulin (ATG, rabbit derived, Thymoglobulin®), may be given according to the following dosing schedule for heart transplant subjects:

1.5 mg/kg/day for 3 to 7 days based on lymphocyte count and markers and platelet count. The first dose is given after organ reperfusion on release of cross-clamp after second dose of steroids (intra-operatively).

Continued daily based on above parameters, will be determined by transplant MD.

Administration: Slow IV infusion over 6 hours for first dose, subsequent doses can be given over 4 hours as tolerated.

In an embodiment, in addition to routine preoperative/intraoperative methylprednisolone for CPB/pump cases, patients may receive a dose of methylprednisolone (Sol-uMedrol) 10 mg/kg (max dose 500 mg) IV to be administered by anesthesia on induction of anesthesia before basiliximab and then a second dose of 10 mg/kg (max 500 mg) on reperfusion (before ATG).

Post-Operative Maintenance Immunosuppression (Maintenance Immunosuppression Regimen)

In an embodiment, post-transplant immunosuppression comprises:

ATG (Thymoglobulin®) 1.5 mg/kg IV daily for 5-7 doses. Hold if WBC<2,000 or platelet count <50,000.

½ dose if WBC 2,000-3,000 or platelet count 50,000-75,000.

Mycophenolate 15-25 mg/kg IV/PO every 12 hrs.

Adjust for GI intolerance or leukopenia/neutropenia.

Can substitute azathioprine if GI intolerance.

Can substitute mycophenolic acid (Myfortic®) if GI intolerance.

Tacrolimus to start at 24-48 hrs after tx depending on renal function & oral tolerance.

Starting dose ~0.05 mg PO q 12 hrs & adjust based on levels.

~10-15 for first 6 months, 8-12 for 6 mo-3 years, 4-8 for >3 years.

Can substitute cyclosporine if IV medication needed or intolerance to tacrolimus.

Methylprednisolone 5 mg/kg IV q 8 hours×6 doses (max dose 125 mg).

Then, 1 mg/kg/dose IV/PO q 12 hours (max 30 mg/dose).

Wean over next 2-3 months based on biopsy results.

In an embodiment, tacrolimus (FK506, Prograf®) may be administered. Usual dosage forms include intravenous solutions of 0.5 mg/ml, and oral capsules of 0.5 mg, 1 mg, and 5 mg per capsule.

A starting dose of ~0.05 mg/kg/dose—is given every 12 hours (maximum 5 mg/dose) when the recipient is PO/NG/SL, usually started at ~24 hours post-operatively if renal function acceptable.

Tacrolimus trough levels are monitored daily until therapeutic dosing is achieved. Increase administration to every 8 hours, if necessary, to achieve therapeutic trough levels. If the drug is given sublingually, the capsule contents are sprinkled under tongue (may result in higher levels). Oral and sublingual doses are not. Generally it will be necessary to administer ~½ of the oral dose to be given sublingually.

Tacrolimus dosing may be administered based on serum whole blood levels measured by mass spectrometry method 10-14 hours (7-9 hours if dosed every 8 hours) following the last dose.

Renal and hepatic function, adverse drug effects, infection and rejection history are all considered in managing a patient's tacrolimus levels. Dose adjustments do not need to be made if levels fall +/−1 within the desired range if the patient is clinically doing well. In these cases the decision is up to the attending transplant physician.

In an embodiment, cyclosporine is administered to patients unable to tolerate tacrolimus. The starting dose: 2 mg/kg/dose by mouth every 12 hours. If unable to achieve therapeutic levels (especially infants and young children) then the dosing frequency is increased to every 8 hours.

General Dosing is based on the following serum whole blood levels measured by mass spectrometry method 10-14 hours (7-9 hours if dosed every 8 hours) following the last dose.

Renal and hepatic function, adverse drug effects, infection and rejection history are all considered in managing a patient's cyclosporine level. Dose adjustments do not need to be made if levels fall +/−10-20 within the desired range if the patient is clinically doing well. In these cases the decision is up to the transplant attending. Every effort should be made to document the patient's goal cyclosporine level in the chart. The IV dose is generally equal to ⅓ the oral dose.

In an embodiment, Mycophenolate mofetil (Cellcept®) (200 mg/ml, 250 mg or 500 mg tabs) may be administered:

Begin 30-50 mg/kg/day in two divided doses (maximum dose children 2 g/day, adults 3 g/day).

IV dose=PO dose.

No therapeutic drug monitoring is required but can be done if concerns about toxicity.

Mycophenolate may cause bone marrow suppression and neutropenia.

The dose may be held when ANC<500 or WBC<1000; may need to decrease dose in setting of decreasing ANC (<1000) or WBC (<3000). In practice dosages of Cellcept 500 mg=Myfortic (mycophenolate) 360 mg.

In an embodiment, Mycophenolate (Myfortic® dosage forms 180 mg tablet, 360 mg tablet) may be administered in lieu of Mycophenolate mofetil, according to the following dosage parameters:

Begin delayed-release tablet: 400 mg/m2/dose twice daily; maximum dose: 720 mg OR BSA 1.19-1.58 m2: 540 mg twice daily, BSA>1.58 m2: 720 mg twice daily.

No IV or suspension available. If IV or suspension is necessary then the drug is converted to Cellcept. (Cellcept 500 mg=Myfortic 360 mg). Mycophenolate may cause the same bone marrow suppression as Mycophenolate mofetil.

In an embodiment, if Mycophenolate mofetil cannot be tolerated, azathioprine may be administered in the following manner:

Begin 2-4 mg/kg/day, given once daily

Azathioprine causes bone marrow suppression and dose may need to be reduced based on WBC/ANC. The IV dose equals the oral dose.

In an embodiment steroid may be administered, as methylprednisolone (Solu-Medrol®), prednisone or prednisolone.

Intravenous steroids are started intraoperatively (as induction immunosuppressive therapy), and the continued postoperatively at 5 mg/kg/dose (maximum 125 mg/dose) IV every 8 hours×6 doses.

Oral steroids may begin thereafter as prednisone tablets or prednisolone suspension 3 mg/ml. Intravenous methylprednisolone is continued if the transplant recipient is unable to tolerate the immunosuppression treatment regimen orally. A switch over to oral therapy may be made the recipient can tolerate oral medications. Exemplary dosing ranges of steroids are:

0-10 kg, start at 2 mg/kg/day divided BID, wean every 2 days, holding at 6 mg daily 0-30 kg, start at 2 mg/kg/day divided BID (max single dose of 30 mg, see below), wean by 5 mg/day every two days then hold at 10 mg daily.

>30 kg, 30 mg BID×4 doses, 25 mg BID×4 doses, 20 mg BID×4 doses, 15 mg BID×4 doses, 10 mg BID×4 doses, then start 15 mg daily to be further weaned by transplant cardiologist Continue to wean steroids to off over first month after transplant based on biopsy results. If rejection develops, then steroids will be restarted at the discretion of the transplant cardiologist and continued indefinitely based on further biopsy results and patient clinical status.

Other drugs in the second immunosuppression regimen include the following:

Sirolimus (Rapamune®) (0.5 mg, 1 mg, 2 mg caps): Initiated after diagnosis of coronary allograft vasculopathy or as otherwise clinically indicated by the transplant cardiologist.

Starting dose: 1 mg/m2 (maximum dose: 3 mg) once daily or divided into 2 daily doses if difficulty achieving adequate levels.

Therapeutic level goal is 4-8, accept lower tacrolimus level (same 4-8 range) if on both drugs.

Trough level drawn 23-25 hours following last dose or 11-13 hours following last dose if dosing every 12 hours.

Discontinue mycophenolate (Cellcept®, Myfortic®), azathioprine when starting sirolimus.

Start Bactrim prophylaxis: Can cause troublesome mouth sores, and delayed wound healing.

Pravastatin (Pravachol®)—used in teenagers/older children and those with CAV

Begin 0.2 mg/kg/day administered once daily (comes in tablet form, can give ¼, ½ or up to 1-2 tabs per day at night.

Titrate up dose as weight changes (maximum dose 20 mg/day).

Monitor LFT's, CK every 8 weeks.

Discontinue drug if joint or muscle pain develops.

Ganciclovir IV—given for CMV prevention if recipient or donor is CMV IgG positive.

Induction therapy: 5 mg/kg IV q 12 hours×7-14 days.

Maintenance therapy: 5 mg/kg IV daily.

Monitor WBC and renal function.

Transition to oral valganciclovir when tolerable.

Valganciclovir (Valcyte®)—for CMV prevention in all CMV+ recipient or donor.

450 mg tabs or 50 mg/ml suspension.

4 months-16 years: total daily oral dose (mg)=[7×BSA× Cr Clearance].

>16 years: 900 mg orally daily.

Monitor CMV PCR at each visit.

Trimethoprim-Sulfamethoxazole (Bactrim®, Septra®):

Single strength tablets 80 mg/400 mg, double strength tab 160 mg/800 mg, suspension 40 mg/200 mg per 5 ml.

Start when taking oral meals as well, prior to discharge for PCP/Toxo prevention.

1 mo-12 yr: 5-10 mg/kg/day TMP div BID 3×/week on consecutive days.

>12 yr: 80-160 mg TMP orally daily or 160 mg TMP orally 3×/week.

Monitor for drugs which may increase or decrease tacrolimus and cyclosporine levels, as known to the person of ordinary skill in the art.

Also monitor for drugs having a synergistic nephrotoxicity with tacrolimus and cyclosporine.

Acute Transplant Rejection Treatment

In an embodiment, the subject is treated in the following manner in the event transplant rejection is noted.

In an embodiment, if the transplant recipient is Grade 0, 1R without hemodynamic compromise: no treatment is required and consideration may be given to weaning steroids.

If the patient presents with Grade 2R cellular rejection without hemodynamic compromise, the following treatment regimen is followed:

Optimize maintenance immunosuppression.

Administer methylprednisolone 15 mg/kg/day IV×3 days (maximum 1000 mg), can divide into every 12 hr dosing or give once every 24 hr.

Repeat biopsy in 1 to 2 weeks, for refractory cellular rejection repeat methylprednisolone and optionally Thymoglobulin®.

If rejection resolved then repeat biopsy 1 month later (6 weeks post-rejection) and resume previously defined biopsy protocol if rejection was successfully treated.

For refractory cellular rejection repeat methylprednisolone and consider thymoglobulin.

If the patient presents with Grade 2R cellular rejection without hemodynamic compromise or higher grade rejection.

Optimize immunosuppression with higher levels (10-15).

Administer methylprednisolone 15 mg/kg/day IV×3 days (maximum 1000 mg).

Administer Thymoglobulin®.

Perform plasmapheresis if evidence of or concern for antibody mediated rejection.

If the patient presents with antibody-mediated rejection with or without hemodynamic compromise:

Administer methylprednisolone 15 mg/kg/day IV×3 days (maximum 1000 mg).

Perform plasmapheresis×5 runs (daily or every other day).

Administer IVIG 1-2 gm/kg IV monthly×6 months.

Evidence of graft dysfunction or hemodynamic compromise warrants a biopsy (when patient is stabilized) for cellular rejection and antibody-mediated rejection, including C4d staining. Start methylprednisolone (SoluMedrol) while awaiting biopsy results, consider starting thymoglobulin and plasmapheresis.

Treat grade 3R biopsies or hemodynamic compromise as a high-grade rejection episode.

Methylprednisolone (SoluMedrol) 15 mg/kg/day IV×3 days (maximum 1000 mg). Consider inotrope therapy, thymoglobulin; and/or plasmapheresis.

Antibody-mediated rejection with or without hemodynamic compromise. Diagnosis: identification of C4d deposition in myocardial tissue with presence of donor-specific antibodies in peripheral serum sample. Consider steroids, ATG pheresis for AMR.

Kidney and Pancreas Immunosuppression Management

Exemplary induction immunosuppressive regimens and maintenance immunosuppressive regimens for kidney and pancreas transplantation procedures are presented below. In an embodiment, transplant recipients receive belatacept as maintenance therapy as part of the second immunosuppressive regimen. This protocol is typically employed when the recipient is Epstein Barr Virus (EBV) Ig+, exhibits no DSA (donor specific alloantibody); irrespective of absolute or calculated panel reactive antibodies (PRA), the transplant involves a negative cross-match and the recipient is <70 years old with a BMI of ≤35. Further considerations include the recipient's ability to tolerate induction (if they would not otherwise receive thymoglobulin). The recipient should have no history of idiopathic focal segmental glomerulosclerosis (FSGS) and no previous non-kidney solid organ transplant. The protocol is for kidney transplants only.

In an embodiment, the induction immunosuppressive regimen comprises administration of methylprednisolone 500 mg intravenously intra-operatively. Alemtuzumab 30 mg is administered by intravenous infusion over a period of three hours (2 hours post administration of steroids). Belatacept 10 mg/kg is administered (TBW) (rounded to the nearest 12.5 mg) after the prior drug administrations.

In an embodiment, the maintenance immunosuppressive regimen comprises belatacept 10 mg/kg TBW on POD 4 and end of week 2, 4, 8, and 12; then 5 mg/kg every month (rounded to nearest 12.5 mg). Sirolimus is administered 2 mg daily with first trough level taken after 2 weeks (goal 8-10 ng/ml). No steroid maintenance therapy is normally required.

In an embodiment in low risk renal transplants where the recipient is not a candidate for belatacept, the induction immunosuppressive regimen may comprise no induction immunosuppressive regimen, i.e., the induction immunosuppressive regimen is optional. The maintenance immunosuppressive regimen may comprise mycophenolic acid 1000 mg administered every 12 hours and tacrolimus administered 0.1 mg/kg/day with a maximum of 5 mg every 12 hours.

In an embodiment when the recipient is high risk and ATG contraindicated, frail, an age >70 and who has evidence of recent infection and recent cancer activity, the induction immunosuppressive agent may comprise basiliximab 20 mg to start in the operating room and post-operative day (POD) 4. The maintenance immunosuppressive regimen may comprise mycophenolic acid 1000 mg every 12 hours and tacrolimus 0.1 mg/kg/day with a maximum of 5 mg every 12 hours with tapering dosages of steroids.

In an embodiment involving high risk renal transplants or kidney and pancreas transplants the following parameters are considered. Recipients having a historic peak PRA>30, a historic donor specific antibody (DSA, irrespective of absolute or calculated PRA), 2nd transplant with early graft loss due to presumed immunological reason, 3rd or greater transplant, Pediatric en bloc (adult) recipients, kidney/pancreas, Pancreas alone and if high risk for DGF or high risk biopsy. In such a transplant, the induction immunosuppressive regimen (induction therapy) may comprise Thymoglobulin 1.5 mg/kg IBW (rounded to nearest 25 mg)×4 doses started in the operating room.

In an embodiment, where the recipient has zero PRA, no autoimmune diseases and a high BMI, the induction immunosuppressive regimen may comprise thymoglobulin 1.5 mg/kg IBW (rounded to nearest 25 mg)×4 doses started in the operating room. The second immunosuppressive regimen (maintenance therapy) may comprise tapering dosages of steroids, such as 500 mg in the OR, 240 mg POD 1, 125 mg POD 2, 125 mg POD 3, 90 mg POD 4, with mycophenolic acid 1000 mg every 12 hours starting POD 4 and tacrolimus 0.1 mg/kg/day with a maximum of 5 mg every 12 hours.

In an embodiment where a pancreas transplant is performed after a kidney transplant, the induction immunosuppressive regimen may comprise thymoglobulin 1.5 mg/kg IBW (rounded to nearest 25 mg)×4 doses started in the operating room. The second immunosuppressive regiment may comprise a steroid taper to lowest of 5 mg daily, mycophenolic acid 1000 mg administered every 12 hours starting POD 4 and tacrolimus administered 0.8 mg/kg/day with a maximum of 4 mg every 12 hours.

For all immunosuppressive regimens involving administration of mycophenolic acid, the initial dose may be chosen based on an assessment of patient and transplant factors.

Adult Heart Transplant Immunosuppression Management

In an embodiment, induction immunosuppressive regimens are normally administered. Exceptions may occasionally be made when the risks of induction therapy are thought to outweigh the benefits of such therapy (i.e., the induction immunosuppressive regimen is optional).

In an embodiment, when an induction immunosuppressive regimen is administered, the regimen may comprise Simulect® (basiliximab): 20 mg IV given in the OR after reperfusion (cross-clamp removal) and repeated on post-operative day 4. In patients receiving induction immunosuppressive therapy, the calcineurin inhibitor (CNI) administered in the second immunosuppressive regiment should be initiated at 48 hours post-operatively, but may be delayed further depending upon the patient's renal condition. Steroids may be administered in the peri-operative period, typically methylprednisolone 500 mg intravenously at induction of general anesthesia and 500 mg IV before reperfusion (cross-clamp removal).

In an embodiment, the maintenance immunosuppressive regimen (post-operative maintenance immunosuppressive treatment), the regimen may comprise steroids, for example, methylprednisolone 125 mg IV q8 hours×3 doses (Start 8 hours after reperfusion) followed by prednisone: 0.5 mg/kg twice daily beginning post-operative day 2; decrease dose by 5 mg twice daily every 2 days to 10 mg twice daily (or 20 mg daily) and maintain this dose to 30 days post-transplant. The second immunosuppressive regimen may also comprise calcineurin inhibitors (CNI), for example, Tacrolimus/FK506/Prograf® (Preferred Agent): 1 mg by mouth every 12 hours. The dose is titrated to trough goal level of 10-15 ng/ml. Typical dose adjustments are made after 5 doses of the calcineurin inhibitor to establish steady state. Daily levels of the CNI are monitored initially to evaluate for CNI toxicity.

In an alternative embodiment cyclosporine/CyA/Neoral® is administered at a dosage of 100 mg (1.5 to 5 mg/kg) by mouth every 12 hours. The dose is typically titrated to a trough goal level of 33 ng/ml. The maintenance immunosuppressive regimen may also comprise an antiproliferative agent such as mycophenolate mofetil (Cellcept®) 1,000 to 1,500 mg orally, with the dosage adjusted to maintain a WBC count >3,000. In the alternative, the antiproliferative agent may be mycophenolate (Myfortic®) 360 mg-720 mg administered orally twice a day, with the dosage adjusted to maintain a WBC count >3,000. In another embodiment, the antiproliferative agent is azathioprine (Imuran®) administered orally in a dosage of 2 mg/kg daily, with the dosage adjusted to maintain a WBC count >3,000.

In an embodiment, the maintenance immunosuppressive regimen may comprise sirolimus (Rapammune®) (TOR-I) administered orally at a dosage of 2 mg daily. The dosage is typically titrated to maintain a trough of 4-12 µg/ml.

In an embodiment, the maintenance immunosuppressive regimen may comprise a tapering dosage of steroids, for example, Month 1, decrease dose to 15.0 mg PO daily; Month 2, decrease dose to 12.5 mg PO daily; Month 3, decrease dose to 10.0 mg PO daily; Month 4, decrease dose to 7.5 mg PO daily; Month 5, decrease dose to 5.0 mg PO daily; Month 6, decrease dose to 2.5 mg PO daily. The steroid taper should be reevaluated following ≥ISHLT Grade 1R with evidence of myocyte necrosis. The taper may be resumed after improvement in histological rejection guidelines.

In an embodiment, the maintenance immunosuppressive regimen may comprise the following additional/adjunctive agents: methotrexate (MTX) administered 2.5 to 5 mg twice weekly for cell-mediated rejection. MTX should be considered for 3 or more consecutive biopsies with ≥grade 1R/2 or 2 consecutive biopsies with grade 2R/3A.

Adult Liver and Intestine Immunosuppressive Management

In an embodiment, a liver transplant with no renal dysfunction may be performed without any induction immunosuppressive regimen, i.e. such induction immunosuppressive regimen is optional. The maintenance immunosuppressive regimen may comprise, administration of mycophenolate 1 g every 12 hours and tacrolimus 2-3 mg every 12 hours along with a tapering dosage of steroids. A typical tapering dosage of steroids is: methylprednisolone 500 mg IV intra-operatively; methylprednisolone 250 mg IV 6 hours post-operatively once; methylprednisolone 180 mg IV once POD 1; methylprednisolone 90 mg IV once POD 2; methylprednisolone 60 mg IV once POD 3; methylprednisolone 30 mg IV once POD 4; prednisone 20 mg PO daily POD 5-14; decrease by 2.5 mg every 2 weeks. In an embodiment, the tapering dosage of prednisolone may be administered as 20 mg daily for the first 2 weeks; 17.5 mg daily for weeks 2-4; 15 m daily for weeks 4-6, 12.5 mg daily for weeks 6-8; 10 mg daily for weeks 8-10; 7.5 mg daily for weeks 10-12; 5 mg daily for weeks 12-14; 2.5 mg daily for weeks 14-16. Stop at 16 weeks. In certain circumstances the prednisolone is weaned to 5 mg daily and held for one year.

In an embodiment, a renal sparing liver transplant is performed where there is preoperative dysfunction requiring HD or CVVHD/F. In another embodiment, a renal sparing liver transplant is performed where there is post-operative renal dysfunction with serum creatinine levels of >2 mg/dL on POD 0-1.

In an embodiment, the induction immunosuppressive regimen comprises thymoglobulin 1.5 mg/kg (rounded to the nearest 25 mg) every 48 hours for 4 doses. In an embodiment, dosage reductions are made for pancytopenia or neutropenia. If WBC count is 2-3 or platelets are 30-50, give ½ dosage. If WBC is <2 or platelets are <30, hold the dosage.

In an embodiment, when premedication is indicated, the premedication may be administered 30-60 minutes prior to ATG infusion, acetaminophen 650 mg VT or orally, diphenhydramine 25-50 mg; and methylprednisolone 40 mg IV (or may use taper described above).

In an embodiment, the transplant is an intestine or multivisceral transplant such as a liver, intestine, pancreas transplant where the recipient is at high immunologic risk (PRA>0, prior pregnancy or transplant of isolated intestine, or where there is a low immunologic risk but a high risk of infection, the induction immunosuppressive regimen may comprise premedication, as described above, and may also comprise thymoglobulin 1.5 mg/kg (rounded to the nearest 25 mg every 24 hours for a total of 6 mg/kg, and basiliximab 20 mg in POD 0 and 4. The maintenance immunosuppressive regimen may comprise a tapering dosage of steroids as described above and mycophenolate 1 g every 12 hours and tacrolimus 1 mg SL every 12 hours (goal 12-16 mg/ml).

In certain embodiments, the tacrolimus is administered at a dosage to achieve target levels of 5-8 (liver) or 12-17 (intestine, liver-intestine) while patient is on mycophenolate mofetil (Cellcept). The target may be altered if the patient is participating in a drug study trial, has rejection, renal compromise, or for advancing age.

In certain embodiments where mycophenolate mofetil (MMF, Cellcept) is administered the standard dosage for adults is 1,000 mg every 12 hours. Dosage reductions may be made in patients with pancytopenia or neutropenia in accordance with the following: WBC 2-3 or platelets 30-50: consider giving ½ dose; for WBC<2 or platelets <30; consider holding dose.

In certain embodiments involving treatment of acute Liver allograft rejections, the following treatment may be administered: methylprednisolone 500 mg IV daily for 3 doses. If liver function tests are not improving, an additional two doses may be given (total of 5 doses of 500 mg IV daily), with a repeat lover biopsy performed on the eve of POD 3 or the morning of POD 4.

In certain embodiments, patients treated with SoluMedrol® or Thymoglobulin® whose CMV IgG was previously negative, should have a CMV IgG rechecked at the beginning of treatment.

Immunosuppressive Management in Lung Transplants

In certain embodiments, immunosuppressive management in lung implants follows the following induction and maintenance immunosuppressive regimens. Induction immunosuppressive regimens may follow an induction immunosuppressive regimen described previously. Maintenance immunosuppressive regimens may comprise the following:

Calcineurin Inhibitors: tacrolimus every 12 hours with dosing adjusted to maintain trough tacrolimus levels. See Table 5 below.

TABLE 5

Tacrolimus Trough Levels

| Time since transplant | Clinical factors | Target trough |
|---|---|---|
| 1st year | Young, high rejection risk, normal renal function | 12-15 ng/ml |
| 1st year | ≥65 yrs and/or CKD | 8-12 ng/ml |
| 1-3 years | Young, recurrent rejection, normal renal function | 10-14 ng/ml |
| 1-3 years | Stage 2-3 CKD | 8-10 ng/ml |
| 1-3 years | Stage 3-4 CKD | 6-8 ng/ml |
| >3 years | Stage 2-3 CKD | 6-8 ng/ml |
| >3 years | Stage 4 CKD | 6 ng/ml |
| Post Campath | | 8 ng/ml or lower, depending on renal function. |

Cyclosporine administered every 12 hours with dosing adjusted to maintain trough CyA levels according to Table 6 below.

TABLE 6

Cyclosporine Trough Levels

| Time since transplant | Clinical factors | Target trough |
|---|---|---|
| 1st year | Young, high rejection risk, normal renal function | 250-300 ng/ml |
| 1st year | ≥65 yrs and/or CKD | 150-200 ng/ml |
| 1-3 years | Young, recurrent rejection, normal renal function | 250-300 ng/ml |
| 1-3 years | Stage 2-3 CKD | 150-200 ng/ml |
| 1-3 years | Stage 3-4 CKD | 100-150 ng/ml |
| >3 years | Stage 2-3 CKD | 100-150 ng/ml |
| >3 years | Stage 4 CKD | 75-125 ng/ml |
| Post Campath | | 150 ng/ml or lower, depending on renal function. |

Steroid tapering dosage of 0-3 months post-transplant, 20 mg administered orally on a daily basis; 3-6 months post-transplant, 15 mg administered orally on a daily basis; 6-9 months post-transplant, 10 mg administered orally on a daily basis; and >9 months post-transplant, 5 mg administered orally on a daily basis.

Azathioprine 2 mg/kg may be administered orally on a daily basis. Important to ensure normal TMPT enzyme levels prior to start and to follow LFTs/CBC. Dosage adjustments may be considered if leukopenia is observed.

Mycophenolate mofetil (Cellcept®) may be administered at a usual dosage of 1,000 mg twice daily. The usual dosage for heart and lung transplants is 1,500 mg daily administered orally. CBC should be followed and dosage adjustments should be considered if leukopenia is observed.

Sirolimus is generally contraindicated in the first 3 months following transplantation due to concerns for anastomotic dehiscence. If administered, sirolimus is typically administered 1 mg daily by oral administration, which is adjusted based on trough levels. For example, administered as a $3^{rd}$ agent or for CNI sparing, a target trough is 4-8 ng/ml; and as a CNI alternative, the trough level is 10-15 ng/ml.

EXAMPLES

Example 1: Intra-Thymus Variability Study

Intra-thymus variability was studied to determine whether histology testing results from one part of a thymus could be considered representative of histology testing results in any other part of the same thymus. The results of this test were used to determine how many samples should be tested during both routine release testing and for process validation testing.

Histology acceptance criteria were established, as noted previously, including the assessment of: areas positive for keratin AE1/AE3 scattered throughout tissue on days 5-9; at least 1 Hassall body identified; CK14 staining scattered throughout tissue; and intact nuclei observed.

Figure 5A:
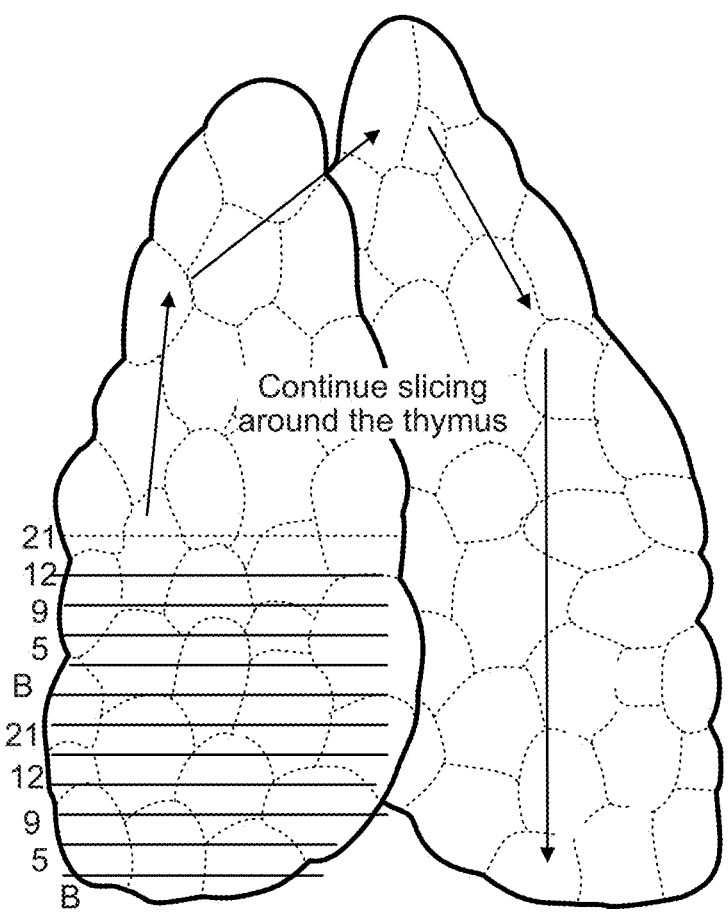
FIG. 5A shows a schematic showing the slicing of thymus tissue for characterization testing, as discussed in section [00766].
Figure 5B:
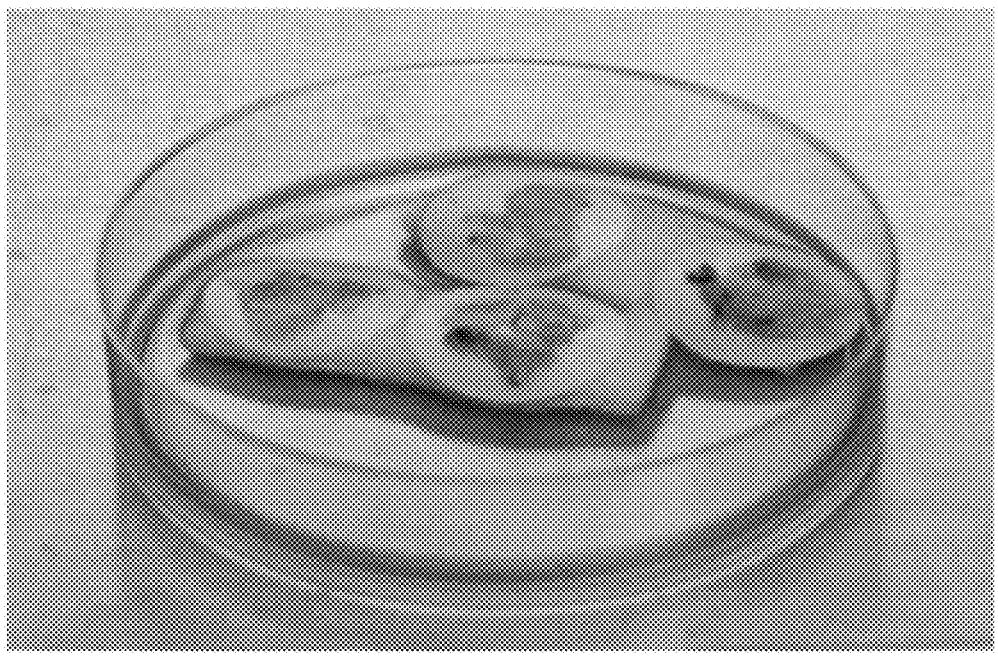
FIG. 5B is a figure showing slices of thymus tissue on cellulose filters on surgical sponges in a tissue culture dish as is used for culture of the thymus.

For this study, three thymuses were sliced in a directional manner and the location of the slices within each thymus was tracked. Slices were cultured in 6-well plates to allow tracking of each slice. Slicing was conducted as shown in FIG. 5A.

For each thymus in the study, slices were dedicated for analysis at each of the following time points, baseline (day 0), day 5, day 9, day 12 and day 21.

Between 5-11 slices were cultured at each time point for each thymus. Slices were cultured per the methods described above with daily media changes. Slices were submitted for H&E staining in the pathology lab and analyzed for identity, potency and viability. All slices in this study met the release acceptance criteria for histology testing as designated above, namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each H&E and AE1/AE3 slide was made by the pathologist. Images of some of these slides for cultured thymus tissue lot MFG-056 are shown in FIGS. 6A-H. The following observations were noted.

All slices derived from the same donor thymus met the acceptance criteria at each time point. In different slices, areas of cortex resemble each other and areas of medulla resemble each other. However, variations were observed in the relative proportion of cortex and medulla between slices.

The differences observed between different slices derived from the same thymus as a function of culture time were primarily related to the amount of necrosis, primarily of thymocytes (which increased as culture time increased) and the numbers of residual thymocytes (which decreased as culture time increased).

Based on these observations, any one slice from a thymus was representative of the entire thymus. In addition, the histologic appearance of the tissue slices at day 5 reflects what is observed at each of the later time points (day 9, 12 and 21).

Example 2: Whole Thymus Time-Course Study

Figure 7A:
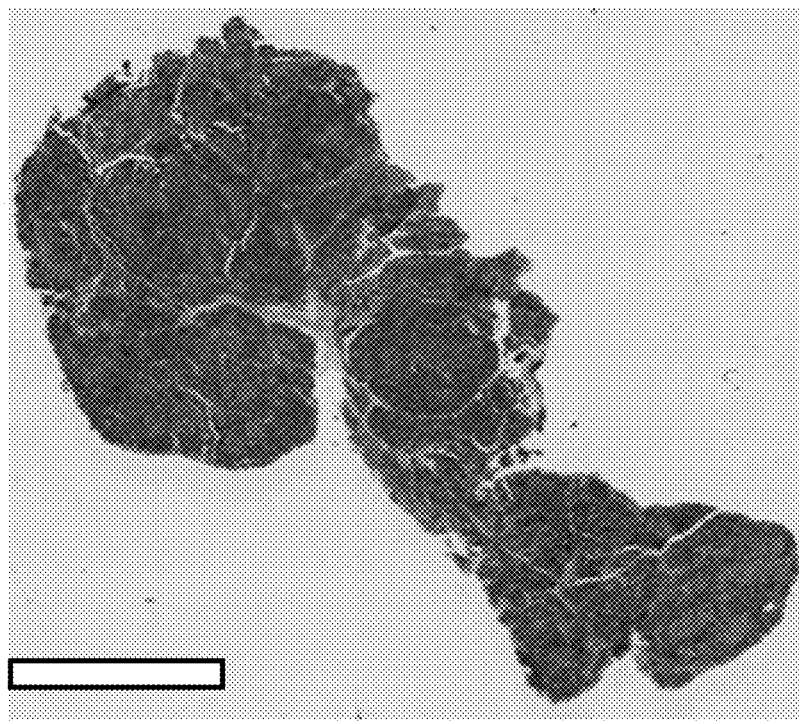
FIGS. 7A and 7B depict the histology of thymus tissue slices on day 0 of the time course in a scale of 5 mm (FIG. 9A) and 100 µm (FIG. 7B), respectively. This shows the thymus and thymocytes at low power (bar 5 mm) and high power (bar 100 um) on day 0. This is normal thymus. At this time the cortex and medulla both have large numbers of thymocytes with dark blue nuclei contributing to the overall dark blue appearance of the tissue. Photo by Laura P. Hale, MD, PhD, Department of Pathology, Duke University.
Figure 7B:
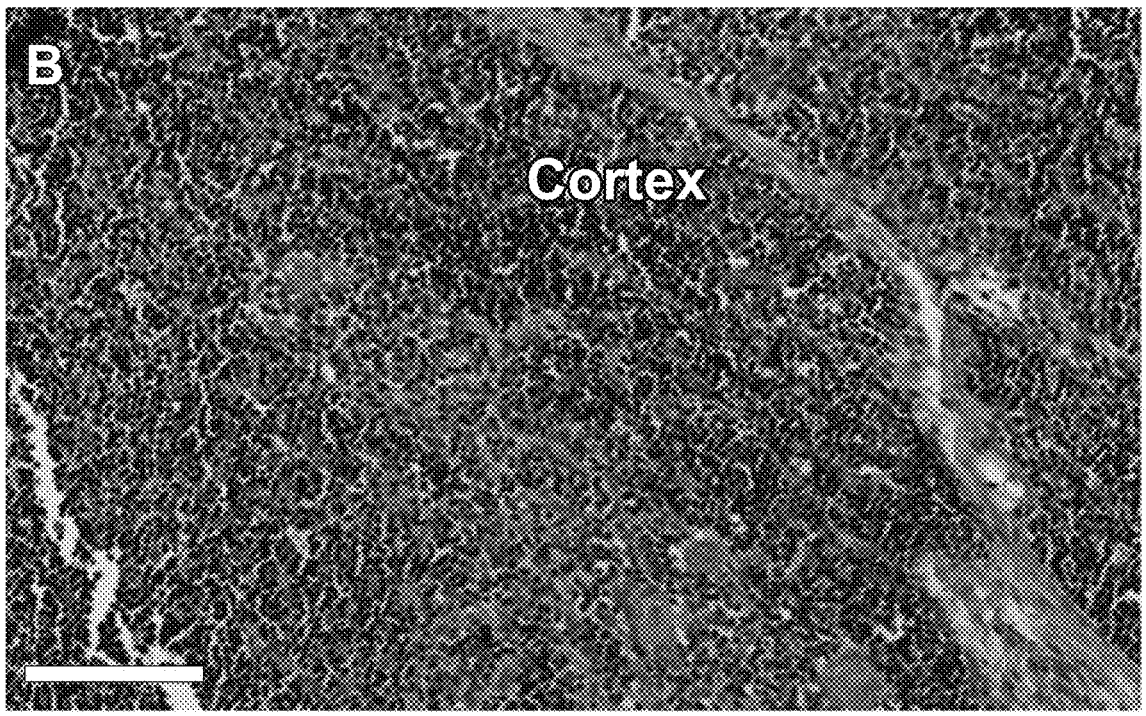
Figure 8A:
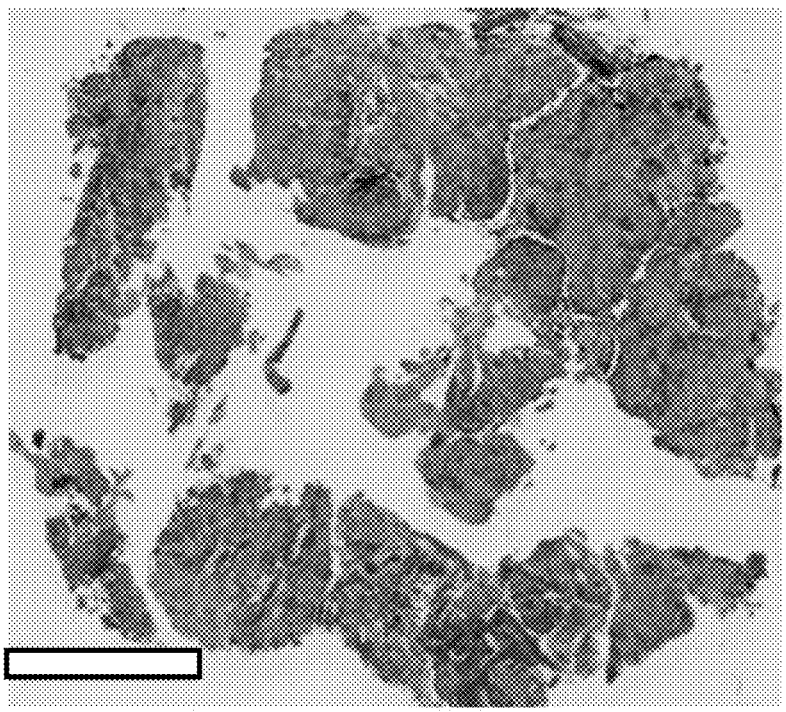
FIGS. 8A and 8B are images from H&E stained slide that depict the histology of thymus tissue slices on day 5 of the time course in a scale of 5 mm (FIG. 8A) and 100 µm (FIG. 8B), respectively. Progression of depletion of the thymocytes results in a more eosinophil (pink) appearance of the tissue. Photo by Laura P. Hale, MD, PhD, Department of Pathology, Duke University.
Figure 8B:
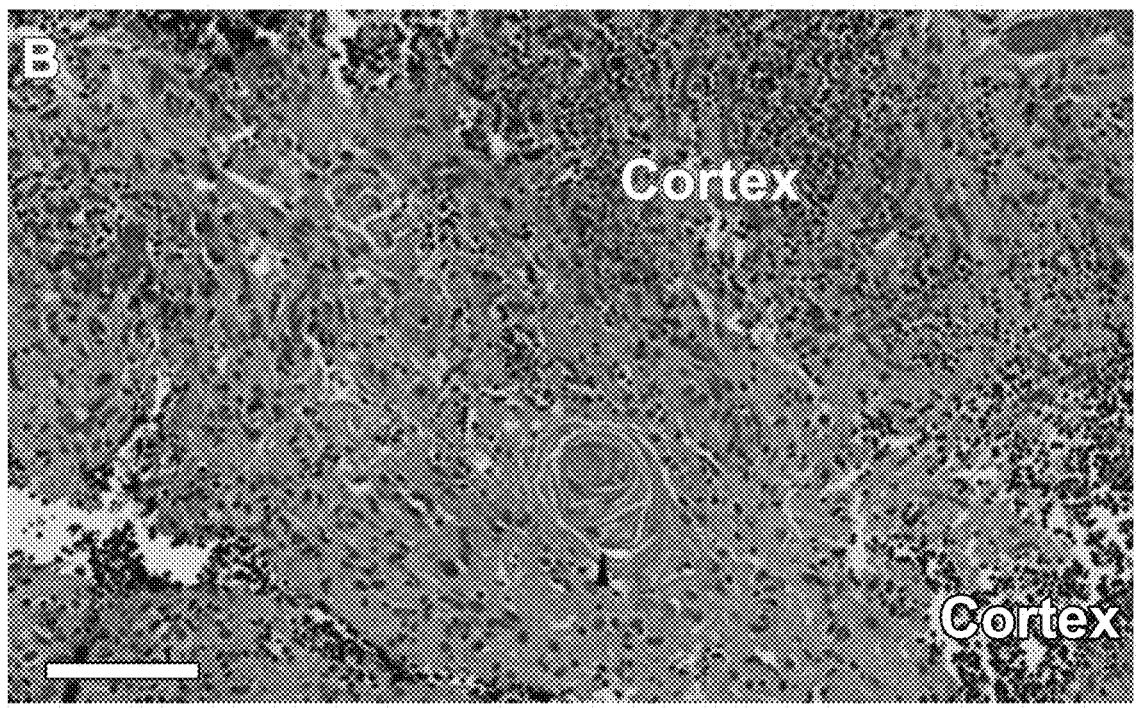
Figure 9A:
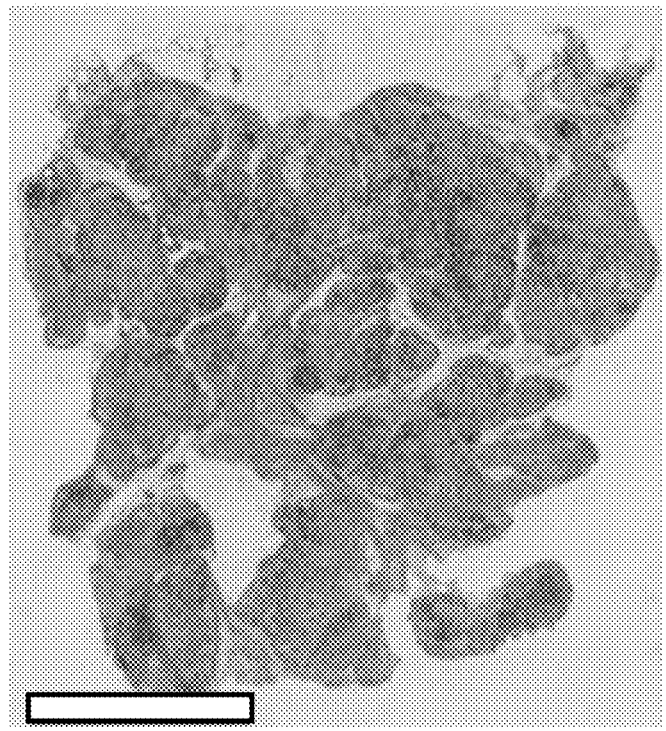
FIG. 9A and FIG. 9B depict H&E staining of the thymus tissue slices on day 12 of the time course in a scale of 5 mm (FIG. 9A) and 100 µm (FIG. 9B), respectively. We see progressive depletion of thymocytes. The higher magnification shows numerous eosinophilic cell bodies lacking nuclei which are diagnostic of necrotic cells that have undergone karyolysis (dissolution of the nuclei). This degree of necrosis is expected at this time in culture. Photo by Laura P. Hale, MD, PhD, Department of Pathology, Duke University.
Figure 9B:
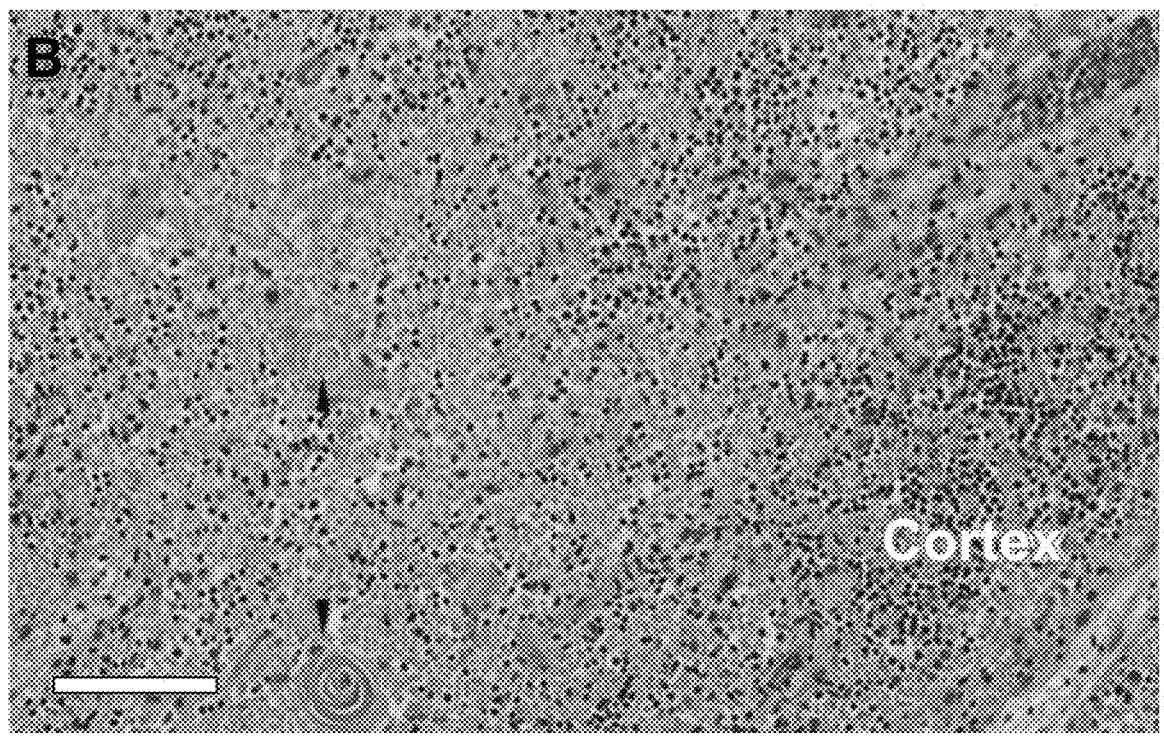

For this study, five thymuses were sliced and cultured per SOP. On the day of slicing, the first, middle and last slices were prepared for immunohistochemistry. The remainder of each thymus was sliced and cultured in 6-well plates. Each thymus was designated for one of the following time points:

baseline (day 0), day 5, day 9, day 12 and day 21. See FIG. 7 for a day 0 thymus slice, FIG. 8 for a day 5 slice, FIG. 9 for a day 12 slice, and FIG. 10 for a day 21 slice.

The total number of slices from each thymus ranged from 21 to 62 slices. Slices were cultured per the procedures outlined above with daily media changes. Slices were submitted for H&E staining in the pathology lab and analyzed for identity, potency and viability. All slices in this study met the release acceptance criteria for histology testing, namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each H&E and AE1/AE3 slide was made by the pathologist. The following observations were noted.

All slices derived from the same donor thymus and tested at the same time point similarly met the acceptance criteria for that time point with variations in the relative amounts of cortex and medulla, residual thymocytes and/or necrosis, as described above.

Differences noted were the relative size, shape, relative content of thymus cortex versus medulla, amount of necrosis, condensation of the thymus epithelium and numbers of residual thymocytes.

In addition, lots from different donors tested at different time points were also qualitatively similar to each other. Differences observed were related to the amount of necrosis (which increased as culture time increased) and numbers of residual thymocytes (which decreased as culture time increased).

Histologic examination of any one slice resulted in the same conclusion regarding acceptability of the entire lot. Based on these observations, the relevant characteristics of any one slice from a thymus reflect those of the entire thymus. In addition, the histologic appearance of the tissue slices at day 5 reflects what is observed at each of the later time points (day 9, 12 and 21), although more necrosis is observed at later time points. FIG. 11 is a good example showing the similarity of the epithelial network as assessed by antibody AE1/AE3 from day 0 to day 21.

Example 3: Thymus Tissue Forced Degradation Study

In this study, thymus tissue slices were treated to generate tissue slices that were considered degraded or non-viable. Three thymuses were used for these experiments. Control samples were taken from each thymus. The treatment conditions presented in Table 7 were tested.

TABLE 7

Forced Degradation Treatment Conditions

| Condition | Duration of Treatment |
| --- | --- |
| Control | No treatment |
| Heat Shock, 55° C. | 4 hours |
| Freeze/thaw, −20° C./ambient | 4 hours |
| Room Temperature, 20-24° C. (Culture in BSC) | 24 hours |
| Dehydration (Culture in absence of media) | 24 hours |
| | 48 hours |
| Nutritional Depletion, (Culture in Normal Saline) | 24 hours |
| | 48 hours |
| Osmolarity Change, (Culture in 10X PBS) | 24 hours |
| DMSO Exposure, (Culture in 1% DMSO in TOM) | 24 hours |

Heat shock was accomplished by placing the 10 cm culture dish containing the slices into a Ziploc bag, and placing into a 55° C. water bath. The plate rested on a support and was not submerged. Freeze/thaw was accomplished by placing the 10 cm culture dish into a −20° C. freezer for 4 hours followed by thawing at ambient.

Samples were tested for histology on days 5 and 9 in culture. Some samples were also tested on day 21. All slices in this study met the release acceptance criteria for histology testing namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each slide was made by the pathologist. The following observations were noted.

Samples exposed to freeze/thaw or to 10×PBS showed the most necrosis but some cells still appeared intact and met the histologic criteria for viability. See FIG. 12 for an example of exposure to 10×PBS.

Slices that were held at room temperature, dehydrated, incubated in normal saline or 1% DMSO or underwent heat shock showed a lesser degree of histologic changes.

For control samples, the following observations were noted by the pathologist.

Thymocytes are progressively lost as thymus tissue is cultured. However, dead cells may persist in cultured thymus long-term due to inability to recruit phagocytes to clear them. The nuclei of cells undergoing apoptotic cell death initially condense and stain more darkly (blue) with hematoxylin dye. As these cells deplete their energy but are not phagocytosed, they lose their membrane integrity and become necrotic. Karyolysis (dissolution of nuclei in necrotic cells) typically occurs within 2-3 days in vivo, but appears to occur more slowly during thymus culture. Thus, it is not unusual to see large eosinophilic (pink) expanses of necrotic cell debris where thymocyte nuclei have undergone karyolysis. Some dead thymocytes retain their nuclei, which have ragged edges and altered staining characteristics compared to those of viable cells.

As thymocytes are depleted from the tissue, the thymic epithelial cells become more visible. The three-dimensional thymic epithelial (TE) network is normally demonstrated in sections via a light and lacy arrangement of connected epithelial cells and/or (seemingly) scattered TE cells whose connections are not evident in the section being examined. As thymocytes are lost during culture, the three-dimensional network contracts. This results in condensation of the residual epithelium, such that the subcapsular cortical epithelial layer becomes thicker and medullary TE cells become more tightly packed. The nuclei of viable TE cells are typically oval, larger than those of thymocytes, and have a sharply defined nuclear membrane outlined by the hematoxylin (blue) stain, as well as one or more nucleoli. These TE nuclei typically look "open", meaning they do not stain darkly with hematoxylin. This fits with an interpretation that they are alive and metabolically active, since active chromatin ("euchromatin") cannot bind the hematoxylin dye. The presence of nucleoli, which are the sites of ribosome synthesis, in many TE cells further confirms that they are alive and metabolically active. The typical histologic appearance of control sections from days 5, 12 and 21 is shown FIGS. 8, 9 and 10, respectively.

For the treatment conditions including room temperature, dehydration, 1% DMSO and heat shock the pathologist indicated that the appearance of the slices did not differ significantly from those of the control. For the heat shocked sample, the pathologist noted that the heat treatment may have "fixed" the cells, by coagulating proteins that prevent further degradation. Heat treatment has been used as a fixative for tissues, including thymus.

FIGS. 12A and 12B depict the histology of thymus tissue slides after exposure to forced degradation conditions. FIG. 10 depicts the histologic appearance of control thymus tissue slices at day 21.

The general histologic appearance of the forced degradation tissue is similar at these time points, but with fewer residual thymocytes at day 21 (FIG. 12B). Representative Hassall bodies in medullary areas are indicated by arrow heads in FIG. 12B. Representative viable-appearing thymic epithelial cells are indicated by arrows in FIGS. 12A and 12B. The cortical area shown in FIG. 12B consists almost entirely of necrotic lymphocytes day 21. The bars at the lower left represent 100 μm.

Example 4: Thymus Tissue Drug Substance Batch Analysis

Batch analysis data for 10 lots of thymus tissue are shown in Table 8 below.

TABLE 8

| Lot | Year of Manufacture | Weight of incoming thymus (g) | Final dose given to patient (mm$^2$/m$^2$) | Appearance[b] | Histology[c] | Endotoxin | Sterility[d] | Mycoplasma[d] | Gram stain |
|---|---|---|---|---|---|---|---|---|---|
| MLM428 | 2016 | 4.97 | 8.034 | pass | pass | <0.500 EU/mL | No growth | No growth | Negative |
| MLM434 | 2016 | 7.48 | 9.110 | pass | pass | <0.500 EU/mL | No growth | No growth | Negative |
| MLM435 | 2016 | 27.74 | 7.104 | pass | pass | <0.500 EU/mL | No growth | No growth | Negative |
| MLM437 | 2016 | 8.99 | 9.884 | pass | pass | <0.500 EU/mL | No growth | No growth | Negative |
| MLM438 | 2017 | 10.68 | 19.134 | pass | pass | <0.500 EU/mL | No growth | No growth | Negative |
| MLM444 | 2017 | 10.51 | 19.402 | pass | pass | <0.500 EU/mL | No growth | No growth | Negative |
| MLM447 | 2017 | 5.95 | 8.459 | pass | pass | <0.500 EU/mL | No growth | No growth | Negative |
| MLM449 | 2017 | 7.81 | 9.260 | pass | pass | <0.500 EU/mL | No growth | No growth | Negative |
| MLM450 | 2017 | 12.99 | 17.128 | pass | pass | <0.500 EU/mL | No growth | No growth | Negative |
| MLM452 | 2017 | 7.61 | 16.802 | pass | pass | <0.500 EU/mL | No growth | No growth | Negative |

Testing performed on RVT-802[a]

Key:
(a) These lots were tested according to the specification that was in place at the time of manufacture. The drug substance testing results presented in this table also represents the final drug product testing results.
(b) The appearance specification was no evidence of tampering or damage to containers.
(c) The histology assay was used for both identity and potency. The histology specification (tested between days 5-9) was the following:
(d) Areas positive for keratin scattered throughout the tissue.
  i. At least 1 Hassall body identified
  ii. CK14 staining scattered throughout the tissue
  iii. Intact nuclei observed
  iv. Sterility and *mycoplasma* samples were collected on days 1, 7 and 14.

Data for 56 clinical thymuses, 8 thymuses used for intra-thymus variability, inter-thymus variability and time-course testing, and 3 thymuses that had undergone forced degradation were used to generate the current control library. The forced degradation samples in the library (negative controls) were the ones that had undergone degradation by exposure to freeze/thaw or to 10×PBS. The full data set resulted in 14 different clusters. All forced degradation samples clustered together and no clinical samples or characterization samples clustered with the forced degradation samples.

Example 5

Figure 20:
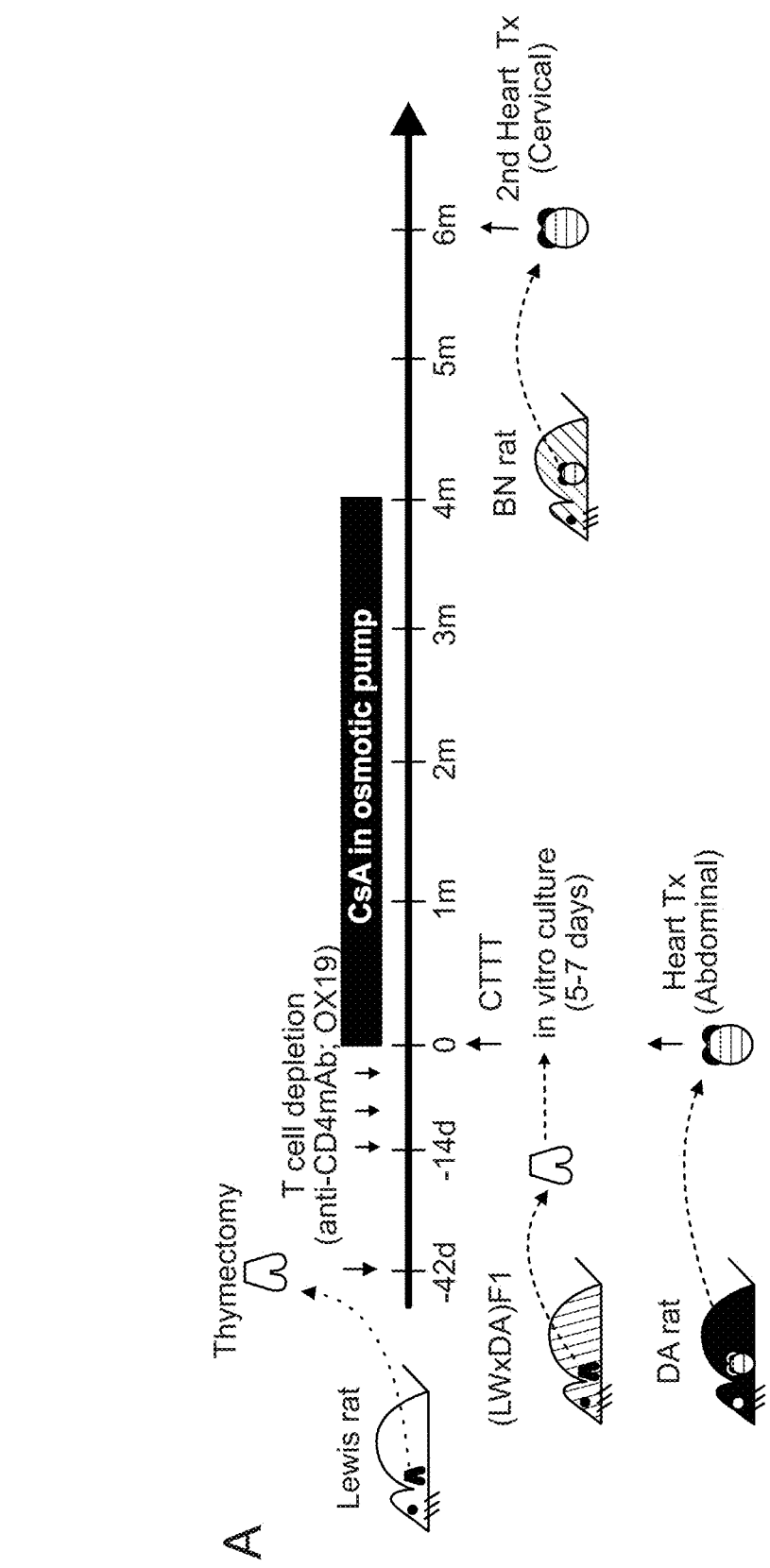
FIG. 20 is a schematic of the experimental design of the experiment reported in Example 5. This figure appears in Kwun, J. et al., JCI Insight (2020) June 4; 5(11).

The overall experimental design of Example 5 is depicted in FIG. 20. A schematic representation of surgical procedures and treatment schedule is presented. The figures and much of the text below come from a manuscript in preparation for submission for publication: Kwun, J. et al., JCI Insight. 2020 June 4; 5(11).

The schematic presentation of the experimental design depicts naïve T cell reconstitution, thymopoiesis, and donor-specific tolerance induced by the surgical insertion of CTT. All Lewis (LW) rats were thymectomized and T cell depleted via anti-CD5 mAb prior to heart transplantation and surgical insertion of a CTT. CTT from F1 (LW×DA) rats and hearts from DA rats were transplanted into thymectomized LW recipients. Cyclosporine (CsA) was given for four months after transplantation via osmotic pump. The third-party BN heart was transplanted into the neck 2 to 3 months after CsA discontinuation. Control rats experienced identical procedures except they did not receive a surgical insertion of CTT Example 5 demonstrates that CTT implanted in an immunoincompetent rat model, as described below, can induce tolerance to a transplanted solid organ. We performed haplomatched F1 (Lewis×Dark Agouti, LW×DA) a implant of CTT (cultured as described below) with vascularized mismatched DA heart transplants into Lewis rats.

Prior to the implant of CTT, recipients were thymectomized and T cell depleted.

Figure 23:
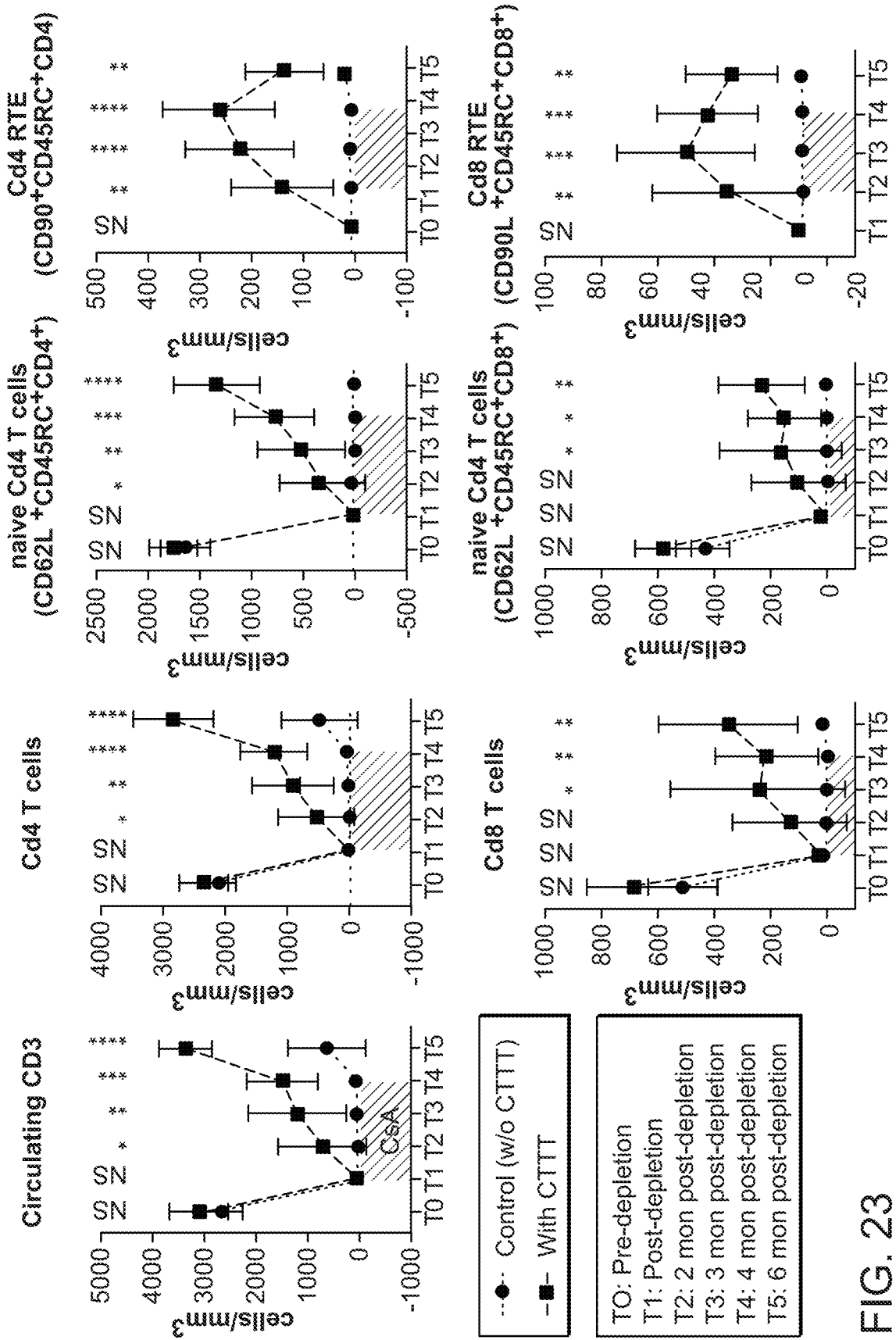
FIG. 23 shows plots of significantly increased numbers of circulating CD4 and CD8 T cells compared to control animals without implantation of CTT. It also shows significantly increased numbers of naïve CD4 and naïve CD8 T cells in the cultured thymus tissue implantation (CTT) group compared to the control group that did not receive CTT and significantly increased numbers of CD4 and CD8 recent thymus emigrants (RTE) in the cultured thymus tissue implantation (CTT) group compared to the control group that did not receive CTT. This figure appears in Kwun, J. et al., JCI Insight (2020) June 4; 5(11).
Figure 25:
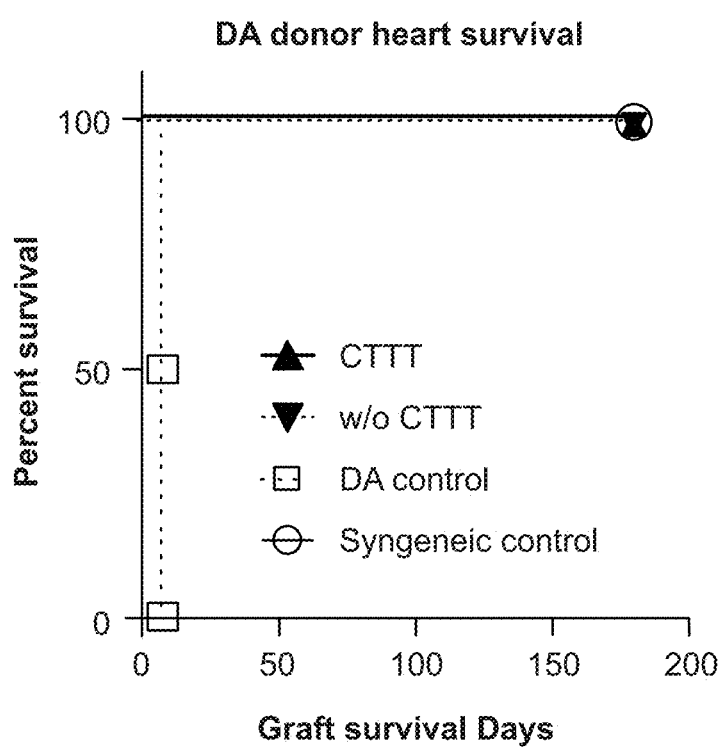
FIG. 25 shows survival percentages of LW rats after thymectomy and immunosuppression with DA heart transplants with CTT (solid triangles, blue line) and without CTT (upside down triangles, red lines) transplants (CTT). The LW rats with CTT are tolerant; the LW rats without CTT are immunodeficient and thus do not reject the DA heart. The control shows complete rejection of DA heart transplants in LW unmanipulated rats (open squares). LW control animals also did not reject an LW cardiac graft (open circle with horizontal line) (n=9). This figure appears in Kwun, J. et al., JCI Insight (2020) June 4; 5(11).

Cyclosporine was administered for 4 months starting on the day of heart transplantation. The control group did not receive a implant of CTT. Two months after discontinuation of immunosuppression, recipients implanted with CTT showed repopulation of naïve CD4 (CD62L+CD45RC+) T cells in the peripheral blood; control rats had none (FIG. 23). Even after developing recent thymic emigrant CD4 (CD90+CD45RC+) T cells, recipients transplanted with CTT did not reject the DA cardiac allografts (FIG. 25). Controls did not reject the DA grafts, due to lack of functional T cells (FIG. 25).

Figure 24A:
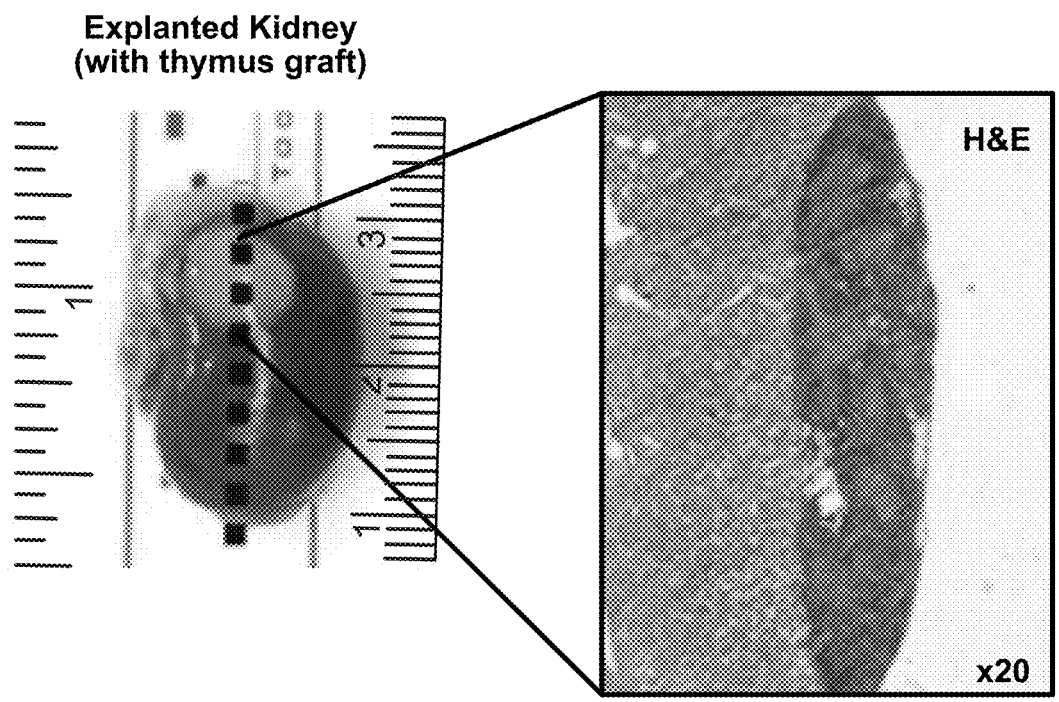
FIG. 24A shows immunohistologic analysis of implanted CTT explanted on day 180 showing normal thymus histology under the capsule of the kidney (right hand side of FIG. 24A).
Figure 27:
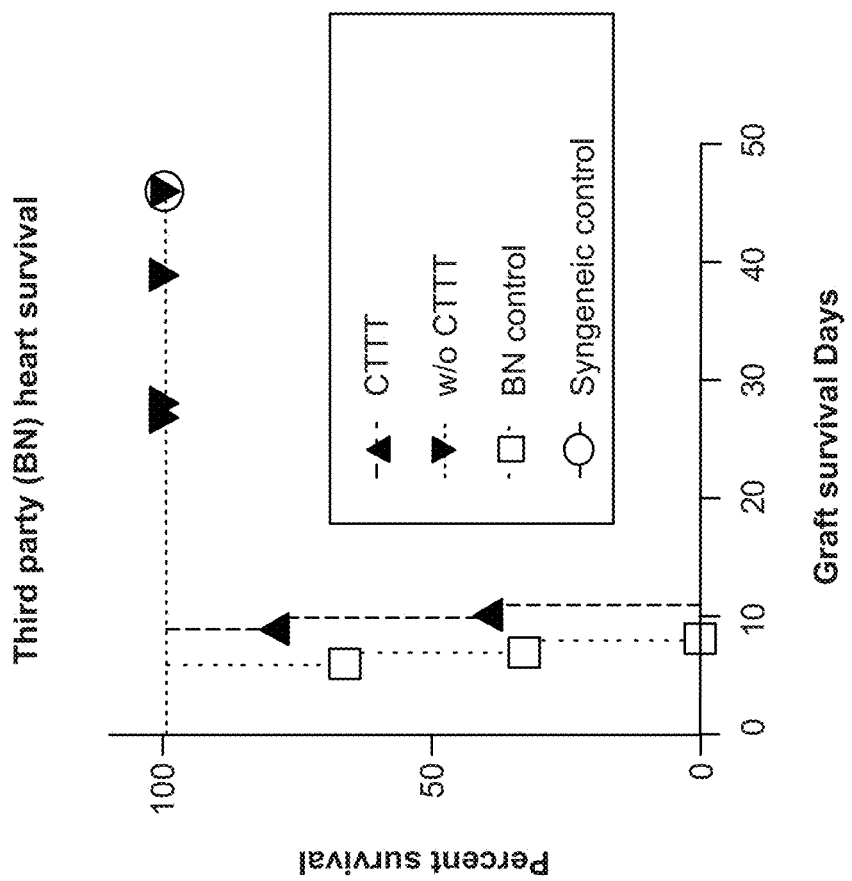
FIG. 27 is a plot of BN heart graft survival in the neck percentage animal survival vs. graft survival days in LW rats with CTT (that were immunocompetent and rejected the cervical allogeneic BN heart) and control LW animals without CTT (that were immunodeficient because of lack of thymus and could not reject the cervical BN heart) inserted vs. BN control (LW rat rejecting a cervical BN heart) and syngeneic controls (LW rats do not reject cervical LW hearts). This figure appears in Kwun, J. et al., JCI Insight (2020) June 4; 5(11).
Figure 32A:
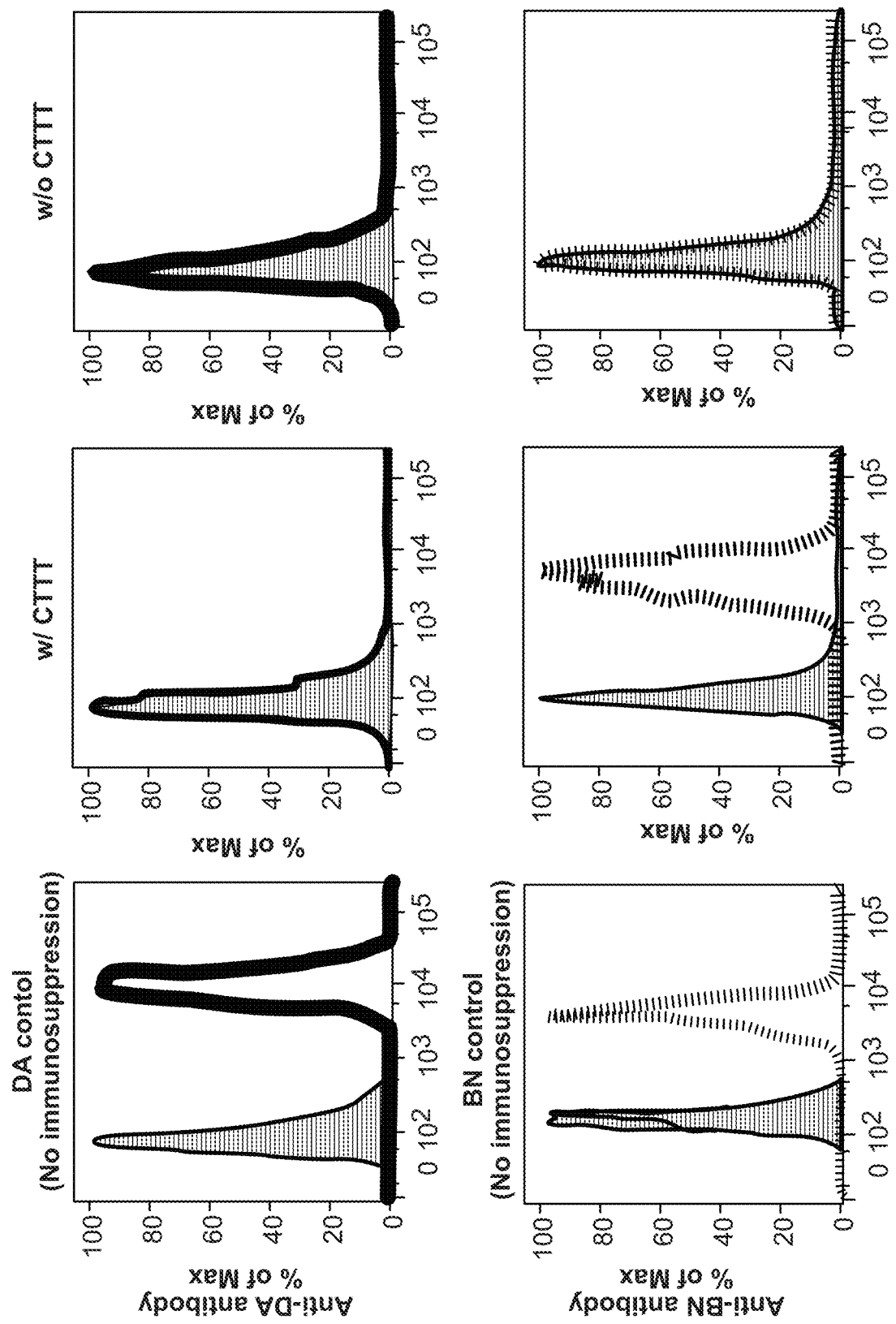
FIG. 32A to FIG. 32C: Humoral tolerance after CTT.

To confirm donor-specific unresponsiveness, an MHC-mismatched Brown Norway (BN) heart was transplanted on day 180 after the initial mismatched DA heart transplant. LW rats with F1 (LW×DA) transplants of CTT rapidly rejected the third-party BN heart (mean time of rejection, 10d; n=5) (FIG. 27). Controls did not reject the third-party heart (n=5). Recipients of CTT were able to produce antibody against third party BN donor but not against the DA thymus donor demonstrating humoral donor-specific tolerance (FIG. 32A). Immunohistochemistry of the transplanted CTTs at necropsy showed functional thymus tissue (FIG. 24). Taken together, F1(LW×DA) CTT given to Lewis rats resulted in specific tolerance to the allogeneic DA MHC expressed in the donor thymus with resulting long-term survival of DA heart transplants after withdrawal of all immunosuppression.

Materials and Methods.

Animal Models

Figure 17A:
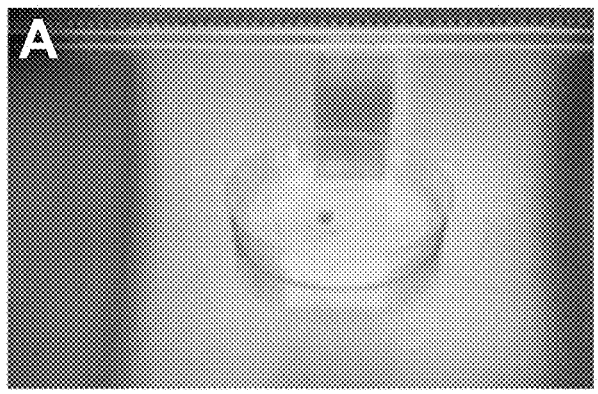
FIGS. 17A-D present photographs of the harvesting of thymus tissue from 3-day old F1 (LW×DA) rats that was cut into four pieces as described in Example 5 (FIG. 17A). A photograph of thymus pieces cultured on sterile mixed cellulose ester filters with thymus organ medium for 5-7 days in a 37° C. $CO_2$ incubator, as described in Example 5 (FIG. 17B).

In this Example 5, allogeneic CTT was harvested and cultured from 3-day old F1 (Lewis×Dark Agouti ray pups (FIGS. 17A and 17B), as described below, and then implanted into thymectomized Lewis (RT-1) recipient rats in a manner comparable to the treatment of human infants with athymic cDGA, as described previously. (Markert, M L, et al., 2008; Market, M L, et al., 2010).

Lewis (RT-1l) and BN (RT-1n) rats were purchased from Charles River. DA (RT-1av1) rats were purchased from Envigo. F1(LEW/DA; RT-1l/av1) were bred by protocol staff at the Duke Breeding Core Division of Laboratory Animal Resources facility. Lewis recipients received thymectomies as described in Rendell V R, Giamberardino C, Li J, Markert M L, & Brennan T V, 2014, "Complete thymectomy in adult rats with non-invasive endotracheal intubation." *J Vis Exp* (94).

Briefly, the submandibular glands and sternohyoid muscle were separated with blunt forceps to expose the tissue overlying the trachea. A 1- to 1.5-cm incision was made in the sternal manubrium. A 7 cm alms-type retractor was used to retract the manubrium and the two halves of the sternohyoid muscles to expose the thymus. The thymus was grasped with blunt forceps and extracted. The cut ends of the sternum were closed with a single 3 to 4-0 silk suture. Two drops of 2.5 mg/ml bupivacaine were applied on the incision and the outer layer of skin was closed with three or four 9-mm wound clips.

All thymectomized rats were maintained on a diet containing Septra (PMI Nutrition International, LLC). To induce T cell depletion in vivo, 1 mg anti-CD5 mAb (OX19; BioXCell, NH) was intraperitoneally administered on days 0, 5, and 10 after thymectomy and suppression with 0.25 mg/kg/d cyclosporine pump was given from day 0 (heart transplant & CTT time point) to 4 months with respect to heart transplantation. All rats were used and maintained in accordance with the guidelines and compliance of the Duke Institutional Animal Research Ethics Committee.

In Vitro Thymus Culture and CT

Figure 17B:
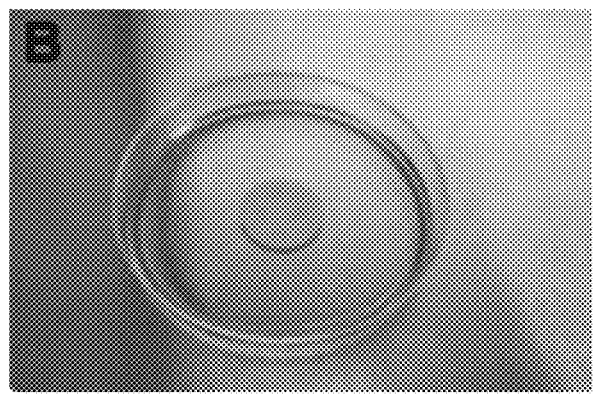
Figures 17C, 17D:
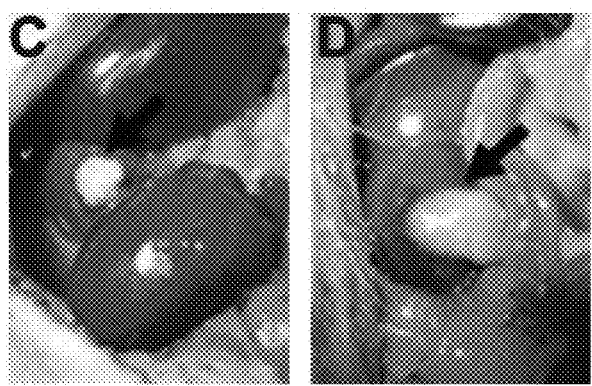

Thymuses from three day's old neonatal F1 (LEW/DA) rat pups were harvested sterilely, cut into four pieces along the longitude natural seam, and transferred onto sterile nitrocellulose filters (MF-Millipore, Millipore Sigma) in a tissue culture dish with TOM medium (FIG. 17B). Thymus tissue was cultured in a $CO_2$ incubator with 5% $CO_2$ at 37° C. for the desired length of time (5 to 7 days). The medium was changed daily. The thymus organ medium (TOM) was composed of HAMS F12 (Life Technologies) at 86.5%; Hepes (Life Technologies) at 25 mM; L-Glutamine (Life Technologies) at 2 mM; Fetal Bovine Serum (Life Technologies) at 10%; and Pen-strep (Life Technologies) at 1×. On the day of transplantation, the thymus pieces were rinsed with fresh medium and transplanted under the kidney capsule of a Lewis rat with one secure suture (10-0 monofilament). See FIG. 17C. All manipulations took place under sterile conditions in a biological safety cabinet.

Abdominal and Cervical Heart Transplantations

Full MHC mismatched DA (RT-1$^{av1}$) donor hearts were transplanted into thymectomized Lewis (RT-1$^l$) recipients. Abdominal heart transplantation was performed using a modified technique of the methods described by Schmid C, Binder J, Heemann U, & Tilney N L, 1994, "Successful heterotopic heart transplantation in rat," *Microsurgery* 15(4):279-281.

Briefly, the donor heart was transplanted into the abdominal cavity of the recipient after a short period of cold ischemia in Euro-Collins solution. The donor pulmonary artery and aorta were anastomosed to the recipient inferior vena cava and descending aorta with an end-side fashion as the inflow and outflow vessels for circulation, using running 9/0 non-absorbable monofilament sutures. Cyclosporine A (CsA) was given via the osmotic pump (Model 2ML4, Alzet). The recipients also received cyclosporine (CsA), approximately 2.5 mg/kg/day after thymus transplantation using osmotic pumps. CsA was discontinued 4 months after thymus transplantation when the test group had naïve T cells over 10%. The pump was loaded sterilely and surgically inserted subcutaneously to mid-dorsal area of recipients. The osmotic pump was replaced every month for 4 months. For full MHC mismatched BN (RT-1$^n$) third-party heart transplantation to the DA heart bearing Lewis recipients the cervical vascularized heart transplantation method described by Heron, et al. (Heron I., 1971, "A technique for accessory cervical heart transplantation in rabbits and rats," *Acta Pathol Microbiol Scand A* 79(4):366-372) was used in modified fashion.

At 6 to 7 months, the 3rd party BN heart was transplanted in the neck. Briefly, the third-party heart was transplanted into the right side of cervical area via a longitudinal incision from submaxilla to the xiphoid. The donor pulmonary artery and external jugular vein were anastomosed end to end and the aorta was anastomosed to the right common carotid artery by cuffing technique. The grafts were monitored by daily palpation and later confirmed by laparotomy at the time of sacrifice. Animals were sacrificed on the day of rejection (cessation of beating) or a designated time point.

Flow Cytometric Analysis and Monitoring DSA

Peripheral blood was obtained from the cranial vena cava and stained with antibodies. To analyze naïve and recent thymic emigrants, we used the combination of anti-Rat CD3 APC (BD Biosciences); anti-Rat CD4 APC-Cy7 (Biolegend); anti-Rat CD8a V450 (BD); anti-Rat CD45 PE-Cy7 (BD); anti-Rat CD45RC-PE (BD); anti-Rat CD62L FITC (BD); and anti-Rat CD90 BV 510 (Biolegend). To assess percentages of T, B, and NK cells, we used the combination of anti-Rat TCR FITC (BD); anti-Rat CD4 APC-Cy7(Biolegend); anti-Rat CD8a V450 (BD); anti-Rat CD45 PE-Cy7 (BD); anti-Rat CD45RA PE (Invitrogen); anti-Rat NKR-P1A-APC (Invitrogen). For host vs donor discrimination, we used the combination of anti-Rat TCR APC (Biolegend), anti-Rat CD45 PE-Cy7 (BD); MHC Class I RT1Aa (Santa Cruz Biotechnology). We also used a secondary goat anti-mouse IgG (Invitrogen) for the non-conjugated MHC Class I RT1Aa. Donor-specific alloantibody (DSA) was assessed by flow cross-match from serially collected recipient serum samples with DA donor or BN third party rats. FITC-conjugated pan-rat immunoglobulin antibody was added to the samples and incubated after washing. The T cells were stained with APC-conjugated anti-CD3. Samples were analyzed on a LSR fortessa (Beckman Coulter).

Necropsy

Figure 21:
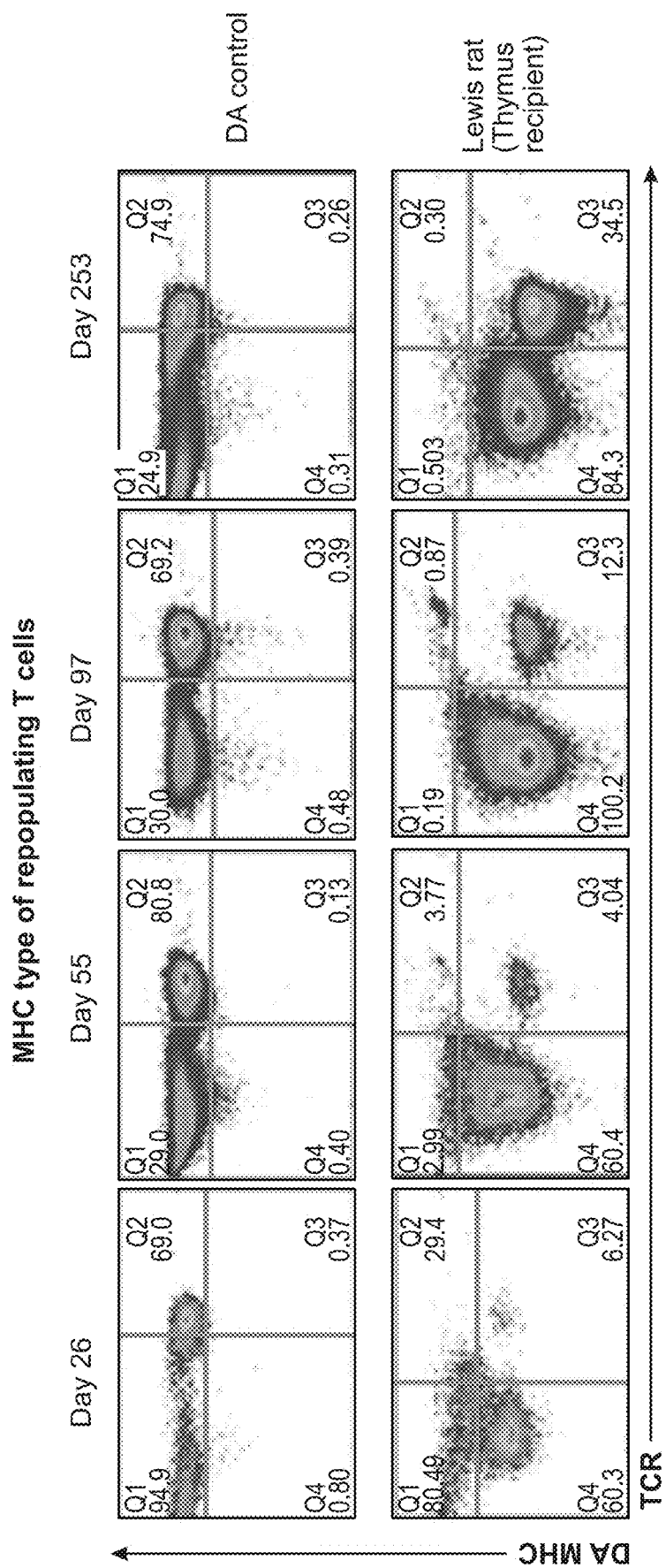
FIG. 21 shows repopulating recipient-type T cells are seen in the lower right quadrant after CTT imallogernicplantation. This figure appears in Kwun, J. et al., JCI Insight (2020) June 4; 5(11).

The thymus graft and all hearts were evaluated at necrocopy 8 months after CTT when the test group rejected the cervical BN heart. As predicted, recipient-derived T cells, not expressing DA MHC, appeared in the peripheral blood of thymus transplant recipients (FIG. 21).

Histology, Immunohistochemistry (IHC), and Morphological Analysis

All cultured thymus and CTT samples from under the kidney capsule were frozen in OCT (Optimal Cutting Compound; Tissue Tek). Control thymus tissue was obtained from newborn to 5-day-old rat pups. Four to five mm sections were stained for CD3 (polyclonal; Dako), Ki-67 (clone: SP6; Thermo), CK, (polyclonal; Invitrogen). IHC images were obtained using an Olympus Vanox AH-3 Microscope of the Olympus DP-70 Digital Camera System. The explanted hearts underwent serial sectioning (5 μm) from the midventricular level to the base. H&E stains were performed for routine examination and grading of rejection. Graft infiltrating T cells were evaluated with polyclonal anti-CD3 (Dako) staining. Whole slides of grafts were scanned with an Aperio ScanScope XT (Aperio Technologies, Inc., Vista, CA).

Statistical Analysis

Experimental results were analyzed by a GraphPad Prism (GraphPad Software 7.0, San Diego, CA). The log-rank test for differences in graft survival and student t-test or Mann-Whitney U test were used for other data. All the data were presented as mean±SD. Values of p which were less than 0.05 were considered as statistically significant.

Results

Figure 18A:
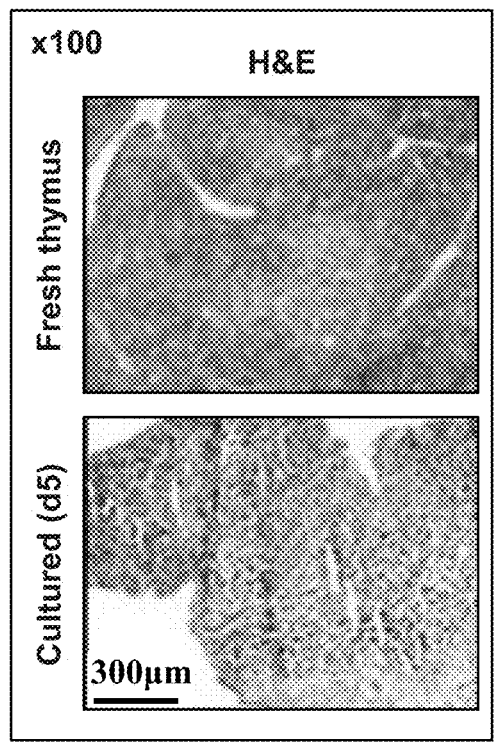
FIGS. 18A-D are photographs depicting the histologic appearance of fresh thymus tissue (top frames) and CTT (bottom frames) at 100× magnification.
Figure 18C:
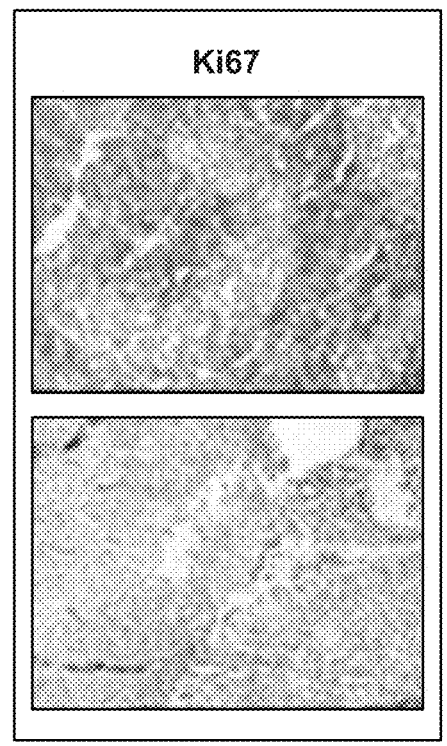
Figure 18B:
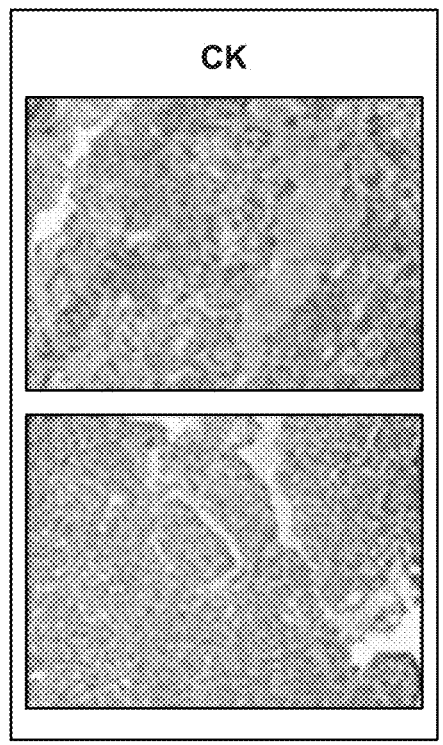
Figure 18D:
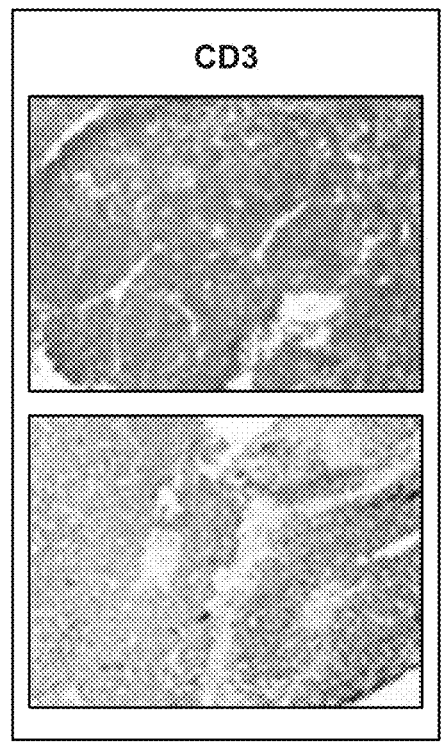
Figure 19A:
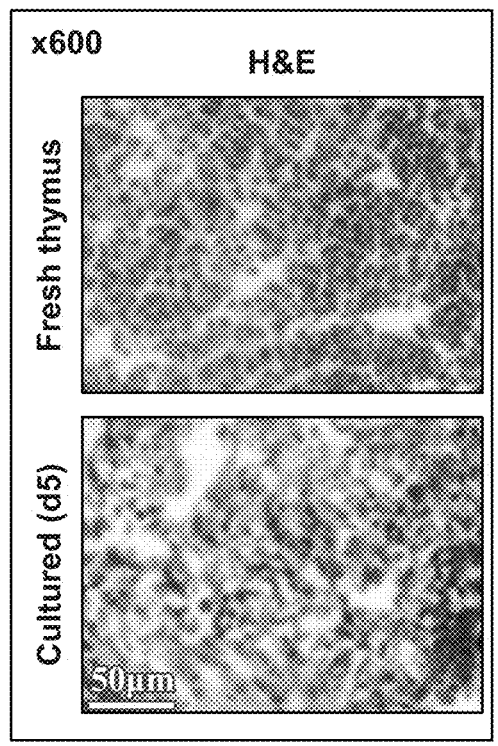
FIGS. 19A-D are photographs depicting the histologic appearance of fresh thymus tissue (top frames) and CTT (bottom frames) at 600× magnification.
Figure 19C:
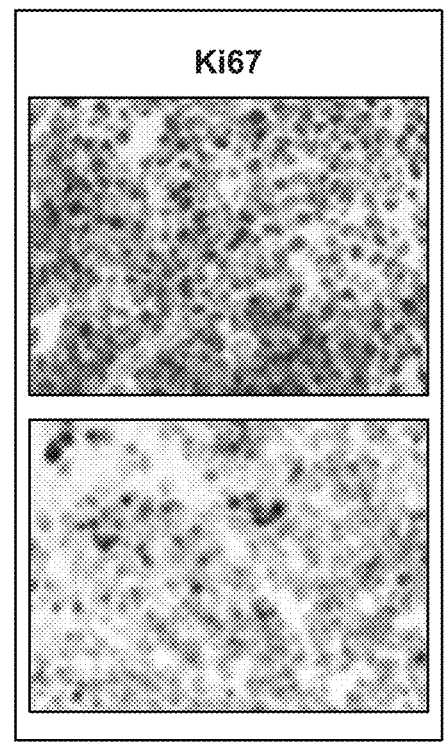
Figure 19B:
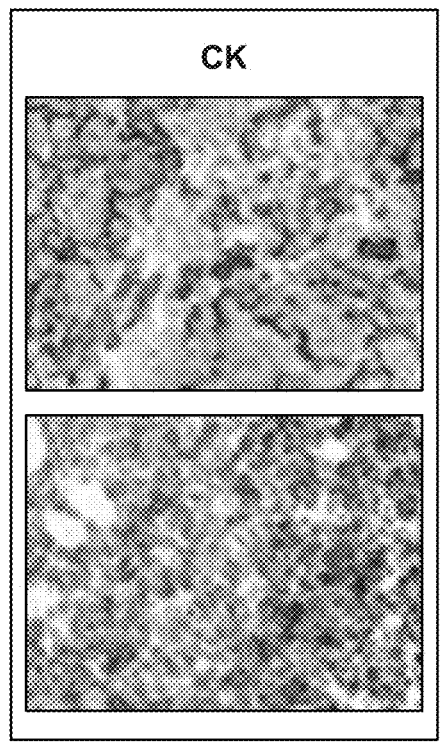
Figure 19D:
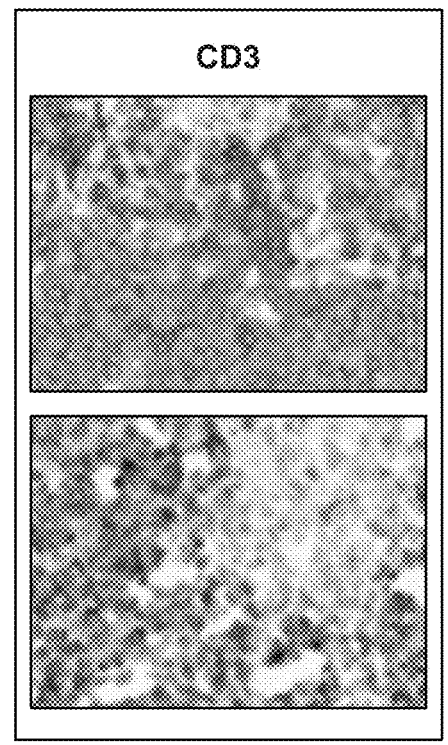

Histologic analysis (FIGS. 18C and 18D (100× magnification) and FIGS. 19C and 19D (600× magnification) showed reduced Ki67+, CD3+ cells in the thymus after culturing, similar to the changes seen after culturing of thymus tissue used for patients (Markert M L, et al., 2008), "Use of allograft biopsies to assess thymopoiesis after thymus transplantation." J Immunol 180(9):6354-6364). As in cultured human thymus, the network of thymic epithelial cells (TEC) was preserved in the rat cultured thymus tissue based on cytokeratin (CK) staining (FIG. 18B (100× magnification) and FIG. 19B (600× magnification).

As predicted, recipient-derived T cells, not expressing DA MHC, appeared in the peripheral blood of thymus implant recipients (FIG. 21). After implantation of CTT, increasingly repopulating recipient-type T cells are seen in the lower right quadrant of FIG. 21 at days 26, 55, 97 and 253.

Immunohistochemical Analysis of Engrafted Allogeneic Thymic Tissue.

Circulating T cell repopulation after T cell depletion and thymus and heart transplantation are depicted in FIG. 23. All animals showed dramatic reduction of circulating T cells after T cell depletion. Cardiac allograft recipients with a CTT insertion (blue/dashed line) showed gradual repopulation of circulating T cells. Animals without a CTT insertion also showed some degree of circulating T cells (red/dotted line). However, naïve and recent thymic emigrants CD4 and CD8 T cells were significantly increased (p<0.01) in animals with a CTT insertion while control animals showed no circulating naïve nor RTE CD4 and CD8 T cell.

Figure 22A:
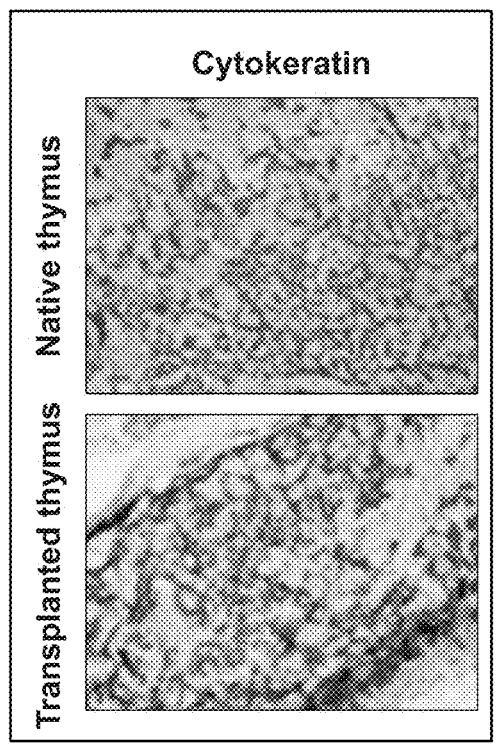
FIG. 22A and FIG. 22B show implanted thymus explanted at 8.5 month after implantation showing positive cytokeratin staining (FIG. 22A), as well as T cell staining similar to native thymus (FIG. 22B). Original magnification ×400. This figure appears in Kwun, J. et al., JCI Insight (2020) June 4; 5(11).
Figure 22B:
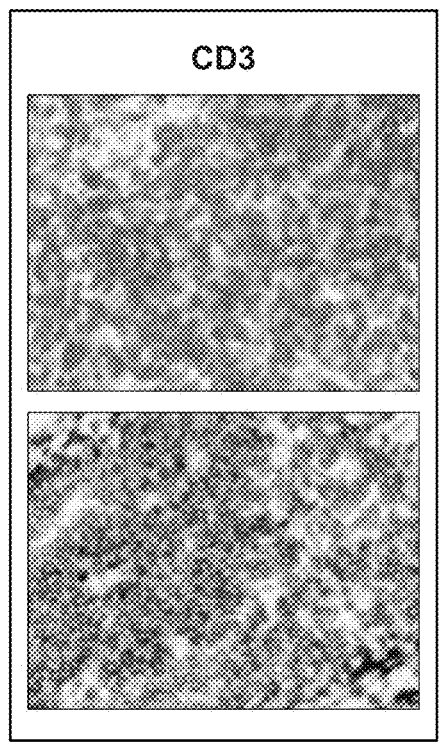

Implanted thymus explanted at 8.5 month after implantation showed positive cytokeratin staining (FIG. 22A) as well as T cell staining similar to native thymus (FIG. 22B). Original magnification ×400.

Animals with insertion of CTT showed significantly increased repopulation of naïve (CD62L+CD45RC+) CD4 and CD8 T cells as well as recent thymic emigrant (RTE) T cells in the peripheral blood while control groups without thymus implantation showed low level of circulating naïve CD4 and CD8 T cells and did not show circulating RTE CD4 and CD8 T cells (FIG. 23). Total circulating CD3 T cell numbers were not significantly different in between groups prior to implantation. As expected, LW recipients with a CTT implant showed significantly increased numbers of circulating CD4 and CD8 T cells compared to control animals without implantation of CTT (FIG. 23).

Engrafted cultured thymus tissues under the renal capsule on day 180 in a recipient of cardiac allograft recipients is depicted in FIG. 24.

Figure 24B:
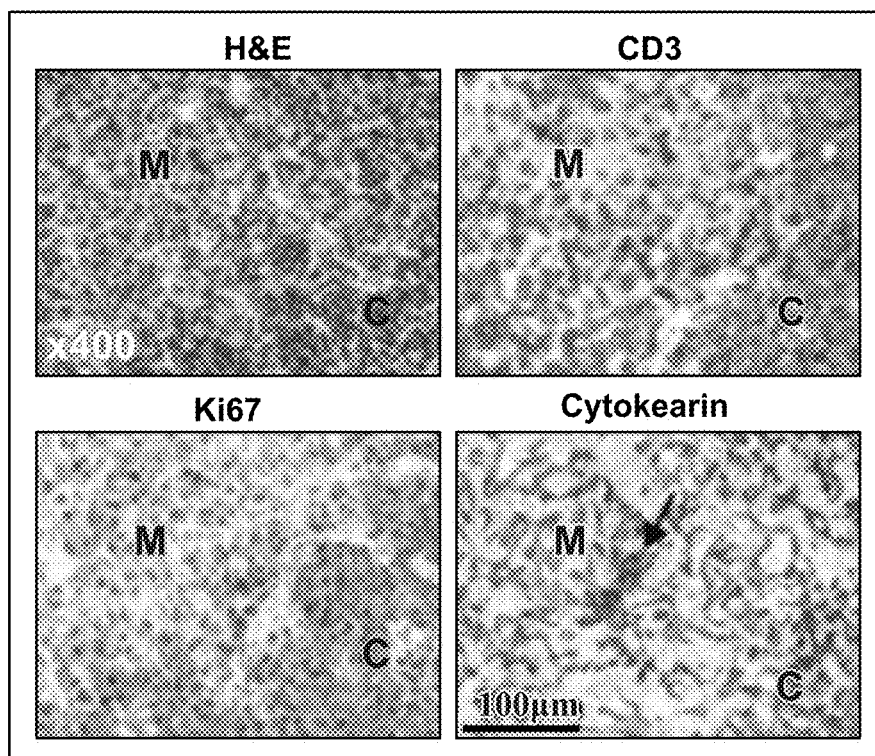
FIG. 24B shows the explanted graft on H&E. Strains for viable T cells (CD3), T cell proliferation (Ki67), and cytokeratin (detected by a rabbit polyclonal antibody) are shown. In the panel stained for cytokeratin, a lacy pattern is seen with Hassall body formation (arrow) on TECs. This figure appears in Kwun, J. et al., JCI Insight (2020) June 4; 5(11).

Histology showed distinct structures separate from renal tissue (Original magnification, ×20). Engrafted cultured thymus tissue showed a normal thymus structure (H&E), viable T cells (CD3), T cell proliferation (Ki67), and Hassall body formation (Black arrow) with a lacy pattern (Cytokeratin) on epithelial cells, confirming the viability of thymus with thymopoiesis (FIG. 24B). Original Magnification, ×200. (Data are presented as means SD; n=8-9 animals per group; student's t-test, *P<0.05; P<0.01; *P<0.001, ****P<0.0001; NS, not significant (p>0.05).

In addition, immunohistologic analysis of implanted CTT explanted on day 180 showed normal thymus histology, viable T cells (CD3), T cell proliferation (Ki67), and a lacy pattern of CK with Hassall body formation (arrow) on TECs from the surgical insertion of CTT (FIG. 24B). These observations confirm the viability and function (thymopoiesis) of the transplanted thymus in the animals receiving allogeneic heart transplantation.

Taken together, rats transplanted with CTT demonstrated thymopoiesis with naïve T cell development in cardiac allograft recipients.

It was expected that T cells reactive to the DA donor would not develop since the T cells developed in CTT expressing DA as well as LW.

The DA heart was evaluated for evidence of rejection. FIG. 25 shows LW rats with DA heart transplants and without any immunosuppressive treatment rejected the DA heart grafts within 10 days (the DA control, open squares). However, even after developing RTE (CD90$^+$CD45RC$^+$) T cells, LW recipients with surgically inserted CTT did not reject (no cessation of beating) the DA cardiac allografts (n=8, filled triangles). Unexpectedly, LW control animals without a CTT insertion also did not reject the DA cardiac graft (n=9, upside down filled triangles). Both groups showed good beating quality for the entire study period (day 180). Since continuous graft beating does not necessarily imply absence of rejection, two recipient rats were sacrificed two months after cessation of immunosuppression (i.e., prior to 3$^{rd}$ party BN cervical heart transplantation) to confirm that there was no rejection. The explanted cardiac allografts (DA hearts) from both animals showed minimal mononuclear cell infiltration (FIG. 26A, with CTT insertion; and FIG. 26B, without CTT insertion), with no signs of rejection by 2004 International Society for Heart &Lung Transplantation (ISHLT) grading FIG. 26C.

Figure 26A:
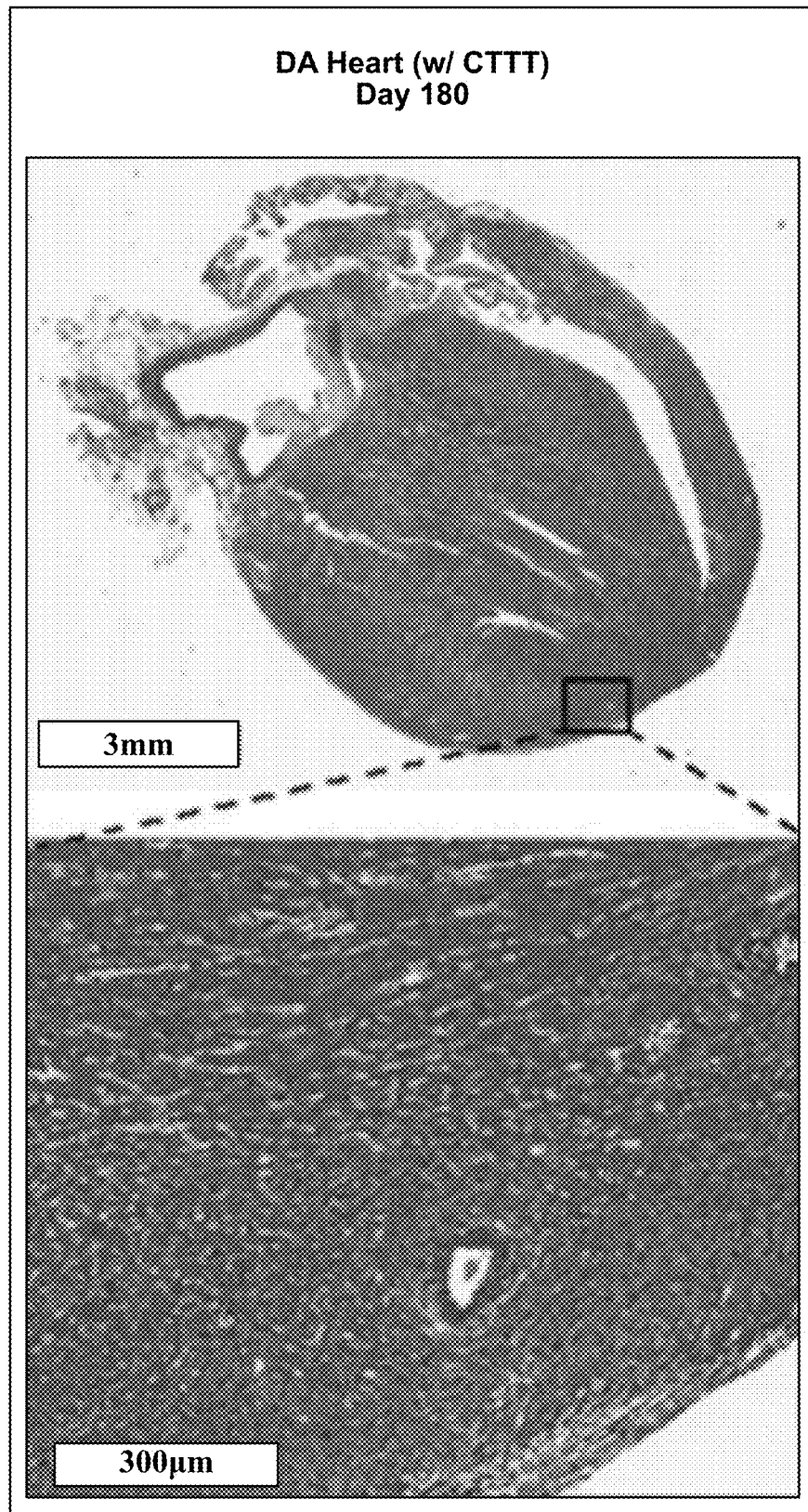
FIGS. 26A and 26B are photographs of transplanted allografts (DA hearts) from animals implanted with (FIG. 26A) and without (FIG. 26B) CTT showing mononuclear cell infiltration with no signs of rejection by 2004 International Society for Heart &Lung Transplantation (ISHLT) depicted in FIG. 26C (the solid blue squares and solid red triangles). This figure appears in Kwun, J. et al., JCI Insight (2020) June 4; 5(11).
Figure 26B:
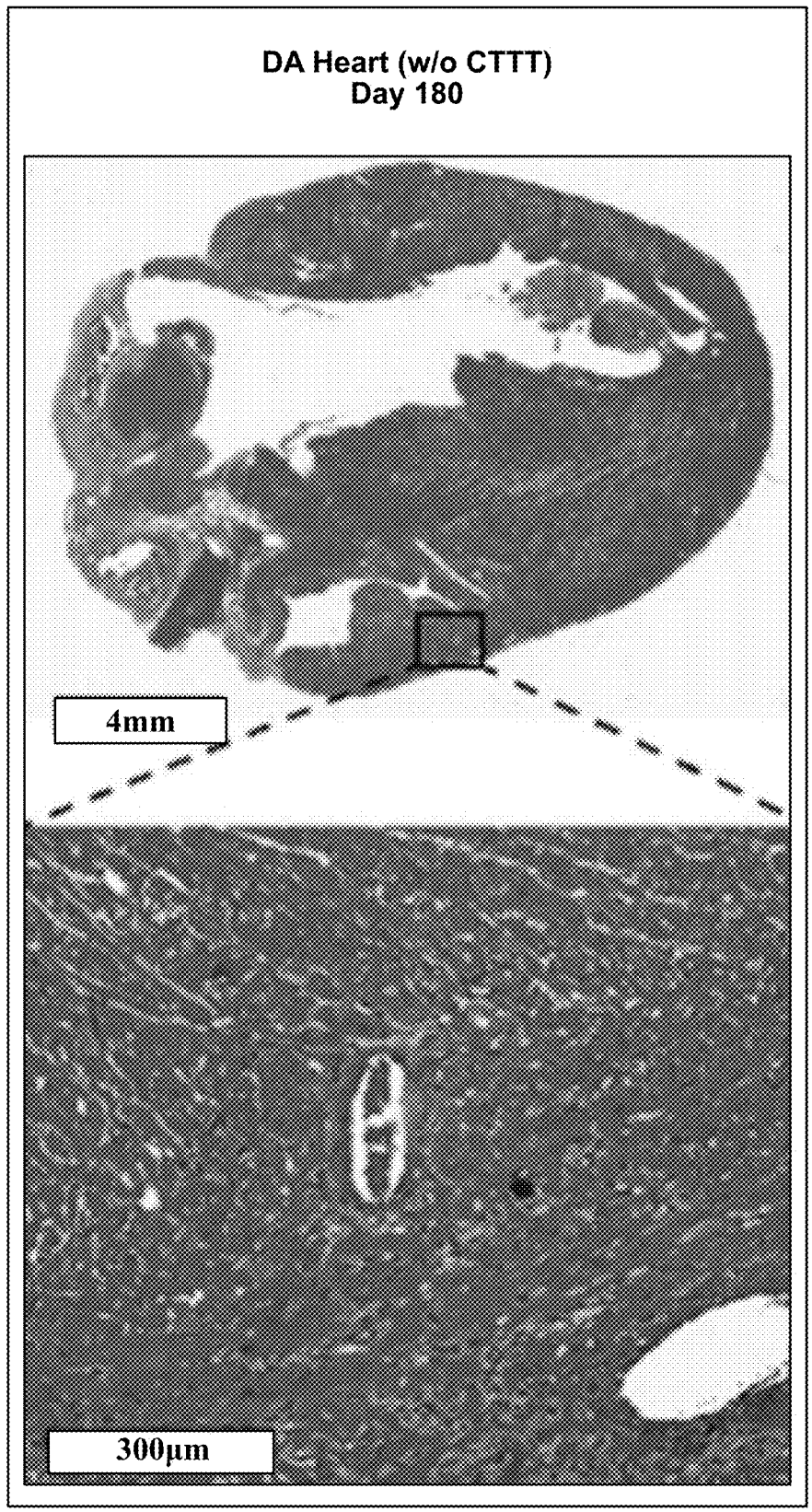

A Kaplan-Meier survival curve (FIG. 25) showed significantly prolonged graft survival from animals with or without CTT and syngeneic controls (LW heart into LW rat) as compared to LW rats with DA heart transplants without any immunosuppression (DA control). Representative scanned images of explanted graft at day 180 from animals with and without CTT are shown in FIGS. 26A and 26B. The images were adapted from whole slide scan.

Figure 26C:
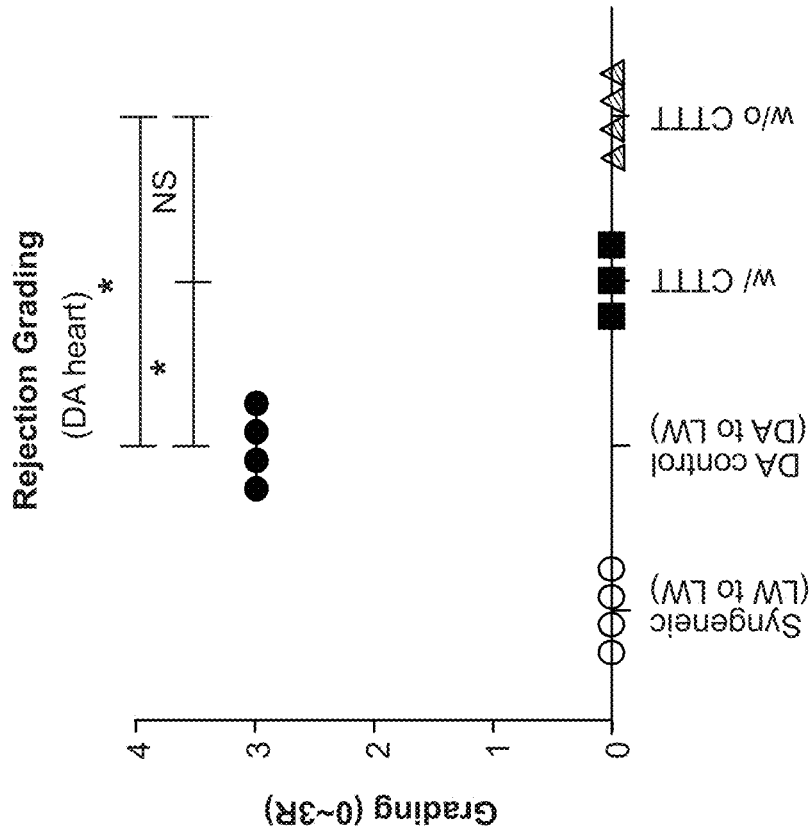

The ISHLT grading showed no difference in rejection grading between cardiac allografts from recipients with CTT vs. without CTT (n=3-4 per group) (FIG. 26C). Mann-Whiney U test, *P<0.05; NS, not significant (p>0.05).

Based on the reconstitution of naïve T cells after CTT, we believe that animals with CTT lost their donor-reactive T cell repertoire while animals without thymus implantation did not fully reconstitute their T cell populations (general hypo-responsiveness).

Alloreactivity Against Third-Party Vascularized Heart Transplantation

To confirm that donor-specific unresponsiveness (tolerance) was achieved as opposed to general hypo-responsiveness, additional fully MHC mismatched BN heart transplantation was performed in both groups of animals at 6 to 7 months (day 180 to 210) after DA heart transplantation.

LW rats with CTT inserted (solid triangles. FIG. 27) rapidly rejected (cessation of graft beating) the third-party BN heart (n=5, median survival time (MST)=101.0 days). However, the control LW animals without CTT inserted did not reject the third-party hearts (n=6, MST≤38.5±8.9 days), possibly due to the lack of any alloreactive T cells.

Figure 28A:
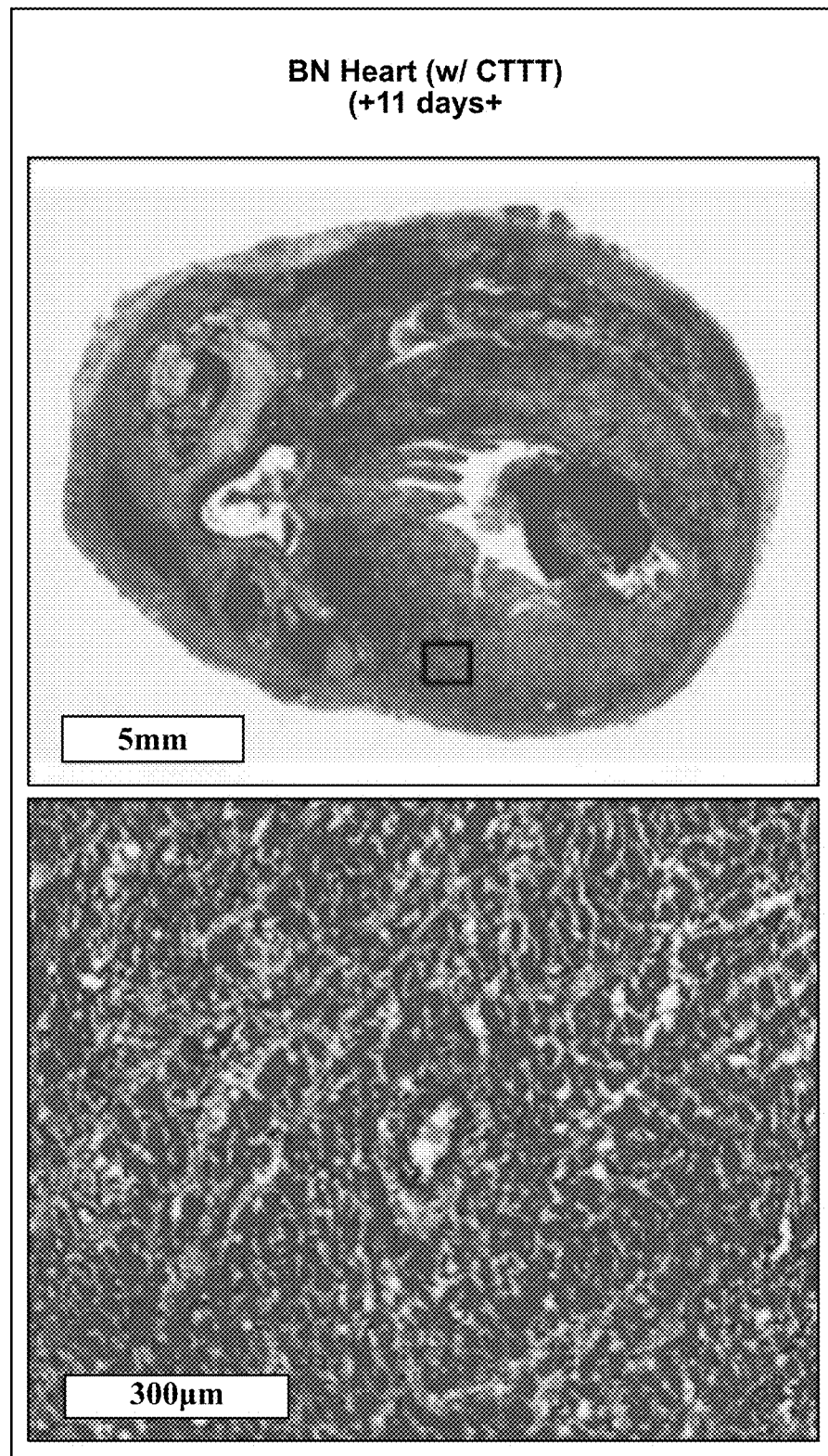
FIG. 28A and FIG. 28B are photographs of BN heart tissue with (FIG. 28A) and without (FIG. 28B) CTT insertions at 11 and 46 days, respectively. These pictures are the basis of the data in FIG. 27 and FIG. 29. The heart in FIG. 28A is not rejected because of tolerance. The heart in FIG. 28B is not rejected because of immunodeficiency from lack of thymus. This figure appears in Kwun, J. et al., JCI Insight (2020) June 4; 5(11).
Figure 28B:
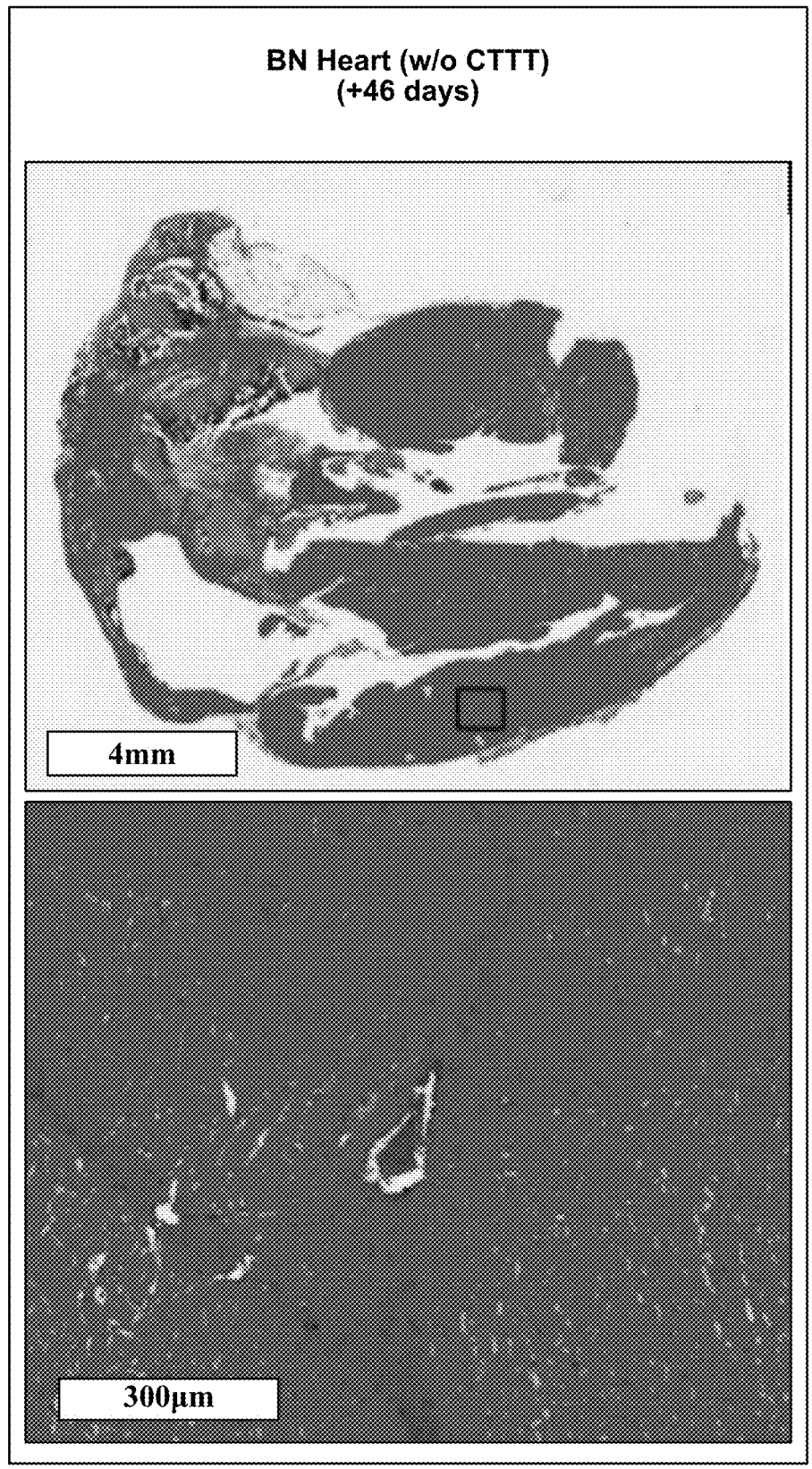

In accordance with this lack of rejection of the third party heart, histological analysis confirmed that animals with CTT inserted (upside down filled triangles, FIG. 27) showed increased mononuclear cell infiltration in the heart allograft (FIG. 28A), while animals without CTT inserted showed a pristine BN heart allograft (FIG. 28B). Recipients with CTT rejected the BN heart rapidly (MST=10±1.0 days) (filled squares, FIG. 29), while recipients without CTT did not reject the third-party BN hearts (dashed triangles, FIG. 29). The BN control (filled circles, FIG. 29) shows rejection of BN hearts by LW rats. The syngeneic control (open circles, FIG. 29) shows lack of rejection of LW hearts by LW rats. Kaplan-Meier survival curve (FIG. 27) showed significant differences in the graft survival. Representative scanned images of explanted BN heart graft at the time of rejection or 46 days post-transplantation are shown in FIGS. 28A and 28B, respectively. BN heart grafts from animals with CTT inserted showed severe mononuclear cell infiltration (FIG. 28A), while BN heart grafts from animals without CTT inserted showed no sign of rejection (FIG. 28B). Images were adapted from whole slide scan.

Figure 29:
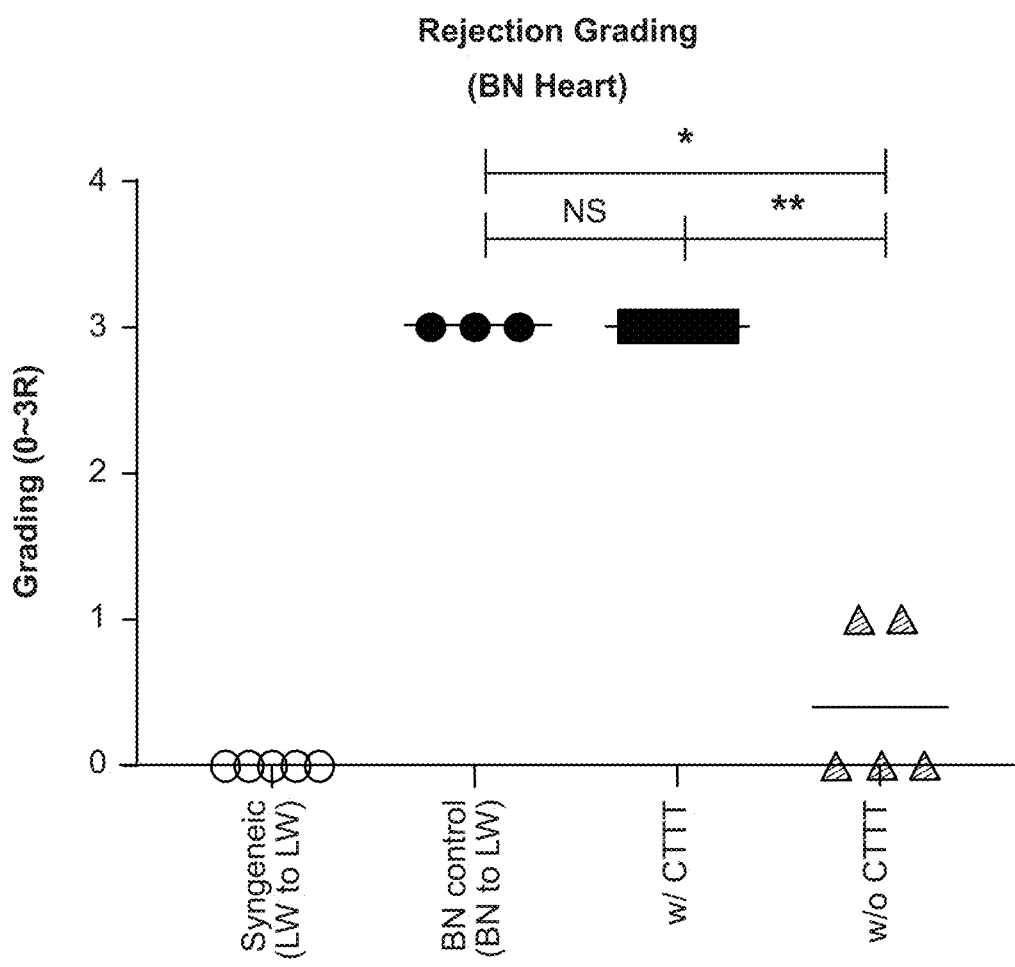
FIG. 29 shows rejection grading of the cervical BN hearts. Syngeneic L W hearts placed into LW rats (open circles) were not rejected. BN hearts placed into LW rats (filled circles) were rejected. BN hearts placed in LW rats who received CTT were rejected (filled squares). BN hearts placed in LW rats who did not receive CTT were weakly rejected (shaded triangles) in 2 rats and not rejected by the other three rats. These data show that the rats with CTT were able to strongly reject $3^{rd}$ party hearts even while they accepted DA hearts (FIG. 26C) as the CTT expressed DA. The rats without CTT were immunodeficient and didn't reject either the DA (FIG. 26C) or the BN hearts. This figure appears in Kwun, J. et al., JCI Insight (2020) June 4; 5(11).

Histological analysis (ISHLT grading) of explanted BN hearts from rats with CTT inserted (filled squares, FIG. 29) showed grade 3R rejection with significantly increased inflammatory cell infiltration compared to syngeneic controls or rats without CTT inserted (shaded triangles, FIG. 29). ISHLT grading showed significantly higher rejection grading from BN hearts from animals with CTT compared to BN hearts from animals without CTT (n=3-5 per group). Mann-Whiney U test, *P<0.05; **P<0.01; NS, not significant (p>0.05).

Figure 30A:
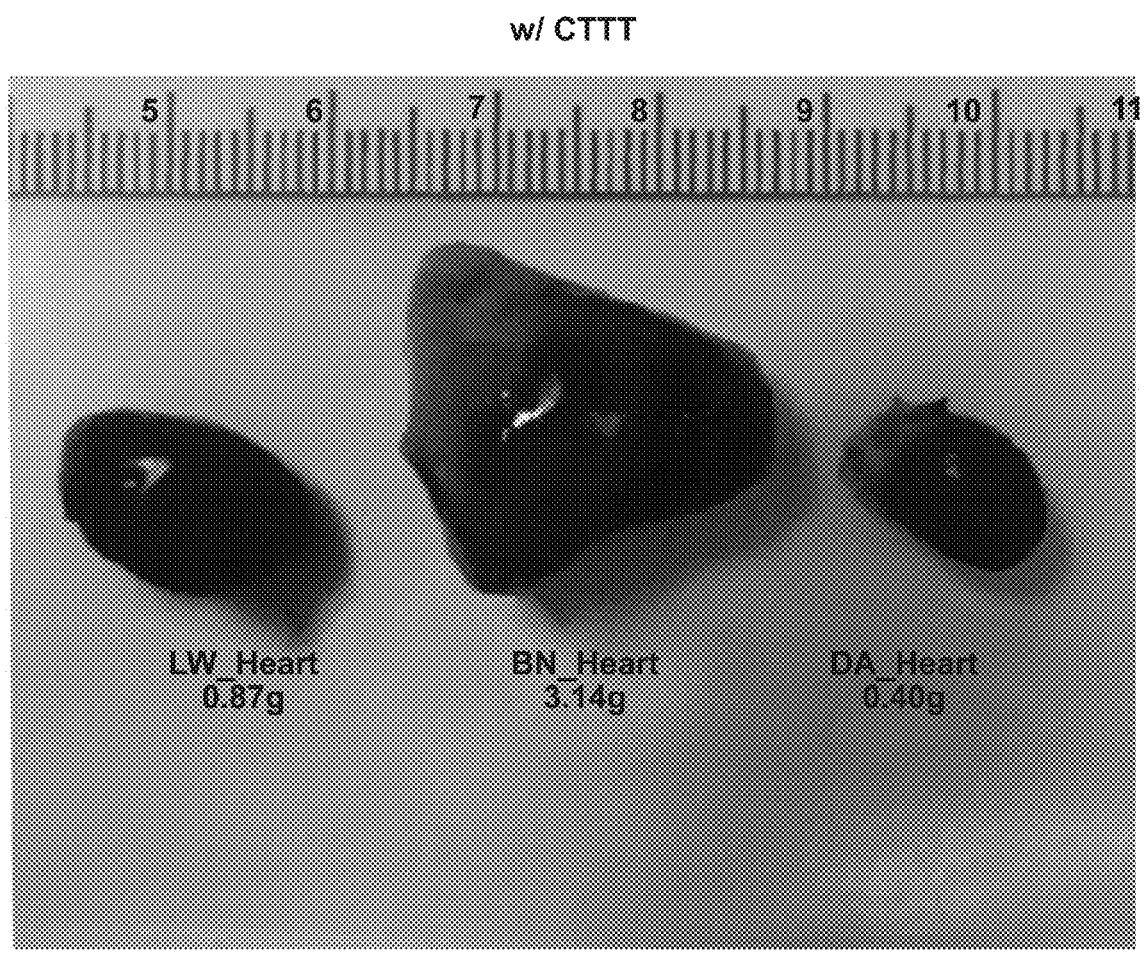
FIG. 30A and FIG. 30B are photographs of BN hearts in which rats received or did not receive CTT insertions compared to LW and DA hearts, respectively.
Figure 30B:
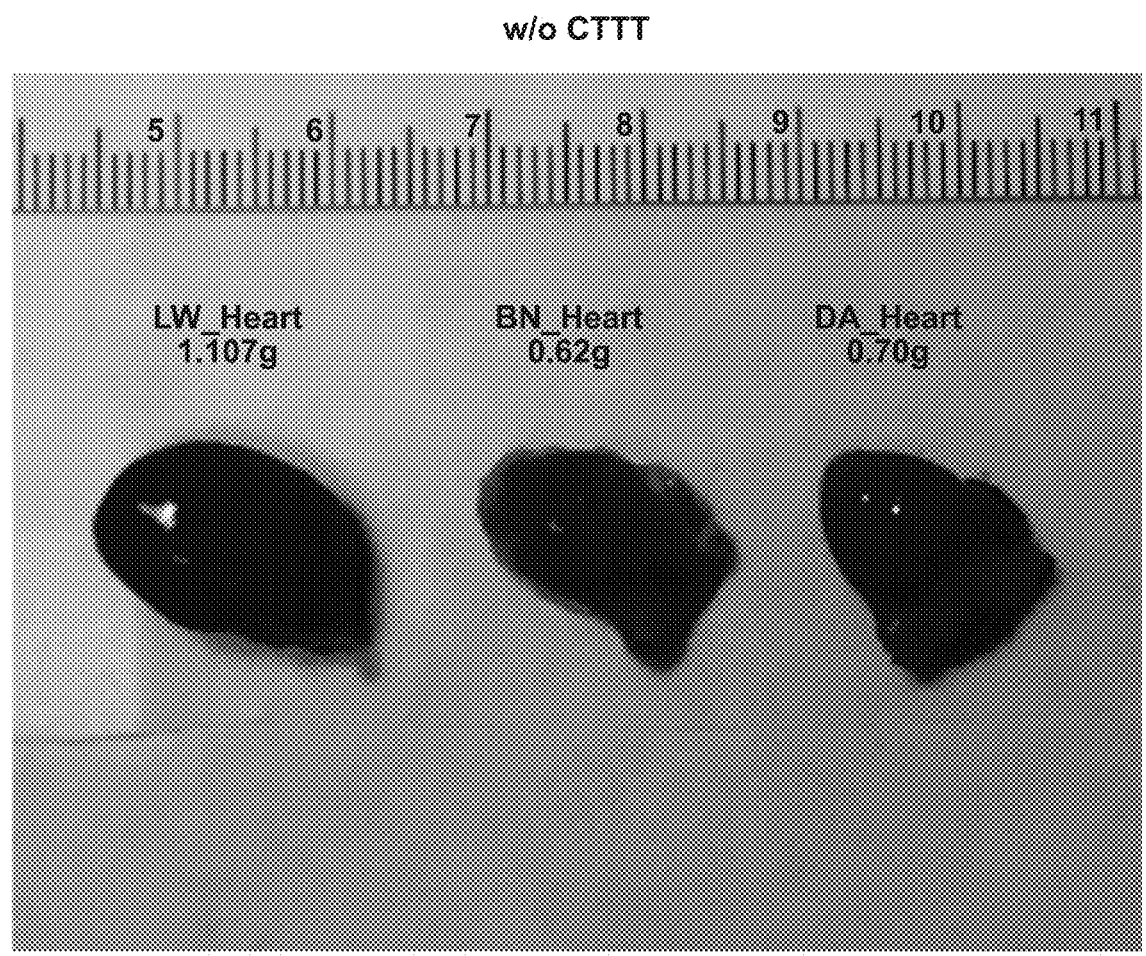

It is also notable that the cervical BN hearts in the recipients with CTT inserted were greatly enlarged (FIG. 30A), while the abdominal DA hearts were smaller than the native hearts (FIG. 30A). BN hearts from recipients without CTT inserted did not show any increase in size (FIG. 30B) compared to BN hearts from recipients with CTT.

Selective T Cell Infiltration in the Third-Party Hearts but not in the DA Hearts that Shared the DA MHC of the CTT Two conventional ways were used to define graft rejection in this rat heart transplantation model: heart beating/cessation measurements and the ISHLT human grading system. The former is insensitive with respect to low-grade rejection, while the latter is insensitive with respect to high-grade rejection. As a result, inflammatory cell infiltration was measured in DA hearts from 3 rats at day 180 and in BN hearts at the time of sacrifice at 7 to 8 months in 5 rats. Inflammatory cell infiltration was therefore measured in DA hearts from 3 rats at day 180 and in BN hearts at the time of sacrifice at 7 to 8 months in 5 rats.

Figure 31B:
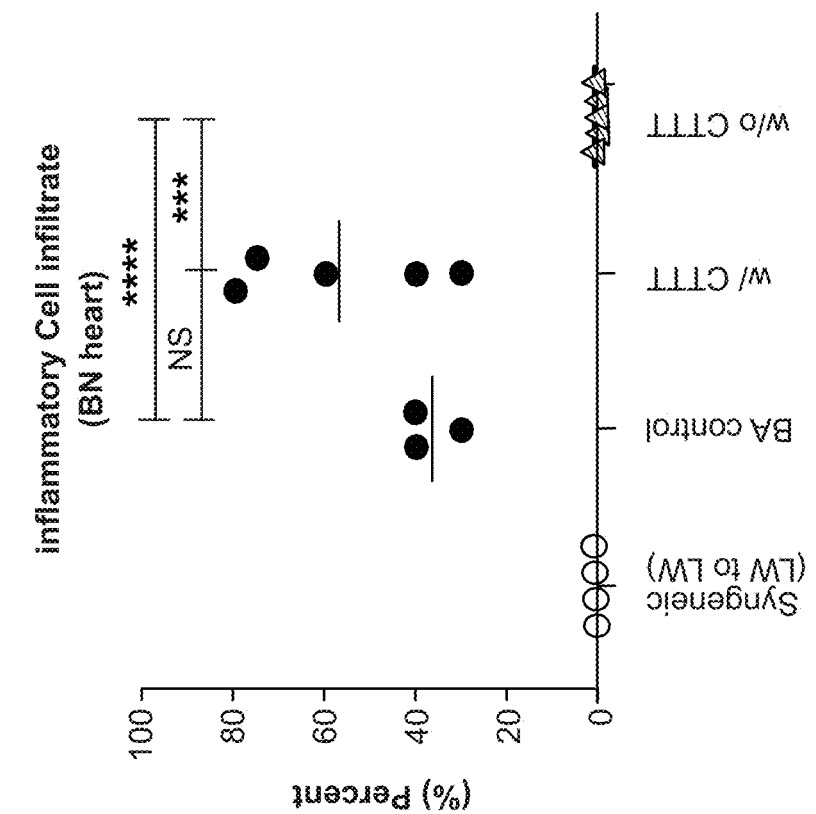
FIG. 31A and FIG. 31B are plots of rejection grading for explanted cervical BN hearts from rats with and without CTT insertions vs. BN controls and syngeneic control rats.
Figure 31A:
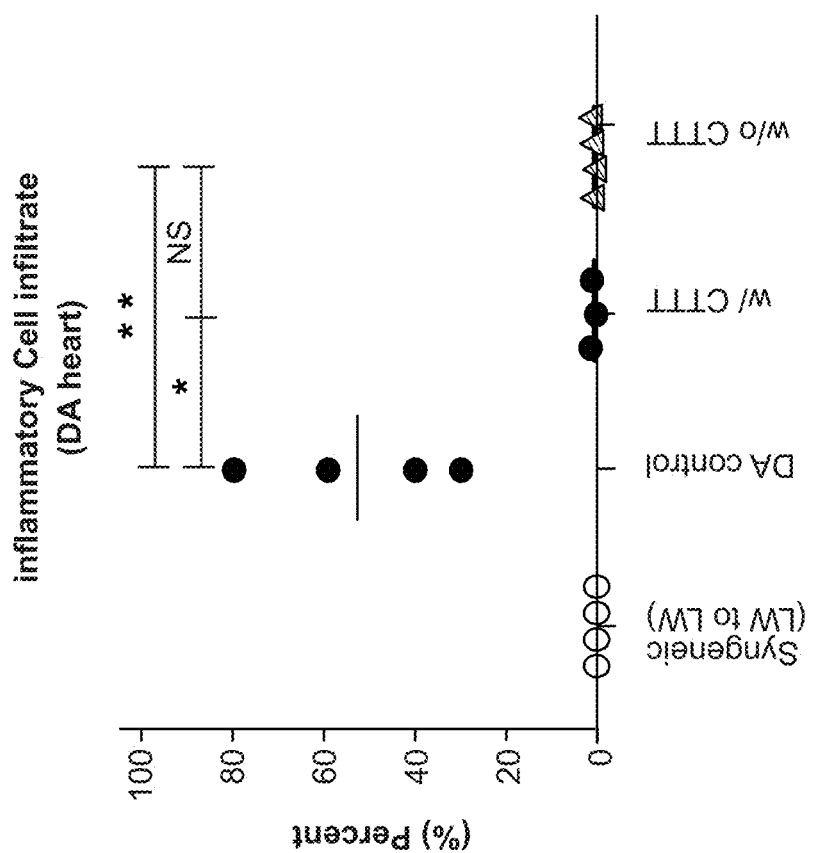

Rats that were treated with T cell depletion, surgical insertion of CTT, and CsA administered for four months, did not show an increased level of inflammatory cell infiltration in the DA hearts after T cell repopulation (FIG. 31A). DA control grafts (in LW rats with no immunosuppression) showed a significantly increased graft infiltration of immune cells in the DA heart compared to the infiltration of immune cells in DA hearts in rats with CTT or without CTT. Animals inserted with CTT showed massive inflammatory cell infiltration in the third-party cardiac allograft (BN heart) (FIG. 31B). The BN control grafts (in LW rats with no immunosuppression) and BN grafts from recipients with CTT showed significantly elevated inflammatory cell infiltration compared to those in BN grafts from animals without CTT. Rats not inserted with CTT showed no infiltrates in the BN heart (FIG. 31B) shaded triangles) because of their immunoincompetence.

Figure 31C:
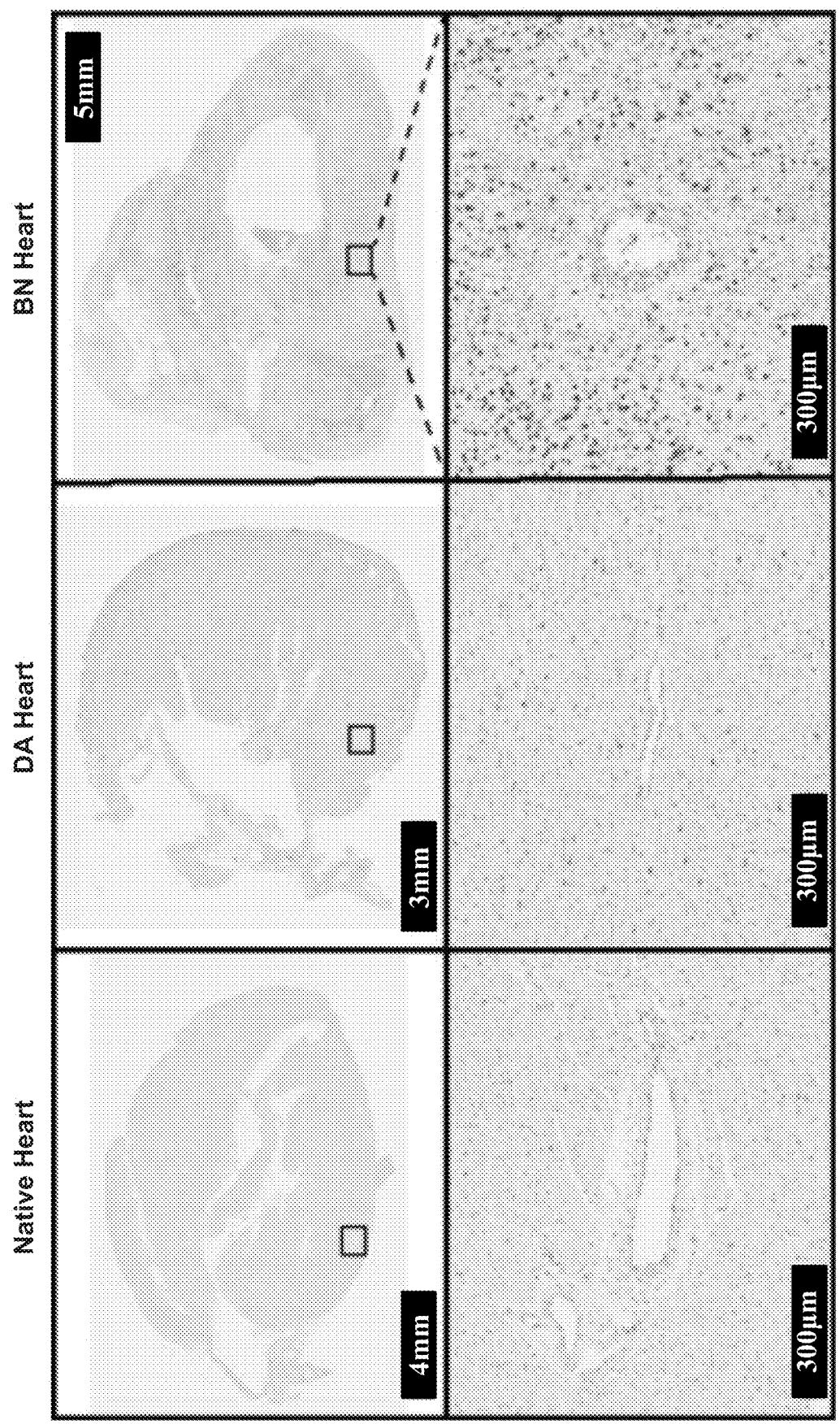
FIG. 31C shows DA and BN heart rats that were harvested from the LW recipients along with the native LW heart at the time of the cervical BN heart rejection. The lower right panel shows the T cells (brown) in the BN heart leading to its rejection.
Figure 31D:
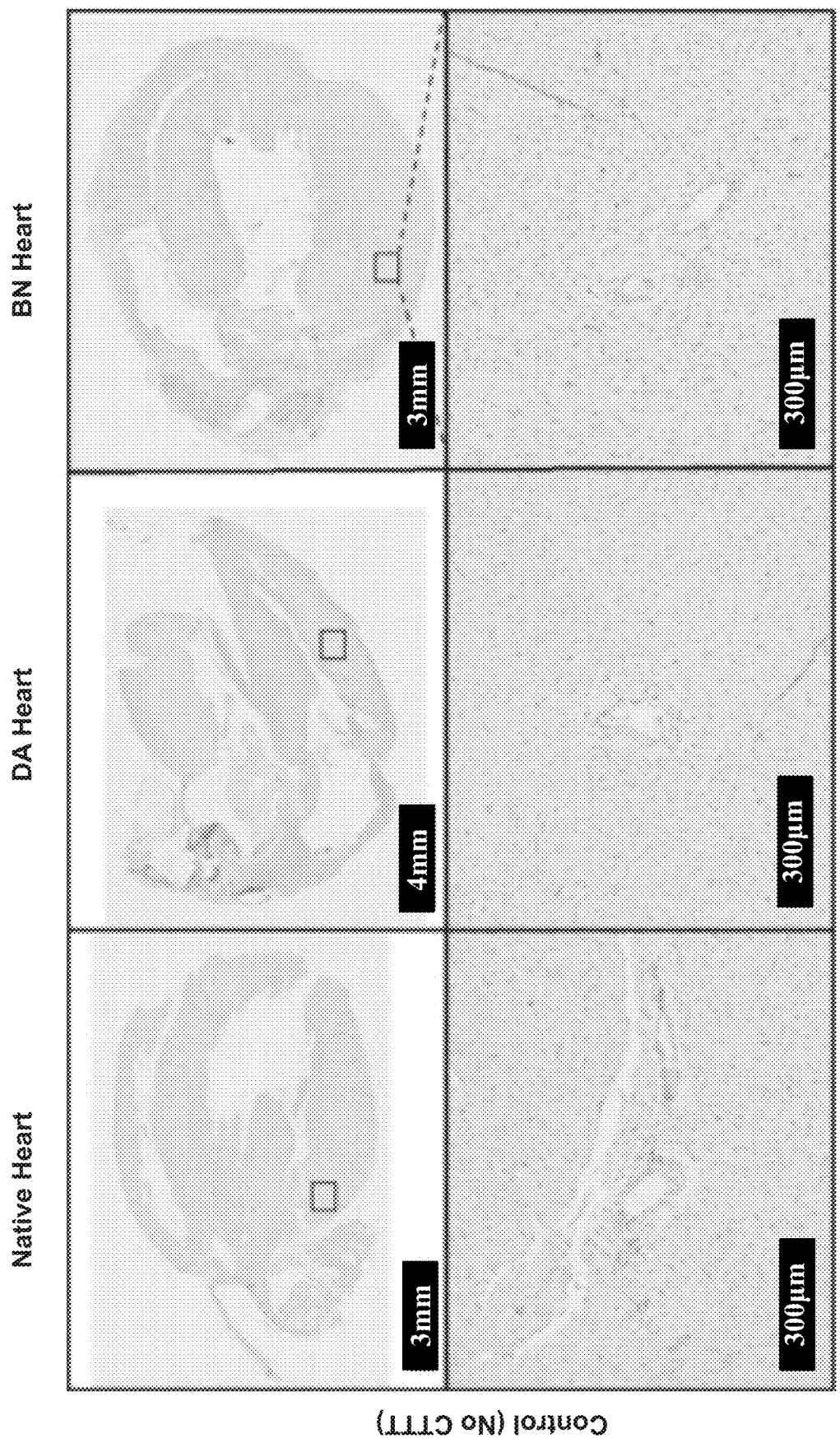
FIG. 31D shows T cell infiltration in the LW, DA, and BN hearts from control animals without insertion of CTT. There is no T cell infiltration because the animals are immunodeficient. This figure appears in Kwun, J. et al., JCI Insight (2020) June 4; 5(11).

T cell infiltration was evaluated with immunohistochemistry and confirmed a selective T cell infiltration in the BN (right hand panels, FIG. 31C), but not DA (middle panels, FIG. 31C) hearts of the animals inserted with CTT and a lack of T cell infiltration in both hearts of animals without CTT inserted (FIG. 31D). Heart allografts from DA and BN rats were harvested with native heart at the time of BN heart rejection. Grossly, native heart and DA heart (POD 196) did not show dramatic increase of T cells, while BN heart (POD14) showed a massive amount of T cells in recipients with CTT inserted. Images were adapted from whole slide scan. Total 3-5 animals per group were analyzed; student's t-test, *P<0.05; P<0.01; *P<0.001; ****P<0.0001; NS, not significant (p>0.05).

These data confirm that for the group receiving CTT the T cell infiltration occurs only in the third-party BN graft, but not in the graft sharing MHC (DA) with the implanted thymus, possibly due to lack of T cell repertoire (by negative selection) against (DA heart) donor antigens.

Humoral Response Against Donor Antigens after Thymus Implantation

Anti-donor antibody responses were evaluated to determine whether the allogeneic T cell unresponsiveness noted in thymectomized LW rats followed by LW×DA transplants and the surgical insertion of CTT, was associated with humoral tolerance against donor DA MHC. Serially collected recipient serum samples were collected and flow cross-match with PBMCs from DA and BN rats was performed. Animals that received DA or BN heart transplants without immunosuppression developed antibody against their donors (DA or BN, respectively). Animals with a syngeneic cardiac allograft did not produce antibody against either DA or BN MHC, as reported in FIG. 32A (horizontal shaded peaks in the left hand column, on top for DA, and on the bottom for BN). Representative histogram plots for post-transplant donor-specific alloantibody (anti-DA and anti-BN antibodies) measured by T cell flow cross-match are shown in FIG. 32A. Recipients with or without CTT did not generate any antibodies against DA antigen (the top row, middle and right hand columns in FIG. 32A), while animals with CTT were able to generate antibody against BN antigen (lower row, middle panel, FIG. 32A). Serum samples from recipients of DA heart transplantation without immunosuppression and from LW recipients of BN heart transplantation without immunosuppression were used as positive controls (DA control and BN control) for anti-DA (top row, left panel, bold line or anti-BN antibody (bottom row, left panel, dashed line), respectively.

Figure 32B:
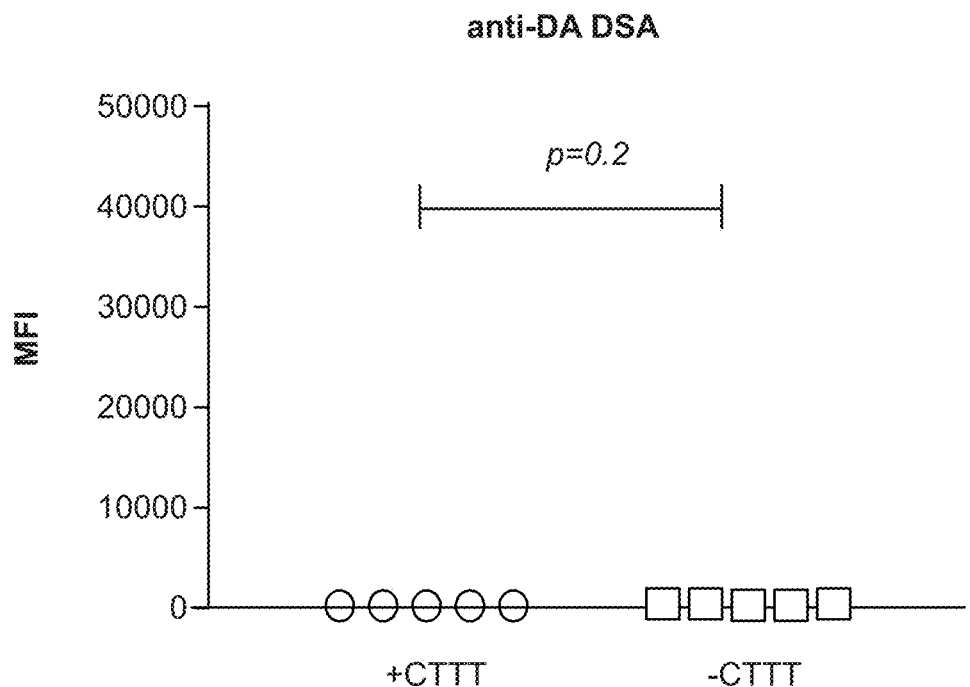
Figure 32C:
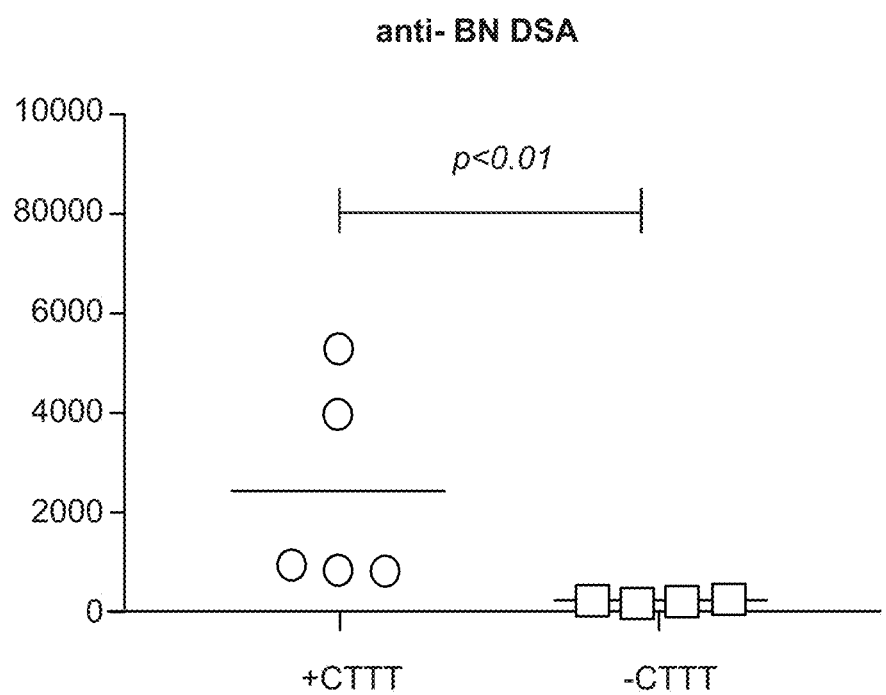

Interestingly, similar to T cell hypo-responsiveness, no anti-DA Ab was detected in animals with or without CTT (FIG. 32B). Anti-BN Ab was readily detected in animals with LW×DA with CTT inserted, but not in animals without CTT inserted, p<0.01 (FIG. 32C). The animals without CTT were generally immunodeficient. The animals with CTT had specific tolerance to DA.

Taken together, thymus co-transplantation resulted in specific tolerance to the allogeneic DA MHC expressed in the donor thymus, and thus long-term survival of the DA heart transplant via preventing development of both the donor-specific anti-DA T cell repertoire as well as preventing the donor (DA)-specific humoral response. Immunocompetence was demonstrated in these rats by the rapid rejection of third-party BN hearts as well as alloantibody response against BN donor cells.

Further support for the treatment described above may be deduced from a clinical experience with a DiGeorge anomaly patient.

Patient 1 is a child born with complete DiGeorge anomaly. He had no T cells at birth. A major problem for Patient 1 was profound hypoparathyroidism leading to many hospitalizations for hypocalcemia. Patient 1 was given both a cultured thymus tissue transplant (CTT) and a parental parathyroid gland transplant on the same day. There were three other patients given thymus plus parental parathyroid in a small clinical trial. Patient 1 received the two transplants at 4 months of life. Although Patient 1 had no T cells, Patient 1 was given RATGAM for immunosuppression prior to transplantation per protocol. No other immunosuppression was given. Patient 1 developed naïve T cells and normal proliferative T cell responses to mitogens. All four patients who received both thymus and parathyroid in the trial developed normal parathyroid hormone levels. Patient 1 was the only subject who was able to come off calcium supplementation long term (10 years). Of the three other Patients, one died prior to one year from pulmonary problems, and the other two with complete DiGeorge anomaly had to return to calcium supplementation by approximately one year. Patient 1 was the only subject who had a negative mixed lymphocyte reaction (MLR) against the parental parathyroid donor at all time points. The other three subjects had positive MLRs starting with their first assay.

The possible explanation for Patient 1 maintaining parathyroid function is that the parathyroid donor of Patient 1 had HLA-Class II alleles that matched either the recipient HLA-Class II alleles ("*" in Table 9 below) or the thymus donor HLA-Class II alleles ("†" in Table 9 below).

The CLPs in Patient 1 developed into thymocytes in the thymus gland.

Dendritic cells from Patient 1 migrate to the thymus and delete T cells that bind tightly to the MHC on patient 1 DCs. There is tolerance to the alleles marked "*" in Table 9 below. See Table 9.

The thymus donor thymic epithelial cells also delete thymocytes that bound tightly to them (marked "†" in Table 9 below). This is the mechanism of tolerance toward the alleles marked "†" in Table 9 below.

TABLE 9

|  | HLA-A | HLA-B | HLA-C | HLA-DRB1 | HLA-DQB1 | HLA-DQA1 | HLA-DPB1 |
| --- | --- | --- | --- | --- | --- | --- | --- |
| Patient 1 | 24:02* | 08:01 | 07:02 | 03:01 | 02:01 | nt | 04:01 |
|  | 02:01* | 44:05* | 02:02* | 16:01* | 05:02* | Nt* | 04:02* |
| Parathyroid Donor | 02:01* | 44:05* | 02:02* | 16:01* | 05:02/05* | 01:02* | 04:02* |
|  | 24:01* | 35:03 | 04:01 | 11:04† | 03:01/19† | 05:05/09† | 04:02† |
| Thymus Donor | 02:01* | 44:03 | 02:02 | 11:01† | 03:01† | 05:05/09† | 04:01† |
|  | 32:01 | 40:02 | 14:03 | 04:05 | 03:03 | 03:02/03 | 02:01 |

Of note, one can see that there is one HLA-B and one HLA-C allele in the parathyroid donor that were not matched to the recipient nor to the thymus donor. We did not understand why the parathyroid gland was not rejected. However, after 10 years passed, the child was given a live measles/mumps/rubella vaccine. The parathyroid function was destroyed within two weeks and Patient 1 returned to calcium supplementation.

We conclude that the live vaccine activated the CD8 T cells in Patient 1. One third of CD8 T cells have inherent alloreactivity. The alloreactive CD8 T cells reacted against the mismatched HLA-B and C alleles in the parathyroid donor (large bold HLA-B and HLA-C alleles in Table 9).

With the data from this patient, it is clear that matching for both HLA-Class I and HLA-Class II are needed to induce long term tolerance. The recipient had tolerance to the DPB1*04:02 allele in the parathyroid donor because the patient expresses DPB1*0402. The patient's dendritic cells went to the thymus and deleted any cells that bound too tightly to DPB1*0402. The recipient did not reject the parathyroid because the DQA1 allele DQA1*05:05/08 is expressed in the thymus. Likely the DQA1*01:02 allele was inherited by the patient from the mother and thus the child was tolerant to that specificity. The Child did not react against the DRB!*11:04 allele in the parathyroid donor because it was so closely related to the 111:01 allele in the mother. Regarding Class I, the B*35:03 and C*04:01 alleles, the thymus had not deleted thymocytes reactive to those alleles because they were not expressed either in the recipient, not in the thymus donor. Ten years after receiving the implant, the child received the MMR vaccine. Measles is a very strong stimulus. Approximately one third of circulating T cells have inherent alloreactivity. When recipient CD8 T cells were exposed to measles vaccine, they reacted against the parathryoid and destroyed it quickly. This patient's course shows that both Class I and Class II alleles in the solid organ recipient must be expressed in the recipient or in the thymus donor for their to be tolerance to the solid organ. This child is thriving with good T cell numbers and function and normal immunoglobulin levels. Patient 1, however, remains on calcium, as the parental parathyroid gland was rejected.

Example 6. Evaluation of Architecture and Viability of Freshly Cultured NHP Thymic Tissue To develop a cultured thymic tissue implantation (CTT) platform in non-human primates (NHPs), NHP donor thymus is resected and cultured, and evaluated for normal tissue appearance and structure.

Methods

Figure 36:
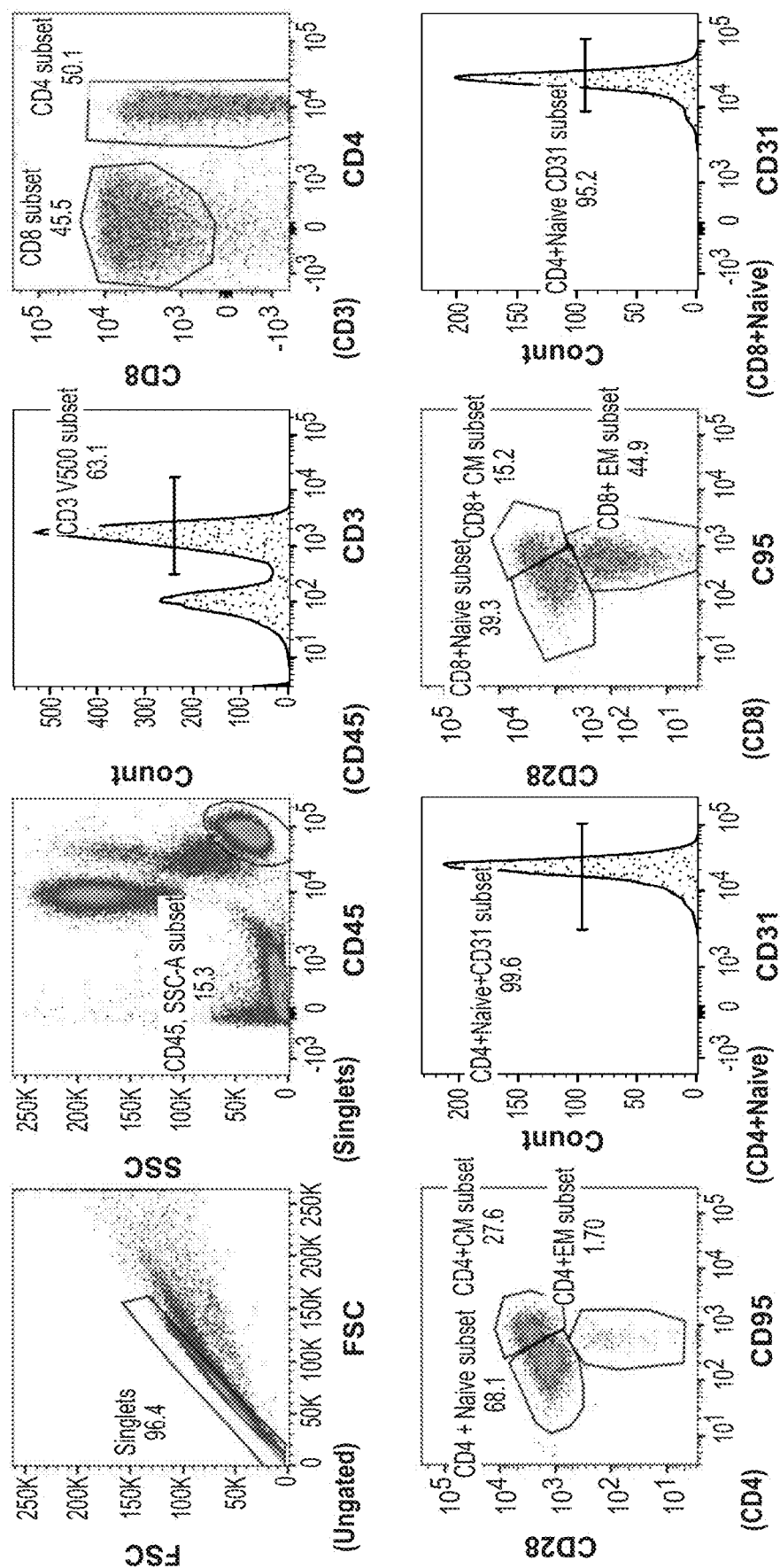
FIG. 36 shows graphs of results from flow cytometry experiments that describe the general gating strategy for identifying recent thymic emigrants (RTEs). Nonhuman primate peripheral blood mononuclear cells are collected and analyzed using polychromatic flow cytometry. The first step is identification of single cells in the first panel top row. The "Singlets" are used to identify the lymphocytes (low SSC, side scatter, and high CD45) in the second panel in top row. The CD3 T cells in the lymphocytes are identified in the 3rd panel, in top row. The CD4 and CD8 cells are gated off the CD3 cells as shown in the 4th panel of the top row. In the bottom row, 1st panel, CD28 and CD95 are used to identify, using the CD4 gate, the CD4+ naïve subset, the central memory subset and the effector memory subset. In the 2nd panel of the bottom row, CD31 is used to show the percentage of CD4+ naïve cells that are RTEs. The 3rd and fourth panels on the bottom row show the same approach to RTEs but for CD8 naïve T cells. As can be seen, the RTEs are 99.6% and 95.2% of the CD4 and CD8 naïve subsets.

Thymus is surgically resected from rhesus macaque NHPs through a limited upper sternotomy, sliced, and cultured identically to the established pediatric techniques described herein above. Two antibody panels have been developed for experimental and tissue assessment purposes. One panel, comprising CD3, CD4, CD8, CD28, CD31, CD45RA, and CD197, is used to assess the presence of recent thymic emigrants (RTEs) and naïve T cells in the blood via flow cytometry (FIG. 36). A second antibody panel comprising AE/AE3 (pan-cytokeratin), cytokeratin (CK) 14, Ki-67 (proliferation), CD3 (T-cell content), and CCL21 (chemokine production) is used for immunohistochemical (IHC) assessment of harvested fresh thymus, cultured thymus, and thymus graft biopsies that are obtained as described herein above and in Examples 8 and 9 below. The IHC antibody panel on fresh NHP thymus is performed to document the adequacy of the tissue. Lot release criteria established for clinical samples, as described herein above, is used for the cultured thymus tissue prior to implantation in the thigh muscle. Evaluation of biopsies of the grafted thymus tissue as shown in FIG. 33A-J also uses the criteria established for clinical samples.

Results

Figure 33:
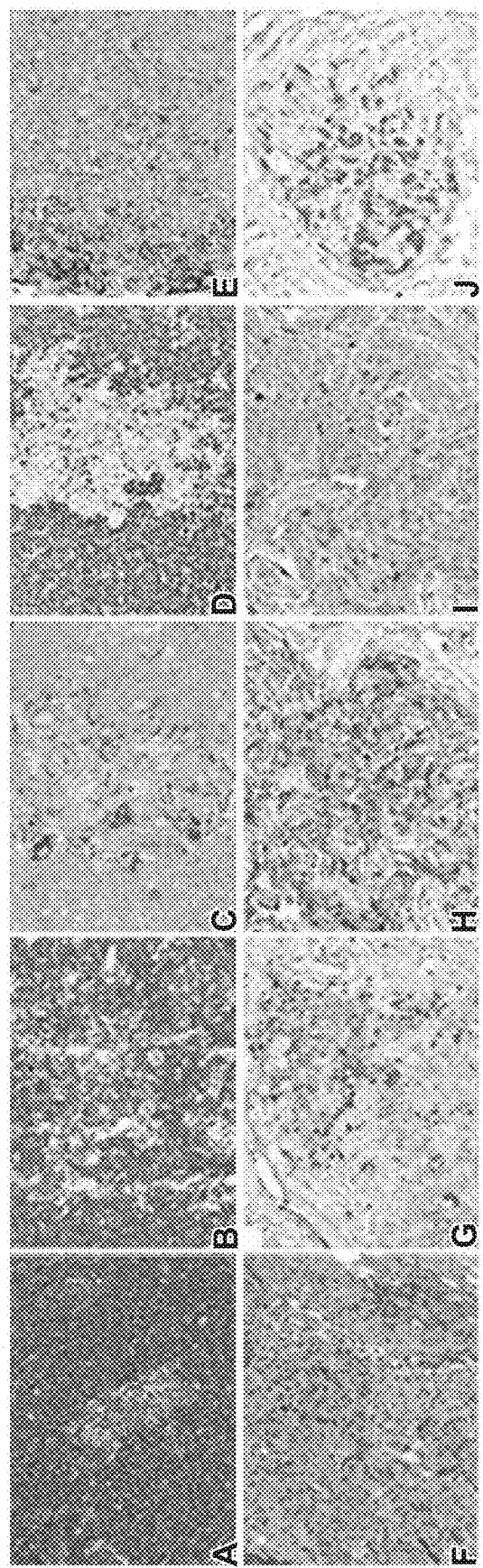
FIGS. 33A-J present photomicrographs of immunohistochemical assessment of fresh and cultured non-human primate (NHP) thymus tissue from an 8-month old NHP. The top row is NHP thymus on the day of harvest and the bottom row is NHP thymus after culture for 12 days. The tissue was stained with hematoxylin and eosin (FIG. 33A and FIG. 33F), CD3 (FIG. 33B and FIG. 33G), pan cytokeratin (CK) antibody AE1/AE3 (FIG. 33C and FIG. 33H), Ki-67 (FIG. 33D and FIG. 33I), and CK14 (FIG. 33E and FIG. 33J). All pictures are at 20× magnification.

As shown in FIG. 33A-E, fresh NHP thymus sections closely resemble fresh human thymus sections. FIG. 33A shows normal NHP thymus morphology: densely packed cortical thymocytes are seen with a central medulla, and less densely packed, with a Hassall body in the center. FIG. 33B shows CD3 staining on T cells throughout the thymus. Viable T cells appear as brown rings. FIG. 33C shows cytokeratin mostly seen in the medulla as lacy extensions and Hassall bodies. The cytokeratin is not seen in the cortex of fresh thymus because there are so many thymocytes. FIG. 33D shows brown staining reflecting Ki-67 antigen in the cortex. The Ki-67 molecule indicates nuclear proliferation. This panel shows the classic appearance of replicating thymocytes in the cortex with little in the medulla. FIG. 33E shows CK14 in the cortex and less in the medulla. The staining in FIG. 33F-J after 12 days of culture, is dramatically different from that in FIG. 33A-E, and is remarkably similar to findings in human samples after in vitro culture. FIG. 33F shows dramatic loss of thymocytes, with retained viable thymic epithelial cells. FIG. 33G demonstrates marked depletion of T cells (CD3+). The antigen targeted is CD3 epsilon which remains quite stable even after T cell death. The dead T cells have CD3 staining throughout, not just on the cell surface (which appears as a ring in the image). There are some viable T cells in the section, but very few compared to the day of harvest. FIG. 33H is stained with the AE1/AE3 cytokeratin antibody. The cytokeratin-positive epithelial cells are viable with normal nuclei. They are partially condensed because there are very few T cells left in the thymus. FIG. 33I is stained with Ki-67. There are essentially no proliferating thymocytes in this section. The cortical thymocytes have mostly died. FIG. 33J has viable CK14-positive epithelial cells. These epithelial cells have space between them to surround early thymic progenitors that will arrive from the bone marrow after CTT. The 12 days of culture is within the range used for clinical CTT (12-21 days).

Example 7. Evaluation of Architecture and Viability of Cryopreserved NHP Thymic Tissue Cryopreservation is needed for the clinical application of induction of tolerance for cultured thymus tissue, in order to provide backup thymus tissue. Approximately half of the cultured thymus is cryopreserved for future use in the event of post-transplantation rejection or damage to the CTT by the high-dose steroid(s) used to reverse the heart rejection episode.

Methods

For cryopreservation, NHP thymus tissue is cultured as described in Example 6. After 12 days of culture, the NHP thymic tissue is cryopreserved per standard methods in the art. In the experiment shown in FIG. 34A-P, the tissue was cryopreserved for 35 days, however, the cryopreserved time can extend to years. In this experiment the cryopreserved tissue was then thawed, formalin fixed, and paraffin embedded. Immunohistochemistry was performed using the same antibody panel as in Example 6.

Results

Figure 34L:
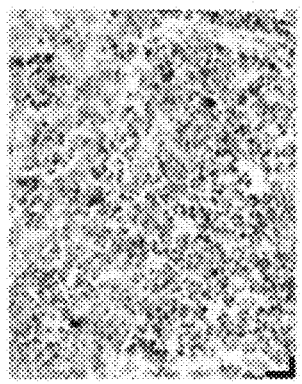
FIG. 34L is similar to panel FIG. 34K in having very few T cells. The fourth row FIG. 34M, FIG. 34N, FIG. 34O
Figure 34K:
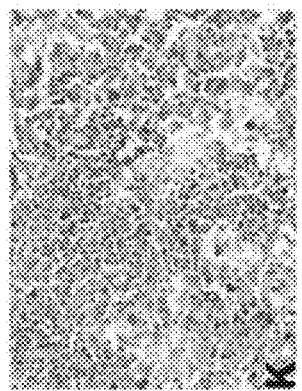
FIGS. 34A-P present analysis of cryopreserved cultured thymus tissue from an 8-month-old non-human primate (NHP) after 12 days of culture. The top row is cytokeratin at harvest (FIG. 34A), day 6 of culture (FIG. 34B), day 12 of culture (FIG. 34C), and after 12 days of culture followed by 35 days cryopreservation then thawing for the photo (FIG. 34D). The cytokeratin (AE1/AE3) in FIG. 34D resembles the cytokeratin in FIG. 34C. The second row shows CK14 staining with the same time points in FIG. 34E (harvest), FIG. 34F (day 6 of culture), FIG. 34G (day 12 of culture) and FIG. 34H (after 12 days of culture followed by 35 days of cryopreservation then thawing), respectively. The CK14 in FIG. 34H is very similar to that in panel FIG. 34G. The third row shows CD3 staining in FIG. 34I, FIG. 34J, FIG. 34K and FIG. 34L at the same time points, which has the expected loss of viable T cells through time. Panel
Figure 34J:
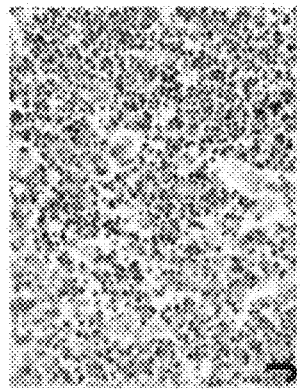
Figure 34I:
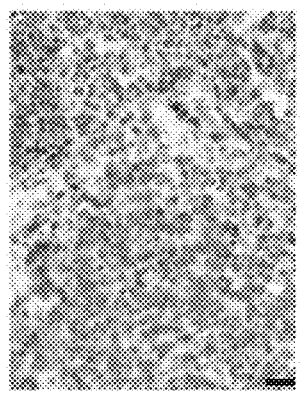
Figure 34P:
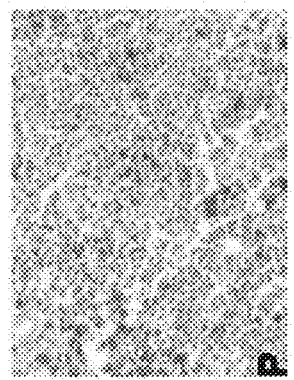
Figure 34O:
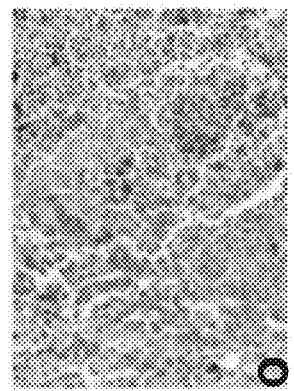
Figure 34N:
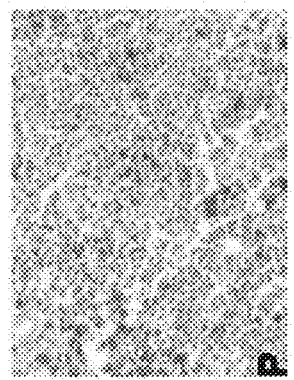
Figure 34M:
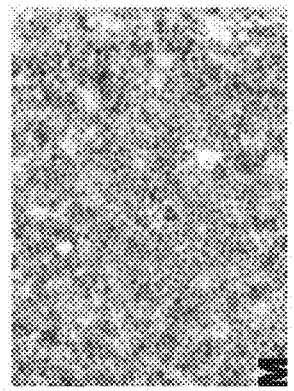

The data shown in FIG. 34A-P highlight the important comparison between the tissue cultured for 12 days (the minimum allowed per protocol; shown in FIG. 34C, FIG. 34G, FIG. 34K, and FIG. 34O), and the tissue cultured for 12 days and then cryopreserved for 35 days (shown in FIG. 34D, FIG. 34H, FIG. 34L, and FIG. 34P). Comparing the cytokeratin in FIG. 34C with that in FIG. 34D shows that FIG. 34C demonstrates a lacier pattern than FIG. 34D, and that the cytokeratin in FIG. 34D is slightly condensed. CK14 cytokeratin staining in FIGS. 34G and 34H is quite similar. The CD3 staining in FIG. 34K and FIG. 34L is also very similar. Ki-67 staining is absent in both FIG. 34O and FIG. 34P, consistent with the findings in FIG. 33I. The thymus tissue cultured for 12 days and the cryopreserved thymus tissue both met lot release criteria for clinical samples.

Example 8. Assessment of Successful Engraftment of Cultured Thymic Tissue in a CMV-Free NHP Model These experiments involve performing heart transplant and CTT in an NHP (rhesus macaque) model with the goal of establishing tolerance of the transplanted heart, and achieving long-term rejection-free graft survival without the need for ongoing immunosuppressive drugs. Animals will be maximally mismatched.

Methods

As an overview of the experiment, maximally MHC-mismatched CMV-free rhesus macaques are used. Recipient animals (Y) undergo complete thymectomy. Donor animals (X) donate both cultured thymic tissue and a heart placed in a heterotopic position into recipient Y (first Tx and second Tx). Immunosuppressive drugs are then withdrawn and donor-specific tolerance is demonstrated by i) continued beating of the donor heart, ii) tolerance to the donor in MLR with reactivity against third party and iii) rejection of skin transplant from $3^{rd}$ party donor animal Z (third Tx).

All experimental NHPs are males. Given the possible interference of commonly used antiviral prophylactic drugs with thymopoiesis, CMV seronegative NHPs raised in a specific pathogen-free colony at the University of California at Davis are used. Based on the experience of other investigators at Duke, involved with non-human primate transplant research, meaningful analysis can come from a 3 recipient animals. This low number is because tolerance should be present in every recipient animal (excepting technical difficulties).

Approximately one month prior to transplantation, the recipient animal undergoes complete thymectomy via a partial sternotomy in preparation for eventual donor thymus transplant. The recipient's T cells are depleted with rhesus-specific anti-thymocyte globulin (rhATG). The animal is fully recovered and undergoes weekly flow cytometry until RTEs are no longer detectable (estimated 2-3 weeks) in the peripheral blood, thus indicating a complete native thymectomy. The flow cytometry panel identifies CD4+ RTEs that are CD3+, CD4+CD45+CD28+CD95−, and CD31+. Refer to the gating strategy as shown in FIG. 36. See the following references for exemplary experimental protocols Markert M L, Sarzotti M, Ozaki D A, Sempowski G D, Rhein M E, Hale L P, et al. *Thymic transplantation in complete DiGeorge syndrome: Immunologic and safety evaluation in twelve patients. Blood.* 2003; 102: 1121-1130, Markert M L, Alexieff M J, Li J, Sarzotti M, Ozaki D A, Devlin B H, et al. *Postnatal thymus transplantation with immunosuppression as treatment for DiGeorge syndrome. Blood.* 2004; 104: 2574-2581, Markert M L, Devlin B H, McCarthy E A. *Thymus transplantation. Clin Immunol.* 2010; 135: 236-246.

Recipient animals carrying MAMU A01 were selected because there is an antibody to that allele for flow cytometry, allowing for easy distinction of RTEs of recipient origin. The donors will not express MAMU A01, excepting when the initial thymectomy in the recipient is not complete; then the original recipient will become the donor and the original donor will become the recipient.

Stage 1: Please refer to FIG. 38 for a detailed outline and time line for the experiment performed in Example 8.

Blood from donor NHP (MAMU-A:01 negative and recipient NHP (MAMU-A:01 positive) is tested by flow cytometry, CBC differential (CBC diff), blood chemistry and CMV levels are determined. Similar testing will be performed in a control NHP. After confirming that the donor and recipient have positive mixed lymphocyte reactions (MLRs) to each other in Stage 1, the donor NHP donates both thymic tissue, and later a heart to a single recipient (refer to Stage 4 described below).

Stage 2: A thymectomy is performed on the recipient NHP on week 1, day 3 of Stage 2 and the recipient NHP thymus is cultured for 12 days, as described elsewhere in this specification. The recipient CTT is then cryopreserved on day 12 of the culturing.

During Stage 2, CMV levels of the recipient are determined in weekly. A DSA (2 ml) blood sample for storage is taken in week 2. CBC diff is measured on day 1 of week 3 in the recipient NHP. Flow cytometry is performed weekly in the donor NHP until recipient shows no RTEs. Flow cytometry in the recipient NHP is performed on day 1 of week 3 of Stage 2 to show no RTE 3 in the recipient NHP. If positive for RTEs, the flow cytometry is continued in weeks 4 and 5, if needed. CBC, levels CMV are determined in the donor NHP at the same time. Weekly CBC differential, CMC levels and flow cytometry are also monitored until the recipient NHP has no RTEs. When no RTEs are found, the experiment proceeds to Stage 3.

If the thymectomy is insufficient because the recipient continues to demonstrate recent thymic emigrants (RTE), the NHP will be deemed to have an incomplete thymectomy. The recipient and donor will then be switched, with the donor being MAMU-A:01 positive and the recipient MAMU-A:01 negative. CMV levels are monitored in the control NHP in Stage 2.

Stage 3: Stage 3 commences with the administration of tacrolimus every twelve hours to the recipient NHP starting on week 1, day 1 of Stage 3. On day 3, a thymectomy is performed on the donor. The removed donor thymus is cultured, as elsewhere described in the specification and prior Examples, for a period of 12 days when half is cryopreserved. The other half can be cultured through day 21 and implanted in the recipient's quadriceps any day from day 12 to 21 of culturing In Stage 3.

To summarize, the recipient undergoes native thymectomy approximately one to two months prior to cultured donor thymus tissue implantation in the quadriceps (and subsequent heart transplantation). The thymectomy must be confirmed to be complete by the lack of recent thymic emigrants (RTEs) in peripheral blood. The recipient's immunosuppressive medications are eventually (after CD4 naïve T cells are 15% or greater), completely withdrawn and donor-specific tolerance is demonstrated using third party MLRs and skin transplants, which should demonstrate both immune competence against third party donor tissue in the setting of specific tolerance of tissue from the thymus and heart donor animal.

Chemistry, CMV levels are measured in the donor NHP throughout Stage 3 until a non-survival heart transplant takes place in Stage 4. CBC diff, CMC levels, and blood chemistry are performed in the recipient NHP in week 1 of Stage 3. A blood sample is drawn for storage. Flow cytometry is performed on day 4 of week 2 to document T cell depletion. CBC diff, tacrolimus levels and CMV levels are measured in week 2 of Stage 3.

Flow cytometry, CBC diff and CMV levels are monitored in the control NHP periodically throughout Stages 3 and 4, until a skin graft is obtained in week 10 of Stage 4.

On Stage 3, day 1 of week 3, approximately half of the CTT is then implanted into the quadriceps muscle of the recipient NHP and the remainder is cryopreserved. The procedure is done per human protocol. Markert M L, Devlin B H. Thymic reconstitution. In: Rich R R, Shearer W T, Fleischer T, Schroeder H W, Weyand C M, Frew A, editors. Clinical Immunology 3rd edition. Edinburgh: Elsevier; pp. 2008. pp. 1253-1261. Skin biopsies are also performed. In Stage 3, on day 3 of week 10, a biopsy of the CTT implant is performed and the Cryo-CTT is then implanted into the quadriceps muscle of the other leg approximately 7 weeks after the first CTT implant to increase the chance of engraftment ad to assess cryopreserved CTT potency. Both freshly cultured and cryopreserved implanted thymic tissue is biopsied approximately 6 weeks after the implantation to verify viability and normal tissue architecture.

The recipient NHP is administered tacrolimus BID starting on day 1 of week 1.

ATG is started in the recipient in Stage 3, on day 1 of week 2. On day 3 of week 2, flow cytometry is performed to show T cell depletion. The last dose of ATG is administered to the recipient on day 5 of week 2, i.e., 2 days rest before CTT implant. Tacrolimus is continued throughout Stage 3 until naïve T cells <15% are observed. The experiment proceeds to Stage 4 if T cells comprise >15% naïve T cells. If naïve T cells are <15% the experiment proceeds to Stage 5. Tacrolimus levels, CMV levels, CBC diff are monitored throughout Stage 3 and blood samples are preserved for future analysis. Tacrolimus levels, CMV levels, CMC diff, creatinine and ALT levels are measured weekly during Stage 3 in the recipient and Control NHP.

Stage 4: A non-survival heart donation is performed on the donor NHP in on day 1 of week 4 of Stage 4 (as previously mentioned). A heterotopic heart transplant from the donor NHP is performed on day 1 of week 4 of Stage 4. Donor blood is used for transfusion into the recipient NHP, if needed. The heart beat in the recipient is monitored twice weekly for two weeks and then weekly throughout Stage 4 by ECHO cardiogram. If the heart stops beating, the recipient NHP is to be sacrificed.

On days 1, 2, 5 and 7 of week 1 the recipient NHP is weighed and the thymus biopsy is checked.

In Stage 4, on day 1 of week 4, a biopsy is performed of Cryo-CTT at the time of the heart transplantation. Tacrolimus levels, CMV levels and CBC diff is performed throughout Stage 4 in the recipient NHP on a weekly basis.

In week 10 of Stage 4, MLR is performed using cryopreserved blood from the heart donor, recipient blood and third party blood. The recipient should be tolerant to the donor and self and reject third party skin tissue. Third party fresh NHP skin tissue and recipient NHP skin tissue will be grafted on recipient. This is done in week 10 of Stage 4. Monitoring of the recipient NHP by flow cytometry, CBC diff, and CMV levels continue monthly (with the control NHP as an assay control.

The recipient NHP may be sacrificed 180 days after heart transplantation. Pathology will be performed on the transplanted heart and the native heart in the recipient. The donor cultured and cryopreserved-cultured thymus transplants will be analyzed by IHC as well as the thoracic tissue, also by IHC. Of note, if the donor heart is beating, the PI has the option of allowing the animal to live longer to see how long the donor heart will continue to beat.

Stage 5: As noted previously, if naïve T cells in the recipient do not reach 15% in Stage 3, tacrolimus will be continued throughout Stages 4 and 5. Once naïve T cells reach >15%, the experiment will proceed to Stage 4. During Stage 5, CBC diff, tacrolimus levels, blood chemistry and CMV levels are monitored.

Stage 6: If naïve T cells in Stage 5 are <10%, the experiment proceeds to Stage 6. During Stage 6, tacrolimus is weaned off in the recipient NHP over a period of 4 weeks. During that period, flow cytometry, CBC diff, CMV levels and blood chemistry measurements are obtained and blood samples are saved. Cryo-CTT from the recipient is transplanted, and in week 9 of Stage 6, a biopsy of the Cryo-CTT is performed and the NHP is sacrificed and its organs are harvested. The purpose is to show that the native thymus can successfully function in the recipient (thus, technical issues are not the reason for failure of the donor thymus tissue transplant. Flow cytometry, CBC diff and CMV levels continue to be monitored in the control NHP.

Figure 35:
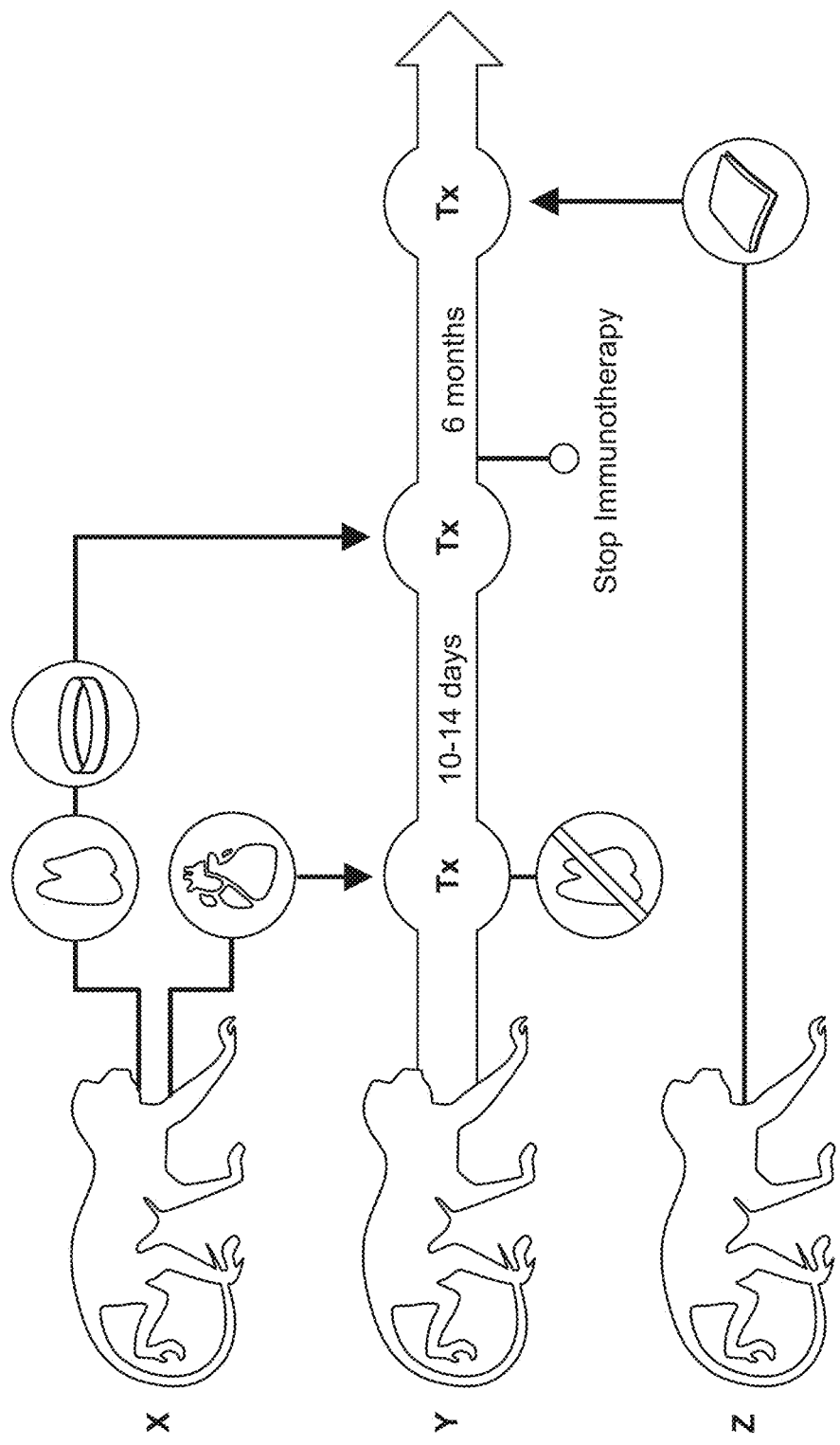
FIG. 35 presents a schematic diagram of the experimental transplantation strategy using maximally MHC-mismatched CMV-free rhesus macaques. Recipient animals (Y) undergo complete thymectomy. Donor animals (X) donate both cultured thymic tissue and a heart placed in a heterotopic position into recipient Y (first Tx and second Tx). Immunosuppressive drugs are then withdrawn and donor-specific tolerance is demonstrated by i) continued beating of the donor heart, ii) tolerance to the donor in nMLR with reactivity against third party and iii) rejection of skin transplant from $3^{rd}$ party donor animal Z (third Tx).

FIG. 35 shows a schematic of the overall experimental design.

Example 9. Assessment of the Ability of CIT to Induce Tolerance to a Same Donor Heart Transplant This example performed in NHPs parallels the disclosed surgical procedures and treatments set forth for pediatric heart transplants in human subjects, as disclosed elsewhere in this specification.

Methods

Stage 1: Please refer to FIG. 39 for a detailed outline and time line for the experiment performed in Example 9.

Recipient and donor NHP blood testing are performed in Stage 1. Blood from donor NHP (MAMU-A:01 negative and recipient NHP (MAMU-A:01 positive) is tested by flow cytometry, CBC differential (CBC diff), blood chemistry and CMV levels are determined. Similar testing will be performed in a control NHP. After confirming that the donor and recipient have positive mixed lymphocyte reactions (MLRs) to each other in Stage 1, the donor NHP donates both thymic tissue, and later a heart to a single recipient (refer to Stage 4 described below).

Stage 2: On day 3 of week 1 in Stage 2, a thymectomy and skin biopsies are surgically performed in the recipient Mamu-A:01 positive recipient NHP. The recipient thymus is cultured from week 1, day 3 to Week 3, day 1. Skin from the skin biopsies is cryopreserved on day 3 of week 1. Flow cytometry is performed weekly on the recipient NHP until no RTEs are shown. Id negative on day 1 of week 2 of Stage 2, it RTEs are negative, the experiment proceeds to Stage 3. CMV levels are monitored biweekly and a DSA (5 ml) is taken in week 2 of Stage 2.

Stage 3: A thymectomy and skin biopsies are performed in the donor NHP on day 3 of week 1. The donor thymus is cultured from 12 days (from day 3 of week 1 to day 1 of week 3). One-half of the cultured thymus will be implanted and the remaining one-half will be cryopreserved. No other procedures are performed on the donor NHP until Stage 4.

The procedures performed on the recipient NHP include a cultured thymus implant from the donor to the recipient on day 1 of week 3. At that time tacrolimus and MMF are started on day 1 of week 3. Tacrolimus and MMF are continued throughout Stage 3. ATG is also administered on day 1 of week 3 for five days to deplete T cells. Also during Stage 3, recipient blood testing is regularly performed. Tacrolimus levels are monitored weekly as well as CMV levels, DSA is tested in week 3, 7 and 16. CBC diff is alternated biweekly with creatinine and ALT in alternating weeks.

Tacrolimus and MMF are continued in Stage 3 until naïve T cells are >15%, then the experiment proceeds to Stage 4. Alternatively, if naïve T cells do not reach 15%, the experiment proceeds to Stage 5 (described below).

Stage 4 entails MLR determination of the donor, recipient and Control NHPs in week 1 and week 6. If MLR shows tolerance to donor and response to third party (Control), the experiment proceeds to week 2. If no tolerance is shown, the experiment proceeds to Stage 6. The purpose is to show that the recipient is tolerant of the donor and the donor is still reactive against the recipient (which should be the case even without thymus in the donor).

Flow cytometry is performed in week 2 to watch for thymus rejection, and is repeated weekly. Tacrolimus is then continued until it is weaned over 4 weeks starting in week 9.

If the experiment proceeds to week 2 tacrolimus is continued and MMF is lowered to BID administration and then daily over weeks 2 and 3, and then stopped.

In week 7, a non-survival heart donation and skin biopsies are performed in the donor NHP and blood is saved for transfusion into the recipient NHP, if necessary. A heterotopic heart transplant is performed in the recipient NHP on day 1 of week 7. On the day of transplantation, the donor heart is procured via a median sternotomy after general anesthesia induction and endotracheal intubation. Concurrently, the recipient NHP is prepared and undergoes general anesthesia induction and endotracheal intubation. The abdomen is prepared and entered via a median laparotomy. The NHP is an administered induction immunotherapy with intravenous methylprednisolone given as a single bolus at a dose of 20 mg/kg. The abdominal aorta and inferior vena cava are secured below the renal arteries and prepared for the anastomosis of the donor allograft. The aorta and inferior vena cava are then clamped and a 5000 unit heparin intravenous bolus administered. The pulmonary artery from the allograft is anastomosed in an end to side fashion to the inferior vena cava, and the ascending aorta from the allograft anastomosed in a similar fashion to the infra-renal abdominal aorta. After de-airing, and ensuring sinus rhythm, the abdomen is closed. Cardioversion is used as needed using internal pads.

In the postoperative period, graft function in the transplanted heart is assessed by regular palpation and by weekly echocardiogram for any signs of rejection (decreased contractility, arrhythmia, etc.). Both immunosuppressive drugs (tacrolimus and mycophenolate mofetil) are weaned over a period of 4 to 8 weeks. Based on the rodent model work described in preceding Examples, normal graft function is expected after withdrawal of immunosuppression, indicating tolerance of the transplanted heart. Several weeks after the full withdrawal of immunosuppression, the recipient undergoes skin transplantation from a third-party NHP that is also maximally MHC mismatched. Around the same time, the recipient undergoes MLR testing using cells from both the thymus and heart donor as well as from the third party (Control) NHP. These tests are used to demonstrate true tolerance rather than simply functional tolerance: recipient animals should mount an immune response measured by MLR to the third party donor but not to their thymic tissue and heart donor. Likewise, continued tolerance of the donor heart is expected, along with rejection of the third party skin transplant. At the conclusion of the experiments (6 months without immunosuppression or death), or with signs of significant graft rejection (complete cessation of activity), the allograft, native heart, and samples from other organs (liver, lungs, spleen, psoas muscle) are procured. The site of cultured thymus tissue transplantation is also harvested for analysis. Tissue histology is performed to identify evidence of cellular or antibody mediated rejection. The architecture and viability of transplanted thymic tissue are assessed by immunohistochemistry. Finally, flow cytometry is used to characterize lymphocyte phenotypes in the spleen, lymph nodes, bone marrow, and peripheral blood.

The Cryo-CTT is biopsied at this time on day 3 of week 10. The transplanted heart is monitored for beating in weeks 8 through 12. If the heart stops beating, the recipient NHP is sacrificed.

In week 12, MLR is performed on a skin graft from a skin biopsy of the donor, recipient, and Control NHP. If the heart is still beating, skin graphs are made of fresh recipient skin, cryopreserved recipient skin, cryopreserved donor skin and fresh and cryopreserved third party (Control) skin in week 12.

During Stage 4, tacrolimus levels are regularly monitored. CMV levels are measured biweekly alternating with flow cytometry measurements and CBC diff measurements. ALT, creatinine and DSA are also periodically monitored. The experiment is terminated 180 days after the heterotopic heart transplant and the recipient NHP is sacrificed and the heart is harvested for pathology. Recipient and donor thymus are sent for IHC and thoracic tissue is also procured and analyzed by IHC.

Stage 5: If continued immunosuppression is needed because naïve T cells are not >15%, return to Stage 4 (although MMF has already been weaned). Tacrolimus is continued until naïve T cells are >15%. If naïve T cells are >10%, return to Stage 4. If naïve T cells are <10%, go to Stage 6. During Stage 5, tacrolimus levels are monitored weekly, and CMV levels and CBC diff, creatinine, and ALT levels are monitored biweekly on an alternating basis. Flow cytometry and CBC diff are monitored in Control NHP on a biweekly basis.

Stage 6: Cryo-CTT from the recipient on day 1 of week 1 is grafted to the recipient to show that the thymus implant may be made in an NHP. A biopsy is performed in the recipient Cryo-CTT graft when the NHP is sacrificed. Flow cytometry and CBC diff levels are measured biweekly in the Control NHPs during Stage 6.

As in the preceding Stage flow cytometry, DSA and CBC diff levels are monitored biweekly alternating with determination of CMC levels, creatinine and ALT levels.

Example 10. Assessment of Architecture, Viability and Functionality of Cultured Human Thymic Tissue Across Multiple Age Ranges to Define the Culturability of Human Thymic Tissue Across Multiple Age Ranges Developing rational inclusion criteria for expanding the human thymus donor pool requires determining the culturability and functional and molecular characteristics of donor human thymus tissues across the broad age range of potential cardiac donors.

The human thymus increases steadily in size in infancy, stabilizes, and eventually begins to involute. Despite this well-known process of age-related involution, it has been shown that the thymus of older children and adults may continue to retain substantial T cell production capacity into the 8th decade, Hong R, Moore, A L. 1996, "Organ culture for thymus transplantation," Transplantation, 61: 444-448; Rice H E, Skinner M A, Mahaffey S M, Oldham K T, Ing R J, Hale L P, et al., 2004, "Thymic transplantation for complete DiGeorge syndrome: medical and surgical considerations," J Pediatr Surg. 2004; 39: 1607-1615. The rationale for these experiments is to determine the donor age ranges that can potentially provide thymus tissues suitable for transplantation. Human thymus implanted to date has come from donors ≤9 months of age. At that age, the thymus is composed almost entirely of cortical and medullary tissue that is active in thymopoiesis. However, because few infant donors are available, most heart transplant recipients receive hearts from older donors. Although adult thymus continues to retain substantial T cell production capacity, thymus derived from older donors typically has less area active in thymopoiesis, Id.; Taub D D, Longo D L, 2009, "Insights into thymic aging and regeneration," Trends Immunol. 30(7):366-373, with correspondingly lower numbers of recently produced naïve T cells in the peripheral blood. Hong R, Moore, A L., 1996, "Organ culture for thymus transplantation," *Transplantation,* 61: 444-448, Rice H E et al, 2004, *J Pediatr Surg.* 2004; 39: 1607-1615; Taub D D, Longo D L, 2009, *Trends Immunol.* 30(7):366-373. Thus, these studies are necessary for determining the donor age range within which thymus retains appropriate functional characteristics to be safe and effective if cultured then co-transplanted into cardiac allograft recipients.

Methods

Thymus tissue is collected prospectively from cardiac surgery patients across three distinct age groups: 9 months to 9 years; 10 years to 25 years; and 26 years to 49 years, for a total of 30 samples following informed consent. As part of the preliminary studies for this project, novel custom instrumentation for slicing fatty tissues was developed. Traditional slicing, with a Stadie-Riggs microtome, of fatty tissues from older thymuses does not yield slices that can be assessed by immunohistochemistry. For fatty thymus, therefore, single edged razor blades (approximately 10) are wired together and sterilized. The distance between blades is approximately 1 mm. Pieces of thymus tissue approximately 1 cm×1 cm×1 cm are put in the bottom of a sterile tissue culture dish. The bound razor blades are pressed into the thymus tissue. Individual slices are removed from the between the razor blades and used for staining. Slicing and culture of human thymus tissues for 21 days is carried out as described in preceding Examples. Tissue slices and spent media from days 1, 5, 12, and 21 are frozen for further analysis. Tissue slices from day 0 and day 21 are also processed into formalin-fixed and paraffin-embedded (FFPE) blocks to facilitate immunohistologic studies, as described below.

Figure 37:
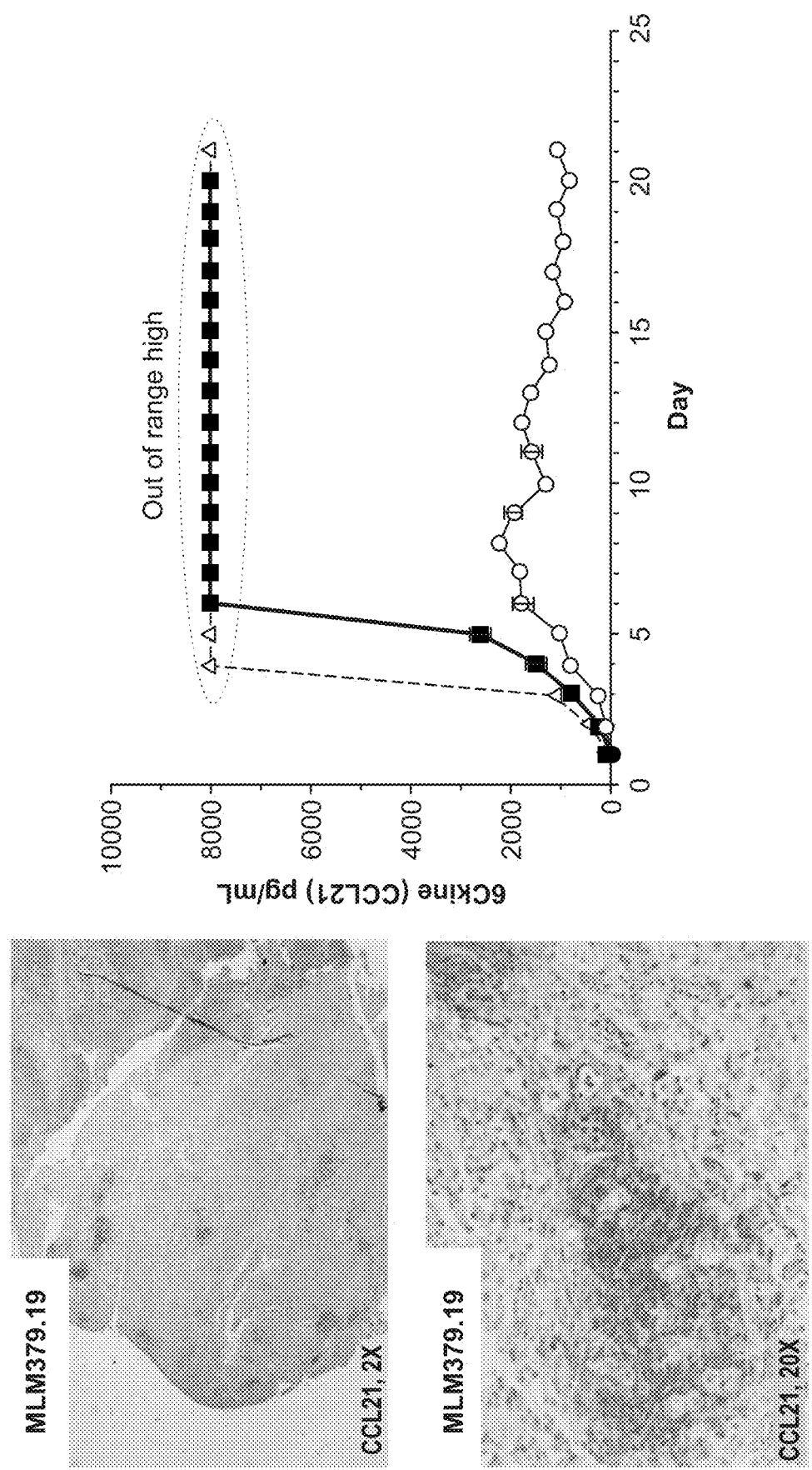
FIG. 37 presents photomicrographic images and a graph of CCL21 assessment in cultured infant thymus. CCL21 is produced at high levels by cultured infant thymus. Immunohistochemical reactivity with CCL21 antibody (Ab) (brown staining) on day 16 of culture is shown in the left panels (upper left panel, 2× magnification; lower left panel, 20× magnification). A corresponding time course measuring daily CCL21 secretion into culture media is shown on the right for 3 infant thymus cultures (R&D Systems Duo-Set ELISA). Thus, the cultured thymus tissue can produce a functionally important biomolecule, CCL21, the chemokine responsible for attracting immature thymocyte precursors to the thymus.

Analysis begins with the FFPE blocks from days 0 and 21, using hematoxylin and eosin (H&E) stained sections as well as immunohistochemistry (IHC) for cytokeratin (AE/AE3 cocktail), cytokeratin (CK) 14, proliferation (Ki-67), T cell content (CD3), and production of chemokine (CCL21). Histologic characteristics of acceptable donor thymus on day 0 include an organized thymic epithelial (TE) network, presence of TE cells that express CK14 as a marker of repopulating potential, presence of immature thymocytes and Hassall bodies as a marker of thymopoiesis at the time of procurement, and >90% intact nuclei as an indicator of tissue viability. Cultured thymus slices should similarly demonstrate thymic epithelial cell viability, maintenance of TE architecture, marked depletion of viable thymocytes, and production of functionally important biomolecules, including high production of CCL21, the chemokine responsible for attracting immature thymocyte precursors to the thymus. Production of CCL21 by thymus slices is assessed via IHC of FFPE slices as well as enzyme immunoassay of spent media (FIG. 37).

Because the thymus tissues used may exhibit varying degrees of age-related atrophy, determining baseline thymus function is essential. Baseline thymus function is determined by image analysis of scanned tissue sections from day 0, as previously described (Hale L P, Markert ML, 2004. "Corticosteroids regulate epithelial cell differentiation and Hassall body formation in the human thymus," *J Immunol.* 2004; 172: 617-624). In addition, thymic output of naïve T cells is determined using donor peripheral blood. Peripheral blood mononuclear cells are purified and preserved; T cell phenotype is determined by 10-color flow cytometry using the following markers: viability, CD3, CD4, CD8, CD19, CD16+CD56, CD45RA, CD57, and CD197. Signal joint T-cell receptor rearrangement excision circles (sjTRECs) present in peripheral blood T cells are quantitated as a marker for thymic origin Lee E N, Park J K, Lee J-R, Oh S-O, Baek S-Y, Kim B-S, et al., 2011, "Characterization of the expression of cytokeratins 5, 8, and 14 in mouse thymic epithelial cells during 2011; 44: 14-24. thymus regeneration following acute thymic involution," *Anat Cell Biol.*

Example 11. Histopathologic Assessment of Cultured Human Thymus

These experiments were performed to assess and describe the histopathologic changes that occur in human thymus slices when cultured according to protocols used for implanted tissues. Understanding these changes can potentially lead to the development and validation of histopathologic criteria for prospective assessment of the quality of cultured thymus slices prior to implantation, based on characteristics of tissues that have successfully generated immune reconstitution in prior recipients Markert M L, Devlin B H, McCarthy E A., 2010, "Thymus transplantation," *Clin Immunol.* 2010; 135: 236-246. Taken together, these results can be used to develop diagnostic criteria based on structural features of the tissue identifiable via hematoxylin and eosin staining and cytokeratin immunohistochemistry that can potentially serve to evaluate the quality of slices used for implanted.

Materials and Methods

Thymic tissue was obtained from immunocompetent infant donors <9 months of age who were undergoing corrective cardiac surgery where removal of a portion of the thymus was routinely required to facilitate the cardiac repair. The parent(s) of each donor provided written informed consent to allow any thymic tissue that was removed and otherwise would be discarded to be potentially used for implantation or research. These studies were approved by the Institutional Review Board of Duke University Medical Center. The donor thymus was sliced and cultured in a Good Manufacturing Process (GMP)-compliant cell manufacturing laboratory for up to 21 days before release to the operating room for surgical implantation into the muscle of the recipient. The details of the donor qualification, culture, and surgical implantation processes have been described elsewhere Markert M L, Sarzotti M, Ozaki D A, Sempowski G D, Rhein M E, Hale L P, et al., 2003, "Thymic transplantation in complete DiGeorge syndrome: Immunologic and safety evaluation in twelve patients," *Blood,* 102: 1121-1130. Markert M L, Alexieff M J, Li J, Sarzotti M, Ozaki D A, Devlin B H, et al., 2004, "Postnatal thymus transplantation with immunosuppression as treatment for DiGeorge syndrome," *Blood,* 104: 2574-2581; Markert M L, Devlin B H, Alexieff M J, Li J, McCarthy E A, Gupton S E, et al., 2007, "Review of 54 patients with complete DiGeorge anomaly enrolled in protocols for thymus transplantation: Outcome of 44 consecutive transplants," *Blood,* 109: 4539-4547; Hong R, wt al., 1996; Rice H E, eSkinner M A, Mahaffey S M, Oldham K T, Ing R J, Hale L P, et al., 2004, "Thymic transplantation for complete DiGeorge syndrome: medical and surgical considerations," *J Pediatr Surg.,* 39: 1607-1615. At specific time points during culture, one or more slices from each donor thymus were fixed in 10% neutral buffered formalin then processed and embedded into formalin-fixed paraffin embedded blocks for histopathologic evaluation. Hematoxylin and eosin (H&E)-stained sections and an immunohistochemical panel were obtained for each tissue block. Antibodies used included pan-cytokeratin (clones AE1/AE3; Leica), cytokeratin (CK) 14 (clone LL02; Leica), CD3 (clone LN10; Leica), and Ki-67 (clone MIB-1; Dako). Automated immunohistochemistry was performed using standard immunoperoxidase methodologies and 3, 3'-diaminobenzidine (brown) substrate, with a hematoxylin counterstain. To assess variability within thymus samples over time in culture, lots were generally examined histologically at ≥3 time points within the following ranges: day 0 (day of receipt), day 5-9, and day 12-21.

Results and Discussion

As thymic organ cultures progressed from days 0 through 21, slices developed increasing amounts of necrosis, increasing condensation of thymic epithelium, and decreasing numbers of residual T cells. The architecture of the thymic epithelial network remained generally well-preserved throughout the 21 days of culture, with focal expression of cytokeratin 14, a putative biomarker of thymic epithelial cells with long-term organ-repopulating potential. All organ slices derived from the same donor thymus closely resembled one another, with minor differences in size, shape, and relative content of cortex versus medulla. Similarly, slices derived from different donors showed similar histopathologic characteristics when examined at the same culture time point.

Initial Identification of Tissue as Thymus

The thymus possesses a thin connective tissue capsule that is typically removed during laboratory processing. However, extensions of the capsule (trabeculae) and associated blood vessels, fibrous tissue, adipose tissue, and variable numbers of mature hematopoietic cells may still be observed in thymus slices. The trabeculae divide the thymus tissue into lobules that are composed of a lacy-appearing three-dimensional network of thymic epithelial cells with intervening spaces containing the developing T cells (thymocytes). The lobules typically demonstrate an outer cortex and an inner medulla, which vary in their histologic appearance as well as phenotype and function of the cells they contain. The thymic cortex is very basophilic (blue) due to densely packed immature thymocytes that stain very darkly with hematoxylin. The density of the more mature thymocytes that are present in the thymic medulla is lower than that of the cortex, so the medulla tends to appear more eosinophilic (pink). The thymic medulla also contains pathognomonic eosinophilic cytokeratin-containing structures called Hassall bodies. Macrophages present within the thymus may form "tingible bodies" that appear as a light-colored circular area against a background of darkly staining thymocytes (a "starry sky" pattern). Large numbers of tingible bodies are characteristic of stress involution, which may occur in normal thymus donors due to the stress of severe cardiac defects, surgery, and/or corticosteroid treatment and does not disqualify a thymus for implantation. The typical histologic features of sliced normal thymus prior to culture (day 0) are shown in FIGS. 40A-D.

Assessment of Hassall Bodies

The thymic medulla contains characteristic structures called Hassall bodies that are composed of terminally differentiated thymic epithelial cells that react with monoclonal antibodies that also react with the terminally differentiated upper layers of the epidermis. Hale L P, et al., 2004; 172: 617-624.

Hassall bodies may serve as a marker of tissue identity, since they are found only in thymus. They may also reflect the quality of the input donor tissue, since the terminal differentiation process is normally triggered by thymocyte-thymic epithelial cell interactions. Id. Hassall bodies are usually readily identified by their appearance as eosinophilic whorls of epithelial cells on H&E-stained slides (FIG. 41A-D). The central-most layers typically lack nuclei. Variable amounts of cellular debris may also be present in the center of the Hassall bodies. Hassall bodies stain very strongly with pan-cytokeratin AE1/AE3 antibodies, which can be used as secondary confirmation of the identity of these structures if not definitively identified in hematoxalin and eosin (H&E)-stained slides.

General Thymocyte Changes During Culture

Figure 43:
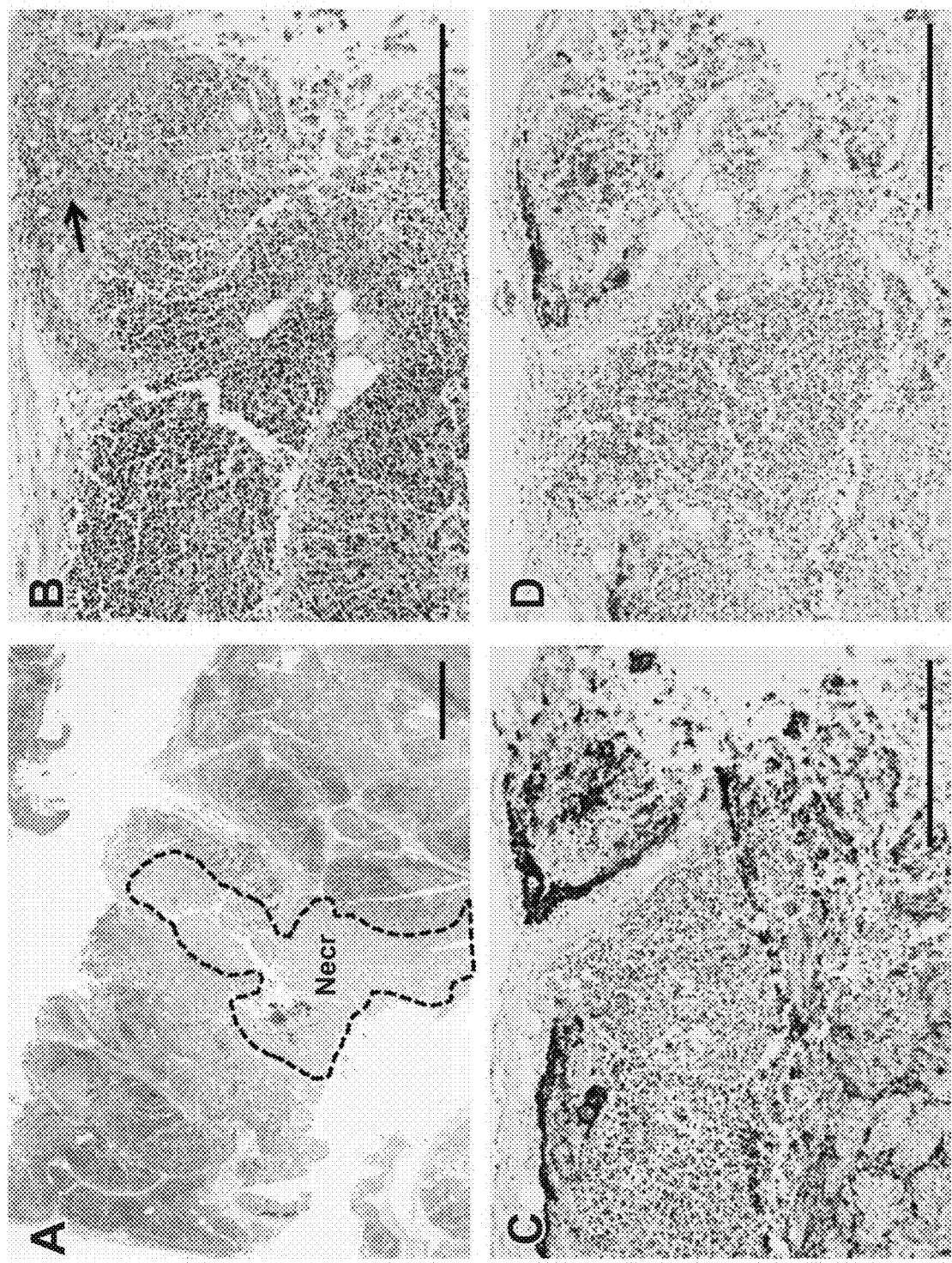

Thymocytes are progressively lost as thymus tissue is cultured, either from being flushed out during media changes or from thymocyte death followed by degradation within the tissue (FIG. 42-FIG. 45). However, unlike what occurs in vivo, dead cells may persist in cultured thymus long-term due to inability to recruit phagocytes to clear them. Thymocyte nuclei undergoing cell death may show pyknosis (chromatin condensation) and karyorrhexis (nuclear fragmentation) but typically, as these cells deplete their energy but are not phagocytosed, they show ragged nuclear edges with loss of nuclear membrane integrity. Karyolysis (complete dissolution of nuclei in necrotic cells) typically occurs within 2-3 days in vivo, but appears to occur more slowly during thymus culture. After 5-9 days in culture, most thymocytes have retained nuclei, but nuclear membranes are not intact, indicating early necrosis (FIG. 43). These altered nuclear characteristics facilitate the distinction between viable and non-viable thymocytes, even when nuclei are retained. Large foci of eosinophilic necrotic cell debris where thymocyte nuclei have undergone karyolysis may also be seen (FIG. 43A).

Histologic Assessment of Cell Integrity and Tissue Architecture

When cultured thymus tissue is to be implanted, it is critical to be able to accurately distinguish between slices with extensive thymocyte necrosis but thriving thymic epithelial cells (the optimal tissue for implantation) versus slices with similar amounts of necrosis where thymic epithelial cells are also compromised. Although it cannot directly assess viability, histologic examination of H&E slides can assess the degree of preservation of normal structures and the presence or absence of indicators of cell death. As described above, thymocytes are expected to be depleted during the culture process. Many thymocytes are washed from the slice during the daily media changes. Many others will die in situ, where their nuclei and cell bodies may remain for prolonged periods of time. However, the membrane integrity of dead thymocytes is compromised and their nuclei exhibit "ragged" edges. Thymocyte debris may clump together, making it impossible to discern individual cell borders. Thymocyte death and depletion is an expected and desirable consequence of culture and relative lack of intact thymocyte nuclei is potentially reflective of slice quality.

Thymic epithelial cells are more easily visualized as thymocytes are depleted from the tissue. Nuclei of viable thymic epithelial cells are typically oval, larger than those of thymocytes, and have a sharply defined nuclear membrane outlined by the hematoxylin stain, with one or more nucleoli. These thymic epithelial nuclei typically look "open," meaning they do not stain darkly with hematoxylin. This fits with an interpretation that they are alive and metabolically active, since active chromatin ("euchromatin") does not bind the hematoxylin dye. The presence of nucleoli, which are the sites of ribosome synthesis, in many thymic epithelial cells further confirms that they were alive and metabolically active at the time of fixation. Examples of intact and viable-appearing thymic epithelial cells are shown in FIG. 46A-B.

Careful microscopic examination of multiple thymus slices at any given time point from day 0-21 showed that all slices derived from the same donor thymus closely resembled one another. The differences observed between different slices derived from the same thymus as a function of culture time were primarily related to the amount of necrosis (increased as culture time increased) and numbers of residual thymocytes (decreased as culture time increased). Slices derived from different donors were also qualitatively similar to each other when examined at the same time points. Differences between different donor tissues included relative size, shape, relative content of thymus versus medulla (but both were always present on each slice examined), amount of necrosis, condensation of thymic epithelium, and numbers of residual T cells. Most changes in histologic appearance had already occurred by day 5 of culture, with generally only additional depletion of thymocytes as cultures progressed.

Assessment of Thymic Epithelial Architecture

A cocktail containing anti-cytokeratin antibodies AE1 and AE3 (AE1/AE3) detects essentially all thymic epithelial cells. In contrast, an antibody reactive with CK14 detects a subset of thymic epithelial cells that are present in the subcapsular cortex and seemingly scattered throughout the remainder of the cortex and medulla. Some of these CK14+ cells have been suggested to have the potential to differentiate into both cortical and medullary epithelial cells, Lee E N, Park J K, Lee J-R, Oh S-O, Baek S-Y, Kim B-S, et al., 2011, "Characterization of the expression of cytokeratins 5, 8, and 14 in mouse thymic epithelial cells during thymus regeneration following acute thymic involution," *Anat Cell Biol.* 44: 14-24, and thus to represent long-term repopulating cells. As thymocytes are depleted from the tissue, the thymic epithelial cells become more visible. The three-dimensional thymic epithelial network is normally demonstrated in sections via a light and lacy arrangement of connected epithelial cells and/or seemingly scattered thymic epithelial cells whose connections are not evident in the section being examined. The three-dimensional thymic epithelial network contracts to varying degrees as thymocytes are lost during culture. This can result in condensation of the residual epithelium, such that the subcapsular cortical epithelial layer becomes thicker and medullary thymic epithelial cells become more tightly packed. Examples of these changes are shown in FIG. 40 and FIGS. 42-45 for a single thymus lot examined on days 0 (day of receipt), 7, 9, 12, and 20. Despite the loss of numerous thymocytes and potentially large areas containing necrotic debris, the overall architecture of the thymic epithelial cell network remains generally well-preserved through at least 21 days of culture (FIGS. 47A-E).

Assessment of Residual T Cells

As described above, the primary purpose of culture of donor thymus tissues that are intended for implantation is to partially deplete T cells to facilitate colonization of the implanted slices with recipient thymocyte precursors and to decrease the risk of graft-versus-host disease. Immature T cells (thymocytes) and mature T cells can be identified in histologic sections by their morphology as well as by immunohistochemical stains that detect proteins specifically expressed by these cell types. CD3 is a component of the T cell receptor for antigen that is present on >95% of cortical and medullary thymocytes as well as on all mature T cells. On day 0, the plasma membranes of essentially all immature T cells in the cortex and the medulla appear strongly reactive with CD3 antibody in a membrane pattern (FIGS. 48A-B). Viable thymocytes/T cells continue to react with CD3 antibody in a membrane pattern as cultures continue. However, the CD3 antibody also reacts strongly with dead thymocytes, including the anucleate debris that remains after dead thymocytes undergo karyolysis (FIG. 48D, FIG. 48G, and FIGS. 48I-K). So much thymocyte debris remains that slices may still appear strongly and uniformly brown when viewed at low magnification (FIG. 48C, FIG. 48F, FIG. 48H, FIG. 48J), although examination of the slide at higher power (e.g. 40× objective) confirms that relatively few intact potentially viable thymocytes are present at these time points. Non-viable cells and cellular debris will be cleared by recipient phagocytes after implantation and therefore convey no risk of graft-versus-host disease. It is not generally possible to accurately identify CD3+ membrane immunoreactivity in tissue areas where considerable amounts of strongly staining debris prevents assessment of cellular membranes of adjacent cells. However, even at late time points during culture, CD3 immunohistochemistry typically highlights at least some thymocytes/T cells that have intact plasma membranes suggesting that they may still be viable (FIG. 48E, FIG. 48G, FIGS. 48I-K).

Assessment of Cellular Proliferation

The Ki-67 antigen is expressed in the nucleus of all cells that are proliferating (i.e., not in the GO phase of the cell cycle). On day 0, the majority of the immature thymocytes present within the thymic cortex are proliferating and their nuclei react strongly with antibody specific for the Ki-67 proliferation antigen. In contrast, only rare more mature medullary thymocytes and/or epithelial or stromal cells react with this antibody (FIGS. 49A-B). The pattern of immunoreactivity observed after day 1-2 of culture is of scattered rare positive cells, almost all of which have the larger nuclei characteristic of thymic epithelial cells (FIGS. 49C-K). Thus, the Ki-67 stain may be a useful adjunctive stain for documenting the viability of thymic epithelial cells within the slice.

DISCUSSION

These experiments describe histopathologic changes that occur when postnatal human thymus is cultured for up to 21 days and demonstrate that histopathologic examination using H&E and cytokeratin immunoreactivity can be useful for assessing the quality of cultured thymus slices intended for implantation. As thymic cultures progressed, slices developed increasing amounts of necrosis, increasing condensation of thymic epithelium, and decreasing numbers of residual T cells. The thymic epithelial network remained intact throughout the 21 days of culture, with continued expression of cytokeratin 14, a putative biomarker of thymic epithelial cells with long-term organ-repopulating potential. Slices from the same thymus were qualitatively similar, such that a single slice could adequately represent the entire thymus. Variability in histologic appearance of cultured thymus slices derived from different donors was also minimal at any given time point. Tissue histology observed early during culture (e.g., days 5-9) closely reflected what was observed later in culture (e.g., days 12-21), although more thymocyte depletion and necrosis were observed at the later time points.

Immunohistochemistry for antibodies that recognize CK14 or all types of cytokeratins (AE1/AE3) was useful in evaluation of cultured thymus slices. Cytokeratin intermediate filaments are important components of the cytoskeleton of all epithelial cells. The pan-cytokeratin AE1/AE3 stain demonstrates the epithelial network within the examined thymus slice, which may not be easily discernable at later time points using H&E stain alone. The specific type of cytokeratin expressed by a particular thymic epithelial cell has been shown to depend on its stage of development and differentiation and functional state. In mice, antibodies that react with CK5, CK8, and CK14 have been most commonly used to identify thymic epithelial cell subtypes, Lee E N, et al., 2011, *Anat Cell Biol.*, 44: 14-24. Expression of CK14 was determined in this study, based on previous studies where CK14 expression was hypothesized to be a characteristic of thymic epithelial cells with the potential to differentiate toward either cortical or medullary lineages Li B, Li J, Devlin B H, Markert M L., 2011, "Thymic microenvironment reconstitution after postnatal human thymus transplantation," *Clin Immunol.* 140: 244-259. While the clinical outcome of long-lasting immune reconstitution Markert M L, et al., *Blood,* 109: 4539-4547 suggests that thymic epithelial progenitors are likely present within implanted thymus slices, the precise phenotype for such progenitors has not been definitively identified in humans. The phenotype of thymic epithelial progenitors in mice is still controversial Bennett A R, Farley A, Blair N F, Gordon J, Sharp L, Blackburn C C., 2002, "Identification and characterization of thymic epithelial progenitor cells," *Immunity* 16: 803-814; Wong K, Lister N L, Barsanti M, Lim J M C, Hammett M V, Khong D M, et al., 2014, "Multilineage potential and self-renewal define an epithelial progenitor cell population in the adult thymus," *Cell Rep.* 8: 1198-1209; Ucar A, Ucar O, Klug P, Matt S, Brunk F, Hofmann T G, et al., 2014, "Adult thymus contains FoxN1 (−) epithelial stem cells that are bipotent for medullary and cortical thymic epithelial lineages," *Immunity,* 41: 257-269; Ulyanchenko S, O'Neill K E, Medley T, Farley A M, Vaidya H J, Cook A M, 2016, "Identification of a bipotent epithelial progenitor population in the adult thymus," *Cell Rep.,* 14: 2819-2832, and only low numbers have been detected using multiple antibodies and multi-color flow cytometry. Thus direct detection of thymic epithelial progenitors in human tissue sections is not currently feasible.

These experiments identified potentially large amounts of necrotic cellular material remaining within thymic slices at culture days 12-21, the time points when the tissue might be implanted. Biopsy examination several months after implantation shows no evidence of this necrotic material Markert M L, et al., 2008, 180: 6354-6364. While not desiring to be bound by any particular theory, Applicant submits that the initial presence of this necrotic debris and its underlying extracellular matrix at the time of implantation may serve to preserve the functional architecture of the slices, including the cortical and medullary niches for developing thymocytes. The recent use of thymus decellularization approaches that preserve extracellular matrix to recreate murine thymic "organoids" that can support cellular differentiation of both epithelial cells and hematopoietic precursors Hun M, Barsanti M, Wong K, Ramshaw J, Werkmeister J, Chidgey A P, 2017, "Native thymic extracellular matrix improves in vivo thymic organoid T cell output, and drives in vitro thymic epithelial cell differentiation," *Biomaterials,* 118: 1-15, supports this hypothesis.

Previous studies demonstrated that the growth potential of thymic epithelial cells was robustly maintained under the culture conditions used, such that cyokeratin-positive epithelial monolayers could be established from the slices up to 12 weeks after initiation of organ culture Markert M L, et al., 1997, *Clinical Immunol Immunopathol.,* 82: 26-36. The experiments described in this example did not directly assess epithelial cell viability, but instead used the presence of intact nuclei as a surrogate marker.

For the Example that follow relating to biomarkers for cultured thymus tissue the followings procedures were followed.

Example 12: Source of Human Thymus Tissue

Thymus tissue was obtained from immunocompetent human donors who were undergoing medically necessary surgery where removal of a portion of the thymus was required to facilitate exposure of the operative field. No tissues were obtained specifically for the purposes of this study. The majority of tissues studied were obtained anonymously from infant, pediatric, and adult donors as tissue that would otherwise be discarded, with retention only of age, sex, and indication for surgery. This use was determined by Institutional Review Board (IRB) of Duke University Medical Center to not constitute human subjects research and to be exempt from IRB review. However, written informed consent was provided by the parent(s) of some infants to allow any thymic tissue that was removed and otherwise would be discarded to be potentially used for research. These consented tissues were coded so the research team had no access to identifying information other than age and sex. This use of consented discarded tissue was approved by the IRB of Duke University Medical Center (Pro00103028).

Thymus Processing and Culture

Representative portions of each thymus were fixed in 10% neutral buffered formalin then processed and embedded into paraffin blocks (FFPE) for histopathologic evaluation. Hematoxylin and eosin (H&E)-stained sections and an immunohistochemical panel were obtained for each tissue block. Antibodies potentially used recognized pan-cytokeratin (clones AE1/AE3; Leica), cytokeratin (CK) 14 (clone LL02; Leica), CD3 (clone LN10; Leica), Ki-67 (clone MIB-1; Dako), CD1a (clone; supplier), and CCL21 (clone; supplier). Automated or manual immunohistochemistry was performed using standard immunoperoxidase methodologies and 3, 3'-diaminobenzidine (brown) substrate, with a hematoxylin counterstain.

For some specimens from infant donors <9 months of age, thymus tissue was sliced ~0.5 mm thick and cultured for up to 21 days, as described in detail elsewhere (Hong and Moore 1996) (Markert et al. 2003). Briefly, thymus slices were placed on filters supported by absorbable gelatin sponge rafts and cultured in Ham's F12 culture medium+ 10% fetal bovine serum at the media/air interface for up to 21 days. Culture medium was replaced daily (24±4 hours) with fresh material dispensed over each tissue slice. Aliquots of spent/conditioned media collected from individual slices or pooled from all slices from a given donor thymus (2.5 mL per slice) were frozen at −20° C. until analysis. Representative slices of cultured thymus slices were fixed in 10% neutral buffered formalin and processed into paraffin blocks at ≥3 time points, generally within the following ranges: day 0 (day of receipt, sliced but not cultured), days 5-9, and days 12-21.

Multiplex Antibody Microarrays and Enzyme Immunoassays

Levels of 200 analytes present in aliquots of conditioned culture medium obtained on days 1-21 from three independent thymus cultures were determined using multiplex antibody microarrays (RayBiotech), per the manufacturer's protocol. Analytes that had at least two measures above the lower limit of detection for at least one thymus (n=127) were natural log (ln)-transformed and subjected to area-under-the curve and regression analyses (FIG. 56).

Selection criteria to identify analytes for further study included initially low levels that consistently increased (a hypothesized characteristic of thymic epithelial (TE)-derived biomarkers) or initially high levels that consistently decreased (a hypothesized characteristic of thymocyte-derived biomarkers), a similar pattern of expression in all three of the thymus cultures analyzed, and published evidence of functional relevance of the analyte to the hypothesized cell of origin and/or thymus biology. Preference was given to those analytes that were highly expressed (as indicated by the area under the curve) and had changes that were statistically significant ($p \leq 0.05$), with or without correction for false discovery. Levels of L-selectin in conditioned medium were quantitated by antibody microarray as described above or a Luminex™ bead-based immunoassay (R&D Systems) that had a lower limit of quantitation (LLOQ) of 3952 pg/mL and an upper level of quantitation of 4,656,306 pg/mL for each sample, factoring in dilution factors. CCL21 secretion was determined in pg/mL using the DuoSet human CCL21 ELISA kit (R&D Systems), based on a standard curve using sigmoidal, best-fit values and a logarithmic scale ($r2=0.9986$).

Multiplex Gene Expression Assay

Multiplex gene expression was measured on FFPE blocks derived from human thymus tissues, using the QuantiGene Plex assay (Thermo-Fisher) per the manufacturer's specifications. Briefly, 6-8 mm3 thymus tissue was macro-dissected from 10 μm thick FFPE sections, placed into assay tubes, and lysed to release target RNAs. Fluorescent Luminex™ beads were incubated with capture extenders, label extenders, blocking probes, and the tissue lysate to capture specific mRNAs to beads with defined fluorescence profiles. Branched DNA technology was used to amplify the signal associated with each bound mRNA followed by hybridization with streptavidin-phycoerythrin. Fluorescence of each bead and its associated phycoerythrin signal were measured using a Bio-Plex 200 instrument (Bio-Rad). The background-corrected fluorescence signal for each analyte of interest was normalized to that of GAPDH for each thymus sample, then further normalized based on tissue composition as described below.

Tissue Morphometry

H&E, pan-cytokeratin (CK) (AE1/AE3), and CD1a immunohistochemical slides were digitally scanned at 40× magnification using a Leica SCN slide scanner (Leica Microsystems), and examined by a pathologist (LPH) using virtual microscopy (ImageScope software; Leica Biosystems). The total area of thymus tissue on the slide ("total area") as defined by H&E stain, the area containing thymic epithelium ("TE area", as defined by CK immunohistochemistry), and the area containing immature thymocytes ("cortical area", as defined by CD1a immunohistochemistry) were determined by outlining them using the "pen tool" provided by the ImageScope software, as described previously (Ito et al. 2017) (FIG. 57A to 57C). Individual areas identified for each tissue (in μm2) were imported into Microsoft Excel for summation, then rounded to the nearest mm2 for data presentation. To adjust for differences in amounts of thymus tissue on each slide, TE, and cortical areas were converted to % of total area by dividing by the total area of thymus tissue examined. Tissue content of developing thymocytes was defined by the % cortical area, i.e. the percentage of the tissue that contained CD1a+ immature thymocytes.

Statistical Analysis

A total of 127 of the 200 analytes had measures above the assay limit of detection on at least two days for at least one thymus. In total, 14 analytes were measured in media from one thymus, 17 were measured in media from two thymi, and 96 in media from three thymi. Separate hierarchical linear regression models were fit for each analyte, predicting ln (pg/mL) by day with responses clustered by thymus. The slope parameter from each model, reflecting the mean change/day in ln (ng/mL), was reported along with the exponentiated slope, which reflects the average daily multiplicative change in pg/mL. P-values were reported with and without adjustment for false discovery using the Benjamini-Hochberg procedure. Model results were also reported along with estimates of the trapezoidal area under the curve (AUC) for each analyte, calculated based on the ln (pg/mL) over the 21-day culture period.

Since QuantiGene expression analysis was performed on whole thymus tissues across a wide range of ages, the percent of the tissue studied that contained thymic epithelium and/or was active in thymopoiesis varied. To address this, the initial QuantiGene results were additionally normalized to the percent area with thymic epithelial cells or the percent area with active cortex as determined by morphometry.

Results

Soluble Molecules Produced by Cultured Human Thymus

Samples of conditioned media obtained on days 1-21 of culture from three consecutive thymus cultures from different donors were screened for 200 molecules via multiplex antibody microarrays. The 127 analytes that had at least two measures above the lower limit of detection for at least one thymus were further analyzed by area-under-the-curve and regression analyses (FIG. 56). Forty-two analytes showed either significantly increased (n=15) or decreased (n=27) release into the culture media as the cultures progressed, as indicated by uncorrected p values <0.05 (FIG. 56). Five of these analytes (L-selectin, CXCL16, M-CSF, CCL21/6Ckine, and galectin-7) showed a similar pattern of expression in all three thymus cultures and continued to have p<0.05 for correlation with time in culture when a false detection rate (FDR) correction was applied (FIG. 56).

Levels of galectin-7, M-CSF, and L-selectin decreased with time, meeting the pre-specified criteria for possible thymocyte-produced soluble molecules (FIGS. 50A, 50B, and 50C).

Although galectin-7 (encoded by the LGAGS7 gene) has been reported to be expressed by terminally differentiated TE cells that are present in Hassall bodies (Kuwabara et al. 2002), its levels in media decreased with culture as expected for a biomarker of thymocytes. Since galectin-7 is a p53-induced protein that triggers apoptosis in multiple cell types (Biron-Pain et al. 2013), it may also be related to thymocyte loss during culture but is unlikely to be specific for thymocytes. Likewise, M-CSF has been shown to be produced by TE cells (Le et al. 1988) and may also be produced by multiple other cell types present within thymus. In contrast, expression of L-selectin is limited to hematopoietic cells and is well-known to be expressed on thymocytes. While not secreted per se, L-selectin is a type I transmembrane glycoprotein that is shed constitutively as well as during leukocyte adhesion and migration (Hafezi-Moghadam et al. 2001; Ivetic et al. 2019), then rapidly re-expressed (Fitzhugh et al. 2008). Soluble L-selectin in conditioned culture media was thus chosen for further validation as a soluble biomarker that may potentially relate to numbers of viable thymocytes present within the thymus cultures.

Levels of CCL21, CXCL16, and CXCL12 secreted into culture media increased with time, meeting the pre-specified criteria for possible TE-produced soluble molecules (FIGS. 50D, 50E, and 50F). All three of these chemokines have been previously shown to be expressed in TE cells (Bunting et al. 2011; Liu et al. 2005). CCL21 has also been shown to be functionally important in thymus due to its chemotactic effects on both early thymocyte progenitors and thymocytes (Hu et al. 2015; Kozai et al. 2017). Thus we chose to further validate CCL21 as a potential biomarker that may reflect content and function of thymic epithelium within cultured thymus slices.

Conditioned media levels of L-selectin decreases during human thymus organ culture and is associated with viable thymocytes.

The pattern of L-selectin release into organ culture medium identified by the screening microarrays was confirmed by determining the levels of soluble L-selectin present in conditioned media from one previously analyzed (MFG-026) and three additional thymus organ cultures as a function of time in culture, using both antibody microarray and cc bead-based multiplex immunoassay. As suggested by the initial screening arrays, levels of L-selectin in conditioned culture media were generally very high initially (e.g. day 1), but by day 5 had rapidly decreased to low levels that were maintained for the remainder of the 21 day culture period (FIG. 51A, 51B). These changes in L-selectin levels paralleled changes observed in viable thymocytes that occurred during culture. Immunohistochemistry with anti-CD3 antibodies that identify cells as T lineage and with anti-Ki-67 antibody that identifies proliferating cells, demonstrates the rapid loss of thymocyte viability early in culture (FIG. 52). On day 0, the plasma membranes of essentially all immature T cells in the cortex and the medulla appear strongly reactive with anti-CD3 in a membrane pattern (FIG. 52B). After several days of culture, the majority of the brown color is due to the anucleate, but still immunoreactive, debris that remains after dead thymocytes undergo karyolysis/nuclear dissolution (FIG. 52E) but their debris remains in the tissue slices. However, rare thymocytes/T cells that appear to have intact plasma membranes may potentially be identified by CD3 immunohistochemistry even after ~3 weeks in culture [not shown; (Hale 2020) (Markert et al. 1997a). Similarly, immunohistochemistry using antibody specific for the Ki-67 proliferation marker shows abundant reactivity with cortical thymocytes on day 0 (FIG. 52C), consistent with the marked proliferation/clonal expansion that occurs in the cortex. However, the thymocyte death that occurs during organ culture results in Ki-67 immunoreactivity only with larger cells morphologically consistent with TE cells at later time points during culture (FIG. 52F).

CCL21 Secretion Increases During Organ Culture

The pattern of increased CCL21 release into organ culture media with time identified by the screening microarrays (FIG. 50E) was validated by quantitation of CCL21 in additional thymus organ cultures using enzyme immunoassays. Thymus specimens were serially sliced as shown in FIG. 53B, then cultured for up to 21 days, with analysis of spent media pooled daily from all slices derived from each thymus sample or from individual slices according to a pre-specified sampling plan. The CCL21 content of pooled daily samples of spent media showed a pattern of increase with increasing time in culture to a steady state level that was markedly increased over baseline (FIG. 53A; n=8 cultures). Secretion by individual slices varied quantitatively, but the overall secretion patterns were similar for all slices derived from a given thymus, with initially low CCL21 secretion that increased to a sustained much higher level as cultures continued (FIG. 53C).

CCL21 is Produced Primarily by TE Cells in Human Thymus Slices

Next, FFPE sections from fresh and cultured human thymus tissues were reacted with CCL21-specific antibodies to determine the cell type(s) that were responsible for the increased secretion of this chemokine that was observed as cultures progressed. TE cells in freshly sliced non-cultured thymus (day 0) showed moderate reactivity with CCL21 antibody, in a pattern that was strongest in medullary regions (FIGS. 54A, 54B), but also included the TE cells scattered in the cortex. A similar pattern of reactivity was seen in cultured thymus, with moderate to strong immunoreactivity of TE cells in medullary regions as well as in scattered TE cells in cortical areas (FIGS. 54C, 54D).

Determination of Thymus Gene Expression Across the Lifespan

To determine how these results from T cell-depleted cultured human infant thymus might relate to changes in aging human thymus, FFPE thymus tissues derived from 47 donors across the lifespan were studied using the QuantiGene multiplex gene expression assay. The cohort studied included 19 males from 5 days to 70 years of age, 27 females from 5 days to 78 years of age, and one sample from a 29-year-old donor whose sex was not recorded. The age and sex distributions for these samples are shown in FIG. 59A.

Thymus tissues obtained from donors ≤18 years (n=XX) showed higher expression of mRNAs encoding the T cell marker CD3E and the cortical thymocyte marker CD1a (FIGS. 55A, 55B) relative to GAPDH when compared to donors older than 18 years (n=XX; p=0.yy), consistent with the increased cortical area involved in active thymopoiesis observed in the younger tissues by CD1a immunohistochemistry (FIG. 59C). The percentage of the thymus tissue section that contained thymic epithelium was also higher in donors ≤18 years compared with older adults (p=0.zz). However, mRNAs encoding cytokeratins 8 (KRT8) and 14 (KRT14) were decreased relative to GAPDH in donors ≤18 years compared with older adults (FIGS. 55C, 55D), an observation that was unexpected given the higher percentage of area containing thymic epithelium in younger donors (FIG. 59B).

Figure 55:
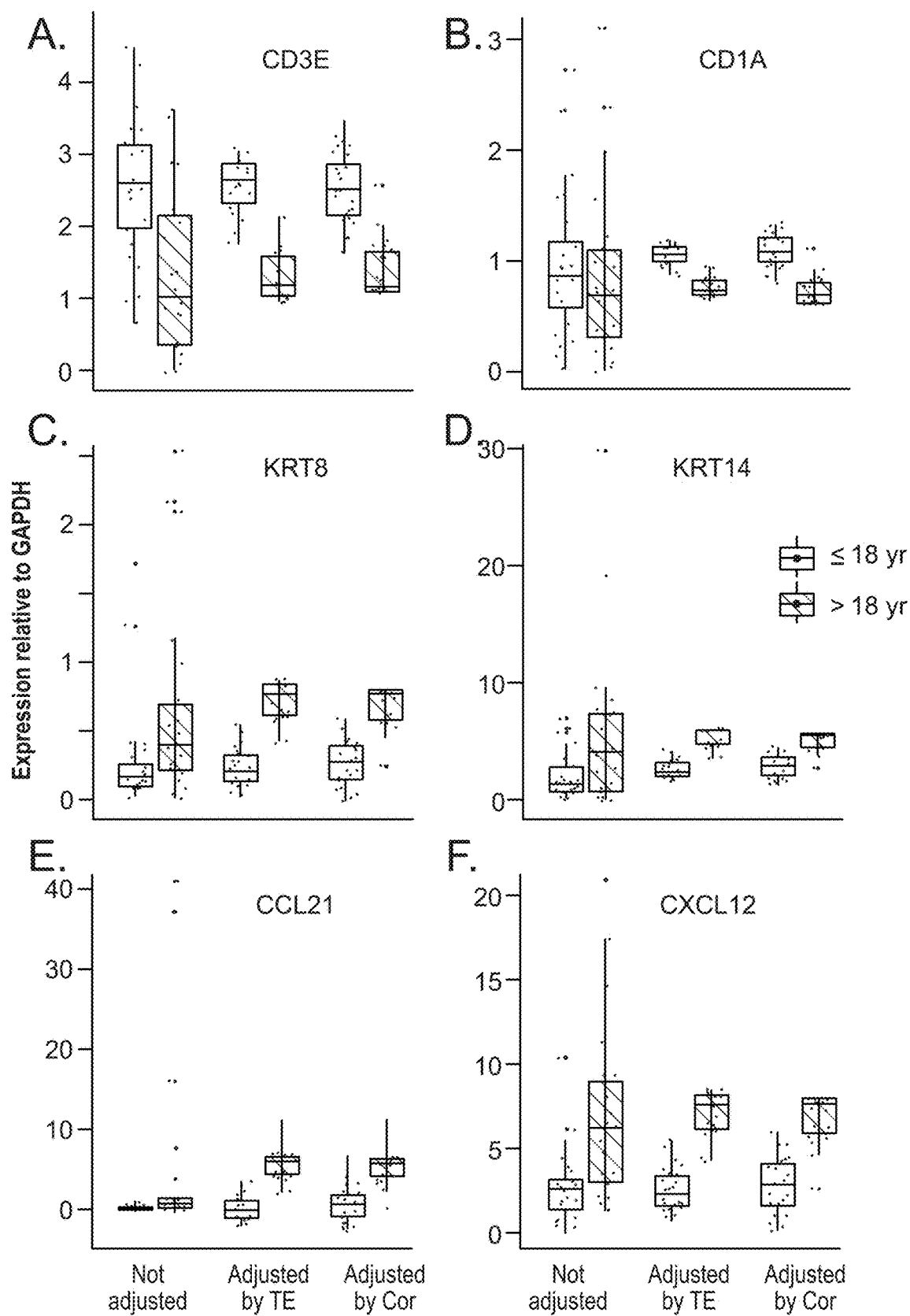
Figure 59:
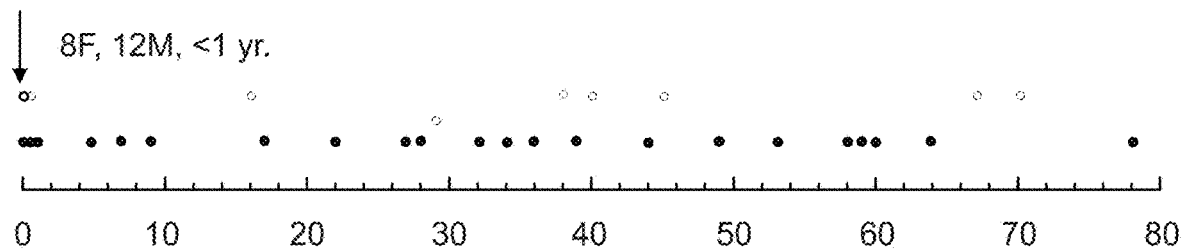
Figure 59:
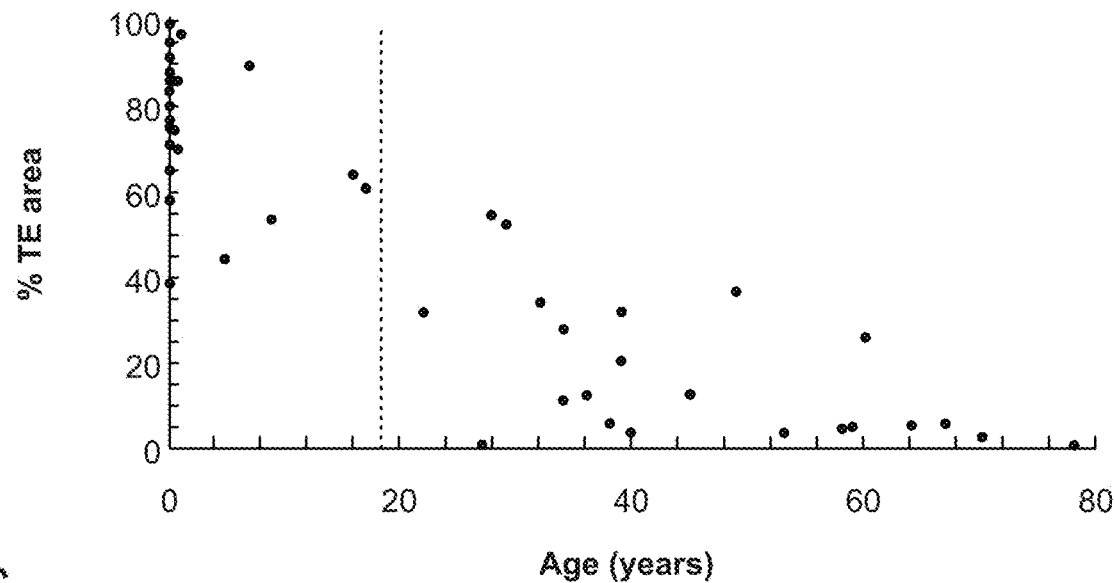
Figure 59:
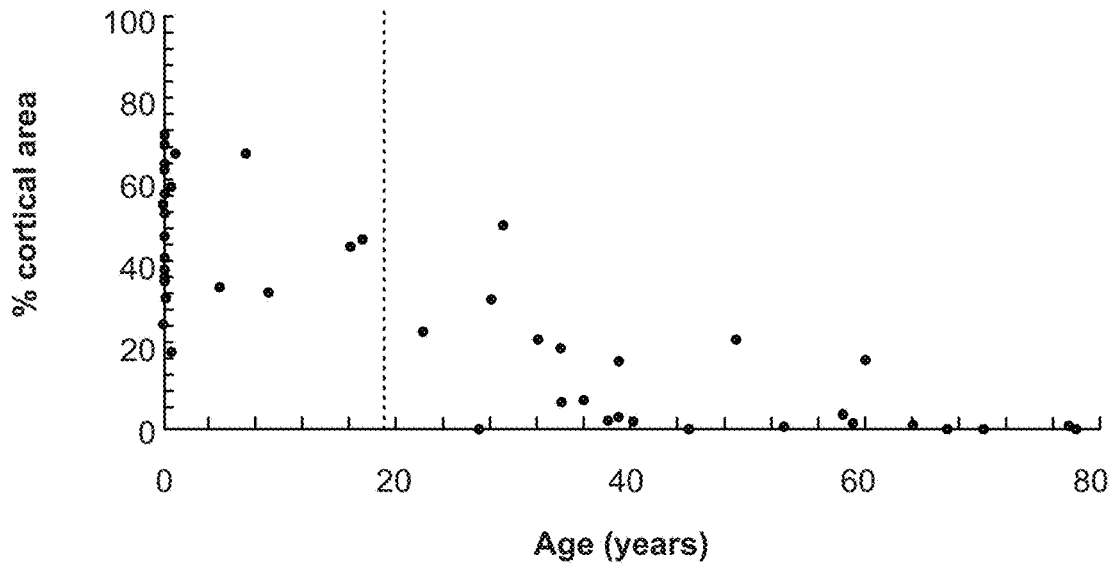

To address this issue, gene expression results were additionally normalized based on their percent of area containing thymic epithelium as indicated by pan-cytokeratin immunohistochemistry and by their percentage of cortical area with active thymopoiesis, as indicated by CD1a immunohistochemistry (FIG. 59). As shown in FIG. 55, these two normalization methods essentially eliminated the outliers that were seen with the non-adjusted data and resulted in very similar ratios. Interestingly, after both normalization methods, thymus tissues from donors ≤18 years continued to express more CD3E and CD1A mRNAs and less KRT8 and KRT14 mRNAs than thymus from older adults.

Figure 6A:
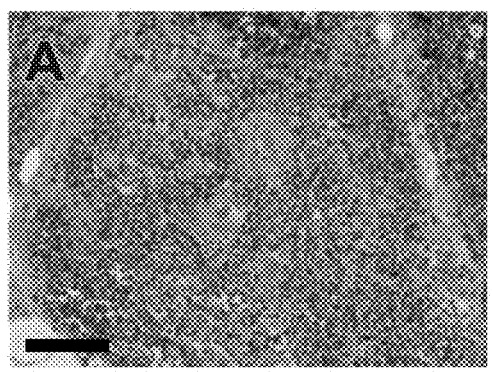
FIGS. 6A-H depict histology testing of thymus tissue slices from a lot (MFG-056) of cultured thymus tissue on day 5, 9, 12 and 21 after harvest of the thymus from a donor. Hematoxylin and eosin-stained slices (left panels) and their corresponding reactivity with a cocktail of the anti-cytokeratin antibodies AE1/AE3 (right panels; brown color denotes positive reactivity) are shown at day 5 (FIG. 6A, FIG. 6B), day 9 (FIG. 6C, FIG. 6D), day 12 (FIG. 6E, FIG. 6F), and day 21 (FIG. 6G, FIG. 6H), respectively. Bars in the lower left of each panel represent 100 µm. Panels with H&E show progression depletion of T cells with time.
Figure 6B:
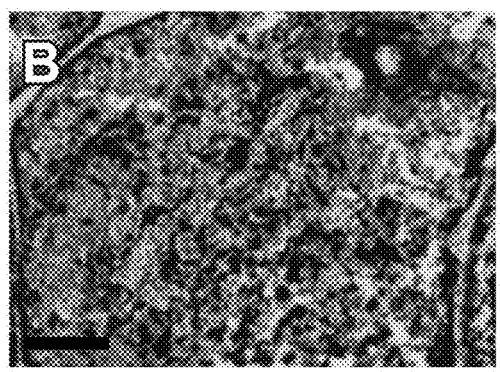
Figure 6C:
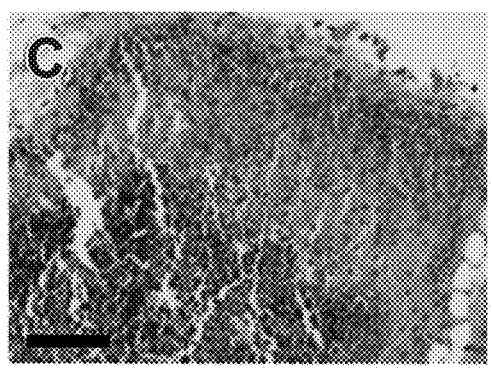
Figure 6D:
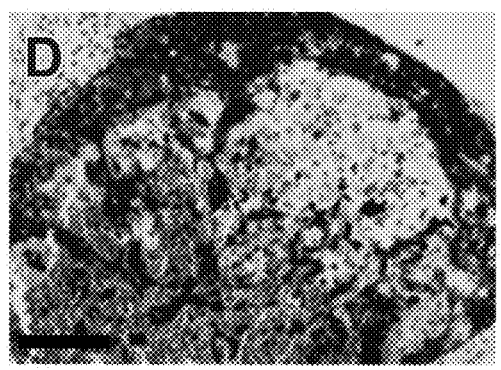
Figure 6E:
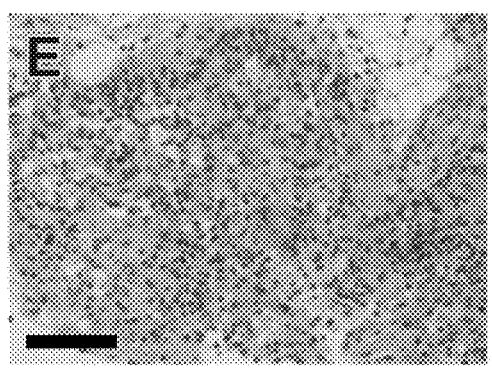
Figure 6F:
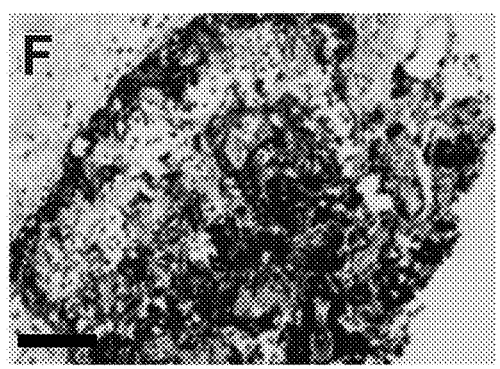
Figure 6G:
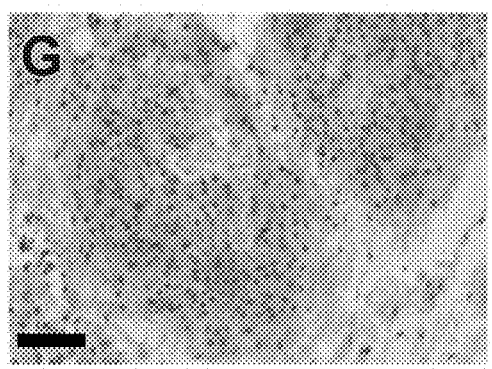
Figure 6H:
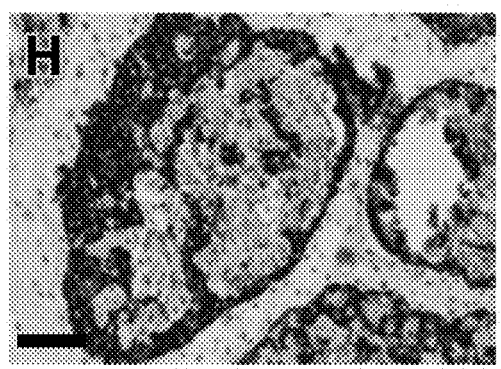

Whole Thymus Expression of CCL21 and CXCL12 Increases as Thymocytes Decrease Due to Aging Unadjusted CCL21 gene expression was consistently low relative to GAPDH in thymus from donors ≤18 years of age (FIG. 6E). In contrast, unadjusted CCL21 expression was higher and more variable in the older adult group, with numerous outliers. Normalization based on TE.

Whole thymus expression of CCL21 and CXCL12 increases as thymocytes decrease due to aging.

Unadjusted CCL21 gene expression was consistently low relative to GAPDH in thymus from donors ≤18 years of age (FIG. 55E). In contrast, unadjusted CCL21 expression was higher and more variable in the older adult group, with numerous outliers. Normalization based on TE area or cortical area eliminated the outliers, and resulted in increased separation between the two donor age groups (FIG. 55E). Similar results were seen for the chemokine CXCL12 (FIG. 55F).

Example 13

Intra-thymus variability was studied to determine whether histology testing results from one part of a thymus could be considered representative of histology testing results in any other part of the same thymus. The results of this test were used to determine how many samples should be tested during both routine release testing and for process validation testing.

Histology acceptance criteria were established, as noted previously, including the assessment of: areas positive for keratin AE1/AE3 scattered throughout tissue on days 5-9; at least 1 Hassall body identified; CK14 staining scattered throughout tissue; and intact nuclei observed.

For this study, three thymuses were sliced in a directional manner and the location of the slices within each thymus was tracked. Slices were cultured in 6-well plates to allow tracking of each slice. Slicing was conducted as shown in FIG. 62A.

For each thymus in the study, slices were dedicated for analysis at each of the following time points, baseline (day 0), day 5, day 9, day 12 and day 21.

Between 5-11 slices were cultured at each time point for each thymus. Slices were cultured per the methods described above with daily media changes. Slices were submitted for H&E staining in the pathology lab and analyzed for identity, potency and viability. All slices in this study met the release acceptance criteria for histology testing as designated above, namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each H&E and AE1/AE3 slide was made by the pathologist. Images of some of these slides for cultured thymus tissue lot MFG-056 are shown in FIGS. 63A-H. The following observations were noted.

All slices derived from the same donor thymus met the acceptance criteria at each time point. In different slices, areas of cortex resemble each other and areas of medulla resemble each other. However, variations were observed in the relative proportion of cortex and medulla between slices.

The differences observed between different slices derived from the same thymus as a function of culture time were primarily related to the amount of necrosis, primarily of thymocytes (which increased as culture time increased) and the numbers of residual thymocytes (which decreased as culture time increased).

Based on these observations, any one slice from a thymus was representative of the entire thymus. In addition, the histologic appearance of the tissue slices at day 5 reflects what is observed at each of the later time points (day 9, 12 and 21).

Example 14: Whole Thymus Time-Course Study

For this study, five thymuses were sliced and cultured per SOP. On the day of slicing, the first, middle and last slices were prepared for immunohistochemistry. The remainder of each thymus was sliced and cultured in 6-well plates. Each thymus was designated for one of the following time points: baseline (day 0), day 5, day 9, day 12 and day 21. See FIG. 64A for a day 0 thymus slice, FIG. 65A for a day 5 slice, FIG. 66A for a day 12 slice, and FIG. 67A for a day 21 slice.

The total number of slices from each thymus ranged from 21 to 62 slices. Slices were cultured per the procedures outlined above with daily media changes. Slices were submitted for H&E staining in the pathology lab and analyzed for identity, potency and viability. All slices in this study met the release acceptance criteria for histology testing, namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each H&E and AE1/AE3 slide was made by the pathologist. The following observations were noted.

All slices derived from the same donor thymus and tested at the same time point similarly met the acceptance criteria for that time point with variations in the relative amounts of cortex and medulla, residual thymocytes and/or necrosis, as described above.

Differences noted were the relative size, shape, relative content of thymus cortex versus medulla, amount of necrosis, condensation of the thymus epithelium and numbers of residual thymocytes.

In addition, lots from different donors tested at different time points were also qualitatively similar to each other. Differences observed were related to the amount of necrosis (which increased as culture time increased) and numbers of residual thymocytes (which decreased as culture time increased).

Figure 68:
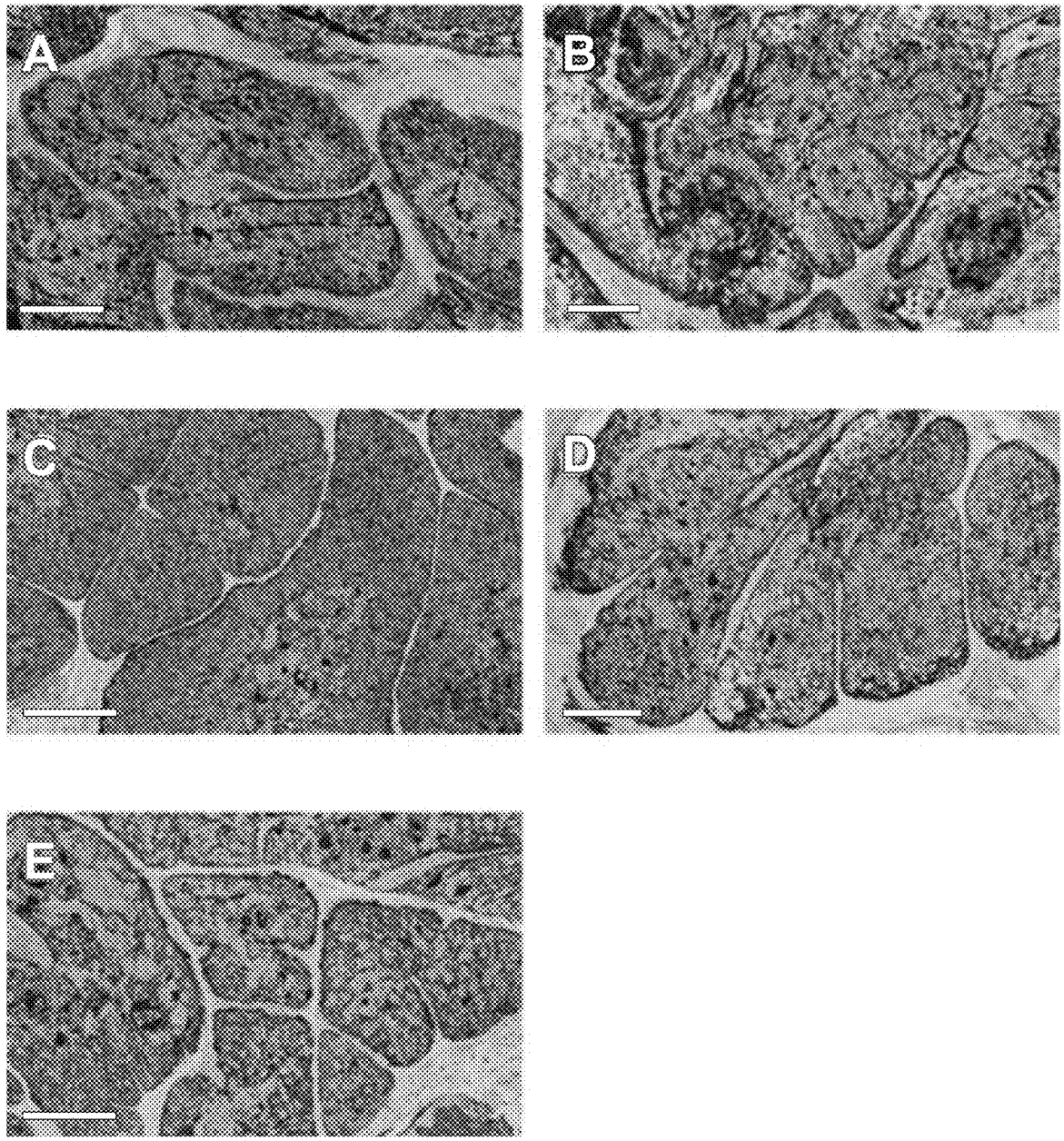

Histologic examination of any one slice resulted in the same conclusion regarding acceptability of the entire lot. Based on these observations, the relevant characteristics of any one slice from a thymus reflect those of the entire thymus. In addition, the histologic appearance of the tissue slices at day 5 reflects what is observed at each of the later time points (day 9, 12 and 21), although more necrosis is observed at later time points. FIG. 68 is a good example showing the similarity of the epithelial network as assessed by antibody AE1/AE3 from day 0 to day 21.

Example 15: Thymus Tissue Forced Degradation Study

In this study, thymus tissue slices were treated to generate tissue slices that were considered degraded or non-viable. Three thymuses were used for these experiments. Control samples were taken from each thymus. The treatment conditions presented in Table 10 were tested.

Example 16: Thymus Tissue Forced Degradation Study

In this study, thymus tissue slices were treated to generate tissue slices that were considered degraded or non-viable. Three thymuses were used for these experiments. Control samples were taken from each thymus. The treatment conditions presented in Table 5 were tested.

TABLE 10

Forced Degradation Treatment Conditions

| Condition | Duration of Treatment |
|---|---|
| Control | No treatment |
| Heat Shock, 55° C. | 4 hours |
| Freeze/thaw, −20° C./ambient | 4 hours |
| Room Temperature, 20-24° C. (Culture in BSC) | 24 hours |
| Dehydration (Culture in absence of media) | 24 hours |
| | 48 hours |
| Nutritional Depletion, (Culture in Normal Saline) | 24 hours |
| | 48 hours |
| Osmolarity Change, (Culture in 10X PBS) | 24 hours |
| DMSO Exposure, (Culture in 1% DMSO in TOM) | 24 hours |

Heat shock was accomplished by placing the 10 cm. culture dish containing the slices into a Ziploc bag, and placing into a 55° C. water bath. The plate rested on a support and was not submerged. Freeze/thaw was accomplished by placing the 10 cm. culture dish into a −20° C. freezer for 4 hours followed by thawing at ambient temperature.

Samples were tested for histology on days 5 and 9 in culture. Some samples were also tested on day 21. All slices in this study met the release acceptance criteria for histology testing namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each slide was made by the pathologist. The following observations were noted.

Samples exposed to freeze/thaw or to 10×PBS showed the most necrosis but some cells still appeared intact and met the histologic criteria for viability. See FIG. 61 for an example of exposure to 10×PBS.

Slices that were held at room temperature, dehydrated, incubated in normal saline or 1% DMSO or underwent heat shock showed a lesser degree of histologic changes.

For control samples, the following observations were noted by the pathologist.

Thymocytes are progressively lost as thymus tissue is cultured. However, dead cells may persist in cultured thymus long-term due to inability to recruit phagocytes to clear them. The nuclei of cells undergoing apoptotic cell death initially condense and stain more darkly (blue) with hematoxylin dye. As these cells deplete their energy but are not phagocytosed, they lose their membrane integrity and become necrotic. Karyolysis (dissolution of nuclei in necrotic cells) typically occurs within 2-3 days in vivo, but appears to occur more slowly during thymus culture. Thus, it is not unusual to see large eosinophilic (pink) expanses of necrotic cell debris where thymocyte nuclei have undergone karyolysis. Some dead thymocytes retain their nuclei, which have ragged edges and altered staining characteristics compared to those of viable cells.

As thymocytes are depleted from the tissue, the thymic epithelial cells become more visible. The three-dimensional thymic epithelial (TE) network is normally demonstrated in sections via a light and lacy arrangement of connected epithelial cells and/or (seemingly) scattered TE cells whose connections are not evident in the section being examined. As thymocytes are lost during culture, the three-dimensional network contracts. This results in condensation of the residual epithelium, such that the subcapsular cortical epithelial layer becomes thicker and medullary TE cells become more tightly packed. The nuclei of viable TE cells are typically oval, larger than those of thymocytes, and have a sharply defined nuclear membrane outlined by the hematoxylin (blue) stain, as well as one or more nucleoli. These TE nuclei typically look "open", meaning they do not stain darkly with hematoxylin. This fits with an interpretation that they are alive and metabolically active, since active chromatin ("euchromatin") cannot bind the hematoxylin dye. The presence of nucleoli, which are the sites of ribosome synthesis, in many TE cells further confirms that they are alive and metabolically active. The typical histologic appearance of control sections from days 5, 12 and 21 is shown FIGS. 65, 66 and 67, respectively.

For the treatment conditions including room temperature, dehydration, 1% DMSO and heat shock the pathologist indicated that the appearance of the slices did not differ significantly from those of the control. For the heat shocked sample, the pathologist noted that the heat treatment may have "fixed" the cells, by coagulating proteins that prevent further degradation. Heat treatment has been used as a fixative for tissues, including thymus.

Figure 10A:
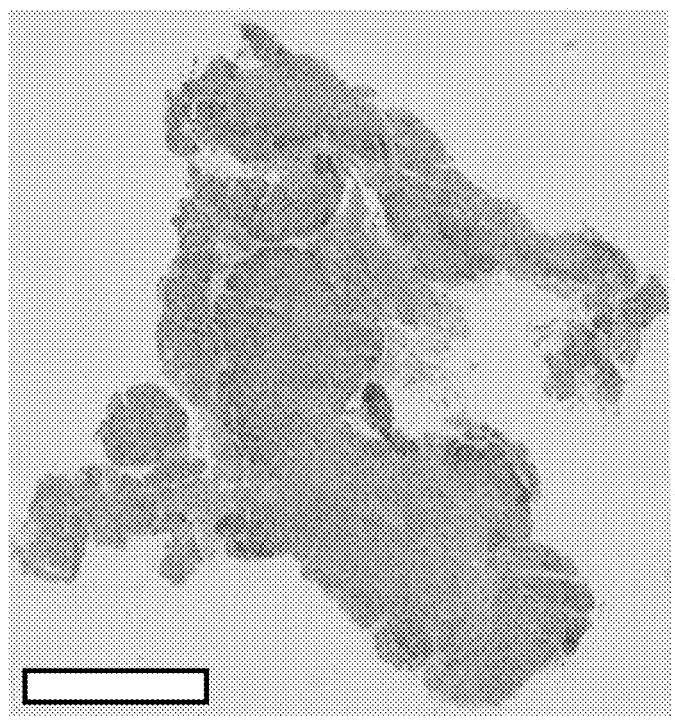
FIG. 10A and FIG. 10B depict H&E staining of thymus tissue slices on day 21 of the time course in a scale of 5 mm (FIG. 10A) and 100 µm (FIG. 10B), respectively. Note the preservation of the overall architecture of the tissue including in FIG. 10B the subcapsular cortex, cortical region and medullary region containing numerous Hassall bodies. The small dark cells are mostly necrotic thymocytes that have not yet undergone karyolysis. Photo by Laura P. Hale, MD, PhD, Department of Pathology, Duke University.
Figure 10B:
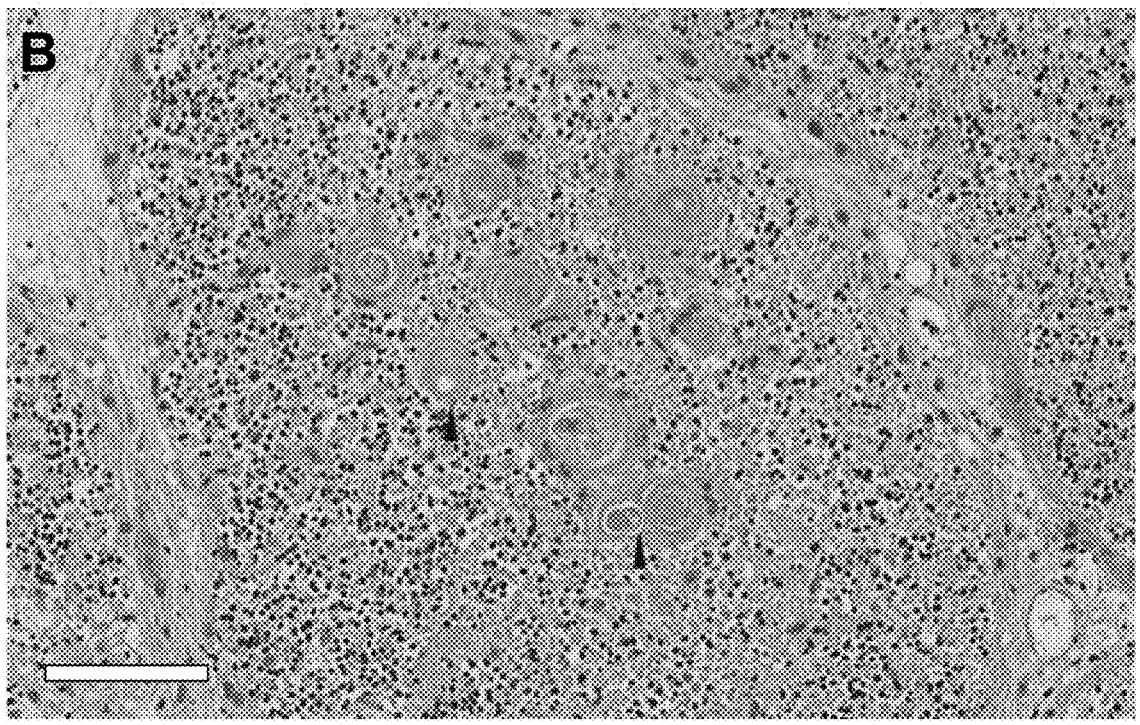
Figure 11A:
FIGS. 11A-E depict representative thymus slices which were immuno-stained with a cocktail of anti-cytokeratin antibodies (AE/AE3).
Figure 11B:
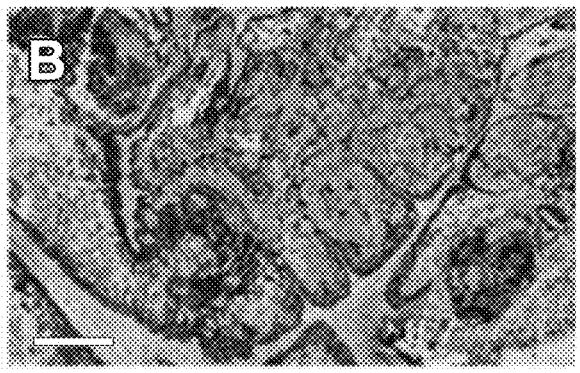
Figure 11C:
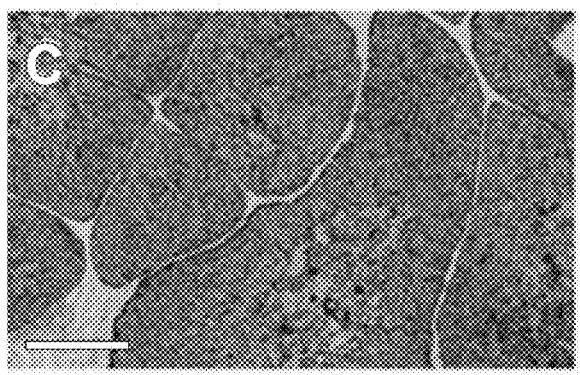
Figure 11D:
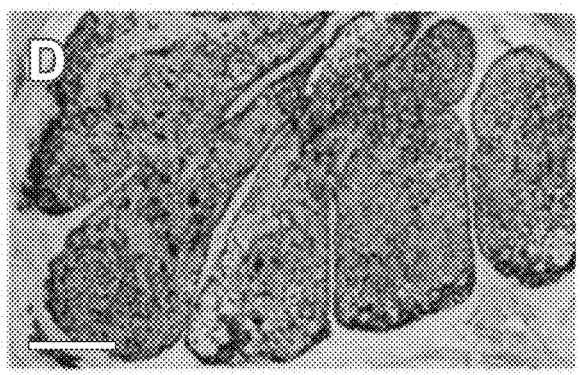
Figure 11E:
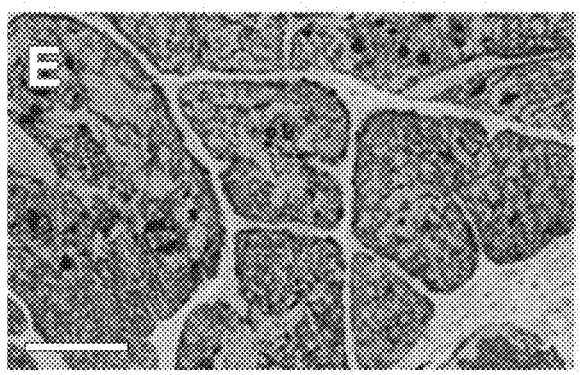

FIGS. 12A and 12B depict the histology of thymus tissue slides after exposure to forced degradation conditions. FIGS. 10A and 10B depicts the histologic appearance of control thymus tissue slices at day 21.

The general histologic appearance of the forced degradation tissue is similar at these time points, but with fewer residual thymocytes at day 21 (FIG. 12B). Representative Hassall bodies in medullary areas are indicated by arrow heads in FIG. 12B. Representative viable-appearing thymic epithelial cells are indicated by arrows in FIGS. 12A and 12B. The cortical area shown in FIG. 12B consists almost entirely of necrotic lymphocytes day 21. The bars at the lower left represent 100 μm.

Example 17: Thymus Tissue Drug Substance Batch Analysis

Batch analysis data for 10 lots of thymus tissue are shown in Table 11 below.

TABLE 11

| Lot | Year of Manufacture | Weight of incoming thymus (g) | Final dose given to patient (mm²/m²) | Testing performed on RVT-802[a] | | | | | |
|---|---|---|---|---|---|---|---|---|---|
| | | | | Appearance[b] | Histology[c] | Endotoxin | Sterility[d] | Mycoplasma[d] | Gram stain |
| MLM428 | 2016 | 4.97 | 8.034 | pass | pass | <0.500 EU/mL | No growth | No growth | Negative |
| MLM434 | 2016 | 7.48 | 9.110 | pass | pass | <0.500 EU/mL | No growth | No growth | Negative |
| MLM435 | 2016 | 27.74 | 7.104 | pass | pass | <0.500 EU/mL | No growth | No growth | Negative |
| MLM437 | 2016 | 8.99 | 9.884 | pass | pass | <0.500 EU/mL | No growth | No growth | Negative |
| MLM438 | 2017 | 10.68 | 19.134 | pass | pass | <0.500 EU/mL | No growth | No growth | Negative |

TABLE 11-continued

| Lot | Year of Manufacture | Weight of incoming thymus (g) | Final dose given to patient (mm²/m²) | Testing performed on RVT-802[a] | | | | |
|---|---|---|---|---|---|---|---|---|
| | | | | Appearance[b] | Histology[c] | Endotoxin | Sterility[d] | Mycoplasma[d] | Gram stain |
| MLM444 | 2017 | 10.51 | 19.402 | pass | pass | <0.500 EU/mL | No growth | No growth | Negative |
| MLM447 | 2017 | 5.95 | 8.459 | pass | pass | <0.500 EU/mL | No growth | No growth | Negative |
| MLM449 | 2017 | 7.81 | 9.260 | pass | pass | <0.500 EU/mL | No growth | No growth | Negative |
| MLM450 | 2017 | 12.99 | 17.128 | pass | pass | <0.500 EU/mL | No growth | No growth | Negative |
| MLM452 | 2017 | 7.61 | 16.802 | pass | pass | <0.500 EU/mL | No growth | No growth | Negative |

Key:
(e) These lots were tested according to the specification that was in place at the time of manufacture. The drug substance testing results presented in this table also represents the final drug product testing results.
(f) The appearance specification was no evidence of tampering or damage to containers.
(g) The histology assay was used for both identity and potency. The histology specification (tested between days 5-9) was the following:
(h) Areas positive for keratin scattered throughout the tissue.
  i. At least 1 Hassall body identified
  ii. CK14 staining scattered throughout the tissue
  iii. Intact nuclei observed
  iv. Sterility and *mycoplasma* samples were collected on days 1, 7 and 14.

Data for 56 clinical thymuses, 8 thymuses used for intra-thymus variability, inter-thymus variability and time-course testing, and 3 thymuses that had undergone forced degradation were used to generate the current control library. The forced degradation samples in the library (negative controls) were the ones that had undergone degradation by exposure to freeze/thaw or to 10×PBS. The full data set resulted in 14 different clusters. All forced degradation samples clustered together and no clinical samples or characterization samples clustered with the forced degradation samples.

Example 18

Methods

Thymus tissue is collected prospectively from cardiac surgery patients across three distinct age groups: 9 months to 9 years; 10 years to 25 years; and 26 years to 49 years, for a total of 30 samples following informed consent. As part of the preliminary studies for this project, novel custom instrumentation for slicing fatty tissues was developed. Traditional slicing, with a Stadie-Riggs microtome, of fatty tissues from older thymuses does not yield slices that can be assessed by immunohistochemistry. For fatty thymus, therefore, single edged razor blades (approximately 10) are wired together and sterilized. The distance between blades is approximately 1 mm. Pieces of thymus tissue approximately 1 cm×1 cm×1 cm are put in the bottom of a sterile tissue culture dish. The bound razor blades are pressed into the thymus tissue.

Individual slices are removed from the between the razor blades and used for staining. Slicing and culture of human thymus tissues for 21 days is carried out as described in preceding Examples. Tissue slices and spent media from days 1, 5, 12, and 21 are frozen for further analysis. Tissue slices from day 0 and day 21 are also processed into formalin-fixed and paraffin-embedded (FFPE) blocks to facilitate immunohistologic studies, as described below.

Analysis begins with the FFPE blocks from days 0 and 21, using hematoxylin and eosin (H&E) stained sections as well as immunohistochemistry (IHC) for cytokeratin (AE/AE3 cocktail), cytokeratin (CK) 14, proliferation (Ki-67), T cell content (CD3), and production of chemokine (CCL21). Histologic characteristics of acceptable donor thymus on day 0 include an organized thymic epithelial (TE) network, presence of TE cells that express CK14 as a marker of repopulating potential, presence of immature thymocytes and Hassall bodies as a marker of thymopoiesis at the time of procurement, and >90% intact nuclei as an indicator of tissue viability. Cultured thymus slices should similarly demonstrate thymic epithelial cell viability, maintenance of TE architecture, marked depletion of viable thymocytes, and production of functionally important biomolecules, including high production of CCL21, the chemokine responsible for attracting immature thymocyte precursors to the thymus. Production of CCL21 by thymus slices is assessed via IHC of FFPE slices as well as enzyme immunoassay of spent media (FIG. 69).

Because the thymus tissues used may exhibit varying degrees of age-related atrophy, determining baseline thymus function is essential. Baseline thymus function is determined by image analysis of scanned tissue sections from day 0, as previously described (Ito, R., Hale, L. P., Geyer, S. M., Li, J., Sornberger, A., Kajimura, J., Kusunoki, Y., Yoshida, K., van den Brink, M. R. M., Kyoizumi, S., Manley, N. R., Nakachi, K., Sempowski, G. D.: *Effects of age and exposure to ionizing radiation on human thymus morphology and function. Radiation Res.*, 187.589-598, 2017. In addition, thymic output of naïve T cells is determined using donor peripheral blood. Peripheral blood mononuclear cells are purified and preserved; T cell phenotype is determined by 10-color flow cytometry using the following markers: viability, CD3, CD4, CD8, CD19, CD16+CD56, CD45RA, CD57, and CD197. Signal joint T-cell receptor rearrangement excision circles (sjTRECs) present in peripheral blood T cells are quantitated as a marker for thymic origin Lee E N, Park J K, Lee J-R, Oh S-O, Baek S-Y, Kim B-S, et al., 2011, "Characterization of the expression of cytokeratins 5, 8, and 14 in mouse thymic epithelial cells during 2011; 44: 14-24. thymus regeneration following acute thymic involution," *Anat Cell Biol*.

Example 19. Histopathologic Assessment of Cultured Human Thymus

These experiments were performed to assess and describe the histopathologic changes that occur in human thymus slices when cultured according to protocols used for implanted tissues. Understanding these changes can potentially lead to the development and validation of histopathologic criteria for prospective assessment of the quality of cultured thymus slices prior to implantation, based on characteristics of tissues that have successfully generated immune reconstitution in prior recipients Markert M L, Devlin B H, McCarthy E A., 2010, "Thymus transplantation," *Clin Immunol.* 2010; 135: 236-246. Taken together, these results can be used to develop diagnostic criteria based on structural features of the tissue identifiable via hematoxylin and eosin staining and cytokeratin immunohistochemistry that can potentially serve to evaluate the quality of slices used for implanted.

Materials and Methods

Thymic tissue was obtained from immunocompetent infant donors <9 months of age who were undergoing corrective cardiac surgery where removal of a portion of the thymus was routinely required to facilitate the cardiac repair. The parent(s) of each donor provided written informed consent to allow any thymic tissue that was removed and otherwise would be discarded to be potentially used for implantation or research. These studies were approved by the Institutional Review Board of Duke University Medical Center. The donor thymus was sliced and cultured in a Good Manufacturing Process (GMP)-compliant cell manufacturing laboratory for up to 21 days before release to the operating room for surgical implantation into the muscle of the recipient. The details of the donor qualification, culture, and surgical implantation processes have been described elsewhere Markert M L, Sarzotti M, Ozaki D A, Sempowski G D, Rhein M E, Hale L P, et al., 2003, "Thymic transplantation in complete DiGeorge syndrome: Immunologic and safety evaluation in twelve patients," Blood, 102: 1121-1130. Markert M L, Alexieff M J, Li J, Sarzotti M, Ozaki D A, Devlin B H, et al., 2004, "Postnatal thymus transplantation with immunosuppression as treatment for DiGeorge syndrome," *Blood,* 104: 2574-2581; Markert M L, Devlin B H, Alexieff M J, Li J, McCarthy E A, Gupton S E, et al., 2007, "Review of 54 patients with complete DiGeorge anomaly enrolled in protocols for thymus transplantation: Outcome of 44 consecutive transplants," *Blood,* 109: 4539-4547; Hong R, wt al., 1996; Rice H E, eSkinner M A, Mahaffey S M, Oldham K T, Ing R J, Hale L P, et al., 2004, "Thymic transplantation for complete DiGeorge syndrome: medical and surgical considerations," *J Pediatr Surg.,* 39: 1607-1615. At specific time points during culture, one or more slices from each donor thymus were fixed in 10% neutral buffered formalin then processed and embedded into formalin-fixed paraffin embedded blocks for histopathologic evaluation. Hematoxylin and eosin (H&E)-stained sections and an immunohistochemical panel were obtained for each tissue block. Antibodies used included pan-cytokeratin (clones AE1/AE3; Leica), cytokeratin (CK) 14 (clone LL02; Leica), CD3 (clone LN10; Leica), and Ki-67 (clone MIB-1; Dako). Automated immunohistochemistry was performed using standard immunoperoxidase methodologies and 3,3'-diaminobenzidine (brown) substrate, with a hematoxylin counterstain. To assess variability within thymus samples over time in culture, lots were generally examined histologically at ≥3 time points within the following ranges: day 0 (day of receipt), day 5-9, and day 12-21.

Results and Discussion

As thymic organ cultures progressed from days 0 through 21, slices developed increasing amounts of necrosis, increasing condensation of thymic epithelium, and decreasing numbers of residual T cells. The architecture of the thymic epithelial network remained generally well-preserved throughout the 21 days of culture, with focal expression of cytokeratin 14, a putative biomarker of thymic epithelial cells with long-term organ-repopulating potential. All organ slices derived from the same donor thymus closely resembled one another, with minor differences in size, shape, and relative content of cortex versus medulla. Similarly, slices derived from different donors showed similar histopathologic characteristics when examined at the same culture time point.

Initial Identification of Tissue as Thymus.

Figure 71:
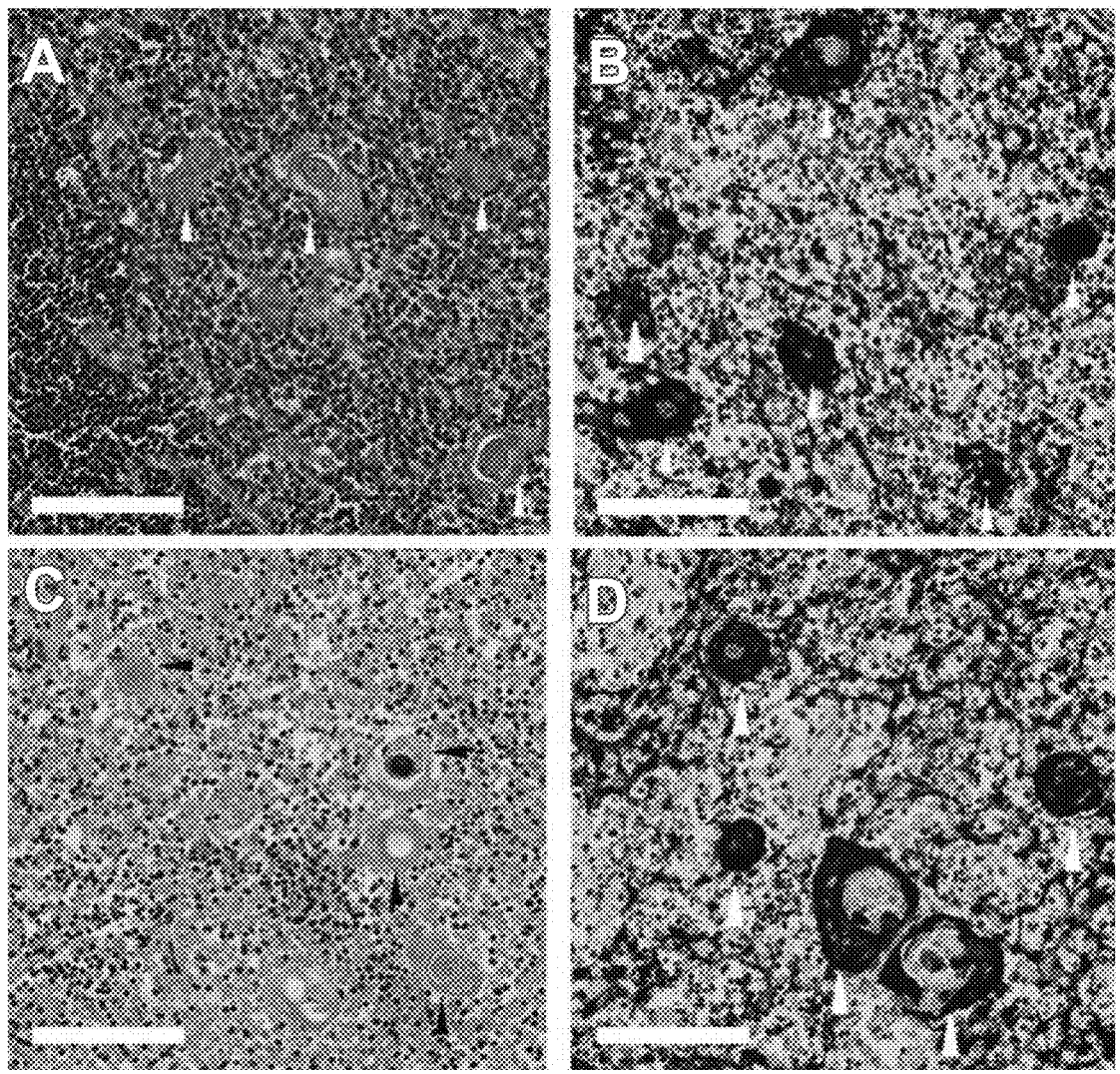

The thymus possesses a thin connective tissue capsule that is typically removed during laboratory processing. However, extensions of the capsule (trabeculae) and associated blood vessels, fibrous tissue, adipose tissue, and variable numbers of mature hematopoietic cells may still be observed in thymus slices. The trabeculae divide the thymus tissue into lobules that are composed of a lacy-appearing three-dimensional network of thymic epithelial cells with intervening spaces containing the developing T cells (thymocytes). The lobules typically demonstrate an outer cortex and an inner medulla, which vary in their histologic appearance as well as phenotype and function of the cells they contain. The thymic cortex is very basophilic (blue) due to densely packed immature thymocytes that stain very darkly with hematoxylin. The density of the more mature thymocytes that are present in the thymic medulla is lower than that of the cortex, so the medulla tends to appear more eosinophilic (pink). The thymic medulla also contains pathognomonic eosinophilic cytokeratin-containing structures called Hassall bodies. Macrophages present within the thymus may form "tingible bodies" that appear as a light-colored circular area against a background of darkly staining thymocytes (a "starry sky" pattern). Large numbers of tingible bodies are characteristic of stress involution, which may occur in normal thymus donors due to the stress of severe cardiac defects, surgery, and/or corticosteroid treatment and does not disqualify a thymus for implantation. The typical histologic features of sliced normal thymus prior to culture (day 0) are shown in FIGS. 71-D.

Assessment of Hassall Bodies

The thymic medulla contains characteristic structures called Hassall bodies that are composed of terminally differentiated thymic epithelial cells that react with monoclonal antibodies that also react with the terminally differentiated upper layers of the epidermis. Hale L P, et al., 2004; 172: 617-624.

Hassall bodies may serve as a marker of tissue identity, since they are found only in thymus. They may also reflect the quality of the input donor tissue, since the terminal differentiation process is normally triggered by thymocyte-thymic epithelial cell interactions. Id. Hassall bodies are usually readily identified by their appearance as eosinophilic whorls of epithelial cells on H&E-stained slides (FIG. 72A-D). The central-most layers typically lack nuclei. Variable amounts of cellular debris may also be present in the center of the Hassall bodies. Hassall bodies stain very strongly with pan-cytokeratin AE1/AE3 antibodies, which can be used as secondary confirmation of the identity of these structures if not definitively identified in hematoxalin and eosin (H&E)-stained slides.

General Thymocyte Changes During Culture

Figure 73:
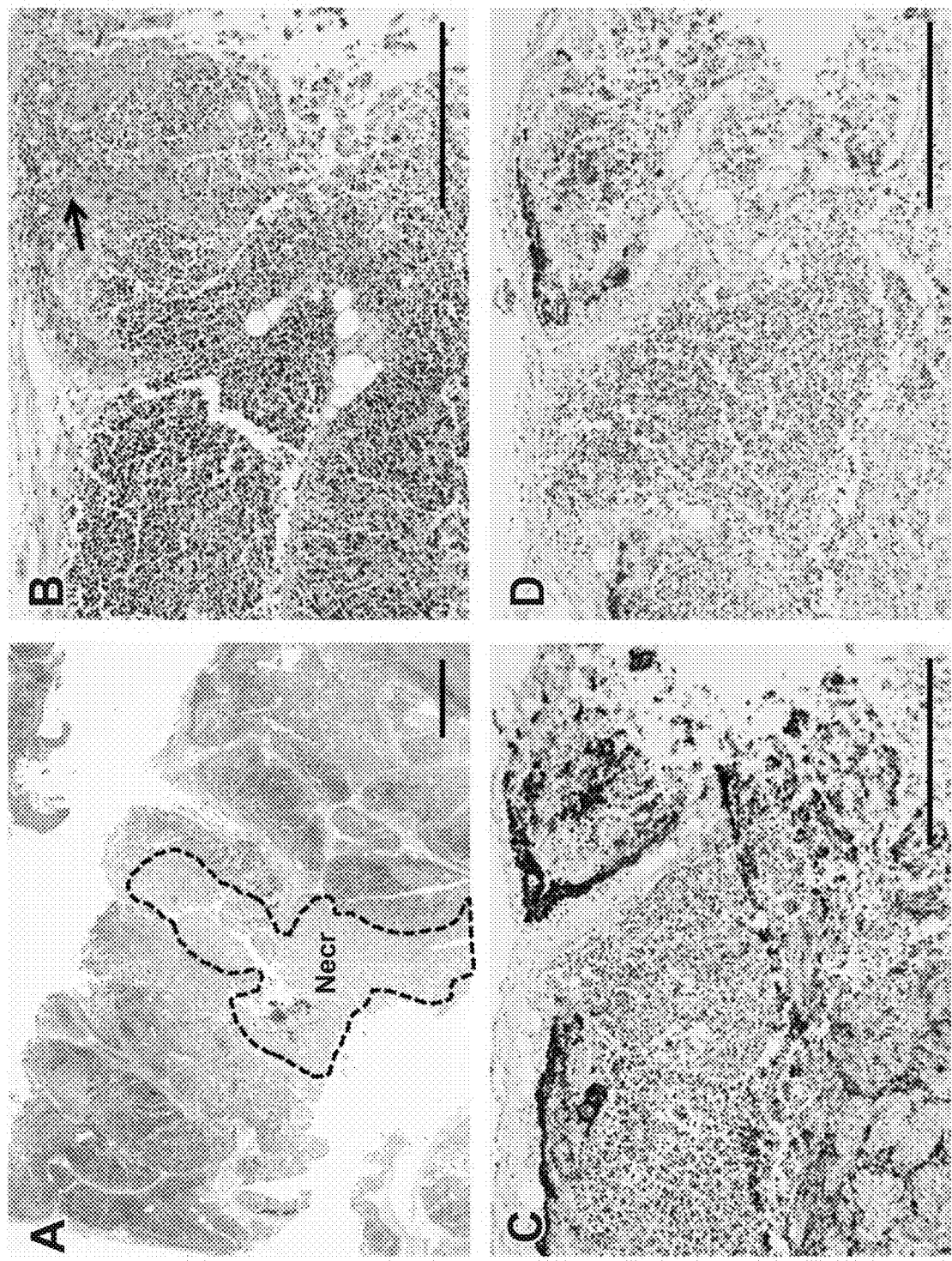

Thymocytes are progressively lost as thymus tissue is cultured, either from being flushed out during media changes or from thymocyte death followed by degradation within the tissue (FIG. 72-FIG. 75). However, unlike what occurs in vivo, dead cells may persist in cultured thymus long-term due to inability to recruit phagocytes to clear them. Thymocyte nuclei undergoing cell death may show pyknosis (chromatin condensation) and karyorrhexis (nuclear fragmentation) but typically, as these cells deplete their energy but are not phagocytosed, they show ragged nuclear edges with loss of nuclear membrane integrity. Karyolysis (complete dissolution of nuclei in necrotic cells) typically occurs within 2-3 days in vivo, but appears to occur more slowly during thymus culture. After 5-9 days in culture, most thymocytes have retained nuclei, but nuclear membranes are not intact, indicating early necrosis (FIG. 24). These altered nuclear characteristics facilitate the distinction between viable and non-viable thymocytes, even when nuclei are retained. Large foci of eosinophilic necrotic cell debris where thymocyte nuclei have undergone karyolysis may also be seen (FIG. 73).

Histologic Assessment of Cell Integrity and Tissue Architecture.

When cultured thymus tissue is to be implanted, it is critical to be able to accurately distinguish between slices with extensive thymocyte necrosis but thriving thymic epithelial cells (the optimal tissue for implantation) versus slices with similar amounts of necrosis where thymic epithelial cells are also compromised. Although it cannot directly assess viability, histologic examination of H&E slides can assess the degree of preservation of normal structures and the presence or absence of indicators of cell death. As described above, thymocytes are expected to be depleted during the culture process. Many thymocytes are washed from the slice during the daily media changes. Many others will die in situ, where their nuclei and cell bodies may remain for prolonged periods of time. However, the membrane integrity of dead thymocytes is compromised and their nuclei exhibit "ragged" edges. Thymocyte debris may clump together, making it impossible to discern individual cell borders. Thymocyte death and depletion is an expected and desirable consequence of culture and relative lack of intact thymocyte nuclei is potentially reflective of slice quality.

Thymic epithelial cells are more easily visualized as thymocytes are depleted from the tissue. Nuclei of viable thymic epithelial cells are typically oval, larger than those of thymocytes, and have a sharply defined nuclear membrane outlined by the hematoxylin stain, with one or more nucleoli. These thymic epithelial nuclei typically look "open," meaning they do not stain darkly with hematoxylin. This fits with an interpretation that they are alive and metabolically active, since active chromatin ("euchromatin") does not bind the hematoxylin dye. The presence of nucleoli, which are the sites of ribosome synthesis, in many thymic epithelial cells further confirms that they were alive and metabolically active at the time of fixation. Examples of intact and viable-appearing thymic epithelial cells are shown in FIG. 77A-B.

Careful microscopic examination of multiple thymus slices at any given time point from day 0-21 showed that all slices derived from the same donor thymus closely resembled one another. The differences observed between different slices derived from the same thymus as a function of culture time were primarily related to the amount of necrosis (increased as culture time increased) and numbers of residual thymocytes (decreased as culture time increased). Slices derived from different donors were also qualitatively similar to each other when examined at the same time points. Differences between different donor tissues included relative size, shape, relative content of thymus versus medulla (but both were always present on each slice examined), amount of necrosis, condensation of thymic epithelium, and numbers of residual T cells. Most changes in histologic appearance had already occurred by day 5 of culture, with generally only additional depletion of thymocytes as cultures progressed.

Assessment of Thymic Epithelial Architecture.

A cocktail containing anti-cytokeratin antibodies AE1 and AE3 (AE1/AE3) detects essentially all thymic epithelial cells. In contrast, an antibody reactive with CK14 detects a subset of thymic epithelial cells that are present in the subcapsular cortex and seemingly scattered throughout the remainder of the cortex and medulla. Some of these CK14+ cells have been suggested to have the potential to differentiate into both cortical and medullary epithelial cells, Lee E N, Park J K, Lee J-R, Oh S-O, Baek S-Y, Kim B-S, et al., 2011, "Characterization of the expression of cytokeratins 5, 8, and 14 in mouse thymic epithelial cells during thymus regeneration following acute thymic involution," *Anat Cell Biol.* 44: 14-24, and thus to represent long-term repopulating cells. As thymocytes are depleted from the tissue, the thymic epithelial cells become more visible. The three-dimensional thymic epithelial network is normally demonstrated in sections via a light and lacy arrangement of connected epithelial cells and/or seemingly scattered thymic epithelial cells whose connections are not evident in the section being examined. The three-dimensional thymic epithelial network contracts to varying degrees as thymocytes are lost during culture. This can result in condensation of the residual epithelium, such that the subcapsular cortical epithelial layer becomes thicker and medullary thymic epithelial cells become more tightly packed. Examples of these changes are shown in FIG. 70A-D and FIG. 73-FIG. 75 for a single thymus lot examined on days 0 (day of receipt), 7, 9, 12, and 20. Despite the loss of numerous thymocytes and potentially large areas containing necrotic debris, the overall architecture of the thymic epithelial cell network remains generally well-preserved through at least 21 days of culture (FIGS. 78A-E).

Assessment of Residual T Cells

As described above, the primary purpose of culture of donor thymus tissues that are intended for implantation is to partially deplete T cells to facilitate colonization of the implanted slices with recipient thymocyte precursors and to decrease the risk of graft-versus-host disease. Immature T cells (thymocytes) and mature T cells can be identified in histologic sections by their morphology as well as by immunohistochemical stains that detect proteins specifically expressed by these cell types. CD3 is a component of the T cell receptor for antigen that is present on >95% of cortical and medullary thymocytes as well as on all mature T cells. On day 0, the plasma membranes of essentially all immature T cells in the cortex and the medulla appear strongly reactive with CD3 antibody in a membrane pattern (FIGS. 79A-B). Viable thymocytes/T cells continue to react with CD3 antibody in a membrane pattern as cultures continue. However, the CD3 antibody also reacts strongly with dead thymocytes, including the anucleate debris that remains after dead thymocytes undergo karyolysis (FIG. 79D, FIG. 79G, and FIGS. 79I-K). So much thymocyte debris remains that slices may still appear strongly and uniformly brown when viewed at low magnification (FIG. 79C, FIG. 79F, FIG. 79H, FIG. 79J), although examination of the slide at higher power (e.g. 40× objective) confirms that relatively few intact potentially viable thymocytes are present at these time points. Non-viable cells and cellular debris will be cleared by recipient phagocytes after implantation and therefore convey no risk of graft-versus-host disease. It is not generally possible to accurately identify CD3+ membrane immunoreactivity in tissue areas where considerable amounts of strongly staining debris prevents assessment of cellular membranes of adjacent cells. However, even at late time points during culture, CD3 immunohistochemistry typically highlights at least some thymocytes/T cells that have intact plasma membranes suggesting that they may still be viable (FIG. 79E, FIG. 79G, FIGS. 79I-K).

Assessment of Cellular Proliferation

The Ki-67 antigen is expressed in the nucleus of all cells that are proliferating (i.e., not in the G0 phase of the cell cycle). On day 0, the majority of the immature thymocytes present within the thymic cortex are proliferating and their nuclei react strongly with antibody specific for the Ki-67 proliferation antigen. In contrast, only rare more mature medullary thymocytes and/or epithelial or stromal cells react with this antibody (FIGS. 66A-B). The pattern of immunoreactivity observed after day 1-2 of culture is of scattered rare positive cells, almost all of which have the larger nuclei characteristic of thymic epithelial cells. Thus, the Ki-67 stain may be a useful adjunctive stain for documenting the viability of thymic epithelial cells within the slice.

Discussion

These experiments describe histopathologic changes that occur when postnatal human thymus is cultured for up to 21 days and demonstrate that histopathologic examination using H&E and cytokeratin immunoreactivity can be useful for assessing the quality of cultured thymus slices intended for implantation. As thymic cultures progressed, slices developed increasing amounts of necrosis, increasing condensation of thymic epithelium, and decreasing numbers of residual T cells. The thymic epithelial network remained intact throughout the 21 days of culture, with continued expression of cytokeratin 14, a putative biomarker of thymic epithelial cells with long-term organ-repopulating potential. Slices from the same thymus were qualitatively similar, such that a single slice could adequately represent the entire thymus. Variability in histologic appearance of cultured thymus slices derived from different donors was also minimal at any given time point. Tissue histology observed early during culture (e.g., days 5-9) closely reflected what was observed later in culture (e.g., days 12-21), although more thymocyte depletion and necrosis were observed at the later time points.

Immunohistochemistry for antibodies that recognize CK14 or all types of cytokeratins (AE1/AE3) was useful in evaluation of cultured thymus slices. Cytokeratin intermediate filaments are important components of the cytoskeleton of all epithelial cells. The pan-cytokeratin AE1/AE3 stain demonstrates the epithelial network within the examined thymus slice, which may not be easily discernable at later time points using H&E stain alone. The specific type of cytokeratin expressed by a particular thymic epithelial cell has been shown to depend on its stage of development and differentiation and functional state. In mice, antibodies that react with CK5, CK8, and CK14 have been most commonly used to identify thymic epithelial cell subtypes, Lee E N, et al., 2011, *Anat Cell Biol.*, 44: 14-24. Expression of CK14 was determined in this study, based on previous studies where CK14 expression was hypothesized to be a characteristic of thymic epithelial cells with the potential to differentiate toward either cortical or medullary lineages Li B, Li J, Devlin B H, Markert M L., 2011, "Thymic microenvironment reconstitution after postnatal human thymus transplantation," *Clin Immunol.* 140: 244-259. While the clinical outcome of long-lasting immune reconstitution Markert M L, et al., *Blood,* 109: 4539-4547 suggests that thymic epithelial progenitors are likely present within implanted thymus slices, the precise phenotype for such progenitors has not been definitively identified in humans. The phenotype of thymic epithelial progenitors in mice is still controversial Bennett A R, Farley A, Blair N F, Gordon J, Sharp L, Blackburn C C., 2002, "Identification and characterization of thymic epithelial progenitor cells," *Immunity* 16: 803-814; Wong K, Lister N L, Barsanti M, Lim J M C, Hammett M V, Khong D M, et al., 2014, "Multilineage potential and self-renewal define an epithelial progenitor cell population in the adult thymus," *Cell Rep.* 8: 1198-1209; Ucar A, Ucar O, Klug P, Matt S, Brunk F, Hofmann T G, et al., 2014, "Adult thymus contains FoxN1 (−) epithelial stem cells that are bipotent for medullary and cortical thymic epithelial lineages," *Immunity,* 41: 257-269; Ulyanchenko S, O'Neill K E, Medley T, Farley A M, Vaidya H J, Cook A M, 2016, "Identification of a bipotent epithelial progenitor population in the adult thymus," *Cell Rep.,* 14: 2819-2832, and only low numbers have been detected using multiple antibodies and multi-color flow cytometry. Thus direct detection of thymic epithelial progenitors in human tissue sections is not currently feasible.

These experiments identified potentially large amounts of necrotic cellular material remaining within thymic slices at culture days 12-21, the time points when the tissue might be implanted. Biopsy examination several months after implantation shows no evidence of this necrotic material Markert M L, Li J, Devlin B H, Hoehner J C, Rice H E, Skinner M A, 2008, "Use of allograft biopsies to assess thymopoiesis after thymus transplantation," *J Immunol,* 180: 6354-6364. While not desiring to be bound by any particular theory, Applicant submits that the initial presence of this necrotic debris and its underlying extracellular matrix at the time of implantation may serve to preserve the functional architecture of the slices, including the cortical and medullary niches for developing thymocytes. The recent use of thymus decellularization approaches that preserve extracellular matrix to recreate murine thymic "organoids" that can support cellular differentiation of both epithelial cells and hematopoietic precursors Hun M, Barsanti M, Wong K, Ramshaw J, Werkmeister J, Chidgey A P, 2017, "Native thymic extracellular matrix improves in vivo thymic organoid T cell output, and drives in vitro thymic epithelial cell differentiation," *Biomaterials,* 118: 1-15, supports this hypothesis.

Previous studies demonstrated that the growth potential of thymic epithelial cells was robustly maintained under the culture conditions used, such that cyokeratin-positive epithelial monolayers could be established from the slices up to 12 weeks after initiation of organ culture Markert M L, et al., 1997, *Clinical Immunol Immunopathol.,* 82: 26-36. The experiments described in this example did not directly assess epithelial cell viability, but instead used the presence of intact nuclei as a surrogate marker.

Example 20

Detection of Cytokines and Chemokines in Spent Media

Spent media samples from the various thymus culture conditions were sent to RayBio, Norcross, Georgia, for a panel analysis of cytokines and chemokines. Testing was performed using Quantibody Arrays using fluorescence detection. Quantibody arrays are sandwich based, glass slide multiplex ELISA (Part Number QAH-CAA-4000 for non-custom kits). All testing was performed using RayBio procedures SOP-TF-QAH-001 and SOP-TF-QAH-003 Three different sets of samples were sent and were tested by RayBio at 2-fold dilution. The first set of samples included manufacturing lots MFG-025, MFG-026, and MFG-027 per testing protocol 060717 QAH-CAA-4000 SA31 Duke U. The second set of samples included MFG-035, MFG-036, and MFG-038 per testing protocol 091117 Cust-H120 SA31 Duke U. The final set of samples included MFG-053, MFG-054, and MFG-066 per testing protocol 050118 QAH-CAA-4000 SA113 Duke U. The first and third set of samples were tested with equivalent kits utilizing different antibody lots. The second set was tested with a custom kit that has different antibody cocktails at different antibody concentrations to target only certain analytes. The custom kit that was used for the second set of testing is the same basis as the other kits, but was testing for only select cytokines and chemokines instead of a broader array of targets. This results in different upper and lower limits of detection for each sample set as they are defined by the mean background. Trends across all three sample submissions should be representative although the data has not been normalized.

Characterization During 21-Day Culture

Samples of the spent medium from Lot MFG-025, MFG-026, MFG-027, MFG-035, MFG-036, and MFG-038 were taken on days 1, 5, 7, 9, 11, 13, 15, 17, 19, and 21 of the routine 21-day culture.

Lot MFG-053

Treatment 1: Control

After thymus receipt in the MC3 facility, the thymus tissue was sliced per the applicable SOPs, as described elsewhere in this specification and cultured for 9 days. Thymus slices were cultured in 10-cm round tissue culture plates with 4 slices per plate. Samples of the spent medium were taken on days 5, 7, and 9 to determine the biomarker levels at each time point as required per protocol.

Treatment 3: −20° C., 4 Hours

After thymus receipt in the MC3 facility, the thymus tissue was sliced per the applicable SOPs, as described elsewhere in this specification and cultured. Thymus slices were cultured in 10-cm round tissue culture plates with 4 slices per plate. Thymus slices were placed on top of a filter per procedure. On day 2, the test thymus slices were subjected to a temperature of −20° C. for 4 hours. The slices were placed back into the 10-cm dish with TOM and cultured for a total of 9 days. Samples of the spent medium were taken on days 5, 7, and 9 to determine the biomarker levels at each time point.

Treatment 5: 55° C., 4 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to a temperature of 55° C. for 4 hours. The slices were placed back into the 10-cm dish with TOM and cultured for a total of 9 days. Samples of the spent medium were taken on days 5, 7, and 9 to determine the biomarker levels at each time point.

Lot MFG-054

Treatment 1: Control.

Treatment 2: Room Temperature, 24 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to room temperature for 24 hours. The slices were placed back into the 10-cm dish with TOM and cultured for a total of 9 days. Samples of the spent medium were taken on days 5, 7, and 9 to determine the biomarker levels at each time point.

Treatment 3: Dehydration, 24 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to dehydration for 24 hours. The slices were placed back into the 10-cm dish with TOM and cultured for a total of 9 days. Samples of the spent medium were taken on days 5, 7, and 9 to determine the biomarker levels at each time point.

Treatment 4: Dehydration, 48 Hours

After thymus receipt in the MC3 facility, the thymus tissue was sliced per the applicable SOPs, as described elsewhere in this specification and cultured. Thymus slices were cultured in 10-cm round tissue culture plates with 4 slices per plate. Thymus slices were placed on top of a filter per procedure. On day 2, the test thymus slices were subjected to a temperature of −20° C. for 4 hours. The slices were placed back into the 10-cm dish with TOM and cultured for a total of 9 days. Samples of the spent medium were taken on days 5, 7, and 9 to determine the biomarker levels at each time point.

Treatment 4: Normal Saline, 24 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to dehydration for 48 hours. TOM was added back to the dish and slices were cultured for a total of 9 days. Samples of the spent medium were taken on days 5, 7, and 9 to determine the biomarker levels at each time point.

Treatment 5: Normal Saline, 24 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were cultured in normal saline for 24 hours instead of TOM. Following treatment, the saline was removed and TOM added per normal procedure and slices were cultured for a total of 9 days. Samples of the spent medium were taken on days 5, 7, and 9 to determine the biomarker levels at each time point.

Treatment 6: Normal Saline, 48 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to a temperature of 55° C. for 4 hours. The slices were placed back into the 10-cm dish with TOM and cultured for a total of 9 days. Samples of the spent medium were taken on days 5, 7, and 9 to determine the biomarker levels at each time point.

Treatment 7: 10×PBS, 24 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of filter per procedure. On day 2, the test thymus slices were cultured in 10×PBS for 24 hours instead of TOM. Following treatment, the 10×PBS was removed and TOM added per normal procedure and slices were cultured for a total of 9 days. Samples of the spent medium were taken on days 5, 7, and 9 to determine the biomarker levels at each time point.

Treatment 8: 1% DMSO, 24 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to 1% DMSO for 24 hours. The slices were placed back into TOM and cultured for a total of 9 days. Samples of the spent medium were taken on days 5, 7, and 9 to determine the biomarker levels at each time point.

Lot MFG-066

Treatment 4: Control

After thymus receipt in the MC3 facility, the thymus tissue was sliced per the applicable SOPs and cultured for 21 days. Thymus slices were cultured in 10-cm round tissue culture plates with 4 slices per plate. Samples of the spent medium were taken on days 2-21 to determine the biomarker levels at each time point.

Treatment 5: −20° C., 4 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to a temperature of −20° C. for 4 hours. The slices were returned to normal conditions and cultured for a total of 21 days. Samples of the spent medium were taken on days 2-21 to determine the biomarker levels at each time point.

Treatment 6: 55° C., 4 Hours.

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to a temperature of 55° C. for 4 hours. The slices were returned to normal conditions and cultured for a total of 21 days. Samples of the spent medium were taken on days 2-21 to determine the biomarker levels at each time point.

Treatment 7: 10×PBS, 24 Hours

After thymus receipt in the MC3 facility, the thymus tissue was sliced per the applicable SOPs and cultured. Thymus slices were cultured in 10-cm round tissue culture plates with 4 slices per plate. Thymus slices were placed on top of a filter per procedure. On day 2, the test thymus slices were subjected to 10×PBS for 24 hours. The slices were placed back into TOM and cultured for a total of 21 days. Samples of the spent medium were taken on days 2 and 4-21 to determine the biomarker levels at each time point.

Results

Based on analysis of the routine and forced degradation data, four biomarkers stood out from the 12 biomarkers studied based on literature and overall trends in data over the time course of culture when compared to forced degraded samples. These were CCL21, CXCL16, L-Selectin, and uPAR. Analysis of the levels of these four biomarkers are discussed in this section.

CCL21 6Ckine

CCL21 6Ckine is a TEC-expressed chemokine that has been shown to be chemotactic for thymocytes (Liu 2005), which is a critical determinant for a successful immune reconstitution of the recipients following implantation of the cultured thymus.

Characterization of CCL21 During 21-Day Culture

Descriptive statistics for the CCL21 levels in the spent media are presented in Table 12. Data from the control samples in the forced degradation studies (Lot MFG-053, MFG-054, and MFG-066) were included with results from 21-day time course samples from Lots MFG-025, MFG-026, MFG-027, MFG-035, MFG-036, and MFG-038. Results greater than the assay ULOQ are not plotted or included in the statistical analysis.

TBLE 12

Descriptive Statistics for CCL21 Levels in Spent Media over 21 days

| Day | N | Mean (pg/mL) | Standard Deviation (pg/mL) | Minimum (pg/mL) | Maximum (pg/mL) |
| --- | --- | --- | --- | --- | --- |
| 1 | 6 | 269.3 | 173.3 | 118.2 | 608.3 |
| 2 | 1 | 1056 | — | 1056 | 1056 |
| 3 | 1 | 1837 | — | 1837 | 1837 |
| 5 | 6 | 9090 | 4584 | 3314 | 16977 |
| 7 | 6 | 9724 | 3918 | 2886 | 13865 |
| 9 | 6 | 11896 | 4579 | 2871 | 15084 |
| 11 | 6 | 17323 | 8668 | 3798 | 30947 |
| 13 | 6 | 16043 | 7541 | 3518 | 24110 |
| 15 | 6 | 19550 | 8611 | 4040 | 28863 |
| 17 | 6 | 16323 | 6478 | 5219 | 23834 |
| 19 | 6 | 18202 | 7765 | 4141 | 25507 |
| 21 | 6 | 17817 | 7570 | 6157 | 27366 |

A scatterplot of the CCL21 levels in the spent media vs. day for each of the lots analyzed is provided in FIG. 85, and a boxplot is provided in FIG. 86. The scatterplot shows that CCL21 levels in the spent media increase over the course of 21 days for each lot analyzed. The boxplot indicates that, in general, the variability of CCL21 levels in the spent media between lots increases as the time spent in culture increases. Variability was lowest on days 5-9. Lot MFG-036 trends lower than other lots in CCL21, there is no apparent reason for any difference as it was manufactured using the same process as other lots. Other biomarkers do not show this lot as apparently different from other lots. Testing of additional lots and additional assay development is recommended to better understand the difference.

Characterization of CCL21 Levels in Forced Degradation Samples

Lot MFG-053 and MFG-054

The CCL21 levels in the spent media during the forced degradation treatments of Lot-053 (1, 3, and 5) and Lot-054 (1-8) are presented in Table 13, and a scatterplot of the data is provided in FIG. 38. The scatterplot contains a plot of the mean CCL21 results from analysis of the control samples (see Table 8). Mean results are plotted (n=6) to exhibit non-degraded lots as forced degraded controls were >ULOQ for that analysis. Note that this does result in oscillation for some days since not all lots had samples collected on all days. Results greater than the assay ULOQ are not plotted.

TABLE 13

CCL21 Levels (pg/mL) in Forced Degradation Study - Lot MFG-053 and MFG-054

| | | Day | | |
| --- | --- | --- | --- | --- |
| Sample | Treatment | 5 | 7 | 9 |
| MFG-053-1 | Control | >ULOQ | >ULOQ | >ULOQ |
| MFG-053-3 | 55° C., 4 hours | 444.44 | 204.91 | 93.23 |

TABLE 13-continued

CCL21 Levels (pg/mL) in Forced Degradation Study - Lot MFG-053 and MFG-054

| | | Day | | |
|---|---|---|---|---|
| Sample | Treatment | 5 | 7 | 9 |
| MFG-053-5 | −20° C., 4 hours | 535.62 | 262.26 | 206.28 |
| MFG-054-1 | Control | >ULOQ | >ULOQ | >ULOQ |
| MFG-054-2 | RT, 24 hours | >ULOQ | >ULOQ | >ULOQ |
| MFG-054-3 | Dehydration, 24 hours | >ULOQ | >ULOQ | >ULOQ |
| MFG-054-4 | Dehydration, 48 hours | >ULOQ | >ULOQ | >ULOQ |
| MFG-054-5 | Normal Saline, 24 hours | >ULOQ | >ULOQ | >ULOQ |
| MFG-054-6 | Normal Saline, 48 hours | >ULOQ | >ULOQ | >ULOQ |
| MFG-054-7 | 10X PBS, 24 hours | 242.90 | 124.75 | 26.54 |
| MFG-054-8 | 1% DMSO, 24 hours | >ULOQ | >ULOQ | >ULOQ |

Lot MFG-066

The CCL21 levels in the spent media during the forced degradation treatments of Lot-066 (4-7) are presented in Table 14, and a scatterplot of the data is provided in FIG. 39. The scatterplot contains a plot of the mean CCL21 results from analysis of the control samples (see Table 7). Mean results are plotted (n=6) to exhibit non-degraded lots as forced degraded controls were >ULOQ for that analysis. Note that this does result in oscillation for some days since not all lots had samples collected on all days. Results greater than the ULOQ are not plotted. Results less than the LOD are plotted at the LOD.

TABLE 14

CCL21 Levels (pg/mL) in Forced Degradation Study - Lot MFG-066

| | Treatment | | | |
|---|---|---|---|---|
| Day | MFG-066-4 Control | MFG-066-5 −20° C., 4 hours | MFG-066-6 55° C., 4 hours | MFG-066-7 10X PBS, 24 hours |
| 2 | 1055.77 | 1218.52 | 1742.07 | 1167.76 |
| 3 | 1836.70 | 1201.87 | 3925.59 | N/A |
| 4 | >ULOQ | 839.84 | 845.34 | 699.39 |
| 5 | >ULOQ | 877.32 | 471.78 | 392.67 |
| 6 | >ULOQ | 754.17 | 256.94 | 396.58 |
| 7 | >ULOQ | 559.68 | 282.62 | 279.21 |
| 8 | >ULOQ | 588.84 | 104.05 | 298.42 |
| 9 | >ULOQ | 688.31 | 161.01 | 201.13 |
| 10 | >ULOQ | 1050.48 | 84.54 | 133.97 |
| 11 | >ULOQ | 829.68 | 81.83 | 93.49 |
| 12 | >ULOQ | 1369.54 | 89.00 | 87.53 |
| 13 | >ULOQ | 1208.39 | 230.84 | 72.30 |
| 14 | >ULOQ | 1256.14 | 48.61 | 62.37 |
| 15 | >ULOQ | 985.02 | 57.27 | <LOD |
| 16 | >ULOQ | 982.11 | 32.06 | <LOD |
| 17 | >ULOQ | 677.25 | <LOD | <LOD |
| 18 | >ULOQ | 1004.75 | 70.45 | 32.59 |
| 19 | >ULOQ | 687.93 | 25.76 | 22.20 |
| 20 | >ULOQ | 703.81 | <LOD | <LOD |
| 21 | >ULOQ | 666.17 | <LOD | <LOD |

ULOQ = 4,444.4 pg/mL; LOD = 22.2 pg/mL.

CXCL16

The CXCL16 chemokine has been shown to be produced by TECs (Bunting 2011). Expression of the receptor is induced during invariant natural killer T cells (iNKT) cell positive selection in the cortex and has also been shown to be detectable in the medulla (Cowan, 2015).

Characterization of CXCL16 During 21-Day Culture

Descriptive statistics for the CXCL16 levels in the spent media are presented in Table 15. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 15

Descriptive Statistics for CXCL16 Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 1219 | 915 | 560 | 2919 |
| 2 | 1 | 858 | — | 858 | 858 |
| 3 | 1 | 625 | — | 625 | 625 |
| 4 | 1 | 815 | — | 815 | 815 |
| 5 | 9 | 1382 | 770 | 367 | 2643 |
| 6 | 1 | 1261 | — | 1261 | 1261 |
| 7 | 9 | 1888 | 696 | 581 | 2735 |
| 8 | 1 | 1880 | — | 1880 | 1880 |
| 9 | 9 | 2262 | 798 | 767 | 3381 |
| 10 | 1 | 2151 | — | 2151 | 2151 |
| 11 | 7 | 2739 | 834 | 1694 | 4154 |
| 12 | 1 | 3036 | — | 3036 | 3036 |
| 13 | 7 | 2887 | 317 | 2439 | 3344 |
| 14 | 1 | 3305 | — | 3305 | 3305 |
| 15 | 7 | 3401 | 774 | 2463 | 4739 |
| 16 | 1 | 2110 | — | 2110 | 2110 |
| 17 | 7 | 2923 | 567 | 2068 | 3777 |
| 18 | 1 | 2224 | — | 2224 | 2224 |
| 19 | 7 | 3146 | 776 | 2496 | 4770 |
| 20 | 1 | 2171 | — | 2171 | 2171 |
| 21 | 7 | 3175 | 630 | 2296 | 3875 |

A scatterplot of the CXCL16 levels in the spent media vs. day for each of the lots analyzed is provided in FIG. 89, and a boxplot is provided in FIG. 90. The scatterplot shows that CXCL16 levels in the spent media increase over the course of 21 days for each lot analyzed. The boxplot indicates that the variability of CXCL16 levels in the spent media between lots is fairly consistent as the time spent in culture increases.

Characterization of CXCL16 Levels in Forced Degradation Samples

Lot MFG-053 and Lot MFG-054

The CXCL16 levels in the spent media during the forced degradation treatments of Lot-053 (1, 3, and 5) and Lot-054 (1-8) are presented in Table 16, and a scatterplot of the data is provided in FIG. 91. The scatterplot contains a plot of the mean CXCL16 results from analysis of the control samples (see Table 9). Mean results are plotted (n=6) to exhibit non-degraded lots as forced degraded controls were >ULOQ for that analysis. Note that this does result in oscillation for some days since not all lots had samples collected on all days. For this analysis, days on which only one lot had data collected was removed as it over represented a single lot resulting in more oscillation that present in the individual data plots. Results less than the LOD are plotted at the LOD.

TABLE 16

CXCL16 Levels (pg/mL) in Forced Degradation Study - Lot MFG-053 and Lot MFG-054

| | | Day | | |
|---|---|---|---|---|
| Sample | Treatment | 5 | 7 | 9 |
| MFG-053-1 | Control | 2189.56 | 2186.22 | 2022.29 |
| MFG-053-3 | 55° C., 4 hours | 30.93 | <LOD | <LOD |
| MFG-053-5 | −20° C., 4 hours | 90.40 | 33.04 | <LOD |
| MFG-054-1 | Control | 366.89 | 581.29 | 767.14 |
| MFG-054-2 | RT, 24 hours | 343.08 | 205.64 | 473.06 |

TABLE 16-continued

CXCL16 Levels (pg/mL) in Forced Degradation Study - Lot MFG-053 and Lot MFG-054

| | | Day | | |
|---|---|---|---|---|
| Sample | Treatment | 5 | 7 | 9 |
| MFG-054-3 | Dehydration, 24 hours | 501.35 | 999.45 | 1593.32 |
| MFG-054-4 | Dehydration, 48 hours | 419.68 | 555.55 | 1672.57 |
| MFG-054-5 | Normal Saline, 24 hours | 297.52 | 913.83 | 748.42 |
| MFG-054-6 | Normal Saline, 48 hours | 448.61 | 897.02 | 657.56 |
| MFG-054-7 | 10X PBS, 24 hours | 83.97 | 16.69 | <LOD |
| MFG-054-8 | 1% DMSO, 24 hours | 387.73 | 450.04 | 910.37 |

Lot MFG-066

The CXCL16 levels in the spent media during the forced degradation treatments of Lot-066 (4-7) are presented in Table 17, and a scatterplot of the data is provided in FIG. 92. The scatterplot contains a plot of the mean CXCL16 results from analysis of the control samples (see Table 9). Mean results are plotted (n=6) to exhibit non-degraded lots as forced degraded controls were >ULOQ for that analysis. Note that this does result in oscillation for some days since not all lots had samples collected on all days. For this analysis, days on which only one lot had data collected was removed as it over represented a single lot resulting in more oscillation that present in the individual data plots. Results less than the LOD are plotted at the LOD.

TABLE 17

CXCL16 Levels (pg/mL) in Forced Degradation Study-Lot MFG-066

| | Treatment | | | |
|---|---|---|---|---|
| Day | MFG-066-4 Control | MFG-066-5 −20° C., 4 hours | MFG-066-6 55° C., 4 hours | MFG-066-7 10X PBS, 24 hours |
| 2 | 858.18 | 642.28 | 982.28 | 858.53 |
| 3 | 624.66 | 474.03 | 405.94 | N/A |
| 4 | 814.60 | 165.71 | 120.34 | 316.00 |
| 5 | 1359.07 | 180.45 | 58.36 | 126.00 |
| 6 | 1260.63 | 157.88 | 26.27 | 91.89 |
| 7 | 1360.16 | 93.07 | 17.81 | 55.73 |
| 8 | 1880.25 | 99.93 | <LOD | 21.82 |
| 9 | 1764.02 | 118.51 | <LOD | <LOD |
| 10 | 2150.67 | 215.01 | <LOD | <LOD |
| 11 | 1694.25 | 153.79 | <LOD | <LOD |
| 12 | 3035.93 | 257.70 | <LOD | <LOD |
| 13 | 2439.40 | 275.28 | <LOD | <LOD |
| 14 | 3304.55 | 361.69 | <LOD | <LOD |
| 15 | 2781.62 | 324.09 | <LOD | <LOD |
| 16 | 2109.69 | 263.37 | <LOD | <LOD |
| 17 | 2067.51 | 269.48 | <LOD | <LOD |
| 18 | 2224.33 | 430.96 | <LOD | <LOD |
| 19 | 2648.50 | 419.62 | <LOD | <LOD |
| 20 | 2170.56 | 420.26 | <LOD | <LOD |
| 21 | 2632.22 | 243.42 | <LOD | <LOD |

L-Selectin.

L-Selectin is expressed at high levels on developing and naïve T cells. It is released from the cell surface when thymocytes are cultured. Usually rapidly re-expressed when shed by healthy cells in vivo (Fitzhugh 2008), progressively decreased levels of shedding likely reflect the progressive loss of thymocyte viability because they normally do not re-express this molecule on the surface during culture (A. Macintyre, unpublished data).

Characterization of L-Selectin During 21-Day Culture

Descriptive statistics for the L-Selectin levels in the spent media over the course of 21 days are presented in Table 18. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 18

Descriptive Statistics for L-Selectin Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 28833 | 10290 | 14966 | 43399 |
| 2 | 1 | 8299 | — | 8299 | 8299 |
| 3 | 1 | 5350 | — | 5350 | 5350 |
| 4 | 1 | 2647 | — | 2647 | 2647 |
| 5 | 9 | 5719 | 3535 | 2306 | 12219 |
| 6 | 1 | 1274 | — | 1274 | 1274 |
| 7 | 9 | 4589 | 3440 | 740 | 12573 |
| 8 | 1 | 695 | — | 695 | 695 |
| 9 | 9 | 3630 | 2678 | 566 | 9924 |
| 10 | 1 | 570 | — | 570 | 570 |
| 11 | 7 | 3130 | 2971 | 448 | 9297 |
| 12 | 1 | 729 | — | 729 | 729 |
| 13 | 7 | 2597 | 3472 | 367 | 10396 |
| 14 | 1 | 790 | — | 790 | 790 |
| 15 | 7 | 2453 | 3110 | 289 | 9385 |
| 16 | 1 | 179 | — | 179 | 179 |
| 17 | 7 | 1834 | 2386 | 446 | 7170 |
| 18 | 1 | 452 | — | 452 | 452 |
| 19 | 7 | 1965 | 1803 | 488 | 5934 |
| 20 | 1 | 496 | — | 496 | 496 |
| 21 | 7 | 1578 | 2307 | 289 | 6755 |

A scatterplot of the L-Selectin levels in the spent media vs. day for each of the lots analyzed is provided in FIG. 93, and a boxplot is provided in FIG. 94. The scatterplot shows that L-Selectin levels in the spent media decrease over the course of 21 days for each lot analyzed. The boxplot indicates that the variability of L-Selectin levels in the spent media between lots, in general, decreases as the time spent in culture increases and as the L-Selectin levels approach zero.

Characterization of L-Selectin Levels in Forced Degradation Sample

Lot MFG-053 and Lot MFG-054

The L-Selectin levels in the spent media during the forced degradation treatments of Lot-053 (1, 3, and 5) and Lot-054 (1-8) are presented in Table 19, and a scatterplot of the data is provided in FIG. 95. The scatterplot contains a plot of the mean L-Selectin results from analysis of the control samples (see Table 18). Mean results are plotted (n=6) to exhibit non-degraded lots as forced degraded controls were >ULOQ for that analysis. For this analysis, days on which only one lot had data collected was removed as it over represented a single lot resulting in more oscillation that present in the individual data plots. Results less than the LOD are plotted at the LOD.

TABLE 19

L-Selectin Levels (pg/mL) in Forced Degradation Study-Lot MFG-053

| Sample | Treatment | Day 5 | Day 7 | Day 9 |
|---|---|---|---|---|
| MFG-053-1 | Control | 9798.40 | 6609.20 | 5079.13 |
| MFG-053-3 | 55° C., 4 hours | 2999.26 | 482.28 | 246.81 |
| MFG-053-5 | −20° C., 4 hours | 5301.16 | 1172.91 | 223.17 |
| MFG-054-1 | Control | 7109.64 | 4058.36 | 3174.80 |
| MFG-054-2 | RT, 24 hours | 7401.82 | 2167.23 | 3192.93 |
| MFG-054-3 | Dehydration, 24 hours | 9755.36 | 7403.73 | 4551.37 |
| MFG-054-4 | Dehydration, 48 hours | 12371.63 | 7316.71 | 4915.73 |
| MFG-054-5 | Normal Saline, 24 hours | 4662.78 | 4475.18 | 2726.21 |
| MFG-054-6 | Normal Saline, 48 hours | 7188.82 | 4556.11 | 1558.68 |
| MFG-054-7 | 10X PBS, 24 hours | 740.20 | 385.16 | <LOD |
| MFG-054-8 | 1% DMSO, 24 hours | 3830.68 | 1806.22 | 2506.04 |

Lot MFG-066.

The L-Selectin levels in the spent media during the forced degradation treatments of Lot-066 (4-7) are presented in Table 19, and a scatterplot of the data is provided in FIG. 96. The scatterplot contains a plot of the mean L-Selectin results from analysis of the control samples (see Table 18). Results less than the LOD are plotted at the LOD.

uPAR (CD87)

uPAR (CD87) is a urokinase receptor (also known as urokinase plasminogen activator receptor) expressed in both soluble and membrane-bound forms based on alternative splicing. It aids in local degradation of extracellular matrix. It has been shown to be expressed in human thymus and by migrating epidermal keratinocytes (EK) at the edge of a wound (Loughner 2016). This latter characteristic is most interesting since TECs mirror EK in expression of many genes (Patel 1995). Progressive increases in secretion by cultured thymus slices may reflect the activation of TE and, thus, may be a marker for TE outgrowth following implantation.

Characterization of uPAR During 21-Day Culture.

Descriptive statistics for the uPAR levels in the spent media over the course of 21 days are presented in Table 20. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 20

Descriptive Statistics for uPAR Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 1168 | 190 | 973 | 1418 |
| 2 | 1 | 226 | — | 226 | 226 |
| 3 | 1 | 354 | — | 354 | 354 |
| 4 | 1 | 373 | — | 373 | 373 |
| 5 | 9 | 3336 | 2475 | 649 | 8285 |
| 6 | 1 | 614 | — | 614 | 614 |
| 7 | 9 | 4166 | 2748 | 577 | 8554 |
| 8 | 1 | 827 | — | 827 | 827 |
| 9 | 9 | 5772 | 3436 | 1086 | 9476 |
| 10 | 1 | 1178 | — | 1178 | 1178 |
| 11 | 7 | 9282 | 4444 | 1180 | 14195 |
| 12 | 1 | 1760 | — | 1760 | 1760 |
| 13 | 7 | 9749 | 4342 | 1759 | 15015 |
| 14 | 1 | 1640 | — | 1640 | 1640 |
| 15 | 7 | 11025 | 5142 | 1434 | 16984 |
| 16 | 1 | 1810 | — | 1810 | 1810 |
| 17 | 7 | 11262 | 5069 | 2286 | 16818 |
| 18 | 1 | 2349 | — | 2349 | 2349 |
| 19 | 7 | 11167 | 5257 | 2728 | 18078 |
| 20 | 1 | 2358 | — | 2358 | 2358 |
| 21 | 7 | 11370 | 4903 | 2432 | 17772 |

A scatterplot of the uPAR levels in the spent media vs. day for each of the lots analyzed is provided in FIG. 97, and a boxplot is provided in FIG. 98. The scatterplot shows that uPAR levels in the spent media increase over the course of 21 days for each lot analyzed, with moderate lot-to-lot variability. The boxplot indicates that the variability of uPAR levels in the spent media between lots, in general, increases as the time spent in culture increases.

Characterization of uPAR Levels in Forced Degradation Samples

Lot MFG-053 and Lot MFG-054

The uPAR levels in the spent media during the forced degradation treatments of Lot-053 (1, 3, and 5) and Lot-054 (1-8) are presented in Table 21, and a scatterplot of the data is provided in FIG. 99. The scatterplot contains a plot of the mean uPAR results from analysis of the control samples (see Table 21). As this data was not normalized between lots, and there was a large amount of lot to lot variability, the average data presented in FIG. 99 is highly dependent on which lots were tested on which days. Days on which only one lot was tested were excluded from the mean on the graph.

TABLE 21 uPAR Levels (pg/mL) in Forced Degradation Study-Lot MFG-053

| Sample | Treatment | Day 5 | Day 7 | Day 9 |
|---|---|---|---|---|
| MFG-053-1 | Control | 1586.63 | 1876.48 | 2209.44 |
| MFG-053-3 | 55° C., 4 hours | 623.75 | 357.64 | 114.32 |
| MFG-053-5 | −20° C., 4 hours | 769.17 | 392.63 | 114.06 |
| MFG-054-1 | Control | 868.64 | 742.05 | 1253.03 |
| MFG-054-2 | RT, 24 hours | 554.80 | 571.46 | 772.94 |
| MFG-054-3 | Dehydration, 24 hours | 970.93 | 960.90 | 1308.89 |
| MFG-054-4 | Dehydration, 48 hours | 1395.64 | 1092.91 | 1438.90 |
| MFG-054-5 | Normal Saline, 24 hours | 684.60 | 1174.55 | 745.63 |
| MFG-054-6 | Normal Saline, 48 hours | 795.46 | 1394.48 | 1047.94 |
| MFG-054-7 | 10X PBS, 24 hours | 187.83 | 131.33 | 81.76 |
| MFG-054-8 | 1% DMSO, 24 hours | 517.56 | 725.97 | 894.00 |

Lot MFG-066

The uPAR levels in the spent media during the forced degradation treatments of Lot-066 (4-7) are presented in Table 22, and scatterplot of the data is provided in FIG. 100. The scatterplot contains a plot of the mean uPAR results from analysis of the control samples (see Table 21). Results less than the LOD are plotted at the LOD

TABLE 21 uPAR Levels (pg/mL) in Forced Degradation Study-Lot MFG-066

| | Treatment | | | |
|---|---|---|---|---|
| Day | MFG-066-4 Control | MFG-066-5 −20° C., 4 hours | MFG-066-6 55° C., 4 hours | MFG-066-7 10X PBS, 24 hours |
| 2 | 226.24 | 310.87 | 238.27 | 269.59 |
| 3 | 354.17 | 552.13 | 244.32 | N/A |
| 4 | 373.38 | 398.20 | 199.96 | 287.12 |
| 5 | 648.60 | 327.72 | 118.72 | 214.89 |
| 6 | 614.27 | 307.83 | 105.12 | 173.27 |
| 7 | 576.95 | 253.79 | 96.84 | 125.15 |
| 8 | 827.26 | 425.72 | 60.88 | 117.14 |
| 9 | 1085.62 | 454.03 | 30.14 | 107.97 |
| 10 | 1177.62 | 573.41 | 33.07 | 86.39 |
| 11 | 1180.05 | 472.15 | 37.90 | 85.87 |
| 12 | 1759.50 | 816.44 | 46.03 | 91.19 |
| 13 | 1758.80 | 687.40 | 109.49 | 57.20 |
| 14 | 1639.73 | 728.67 | 26.22 | 54.81 |
| 15 | 1434.30 | 633.52 | <LOD | 26.11 |
| 16 | 1810.32 | 484.86 | <LOD | <LOD |
| 17 | 2286.43 | 564.93 | <LOD | <LOD |
| 18 | 2349.14 | 973.23 | 27.01 | <LOD |
| 19 | 2728.06 | 707.92 | <LOD | <LOD |
| 20 | 2358.15 | 680.65 | 27.13 | <LOD |
| 21 | 2432.05 | 563.35 | <LOD | <LOD |

LOD = 25.4 pg/mL.

Correlations.

The four sets of biomarker data (CCL21, CXCL16, L-Selectin and uPAR) were subjected to normality tests (Ryan-Joiner). The p-values for CCL21 (>0.087) and CXCL16 (>0.100) indicate that they follow a normal distribution. The p-values for L-Selectin (<0.010) and uPAR (<0.010) indicate that they do not follow a normal distribution. Pearson correlation coefficients were determined for each of the correlations and are presented in Table 22. The coefficients were statistically significant, and all exhibited strong correlations with each other, with the exception of L-Selectin with all other biomarkers. Regression models showing the correlations are provided in FIG. 101 through FIG. 103. The strongest correlation was observed between CCL21 and uPAR. Regressions are shown for visual purposes.

TABLE 22

Pearson Correlation Coefficients for CCL21, CXCL16, L-Selection, and uPAR

| | CCL21 | CXCL16 | L-Selectin |
|---|---|---|---|
| CXCL16 | 0.606 | | |
| L-Selectin | −0.486 | −0.374 | |
| uPAR | 0.817 | 0.727 | −0.278 |

Additional Results

CCL11 (Eotaxin)

The CCL11 chemokine (eotaxin) is produced by medullary TE (Bunting 2011). It was initially named for its ability to attract eosinophils, and it has been shown that eosinophil infiltrates may be prominent in thymus tissues with active thymopoiesis (Flores 1999); however, CCL11 has also been shown to serve as a chemoattractant for both double-positive and single-positive human thymocytes (Bunting 2011).

Characterization of CCL11 During 21-Day Culture

Descriptive statistics for the CCL11 levels in the spent media over the course of 21 days are presented in Table 23. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 23

Descriptive Statistics for CCL11 Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 2.2 | 0.7 | 1.3 | 3.1 |
| 2 | 1 | 9.7 | — | 9.7 | 9.7 |
| 3 | 1 | 9.7 | — | 9.7 | 9.7 |
| 4 | 1 | 9.7 | — | 9.7 | 9.7 |
| 5 | 9 | 22.9 | 41.3 | 1.3 | 131.3 |
| 6 | 1 | 9.7 | — | 9.7 | 9.7 |
| 7 | 9 | 36.5 | 20.7 | 9.7 | 66.0 |
| 8 | 1 | 26.9 | — | 26.9 | 26.9 |
| 9 | 9 | 85.4 | 81.6 | 11.2 | 254.4 |
| 10 | 1 | 31.8 | — | 31.8 | 31.8 |
| 11 | 7 | 98.2 | 69.7 | 22.7 | 234.3 |
| 12 | 1 | 96.2 | — | 96.2 | 96.2 |
| 13 | 7 | 123.6 | 74.4 | 37.8 | 257.4 |
| 14 | 1 | 116.5 | — | 116.5 | 116.5 |
| 15 | 7 | 151.1 | 83.2 | 54.1 | 265.9 |
| 16 | 1 | 160.5 | — | 160.5 | 160.5 |
| 17 | 7 | 176.7 | 103.3 | 77.1 | 384.6 |
| 18 | 1 | 310.6 | — | 310.6 | 310.6 |
| 19 | 7 | 201.0 | 112.7 | 106.1 | 414.7 |
| 20 | 1 | 231.2 | — | 231.2 | 231.2 |
| 21 | 7 | 227.6 | 127.2 | 101.4 | 441.9 |

A scatterplot of the CCL11 levels in the spent media vs. day for each of the lots analyzed is provided in FIG. 104 and a boxplot is provided in 105. The linear regression model is provided in FIG. 106. The scatterplot shows that CCL11 levels in the spent media increase linearly over the course of 21 days for each lot analyzed. The boxplot indicates that the variability of CCL11 levels in the spent media between lots increases as the time spent in culture increases, which is also shown in Table 24 by the increasing standard deviation values over time. Variability was lowest on days 5-9. The adjusted $R^2$ value from regression analysis indicates that the time spent in the culture explains 51.2% of the variability in the CCL11 levels.

Lot MFG-053 and Lot MFG-054

The CCL11 levels in the spent media during the forced degradation treatments of Lot-053 (1, 3, and 5) and Lot-054 (1-8) are presented in Table 24, and a scatterplot of the data is provided in FIG. 107. The scatterplot contains a plot of the mean CCL11 results from analysis of the control samples (see Table 23). Results less than the LOD are plotted at the LOD.

TABLE 24

CCL11 Levels (pg/mL) in Forced Degradation Study-Lot MFG-053

| | | Day | | |
|---|---|---|---|---|
| Sample | Treatment | 5 | 7 | 9 |
| MFG-053-1 | Control | <LOD | 58.88 | 254.39 |
| MFG-053-3 | 55° C., 4 hours | <LOD | <LOD | <LOD |
| MFG-053-5 | −20° C., 4 hours | <LOD | <LOD | <LOD |
| MFG-054-1 | Control | <LOD | <LOD | 11.16 |
| MFG-054-2 | RT, 24 hours | <LOD | <LOD | <LOD |
| MFG-054-3 | Dehydration, 24 hours | <LOD | 14.61 | 35.01 |
| MFG-054-4 | Dehydration, 48 hours | <LOD | 57.41 | 109.19 |

TABLE 24-continued

CCL11 Levels (pg/mL) in Forced Degradation Study-Lot MFG-053

| | | Day | | |
|---|---|---|---|---|
| Sample | Treatment | 5 | 7 | 9 |
| MFG-054-5 | Normal Saline, 24 hours | <LOD | <LOD | <LOD |
| MFG-054-6 | Normal Saline, 48 hours | <LOD | <LOD | <LOD |
| MFG-054-7 | 10X PBS, 24 hours | <LOD | <LOD | <LOD |
| MFG-054-8 | 1% DMSO, 24 hours | <LOD | 16.69 | 32.58 |

Lot MFC-066

The CCL11 levels in the spent media during the forced degradation treatments of Lot-066 (4-7) are presented in Table 25, and a scatterplot of the data is provided in FIG. 108. Results less than the LOD are plotted at the LOD.

TABLE 25

CCL11 Levels (pg/mL) in Forced Degradation Study-Lot MFG-066

| | Treatment | | | |
|---|---|---|---|---|
| Day | MFG-066-4 Control | MFG-066-5 −20° C., 4 hours | MFG-066-6 55° C., 4 hours | MFG-066-7 10X PBS, 24 hours |
| 2 | 0.00 | <LOD | <LOD | <LOD |
| 3 | 0.00 | <LOD | <LOD | N/A |
| 4 | 0.00 | <LOD | <LOD | <LOD |
| 5 | 3.10 | <LOD | <LOD | <LOD |
| 6 | 8.40 | <LOD | <LOD | <LOD |
| 7 | 13.58 | <LOD | <LOD | <LOD |
| 8 | 26.90 | <LOD | <LOD | <LOD |
| 9 | 36.90 | 50.66 | <LOD | <LOD |
| 10 | 31.84 | 140.66 | <LOD | <LOD |
| 11 | 39.28 | 264.99 | <LOD | <LOD |
| 12 | 96.19 | 545.87 | <LOD | <LOD |
| 13 | 101.91 | 797.66 | <LOD | <LOD |
| 14 | 116.49 | 847.03 | <LOD | <LOD |
| 15 | 177.41 | 853.97 | <LOD | <LOD |
| 16 | 160.51 | 980.33 | <LOD | <LOD |
| 17 | 162.22 | 985.17 | <LOD | <LOD |
| 18 | 310.58 | 1367.42 | <LOD | <LOD |
| 19 | 255.68 | 1089.50 | <LOD | <LOD |
| 20 | 231.17 | 1220.33 | <LOD | <LOD |
| 21 | 343.86 | 1124.40 | <LOD | <LOD |

LOD = 9.7 pg/mL.

Osteopontin (OPN)

Osteopontin (OPN) is a cytokine encoded by the SPP1 gene and increases during thymic stress. Increased levels are associated with thymic atrophy (decrease in thymocyte number), which is a desirable state for cultured thymus (Wang 2009; Gridley 2013). OPN is required to make corticosteroids, which have been well-established to induce thymocyte apoptosis.

Characterization of OPN During 21-Day Culture

Descriptive statistics for the OPN levels in the spent media over the course of 21 days are presented in Table 26. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 26

Descriptive Statistics for OPN Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 5592 | 3632 | 2483 | 12084 |
| 2 | 1 | 5941 | — | 5941 | 5941 |
| 3 | 1 | 5124 | — | 5124 | 5124 |
| 4 | 1 | 6688 | — | 6688 | 6688 |
| 5 | 9 | 9589 | 2090 | 7147 | 13717 |
| 6 | 1 | 6471 | — | 6471 | 6471 |
| 7 | 9 | 10283 | 2246 | 6755 | 13942 |
| 8 | 1 | 7503 | — | 7503 | 7503 |
| 9 | 9 | 10254 | 2492 | 6502 | 14907 |
| 10 | 1 | 8358 | — | 8358 | 8358 |
| 11 | 7 | 12962 | 7206 | 7640 | 28982 |
| 12 | 1 | 9975 | — | 9975 | 9975 |
| 13 | 7 | 10993 | 1375 | 9191 | 13367 |
| 14 | 1 | 9790 | — | 9790 | 9790 |
| 15 | 7 | 14107 | 6705 | 9664 | 28982 |
| 16 | 1 | 7629 | — | 7629 | 7629 |
| 17 | 7 | 11386 | 2479 | 8067 | 14821 |
| 18 | 1 | 6954 | — | 6954 | 6954 |
| 19 | 7 | 12416 | 2894 | 8756 | 16660 |
| 20 | 1 | 7662 | — | 7662 | 7662 |
| 21 | 7 | 11404 | 1787 | 9596 | 14642 |

A scatterplot of the OPN levels in the spent media vs. day for each of the lots analyzed is provided in FIG. 109 and a boxplot is provided in FIG. 110. The quadratic regression model is provided in FIG. 111. The scatterplot shows that OPN levels in the spent media increase over the course of 21 days for each lot analyzed. The boxplot indicates that the variability of OPN levels in the spent media between lots does not show a trend as the time spent in culture increases. The adjusted $R^2$ value from regression analysis indicates that the time spent in the culture explains 19.3% of the variability in the OPN levels.

Characterization of OPN Levels in Forced Degradation Samples.

Lot MFG-053 and Lot MFG-054.

The OPN levels in the spent media during the forced degradation treatments of Lot-053 (1, 3, and 5) and Lot-054 (1-8) are presented in Table 27, and a scatterplot of the data is provided in FIG. 112. The scatterplot contains a plot of the mean OPN results from analysis of the control samples (see Table 26). Results less than the LOD are plotted at the LOD

TABLE 27

OPN Levels (pg/mL) in Forced Degradation Study-Lot MFG-053

| | | Day | | |
|---|---|---|---|---|
| Sample | Treatment | 5 | 7 | 9 |
| MFG-053-1 | Control | 9051.16 | 10494.61 | 10257.37 |
| MFG-053-3 | 55° C., 4 hours | 5755.22 | 2447.84 | 323.30 |
| MFG-053-5 | −20° C., 4 hours | 5412.33 | 1356.19 | 311.38 |
| MFG-054-1 | Control | 8204.45 | 7425.51 | 6502.26 |
| MFG-054-2 | RT, 24 hours | 6278.27 | 6259.90 | 7061.52 |
| MFG-054-3 | Dehydration, 24 hours | 7922.19 | 8691.84 | 8161.90 |
| MFG-054-4 | Dehydration, 48 hours | 6772.23 | 6950.47 | 9069.79 |
| MFG-054-5 | Normal Saline, 24 hours | 8284.11 | 8270.36 | 8650.79 |
| MFG-054-6 | Normal Saline, 48 hours | 7884.72 | 9491.01 | 7300.88 |

TABLE 27-continued

OPN Levels (pg/mL) in Forced Degradation Study-Lot MFG-053

| | | Day | | |
|---|---|---|---|---|
| Sample | Treatment | 5 | 7 | 9 |
| MFG-054-7 | 10X PBS, 24 hours | 1199.92 | 303.01 | <LOD |
| MFG-054-8 | 1% DMSO, 24 hours | 8151.87 | 7736.58 | 8673.01 |

Lot MFG-066

The OPN levels in the spent media during the forced degradation treatments of Lot-066 (4-7) are presented in Table, and a scatterplot of the data is provided in FIG. 113. The scatterplot contains a plot of the mean OPN results from analysis of the control samples (see Table). Results less than the LOD are plotted at the LOD.

TABLE 28

OPN Levels (pg/mL) in Forced Degradation Study-Lot MFG-066

| | Treatment | | | |
|---|---|---|---|---|
| Day | MFG-066-4 Control | MFG-066-5 −20° C., 4 hours | MFG-066-6 55° C., 4 hours | MFG-066-7 10X PBS, 24 hours |
| 2 | 5941.42 | 5539.21 | 5421.78 | 6531.38 |
| 3 | 5123.63 | 5976.10 | 5959.32 | N/A |
| 4 | 6688.17 | 3893.95 | 3147.49 | 5729.23 |
| 5 | 7188.12 | 2913.08 | 1763.42 | 2773.82 |
| 6 | 6470.90 | 1639.25 | 662.82 | 1731.26 |
| 7 | 6754.85 | 1006.91 | 322.94 | 550.05 |
| 8 | 7502.70 | 981.05 | 74.27 | 345.42 |
| 9 | 8490.86 | 1753.27 | <LOD | 90.47 |
| 10 | 8357.82 | 2323.33 | <LOD | 90.86 |
| 11 | 7639.75 | 2008.82 | <LOD | <LOD |
| 12 | 9975.27 | 3876.91 | <LOD | <LOD |
| 13 | 9191.25 | 3867.66 | 87.77 | <LOD |
| 14 | 9790.47 | 3446.07 | <LOD | <LOD |
| 15 | 9663.58 | 3608.04 | <LOD | <LOD |
| 16 | 7628.70 | 2761.86 | <LOD | <LOD |
| 17 | 8066.54 | 2377.30 | <LOD | <LOD |
| 18 | 6954.15 | 4060.38 | <LOD | <LOD |
| 19 | 8756.05 | 3549.93 | <LOD | <LOD |
| 20 | 7662.28 | 2800.63 | <LOD | <LOD |
| 21 | 9596.49 | 2620.97 | <LOD | <LOD |

CXCL12 (SDF-1a)

CXCL12 (SDF-1a) has been documented to be produced by subcapsular cortical and medullary TE (Bunting 2011; Hernandez-Lopez 2002; Zaitseva 2002), but also can be made by thymic fibroblasts and endothelial cells present within the thymus. CXCL12 has been shown to recruit B cells and antigen-presenting cells (APC) to the thymus (Weiss 2003), which is expected to be important in generation of full thymic function. It is also involved in localization of thymocyte subsets within the thymus and it enhances thymocyte proliferation to IL-7 (Hernandez-Lopez 2002). Of note, antibodies that neutralize CXCL12 have been shown to decrease thymopoiesis in human thymus organ cultures in vitro, and addition of CXCL12 increases thymopoiesis in these cultures (Hernandez-Lopez 2002).

Characterization of CXCL12 During 21-Day Culture

Descriptive statistics for the CXCL12 levels in the spent media over the course of 21 days are presented in Table 29. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 29

Descriptive Statistics for CXCL12 Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 4.6 | 0.3 | 4.3 | 4.9 |
| 2 | 1 | 6.3 | — | 6.3 | 6.3 |
| 3 | 1 | 6.3 | — | 6.3 | 6.3 |
| 4 | 1 | 6.3 | — | 6.3 | 6.3 |
| 5 | 9 | 5.2 | 0.9 | 4.3 | 6.3 |
| 6 | 1 | 6.3 | — | 6.3 | 6.3 |
| 7 | 9 | 6.0 | 2.5 | 4.3 | 12.3 |
| 8 | 1 | 6.3 | — | 6.3 | 6.3 |
| 9 | 9 | 5.2 | 0.9 | 4.3 | 6.3 |
| 10 | 1 | 6.3 | — | 6.3 | 6.3 |
| 11 | 7 | 5.3 | 1.5 | 4.3 | 8.3 |
| 12 | 1 | 8.6 | — | 8.6 | 8.6 |
| 13 | 7 | 5.5 | 1.6 | 4.3 | 8.8 |
| 14 | 1 | 11.0 | — | 11.0 | 11.0 |
| 15 | 7 | 9.9 | 5.8 | 4.9 | 20.5 |
| 16 | 1 | 7.5 | — | 7.5 | 7.5 |
| 17 | 7 | 12.6 | 8.4 | 4.9 | 29.7 |
| 18 | 1 | 12.9 | — | 12.9 | 12.9 |
| 19 | 7 | 20.1 | 13.2 | 5.7 | 37.4 |
| 20 | 1 | 15.5 | — | 15.5 | 15.5 |
| 21 | 7 | 22.3 | 14.6 | 8.2 | 50.2 |

A scatterplot of the CXCL12 levels in the spent media vs. day for each of the lots analyzed is provided in FIG. 114, and a boxplot is provided in FIG. 115. The cubic regression model is provided in FIG. 116. The scatterplot shows that CXCL12 levels in the spent media increase over the course of 21 days for each lot analyzed. The boxplot indicates that the variability of CXCL12 levels in the spent media between lots, in general, increases as the time spent in culture increases. Variability was lowest on days 5-13. The adjusted $R^2$ value from regression analysis indicates that the time spent in the culture explains 44.5% of the variability in the CXCL12 level Characterization of CXCL12 Levels in Forced Degradation Samples Lot MFG-053 and Lot MFG-054

The CXCL12 levels in the spent media during the forced degradation treatments of Lot-053 (1, 3, and 5) and Lot-054 (1-8) are presented in Table 30, and a scatterplot of the data is provided in FIG. 117. The scatterplot contains a plot of the mean CXCL12 results from analysis of the control samples (see Table 29). Results less than the LOD are plotted at the LOD.

TABLE 30

CXCL12 Levels (pg/mL) in Forced Degradation Study-Lot MFG-053 and Lot MFG-054

| | | Day | | |
|---|---|---|---|---|
| Sample | Treatment | 5 | 7 | 9 |
| MFG-053-1 | Control | 9051.16 | 10494.61 | 10257.37 |
| MFG-053-1 | Control | <LOD | <LOD | <LOD |
| MFG-053-3 | 55° C., 4 hours | <LOD | <LOD | <LOD |
| MFG-053-5 | −20° C., 4 hours | <LOD | <LOD | <LOD |
| MFG-054-1 | Control | <LOD | <LOD | <LOD |
| MFG-054-2 | RT, 24 hours | <LOD | <LOD | <LOD |
| MFG-054-3 | Dehydration, 24 hours | <LOD | <LOD | <LOD |
| MFG-054-4 | Dehydration, 48 hours | <LOD | <LOD | <LOD |
| MFG-054-5 | Normal Saline, 24 hours | <LOD | <LOD | <LOD |

TABLE 30-continued

CXCL12 Levels (pg/mL) in Forced Degradation Study-
Lot MFG-053 and Lot MFG-054

| | | Day | | |
|---|---|---|---|---|
| Sample | Treatment | 5 | 7 | 9 |
| MFG-054-6 | Normal Saline, 48 hours | <LOD | <LOD | <LOD |
| MFG-054-7 | 10X PBS, 24 hours | <LOD | <LOD | <LOD |
| MFG-054-8 | 1% DMSO, 24 hours | <LOD | <LOD | <LOD |

Lot MFG-066.

The CXCL12 levels in the spent media during the forced degradation treatments of Lot-066 (4-7) are presented in Table 31 and a scatterplot of the data is provided in FIG. 118. The scatterplot contains a plot of the mean CXCL12 results from analysis of the control samples (see Table 29). Results less than the LOD are plotted at the LOD.

TABLE 31

CXCL12 Levels (pg/mL) in Forced
Degradation Study-Lot MFG-066

| | Treatment | | | |
|---|---|---|---|---|
| Day | MFG-066-4 Control | MFG-066-5 -20° C., 4 hours | MFG-066-6 55° C., 4 hours | MFG-066-7 10X PBS, 24 hours |
| 2 | <LOD | <LOD | <LOD | <LOD |
| 3 | <LOD | <LOD | <LOD | N/A |
| 4 | <LOD | <LOD | <LOD | <LOD |
| 5 | <LOD | <LOD | <LOD | <LOD |
| 6 | <LOD | <LOD | <LOD | <LOD |
| 7 | <LOD | <LOD | <LOD | <LOD |
| 8 | <LOD | <LOD | <LOD | <LOD |
| 9 | <LOD | <LOD | <LOD | <LOD |
| 10 | <LOD | <LOD | <LOD | <LOD |
| 11 | <LOD | <LOD | <LOD | <LOD |
| 12 | 8.60 | <LOD | <LOD | <LOD |
| 13 | 8.77 | <LOD | <LOD | <LOD |
| 14 | 10.96 | <LOD | <LOD | <LOD |
| 15 | 10.80 | <LOD | <LOD | <LOD |
| 16 | 7.53 | <LOD | <LOD | <LOD |
| 17 | 10.98 | <LOD | <LOD | <LOD |
| 18 | 12.95 | <LOD | <LOD | <LOD |
| 19 | 14.08 | <LOD | <LOD | <LOD |
| 20 | 15.47 | <LOD | <LOD | <LOD |
| 21 | 18.57 | <LOD | <LOD | <LOD |

CCL20 (MIP-3a).

CCL20 (MP-3a) is a chemokine whose pattern corresponded with that hypothesized for thymocytes.

Characterization of CCL20 During 21-Day Culture

Descriptive statistics for the CCL20 levels in the spent media over the course of 21 days are presented in Table 32 Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 32

Descriptive Statistics for CCL20 Levels
in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 22.8 | 16.6 | 8.1 | 54.1 |
| 2 | 1 | 311.9 | — | 311.9 | 311.9 |
| 3 | 1 | 270.1 | — | 270.1 | 270.1 |
| 4 | 1 | 341.9 | — | 341.9 | 341.9 |
| 5 | 9 | 92.4 | 168.0 | 6.6 | 533.0 |
| 6 | 1 | 448.8 | — | 448.8 | 448.8 |
| 7 | 9 | 54.5 | 68.9 | 4.5 | 222.8 |
| 8 | 1 | 366.9 | — | 366.9 | 366.9 |
| 9 | 9 | 58.9 | 87.8 | 2.9 | 283.2 |
| 10 | 1 | 243.7 | — | 243.7 | 243.7 |
| 11 | 7 | 42.5 | 51.0 | 2.5 | 147.4 |
| 12 | 1 | 195.4 | — | 195.4 | 195.4 |
| 13 | 7 | 31.7 | 40.4 | 1.6 | 116.3 |
| 14 | 1 | 141.2 | — | 141.2 | 141.2 |
| 15 | 7 | 21.6 | 22.6 | 1.1 | 62.0 |
| 16 | 1 | 43.7 | — | 43.7 | 43.7 |
| 17 | 7 | 14.3 | 16.7 | 1.1 | 47.2 |
| 18 | 1 | 38.8 | — | 38.8 | 38.8 |
| 19 | 7 | 9.9 | 11.7 | 1.1 | 33.7 |
| 20 | 1 | 17.4 | — | 17.4 | 17.4 |
| 21 | 7 | 7.7 | 7.5 | 1.1 | 19.6 |

A scatterplot of the CCL20 levels in the spent media vs. day for each of the lots analyzed is provided in FIG. 119 and a boxplot is provided in FIG. 120. The cubic regression model is provided in FIG. 121 The scatterplot shows that CCL20 levels in the spent media show no consistent trend over the course of 21 days for each lot analyzed. The boxplot indicates that the variability of CCL20 levels in the spent media between lots, in general, increases until day 9, then decreases. The adjusted $R^2$ value from regression analysis indicates that the time spent in the culture explains 12.4% of the variability in the CCL20 levels.

Characterization of CCL20 Levels in Forced Degradation Samples

Lot MFG-053 and Lot MFG-054.

The CCL20 levels in the spent media during the forced degradation treatments of Lot-053 (1, 3, and 5) and Lot-054 (1-8) are presented in Table 33, and a scatterplot of the data is provided in FIG. 122. The scatterplot contains a plot of the mean CCL20 results from analysis of the control samples Table 32. Results less than the LOD are plotted at the LOD.

TABLE 33

CCL20 Levels (pg/mL) in Forced Degradation
Study - Lot MFG-053 and Lot MFG-054

| | | Day | | |
|---|---|---|---|---|
| Sample | Treatment | 5 | 7 | 9 |
| MFG-053-1 | Control | 81.96 | 51.90 | 40.47 |
| MFG-053-3 | 55° C., 4 hours | <LOD | <LOD | <LOD |
| MFG-053-5 | -20° C., 4 hours | 30.66 | <LOD | <LOD |
| MFG-054-1 | Control | 36.53 | 9.39 | 16.57 |
| MFG-054-2 | RT, 24 hours | 32.98 | 15.88 | 15.36 |
| MFG-054-3 | Dehydration, 24 hours | 76.32 | 44.29 | 25.21 |
| MFG-054-4 | Dehydration, 48 hours | 178.63 | 72.54 | 38.18 |
| MFG-054-5 | Normal Saline, 24 hours | 37.71 | 17.40 | 13.53 |
| MFG-054-6 | Normal Saline, 48 hours | 29.80 | 19.57 | <LOD |
| MFG-054-7 | 10X PBS, 24 hours | 76.22 | <LOD | <LOD |
| MFG-054-8 | 1% DMSO, 24 hours | 57.68 | 38.68 | 28.91 |

Lot MFG-066

The CCL20 levels in the spent media during the forced degradation treatments of Lot-066 (4-7) are presented in Table 34, and a scatterplot of the data is provided in FIG. 123.

TABLE 34

CCL20 Levels (pg/mL) in Forced Degradation Study - Lot MFG-066

| Day | Treatment | | | |
|---|---|---|---|---|
| | MFG-066-4 Control | MFG-066-5 −20° C., 4 hours | MFG-066-6 55° C., 4 hours | MFG-066-7 10X PBS, 24 hours |
| 2 | 311.88 | 528.39 | 516.27 | 672.07 |
| 3 | 270.06 | 745.91 | 154.68 | N/A |
| 4 | 341.94 | 455.90 | 49.55 | 377.65 |
| 5 | 532.95 | 171.73 | 21.34 | 281.59 |
| 6 | 448.83 | 125.63 | 9.69 | 136.92 |
| 7 | 222.80 | 61.26 | <LOD | 32.66 |
| 8 | 366.90 | 43.35 | <LOD | 18.96 |
| 9 | 283.22 | 45.43 | <LOD | <LOD |
| 10 | 243.72 | 45.69 | <LOD | <LOD |
| 11 | 147.41 | 29.46 | <LOD | <LOD |
| 12 | 195.40 | 47.01 | <LOD | <LOD |
| 13 | 116.31 | 40.86 | <LOD | <LOD |
| 14 | 141.19 | 38.75 | <LOD | <LOD |
| 15 | 61.99 | 32.39 | <LOD | <LOD |
| 16 | 43.67 | 19.70 | <LOD | <LOD |
| 17 | 47.21 | 13.72 | <LOD | <LOD |
| 18 | 38.78 | 86.57 | <LOD | <LOD |
| 19 | 33.72 | 81.16 | <LOD | <LOD |
| 20 | 17.44 | 67.62 | <LOD | <LOD |
| 21 | 19.60 | 52.20 | <LOD | <LOD |

IL-16.

IL-16 is a cytokine known to be made by lymphocytes.
Characterization of IL-16 During 21-Day Culture.

Descriptive statistics for the IL-16 levels in the spent media over the course of 21 days are presented in Table 35. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 35

Descriptive Statistics for IL-16 Levels in Spent Media over 21 days.

| Day | N | Mean (pg/mL) | Standard Deviation (pg/mL) | Minimum (pg/mL) | Maximum (pg/mL) |
|---|---|---|---|---|---|
| 1 | 6 | 2168.3 | 719 | 1280.0 | 3039.5 |
| 2 | 1 | 725.4 | — | 725.4 | 725.4 |
| 3 | 1 | 934.5 | — | 934.5 | 934.5 |
| 4 | 1 | 837.9 | — | 837.9 | 837.9 |
| 5 | 9 | 1084.8 | 657 | 392.1 | 2273.7 |
| 6 | 1 | 709.2 | — | 709.2 | 709.2 |
| 7 | 9 | 980.0 | 602 | 369.3 | 2062.4 |
| 8 | 1 | 455.8 | — | 455.8 | 455.8 |
| 9 | 9 | 749.4 | 477 | 155.9 | 1714.8 |
| 10 | 1 | 217.7 | — | 217.7 | 217.7 |
| 11 | 7 | 540.8 | 383 | 83.9 | 1052.9 |
| 12 | 1 | 149.6 | — | 149.6 | 149.6 |
| 13 | 7 | 388.9 | 328 | 72.8 | 976.0 |
| 14 | 1 | 90.1 | — | 90.1 | 90.1 |
| 15 | 7 | 265.3 | 253.4 | 38.5 | 623.3 |
| 16 | 1 | 43.5 | — | 43.5 | 43.5 |
| 17 | 7 | 225.6 | 204.8 | 35.7 | 602.2 |
| 18 | 1 | 55.4 | — | 55.4 | 55.4 |
| 19 | 7 | 155.5 | 125.2 | 33.0 | 346.5 |
| 20 | 1 | 29.2 | — | 29.2 | 29.2 |
| 21 | 7 | 143.9 | 132.4 | 22.3 | 357.3 |

A scatterplot of the IL-16 levels in the spent media vs. day for each of the lots analyzed is provided in FIG. 124, and a boxplot is provided in FIG. 125. A fitted line plot (quadratic regression model) is provided in FIG. 126. The scatterplot shows that IL-16 levels in the spent media decrease over the course of 21 days for each lot analyzed. The boxplot indicates that the variability of IL-16 levels in the spent media between lots, in general, decreases as the time spent in culture increases and as the IL-16 levels approach zero. The adjusted $R^2$ value from regression analysis indicates that the time spent in the culture explains 57.3% of the variability in the IL-16 levels.

Characterization of IL-16 Levels in Forced Degradation Samples

Lot MFG-053 and Lot-MFG-054.

The IL-16 levels in the spent media during the forced degradation treatments of Lot-053 (1, 3, and 5) and Lot-054 (1-8) are presented in Table 36, and a scatterplot of the data is provided in FIG. 127. The scatterplot contains a plot of the mean IL-16 results from analysis of the control samples (see Table 35).

TABLE 36

IL-16 Levels (pg/mL) in Forced Degradation Study - Lot MFG-053 and Lot MFG-054

| Sample | Treatment | Day | | |
|---|---|---|---|---|
| | | 5 | 7 | 9 |
| MFG-053-1 | Control | 1024.16 | 740.06 | 571.75 |
| MFG-053-3 | 55° C., 4 hours | 517.51 | 206.78 | 46.89 |
| MFG-053-5 | −20° C., 4 hours | 1005.73 | 699.75 | 370.09 |
| MFG-054-1 | Control | 639.94 | 560.26 | 498.05 |
| MFG-054-2 | RT, 24 hours | 810.36 | 550.57 | 558.29 |
| MFG-054-3 | Dehydration, 24 hours | 540.44 | 677.36 | 531.92 |
| MFG-054-4 | Dehydration, 48 hours | 857.18 | 456.11 | 684.26 |
| MFG-054-5 | Normal Saline, 24 hours | 644.22 | 614.86 | 477.22 |
| MFG-054-6 | Normal Saline, 48 hours | 683.34 | 664.17 | 412.90 |
| MFG-054-7 | 10X PBS, 24 hours | 506.42 | 572.40 | 138.87 |
| MFG-054-8 | 1% DMSO, 24 hours | 740.35 | 427.49 | 551.14 |

Lot MFG-066.

The IL-16 levels in the spent media during the forced degradation treatments of Lot-066 (4-7) are presented in Table 37 and a scatterplot of the data is provided in FIG. 128. The scatterplot contains a plot of the mean IL-16 results from analysis of the control samples (see Table 36. Results less than the LOD are plotted at the LOD.

IGFBP-1

IGFBP2-6 are known to be expressed by thymic epithelium, which does not express IGFBP-1 (Gosteli-Peter 1994; Ketcha 1999)

Characterization of IGFBP-1 During 21-Day Culture.

Descriptive statistics for the IGFBP-1 levels in the spent media over the course of 21 days are presented in Table 37. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 37

Descriptive Statistics for IGFBP-1 Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 5901.3 | 3312.8 | 2427.2 | 11012.9 |
| 2 | 1 | 124.1 | — | 124.1 | 124.1 |
| 3 | 1 | 76.0 | — | 76.0 | 76.0 |
| 4 | 1 | 39.2 | — | 39.2 | 39.2 |
| 5 | 9 | 383.4 | 504.1 | 29.5 | 1598.7 |
| 6 | 1 | 28.9 | — | 28.9 | 28.9 |
| 7 | 9 | 247.2 | 238.0 | 11.9 | 695.1 |
| 8 | 1 | 18.2 | — | 18.2 | 18.2 |
| 9 | 9 | 106.9 | 130.8 | 5.4 | 352.6 |
| 10 | 1 | 17.8 | — | 17.8 | 17.8 |
| 11 | 7 | 88.3 | 46.8 | 14.1 | 135.0 |
| 12 | 1 | 19.6 | — | 19.6 | 19.6 |
| 13 | 7 | 54.5 | 37.3 | 13.4 | 111.4 |
| 14 | 1 | 11.7 | — | 11.7 | 11.7 |
| 15 | 7 | 37.5 | 24.0 | 12.7 | 79.4 |
| 16 | 1 | 7.3 | — | 7.3 | 7.3 |
| 17 | 7 | 53.8 | 32.7 | 7.7 | 92.5 |
| 18 | 1 | 5.4 | — | 5.4 | 5.4 |
| 19 | 7 | 37.1 | 30.1 | 6.4 | 91.3 |
| 20 | 1 | 5.4 | — | 5.4 | 5.4 |
| 21 | 7 | 45.9 | 42.5 | 6.9 | 128.4 |

A scatterplot of the IGFBP-1 levels in the spent media vs. day for each of the lots analyzed is provided in FIG. 129, and a boxplot is provided in FIG. 130. The cubic regression model is provided in FIG. 131. The scatterplot shows that IGFBP-1 levels in the spent media increase over the course of 21 days for each lot analyzed. The boxplot indicates that the variability of IGFBP-1 levels in the spent media between lots, in general, decreases as the time spent in culture increases and as the IGFBP-1 levels approach zero. The adjusted $R^2$ value from regression analysis indicates that the time spent in the culture explains 61.2% of the variability in the IGFBP-1 levels Characterization of IGFBP-1 Levels in Forced Degradation Samples.

Lot MFG-053 and Lot MFG-054.

The IGFBP-1 levels in the spent media during the forced degradation treatments of Lot-053 (1, 3, and 5) are presented in Table 38, and a scatterplot of the data is provided in FIG. 132. The scatterplot contains a plot of the mean IGFBP-1 results from analysis of the control samples (see Table 37). Results less than the LOD are plotted at the LOD.

TABLE 38

IGFBP-1 Levels (pg/mL) in Forced Degradation Study - Lot MFG-053 and Lot MFG-054

| Sample | Treatment | Day 5 | Day 7 | Day 9 |
|---|---|---|---|---|
| MFG-053-1 | Control | 107.06 | 27.13 | 14.11 |
| MFG-053-3 | 55° C., 4 hours | 54.51 | 26.53 | <LOD |
| MFG-053-5 | −20° C., 4 hours | 81.52 | 27.37 | 6.31 |
| MFG-054-1 | Control | 29.49 | 11.88 | <LOD |
| MFG-054-2 | RT, 24 hours | 68.75 | 6.69 | 10.44 |
| MFG-054-3 | Dehydration, 24 hours | 59.99 | 41.37 | 7.65 |
| MFG-054-4 | Dehydration, 48 hours | 213.65 | 55.75 | 26.13 |
| MFG-054-5 | Normal Saline, 24 hours | 30.71 | 12.24 | 9.74 |
| MFG-054-6 | Normal Saline, 48 hours | 46.47 | 22.17 | <LOD |
| MFG-054-7 | 10X PBS, 24 hours | 26.93 | 10.21 | <LOD |
| MFG-054-8 | 1% DMSO, 24 hours | 43.13 | 13.87 | <LOD |

Lot MFG-066.

The IGFBP-1 levels in the spent media during the forced degradation treatments of Lot-066 (4-7) are presented in Table 39, and a scatterplot of the data is provided in FIG. 133. The scatterplot contains a plot of the mean IGFBP-1 results from analysis of the control samples (see Table 38). Results less than the LOD are plotted at the LOD.

TABLE 39

IGFBP-1 Levels (pg/mL) in Forced Degradation Study-Lot MFG-066

| Day | MFG-066-4 Control | MFG-066-5 −20° C., 4 hours | MFG-066-6 55° C., 4 hours | MFG-066-7 10X PBS, 24 hours |
|---|---|---|---|---|
| 2 | 124.11 | 147.13 | 81.00 | 172.87 |
| 3 | 75.96 | 129.04 | 48.30 | N/A |
| 4 | 39.24 | 87.02 | 30.21 | 35.07 |
| 5 | 45.41 | 20.74 | 13.85 | 17.70 |
| 6 | 28.85 | 23.26 | 9.45 | 14.23 |
| 7 | 12.56 | <LOD | 7.92 | 7.31 |
| 8 | 18.17 | <LOD | <LOD | <LOD |
| 9 | 14.32 | 9.65 | <LOD | <LOD |
| 10 | 17.85 | 9.58 | <LOD | <LOD |
| 11 | 14.11 | 25.07 | <LOD | <LOD |
| 12 | 19.60 | 36.21 | <LOD | <LOD |
| 13 | 13.39 | 41.61 | <LOD | <LOD |
| 14 | 11.66 | 41.36 | <LOD | <LOD |
| 15 | 12.71 | 33.28 | <LOD | <LOD |
| 16 | 7.27 | 27.77 | <LOD | <LOD |
| 17 | 7.72 | 22.93 | <LOD | <LOD |
| 18 | <LOD | 50.22 | <LOD | <LOD |
| 19 | 6.43 | 44.51 | <LOD | <LOD |
| 20 | <LOD | 34.44 | <LOD | <LOD |
| 21 | 6.87 | 43.82 | <LOD | <LOD |

MIF.

MIF is a chemokine whose pattern corresponded with that hypothesized for thymocytes.

Characterization of MIF During 21-Day Culture.

Descriptive statistics for the MIF levels in the spent media over the course of 21 days are presented in Table 40. Data from the control samples from the forced degradation studies (Lot MFG-053, MFG-054, and MFG-066) were included with results from Lot MFG-025, MFG-026, MFG-027, MFG-035, MFG-036, and MFG-038

TABLE 40

Descriptive Statistics for MIF Levels in Spent Media over 21 days

| Day | N | Mean (pg/mL) | Standard Deviation (pg/mL) | Minimum (pg/mL) | Maximum (pg/mL) |
|---|---|---|---|---|---|
| 5 | 3 | 2300 | 908 | 1468 | 3268 |
| 7 | 3 | 1977 | 563 | 1445 | 2567 |

TABLE 40-continued

Descriptive Statistics for MIF Levels in Spent Media over 21 days

| Day | N | Mean (pg/mL) | Standard Deviation (pg/mL) | Minimum (pg/mL) | Maximum (pg/mL) |
|---|---|---|---|---|---|
| 9 | 8 | 2512 | 791 | 1312 | 3341 |
| 10 | 1 | 3087 | — | 3087 | 3087 |
| 11 | 7 | 2152 | 642 | 912 | 3089 |
| 12 | 1 | 3308 | — | 3308 | 3308 |
| 13 | 7 | 1378 | 638 | 492 | 1950 |
| 14 | 1 | 2280 | — | 2280 | 2280 |
| 15 | 7 | 1378 | 528 | 416 | 2023 |
| 16 | 1 | 913 | — | 913 | 913 |
| 17 | 7 | 868 | 339 | 469 | 1185 |
| 18 | 1 | 970 | — | 970 | 970 |
| 19 | 7 | 844 | 226 | 584 | 1115 |
| 20 | 1 | 721 | — | 721 | 721 |
| 21 | 7 | 829 | 305 | 435 | 1211 |

A scatterplot of the MIF levels in the spent media vs. day for each of the lots analyzed is provided in FIG. 134 and a boxplot is provided in FIG. 135. The linear regression model is provided in FIG. 136. The scatterplot shows that MIF levels in the spent media decrease over the course of 21 days for each lot analyzed. The boxplot indicates that the variability of MIF levels in the spent media between lots, in general, decreases as the time spent in culture increases and as the MIF levels approach zero. The adjusted R2 value from regression analysis indicates that the time spent in the culture explains 49.2% of the variability in the MIF levels.

The MIF levels in the spent media during the forced degradation treatments of Lot-053 (1, 3, and 5) and Lot-054 (1-8) are presented in Table 41 and a scatterplot of the data is provided in FIG. 137. The scatterplot contains a plot of the mean MIF results from analysis of the control samples (see Table 36). Results greater than the ULOQ are not plotted.

TABLE 41

MIFF Levels (pg/mL) in Forced Degradation-Lot -053 and Lot-054

| | | Day | | |
|---|---|---|---|---|
| Sample | Treatment | 5 | 7 | 9 |
| MFG-053-1 | Control | >ULOQ | >ULOQ | 3233.27 |
| MFG-053-3 | 55° C., 4 hours | >ULOQ | >ULOQ | 1104.83 |
| MFG-053-5 | −20° C., 4 hours | >ULOQ | >ULOQ | 1649.46 |
| MFG-054-1 | Control | >ULOQ | 2567.42 | 2464.25 |
| MFG-054-2 | RT, 24 hours | >ULOQ | 3612.80 | 3374.70 |
| MFG-054-3 | Dehydration, 24 hours | >ULOQ | >ULOQ | >ULOQ |
| MFG-054-4 | Dehydration, 24 hours | >ULOQ | >ULOQ | >ULOQ |
| MFG-054-5 | Normal Saline, 24 hours | >ULOQ | >ULOQ | >ULOQ |
| MFG-054-6 | Normal Saline, 48 hours | >ULOQ | >ULOQ | 3316.32 |
| MFG-054-7 | 10X PBS, 24 hours | >ULOQ | >ULOQ | 3637.27 |
| MFG-054-8 | 1% DMSO, 24 hours | >ULOQ | >ULOQ | 3668.38 |

Lot MFG-066.

The MIF levels in the spent media during the forced degradation treatments of Lot-066 (4-7) are presented in Table 42, and a scatterplot of the data is provided in FIG. 138. The scatterplot contains a plot of the mean MIF results from analysis of the control samples (see Table 41). Results greater than the ULOQ are not plotted.

TABLE 42

MIF Levels (pg/mL) in Forced Degradation Study-Lot MFG-066

| | Treatment | | | |
|---|---|---|---|---|
| Day | MFG-066-4 Control | MFG-066-5 −20° C., 4 hours | MFG-066-6 55° C., 4 hours | MFG-066-7 10X PBS, 24 hours |
| 2 | >ULOQ | >ULOQ | >ULOQ | >ULOQ |
| 3 | >ULOQ | >ULOQ | >ULOQ | N/A |
| 4 | >ULOQ | >ULOQ | >ULOQ | >ULOQ |
| 5 | >ULOQ | >ULOQ | >ULOQ | >ULOQ |
| 6 | >ULOQ | >ULOQ | >ULOQ | >ULOQ |
| 7 | >ULOQ | >ULOQ | >ULOQ | >ULOQ |
| 8 | >ULOQ | 3756.95 | 2724.06 | >ULOQ |
| 9 | 3341.28 | 3129.52 | 2230.04 | >ULOQ |
| 10 | 3086.91 | 2153.04 | 1543.57 | >ULOQ |
| 11 | 2090.07 | 1458.60 | 946.02 | 2042.93 |
| 12 | 3307.79 | 1655.69 | 1334.31 | 3553.31 |
| 13 | 1949.83 | 1776.58 | 3170.68 | 1706.88 |
| 14 | 2280.45 | 1237.27 | 875.61 | 1604.87 |
| 15 | 1421.79 | 921.58 | 795.98 | 877.94 |
| 16 | 912.75 | 780.77 | 489.52 | 647.60 |
| 17 | 999.58 | 498.76 | 398.93 | 421.43 |
| 18 | 970.10 | 925.19 | 731.72 | 906.22 |
| 19 | 1098.03 | 752.08 | 410.44 | 399.31 |
| 20 | 721.44 | 585.77 | 205.49 | 361.21 |
| 21 | 1080.61 | 578.89 | 164.08 | 213.77 |

CCL25 (TECK).

CCL25 (TECK) is a chemokine that has been shown to be chemotactic for thymocytes (Liu 2005). It is known to be expressed by thymic dendritic cells and by both FoxN1$^+$ and FoxN1$^-$ TE cells (Bunting 2011); however, its activity does not appear to be critical for thymus development based on studies of mice in which CCR9, the sole receptor for this chemokine, was deleted (Wurbel 2001).

Characterization of CCL25 During 21-Day Culture.

Descriptive statistics for the CCL25 levels in the spent media over the course of 21 days are presented in Table 43. Data from the control samples from the forced degradation studies (Lot MFG-053, MFG-054, and MFG-066) were included with results from Lot MFG-025, MFG-026, MFG-027, MFG-035, MFG-036, and MFG-038.

TABLE 43

Descriptive Statistics for CCL25 Levels in Spent Media over 21 days

| Day | N | Mean (pg/mL) | Standard Deviation (pg/mL) | Minimum (pg/mL) | Maximum (pg/mL) |
|---|---|---|---|---|---|
| 1 | 6 | 85.5 | 24.2 | 63.9 | 113.6 |
| 2 | 1 | 242.2 | — | 242.2 | 242.2 |
| 3 | 1 | 242.2 | — | 242.2 | 242.2 |
| 4 | 1 | 242.2 | — | 242.2 | 242.2 |
| 5 | 9 | 138.4 | 80.3 | 63.9 | 242.2 |
| 6 | 1 | 242.2 | — | 242.2 | 242.2 |
| 7 | 9 | 138.4 | 80.3 | 63.9 | 242.2 |
| 8 | 1 | 242.2 | — | 242.2 | 242.2 |
| 9 | 9 | 138.4 | 80.3 | 63.9 | 242.2 |
| 10 | 1 | 242.2 | — | 242.2 | 242.2 |
| 11 | 7 | 132.8 | 89.7 | 63.9 | 277.5 |
| 12 | 1 | 242.2 | — | 242.2 | 242.2 |
| 13 | 7 | 108.8 | 63.0 | 63.9 | 242.2 |
| 14 | 1 | 242.2 | — | 242.2 | 242.2 |
| 15 | 7 | 121.4 | 69.0 | 63.9 | 242.2 |
| 16 | 1 | 242.2 | — | 242.2 | 242.2 |
| 17 | 7 | 108.8 | 63.0 | 63.9 | 242.2 |
| 18 | 1 | 242.2 | — | 242.2 | 242.2 |
| 19 | 7 | 111.7 | 61.0 | 63.9 | 242.2 |
| 20 | 1 | 242.2 | — | 242.2 | 242.2 |
| 21 | 7 | 123.6 | 74.3 | 63.9 | 242.2 |

A scatterplot of the CCL25 levels in the spent media vs. day for each of the lots analyzed is provided in FIG. 139 and a boxplot is provided in FIG. 140. The linear regression model is provided in FIG. 141. The scatterplot shows that CCL25 levels in the spent media increase over the course of 21 days for each lot analyzed. The boxplot indicates that the variability of CCL25 levels in the spent media between lots, in general, increases as the time spent in culture increases. The adjusted R2 value from regression analysis indicates that the time spent in the culture explains 49.2% of the variability in the CCL25 levels.

Characterization of CCL25 Levels in Forced Degradation Samples.

Lot MFG-053 and Lot MFG-054.

The CCL25 levels in the spent media during the forced degradation treatments of Lot-053 (1, 3, and 5) and Lot-054 (1-8) are presented Table 44, and a scatterplot of the data is provided in 142. The scatterplot contains a plot of the mean CCL25 results from analysis of the control samples (see Table 43). Results less than the LOD are plotted at the LOD.

TABLE 44

CCL25 Levels (pg/mL) in Forced Degradation Study-Lot MFG-053 and Lot MFG-054

| Sample | Treatment | Day 5 | Day 7 | Day 9 |
|---|---|---|---|---|
| MFG-053-1 | Control | <LOD | <LOD | <LOD |
| MFG-053-3 | 55° C., 4 hours | <LOD | <LOD | <LOD |
| MFG-053-5 | −20° C., 4 hours | <LOD | <LOD | <LOD |
| MFG-054-1 | Control | <LOD | <LOD | <LOD |
| MFG-054-2 | RT, 24 hours | <LOD | <LOD | <LOD |
| MFG-054-3 | Dehydration, 24 hours | <LOD | <LOD | <LOD |
| MFG-054-4 | Dehydration, 48 hours | <LOD | <LOD | <LOD |
| MFG-054-5 | Normal Saline, 24 hours | <LOD | <LOD | <LOD |
| MFG-054-6 | Normal Saline, 48 hours | <LOD | <LOD | <LOD |
| MFG-054-7 | 10X PBS, 24 hours | <LOD | <LOD | <LOD |
| MFG-054-8 | 1% DMSO, 24 hours | <LOD | <LOD | <LOD |

Lot MFG-066.

The CCL25 levels in the spent media during the forced degradation treatments of Lot-066 (4-7) are presented in Table 45, and a scatterplot of the data is provided in FIG. 143. The scatterplot contains a plot of the mean CCL25 results from analysis of the control samples (see Table 44). Results less than the LOD are plotted at the LOD.

TABLE 45

CCL25 Levels (pg/mL) in Forced Degradation Study-Lot MFG-66.

| Day | MFG-066-4 Control | MFG-066-5 −20° C., 4 hours | MFG-066-6 55° C., 4 hours | MFG-066-7 10X PBS, 24 hours |
|---|---|---|---|---|
| 2 | <LOD | <LOD | <LOD | <LOD |
| 3 | <LOD | <LOD | <LOD | N/A |
| 4 | <LOD | <LOD | <LOD | <LOD |
| 5 | <LOD | <LOD | <LOD | <LOD |
| 6 | <LOD | <LOD | <LOD | <LOD |
| 7 | <LOD | <LOD | <LOD | <LOD |
| 8 | <LOD | <LOD | <LOD | <LOD |
| 9 | <LOD | <LOD | <LOD | <LOD |
| 10 | <LOD | <LOD | <LOD | <LOD |
| 11 | <LOD | <LOD | <LOD | <LOD |
| 12 | <LOD | <LOD | <LOD | <LOD |
| 13 | <LOD | <LOD | <LOD | <LOD |
| 14 | <LOD | <LOD | <LOD | <LOD |
| 15 | <LOD | <LOD | <LOD | <LOD |
| 16 | <LOD | <LOD | <LOD | <LOD |
| 17 | <LOD | <LOD | <LOD | <LOD |
| 18 | <LOD | <LOD | <LOD | <LOD |
| 19 | <LOD | <LOD | <LOD | <LOD |
| 20 | <LOD | <LOD | <LOD | <LOD |
| 21 | <LOD | <LOD | <LOD | <LOD |

APPENDICES

Appendix 1

TABLE 46

Biomarker Data for 21-day Culture Characterization. Lot MFG-025 Data

| Day | CCL11 | IL-16 | IGFBP-1 | CCL21 | CXCL16 | MIF | CCL20 | OPN | CXCL12 | CCL25 | L-Selectin | uPAR |
|---|---|---|---|---|---|---|---|---|---|---|---|---|
| 1 | 3.1 | 3039.5 | 3480.3 | 216.0 | 591.3 | >4000 | 12.8 | 2655.1 | <4.3 | <63.9 | 20322.8 | 1311.2 |
| 5 | 4.7 | 2273.7 | 239.5 | 7646.8 | 906.0 | >4000 | 6.6 | 7147.3 | <4.3 | <63.9 | 4768.4 | 3956.7 |
| 7 | 40.2 | 1470.5 | 170.8 | 12787.3 | 2219.8 | >4000 | 4.5 | 8800.9 | <4.3 | <63.9 | 4590.3 | 6475.0 |
| 9 | 81.9 | 949.8 | 41.7 | 12791.6 | 2317.4 | 2829.6 | 2.9 | 7838.6 | <4.3 | <63.9 | 3133.3 | 7145.7 |
| 11 | 102.4 | 791.2 | 55.0 | 19295.9 | 2607.5 | 2296.3 | 2.5 | 9507.4 | <4.3 | <63.9 | 1792.8 | 9765.5 |
| 13 | 113.5 | 456.5 | 22.6 | 15618.0 | 2721.2 | 1332.7 | 1.6 | 9764.4 | <4.3 | <63.9 | 1261.9 | 8664.8 |
| 15 | 126.5 | 378.9 | <18.5 | 23809.5 | 4739.1 | 1222.2 | 2.4 | 10424.8 | 6.5 | 72.4 | 1144.6 | 10071.4 |
| 17 | 135.9 | 178.2 | 41.7 | 16747.1 | 2628.4 | 599.1 | <1.1 | 9615.1 | 15.7 | <63.9 | 891.9 | 7324.9 |
| 19 | 109.5 | 98.6 | 52.9 | 18783.3 | 2495.7 | 621.1 | <1.1 | 11514.1 | 37.4 | <63.9 | 1316.4 | 8900.9 |
| 21 | 146.3 | 98.3 | 64.1 | 15618.6 | 2295.9 | 659.0 | <1.1 | 11163.2 | 32.3 | <63.9 | 693.3 | 10138.6 |

TABLE 47

Biomarker Data for 21-day Culture Characterization. Lot MFG-026 Data.

| Day | CCL11 | IL-16 | IGFBP-1 | CCL21 | CXCL16 | MIF | CCL20 | OPN | CXCL12 | CCL25 | L-Selectin | uPAR |
|---|---|---|---|---|---|---|---|---|---|---|---|---|
| 1 | <1.3 | 2251.4 | 8588.2 | 238.8 | 1487.3 | >4000 | 54.1 | 6811.7 | <4.3 | <63.9 | 27797.8 | 1417.8 |
| 5 | 7.9 | 459.9 | 207.1 | 3314.4 | 1066.8 | 2165.6 | 9.4 | 9773.0 | <4.3 | <63.9 | 2305.7 | 1658.3 |

TABLE 47-continued

Biomarker Data for 21-day Culture Characterization. Lot MFG-026 Data.

| Day | CCL11 | IL-16 | IGFBP-1 | CCL21 | CXCL16 | MIF | CCL20 | OPN | CXCL12 | CCL25 | L-Selectin | uPAR |
|---|---|---|---|---|---|---|---|---|---|---|---|---|
| 7 | 45.1 | 493.2 | 148.5 | 8526.8 | 2735.3 | 1918.5 | 13.0 | 11388.9 | <4.3 | <63.9 | 4011.4 | 4648.4 |
| 9 | 60.4 | 420.6 | 44.9 | 12138.9 | 3044.0 | 1316.6 | 7.6 | 11736.5 | <4.3 | <63.9 | 3862.2 | 8738.9 |
| 11 | 72.6 | 208.6 | 53.8 | 15708.8 | 3476.5 | 911.6 | 6.2 | 12228.6 | <4.3 | <63.9 | 4169.7 | 14194.9 |
| 13 | 54.7 | 91.6 | <18.5 | 12209.1 | 3343.8 | 492.0 | 3.2 | 11332.6 | <4.3 | <63.9 | 1601.7 | 11235.8 |
| 15 | 62.4 | 57.1 | <18.5 | 16698.5 | 3718.1 | 416.2 | 2.2 | 13547.0 | 7.2 | <63.9 | 1629.4 | 14894.4 |
| 17 | 77.1 | 65.2 | <18.5 | 14276.9 | 3776.6 | 477.2 | 1.8 | 12756.0 | 12.3 | 69.9 | 473.3 | 14092.6 |
| 19 | 106.1 | 71.5 | <18.5 | 18004.7 | 4770.0 | 651.3 | 1.7 | 15975.3 | 30.1 | 84.4 | 1714.4 | 14362.4 |
| 21 | 101.4 | 46.5 | <18.5 | 14976.8 | 3875.2 | 434.7 | 1.4 | 11138.3 | 20.3 | <63.9 | 709.6 | 13016.9 |

TABLE 48

Biomarker Data for 21-day Culture Characterization. Lot MFG-027 Data.

| Day | CCL11 | IL-16 | IGFBP-1 | CCL21 | CXCL16 | MIF | CCL20 | OPN | CXCL12 | CCL25 | L-Selectin | uPAR |
|---|---|---|---|---|---|---|---|---|---|---|---|---|
| 1 | <1.3 | 2972.5 | 5893.5 | 256.7 | 1162.9 | >4000 | 21.4 | 3612.7 | <4.3 | <63.9 | 35738.2 | 1026.1 |
| 5 | <1.3 | 1951.9 | 629.1 | 7652.5 | 693.5 | >4000 | 10.7 | 10758.7 | <4.3 | <63.9 | 6685.3 | 4767.6 |
| 7 | 12.1 | 2062.4 | 357.7 | 11056.7 | 1364.7 | >4000 | 6.1 | 10985.0 | <4.3 | <63.9 | 3937.7 | 5262.3 |
| 9 | 47.0 | 1127.3 | 81.3 | 13434.9 | 1783.4 | 2927.2 | 5.0 | 11227.9 | <4.3 | <63.9 | 2897.3 | 8194.7 |
| 11 | 90.5 | 1052.9 | 135.0 | 17599.4 | 2226.2 | 2325.3 | 2.7 | 10714.1 | <4.3 | <63.9 | 3065.3 | 9295.3 |
| 13 | 125.2 | 976.0 | 60.6 | 22579.7 | 2753.5 | 1950.4 | 2.4 | 13367.5 | 6.6 | <63.9 | 1921.8 | 13471.9 |
| 15 | 125.1 | 567.3 | 32.7 | 23637.2 | 2463.1 | 1319.4 | <1.1 | 13023.8 | 14.7 | <63.9 | 2195.0 | 13678.3 |
| 17 | 180.4 | 359.2 | 82.8 | 21395.9 | 2737.2 | 1173.2 | <1.1 | 12720.5 | 29.7 | <63.9 | 1098.7 | 15640.8 |
| 19 | 178.9 | 314.6 | 53.2 | 25506.7 | 2932.2 | 1114.8 | 1.1 | 12447.5 | 33.5 | <63.9 | 1826.7 | 15449.1 |
| 21 | 172.9 | 155.0 | 51.6 | 27366.0 | 2710.8 | 899.4 | 1.7 | 10874.7 | 50.2 | <63.9 | <288.7 | 13585.4 |

TABLE 49

Biomarker Data for 21-day Culture Characterization. Lot MFG-035 Data.

| Day | CCL11 | IL-16 | IGFBP-1 | CCL21 | CXCL16 | MIF | CCL20 | OPN | CXCL12 | CCL25 | L-Selectin | uPAR |
|---|---|---|---|---|---|---|---|---|---|---|---|---|
| 1 | <2.4 | 171.3 | 4005.8 | 118.2 | 591.9 | >4000 | 8.1 | 2483.1 | <4.9 | <109.2 | 43398.9 | 972.9 |
| 5 | 5.3 | 1365.1 | 534.5 | 11062.5 | 1077.8 | >4000 | 23.7 | 11167.6 | <4.9 | <109.2 | 12218.9 | 5028.7 |
| 7 | 34.7 | 1604.8 | 304.4 | 13864.8 | 1885.0 | >4000 | 44.0 | 11319.2 | <4.9 | <109.2 | 12573.3 | 8553.5 |
| 9 | 53.0 | 911.8 | 100.1 | 15084.4 | 2345.3 | 2672.3 | 39.5 | 11533.4 | <4.9 | <109.2 | 9924.4 | 8717.3 |
| 11 | 125.6 | 702.3 | 112.5 | 16587.6 | 2778.5 | 2138.7 | 42.1 | 10908.4 | <4.9 | <109.2 | 9297.0 | 10260.6 |
| 13 | 175.0 | 589.9 | 79.5 | 18225.6 | 2814.2 | 1623.0 | 38.0 | 10378.6 | <4.9 | <109.2 | 10396.4 | 10335.1 |
| 15 | 246.4 | 623.3 | 49.0 | 20254.9 | 2907.1 | 1318.9 | 32.7 | 10998.3 | <4.9 | <109.2 | 9385.0 | 11838.6 |
| 17 | 209.4 | 273.3 | 77.7 | 16463.8 | 2669.5 | 1185.3 | 19.9 | 9030.6 | <4.9 | <109.2 | 7169.9 | 11185.4 |
| 19 | 233.8 | 346.5 | 21.9 | 17536.0 | 2949.5 | 889.2 | 13.3 | 10862.7 | 5.7 | <109.2 | 5934.2 | 7542.2 |
| 21 | 263.3 | 357.3 | 42.5 | 18157.2 | 3316.7 | 1029.1 | 12.0 | 9639.3 | 8.2 | <109.2 | 6755.4 | 8659.6 |

TABLE 50

Biomarker Data for 21-day Culture Characterization. Lot MFG-036 Data.

| Day | CCL11 | IL-16 | IGFBP-1 | CCL21 | CXCL16 | MIF | CCL20 | OPN | CXCL12 | CCL25 | L-Selectin | uPAR |
|---|---|---|---|---|---|---|---|---|---|---|---|---|
| 1 | <2.4 | 1755.0 | 2427.2 | 608.3 | 2919.1 | >4000 | 25.6 | 12083.9 | <4.9 | 113.6 | 30773.2 | 1275.9 |
| 5 | 131.3 | 814.1 | 59.4 | 16977.2 | 2642.8 | 1467.7 | 40.3 | 9295.7 | <4.9 | <109.2 | 3730.5 | 8284.6 |
| 7 | 66.0 | 1041.3 | 695.1 | 2886.3 | 1938.6 | >4000 | 54.2 | 11436.4 | 12.3 | <109.2 | 3206.4 | 3260.5 |
| 9 | 190.2 | 1714.8 | 307.5 | 2871.3 | 2938.0 | >4000 | 61.9 | 9787.9 | 5.3 | <109.2 | 1956.0 | 5128.1 |
| 11 | 234.3 | 789.7 | 128.5 | 3798.2 | 2237.0 | 3089.5 | 44.5 | 10757.3 | <4.9 | <109.2 | 1610.9 | 6531.0 |
| 13 | 257.4 | 407.7 | 111.4 | 3517.8 | 2866.5 | 1796.6 | 30.2 | 11336.1 | <4.9 | <109.2 | 1240.1 | 7761.4 |
| 15 | 265.9 | 117.7 | 79.4 | 4039.8 | 3353.5 | 1921.6 | 32.5 | 12110.2 | <4.9 | <109.2 | 1156.0 | 8272.5 |
| 17 | 384.6 | 602.2 | 92.5 | 5219.5 | 3380.9 | 1175.0 | 19.6 | 12693.3 | 8.2 | <109.2 | 1185.0 | 11488.1 |
| 19 | 414.7 | 152.3 | 91.3 | 4140.5 | 2777.9 | 951.0 | 12.0 | 10699.5 | 6.6 | <109.2 | 1224.3 | 11109.2 |
| 21 | 441.9 | 291.3 | 128.4 | 6156.5 | 3550.4 | 1211.5 | 14.1 | 12773.7 | 11.0 | 212.8 | 1108.4 | 13987.1 |

TABLE 51

Biomarker Data for 21-day Culture Characterization. Lot MFG-038 Data.

| Day | CCL11 | IL-16 | IGFBP-1 | CCL21 | CXCL16 | MIF | CCL20 | OPN | CXCL12 | CCL25 | L-Selectin | uPAR |
|---|---|---|---|---|---|---|---|---|---|---|---|---|
| 1 | <2.4 | 1280.0 | 11012.9 | 177.6 | 559.7 | >4000 | 14.8 | 5907.6 | <4.9 | <109.2 | 14966.5 | 1001.6 |
| 5 | 26.5 | 392.1 | 1598.7 | 7884.9 | 2139.7 | 3268.1 | 89.6 | 13716.5 | <4.9 | <109.2 | 2521.2 | 3221.0 |
| 7 | 48.5 | 369.3 | 497.0 | 9224.8 | 2724.7 | 1445.4 | 84.5 | 13942.3 | <4.9 | <109.2 | 1577.3 | 6094.5 |
| 9 | 33.6 | 155.9 | 352.6 | 15056.1 | 3380.5 | 1312.2 | 72.8 | 14906.8 | <4.9 | <109.2 | 2072.6 | 9476.4 |
| 11 | 22.7 | 83.9 | 119.2 | 30946.6 | 4153.6 | 2212.1 | 52.0 | 28981.8 | 8.3 | 277.5 | 1525.3 | 13747.2 |
| 13 | 37.8 | 72.8 | 75.8 | 24110.2 | 3267.1 | 502.7 | 29.9 | 11577.3 | <4.9 | <109.2 | 1393.2 | 15015.5 |
| 15 | 54.1 | 38.5 | 51.6 | 28862.9 | 3843.4 | 2023.0 | 18.2 | 28982.0 | 20.5 | 189.4 | 1374.0 | 16983.8 |
| 17 | 87.2 | 35.7 | 56.0 | 23833.9 | 3199.4 | 469.3 | 9.6 | 14821.0 | 6.1 | <109.2 | 1570.4 | 16818.3 |
| 19 | 108.1 | 33.0 | 15.5 | 25243.3 | 3445.8 | 584.3 | 6.1 | 16660.4 | 13.5 | <109.2 | 1252.4 | 18078.0 |
| 21 | 123.5 | 22.3 | <9.1 | 24625.4 | 3842.7 | 485.7 | 3.8 | 14642.2 | 15.2 | <109.2 | 1134.2 | 17772.4 |

The foregoing embodiments and advantages are merely exemplary and are not to be construed as limiting the present invention. The present teachings can be readily applied to other types of apparatuses, experiments and surgical procedures. Also, the description of the embodiments of the present invention is intended to be illustrative and not to limit the scope of the claims. Many alternatives, modifications, and variations will be apparent to those skilled in the art.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

References discussed in the application, which are incorporated by reference in their entirety, for their intended purpose, which is clear based upon its context.

All patents, patent applications and publications cited herein are hereby incorporated by reference in their entirety. The disclosures of these publications in their entireties are hereby incorporated by reference into this application.

The disclosures of each and every patent, patent application, publication, and accession number cited herein are hereby incorporated herein by reference in their entirety.

While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

REFERENCES

Ahonen, P., 1985, "Autoimmune polyendocrinopathy-candidosis-ectodermal dystrophy (APECED): autosomal recessive inheritance," Clinical Genetics, 27: 535-542

Ahonen, P., et al., 1987, "Adrenal and steroidal cell antibodies in patients with autoimmune polyglandular disease type I and risk of adrenocortical and ovarian failure," J. Clin. Endocrinology and Metabolism, 64: 494-500.

Ahonen, P., et al., 1987, "Adrenal and steroidal cell antibodies in patients with autoimmune polyglandular disease type I and risk of adrenocortical and ovarian failure," J. Clin. Endocrinology and Metabolism, 64: 494-500.

Ahonen, P., et al., 1988, J. Clin. Endocrinology and Metabolism, 66: 1152-1157.

Ahonen, P., et al., 1990, "Clinical variation of autoimmune polyendocrinopathy-candidiasis-ectodermal dystrophy (APECED) in a series of 68 patients," New Engl. J. Med. 322: 1829-1836.

Arulanantham, K., et al., 1979, "Evidence for Defective Immunoregulation in the Syndrome of Familial Candidiasis Endocrinopathy," New Eng. J. Med. 300:164-168.

Bennett A R, Farley A, Blair N F, Gordon J, Sharp L, Blackburn C C., 2002, "Identification and characterization of thymic epithelial progenitor cells, Immunity, 16: 803-814.

Bernstock, Joshua D, Totten, A, and Atkinson, T. Prescott, "Recurrent microdeletions at chromosome 2p11.2," Bernstock, Joshua D, Totten, A, and Atkinson, T. Prescott, JACI 145:358-367.

Biron-Pain K, Grosset A A, Poirier F, Gaboury L, St-Pierre Y (2013) Expression and functions of galectin-7 in human and murine melanomas PLoS One 8:e63307 doi:10.1371/journal.pone.0063307.

Blizzard, R. M. and Kyle M., 1963, "Studies of the Adrenal Antigens and Antibodies in Addison's Disease," J. Clin. Invest. 42: 1653-1660 Boehm T, Takahama Y. 2014. Thymic Development and Selection of T Lymphocytes. Heidelberg: Springer-Verlag.

Boehm T, Takahama Y. 2014. Thymic Development and Selection of T Lymphocytes. Heidelberg: Springer-Verlag.

Bunting M D, Comerford I, McColl S R. Finding their niche: chemokines directing cell migration in the thymus. Immunol Cell Biol. 89:185-196, 2011.

CFR Title 21; 1271 Human cells, tissues, and cellular and tissue-based products.

Chinn I, Devlin B, Li Y J, et al., 2008. "Long-term tolerance to allogeneic thymus transplants in complete DiGeorge anomaly," Clin Immunol. 126(3): 277-281.

Davis C M, McLaughlin T M, Watson T J, Buckley R H, Schiff S E, Hale L P, et al., 1997, "Normalization of peripheral blood T cell receptor V-beta repertoire after postnatal thymic transplantation in DiGeorge syndrome," J. Clinical Immunol., 17: 167-175.

Davies, E G, Cheung M, Gilmour K, Maimaria J, Curry J, Furmanski A, et al., 2017, "Thymus transplantation for complete DiGeorge syndrome: European experience," *J Allergy Clin Immunol.* 140: 1660-1670.

Dudal S et al. (2015) Integrated pharmacokinetic, pharmacodynamic and immunogenicity profiling of an anti-CCL21 monoclonal antibody in cynomolgus monkeys MAbs 7:829-837 doi:10.1080/19420862.2015.1060384.

Fitzhugh D J, Shan S, Dewhirst M W, Hale L P (2008) Bromelain treatment decreases neutrophil migration to sites of inflammation Clin Immunol 128:66-74 doi: 10.1016/j.clim.2008.02.015.

Flores K G, Li J, Sempowski G D, Haynes, B F, Hale L P. Analysis of the human perivascular space during aging. J Clin Invest. 104:1031-1039, 1999.

Gosteli-Peter M A, Winterhalter K H, Schmid C, Froesch F R, Zapf J. Expression and regulation of insulin-like growth factor-1 (IGF-1) and IGF-binding protein messenger ribonucleic acid levels in tissues of hypophysectomized rats infused with IGF-1 and growth hormone. Endocrinol. 135:2558-2567, 1994.

Gridley D S, Mao X W, Stodieck L S, Ferguson V L, Bateman T A, Moldovan M, et al. Changes in mouse thymus and spleen after return from the STS-135 mission in space. PLOS One. 8: e75097, 2013. doi:10.1371/journal.pone.007509.

Gruver A L, Hudson L L, Sempowski G D (2007) Immunosenescence of ageing J Pathol 211:144-156 doi: 10.1002/path.2104.

Hafezi-Moghadam A, Thomas K L, Prorock A J, Huo Y, Ley K (2001) L-selectin shedding regulates leukocyte recruitment J Exp Med 193:863-872 doi:10.1084/jem.193.7.863.

Hale L P, Markert M L., 2004, "Corticosteroids regulate epithelial cell differentiation and Hassall body formation in the human thymus," *J Immunol.,* 172: 617-624.

Hernandez-Lopez C, Varas A, Sacedon R, Jimenez E, Munoz J J, Zapata A G, Vicente A. Stromal cell-derived factor 1/CXCR4 signaling is critical for early human T-cell development. Blood. 99:546-554, 2002.

Heron I., 1971, "A technique for accessory cervical heart transplantation in rabbits and rats," *Acta Pathol Microbiol Scand A* 79(4):366-372.

Hong R, Schulte-Wissermann H, Jarrett-Toth E, Horowitz S D, Manning D D, 1979, "Transplantation of cultured thymic fragments. II. Results in nude mice," *J Exp Med.* 149(2): 398-415.

Hong R, Moore, A L. 1996, "Organ culture for thymus transplantation," *Transplantation,* 61: 444-448.

Hu Z, Lancaster J N, Ehrlich L I (2015) The Contribution of Chemokines and Migration to the Induction of Central Tolerance in the Thymus Front Immunol 6:398 doi: 10.3389/fimmu.2015.00398.

Hun M, Barsanti M, Wong K, Ramshaw J, Werkmeister J, Chidgey A P., 2017, "Native thymic extracellular matrix improves in vivo thymic organoid T cell output, and drives in vitro thymic epithelial cell differentiation," *Biomaterials,* 118: 1-15.

Ito, R., Hale, L. P., Geyer, S. M., Li, J., Sornberger, A., Kajimura, J., Kusunoki, Y., Yoshida, K., van den Brink, M. R. M., Kyoizumi, S., Manley, N. R., Nakachi, K., Sempowski, G. D.: Effects of age and exposure to ionizing radiation on human thymus morphology and function. Radiation Res., 187:589-598, 2017.

Ito R et al. (2017) Late Effects of Exposure to Ionizing Radiation and Age on Human Thymus Morphology and Function Radiat Res 187:589-598 doi:10.1667/RR4554.1.

Ivetic A, Hoskins Green H L, Hart S J (2019) L-selectin: A Major Regulator of Leukocyte Adhesion, Migration and Signaling Front Immunol 10:1068 doi:10.3389/fimmu.2019.01068.

Ketcha O, Martens H, Franchimont N, Achour I, Hazee-Hagelstein M-T, Charlet-Renard C, et al. Characterization of the insulin-like growth factor axis in the human thymus. J Neuroendocrinol. 11:435-440, 1999.

Kozai M et al. (2017) Essential role of CCL21 in establishment of central self-tolerance in T cells J Exp Med 214:1925-1935 doi:10.1084/jem.20161864.

Krohn, K., et al., 1992, "Identification by molecular cloning of an autoantigen associated with Addison's disease as steroid 17α-hydroxylase," *Lancet* 339:770-773.

Kuwabara I et al. (2002) Galectin-7 (PIG1) exhibits pro-apoptotic function through JNK activation and mitochondrial cytochrome c release J Biol Chem 277:3487-3497 doi:10.1074/jbc.M109360200.

Kuwabara I, Kuwabara Y, Yang R-Y, Schuler M, Green D R, Zuraw B I, et al. Galectin-7 (PIG1) exhibits pro-apoptotic function through JNK Lee E N, Park J K, Lee J-R, Oh S-O, Baek S-Y, Kim B-S, et al., 2011, "Characterization of the expression of cytokeratins 5, 8, and 14 in mouse thymic epithelial cells during thymus regeneration following acute thymic involution," *Anat Cell Biol.* 44: 14-24.

Kwun, Jean, Li, Jie, Rouse, Clay, Park, Jae Berm, Farris, Alton B., Kuchibhatla, Maragatha, Turek, Joseph W. Knechtle, Stuart J. Kirk, Allan D. and Markert, M Louise, *Cultured thymus tissue implantation promotes donor-specific tolerance to allogeneic heart transplants,* JCI Insight. 2020 Jun. 4; 5(11):e129983. doi: 10.1172/jci.insight.129983.

Le P T, Kurtzberg J, Brandt S J, Niedel J E, Haynes B F, Singer K H (1988) Human thymic epithelial cells produce granulocyte and macrophage colony-stimulating factors J Immunol 141:1211-1217.

Lee E N, Park J K, Lee J-R, Oh S-O, Baek S-Y, Kim B-S, et al., 2011, "Characterization of the expression of cytokeratins 5, 8, and 14 in mouse thymic epithelial cells during thymus regeneration following acute thymic involution," *Anat Cell Biol.* 44: 14-24.

Li B, Li J, Hsieh C S, Hale L P, Li Y J, Devlin B H, Markert M L. 2009 "Characterization of cultured thymus tissue used for transplantation with emphasis on promiscuous expression of thyroid tissue-specific genes," 2009, *Immunol Res.* 2009, 44(1-3):71-83.

Li B, Li J, Devlin B H, Markert M L. 2011, "Thymic microenvironment reconstitution after postnatal human thymus transplantation," *Clin Immunol. September;* 140 (3): 244-59.

Liu C, Ueno T, Kuse S, Saito F, Nitta T, Piali L, et al. The role of CCL21 in recruitment of T-precursor cells to fetal thymi. Blood. 105:31-39, 2005.

Lkhagvasuren E, Sakata M, Ohigashi I, Takahama Y (2013) Lymphotoxin beta receptor regulates the development of CCL21-expressing subset of postnatal medullary thymic epithelial cells J Immunol 190:5110-5117 doi:10.4049/jimmunol.1203203.

Loughner C L, Bruford E A, McAndrews M S, Delp E E, Swamynathan S, Swamynathan S K. Organization, evolution and functions of the human and mouse Ly6/uPAR family genes. Human Genomics 10:10, 2016.

Markert M L, Kostyu D D, Ward F E, McLaughlin T M, Watson T J, Buckley R H, Schiff S E, Ungerleider R M, Gaynor J W, Oldham K T, Mahaffey S M, Ballow M, Driscoll D A, Hale L P, Haynes B F. "Successful formation of a chimeric human thymus allograft following transplantation of partially HLA-matched postnatal thymus," 1997, *Journal of Immunology*, 158:998-1005.

Markert M L, Watson T J, Kaplan I, Hale L P, Haynes B F, "The human thymic microenvironment during organ culture," 1997, *Clin Immunol Immunopathol.*, January; 82(1): 6354-6364.

Markert M L, Boeck A, Hale L P, Kloster A L, McLaughlin T M, Batchvarova M N, et al., "Transplantation of thymus tissue in complete DiGeorge syndrome," 1999, *N Engl J Med.* 341(16): 1180-9.

Markert M L et al. (2003) Thymus transplantation in complete DiGeorge syndrome: immunologic and safety evaluations in 12 patients Blood 102:1121-1130 doi:10.1182/blood-2002-08-2545.

Markert M L, et al., 2004, "Postnatal thymus transplantation with immunosuppression as treatment for DiGeorge syndrome," *Blood* 104(8):2574-2581.

Markert M L, Devlin B H, Alexieff M J, Li J, McCarthy E A, Gupton S E, et al., "Review of 54 patients with complete DiGeorge anomaly enrolled in protocols for thymus transplantation: outcome of 44 consecutive transplants," 2007, *Blood*, 109(10): 4539-47.

Markert M L, Devlin B H., 2008, "Thymic reconstitution. In: Rich R R, Shearer W T, Fleischer T, Schroeder H W, Weyand C M, Frew A, editors. Clinical Immunology 3rd edition. Edinburgh: Elsevier; pp. 2008. pp. 1253-1261.

Markert M L, Li J, Devlin B H, Hoehner J C, Rice H E, Skinner M A, 2008, "Use of allograft biopsies to assess thymopoiesis after thymus transplantation," *J Immunol*, 180: 6354-6364.

Markert M L, Devlin B H, McCarthy E A, 2010, "Thymus transplantation," *Clin Immunol.*, 135(2):236-46.

Markert M L, Marques J G, Neven B, Devlin B H, McCarthy E A, Chinn I K, 2011, "First use of thymus transplantation therapy for FOXN1 deficiency (nude/SCID): A report of 2 cases," Blood, 117: 688-696.

Markert M L, Devlin B H, McCarthy E A. Chapter 84 *Thymic reconstitution.* 2013. In: Fleisher T A, Shearer W T, Schroeder H W, Frew A J, Wey and C M, editors. Clinical Immunology (Fourth Edition). London pp. 1032-8.

Markert M L. 2014. "Thymus Transplantation," *Stiehm's Immune Deficiencies*, eds Sullivan K E & Stiehm E R (Academic Press), 1st Ed, pp 1059-1067.

Neufeld, M. et al., 1981, "Two types of autoimmune Addison's disease associated with different polyglandular autoimmune (PGA) syndromes," *Medicine* 60: 355-362.

Palmer S, Albergante L, Blackburn C C, Newman T J (2018) Thymic involution and rising disease incidence with age Proc Natl Acad Sci USA 115:1883-1888 doi:10.1073/pnas.1714478115.

Parker W, Yu P B, Holzknecht Z E, Lundberg K, Buckley R H, Platt J L, "Specificity and function of 'natural' antibodies in immunodeficient subjects: Clues to B cell lineage and development," 1997, *J Clin Immunol.*, 17:311-321.

Patel D D, Whichard L P, Radcliffe G, Denning S M, Haynes B F. Characterization of human thymic epithelial cell surface antigens: Similarity of thymic epithelial cells to epidermal keratinocytes. J Clin Immunol. 15:80-92, 1995.

Perheentupa J., 2002, *Endocrinol. Metab. Clin. North Am.* 31: 295-320 Rota I A and Dhalla F. FOXN1 deficiency nude severe combined immunodeficiency. Orphanet Journal of Rare Diseases. 2017; 12:6.

Rendell V R, Giamberardino C, Li J, Markert M L, & Brennan T V, 2014, "Complete thymectomy in adult rats with non-invasive endotracheal intubation," *J Vis Exp* (94).

Rice H E, Skinner M A, Mahaffey S M, Oldham K T, Ing R J, Hale L P, 2004, "Thymic transplantation for complete DiGeorge syndrome: medical and surgical considerations," *J Pediatr Surg.*, 39: 1607-1615.

Schmid C, Binder J, Heemann U, & Tilney N L, 1994, "Successful heterotopic heart transplantation in rat," *Microsurgery* 15(4):279-281.

Schoenecker J G, Hauck R K, Mercer M C, Parker W, Lawson J, 2000, "Exposure to topical bovine thrombin during surgery elicits a response against the xenogeneic carbohydrate galactose α1-3Galactose," *J Clin Immunol.*, 20:434-444.

Sun D P et al. (2016) Thymic hyperplasia after chemotherapy in adults with mature B cell lymphoma and its influence on thymic output and CD4(+) T cells repopulation Oncoimmunology 5:e1137417 doi:10.1080/2162402X.2015.1137417.

Ucar A, Ucar O, Klug P, Matt S, Brunk F, Hofmann T G, 2014, "Adult thymus contains FoxN1(-) epithelial stem cells that are bipotent for medullary and cortical thymic epithelial lineages," *Immunity*, 41: 257-269.

Uibo R., et al., 1994, "Autoantibodies to cytochrome P450 enzymes P450scc, P450c17, and P450c21 in autoimmune polyglandular disease types I and II and in isolated Addison's disease," *J. Clin. Endocrinol. Metab.* 78: 323-328.

Ulyanchenko S, O'Neill K E, Medley T, Farley A M, Vaidya H J, Cook A M, 2016, "Identification of a bipotent epithelial progenitor population in the adult thymus," *Cell Rep.* 14: 2819-2832.

Wang K X, Shi Y F, Ron Y, Kazanecki C C, Denhardt D T. Plasma osteopontin modulates chronic restraint stress-induced thymus atrophy by regulating stress hormones: Inhibition by an anti-osteopontin monoclonal antibody. J Immunol. 182:2485-2491, 2009.

Weiss J M, Cuf P, Bismuth J, Eymard B, Fadel E, Berrih-Aknin S, et al. SDF-1/CXCL12 recruits B cells and antigen-presenting cells to the thymus of autoimmune myasthenia gravis patients. Immunobiol. 218:373-381, 2013.

Wickemeyer J L, Sekhsaria S (2014) Prolonged severe immunodeficiency following thymectomy and radiation: a case report J Med Case Rep 8:457 doi:10.1186/1752-1947-8-457.

Wong K, Lister N L, Barsanti M, Lim J M C, Hammett M V, Khong D M, 2014, "Multilineage potential and self-renewal define an epithelial progenitor cell population in the adult thymus," *Cell Rep.* 8: 1198-1209.

Wurbel M-A, Malissen M, Guy-Grand D, Meffre E, Nussenzweig M C, Richelme M, Carrier A, Malissen B. Mice lacking the CCR9 CC-chemokine receptor show a mild impairment of early T- and B-cell development and a reduction in T-cell receptor γδ+ gut intraepithelial lymphocytes. Blood 98:2626-2632, 2001.

Yu X, Almeida J R, Darko S, van der Burg M, DeRavin S S, Malech H, 2014, "Human syndromes of immunodeficiency and dysregulation are characterized by distinct defects in T-cell receptor repertoire development," *J Allergy Clin Immunol.* 133: 1109-1115.

Zaitseva M, Kawamura T, Loomis R, Goldstein H, Blauvelt A, Golding H. Stromal-derived factor 1 expression in the human thymus. J Immunol. 168:2609-2617, 2002.

Zlotogora, J., et al., 1992, "Polyglandular autoimmune syndrome type I among Iranian Jews," *J. Med. Genet,* 29, 824-826.

Abbreviations

AIRE: autoimmune regulator gene.
Ab: Antibody.
Ag: Antigen.
ALCAM, Activated leukocyte cell adhesion molecule.
ANG-1, Angiopoietin 1.
APC: Antigen Presenting Cell.
ATG: thymoglobulin.
BCMA, B-cell maturation antigen/tumor necrosis factor receptor superfamily member 17 (TNFRSF17).
b.i.d.: twice daily.
BMI: body weight index.
BSA: body surface area.
BSC: biological safety cabinet.
CCL11, Eotaxin.
CCL20, chemokine (C-C motif) ligand 20; MIP-3a.
CCL21/6Ckine, Chemokine (C-C motif) ligand 21.
cDGA: complete DiGeorge anomaly.
CEACAM-1, Carcinoembryonic antigen-related cell adhesion molecule 1.
CFR: Code of Federal Regulations.
cGMP: Current Good Manufacturing Practices.
CK: cytokeratin.
CNI: calcineurin inhibitor.
CTACK, CCL27, C-C motif chemokine ligand 27.
CTT: allogeneic cultured postnatal thymus tissue-derived product.
CVVHD/F: continuous veno-venous hemodiafiltration.
CXCL12/SDFF-1a, Stromal cell-derived factor 1.
CXCL16, chemokine ligand 16.
DC: Dendritic Cell.
DSA: Donor-specific Antibody.
DGF: Delayed Graft Function.
DKK-1, Dickkopf-related protein 1.
DMSO: dimethyl sulfoxide.
EBV: Epstein Barr virus.
EGF R, Epidermal growth factor rector.
EU: endotoxin unit.
FBS: fetal bovine serum.
FDA: Food and Drug Administration.
FSGS: focal segmental glomerulosclerosis.
Galectin-7.
GAPDH: glyceraldehyde 3-phosphate dehydrogenase.
GCP-2, Granulocyte chemotactic protein-2, (or C-X-C motif chemokine ligand 6).
GDF-15, Growth differentiation factor-15.
GDNF, Glial cell line-derived neutrophic factor.
H&E: Hematoxylin and Eosin.
HD: hemodialysis.
HEPES: N-2-Hydroxyethyl peperazine N'-2-ethane-sulfonic acid.
HI: HI—Heat inactivation.
HIP: Intraperitoneal.
HIV: human immunodeficiency virus.
HVEM, Herpesvirus entry mediator.
ICAM-1, Intercellular Adhesion Molecule 1, CD54.
ICAM-3, Intercellular adhesion molecule 3.
IBW: ideal body weight.
IDDM: insulin dependent diabetes mellitus.
IGFBP-1, Insulin line growth factor binding protein 1.
IGFBP-6, Insulin Like Growth Factor Binding Protein 6.
IL-1b, Interleukin 1 beta.
IL-2Ra, Interleukin-2 receptor alpha chain.
IL-2Rg, Interleukin 2 Receptor Subunit Gamma.
IL-12p40, Interleukin-12 subunit beta.
IL-16, Pro-interleukin-16.
ISHLT: International Society for Heart & Lung Transplantation.
ISO: International Organization for Standardization.
LAL: limulus amebocyte lysate.
LIGHT, a member of the TNF superfamily expressed on activated T cells and immature DCs.
LOD: lower limit of detection.
M-CSF, Macrophage colony-stimulating factor.
MC3: Marcus Center for Cellular Cures.
mAb: monoclonal antibody.
MHC: Major Histocompatibility Complex.
MICA, MHC Class I Polypeptide-Related Sequence A.
MIF, Macrophage migration inhibitory factor.
MIP-3b, Macrophage inflammatory Protein-3 Beta (CCL 19, chemokine ligand 19).
MIP-1b, Macrophage inflammatory protein-1β.
MST: mean survival time.
NRGi-B1, Neuregulin.
OPN, Osteopontin
PBMC: peripheral blood mononuclear cells.
PBS: phosphate buffered saline.
PDGF-AA, platelet-derived growth factor AA.
PECAM-1, Platelet endothelial cell adhesion molecule-1 (CD31).
PF4, platelet factor 4.
PIGF, Phosphatidylinositol-glycan biosynthesis class F protein.
POD: Post-Operative Day.
PRA: panel reactive antibodies.
RANTES, Regulated upon Activation, Normal T cell Expressed and Presumably Secreted.
SCF R, Stem cell factor Receptor.
SL: sublingual.
TBW: total body weight.
TC: tissue culture.
Tfh: T follicular helper.
TOM: thymus organ medium.
uPAR (CD87), Urokinase plasminogen activator receptor.
USP: United States Pharmacopeia.
ULOQ: upper limit of quantitation.
USP: United States Pharmacopeia.

What is claimed is:

1. A method of producing an allogeneic cultured postnatal thymus tissue-derived product suitable for implantation into a human, comprising the steps of:
(a) slicing the donor thymus into slices, placing the donor thymus slices on a support structure, and culturing the donor thymus tissue slices in a thymus organ medium for a period of from about 6 days to about 21 days to produce partially T-cell depleted donor thymus tissue slices;
(b) detecting the level of CCL21 in the thymus organ medium during the culturing step and comparing the level of CCL21 to a baseline level determined at day 0 of the culturing step; and
(c) if the level of CCL21 is increased as compared to the baseline level and if the thymus tissue slices show areas positive for cytokeratin (CK) staining, the presence of at least one Hassall body, and the presence of intact nuclei of thymic epithelial cells and other stromal cells, recovering the partially T-cell depleted donor thymus tissue slices as the allogeneic cultured postnatal thymus tissue-derived product suitable for implantation.

2. The method according to claim 1, the method further comprising detecting the levels of one or more of L-selectin, M-CSF, galectin-7 or IL-16 in the thymus organ medium during the culturing step, comparing the levels of one or more of L-selectin, M-CSF, galectin-7 or IL-16 with baseline levels determined at day 0 of the culturing step for L-selectin, M-CSF, galectin-7 or IL-16, wherein the levels of one or more of L-selectin, M-CSF, galectin-7 or IL-16 are decreased as compared to the baseline levels.

3. The method according to claim 2, the method further comprising detecting the levels of one or more of CXCL12, CXCL16, or CCL11 in the thymus organ medium during the culturing step, comparing the levels of one or more of CXCL12, CXCL16, or CCL11 with baseline levels determined at day 0 of the culturing step for XCL12, CXCL16, or CCL11, wherein the levels of one or more of CXCL12, CXCL16, or CCL11 are increased as compared to the baseline levels.

4. The method according to claim 1, wherein the culturing step is for a period of six days, or seven days, or eight days, or nine days, or 10 days, or 11 days, or 12 days, or 13 days, or 14 days, or 15 days, or 16 days, or 17 days or 18 days or 19 days, or 20 days, or 21 days; or for a period of 5-6 days, or 5-7 days, or 5-8 days, or 5-9 days, or 5-10 days, or 6 to 7 days, or 6 to 8 days, or 6 to 9 days, or 6 to 10 days, or 6 to 11 days, or 6 to 12 days, or 6 to 21 days, or 7 to 21 days, or 8 to 21 days, or 9 to 21 days, or 10 to 21 days, or 11 to 21 days, or 12 to 21 days, 13 to 21 days or 14 to 21 days, or 15 to 21 days, or 16 to 21 days or 17 to 21 days or 18 to 21 days, or 19 to 21 days, or 20 to 21 days.

5. The method of claim 1, wherein the thymus tissue slices of step (c) show cytokeratin 14 (CK 14) staining.

6. The method of claim 1, wherein the thymus tissue slices show areas positive for CK staining in a lacy pattern.

7. The method of claim 5, wherein the thymus tissue slices show areas positive for CK14 staining in a lacy pattern.

* * * * *